US007879551B2

(12) United States Patent
Brody et al.

(10) Patent No.: US 7,879,551 B2
(45) Date of Patent: Feb. 1, 2011

(54) METHODS AND MATERIALS FOR IDENTIFYING POLYMORPHIC VARIANTS, DIAGNOSING SUSCEPTIBILITIES, AND TREATING DISEASE

(75) Inventors: Lawrence C. Brody, Baltimore, MD (US); Anne Parle-McDermott, Dublin (IE); John Scott, Dublin (IE); Peadar Kirke, Dublin (IE); James Mills, Rockville, MD (US); Faith Pangilinan, Rockville, MD (US); Anne Molloy, Dublin (IE)

(73) Assignees: The United States of America as represented by the Department of Health and Human Services, Washington, DC (US); The Provost Fellows and Scholars of the College of the Holy and Undivided Trinity of Queen Elizabeth Near Dublin, Dublin (IE); The Health Research Board, Dublin (IE)

( * ) Notice: Subject to any disclaimer, the term of this patent is extended or adjusted under 35 U.S.C. 154(b) by 308 days.

(21) Appl. No.: 11/958,126

(22) Filed: Dec. 17, 2007

(65) Prior Publication Data

US 2008/0213775 A1 Sep. 4, 2008

Related U.S. Application Data

(63) Continuation-in-part of application No. PCT/US2005/021288, filed on Jun. 16, 2005.

(51) Int. Cl.
*C07H 21/04* (2006.01)
*C12Q 1/68* (2006.01)

(52) U.S. Cl. .......................... 435/6; 435/91.1; 435/91.2; 536/23.1; 536/24.3

(58) Field of Classification Search ........................ None
See application file for complete search history.

(56) References Cited

U.S. PATENT DOCUMENTS

| 6,664,062 B1 | 12/2003 | Stanton, Jr. |
| 6,833,243 B2 | 12/2004 | Rozen |
| 6,838,276 B2 | 1/2005 | Falco et al. |

OTHER PUBLICATIONS

Parle-McDermott et al. (AM. Journal of Medical Genetics, vol. 132 A: 365-368, Jan. 6, 2005).*
Aguiar et al., "Neural Tube Defects and Associated Factors in Liveborn and Stillborn Infants," *J. Pediatr. (Rio J.)*., 79 (2), 129-134 (2003).
Christensen et al., Disruption of the Mthfd1 Gene Reveals a Monofunctional 10-Formyltetrahydrofolate Synthetase in Mammalian Mitochondria, *J. Biol. Chem.*, 280 (9), 7597-7602 (2005).
Kirke et al., "Impact of the MTHFR C677T Polymorphism on Risk of Neural Tube Defects: Case-Controlled Study," *BMJ*, 328, 1535-1536 (2004).
Konrad et al., "Plasma Homocystein, 'MTHFR C677T, CBS 844inds68bp, and MTHFD1 G1958A Polymorphisms in Spontaneous Cervical Artery Dissections," *J. Neurol.*, 251, 1242-1248 (2004).
Krajinovic et al., "Role of Polymorphisms in MTHFR and MTHFD1 Genes in the Outcome of Childhood Acute Lymphoblastic Leukemia," *The Pharmacogenomics Journal*, 4, 66-72 (2004).
O'Leary et al., "Analysis of the Human Folate Receptor Beta Receptor Gene for an Association with Neural Tube Defects," *Molecular Genetics and Metabolism*, 29, 129-133 (2003).
Online Mendelian Inheritance in Man (OMIM), "+172460 Methylenetetrahydrofolate Dehydrogenase 1; MTHFD1" http://www.ncbi.nlm.nih.gov/entrez/dispomim.cgi?id=172460.
Parle-McDermott et al., "Analysis of MTHFR 1298A=>C and 677C=>T Polymorphisms as Risk Factors for Neural Tube Defects," *J. Hum. Genet.*, 48, 190-193 (2003).
Parle-McDermott et al., "Polymorphisms Within the Vitamin B12 Dependent Methylmalonyl-CoA Mutase Are Not Risk Factors for Neural Tube Defects," *Molecular Genetics and Metabolism*, 80, 463-468 (2003).
Prasannan et al., "Human Mitochondrial C1-Tetrahydrofolate Synthase," *J. Biol. Chem.*, 278, 43178-43187 (2003).
Stanek et al., "Premature Closure of Foramen Ovale and Renal Vein Thrombosis in a Stillborn Twin Homozygous for Methylene Tetrahydrofolate Reductase Gene Polymorphism: A Clinicopathologic Case Study," *J. Perinat. Med.*, 28, 61-68 (2000).
Zetterberg et al., "The transcobalamin codon 259 polymorphism influences the risk of human spontaneous abortion," *Hum. Reprod.*, 17 (12), 3033-3036 (2002).
Zetterberg et al., "Gene-gene interaction between fetal MTHFR 677C>T and transcobalamin 776C>G polymorphisms in human spontaneous abortion," *Hum. Reprod.*, 18 (9), 1948-1950 (2003).
Brody et al., *Am. J. Hum. Genet.*, 71(5): 1207-1215 (2002).
Chen et al., *Int. J. Cancer*, 110(4): 617-620 (2004).
Chowdary et al., *Genetic Testing*, 7(3): 255-257 (2003).
De Marco et al., *J. Hum. Genet.* 51(2): 98-103 (2006).
Di Pietro et al., *Molecular and Cellular Biology*, 22(12): 4158-4166 (2002).
GENBANK Database Accession No. BC017477 (Apr. 27, 2005).
Hol et al., *Clin. Genet.*, 53(2): 119-125 (1998).
JSNP Database Accession No. IMS-JST088187 (Aug. 9, 2001).
Parle-McDermott et al., *Am. Journal of Medical Genetics*, 132(4): 365-368 (2005).

(Continued)

Primary Examiner—Jeanine A Goldberg
(74) Attorney, Agent, or Firm—Leydig, Voit & Mayer

(57) ABSTRACT

The invention is directed to materials and methods associated with polymorphic variants in two enzymes involved in folate-dependent and one-carbon metabolic pathways: MTHFD1 (5,10-methylenetetrahydrofolate dehydrogenase, 5,10-methenyltetrahydrofolate cyclohydrolase, 10-formyltetrahydrofolate synthetase) and methylenetetrahydrofolate dehydrogenase (NADP+dependent) 1-like (MTHFD1L). Diagnostic and therapeutic methods are provided involving the correlation of polymorphic variants in MTHFD1, MTHFD1, and other genes with relative susceptibility for various pregnancy-related and other complications.

2 Claims, No Drawings

OTHER PUBLICATIONS

Parle-McDermott et al., *Molecular Human Reproduction*, 11(7): 477-480 (2005).

Zetterberg, *Reproductive Biology and Endocrinology*, 2(7): 1-8 (2004).

* cited by examiner

SEQUENCE LISTING

```
<160> NUMBER OF SEQ ID NOS: 28

<210> SEQ ID NO 1
<211> LENGTH: 3110
<212> TYPE: DNA
<213> ORGANISM: Homo sapiens
<220> FEATURE:
<221> NAME/KEY: CDS
<222> LOCATION: (54)..(2861)
<220> FEATURE:
<221> NAME/KEY: misc_feature
<222> LOCATION: (653)..(653)
<223> OTHER INFORMATION: Xaa at position 653 of the amino acid
      sequence = Arg or Gln
<220> FEATURE:
<221> NAME/KEY: misc_feature
<222> LOCATION: (2011)..(2011)
<223> OTHER INFORMATION: n at position 2011 of the nucleic
      sequence = g or a
```

<400> SEQUENCE: 1

```
gtggaacctc gatattggtg gtgtccatcg tgggcagcgg actaataaag gcc atg          56
                                                         Met
                                                         1 gcg cca gca gaa atc ctg aac ggg aag gag atc tcc gcg caa ata agg         104
Ala Pro Ala Glu Ile Leu Asn Gly Lys Glu Ile Ser Ala Gln Ile Arg
        5                  10                  15 gcg aga ctg aaa aat caa gtc act cag ttg aag gag caa gta cct ggt         152
Ala Arg Leu Lys Asn Gln Val Thr Gln Leu Lys Glu Gln Val Pro Gly
     20                  25                  30 ttc aca cca cgc ctg gca ata tta cag gtt ggc aac aga gat gat tcc         200
Phe Thr Pro Arg Leu Ala Ile Leu Gln Val Gly Asn Arg Asp Asp Ser
 35                  40                  45 aat ctt tat ata aat gtg aag ctg aag gct gct gaa gag att ggg atc         248
Asn Leu Tyr Ile Asn Val Lys Leu Lys Ala Ala Glu Glu Ile Gly Ile
 50                  55                  60                  65 aaa gcc act cac att aag tta cca aga aca acc aca gaa tct gag gtg         296
Lys Ala Thr His Ile Lys Leu Pro Arg Thr Thr Thr Glu Ser Glu Val
             70                  75                  80 atg aag tac att aca tct ttg aat gaa gac tct act gta cat ggg ttc         344
Met Lys Tyr Ile Thr Ser Leu Asn Glu Asp Ser Thr Val His Gly Phe
         85                  90                  95 tta gtg cag cta cct tta gat tca gag aat tcc att aac act gaa gaa         392
Leu Val Gln Leu Pro Leu Asp Ser Glu Asn Ser Ile Asn Thr Glu Glu
        100                 105                 110 gtg atc aat gct att gca ccc gag aag gat gtg gat gga ttg act agc         440
Val Ile Asn Ala Ile Ala Pro Glu Lys Asp Val Asp Gly Leu Thr Ser
    115                 120                 125 atc aat gct ggg aga ctt gct aga ggt gac ctc aat gac tgt ttc att         488
Ile Asn Ala Gly Arg Leu Ala Arg Gly Asp Leu Asn Asp Cys Phe Ile
130                 135                 140                 145 cct tgt acg cct aag gga tgc ttg gaa ctc atc aaa gag aca ggg gtg         536
Pro Cys Thr Pro Lys Gly Cys Leu Glu Leu Ile Lys Glu Thr Gly Val
                150                 155                 160 ccg att gcc gga agg cat gct gtg gtg gtt ggg cgc agt aaa ata gtt         584
Pro Ile Ala Gly Arg His Ala Val Val Val Gly Arg Ser Lys Ile Val
            165                 170                 175 ggg gcc ccg atg cat gac ttg ctt ctg tgg aac aat gcc aca gtg acc         632
Gly Ala Pro Met His Asp Leu Leu Leu Trp Asn Asn Ala Thr Val Thr
        180                 185                 190 acc tgc cac tcc aag act gcc cat ctg gat gag gag gta aat aaa ggt         680
Thr Cys His Ser Lys Thr Ala His Leu Asp Glu Glu Val Asn Lys Gly
    195                 200                 205 gac atc ctg gtg gtt gca act ggt cag cct gaa atg gtt aaa ggg gag         728
Asp Ile Leu Val Val Ala Thr Gly Gln Pro Glu Met Val Lys Gly Glu
210                 215                 220                 225 tgg atc aaa cct ggg gca ata gtc atc gac tgt gga atc aat tat gtc         776
Trp Ile Lys Pro Gly Ala Ile Val Ile Asp Cys Gly Ile Asn Tyr Val
                230                 235                 240 cca gat gat aaa aaa cca aat ggg aga aaa gtt gtg ggt gat gtg gca         824
Pro Asp Asp Lys Lys Pro Asn Gly Arg Lys Val Val Gly Asp Val Ala
            245                 250                 255 tac gac gag gcc aaa gag agg gcg agc ttc atc act cct gtt cct ggc         872
Tyr Asp Glu Ala Lys Glu Arg Ala Ser Phe Ile Thr Pro Val Pro Gly
        260                 265                 270 ggc gta ggg ccc atg aca gtt gca atg ctc atg cag agc aca gta gag         920
Gly Val Gly Pro Met Thr Val Ala Met Leu Met Gln Ser Thr Val Glu
    275                 280                 285
```

| | | |
|---|---|---|
| agt gcc aag cgt ttc ctg gag aaa ttt aag cca gga aag tgg atg att<br>Ser Ala Lys Arg Phe Leu Glu Lys Phe Lys Pro Gly Lys Trp Met Ile<br>290                        295                        300                        305 | | 968 |
| cag tat aac aac ctt aac ctc aag aca cct gtt cca agt gac att gat<br>Gln Tyr Asn Asn Leu Asn Leu Lys Thr Pro Val Pro Ser Asp Ile Asp<br>                                310                        315                        320 | | 1016 |
| ata tca cga tct tgt aaa ccg aag ccc att ggt aag ctg gct cga gaa<br>Ile Ser Arg Ser Cys Lys Pro Lys Pro Ile Gly Lys Leu Ala Arg Glu<br>                        325                        330                        335 | | 1064 |
| att ggt ctg ctg tct gaa gag gta gaa tta tat ggt gaa aca aag gcc<br>Ile Gly Leu Leu Ser Glu Glu Val Glu Leu Tyr Gly Glu Thr Lys Ala<br>                                340                        345                        350 | | 1112 |
| aaa gtt ctg ctg tca gca cta gaa cgc ctg aag cac cgg cct gat ggg<br>Lys Val Leu Leu Ser Ala Leu Glu Arg Leu Lys His Arg Pro Asp Gly<br>355                        360                        365 | | 1160 |
| aaa tac gtg gtg gtg act gga ata act cca aca ccc ctg gga gaa ggg<br>Lys Tyr Val Val Val Thr Gly Ile Thr Pro Thr Pro Leu Gly Glu Gly<br>370                        375                        380                        385 | | 1208 |
| aaa agc aca act aca atc ggg cta gtg caa gcc ctt ggt gcc cat ctc<br>Lys Ser Thr Thr Thr Ile Gly Leu Val Gln Ala Leu Gly Ala His Leu<br>                                390                        395                        400 | | 1256 |
| tac cag aat gtc ttt gcg tgt gtg cga cag cct tct cag ggc ccc acc<br>Tyr Gln Asn Val Phe Ala Cys Val Arg Gln Pro Ser Gln Gly Pro Thr<br>                        405                        410                        415 | | 1304 |
| ttt gga ata aaa ggt ggc gct gca gga ggc ggc tac tcc cag gtc att<br>Phe Gly Ile Lys Gly Gly Ala Ala Gly Gly Gly Tyr Ser Gln Val Ile<br>                        420                        425                        430 | | 1352 |
| cct atg gaa gag ttt aat ctc cac ctc aca ggt gac atc cat gcc atc<br>Pro Met Glu Glu Phe Asn Leu His Leu Thr Gly Asp Ile His Ala Ile<br>435                        440                        445 | | 1400 |
| act gca gct aat aac ctc gtt gct gcg gcc att gat gct cgg ata ttt<br>Thr Ala Ala Asn Asn Leu Val Ala Ala Ala Ile Asp Ala Arg Ile Phe<br>450                        455                        460                        465 | | 1448 |
| cat gaa ctg acc cag aca gac aag gct ctc ttt aat cgt ttg gtg cca<br>His Glu Leu Thr Gln Thr Asp Lys Ala Leu Phe Asn Arg Leu Val Pro<br>                                470                        475                        480 | | 1496 |
| tca gta aat gga gtg aga agg ttc tct gac atc caa atc cga agg tta<br>Ser Val Asn Gly Val Arg Arg Phe Ser Asp Ile Gln Ile Arg Arg Leu<br>                        485                        490                        495 | | 1544 |
| aag aga cta ggc att gaa aag act gac cct acc aca ctg aca gat gaa<br>Lys Arg Leu Gly Ile Glu Lys Thr Asp Pro Thr Thr Leu Thr Asp Glu<br>                      500                        505                        510 | | 1592 |
| gag ata aac aga ttt gca aga ttg gac att gat cca gaa acc ata act<br>Glu Ile Asn Arg Phe Ala Arg Leu Asp Ile Asp Pro Glu Thr Ile Thr<br>515                        520                        525 | | 1640 |
| tgg caa aga gtg ttg gat acc aat gat aga ttc ctg agg aag atc acg<br>Trp Gln Arg Val Leu Asp Thr Asn Asp Arg Phe Leu Arg Lys Ile Thr<br>530                        535                        540                        545 | | 1688 |
| att gga cag gct cca acg gag aag ggt cac aca cgg acg gcc cag ttt<br>Ile Gly Gln Ala Pro Thr Glu Lys Gly His Thr Arg Thr Ala Gln Phe<br>                                550                        555                        560 | | 1736 |
| gat atc tct gtg gcc agt gaa att atg gct gtc ctg gct ctc acc act<br>Asp Ile Ser Val Ala Ser Glu Ile Met Ala Val Leu Ala Leu Thr Thr<br>                        565                        570                        575 | | 1784 |
| tct cta gaa gac atg aga gag aga ctg ggc aaa atg gtg gtg gca tcc<br>Ser Leu Glu Asp Met Arg Glu Arg Leu Gly Lys Met Val Val Ala Ser<br>                                580                        585                        590 | | 1832 |
| agt aag aaa gga gag ccc gtc agt gcc gaa gat ctg ggg gtg agt ggt<br>Ser Lys Lys Gly Glu Pro Val Ser Ala Glu Asp Leu Gly Val Ser Gly<br>595                        600                        605 | | 1880 |

```
                                                          -continued gca ctg aca gtg ctt atg aag gac gca atc aag ccc aat ctc atg cag    1928
Ala Leu Thr Val Leu Met Lys Asp Ala Ile Lys Pro Asn Leu Met Gln
610                 615                 620                 625 aca ctg gag ggc act cca gtg ttt gtc cat gct ggc ccg ttt gcc aac    1976
Thr Leu Glu Gly Thr Pro Val Phe Val His Ala Gly Pro Phe Ala Asn
                630                 635                 640 atc gca cat ggc aat tcc tcc atc att gca gac cng atc gca ctc aag    2024
Ile Ala His Gly Asn Ser Ser Ile Ile Ala Asp Xaa Ile Ala Leu Lys
            645                 650                 655 ctt gtt ggc cca gaa ggg ttt gta gtg acg gaa gca gga ttt gga gca    2072
Leu Val Gly Pro Glu Gly Phe Val Val Thr Glu Ala Gly Phe Gly Ala
        660                 665                 670 gac att gga atg gaa aag ttt ttt aac atc aaa tgc cgg tat tcc ggc    2120
Asp Ile Gly Met Glu Lys Phe Phe Asn Ile Lys Cys Arg Tyr Ser Gly
    675                 680                 685 ctc tgc ccc cac gtg gtg gtg ctt gtt gcc act gtc agg gct ctc aag    2168
Leu Cys Pro His Val Val Val Leu Val Ala Thr Val Arg Ala Leu Lys
690                 695                 700                 705 atg cac ggg ggc ggc ccc acg gtc act gct gga ctg cct ctt ccc aag    2216
Met His Gly Gly Gly Pro Thr Val Thr Ala Gly Leu Pro Leu Pro Lys
                710                 715                 720 gct tac ata cag gag aac ctg gag ctg gtt gaa aaa ggc ttc agt aac    2264
Ala Tyr Ile Gln Glu Asn Leu Glu Leu Val Glu Lys Gly Phe Ser Asn
            725                 730                 735 ttg aag aaa caa att gaa aat gcc aga atg ttt gga att cca gta gta    2312
Leu Lys Lys Gln Ile Glu Asn Ala Arg Met Phe Gly Ile Pro Val Val
        740                 745                 750 gtg gcc gtg aat gca ttc aag acg gat aca gag tct gag ctg gac ctc    2360
Val Ala Val Asn Ala Phe Lys Thr Asp Thr Glu Ser Glu Leu Asp Leu
    755                 760                 765 atc agc cgc ctt tcc aga gaa cat ggg gct ttt gat gcc gtg aag tgc    2408
Ile Ser Arg Leu Ser Arg Glu His Gly Ala Phe Asp Ala Val Lys Cys
770                 775                 780                 785 act cac tgg gca gaa ggg ggc aag ggt gcc tta gcc ctg gct cag gcc    2456
Thr His Trp Ala Glu Gly Gly Lys Gly Ala Leu Ala Leu Ala Gln Ala
                790                 795                 800 gtc cag aga gca gca caa gca ccc agc agc ttc cag ctc ctt tat gac    2504
Val Gln Arg Ala Ala Gln Ala Pro Ser Ser Phe Gln Leu Leu Tyr Asp
            805                 810                 815 ctc aag ctc cca gtt gag gat aaa atc agg atc att gca cag aag atc    2552
Leu Lys Leu Pro Val Glu Asp Lys Ile Arg Ile Ile Ala Gln Lys Ile
        820                 825                 830 tat gga gca gat gac att gaa tta ctt ccc gaa gct caa cac aaa gct    2600
Tyr Gly Ala Asp Asp Ile Glu Leu Leu Pro Glu Ala Gln His Lys Ala
    835                 840                 845 gaa gtc tac acg aag cag ggc ttt ggg aat ctc ccc atc tgc atg gct    2648
Glu Val Tyr Thr Lys Gln Gly Phe Gly Asn Leu Pro Ile Cys Met Ala
850                 855                 860                 865 aaa aca cac ttg tct ttg tct cac aac cca gag caa aaa ggt gtc cct    2696
Lys Thr His Leu Ser Leu Ser His Asn Pro Glu Gln Lys Gly Val Pro
                870                 875                 880 aca ggc ttc att ctg ccc att cgc gac atc cgc gcc agc gtt ggg gct    2744
Thr Gly Phe Ile Leu Pro Ile Arg Asp Ile Arg Ala Ser Val Gly Ala
            885                 890                 895 ggt ttt ctg tac ccc tta gta gga acg atg agc aca atg cct gga ctc    2792
Gly Phe Leu Tyr Pro Leu Val Gly Thr Met Ser Thr Met Pro Gly Leu
        900                 905                 910 ccc acc cgg ccc tgt ttt tat gat att gat ttg gac cct gaa aca gaa    2840
Pro Thr Arg Pro Cys Phe Tyr Asp Ile Asp Leu Asp Pro Glu Thr Glu
```

```
              915                 920                 925
cag gtg aat gga tta ttc taa acagatcacc atccatcttc aagaagctac      2891
Gln Val Asn Gly Leu Phe
930                 935 tttgaaagtc tggccagtgt ctattcaggc ccactgggag ttaggaagta taagtaagcc   2951
aagagaagtc agcccctgcc cagaagatct gaaactaata gtaggagttt ccccagaagt   3011
cattttcagc cttaattctc atcatgtata aattaacata aatcatgcat gtctgtttac   3071
tttagtgacg ttccacagaa taaaaggaaa caagtttgc                         3110

<210> SEQ ID NO 2
<211> LENGTH: 2808
<212> TYPE: DNA
<213> ORGANISM: Homo sapiens
<220> FEATURE:
<221> NAME/KEY: misc_feature
<222> LOCATION: (1958)..(1958)
<223> OTHER INFORMATION: n at position 1958 of the nucleic
      sequence = g or a

<400> SEQUENCE: 2
atggcgccag cagaaatcct gaacgggaag gagatctccg cgcaaataag ggcgagactg     60
aaaaatcaag tcactcagtt gaaggagcaa gtacctggtt tcacaccacg cctggcaata    120
ttacaggttg gcaacagaga tgattccaat ctttatataa atgtgaagct gaaggctgct    180
gaagagattg ggatcaaagc cactcacatt aagttaccaa gaacaaccac agaatctgag    240
gtgatgaagt acattcatcc tttgaatgaa gactctactg tacatgggtt cttagtgcag    300
ctacctttag attcagagaa ttccattaac actgaagaag tgatcaatgc tattgcaccc    360
gagaaggatg tggatggatt gactagcatc aatgctggga gcttgctag aggtgacctc     420 aatgactgtt tcattccttg tacgcctaag ggatgcttgg aactcatcaa agagacaggg    480
gtgccgattg ccggaaggca tgctgtggtg gttgggcgca gtaaaatagt tggggccccg    540
atgcatgact tgcttctgtg gaacaatgcc acagtgacca cctgccactc caagactgcc    600
catctggatg aggaggtaaa taaggtgac atccctggtgg ttgcaactgg tcagcctgaa    660
atggttaaag gggagtggat caaacctggg gcaatagtca tcgactgtgg aatcaattat    720
gtcccagatg ataaaaaacc aaatgggaga aaagttgtgg gtgatgtggc atacgacgag    780
gccaaagaga gggcgagctt catcactcct gttcctggcg gcgtagggcc catgacagtt    840
gcaatgctca tgcagagcac agtagagagt gccaagcgtt tcctggagaa atttaagcca    900
ggaaagtgga tgattcagta taacaacctt aacctcaaga cacctgttcc aagtgacatt    960
gatatatcac gatcttgtaa accgaagccc attggtaagc tggctcgaga aattggtctg   1020
ctgtctgaag aggtagaatt atatggtgaa acaaaggcca agttctgct gtcagcacta   1080 gaacgcctga gcaccggcc tgatgggaaa tacgtggtgg tgactggaat aactccaaca   1140
cccctgggag aagggaaaag cacaactaca atcgggctag tgcaagccct tggtgcccat   1200
ctctaccaga atgtctttgc gtgtgtgcga cagccttctc agggcccac ctttggaata   1260 aaaggtggcg ctgcaggagg cggctactcc caggtcattc ctatggaaga gtttaatctc   1320
cacctcacag gtgacatcca tgccatcact gcagctaata acctcgttgc tgcggccatt   1380
gatgctcgga tatttcatga actgacccag acagacaagg ctctctttaa tcgtttggtg   1440
ccatcagtaa atggagtgag aaggttctct gacatccaaa tccgaaggtt aaagagacta   1500
ggcattgaaa agactgaccc taccacactg acagatgaag agataaacag atttgcaaga   1560
```

-continued

```
ttggacattg atccagaaac cataacttgg caaagagtgt tggataccaa tgatagattc      1620
ctgaggaaga tcacgattgg acaggctcca acgagaagg gtcacacacg dacggcccag       1680
tttgatatct ctgtggccag tgaaattatg gctgtcctgg ctctcaccac ttctctagaa      1740
gacatgagag agagactggg caaaatggtg gtggcatcca gtaagaaagg agagcccgtc      1800
agtgccgaag atctgggggt gagtggtgca ctgacagtgc ttatgaagga cgcaatcaag      1860
cccaatctca tgcagacact ggagggcact ccagtgtttg tccatgctgg cccgtttgcc      1920
aacatcgcac atggcaattc ctccatcatt gcagaccnga tcgcactcaa gcttgttggc      1980
ccagaagggt ttgtagtgac ggaagcagga tttggagcag acattggaat ggaaaagttt      2040
tttaacatca aatgccggta ttccggcctc tgccccacg tggtggtgct tgttgccact       2100
gtcagggctc tcaagatgca cggggggcggc cccacggtca ctgctggact gcctcttccc      2160
aaggcttaca tacaggagaa cctggagctg gttgaaaaag gcttcagtaa cttgaagaaa      2220
caaattgaaa atgccagaat gtttggaatt ccagtagtag tggccgtgaa tgcattcaag      2280
acggatacag agtctgagct ggacctcatc agccgccttt ccagagaaca tggggctttt      2340
gatgccgtga agtgcactca ctgggcagaa ggggggcaagg gtgccttagc cctggctcag      2400
gccgtccaga gagcagcaca agcacccagc agcttccagc tcctttatga cctcaagctc      2460
ccagttgagg ataaaatcag gatcattgca cagaagatct atggagcaga tgacattgaa      2520
ttacttcccg aagctcaaca caaagctgaa gtctacacga agcagggctt tgggaatctc      2580
cccatctgca tggctaaaac acacttgtct ttgtctcaca acccagagca aaaaggtgtc      2640
cctacaggct tcattctgcc cattcgcgac atccgcgcca gcgttggggc tggttttctg      2700
taccccttag taggaacgat gagcacaatg cctggactcc ccacccggcc ctgttttat      2760 gatattgatt tggaccctga aacagaacag gtgaatggat tattctaa                  2808
```

<210> SEQ ID NO 3
<211> LENGTH: 935
<212> TYPE: PRT
<213> ORGANISM: Homo sapiens
<220> FEATURE:
<221> NAME/KEY: misc_feature
<222> LOCATION: (653)..(653)
<223> OTHER INFORMATION: Xaa at position 653 of the amino acid
      sequence = Arg or Gln

<400> SEQUENCE: 3

```
Met Ala Pro Ala Glu Ile Leu Asn Gly Lys Glu Ile Ser Ala Gln Ile
1               5                   10                  15

Arg Ala Arg Leu Lys Asn Gln Val Thr Gln Leu Lys Glu Gln Val Pro
            20                  25                  30

Gly Phe Thr Pro Arg Leu Ala Ile Leu Gln Val Gly Asn Arg Asp Asp
        35                  40                  45

Ser Asn Leu Tyr Ile Asn Val Lys Leu Lys Ala Ala Glu Glu Ile Gly
    50                  55                  60

Ile Lys Ala Thr His Ile Lys Leu Pro Arg Thr Thr Thr Glu Ser Glu
65                  70                  75                  80

Val Met Lys Tyr Ile Thr Ser Leu Asn Glu Asp Ser Thr Val His Gly
                85                  90                  95

Phe Leu Val Gln Leu Pro Leu Asp Ser Glu Asn Ser Ile Asn Thr Glu
            100                 105                 110

Glu Val Ile Asn Ala Ile Ala Pro Glu Lys Asp Val Asp Gly Leu Thr
        115                 120                 125
```

-continued

```
Ser Ile Asn Ala Gly Arg Leu Ala Arg Gly Asp Leu Asn Asp Cys Phe
130                 135                 140

Ile Pro Cys Thr Pro Lys Gly Cys Leu Glu Leu Ile Lys Glu Thr Gly
145                 150                 155                 160

Val Pro Ile Ala Gly Arg His Ala Val Val Gly Arg Ser Lys Ile
            165                 170                 175

Val Gly Ala Pro Met His Asp Leu Leu Leu Trp Asn Asn Ala Thr Val
            180                 185                 190

Thr Thr Cys His Ser Lys Thr Ala His Leu Asp Glu Glu Val Asn Lys
        195                 200                 205

Gly Asp Ile Leu Val Val Ala Thr Gly Gln Pro Glu Met Val Lys Gly
    210                 215                 220

Glu Trp Ile Lys Pro Gly Ala Ile Val Ile Asp Cys Gly Ile Asn Tyr
225                 230                 235                 240

Val Pro Asp Asp Lys Lys Pro Asn Gly Arg Lys Val Val Gly Asp Val
                245                 250                 255

Ala Tyr Asp Glu Ala Lys Glu Arg Ala Ser Phe Ile Thr Pro Val Pro
            260                 265                 270

Gly Gly Val Gly Pro Met Thr Val Ala Met Leu Met Gln Ser Thr Val
        275                 280                 285

Glu Ser Ala Lys Arg Phe Leu Glu Lys Phe Lys Pro Gly Lys Trp Met
290                 295                 300

Ile Gln Tyr Asn Asn Leu Asn Leu Lys Thr Pro Val Pro Ser Asp Ile
305                 310                 315                 320

Asp Ile Ser Arg Ser Cys Lys Pro Lys Pro Ile Gly Lys Leu Ala Arg
                325                 330                 335

Glu Ile Gly Leu Leu Ser Glu Glu Val Glu Leu Tyr Gly Glu Thr Lys
            340                 345                 350

Ala Lys Val Leu Leu Ser Ala Leu Glu Arg Leu Lys His Arg Pro Asp
        355                 360                 365

Gly Lys Tyr Val Val Val Thr Gly Ile Thr Pro Thr Pro Leu Gly Glu
    370                 375                 380

Gly Lys Ser Thr Thr Thr Ile Gly Leu Val Gln Ala Leu Gly Ala His
385                 390                 395                 400

Leu Tyr Gln Asn Val Phe Ala Cys Val Arg Gln Pro Ser Gln Gly Pro
                405                 410                 415

Thr Phe Gly Ile Lys Gly Gly Ala Ala Gly Gly Gly Tyr Ser Gln Val
            420                 425                 430

Ile Pro Met Glu Glu Phe Asn Leu His Leu Thr Gly Asp Ile His Ala
        435                 440                 445

Ile Thr Ala Ala Asn Asn Leu Val Ala Ala Ile Asp Ala Arg Ile
    450                 455                 460

Phe His Glu Leu Thr Gln Thr Asp Lys Ala Leu Phe Asn Arg Leu Val
465                 470                 475                 480

Pro Ser Val Asn Gly Val Arg Arg Phe Ser Asp Ile Gln Ile Arg Arg
                485                 490                 495

Leu Lys Arg Leu Gly Ile Glu Lys Thr Asp Pro Thr Thr Leu Thr Asp
            500                 505                 510

Glu Glu Ile Asn Arg Phe Ala Arg Leu Asp Ile Asp Pro Glu Thr Ile
        515                 520                 525

Thr Trp Gln Arg Val Leu Asp Thr Asn Asp Arg Phe Leu Arg Lys Ile
    530                 535                 540

Thr Ile Gly Gln Ala Pro Thr Glu Lys Gly His Thr Arg Thr Ala Gln
```

```
                545                 550                 555                 560
Phe Asp Ile Ser Val Ala Ser Glu Ile Met Ala Val Leu Ala Leu Thr
                565                 570                 575
Thr Ser Leu Glu Asp Met Arg Glu Arg Leu Gly Lys Met Val Val Ala
                580                 585                 590
Ser Ser Lys Lys Gly Glu Pro Val Ser Ala Glu Asp Leu Gly Val Ser
                595                 600                 605
Gly Ala Leu Thr Val Leu Met Lys Asp Ala Ile Lys Pro Asn Leu Met
                610                 615                 620
Gln Thr Leu Glu Gly Thr Pro Val Phe Val His Ala Gly Pro Phe Ala
625                 630                 635                 640
Asn Ile Ala His Gly Asn Ser Ser Ile Ile Ala Asp Xaa Ile Ala Leu
                645                 650                 655
Lys Leu Val Gly Pro Glu Gly Phe Val Val Thr Glu Ala Gly Phe Gly
                660                 665                 670
Ala Asp Ile Gly Met Glu Lys Phe Phe Asn Ile Lys Cys Arg Tyr Ser
                675                 680                 685
Gly Leu Cys Pro His Val Val Leu Val Ala Thr Val Arg Ala Leu
                690                 695                 700
Lys Met His Gly Gly Pro Thr Val Thr Ala Gly Leu Pro Leu Pro
705                 710                 715                 720
Lys Ala Tyr Ile Gln Glu Asn Leu Glu Leu Val Glu Lys Gly Phe Ser
                725                 730                 735
Asn Leu Lys Lys Gln Ile Glu Asn Ala Arg Met Phe Gly Ile Pro Val
                740                 745                 750
Val Val Ala Val Asn Ala Phe Lys Thr Asp Thr Glu Ser Glu Leu Asp
                755                 760                 765
Leu Ile Ser Arg Leu Ser Arg Glu His Gly Ala Phe Asp Ala Val Lys
                770                 775                 780
Cys Thr His Trp Ala Glu Gly Gly Lys Gly Ala Leu Ala Leu Ala Gln
785                 790                 795                 800
Ala Val Gln Arg Ala Ala Gln Ala Pro Ser Ser Phe Gln Leu Leu Tyr
                805                 810                 815
Asp Leu Lys Leu Pro Val Glu Asp Lys Ile Arg Ile Ala Gln Lys
                820                 825                 830
Ile Tyr Gly Ala Asp Asp Ile Glu Leu Leu Pro Glu Ala Gln His Lys
                835                 840                 845
Ala Glu Val Tyr Thr Lys Gln Gly Phe Gly Asn Leu Pro Ile Cys Met
                850                 855                 860
Ala Lys Thr His Leu Ser Leu Ser His Asn Pro Glu Gln Lys Gly Val
865                 870                 875                 880
Pro Thr Gly Phe Ile Leu Pro Ile Arg Asp Ile Arg Ala Ser Val Gly
                885                 890                 895
Ala Gly Phe Leu Tyr Pro Leu Val Gly Thr Met Ser Thr Met Pro Gly
                900                 905                 910
Leu Pro Thr Arg Pro Cys Phe Tyr Asp Ile Asp Leu Asp Pro Glu Thr
                915                 920                 925
Glu Gln Val Asn Gly Leu Phe
                930                 935

<210> SEQ ID NO 4
<211> LENGTH: 30
<212> TYPE: DNA
<213> ORGANISM: Homo sapiens
```

```
<220> FEATURE:
<221> NAME/KEY: misc_feature
<222> LOCATION: (15)..(15)
<223> OTHER INFORMATION: n = g or a

<400> SEQUENCE: 4
catcattgca gaccngatcg cactcaagct                                          30

<210> SEQ ID NO 5
<211> LENGTH: 71629
<212> TYPE: DNA
<213> ORGANISM: Homo sapiens
<220> FEATURE:
<221> NAME/KEY: misc_feature
<222> LOCATION: (53753)..(53753)
<223> OTHER INFORMATION: n at position 53753 of the nucleic
      sequence = g or a

<400> SEQUENCE: 5
gtggaacctc gatattggtg gtgtccatcg tgggcagcgg actaataaag gccatggcgc          60
cagcagaaat cctgaacggg aaggagatct ccgcgtaagc acctgacatt gttgttgagt         120
gtggggctgt ggacgagggc tctgagggtg tgcaggtccc ccggacccat tttttgcggg         180
agggacactt gtagcggaag agttaggccc ataacacctg aagacctgca gccaaagaaa         240
gagaacccgg gcacaacctg cgtttgcaag tggactgcct agtggctgta gccgctggct         300
cctgtgcttc ggggaaaagt cctgtgccga ctatgctccc aaacgcgcag ctgctggtga         360 cttttctgccg ggagagtggg tagttgcggc ttcctggagc cccccctagtc agaactcaga        420 aatccaatct acttaattcc cgttaatttg gaggtgagta gatggagact agtgaggtga         480
caaggcttga caagactaca aggctgataa tgacagaggg tccttccagc tcatagcttt         540
tcccactata ccatagtctt atcatacgct aagtgaaatc taatacattt ttcctttctc         600
ttcaatctcg tgcttctctc taacagccat ctctctgccc tggtcctaga gttacttgaa         660
acgtaatttg gctcctgagt cctgagaata ttctgcattc cacttgacct ctgcctgttc         720 taccccttgcg ggacatctga atgcttaatt agtgggtatc gttgccagct ttactcccag        780
gaagtaacac tggctgcttt ttgtctggga ggtgactggt gaggaaaaat gagagtagaa         840
ggaagaggga aaaatatatt ccctctagta gatgaaggag ggaaagatat attctgtgtg         900
accttactga gtttgctctt gggacctttc acatcacccg ttatgtaagt aactgttgcc         960
agccacagca gttactaaat tgtaattgtc ctgtaactcc taactttgta ataggttttt        1020
gagtgaatta caaagtcatc ggtggtgaaa agtccgggcc cagtggctca tgcctgtaat        1080
cccagcactt tgggaggccg aggtgggtgg atcacctgag gtctggagtt caagaccagc        1140
ctatccaaaa tggtgaaacc ccatctctac taaaaataca aaaaattagc cgagtgtggt        1200
ggcaggcatc tgtaatccca gctacttggg aggctgaggc aggagaatca cttgaacctg        1260
gggggcagag gttgcagtga gctgagatgc gccattgcac tccagcctgg gcaacaagag        1320
cgaaactccg tctaagaaaa aaaaaaaag aaatcacaat acttactgct tagtgctttt        1380
caacatgtgg cttgctaaac tgtatttctg ctttactttc tgttttgttt tgcttgtatt        1440
caaacttact tcctttttcca gtggcttttt gttttaatat aaaaatcttc cttttagaaa        1500
gactgattgt gaagagataa tttagtgcat aataatagtg cagataattt agtcaataa        1560 taatgcatct gggccagtac tgagaatagg tgctcactga atatactttc gttaattgga        1620
gagcaaatta aatatgttta tcaactccat aagggcaaat acatgtattg tcttattttt        1680
gtctatatcc taaacaccctg gaaaccctgt ttcctgcctt actacttgtg tggttttaag        1740
```

```
caaattaatt aacctttctg tgccaaagtt tcctcaaatg ttaagtaaaa gtaatgtcta    1800
ggtcattggg atgttagtag aattaaatgg gttcctaaca gatgatcatt tataattctt    1860
cctggcacat aataagtatt cgatatatgt tgtattaata atcagtaatt agttaatgta    1920
tatatgaatg attcattatc tttttttttt tttacatggt agctgctgcc ttgagatcta    1980
tttttttttt tgagatgaag tcttgctgtg tccaatcttg gctcactgca acctctgcct    2040
cctgcataca agcaattctc tcatatcagc ctcctgagta cctgggatta caggtgcccg    2100
ccatcacgcc tagctaattt ttttttttga gatggagttt cactcgtcgc ccagactgga    2160
gtacaatggc gtgatctcgg ctcactgcaa cctctgcctc ctgggttcaa gcgattctcc    2220
tgcctcagcc tcccaagtag ctgggattac aggcgtccgc caccatgtcc agctagtttg    2280
tttgtttgtt tgagacagag tttcactctt gttgcccagg ctggagtgca atggcatgat    2340
cttggctcac tgcaacctcc acctcccagg ttcaagcgat tctcctgcct cagcctcccg    2400
agtagctgag actacaggtg tgtgccaccc cgtccggcta atttttgtat ttttagtaga    2460
gacgggcttt caccatgttg gtcaggctgg tctgtaactc ctgacccat gtgatccacc    2520 cacctcggcc tcccaaagtg ctgggattac aggcatgagc cactgcaccg tcctagaat    2580 ttcttaaaaa tccagcccac ttcccacatt ccatcctgcg gattaggaaa tcatttgagg    2640
ccagaaaagt gatgtgattt gtccaagggt gaatggcaat ggctcaacta aaactaaggt    2700
cttcacccag tatatgatgt ttttcattct aaccagcact tactacttgc taaaaggaat    2760
ttcgtaagct tttcttttc ttttctttct ttctttcttt ttattttca gacaaggtct    2820 tgctctgttg ctcaggctgg agtgcaatgg cacgatgttg tctcactgta acctccactt    2880
cctgggttca aacgattctc ctgcctcagc ctcccaggta gctgggacta cgggcatgca    2940
ctactatgcc cggctaattt ttgaatttt agtagagatg gggtttcgcc atgttggtca    3000
agctggtctt gaactcctga cctcaagtga tctgtccacc tccacctcct aaagtgctag    3060
gattacaggt gtgagccact gcgccccgc tggcgctttg cttttctttt acagtcttcc    3120
tctcattagc atgtttccca ccctgctgag aatgctatcc ctgactcgtc ctcttctatt    3180
attattctcc ttttatgcct tcctgggagc tcggacatca acaaagttca gcattccaga    3240
ttccttctct acctgctcta ctctgtggga aactgggtac ttacatgatg gatttagttg    3300
ccaaattatc tttctttgga agtaacagcc ccttttctcc ctcacgggga attctaagtt    3360
tgcagcctga atttgacaac cggggggaagg tctgagagtt agagacaagt atctgttctt    3420
tgtgggtatt tattcactta ctcaacaagt agctgtatgt gtcccctaag ccaggcaatc    3480
ttcaaagctc tgagagtcta atagtgaaca aaacagccca aatccctacc ctcatgaaac    3540
ttgcatactg atgggtagag acagacattt aaataggtga aacacattgt gagctggtgg    3600
gaagcacaaa gagaacacca gagcagaaaa gagggacagg agtttctgtg gtatggtggc    3660 tgcaattta aatatgggag tcatagtctt tgtaaaagtg acttacgggc aaagacttga    3720
aggaggtgga gccttaagcc tgccaatgtt gtgagggaaa tagctcctga ccaaaaacac    3780
agcctgtgcc atagaccttt gtcctcacca gttactaact tactgctttg ggggtcaat    3840 ggcaatggcc ctgtgagaag ctgaccgagt ggaggctcct gagtagagga acctgaccct    3900
gccctgggca gaagggtggt gtcttttaaa agattatgca aagtgggaga aggatgtgca    3960
ttagtgttgg aagacccacc ttgctttgta ggcaagaaag catagttgtt ctataagtgg    4020
gcctttcaaa gggggggctta ctacatttat atgatttgtt tggttttcc ttcccttagt    4080
```

```
ttgctataat taagcctgct ctctccattg gtggcatttt tcttgattaa gtctcctttc   4140
taaagagact ggttgtgaag aggcagatgg tttgagtagg tgctgcgagt gtttgctggc   4200
caagtgcagg gcaagttggg tatatttgta agctcgctgt ggatggtagc tccagagcct   4260
aagcacggtg ctgcctcctc tgtgcatcac tgggtcatgc aatttacctc tgtgccttag   4320
cttctgtata ttggggtagt aatgtcacct aactcataag gttgttagaa ttaaatgagt   4380
ttaataccta taaagcattt agagaagttg ttggtacatg gtaagttta ataaataggt    4440 acttagaaag tactcattga ataaaaaagt gatgtttgtg tttatccagg ctgtaccttt   4500
gggagctggc ttataatctt gagacttaaa attagaattt atcctagtga tcaaagataa   4560
aagtttggaa ccttggctgt acatttagct acagggctag aagaactgtt tttgtgaaaa   4620
taatttgctt accatagtga agggcaggtc ttccttggtta ctaagttaac atggataaga   4680
cttttacttt gtcctgtaga ttaaatacat gtaggccctt ttgtgcttaa aaagatttgt   4740
ctgggcaggg cgtggtggct catgcctgta atcctaggac tttgggaggc ccaggcagga   4800
ggatcacctg agatcaggag ttggagacca gcctgactaa catggtgaaa ccccatctct   4860
actaaaaata caaaattagc tgggcatggt ggcccatgcc tgtaatccca gctactccag   4920
aggctgagac aggagaatgg cttgaacctg ggaggaggag gttgcagtga gccagtgagc   4980
caagatggcg ccattgcact ccagcctggg caacaagagc aaaacttcat ctcagaaaga   5040
aaaaaaaaaa aaatttgcct gtaatgaact ccaaagtgca ggttgctcaa aagttacatg   5100
gaaacttgac tgtcatagct ggattgattc tggaagcctg tgcaggagag gtcggagttc   5160
cagagaggct gggaccttca gctaggaccc cagccaggct gttgggcagg ttgcagcgat   5220
agtgcagcag agcccagagc tggcagccaa ctactatggt catggcacct gattggggat   5280
gtggtttgca ataagtgtc tgtccttgtc catcagggga gttgggatca ggcagtttgg    5340
gatttgggta gtgggttttt gagcagaggt ctgtggttcc ctgttacatc ccctatttgc   5400
atgaagaatc ttctagaagg aaagctggcc tagtacagag gagggtcctt ggagtggaag   5460
caaatggctc ccttctcctc taattgactc agtagaggtt ggtagaatag aggttaaggg   5520
gcagggatgc ttgtgtggcc ttggaaaagt tagcttcact ttcctttctg tgcagtaggg   5580
atgatgagaa ctgtctactt cctgacgttg ccccaaggat taaaagaatg taagactctc   5640
aaaacaagct tctttgacgt cccatccaca gtgcagaagg cccccattac ccctgcactg   5700
tgcggttggc tctccttttgc accccttaat tgaccaaaaa gcagcttctg tcaccctgta   5760
aatccttgac cttgaagaag tgggtggcta aaggtgccac agtcaagatt cctcagccac   5820
tcggctacta cccttaccct caattttgca gtttatgaca cttttagccag aagctaagtg   5880 acttgcccag gtgttccaag gtaggtggca gaggctcgat ggtgcatttc tttccctacc   5940
atgggcttgt cattggcttg ctagaaggaa ttgcaaactt ctaccctcca gcaggagaca   6000
ccctgggttt ggttctccct gaggcctttc cattgtgagg aaatcattcc acccatcagt   6060
ctggttggga agcacccaaa cagattctct tcaaaaagtc attttgaag ttatagtcca    6120 attttgactg gttagagaca ggtcagacct acttactttg ctggctaagc ttttttttttt  6180 tctttgcccc tcaccacaag cctggacggg agacgtactg cttggtatct ggtgcttgag   6240
aggtcccagg agataaggga gcattctgt gaaaggtttt gccagagcct gtcaggaact    6300
taatcttgac tgcaatgaat gacttaacat tataagtgat cttgggttt aggtgcccaa    6360 ataccagtcc ctccttagta agcagccttt tagacctaac ctttctctacc taaggttttg  6420 ttcagtcttt ttgaaaagca ggaaggccag gtccttgtga ggcttttctc attacaagct   6480
```

```
cttggcaggt tcttccctcc aagtggagaa cccttacctt ccccattctt tctaccttcc    6540
cctctgatga tccagagggc tgcaagggac ctagagctgt tcattggagc cctagtcagc    6600
tctagcggcc agatctatgg ttaggtaatc ctccaatagt gagactaatt ctcagtgtta    6660
gaattagggg tctgcctgtt ctcaccagca gacccactgg catcaactct cctttgttga    6720
catatagtta agcaccgctt cttacagatc ctcatactca gagccaacct tgtcttgtct    6780
cataactctt gctactggca gaaggtgata aaattgtggc ctagaggcca aatgttttttt   6840 gtttggctta cagaattaga ttacttctca acacatttat tactttacaa cattagatta    6900
cttcttaaca cacttatgcc tgtagttaca cataaaaatc tggatgcttg acttttttgaa  6960 agatgtgaac agtttagcaa tactgtactg tctatcttca tgccatcaat ttgttggatc    7020
tgagtagatg ctgcctaccc cctcatcctt gagtgggtgg gggtggggga ggtgggacct    7080
cattgttcag gaatcctacc acacttggtt gcctgtacca ggactccgaa ggttctttcc    7140
tctttgagac ctttttctga atgaacttat ggtccacttt taaaatccta aattttataa    7200
agccttaacc agtccaacct agtccgttta ttgcattaga tcagaggttg tcaaatgggg    7260
cagttttttc ctccctctac ctcagggcat tgggcatgcc tggagtcttt tgggttgtca    7320
tatggggaag gggtatgcta ttggcatcta gcagtagagg ccaggactgg tgccgagcat    7380
cctgcagtgc acaggatagt ccccataaca aaggatgatc tggtccaaat gtcagtggtg    7440
ctgagatcga aaaccctga tcaagaagct taatgtgagt tattgtgtca ttgtgtgtgt      7500
ggattaatga tggactttac cctcactaag aattatagga ttcattaaaa ttttacacta    7560
ttctgactta ttttcatgtc ataaatatca agcagtttac ctttgctttc ttagggcttt    7620
gagttagaga caattggatg gaagaacttt acattataaa ctttcaatga agcataaaat    7680
agcttcctca cattaagctt tcaaatacgt atttgaggta actgtcaaat ttggtaaatg    7740
tctgggttaa attataataa tttttttagt aaatattctt atgtaataat agtactattg    7800
tcagttgact gtcttgtata ctgatatagc ttttgctata ttagtgatag gtgaaaatca    7860
gttttctttc aacaagaagg taattagtg ttttaatttg acttaaatga ctagcaattt     7920
gaaatatatg tatttcttgg aacactaggt ggccttacaa tcacaattat ttttacaagg    7980
aactacatat taagttttta aaatttttt gaaggttttt ttttttttt ttttgagatg      8040 gagtttcact cttgttgcct aggctggagt gcaatggcgc gatctcggct caccgcaacc    8100
tctgcctccc gggttcaagc gattcccgtg cctcagcctc ccgagtagct gggattacag    8160
gcatgcgcca ccgctcccag ttaatttttt ttttttttt ttgtattttt agtagagacg     8220
gggtttcacc gctcaggctg tgtcaaaccc ccagctcag gtgatccacc cacctcagcc    8280
tcccaaagtg ctgggattat aggcgtgagc caccgtgccc agccgaagta ttttttagta    8340
gtataaaaat tgttaatgaa caaatgaaat aaatcaacaa atgaacaaaa tgggaataaa    8400
acatattaaa taaacatttt gtgttctgca ttttaaaaat cttataatag ctgggcgccg    8460
tggctcactc ctgtaatccc agcactttgg gaggccgagg agggcagatc acgaggtcag    8520
gagatcgaga ccatcttggc taacacggtg aaaccccgtc tctactaaaa aatacaaaaa   8580
attagctggg cgtggtggcg ggcgcctgta gtcccagcta cttgggaggc tgaggcagga   8640
gaatggcttg aacccgggag gcggagcttg cagtgagccg agatcgcgcc actgcactcc   8700
agcctgggag acgagggag actgcgtctc aaaaaaaaaa aaaaaaaaaa aaaaaaaaaa    8760
aaaaatatat atatatatat atatatatat atatatatat atatatatat atatataaaa    8820
```

```
aacagtaatc tattggggca ggggataaat tgtgtccttg tttagaagaa gactttttttt    8880
tttttagaag aagccctgtt gttttttgttg ttgttatttg tttgtttgtt tgttttgaga    8940
cggagtctca gtgggtcgcc caggctggag tgcagtggcg cgatctctgc tcactgcaac    9000
ctctgcctcc cgggttcaag cgattctcct gcctcagcct cctgagtagc tgagactaca    9060
ggcgcgtgcc accacgcctg gctgattttt cgtattttttt agtggagacg gggtttcacc   9120
atattggcca ggctggtctc gaactcctga cctcgtgatc tgcctgcctt ggcctcccaa    9180
agtgctggga ttgcaggcgt gagccatcat gcccggcccg aagccctgta ttttgaaggt    9240
gaatgttttt gcttcttctc tgatcagtta ctaaaagtgt tttccctgtg ccatttgaga    9300
attatttgag aactactcta agcttatggc acatttcagc attttttgttg tctaaaggca   9360
gctgtatttt aatcatgtaa atttcatgct gcctcctttg cctaccatat agcttctgtt    9420
gaaatgtcca tgttatattt tattttattt actcatttttt ctatatccat aataagagtt   9480
aaaggttata ttttagcaat gtgttttttt ctctgtcata acatgttaaa tattttaaat    9540
tcagccatga tgttaaacag agtgaattgg aatttctaac ggatttcggc aggaatgatt    9600
ataaagact tagggccaaa gagagcctgg gtgactgtgt aggggtatta ggctatgccc     9660
agcaccacat ctggttgtca ttcaggggag cagctagggc tggaactgct ggggagtgca    9720
aactgcagta ttccctgttc ccttgtctca gagcagaatt gtggcctcta tccaggtcca    9780
atcccagtta aaaaaaaaaa ttccaatggt ctattcttct tttgagctat attattgtag    9840
agaatactga cttgaaaaaa caaagtcact aactagaaat aaaatttgaa ctgggtgcag    9900
tggcttataa ctgtaatccc agcacttttg ggaggccaag gtgggaggat cacttgagct    9960
caggagttca agatcagcct gggcaacatg gcaaaatccc atctctacaa aaaatacaaa   10020
aattagctga agtgtggtgg tgtgcacctg tagttccagc tacttgggag gctgaagtgg   10080
gaggatggct tgagcccagg aggtggaggt tgcagtgagc tgtgattgca tcactgcact   10140
ccagcctggg tgatagagcc agaccctgtc tcaaaaaata aaataaataa ataaaaatca   10200
aaataaataa aatttgaaaa tcttgggtat gacttctttc ttgtaccatt caacattctt   10260
gatgtttact aggccagtcc aaataatcta tttcttgtgt gcctgtttat gtcagttttt   10320
tgtgacgtgt ggagaagtgg aactgggagt aaccaaatca gaatgaagga agagctgttt   10380
gtgaatgtcc atatgacaaa tgacaaaact ggttttccaa gagggacaga gcatgttcaa   10440
gttgaacatt gtatcatata tcataactgg gcaaggttga gctattcaga tatgtattta   10500
tggatgtaat ttcatttact tgacatccta gtgtattgtt gagaagttgt atgttggtaa   10560
attgatcatc ttagttttgc aagaggttat actttctttc actctaataa ggagactgca   10620
ggaggttata cttttagcct tgtgttaaat tctttgtaaa gaaaattctt ttgtgaatta   10680
gaatataatt tgtaagttta tactgaattt ggagtgggat tcattgattt atcattcaac   10740
cttatgtgga tacgctgtgg tcatcttact agtgcaggtt gagcaaaagg tgtgtgcttg   10800
agtttgttcc tgtaaaattt ttcatgacag cacctggaga gtggaaatgt gaaaaaagat   10860
gagcatcagc actttctaga agtgttggtc taagttttca tttatttact atatgatttt   10920
gaatgccatc aactaataca ttttcaatta tccctgaacc ctgtggctca gttagtgtca   10980
gtgggagtaa gaaaagatcc acgtgtccgg gaacagtggc tcacgcctgt aatcccagca   11040
ctttgggagg ttgagatggg tggatcacga agtcaggagt tcgagaccag cctgaccaac   11100
atggtgaaac cccatctcta ctaaaaatac aaaaattagc cgggcgtggt ggcacgtgcc   11160
tgtaatctca gctactcagg agactgaggc agcagaatcg cttgaaccca ggaggtggag   11220
```

```
gttgcagtga gcagatatcg caccattgca ctccagcctg ggcaaaagcg agtccccatc   11280
tcaaaaaaaa aaaaaaaaaa aagaaaaaag aaaaagattc acatctactt gaggcctgga   11340
aaattgttgg gaagttcctg tacatattaa accagataat gtccattcag tggtgttttt   11400
attttatttt attttatttt ggagacagtc ttgctctatc gtccaggctg gagtgcaatg   11460
gcaccatcat agctcactgc agcctcaacc tcctgggctc cagccatcct cctgccgcag   11520
cctcctgagt agctgggact acaggggcct gccaccactc ccaactaatt ttttattctt   11580
tgtagagatg gggtctcact atgttgccca ggatagtctt aaactcctgt tctaaagcaa   11640
tcctcttgcc ttaggttccc aaagtactga gattacaggc atgaaccatt gcctgctcct   11700
ggccagtgtt tttgatttaa aagagaaata caggccgggt gcagtggctc acgcctgtaa   11760
tcccagcact ttgggaagct gaggtggggg gatcacctga ggtcgggagt cgagaccag   11820 cctgaccaac atagagaatc tccacgttta ctagaaatac aaaattagcc aggcttggtg   11880
gcgcatgcct gtaatcctag ctactcggga ggctgaggca ggagaatcga ttgaacctgg   11940
gaggtggagg ttgtggtaag ctgagatcgc accattgcac tccagcctgg gcaatgagag   12000
caaaacttgg tctcaaaaaa aaagagaaat acaggccggg tgcagtggct cacgcctgta   12060
atcccagcac tttgggaggc cgaggtccta gatcgcttga gcccaggaat tcaagaccag   12120
cttgggcaat ggtgaaaccc atctctacca aaagtacaaa aattagccag gtgtggtggc   12180
acagacctgt aaagtcccag ctactcagga ggctggggcg aaaggatcgc ttgagcccag   12240
gaggtcgagg ctgcagtgag ctttgattgt gccactgtac tcccagcctg ggtgacagag   12300
cgagaccctg tgttaataaa caaacaaaca aataaaagag aaatacatct aataatctgc   12360
atcacttatt tgtgcttgaa acattcagtg ttaaccccac cctttccttt ttctctaggc   12420
aaataagggc gagactgaaa atcaagtca ctcagttgaa ggagcaagta cctggtttca   12480
caccacgcct ggcaatatta caggtattat gatagtgtat tttcattaat gttgtctttg   12540
cttgatttct cagtatcatt tcagacctct ccctctactt tcctccttt tttttggctg   12600 ttgtgtaatc tcatgccttt tcagtctctc ttggcaggct cccccctttg gctcagcttc   12660
taaatgttgg catatcctgg ccctctgctc ttctctgtgg atacccttc tctaggccag   12720 tgtctcttaa ccttttggtct tagtagggcc cctttacaat cttttttttc tttaatttaa   12780
tgtatttatt tatttattta cttttgagag acaaggtctt actctgttgc caggctggaa   12840
tgtagtagtg caatcatagc tcactgtagc gttgaactcc tggcttcaag cagtcctcct   12900
gcctctgcct gccaaagcat gggtattaca ggcgtgagcc actgtacctg ccccgttta   12960 cactcttaaa gatgtaagac ctcaagaagc tattgtttat acagatttat ccattaatgt   13020
ttactatatt agaaattagg aagttttggc cggacacggt ggctcctgcc tgtaatccag   13080
cactttggga ggccgaggtg ggcagatcac ctgaggtcag gagtttgaga ccagcctggc   13140
caacatggtg aaaccccatc tttattaaaa acacaaaaat tagctgggcg tggtggtggg   13200
cgcctgtaat cccagctact ctggaggctg aggcaggaga atcacttgaa cccgggaggt   13260
ggaggttgca gtgagccaag attgtgccac tgcactccag cctgggcgac agagagattc   13320
cgtctcaaaa aaaaaaaaa gagaaattag gaagttttaa aaatgtttat tcatttaaaa   13380
atgccaatag tgagctcatt tattatatgt taacataaat aacatttat ggaacaaaaa   13440 cttttttaaa aagaaaattt agtgaaaaga ggggcattat tttatatttg tgcacacctc   13500
tttcctgtat ggcttagtag aagagagctg gagtcctatc tgcctctgca ttcagtcttt   13560
```

```
tgctgtgtgc tggtttgatt gaaatatatg gagaaaattt ggcttcatac agatgtgtag    13620
ctataaaagg gaagaatttt tttaacagtc cttccaggta attgtgggta ttttctttg    13680 atgttgtacc aggactcagt aagtaaattt taaaagatta gttgcaatgt agaatctgaa    13740
actctatcag tgaactttga tactttgtta catcttctca gacttgcaca ctttgttaca    13800
tcaaaatgtt acatttggaa tgaatattta ccccatgcat ggttttgtaa catcctttgt    13860
tcctcatttg gaaataata gttcccggaa ttatgcagat cttccaaatg ttaacatttc    13920
attatgcaat atgaaagaat tggaatcatt aacatcacca acaagctcat cagagaagtt    13980
ttcaagtatt gagaagctgt caagctcaca ggggtggata aaaaatttta attttcaccc    14040
aaaaactcac attttatcat tggcaacaaa tacaattaat tgtttcccct gaaataccag    14100
tttcacttta ttcattttg agaaaatatt tgtcaaatac tcaagcctga ataatcattg    14160
cttgtcagtt gttatttcaa gtaggtgttt catataaaaa tgcatctgtt tcagctaaca    14220
aggcaaaaaa gcacaagtgc agcctggaca acaaagtgag atcccatctc cacaaaaaaa    14280
ttaaaaaatg agccaggagt ggtcgtatag aggtgtggtc ccaactacat gagagggaga    14340
caggagatca cttgagccca ggaagtcgag gctgcaggga gttgtgttca tgccactgta    14400
ctccagctta ggtgacagtg agatcctgtc tcaaaaaaaa ataaaaataa aaataaaaaa    14460
gcactaatgc tttagtaaca accacaacca ctgtacttct gtatatagca gaagtgcatt    14520
atgagtgctt cccaattcct tacatagact attaaaaaca catgcactca agagttgagg    14580
tttatttata tatatatatt ttttactttt tgggacagag ttttactgt tactcagtgc    14640 agtggcacaa tcttggttca ctgcaacctt catctcccag gctcaagtga tcctcccact    14700
cagcctccag agtagctggg attacaggca tgcgccacca tgcctaattt tttttttga    14760 gacggagtct tgctctgtcg cccaggctgg agtgcagtgg tgcaatcttg gcttactgca    14820
gcctccgctc ccagattcat gcaattctcc tgccttggcc tcctgagtag ctgggattac    14880
aggcacctgc cattgcaccc tgctaatttt ttttttttga acagaatct cgctctatcc    14940 cccaggctgg aatgtaatga cataatctca gctcactgca accttgcct cctgggttca    15000 agtgattctc atgcctcagc ctctggagta gctgggatta caggtgccac gcccagctaa    15060
tttttgtaat tttagtagag atagggtttc accattttgg ccaggctggt ctcgaactct    15120
tgacctcagg tgatccacct gcctcagctt cccaaagtgc tgagattaca ggtgtaagcc    15180
actgcgccca gccttaattt tttgtatttt tttgtagagt ttttttttgc cttgttgccc    15240
tagctggtct tgaactctgg gacccaaagt gatcctccca tttagcctc ccaaagtgct    15300 gggattacag gcatgagcta ctgcgcttgg ccttaatttt ttgtattttt ttgtagagac    15360
ggttttttgc cttgttgccc aggctagtct ccaactcctg ggctcaaagt gatcctcccg    15420
ccttggcctc ccaaagtcct gagattacag gcatgagcca ctgtgctcgg ccaagttgaa    15480
gtttaagaaa attaataatg tatatttctt catcaagggt ggtcctagtg aaactggcat    15540
ttagttttac tgggagtgtg tggtagtgaa ggataccttg actactagtc caaagccatt    15600
gtcttgattt gtgctggttc actagtagtc ttacacacca ttgcttttgc accatcggta    15660
cagacgttaa cacaatgaaa aaggcaaaca acattgtagt ggtattatta tgaagctagt    15720 ctggcccctca taaatctttg aaaaggtctt ggggtccctc aagagtgtgt gggccacatt    15780
atcagaacca ttattttagg cagtttcatc tatcaggcca gtgacttcta aatctagatt    15840
tcttctgagc tccaggctct tggtctggga caccactggt tccttccca ccttcaagtc    15900 tcctttgctt gttgttgctc atcaccctaa tacctaaacc atttgaatgc cttgggctca    15960
```

```
cccttgagat ctcttcccca tcttattctt tccctaagta acctcaccca gtcccatagc   16020
ttcatgaggg aatgcttcca aatttaggtc tctatccagt atttcttccc tgagctccag   16080
attcacccag tagggagata ttcaatacat attttttacgg acaaatgtat gaaggaatgt   16140
ttgcaatctt gatttggatg acaggaaact cacggctttc atttgaaact cccatcagag   16200
tttcacccaa gttggacata gtctccttct caatctcttt atttgtatgt ctccaataga   16260
tcatttaatc ccttgctaaa tttctatccc ttgttcatca agaatgtcaa ggtgggcatg   16320
gtgcggtggc tcatgcctat aatcccagca ctttgggagg ctaaggcggg tagatcactt   16380
aaggtcagga gtttgagact agcctggcca acatggtgag aactcatctc tactcaaaat   16440
acaaaaatta gccaggtgtg gtggtgcaca cctgtgatca cagctactca ggaggctgag   16500
gcaggagaat cgcttgaacc tgggggacag aggttgcagt gagctgagat tgtgccactg   16560
cactccagcc taagactccg tctcaattta aaaaaaaaaa agtcaaagtg aatagtactt   16620
aaatattccc ctctcctcct ctgctgtttg tctaagaggg cttagctgag aagaaaagca   16680
cagaaggcct gtcactctct gcctggcatg ttctctgctg tggtggattt tcccttttt    16740 gcaaattact aagaatcaaa agtatatatt gtgggtgtat actggtacat ttggtggctg   16800
gttatttctt ggcttatttt tgcaaattgt ttgttgtaga aagagtaaat gtcataggca   16860
agaagtatac ccttttaaa gcaacattgg gggtgttttt tttcctccat tttaaaaact    16920
gacttccaac cttgtttttt aaatttattg attacaaatg ttttattac ataaacactg    16980 ttctacagct cgtctcctac gtccttgctg ataaaacagt ggtagaatct tttaatttg    17040 tactttagca ccagagtcaa cagctttctg tgatacaagg tttatataat atgttgtaat   17100
cacatctccc tgcctcagac ctctagtctt tttcgctgtg gtgctggcac caccatcttc   17160
ccacattccc tgagctagaa gcctgaggcc gtctccttag gagctctctt cctcactccc   17220
tgcatccagt tagggctat tgtcctattg attgtgcctc tcatcaactc ttggaatctg    17280
ttgcctcccc ttgattccta tttctcccaa ccctggggcc actatagtta cctgcttaat   17340
gatttggggt tctatctata tacctcctgt ctgtcctcct gactgcaatt gcaatccttg   17400
ttaaaatgca agtctgatca caatctatcc agccacactc actctccatc ctttaccaga   17460
atgatagtac aagttgagta tcccttatcc gaaatgcttg ggacaagagt gttttagatg   17520
ttggaatctg tatatacata gggatgagat ccaattctaa agcaaaattt atttgtgttt   17580
cattatatac cttatacttg tagactgaag gtaattttat atatatgtgt gtgtgtgtat   17640
atatatatat aataataatt attattatta ttatttttt tgagactgag ttttgctctt    17700
gtcacccagg ctgagtgca atggcacgat ctcggcgcac tgcaacctcc acctcctggg    17760
ttcaagtgat tctcctgcct cagcctcctg agtagctggg attacaggtg tgttccacca   17820
cgcctggcta ttttttgtat ttttagttga gatgagattt caccatgttg gtcaggctgg   17880
tcttgaactc ctgacctcag gtgatccgcc tgcctcggcc tctcaaagtg ctaggattac   17940
ggacatgagc cactgctccc ggccaatttt atatattttt aataatattt tgcatgaaat   18000 gcactttta ctgtgttttg actgtaagcc atcacatgag gccaggtgtg gaattttcta    18060
cttttggcgt tgtcagtgct caaagtttct gattttggag cattttttat ttgtggtttt   18120
tttttttttt tttttgaga cagggtctca ctctgttgtc caggctggag tgcaggggtg   18180
tgatcacagt tcattgcagc ctggatctcc caggctcaag ctatcctccc atctcagcct   18240
cctgagtagc tgggactaca ggcatccagc taattttagt atttgagaca gaatttctcc   18300
```

```
atattgccca ggctagtctc agactgagct caagtgatcc acctgccttg gcctcccaaa    18360
gtgccgagtc accgcacctg actgattttg gattttgag ttagggatct tcaacctgta    18420
ctacttatat agagtgtcta caataattca aattgtttgt ttatatttct aatcgttcta    18480
tgttttatac taccctacga tgtaggagat gtccccttat agccatagta actcatgctc    18540
aaagatcttg ggtagcttgc ccaaagccag tcaggaaggg actgagtctg ggaaatgaac    18600
ccagatctgt ctctaaaacc catttgttct tcccctttgt tttcctaatt ccttagcaat    18660
gcattcaaga acattcatga tctggcccaa gtatatattt aaaagttgag ttttcatttt    18720
tttttaataa agtggatgag taacttccca aataactgaa tatttatagg aaattaagac    18780
ttgacttttc attataagag atactaatgg gctaggcatg gtggctcacg cctgtaatcc    18840
caccacttta ggaggccaag gcgagtggat tgcttgagcc caggagttca agaccagcct    18900
gggaaatata gagagacttt gtctccaaaa aaatacaaaa attagctggt tgtggtggtg    18960
cttgcctgta gtccccacta ctgaggaggc tgagctggga ggattgctca cgcctgggag    19020
gttgaggctg cagtgagctg taatcgtgtc attgcactcc agcctgggtg acagagcaag    19080
actttgtctc aaaaaaaaaa aaagttttct ggtaaggtga tagaaataca gcctcagccc    19140
catagcctca ttagtatctc tcactctctc tctttttttt ttttttttga gtcagaatct    19200
tgttctgtca tgcaggctgg agtgcagtga tgtgatctct gctcactgaa acctctgccc    19260
tcccctgtcc cccagggat cctcccacct tagcctccca aatgagctgg gactacaggc    19320
acaccaccat gcccagataa ttttgtatt ttttgtagag atggggtttc gatatgttgc    19380
ccaggctggt ctttaactcc tgggctcaag caatccacac accttgacct cccaaagtgc    19440
tgggagtata ggcatgagcc actgcacctg gccaaaaaac tgatttttaa cagtattcgg    19500
gaactattca gagtgcttta tgtatagtaa ctcattcagt cctcacaaaa tacatggaca    19560
gaatacagtt aataaactca actagcctgt atcttcataa ggttttctga aacagaaaga    19620
aaaatgaacc agtagaccaa tacccaagat atcttacggt gtagaacaca gattagtaaa    19680
ctgtggcccg tatccaaatg ctgcccagtt tataaagagt taaaaaagca atagcagcag    19740
ctgctgtgac acggtatgtg tcccacaaag cctaaaatat acaccgtctg cccctctaca    19800
gaaagtttgc agactcctgg tataaaaaaa aagtgtccct aacctgttct ggaataggat    19860
cttttttgga tgatgtagta ctcagccacc ttcaaggaga aatcagcatt cttttttttt    19920
tttttttttt tgagatggag tttcactctt gtcgcccagg ctggagtgca atggcacgat    19980
cttggctcac tgcaacttct gcccccgggg ttcaagggat tctcctgcct cagcttccca    20040
agtagctggg attacaggtg caccaccatc tgactggcta atatttgtat ttttagtata    20100
gatggggttt caccatcttg gccaggctag tctcgaactc ctgaccttag gtgatctgcc    20160
cgccttagcc tcccaaagtg ctgggattac aggcgtgagc caccatgccc ggccagaata    20220
cacgttcttt aaacattctt tttgcatcta gtctatcaat ggttctataa ccactttccc    20280
ctataaaatg cctatactgg ccaagtgtgg tggctcacac ctacctagca ctttggcagg    20340
ctgaggcagg aggattgctt aagcccaggt gtttgagacc agcctgggca atagagaaac    20400
tccatttcta caaaaaatac aaaaattggc tgtttgtggc agcgtgtact ggtagtccta    20460
gcttcttggg aagctgaggt gggaggattg cttgagccta ggagttgcag gctgcagtga    20520
gccatgatca tgctactgta ctctaggctg ggtggcagag taagaccctg tctcaaaaat    20580
aataaataaa taaataaaac ctatactaag agtgactctt tgaattggct tttagatgtc    20640
ttttccaata aaactttgac atacgctcat aactataact attaagtttt ctttctggaa    20700
```

```
ctggttgtag ttttagtgtt ttagacaaac tccttcagaa atattcaggc cgaaaatagt    20760
tacatgtaaa ggaacaacaa cagcgagaga cttcagactt ctcctgtgtg acattagatg    20820
ccaaagacaa catctccgaa ggaaaatgct gtcactccaa atcaggcaag gccagtcaag    20880
tgcaagggac agcagaaaaa tattttcagt tatacagact tagaaacatg tccacctacc    20940
tttcctggaa aactgactta taagttacat ttcacttact tgaaacatga atgaagataa    21000
attctagaac agagaagttg tggcttcctt actggcagca agtgataaaa caatttaatc    21060
tcagagttaa gactaaataa ctagtggtag gtataaatat gaatgaaatt gtaaaaaaat    21120 aatactttg tatttagaac cacctccttt cctactttga tctaaaaatt ccggaatgta     21180
tcaaatctgg taactgaacc agtgagggtt gggtggtggg gcaaagaaca tacatagaaa    21240
gtgaccaaag aggaaacatg agaggcacga aaagtctagg gaagccccta cgagaagcat    21300
ctaatgtact tagatacaaa taacccatta aaaaaaaagg tagaattccc ctcaaaggac    21360
tcttctggct cttgcaattc aaattagcac cacaaaactg agaactgtct gtataaggga    21420
caactgaagc taagattcag gccatgtcct gagatctgag gagagcgtcc agtaatagca    21480
ccaatatgac aagctcagaa aatcctgtgt tacaaaagcc ggcttctttc tctgccatgg    21540
tcctgttaaa aggagctgtg cttcagttgt ctttgatatg aagggaccac cacctttccc    21600
tctgtgatac cctctgcaat tctgggagaa acacaactta tggtagcatg tatcaacctt    21660
gagaaggaga ataccaacc actggagcat gaaacaatat tagtacaata aaattttaca     21720
aataaatggt tataatgata aactataaat atgttcatgg tcaaagaaac agagggaaca    21780
tagtgagaca ctgcatggtg gttcaaagga tttagcctct gcactacaag tttctccctg    21840
tctctctctt ttttttttaa gagacaaggt ctctctctgt tgcccaggct gcccaggcat    21900
agtaccatga ctcactgtgc actggtgcaa tcatggaaaa actcttgacc tcaagtaatc    21960 ctcccaccctt ggcctcctga gtgctgggac tacaggcagg caccactatg cctggctaat   22020
tttttgtaaa gatgggggg ggggtctcac tatgttgccc aggctggtct cgaactcctg     22080
ggctcaaacg atcctcctcc cttggcctcc caaagtgcag ggattataga cctgagttgc    22140
tgcacccggc ctcctctctg tgttggggcc agcagattgc cctttgtctt gcctggctgt    22200
ttattctgtg taaactagag ggaggtcctt ccaccctcct ttctattgtc tgtgtggcgg    22260
ggccagggag ctttccattg cccctgcggg tggggagag ggtgtggaat gtgccctctg     22320
ggtgctcctg cctctcaggc attttttcttg cctgatgaca gtttctcagc cctccatact   22380
ctgttttcct ggtatggcag cagaaatccc acatgtttct agtaggcctg cagcatcctt    22440
gcttagtttc cagtgcagat gcagatatcc tctactttct gtttgggtt tggcagtggg     22500 aaccaggtgg gccttgttta ggggagggc tgtaacacca tctgtgttca cataatccct     22560
cctgccccca cagcctccct atactcctgt aaaagttctc tgcaacaaga gtcgcatgat    22620
taaacatttc ttttattaaa actaaaattg tagaagcttt tctgtgcact ttgcctttcc    22680
ctaatcatct gatttgcatg catttattat tctaggttgg caacagagat gattccaatc    22740
tttatataaa tgtgaagctg aaggctgctg aagaggtaac gccagaagag ctgtgccatc    22800
accctcccca acctccacct gggtcctatc gattacccct tgccctttt ggtcctccct     22860 gtgaaaactt ttatcaccca caggagacat tagtttatct attttgtaag tcagaaatgg    22920
gtgggttaga tctgtggcct ctggtttgcc cgtgagtttt tgttttctca ttaatgattt    22980
tcttcccaaa gagcaggatg tcaattgagg aaagtgacaa gtctcgatca ttttaggaga    23040
```

```
tttatttgcc aaaattaagg acacacctgg gagacaggtc tataccttc tccgaagatg   23100
atttcgagtt ctccaaattt aaagaggaaa gggtgggtta ttgaaaagta cacgttttca   23160
tgtaagaggt gggtagggaa aaatagtcat tcatgacctt ctctggctca gtgaatctgc   23220
attttttaca taagatgaca gatggccgga cgcggtggct cacgccagta atcccagcac   23280
tttgggaggc cgaggcgggc ggatcacctg aggtcgggag ttttagacca gcctaagaaa   23340
catggagaaa ccccatctct actaaaaata caaaaaatta gctgggtgtg gtggcgcatg   23400
cctgtaatcc cagctactcg ggaggctgag gcaggagaat cgcttgaacc tgggaggcgg   23460
aggttgtggt gagccaagat agtgccattg cactccagcc tgggcaataa gagtgaagct   23520
ccaaccagaa aaaaaaaga cgatatagac aagtggggca gaggaaaaat gcaggcaatc   23580
tgcatttac ataagataac atagacagaa ttgggcaggg gaaaaatcag atatacattt   23640
gtgtctggtg ggctgggggg atttacattg ccatggtgaa attttaacag aaacatcata   23700
aagatgttgc agctcactac gaatttcttt gtgggcaaaa tatgggggag gcatgtagct   23760
tttcatcttg taacatctta tttaggaacc aaaaggggg aggcagattt gcatgaccca   23820
gttcccagct tggcttttcc ctttgactta atgaatttgg ggtcccaaga tttaattcc   23880
tttctcaaga aatagcaagc atgacattgc tgaagtgcag tggtggcaat taacaagtga   23940
atgatgaatg ggttgaagtg agggactcat tcttcagaac atataagggt gaaatgatga   24000
ccaacacctc cttgcttgtt agtcatgtct gtaaagaaaa tggttcaata tctcaagttg   24060
tcttgccatt tacctgcttt taatgtctgt tttgcagatt gggatcaaag ccactcacat   24120
taagttacca agaacaacca cagaatctga ggtgagcttt tatgagttga ttgtgaagag   24180
ggaaggtgaa gtggtttcct ctctggtttt ggtttacggg ggctttgggg actgacacat   24240
ttagccaaga cctccaggta ttttttttt tttttttt gagacacagt tttgctcatg   24300
tcacccaggc tggagagcaa tgatgcgatc tcgactctct gcaacctccg cctcccaggt   24360
tcaagcaatt ctcctgcctc agcctcccga gtagctggga ttacaggcgc ccaccgcctc   24420
acctggctaa ttttatatt tttaatagag acgcggtttc accacgttgg ccaggctggt   24480
cttgaactcc tgacctgagg tgatttaccc gccttggcct cccaaagtgc tgggattaca   24540
ggcgtgagcc accacgcctg gcacctccag gtattctttc ttcacagact cccacagagg   24600
agatggtgca gggatgaaca tttggtactc aaagtgtgac tgcagtactg tttgcttcca   24660
aatcatctgt tgtgttttgtt aaaactgatc cttggagcca ggcacggtgg ctcatgcctg   24720
taatcccagc attttgggag gccgaggtgg gcagatcacc tgaggtcggg agttcgagac   24780
cagcctggcc aacatggaga aaccctgtct ctactaaaaa atacaaaatt gccaggcgt   24840
ggtggcgcat gcctgtaatc ccagctactt ggaaggttga ggcaggagaa tcacttgaac   24900
ccgggaggcg gaggttgcag tgagccaaga tcgtaccatt gcactccaac ctgggaaaaa   24960
agagcaaaac tccgtctcaa aaaaataggt aaaaccgatc cttggcctgt aattatctgc   25020
attctaaaaa ccaaatatgt attccttta tatgaggttc aggactaggc agaacaaatc   25080
agcggtgatt aaagtcagaa ctgtggttgc ctgtaggtgg gagattaatg ctaaactgta   25140
ggaggataaa gcaactttct tgaggttatg gcaatgttcc atatatgcgc tgtccagtat   25200
gggagccact agccccatga ggctatttga atttagttaa aatgaaataa aattaaaaat   25260
tcacttcctt ggttgtacta gccactttgc aaggattaag tagctgctat tgtattgtaa   25320
ggtgcaaatt atagaaaatt tctgccatcg cagaaaagat gattggacat tgctgctcta   25380
catcttgatt tggatgattg taacatgggt attattgctg taataagtta ttagagttct   25440
```

```
tagctcttt   tatttattg   tattgtattt   ttagagacag   ggtctcactc   ttttgcctca   25500
gctgcagcac  agtggtgtga  tcatagctca   ttgtagcctc   aacctcctaa   gctcaagtga   25560
tcctcccacc  ttagcctctt  gagcagctgg   gactataggc   atgagccacc   atgcccagct   25620
aattttattt  tattttgag   gcagagtttt   actcttgtcg   cccaggctag   agtgcagtgg   25680
tgcaatattg  gctcactgca  acctccacct   cccaggttca   agcgattctc   atgcctcagc   25740
ctcctgagta  gctgtgacta  caggcatgcg   ccaccacgcc   cagctaattt   ttgtattttt   25800
aattgcccat  attgcccagg  ctggtctcaa   actactgacc   tcaagtgatc   tgcccactca   25860
agcctcccaa  agtgctggga  ttacaggcgt   gagccaccgc   acctgtcccc   gcttttttt    25920
ttttttttt   tttttgaga   cagagtcttg   ctctgttgcc   caggctggat   gcagtggcat   25980
gatctcagct  cactgcagcc  tccgcttcct   gggttcaagc   gattctcatg   cctcagcctc   26040
ctgagaggct  gagattacag  gcatgcgcca   ctatgcccgg   cttattttt    atattttgt    26100
agagacaggg  tttcaccatg  ttggccaggc   tggtttcaaa   ctcctggctt   caagtgatcc   26160
agtagctgct  attgtattgt  aaggtgcaaa   ttatagaaaa   taattttcta   tattttggga   26220
ggcctgcctt  ggcttcccaa  agtgctggga   tgacaggtgt   gagccaccac   acccagccct   26280
aatttttttt  tttttttt    gaggtggagt   ttcactattg   ttgcccaggc   tggagtgcaa   26340
tggcacaatc  tcaactcact  gctggagtgc   agtggcacta   tctcagcgga   ctgcaacctc   26400
cacctcccag  gttcaagcaa  ttctcctgcc   tcagcctccc   gagtagctag   gattacaggc   26460
atgtgccacc  acacctggct  aattttgtat   ttttagtaga   acagggtttt   cactatgttg   26520
gcccagctgg  tctcaaactc  ccaacctcag   gtgatccacc   cacctcagcc   tcccaaagtg   26580
ctggaattac  agtcgtgaac  caccgcaccc   agccctggc    cctaattttt   aaaaagtttt   26640
tgtagatatc  acatttcact  gtgttgtcca   ggctggtctt   gaactcctgg   gttcaagtaa   26700
tcctcctgac  ttggcctccc  aaagtgctgg   gattacaggc   atgagacacc   tcgcccagcc   26760
tcttagctct  tttatttgat  ggacttctta   ccagacacct   aggggatgca   ttctatgtta   26820
aagtacaggt  gctctcagga  ttcaagggga   aggtacattc   tgaaaggact   ataattaaag   26880
tgttgggggg  aaatagggca  acctaatttt   tgccttagaa   agtgtttctt   cctacctttt   26940
gatttctgtg  tgatatacaa  attatatatg   gtattacttt   taggtgatga   agtacattac   27000
atctttgaat  gaagactcta  ctgtacatgg   gttcttagtg   cagctacctt   tagattcaga   27060
gaattccatt  aacactgaag  aagtgatcaa   tgctattgca   cccgagaagg   atgtggatgg   27120
gtaagtgtgg  cttggcttcc  tatgtctcat   tgcatgcttt   catttataat   atgtttctat   27180
ttggggaata  cagcataaat  gtttctaaag   agtaaagaca   tctaattgcc   tttatttcct   27240
tcttatttcc  atcactttt   taagattgac   tagcatcaat   gctgggaaac   ttgctagagg   27300
tgacctcaat  gactgtttca  ttccttgtac   gcctaaggga   tgcttggaac   tcatcaaaga   27360
gacaggtaaa  aacaacaaac  caaacaacaa   gaaagcacca   tttcctgaat   cctggtcttg   27420
acatgtggtg  gcatagagga  ggtacattgt   gggccataaa   taatggact    tgattggcag   27480
aagggcctgt  ctactaagga  tgttacctaa   attttctctc   aattttctca   gcaactctgt   27540
gaagtaggta  ctgttattgt  tcaactgcta   agaaaatagg   ctcaggccag   gcacagcggc   27600
tcatgcctgt  tatcccagca  ctttgggagg   ctgaagcggg   ctgagatcac   ctgaggtcag   27660
gaattcgaga  ccagcctggt  caacatggtg   aaaccctgtc   tctactaaaa   atacaaaaaa   27720
attatccagg  cagggtggca  tgcacctgta   ttcccagcta   ttcggaggc    agaggtggga   27780
```

```
ggattgattg aacctgggag gcggaggttg cagtgagccg agatcacctg actgcactcc   27840
agcctgggca acagagcgag actctgtctc taaaataaac aaacaaacaa acaaacaaac   27900
aaaaccagct cagagagagc aagtaacttg tctgggagac aacggaacca agatttgaat   27960
tcagagttat ctgagttcaa agcaatttat tttaacctat acagtaataa aaatttggat   28020
agtttaaaag gatatgaagt gaaaagcccc acctccccc accccaaaa tgggcactga     28080
atctccacag tagttccagg actcgacaga tggctggaaa tgggtctcct gcacagttgg   28140
ccatattgtc ccgttactag ttagcacctt gctattttaa tttcattatg aatacttta    28200
gcagaggtta ttttttacaa ggaaatgggt cctggtaaaa agaagtaggt cagaagtttc   28260
aagtggaaag ttttggccag cataaatgaa aattttctgt ggttggcaag aaaaggtcaa   28320
aggtcaagct ttgacagttc atttctacag ttaaatgtat attcttcagc atatttagca   28380
aacattgtag tgccttgctt aaaagaaaaa aatcccacga ggacagcacc tgaaggcctc   28440
ccactgcctc ttattgagtg atgctaccat ttgccctgat gcagctttaa ctcttctgct   28500
gaatcctaaa agtatagaa agttacctt taaaactttg aggtctttac ttctagatgt     28560
tcatgatgtt cacattatta taagagttta tctttttctg aaaaaaaatg attttatgcg   28620
agaagcacaa tttaaaccct tgctgctttg agcaagggtc cactgccctc agccttgact   28680
gccctgagga ctctgatgaa gtcgtcaact tctctctgct ttcttctttg tggacagctc   28740
attttcgggc tccactttgt ggccacaaac acctacagcc tggttccatc ctcatgccta   28800
acagtcatgg gattggatct tatcagctga gggaagaaat atggtcccct gtccactact   28860
gggtactcac tcaggctgtc tttagtagag tatgagtcag ccctgaaaag gacattggta   28920
tattgccaga aaaatggatg ctgtgatagc aaaaagaaag ctttgctgcc acagttcaat   28980
ttccccttta tcacttccct gcaagtaacc ctatggctca ggccctaagc caaaagagaa   29040
atttgggtga ggaactgtat aaacaaactt accaaagtta gaaggaatta ccgatactaa   29100
tctaatttct tacacatctc tccagcctgt tacatacacc ctatttgttt taacttttt    29160
tccccatgta atttaatctg atgtcttctt ccgtatggct gattagctgt atgtcagggt   29220
ttcttttttc tttgagtgta ggttttcttc ccactcccct atgactcaat gaatgatctt   29280
ggcttaagct gctcccaaaa acccacggcc agaaggacac aagtacaagt cccaatttat   29340
agctgaaacc ctagagttga gaatattatt gccaaagaag gaatgctttt aggaaggttt   29400
ctgtttgatg ttaagaacct gttttgtgc acttattcta atttctccac gtggcatgcg    29460
aaggagggca gcttctatcc tccaactctg atgcaggctg gcttttcttt caggggtgcc   29520
gattgccgga aggcatgctg tggtggttgg gcgcagtaaa atagttgggg ccccgatgca   29580
tgacttgctt ctgtggaaca atgccacagt gaccacctgc cactccaaga ctgcccatct   29640
ggatgaggag gtagggtgtc cagaggagag gtaaaggtgt tacggtgggg agggtgggtg   29700
tgccagaggc tgccatgtcc tttacactca tgacctcatt taaccccatc atctcatttt   29760
tacaagatga aaaacaaat tcaaattaaa ggctgagtgg ggtggctgac acctgtagtc    29820
ccaacacttt gggagtctga ggcaggagga ttgtttgagc ccaagagttt ttgagaccag   29880
cctgggcaac atagtgagac gctttctctg caaaaaaaat taaaattag ccagatgggg    29940
tgggcacatg cctgtagtcc cagctactcg ggaggttgag gcaagaggat tgcttgagcc   30000
caggaggtcg aggctgcagt aagctacgat cacaccactg cactccagcc tgggctacag   30060
agcaagaccc tgtctcaaaa aaaaaaaaaa attaattaat taaaaaaac ataaaattaa    30120
aagcatgctg aagtttatac agagtttgtt ctgtgtactt tctctcttcc ttttctttt    30180
```

```
ttctttattt attttttttg agatggagtt tcactcttgt tgcccaggct ggagtgcaat    30240
ggcgcaatct cagctcacca caacctctgc ctcctgggtt caagtgattc tcctgcctca    30300
gcctcctgag tagctgggat tacaggcatg tgccaccacg cctggctaat tttgtatttt    30360
tagtagagac aaggtttctc catgttggtc aggccggtct tgaactcctg acctcaggtg    30420
atccacctgc cttggcctcc caaagtactg ggattacagg catgagccac catgcccgac    30480
ctttgtcttt tttcttttga cagggtctg tgctctgtta tttaggctag agtgcagtgg    30540
cagtccatga gagcccactg cagctttgaa ctcctgggct cgagtgatcc tcctgcatca    30600
accttctgag tagctgggac tacaggcatg tgccaccatg cctggctaat ttttaagctt    30660
tttgtagcga caggggtctc actgtgttgc ccaggctgga ctcaaactcc tggactcaag    30720
cgatcctcct ggttcacctt cctaaagtgc tgagattaca ggcgtgaccc aacatgcctg    30780
gcctctcacc aagtactttc taccctaatc tgcctcgtgg tggacaggga ttagcagtac    30840
aggcactcag attgacctct ggcagccaga tcccatgtgt gtaaaagtgg tggcctcaga    30900
gtgaaggtgc tccagaggca gtcgtgggca gtagtctgct aatagctatg cagcttgtt    30960
ctagatccct gcatcagatt cctgagccca agaatgcgca cacacacaca cgtgcctgtt    31020
gacagtgcag tctcttaaat gtggggagag agcaggagag aggcctagta ctttctcttt    31080
taatcctccc aaagtagtgc tctacattct gtaggagaag gagcagtgtc tggacataac    31140
acgcagggcc ccaagcctgt ttgccctct gccttgcagg ttgacactga tttccctatt    31200
gggtaaaatg gctggtgaaa gggagctctt tggcatgtgt agaaatgagc acggcatgtg    31260
aagggctgtc agaaacagtg tgtggcttac atttgaggcc ttaacccaat atcttatgaa    31320
atagcttatg acacttaaga atttaataca aagctcaggg atatcctttt catttctggg    31380
tttttttttg gtgtgtattt cattatttca tttctgatgt ccaaatcccc taccccctagg    31440
taaataaagg tgacatcctg gtggttgcaa ctggtcagcc tgaaatggtt aaaggggagt    31500
ggatcaaacc tggggcaata gtcatcgact gtggaatcaa ttatgtccca ggtgagtgtt    31560
gttggaggag taaggtggct gctggtattg aggatggtat ctaggtcatc aaaagaagcc    31620
tgagagagaa gcttgtctca ttttatgctt gtagtactaa ggtttaggag actgactagc    31680
ccaagggtgc acagagttag tagatagaag agttgccact tgcaggcagg tctgcctggt    31740
gccagagcct ttgattttca tcatgtgctg tacagcttcc aagatgactt tgtccaggga    31800
gaaagtgaga gggagggcag gagggatata tcactttatc ttcatgtaga gatcaccctt    31860
tattttagca aagttgatgg atggatttaa aatacagtat aattattgca aagtgctatg    31920
agagtccaga agagggactc attctgccaa gaggagggct ttacaaagaa gatatttgac    31980
ctgggttttt ttctaggctg agaggataaa tctagccttt taatcatgtc caaaactgta    32040
ctcggcatcc tcatccccaa gttaccccctt actcccgtct tttggttagt atcaccattc    32100
ttccttcccg caagtctgaa gccttttagt ttccctccca agcattccct atattggacc    32160
agtctctaaa tattaggaat tgttttctct ctcctctgtt ctgagtgtca ccactgagtg    32220
ttaccttctc agctgatggg ctgtgataac ttccttgcag gtgtccctcc ctccagctgc    32280
ttcccactca gatctatccc cgtgctctcg ccttgccacg ttcaccttct ggcatggaac    32340
tctgagcctc ttccttctta cttgccagac tccttagcct cacactaatt tcagtgacct    32400
ctgcagcctg tgatctcact tgcgcatggt gaatacctgt cttcaacttg taaagtggac    32460
cactttccct tccctgcgca tgcctcgttt gccctttgta gttccctcac ctgcattctt    32520
```

```
agtggagtgg gctactcttt caaacagaaa acttcacaga acaatagggc aaaacttgcg    32580
tacgtcctca tagatccaag aaaggaacaa tctttaacgg agcaactact gtgtatccag    32640
cacaatgcca ggccttgggc tacacaactg aataaggttc aacttcacct tcaccttcag    32700
ctgcttcctc cccatctcct ctctgtcatg tctgttattc cttccaaacc ttgtttgatt    32760
tccccttatc aagggatgat ctttccttct ctccctccct cctctcccat agaacatgtg    32820
tattgtatct tttgttgcat gtgtctcatg tacggcgtcc tgtgctctcc tgcctagata    32880
gctcctcaag ggcagtggtc actgtggcgc cacatccagc ttcctgccat ctgaccactg    32940
gcactcatat ctattgaatt gtcgaaggga gttatagctg gaagtctttt ttctcccttc    33000
ccatctcaag tttcagatgt agacgctgag ctgccaggaa cattagtcac tgtcaagcct    33060
tcaccgtttt taacctccct cccactctcc ctaccgtgct tttaagacag tagctcataa    33120
ttgatcactc attttcttgt agtgtaatta tctaacaggc gataaagaaa ttgctctcct    33180
acaactcctc actttgaata cttgcgatat gacattcaag ctcagtcttt ttatttattt    33240
atttttttaa tttttttttt ttttcttgag acggagtctc gctctgttgc ccaggctgga    33300
gtgctgtggc gcgatctcgg ctcactgcaa gctccgcctt cgggttcat gccattctcc    33360 cgcctccgcc tcccgagtag ctgggactac aggcgcccgc caccacgccc ggctaatttt    33420
ttttgtattt ttagtagaga cggggtttca ccatgttagc caggatggtc tcgatctcct    33480
gacctcgtga tccgcccacc tttgcctccc aaagtgctgg gattacaggc gtgagccacc    33540
gcacccagca agctcagtct ttttaaaacc tcgcatcttc tgtatcatat ttctgctttt    33600 ggcattttt ttttggatta catgtgagaa atggagaaga aaaacctgag tggggatctt    33660
gagtgttgca gataggtagg aaatgttgac ttaaacatga aacttgccat ccttttcaca    33720
ttgattcctt atgtagacaa taaaatatga ataaaatcaa agcagtatct tcccttctgg    33780
tcaacagtgt ttttactgat cttgggcata taggcaaatt aatgctgata cagctggatg    33840
ttattgtgtt ccccaaagga tggcagaatc actcagttac agaccagcaa atgggctgca    33900
ggacctaaag actgatattt gcaaatgttc actttagaag caaactttc taccaccgag    33960 ctacttcttg gttcatattt tgattattta aatagtttgc atggtccact cagggataac    34020
attgtaagtc acttgccaaa ttaagaatga atcaaggtgt gtataccttt tacaaagaag    34080 taatatttt aaagattcaa gtgcagggca gaaagtattg gccagagaaa cacataaaag    34140
tgctcttcct gcttggctta ctaaagataa attgagaagg gccagatcaa tagtgttta    34200 tttggaaggg ttaaaagtg ggaacagatt ccccacccta atgcaatcca gtctcaacct    34260
atccagtgta gctgcttctg gactggcctc tattattagg gtccccaaat taaatgtaga    34320
agagtcaggg ctcagctgga tctttagttg attttttgtac atgtgatttc ccaaagaaag    34380
agaaattcta gggctggggg tagataacca aaaggtttgc tcattactga ggtcatatgc    34440
ttaggctgag tagtggtcac ttttttccact gaccacatca tcctatccac gaagcactgc    34500
atgtttagca gtgtctcgtc aaccctgaca gtatttggtt taggagcaaa actgaactca    34560
ccagtgctgc gtttagtcat gtagtcaaag atatgtgtct cttacctgtg ggaaaacgaa    34620
aatgactaac attaacacgt agaaatagat gcagcgggta tttcaagcta actacagtgt    34680
gaagacgatt gaaacttgta cagagggcaa acctctatct atatttcctt ggcattttga    34740
aatgactcta ggggctgtaa gaggaaatgt tctgccagtt tgctgcttta taatcttcta    34800
gaaacttgaa accatcccaa tgagttgtgt tgaccagctc cttttactcc atataaaaaa    34860
tatcttacgt atctgtggtg gaaagagaaa ctcttgcgtt tggaggctgc tttttcaatt    34920
```

```
tcagtaatgt acacattttc tcattttgcc ctcagcaaat tgtgatagg tagtgttaag   34980 ccttctttgc attttggact tcagattaat atggagccca caggagctgc agaactaact   35040
tttttttttg agacggagtt tcgctcttgt tgcccaggct ggagtggaat gctcactgca   35100
gcctccgcct cccgggttca agtgagtctc ctgcctcagc ctctgagcag ctgggattac   35160
aggtgcccgc taccaagccc agctgatttt ttaatatttt tagtagagac ggggtttcac   35220
catgctggcc aggctggtct cggactcctg acctcaggtg atccaccgc cttggcctcc   35280 caaagtgctg gcattacagg tgtgagccac cacacctggc cctaatttt aataaaagag   35340 ctgatgctac agctaatctc ttttttttct gagacagagt ctcgctctgt tgcccaggct   35400
ggagtgcagt gacgcaatct ccgctcactg caagctccgc cccgggtt catgccattc   35460 tcctgcctca gcctcccaag tagctgggac tacaggtgcc cgccaccatg cccagctaat   35520 tttttgtat tttagcaga gacggggttt cactgtgtta gccaggatgg tcttgatctc   35580
ctgatctggt gatccgcccg cctcggcctc ccaaagtgcc tgctaatctc ttaattctgg   35640
cttcttgcct ccaccttgga gcttcttctc agttgtggcg atctgatcag agagaagtgg   35700
tgatgtcgct aaaactacca gatgcagcgc gggagcctta ttgcttcgag gtctaggccc   35760
gcccccagcc cctcctggaa gtgcactgaa gccaagtgta ggatgttctt tgtgtgagtg   35820
agcaatgatg catcattggg ttttgttctc ttgaatagct attctttgct ggtaagattt   35880
gtagttgttc ttgtgtccctt ttaagggaag tgtaattata ttctttgcct ttagcataca   35940
tttaagtagc tgtgtctttg gaattggatg ttgaattgtt cctccagctc acacatggag   36000
ctcacaaaat gctgacagtt gctgtagaaa cgatatctgg cagctgtgac agagttggat   36060
ctttgtgcac ccaaaaaatt tcctttgtag gctttagcaa attaacattt taaaatgggt   36120
gctcattata tactgggtag ttggttttaa gaataaaaaa cagttggtat tttatttgcc   36180
acctgagaga ctacaaaagg attctccagg ttctgtaaaa ccacttatgc atcttgtgaa   36240 ttttttgcagg taaaataatt ttctcccctaa gaaatagcaa acatctgtca ttccatagct   36300
tttaagttaa gtaggcactg gagcctgatg ggactaacac accctacaat tctgctgagt   36360
ttttgtcgta actgatcacc aggactgtga ttctgagact tagttttgat ttctccccca   36420
cttgaccaga tgataaaaaa ccaaatggga gaaaagttgt gggtgatgtg gcatacgacg   36480
aggccaaaga gagggcgagc ttcatcactc ctgttcctgg cggcgtaggg cccatgacag   36540
ttgcaatgct catgcaggta attgtgaata aagtttcta taagagttct gaaaagctga   36600
tcgagttttg gctgcttttc tccccaagta gaaatgtcaa aaacctactc agaagtaaag   36660
atgtgaattt attgagaaaa agggaaggga agaatagaga aataagatca ggcacattaa   36720
tagaggaaag tagggatggc ataattccag tctgttttgg aatataataa ctttgaaaga   36780
agaaaagtgc gatcacactg gcttggccag gtctgttttg gtttgccttc cctttctttt   36840
tttttttttt tttttgagac ggagttttgc tcttgctgcc caggctggag tgcaatggtg   36900
tgatcttggc ttaccgcaac ctccatctcc ctgattcaag tgattctcct gcctcagcct   36960
cctgagtagc tgggattaca ggtgtgcacc accacgcccg gcgaattttg tattttagt   37020 agagacaggt ttctccacgt tggttaggct ggtctggaac tcccgacctc aggtgatccg   37080
cccaccttgg ccttccaaag tgctgggatt agaggtgtga gccaccgtgc ccggcctgtt   37140 ttcccttttct aacatgcacc agctgacagg ggccaggcga gcagcccaa agcatgttag   37200 gtgcctcttg actcttagct aggattgaag catggtaata agtgggtctg aagcagttca   37260
```

```
ttttgtgatt gaactggagt gacctggagc ttgaaactga ggtgaggatt aaaataacca    37320
cctcttctaa gtttcattta tttcattttg cttagagcac agtagagagt gccaagcgtt    37380
tcctggagaa atttaagcca ggaaagtgga tgattcagta taacaacctt aacctcaaga    37440
cacctgttcc aaggtaaaaa taaagtttta ctgatttaaa actttgtgaa ttgttggttt    37500
ttagttgaca gatactgtgg gttcacatat gctccctctg aaggtgcctt cagtggttgg    37560
ggttgggttg ggggcttgtt actactgtgg gattaattaa actcagtgga taaacattaa    37620
tacctatttt ctatgtttcc aaagtgacat tgatatatca cgatcttgta aaccgaagcc    37680
cattggtaag ctggctcgag aaattggtct gctgtctgaa gaggtagaat tatatggtga    37740
aacaaaggcc aaagttctgc tgtcagcact agaacgcctg aagcaccggc ctgatgggaa    37800
atacgtggtg gtgactgggt atgctttta ttcatgttgc catccaaatc ttagtatcag     37860
tcctgatact aaggcgttgc atttgcactt ggcacatgta tgtagaggtg cctttaattt    37920
gattttagca ttttcacccg tatttgatct catttgatcc ttacagcaat cctgagaggt    37980
aggtaagaat agattataat catagatgag aaaattggtc aaggttatcc atctagtaag    38040
tggaagagtt tggtcttaaa acccggtctt aagatagaat cacctttgc tgttgttgtt     38100 gttgttgttg ttttgagaca gagtctcgct ctgttgccca ggctggagtg cagtggcacg    38160
atctcggctc accacaacct ctgtctccca agttcaagcg ttctcctgc ctcagcctcc     38220 cgagtagctg ggactacagg tgcaaggcac cacacccagc taattttgt attttagta     38280 gagagtgtgt ttcactatgt tggccaggct ggtctcgaac tcctgacctt gtgatccacc    38340
cacctcagcc tcccaaagtg ctgggattac aggcgtgagc caccacaccc ggccagaatc    38400 accttttga acccaaaatt cattaattcg atggatttac taagcattca tttttattgc     38460
tgggctgagg ttatattaaa aagctagttt ttgagaatat aaaatgagaa attaaaatta    38520
tagccgtgtc tctacaagat aaagtatatt tgcttcttac agcaagaaga gctaaaatac    38580
aggaatcatt ttttttctta agttttttg gaaattacaa ctaagacttt tgaaaaagat     38640
atctttcagg gcttttgtct ttcttttct ttgtcttttc tttctttttt tttctttaag     38700
agatgggggt ttgctctgtt gcccaggctg gagtacagtg gtgcagtcat agcttactgt    38760
agcctggaac tcctgggctc aagtgatcct cttgcctcag cctcctatat agctgggact    38820
acaggcatac actgctatgc ctgactttgt cttttcttaat ctttagatta cgagtcattc    38880
tctaggatct gctaggtatg acttagtgat tcagatacac ttaattcttt aaaccttttt    38940
ctcttttgct ttcgtcttga agaataactc caacacccct gggagaaggg aaaagcacaa    39000
ctacaatcgg gctagtgcaa gcccttggtg cccatctcta ccagaatgtc tttgcgtgtg    39060
tgcgacagcc ttctcagggc cccacctttg gaataaaagg tactagtgag actggaccat    39120
gggtggtgac aggggacctg cttctccttc agtcctccca ggcccacgca acctatgata    39180
cttatggggt cttcaactca tttcaacacc aggaatgtca ttctcacaaa cctctgtagt    39240
catgcttttg atgaaggctg tcattggatc tccccagctc ctgctgtcac tgttggccac    39300
tgcacaggga ttctctggga tgggtgatat gtagctggag gtgcttttat ttgaccctca    39360
tagtccactg ctacagtaac cataaaggta atcatagcta ctgatcatct tacagacact    39420
ctagagacaa tgcaaaccc cacagatgtt tcaccttgtt gggaataaga aaagcctacc     39480
tttattgaat atatgctttg tgccagatat tgtgctgagc agttttgca tattattcta     39540 tcatccagta cgagatagta ttgtcaccat tttaaaatag cagcaactgg gacttcagag    39600
gtggcttggt caaaggcacc tgtattaagt accagagtga ttcttccatg tctatttcaa    39660
```

```
gctctaaatt actaccatac tcgcacttta ccttcagatt tttattgctg cggtactaag   39720
aacatgtgtt tttttttttt tttttttttt tttgagacag ggtctcactc actctgtcgc   39780
ccaggctgga atgcagtggt gtgatctcgg ctcattgcaa cctctccacc ttctgggttc   39840
aagagactct cctgccacag cctcccgagt agctgggatt acaggcacgc atgaccatgc   39900
ctggctaatt tttgtatttt tggtagagac ggggtttcac catttggcc aggctggtct    39960 tgaacttctg acctcaagtg atctgcctgt ctcagccttc caaactggta ggactatagg   40020
catgagccac cgtgccaagc tgctgtctta attaaaataa tgtttattaa ttatgatagg   40080
ttcttagagt tagctttctc tgcttggtga gggtatcaca ttttgcttgt tctagcaatt   40140
actacaaatg ttgacaccgg gaacaccttc acccttccac ctttttttt tttttttggag   40200 acacagtctc gctctgttgc ctgggctgga gtacagtggc acgatcttgg ctcactgcaa   40260
cctccgcctc ctggtttcaa gcaattctcc tgcctcagcc tcccaagtag ctgggactac   40320
aggtgcgtgc caccatgcct ggctaatttt tgtgttttta gtagagatgg ggtttcacta   40380
tattggccag gctggtcttg aactcctgac cttgtgatct gcccaccttg gcctcccaat   40440
gtgctgggat aataggcatg agccaccgtg cccagcccac ccttccacct attttataaa   40500
tgtaatcact ttgttctgct cttgagcttg tcttaacccc ctttcaactt cagcacgagc   40560
tattccttgt tctgcttatt gaacccatta ttttccttt actcttactg caaattgcct    40620
cactgcacgg tctctgcctc acaaaaacaa aatacatatt aatatatctc tgggctgggt   40680
gcagtggctc atgcctaaaa tcccagcact ttgggagggt gaggtggtag attacttgag   40740
gccaggagtt cgagaccagc caggccaaca tggcaaaccc cgtctctatt aaaaacacaa   40800
aaattagctg gcatggtgg tatgtgcctg taatcccaga ccattaccct ccagcctgtg    40860
agacagtatg agactctgtc taaaaaata tatatctgat ttacatttat gcactgata     40920 atgtggtaac ctggactttt tttgtttgtt tgtttgtttt ttttgagaca gagtcttgct   40980
ctgtctggag tcccagctca ggctggagtg cagtggcatg atcataactc actgcagcct   41040
tgatctccca ggctaggact ataggcatga gcagccatgc ttggtgtcct gaacattttc   41100
aactggcttt tggctaatac agattgagca tcagaaatct agaaacctga atctgaaag    41160 gctccaaaat tctaaacttt ttgagtgctg acacgatgct caaaggacat gctcattgga   41220
tcatttcaga ttttaaatcc tggatttggg atgctggatc agtatgatga aaatattcca   41280
aaatctggaa aacaaaaacc caaatccaaa acccaaatcc aagcatttta ataagggat    41340 actcaacctg taatccaagt agcccaaaaa aatctagcaa ttaggctgct ttctaacagc   41400
ctaatctatt tatctctatt taggaaaaat tatagtcttt ttgttaggtg tatgtatttt   41460
aaatatttct gttttaaaag ccaaagtagc tttatgagag taggaaattg aacaggttgc   41520
ctttatgtaa ctgtcagctg ggtgttttaa caaatgccag taattacaag gaacatattt   41580
ctaaagataa tgagtaggta tatatttgtt catggtttg tcatttaaac tcagatttca    41640
attgagagac tagtattaga aaacacttga tcaaaactgt ccaaatgatt ctaaaaaata   41700
aataaataaa tgtgcttagt agttacaata atgcatttgc atttatttga tttctaagtc   41760
attggagaag catgcttaac tgagcttcca cccttgacct gtcccctagg tggcgctgca   41820
ggaggcggct actcccaggt cattcctatg gaagaggtaa agtattctgg gatttggctg   41880
aattagatcc ccctttttt gtcgggggg agggtgctga attagctccc ttttttttccc    41940 catgacggag tcttgctctg ttgcccagag ctggagtgca atggcgcaat ctcggctcac   42000
```

-continued

```
tgcaacctct gcctcccagg ttcaagcaac tctcctgcgt cagcctcccg agtagctggg    42060
attacaggca tgcaccacca cgctcagcta attttgtatt tttagtagag acggggtttc    42120
accgtgttgg ccaagctggt cttgaactcc tgacctcgtg atccgcccac ctcggcctcc    42180
caaagtgctg gtattatagg cgtgagccac cgcacccagc ctagattctt tattatagct    42240
ttttctctct ggagattagc cttttttgta gagctcttag cggacaaatg acttgtttct    42300
cagcaaaagc aacacctagg gggaaaacaa cttaatttgc agacttgtga tacagcttgg    42360
tttcaaactt tggctttcag tgggaatgat tattataagc aaatgaccaa atgaagcatg    42420
gtatcgggaa gcaccaacac acagcgattt cagaattcat ttatgtaact gcagaaattg    42480
gaacattaca tagacataga gtcggtgctg ctcccgtgca ctcctcctcg ctgttttgag    42540
gtgtgtcctc agtaacccag tgtggctgtt gatcccagtg gtgtggtatt tgtggtctct    42600
ggacatctca ttttggaaaa actgcaagtt ctgtatttgg gaggagattc ttctgtggac    42660
agataattag tcttttatgt tttcttttct tttttctttt tcttttttt tttttttaa    42720
gacagagtct cactctgtca cccaggctgg agtgtagtgg tgtgatcttg gtcactgca    42780
acctccacct cccaagttct cctgcctcag ccttccaagt agctgggatt acaggtgcgc    42840
actaccacac ttggctactt tttatgtttt tagtagagat ggggtttcgc catgttgccc    42900
agggtggtct tgaactcctg gcctgaagtg atccgcccgc ctcggcctcc caaagtgctg    42960
gtattatagt tgtgagctac cacacccagc cagtcattta tgttttcaag aactccctat    43020
attgggtgtt tgtccactaa ctgggctgcc ttcagtattc cattggcttt aaaataggga    43080
ttgagctttg caatagaatg aaagttggaa agatacagag cagctgggag actaatgtgg    43140
cttctgttct tttgtagttt aatctccacc tcacaggtga catccatgcc atcactgcag    43200
ctaataacct cgttgctgcg gccattgatg ctcggatatt tcatgaactg acccagacag    43260
acaaggtagg atgccaaagc cccatgaacc ccattgaaca gttttgaaag tattgaacca    43320
tctgaattag tgttggtgtc ttgggtgctg aggatgcagg tagcaaagca gtgggctcc    43380
tctcatttta aagcccctt cttttcttta aggctctctt taatcgtttg gtgccatcag    43440
taaatggagt gagaaggttc tctgacatcc aaatccgaag gttaaaggta agctttttt    43500
cttccacatt ttttatattg tatggaatct ggaatctgat cattgattag gacataaaag    43560
tcttcttgga gtagcctatt ttagatgaag ttacatcagt aatcatagtc ttaaagtcat    43620
gatatacata gcaaagatgg atggtagagg ttatttctca tttatctata gattagaagt    43680
ggctagtgtg gaataaatag aacactgaca acctgccctc agctaagaaa gaaacgacac    43740
ttcctttata acatgaacaa gagtcaggat gtcactgtgg cggcatagca gcctttggag    43800
tttgcatcat tgggacctta agcaaatttg ttaaatgact tgtttctccg cttacttgtc    43860
tgtaaaataa tacttgcctt gccctgaata gataagggtc tgtgttaaac agttaaaacc    43920
atagttatat ctatatttta tttgaatttc tgtaacaaat acatagttag taagcataca    43980
ccataccacc tgacccagaa atctcaccca aaataaatga aaactctgtt cacataaaaa    44040
tctgtacatt aatgttttta gcagctctat taataatttc caaaaactgg gaactaatct    44100
aaatgtcttt cattggatga ataaataaac aaactggtac atccatccaa taaaataaa    44160
tgagctatta atacaagcaa caacttggat gaatttcagt ggcattatgc tgggtgaaag    44220
aagccagtct caaaagcttg catattgcat gcctccattt atatgatatt ctcaataaga    44280
gaaaactata gtgctaggga acagatcaat agatgttaag ggtatggatg aagggagggt    44340
atgaccataa aggaacagca aaggagaggt gttttgtttt gttttttgtt ttcttttttg    44400
```

```
agacagcgtc tctctctgta acccggctgg agtgcagagg cacaatcaca gctcactata    44460
gcttccacct tccaggttca agcaatcctc tcatcttagc ctcctgagca cctgggacta    44520
taggtacaca caccaccaca cctggctaat ttttattttt attttttttgt agagaccgtg   44580
tctcaccata ttgtccaggc tggtctcaaa ctcctggtct aaagcgatgg tcctgcctca    44640
gcctcccaaa gtgttgggat tactggcgtg agccaccacg tctggccaca agggattttt    44700
tgttttttgtt tttctgtttt ttaattttttc aaaaatttat tggttggttg tttgttttgtt 44760
tgtttaagac agagtctcac tctatctccc aggctggagt gcaatggtgt gatctcagct    44820
cactgcaacc tccacctctc aggttcaagc agttctcctg cctcagcctg aatagctggg    44880
gttacaggtg cctgccacca tgcccagcta attttggtat ttttagtaga gagaaggttt    44940
catcatgttg gccaggctgg tctcgaactc ctgacctcag gtgacccacc cgccttggcc    45000
tctcaaagtg ctgggattac aggcgtgagc cactgtaccc ggcctgtttg tttatgtttt    45060
tgagaaaagc ttttactctg tcacccaggc tggagtgccg tggtgcaatc acatcttact    45120
acagcctcaa cctccaggac tcaagtgatt ctcccacctc acccaactag gtagctgaga    45180
ctacagccag gtaccaccat gcccagattt ttatatattg tgtagagacc gggttttgcc    45240
gtgttgccca ggctgatctc aagcttctgg gctcaagcaa tctgcctacc ttggcatacc    45300
aaagtgctgg gattacttgc atgaaccact gagctcagca ttttttttttt ttttttttt   45360
ttaagagatg aggaggccag gcgtggtggc tcatacctgt aatcccagaa cgttgggaag    45420
ctgaggcagg tggatcacct gaggttggga gtttgagacc agcctgacca acatggagaa    45480
accccatctc tactaaaaat acaaaattag ctgggcatgg tggtgcacgc ctgtagcccc    45540
agctactcga gaggctgaca caagagaatc gcttgaacct gggaggcgga ggttgcagtg    45600
agctgaggat gccccactgc actccagcct gggtgacaga cagagactgt ctcaaaaaaa    45660
attgggtttg tgttttacaa cacttcttgg tcactatgat actatgatta tttaggtcta    45720
ggcttaggga aatcttctgg tgctcagtta tagggacaaa catgttaata ataccttgt    45780
acatgtgtga gtaatgtgaa tttgcagata tcgggataaa atcacttttg tcagacccag    45840
aaaaaacagg gctgggaaaa catgaagaag aggaggctta cacttacgtg tctgtgataa    45900
gaactgtttg caaggcctgt aatcccagca ctttgggagg ccaaggcagg aggatgactt    45960
gagcccagca gttcgagacc agcctgagca atgaagcaaa acctcgtctc tacaaaaaaa   46020
tttaaaaacg agccaggtgt ggtggcatgc acctgtagtt atacccagct actcgggagg   46080
ctaaggcagg agcatcccctt gaacccagaa gttcaaggtt gcagtgagct atcattgggc   46140
cactataatc tagcctaagt gacagaatga gacctcatct caaaaaaaca aaagcaaaaa    46200
ttgtttccaa caactttata aaaccccaaa agaaatccct tcacgtcctt cacacatctc    46260
ctgctttgca cagcttgcac atttcaaatg tatacttatg tttccatgac aagacttatc    46320
actagacatt cttcaggatg ggagtaattc agataagatg ctcttgaaag tacacttatc    46380
cagcaacggc aactgcacca atgaattgac aactctggct ttgagcttct gggagcgatg   46440
aattctgttt ttttttttt tttgagacag ggtcttgctc tgtcacccag gctgtagtgc   46500
agtggcacaa tcatggctca ctgcagcctt gacctgaact ctctaagcag actacgtgaa    46560
gctctccctc ttttctttttt tttttttt ttttttttt tgagatggag tctcacccag     46620
gctggagtgc agtggcgtga tcttggctta ctgcaacctc tacctcctgg gttcaagcag    46680
ttctgctgtc tcagcctccc aagtagctgg gattatagtc acccaccacc atgcccagct    46740
```

```
aatttttgta ttttttagta gagacagggt ttcaccgtgt tggccaggct ggtctcaaac   46800
tcctgacctc aggtgatctg cccatctcag cttcccatag tgctgggatt acaggctcag   46860
ccacaggctg agcttcacgc ctagctgaag ctctccttct ttgctagtaa aatcttccct   46920
tccctcacta ggcatatttg tggcatccca ggttataatc ctcgttgctc attcctgaat   46980
aaactcaacc tacttggaga taattttttg taatgtcttt ctttaggctg acagtaggaa   47040
ataaccccca gctttcagtt tttccttctg aatttaagat ggtttgcatt tcctagaggg   47100
gatcccattt agaggtaggg gtcaaaattt ttgtcttacg tttattgtgc ttctgtttgt   47160 cttatttat  gtttcattt  tcctacactt tcagagacta ggcattgaaa agactgaccc   47220
taccacactg acagatgaag agataaacag atttgcaaga ttggacattg atccagaaac   47280
cataacttgg caaagaggta ccagagcagt atacaagccc cgtttgtttt ggctatattg   47340
cacaccctac accctccaga agagttgtta aaatgtgagg ctcagaagct tccatgttgg   47400 tatttacca  gctaaggcat gaccaagatg gtgacattat ttcttttct  tgccacctct   47460 ctcagtatct ctccttatta gctatcatca aatctctttg ttggattggt cgaacatttt   47520
gctggctatt cagtgttgac tgaaattagg gtagttaaac caaaaatcac attttacaaa   47580
tttaatttta tgcaaaaagt tttagtgtca tgaagtagag aaattatgtt taatcacttc   47640
ttgaatcatg tgtgaccttt attcttagaa ctcttgtgtg gcataaatga cttgattttt   47700
ttctgtagtt ctctagctta cctaatcttt ttttttttga gatggagtct cgctctgtcg   47760
cccaggctag agtgcagtgg cacagtatcg gctcactgca agctctgcct cccaggttca   47820
cgccattctc ctgcctcagc ctcccgagta actgggacta caggcacccg ccatcatgcc   47880
cggctaattt tttgtatttt tagtagagac agggtttcac catgttagct aggatggtct   47940
caatctcctg acctcatgat ccgcccacct caggctccca aagtgctggg attacaggca   48000
tgagccaccg cacccggcct acctaatcat tttttacct  catttatta  aattctctta   48060 tagcatatta ggtagccttc aaggtttaaa tacttaccag ttcagtaagt aggtttcctg   48120
gcttcactgc catatgctac ttttctcaat gcacaactag tgtagcttag atttcacttt   48180
gcatcaacaa tgcaaccttc tattctgtat cactattgag aaagaatctt catccactca   48240
tgcagaatag agctgaaggc cagtttattg actgttttg  tgattttcct tgactcaata   48300
accgttgcta gctaatggcc ttatttagat gacactctca atgtctaaaa ccacattgga   48360
atttctcttc ctttgcttca atagcttag  acaaatggta taatatttta taaggaataa   48420
gctaaaagtc cattttgaag atttagtatc cgatttactt ttcttttgct tcgtgtctca   48480
ttcatgtttt ctaagcaact agaggcagtc atacctattg actagctatt ttttacagaa   48540
atattagtta catgaaacct gatactttt  tcttttgaaa ataagggtt  ggctttaaca   48600 acacattaca gcaagagtgg ggggtgtgtg tgtctgattg ctatataaga cactgctttt   48660
ggtatgaaat tatgacagtc tttatggaaa ataatttggc atattatcaa gtgccttaaa   48720
aatgcttctc ctccttgact catttagagt atgaactggg tttttttgtt catttgtgt   48780 gtgtgtgtgt ttttactttg aaattatttt aattttgaaa tagaaaacat cttgaaaaaa   48840
aaacccacaa aatatatagg caaatttgta ctctgtgagc ttctcacatc cttacactgc   48900
ttcaccaatc tctaagatga aaaactctgt tctaaaacat attcagccat cagcaatgat   48960
gttattagta ggaatatgga tcaattaat  tttgtgtttc tttgatattg tttggcattt   49020
gatactgaaa tggcaactcc tgtttcctct ctatactcat agtactctca gcacctcact   49080
tctgacacca gatgggtagt ttttctcttc cacaacaatt cagctttcac ttctccagtg   49140
```

```
gatattgact gagtatccta tgatttaact caattctgac actaactgtc tggagcagat    49200
cctacaggta aagggctcag tcctaaaaga ctgccccact tcagacacga atcgcaagtc    49260
caggttgtca cctgtgcttc tgaccaactg gttataaact ggagggtccc cacaaccccc    49320
tgctcaggtt catttgctag aatggctcac agaactcaga gaagcatttc acttgtgttt    49380
atggtttatt ataaaggata cagctcagaa acaaccagat ggaagagaag cgtaggggc    49440 atcactctcc cagcacctgg atgtgttcac cagcccagag gctcatcaaa tcatgttgtt    49500
caagagtttt tttttttgaga cggagttttg ttcttgttgc ctaggctaga gtgcaatgga    49560
gtgatctcag ctcactgcaa cctctgcttc ccgggttcaa gcgattctcc tgcctcagcc    49620
tcctgagaag ctgggattac aggcatgcac caccacaccc ggctaatttt gtattttag    49680 tagcgacagg gttttttccat gttggtcagg ctggcctcga acttttgacc tcaggtgatc    49740
tgcccacctt ggcccccaa agtgctggga tttacaggcg tgagccactg tgcccggcct    49800
gttcaagagt tttatacacc cctaacacct tacccagagg ttggtgggtg ggactgaaag    49860
ttccagccct ctaatcattt ggtctttttg gtgaccattc cttcctgag gctgtctagg    49920 agacctacca taagtaactt attaccataa actcaggtgt gatcaaaagg agtttgtaat    49980
gaataacaag acactcctat cacccttgga attccaagag ctctgtgagc ttttgtcag    50040 gaacccatga caaaggtcaa atatatttcc tattcacta cacataccaa aagccagaac    50100
tgagggtaca ctaaaatgtt aacagtagtt agtcctggga ggtcgttagt tggttagttg    50160
cttggtcttt gccatgtttt ttgtggttat ataattggat agatattctg tcatcagaat    50220
aaaaattctc tctgctaagt gtgctatgtt tcctaaattt ccagaccagg cctggcaccc    50280
agcgtgtttc aaaagatatt tgcacttgcc ctgatttgat ggctcctgca tttcttacgg    50340
tggtggaaag tcaatgagtc atcatcccac agaacaacaa cacaaacctc agtcttttga    50400
aaaaatgtag actgctctgt ttttcttata tgtggaatat gctttaaaat agattccaga    50460
tttctagtta actgtttgaa ttctctagat gggataaaac caagccattc cacattcctt    50520
tgctgtaaaa ataactcctg tgtatttatg gtatatgaac atcatttctt aactttaaca    50580
catattctag cttgccatc cattttgaaa tattgataga caatcatgaa attagactta    50640
ttgctttaaa actctgctgc ttcctttaac tttgtggtcc tttactcaa aatcgttcta    50700 tatcttgcct gtctgctgta gtgttggata ccaatgatag attcctgagg aagatcacga    50760
ttggacaggc tccaacggag aagggtcaca cacggacggt aacaatttgt ccctttccaa    50820
ggaaattagt tcagaggcac tagatcttgc tgcttctctc ctcctccatc ctctctcata    50880
cgactgatac tgccaggtgt tgttctgcct tctccctttt aaaatggaag tgagtaggtg    50940
tgtggcattg agcactcctg acagcttttg caataaatcc catgtgtcac ctgtgtgttt    51000
ttcccccggc atttttttcct ggaggtggag agccccaagt gaatatcctt gcatagaaat    51060
tgattaaaat tgcttctttt ttgtggccat ttcactgtat atctccttgg tttaagaggt    51120
accatatatt tcccttgtat atgaaagaaa caataagcgc atgattataa gcggccttca    51180
tagggataaa atcatagctt tttggtccta ctataacatt tattttaaaa aactgacaac    51240
tcagggctgg gcgtggtggc tcacgcctgt aatcccagca ctttgggagg ccgaggcggg    51300
cggatcactt gaggtcagga gttcgagatc agcccggcca aacccatctc tactaaaaa    51360 aatacaaaaa ctagctgggc atggtggcac gcgcctgtaa tcccagctac ttgggaggct    51420
gaggcgcgaa aattgcctga acccaggagg tggatgttgc attgagccaa gattgtgcca    51480
```

```
ctgcactcca gcctgggcaa cagaccgaga ctctgtctcc aaaaaaaaaa aaaaaaaaaa    51540
aaaatgacaa ctcagggtct tggaataatt aattaatata ttttttttgct attagaggat   51600
tattttcatt aagtattttg ggtagtattc tgttattcta tccttttaag ctatttgttt    51660
aagcctcaga tgtaaaagag gatcactttt gcaattcaca cttctggttt aacacaaagt    51720
ttttgctagt acctcttttc cctgcccaca ggcccagttt gatatctctg tggccagtga    51780
aattatggct gtcctggctc tcaccacttc tctagaagac atgagagaga gactgggcaa    51840
aatggtggtg gcatccagta agaaggaga gcccgtcagt gccgaagatc tggtgggtac     51900
ccagacacgc caggcttggc gacatatctg tgtctgttgt cctagggtct ttcagcagtt    51960
attaataaca aaatgtaatg ctgtacttaa gacattgcaa ttaattcatc aatttaatcc    52020
tattttgcta attacaagat aattatgaaa tgtttaaaaa gtacatcaga gtgaataata    52080
gctggtatgc tttagtaata gatcacaagt tccagatgat ttgagtaaca tcttcatcct    52140
gtgggcatct ctaaaagtgg gtgtatgact tcaatttgca gagaacatca agagtaccat    52200
tgctttatct ttgttgctag gtagttcagc tacactttga tggcttaata gagtgacctg    52260
atgttaaaag ttggtattga actcttgcgt aatattgcag tttcagcttt ggaagacaca    52320
tattgagttt ggtatttata gaaatttctg cccagatacc agagttacaa ataactgagt    52380
actctgggaa cgagcattgt cgtgctctaa aatagtctag aatggatttc tcacatcagt    52440
cagcagctga gcttgattaa gatgcttgtt tctagagtta catgttttc cagatattac      52500
atgtgaatgc catttgtatt ctatctggca actttggcca ggcgtggtgg ctcatgcctg    52560
taatcccagc actttgggag gctgaggcgg gtggatcaca aggtcaggag attgagacca    52620
tcctggctaa cacaatgaaa ccctgtctct actaaaaata caaaaaatt agccgggcat      52680
agtggcgggt gcctgtagtc ccagctactc gggaggctga ggcaggagaa tggcgtgaac    52740
ctgggaggtg gagcttgcag tgagccgaga ttgcaccact gcactccagc ctgggcaaca    52800
cagccagact ccgtctcaaa aataaataa tttaataatt ggcaacttca tagcatatcc      52860
agaaaaaaac catgaatggt ccaattcagg tgaaagtatc aattggtcca agatggctaa    52920
catgggtaag cctagaatgt caaatattgg tttcagaagg ttgggttttt ttgctggtgg    52980
gagttgatgc tgcacacatt tgttttgtag ggggtgagtg gtgcactgac agtgcttatg    53040
aaggacgcaa tcaagcccaa tctcatgcag acactggagg tgagcagagt gactcctgcc    53100
ttcttgaatt ggttttggac agtcagagca gagtggttat aaagcacact tgcaaggcgc    53160
ggtggctcac acctgtaatc ccagcacttt gggaggccaa ggtgggcaga tcacaaggtc    53220
aggagatcga gaccatcctg gctaacatgg tgaaacccg tctctactaa aaatacaaaa      53280
aattagccgg gcatggtggc gggcgcctgt agtcccagct gctcggaagg ttgaggcaga    53340
atggcgtgaa cctggaggc agagcttgca gtgagccgag atcacgccac tgcactccag     53400
actgggcgac agagcgagac tccgtgtcaa aaaaaaaaa aaaaattaa gcacacttaa       53460
cctgggtagt caagaccttc tccacttgct catctctttc ttctcattct tcctcacacc    53520
tgtgactggg acgttactga aataaaagag atgactttat attttccctc tgggaagtat    53580
tcttccttcc gattccaaat caattccata ccgttgaatg tgtgatccca ctttgaagca    53640
ggattggcag ctcagctcac ggtgtcctgg tttccacagg gcactccagt gtttgtccat    53700
gctggcccgt ttgccaacat cgcacatggc aattcctcca tcattgcaga ccngatcgca    53760
ctcaagcttg ttgcccaga agggtttgta ggttagtgtt ttttgcaaaa ccagtgaata     53820
gactgtatgt ttctttttaac atcaggggaa ttgggatggc attttactg ttgctttcct    53880
```

```
ctttacagtg acggaagcag gatttggagc agacattgga atggaaaagt tttttaacat    53940
caaatgccgg tattccggcc tctgccccca cgtggtggtg cttgttgcca ctgtcagggc    54000
tctcaagatg cacggggggcg gccccacggt gagtggtggg ttgaagtatc tgattatcgg   54060
cagtgtgctg acggccaaaa ggaagttgga tgacttctgc ctgtttcttc attgagttgc    54120
tcttatcctc gtgattaaca ggcagcaaaa gcaagggacg ggcagacagc ccttgtgttg    54180
gctgccttat cactcacagg caccgtcagc gctcagcatt ttaagagggc caaaatcggc    54240
tgcctggcct acctttcgga ggacatctga caatatctaa acccctccaa ggacgtgtac    54300
tcggctagcc ccacaaaaaa ctgttttacg ttcagactgt tcttttaaa tctgcatccc     54360
tctgtatagt gacactggca accagccaac caaaccagtt agctgagaca gaggtcagcc    54420
ccttcttgag tatactgttc atgctggaca gggcctccac accctaggga gggagtgggg   54480
gagaggagaa tggcagatct gcccagggct gccctgggta acagagaaac aggtggagac    54540
tggctcatcc tcacctccag cctgaatttt gtatttctct gaattcctac tgcttagaaa    54600
ttcctactac tttttatcct agtatttaa  cacctttct  ttagggccta catgaaaaga    54660
catggtgcta ggttttctga aatcatttga aaaactatta aattcctgtc caccaggagc    54720
ttgtattata acttaggaaa taaggactcc ctggcctaca ggataaaaat caaatttgtt    54780
ttggtcaggg tttgtcctaa tgtagcagtt ctctgttttg gcctcagaac ctctttacac    54840
tcttgacagt tattgagagc ctaaaagagt ttttgttcat atgggttata gctattgata    54900
tttaccatat tagaaattaa aactgagtta catgtaaaca taaagaactt tgtaaacatg    54960
aaaatgcatt atcttttccc agcaaaattt aggcattgta cattttttcag atcttctctg   55020
ggtctggctt aattgaagac agcacttgat ctgttgtgac atcacatgtc tcataacctt    55080
tggaaaagtc cattatatgc tcaatgagag aatgataatg agagtaaaag ggccataaga    55140
tgttacagaa tcttatggaa atagtttttga cttcatggac cccttcaaag gattgggtcc   55200
ccggagcaca ctgggaatgc tgccataaca accccagcac ccctatccag tcttagttat    55260
ccctgagtgc caaaggcact cccaacccag cacactcctt tctgctagta gcacaggata    55320
gactcccttt tttttcccag tcacaactaa cattcctctc tcttacaccc ctcactcacc    55380
ctcacaccat cacacctcct ttccttgctt cctcctgacc tcacagtcag gataatgtcc    55440
cataatgctg tgcatggagg ggaacatttg cacatatggc tctgtcaaga gagtaggcct   55500
cctgctctca ttagcttgct gacgggaagc tacctgtaag gtccttgctt cttgctctgc    55560
ctccacacag ccccttctgg agttggagca catagtctca ctgcaatgga agagggcaga   55620
gcttcttaat cactatccac tgcccatggt ggggcccatg aaatggacac cttcacccat    55680
ttgctcattt ctgtggatgc agcagggctg agccacggca tagatcaaga ctggggggctg  55740
gggggcgggg cggggaggca ccagacacct ccatccttta gatatactct acaaaagaga    55800
aagaaaatcc ttctgtattg ttttccctct tgtttgtatt gaccctgcac cacggttcag    55860
ctccaccaat gctaggttgg cactgtggac cagttcatga aaccatggca gggctcatca    55920
cgggctctat cgacagacat cccagggtga cttccgcagg cccgaccgct tcctctttcc    55980
ccacactccc cttgacttcc aaccccactg ctatggcctt cactcgagtc actgcacctg    56040
cttggtacac cccttttccac ctctcctgcc atcgatccgg tccttctcac ctccttaatt   56100
caggtcatag aggtcttcca cgctgcccaa agcagtcgat tttgttctgt gctgtgtgat    56160
tggtcacata ccctaagtcc ttagggcagg aaataatctt atactactgt acagcctgca    56220
```

```
agcattgcag cgtcttgcct ttaacacatg aaaagcacca ttttaagcta ggagatttaa    56280
ataggaaatg cctctgactc tgtttctttt ccttccaggt cactgctgga ctgcctcttc    56340
ccaaggctta catacaggag gtaacctgag ttatttctca tcacgtgtcc tagaaagcac    56400
cacaccttga atcagcattt ctccacctgg cccatgtgga aatgaatggg ttattgctgt    56460
gacccagggt gcagggtgcc aaaaggcctg cagtgtgctg aggagttata ttaaatgagt    56520
agatagggaa gatgtacctc acaaaataga attgtcccac ataggggtgtc aataagccac    56580 tgccctagac cagtggttga ttctcaacag ctgattttga ccccggggac atttggcaat    56640
gtctagagac tttttttatt attacaactg gaggtgggga gtgctactgg aatctagtgg    56700
gtagaaactg gggatgctgg ctaaacatcc tttaatgcac aggacagccc ctacaacatt    56760
atccagctca aatgtcggag tgtgaggctg agaaaccctg tcctagacta atagcagttc    56820
ccttccattg tcttccctgc attggctggg taagttccaa atgccattca gatcagaagc    56880
aagtagagac cttttttgaa atggcttctc ctctgccgat ttaaatccat attaacgggc    56940
caagatatat ggtcaggatt ctggttgttt ttctagacaa agcttcctgg atatttatag    57000
catcaaacag gaggctagag aacaactgtg agctcaaatc ttttcatatt tatgtcattt    57060
accatcaaag aaacatctct aaagccagtt tggggtggtt acaggaaaga caggccatca    57120
gataaggtgg caaggtcacc tgctgtcact gctaattcaa ttttttctgcc tttttggaag    57180 gcttttaaat tatcaagcaa tacagggtca ctgttcaggc cccaaatgaa gtatttcaaa    57240
actggctaga aaaaattgct ggtaccttca gtctgcctgt cttctgagtt atggtttgcc    57300
ttttatggtc atttgtctga ttcacgcgta ggaggggaat tcacagttct ggccctcctg    57360
ccaccccaca gccttttcctg tgtctaatta cagtgactgc ccctagctgg cccagctggt    57420
gtcttcattt aagaaattct acttatttaa aactgttctt gatcagcgtt acatattaat    57480
tggttttcat gtgactagag gtaaagaatt agcagtgttc tttagaagct caaataaatc    57540
ataatctcag ttttcaatta ttaaaggaaa aaagcataaa tcacatttat aatgaaccta    57600
gttgttttcc acctttatc ctacctattt ctgcttttt gggatcaaca aacattagtg    57660
ctgggttttg ctcgatgatt cagtatatgt attttttatag aagactcttt tatttttaaa    57720
atatttaatg tattgttaag cctacaatag taatatatccc tttgtaaaaa ataataatta    57780
aacattataa gaatgtaata tatgtgagtt gagtccccctt aacagttcgg tgcatatttc    57840
tcgacattta aaaattttttc atgaattata tacatgtatt tttgtgtttg tcctaaaatg    57900
gaataattaa gctctccatg gttttgcacc tttagtacat cttggacagg ttccatgtta    57960
acacagatgg gtctcacttt cataacatct gcatgataaa tatttattga gtgtatatgt    58020
cataattcat tggcccagtc cccccttggag gaggtttatg tttataattt tccaatgcta    58080
caagcagggc tgcagtaaac atacttaaag atacatttcc ttaattgctt ccctttagtt    58140
tgtagtactt ggttttggt gggttttttt gtttttgtttt gttttgagat ggagtctggc    58200
tctattaccc aggctggagt gcagtggtgt gatctcggct cactgcaagc tccgcctcct    58260
gggttcacac cattctcctg cctcagcctc ccaagaagct gcgactacaa gcacccacca    58320
tcatgtccgg ctaatttttt tgtatttta gttgagacgg ggtttcaccg tgttagccag    58380
gatggtctcg atctcctgac ctcgtgttcc acccgcctcg gcctcccaaa gtgctgggat    58440
tacaggcatg agccaccacg cccagccggt ttttggggtt ttttttacag acagggtctc    58500
actctgtcac ctaggctgga ctgcagaggc gtgatcatag ctgcagcctc taactcttgg    58560
gcttaagcag tctccccgct tcaacctccc aactagctgg aagaacagga acacgccacc    58620
```

```
acaccaggct aatttttta tttttgtag agacggggtc tccctatgtt gcccaggcag   58680
gctgctgtcg aactcctagg tgcaagtgat cctccgatct cagcctcgca aagtactggg   58740
attacaggtg tgagctacca catccagctc agttcttttt ttttttttt tttttttttt   58800 gagacagagt cttgctctgt caccaggctg gagtgcagtg gtgcaatttc aactcactgc   58860
aacctccgcc tctgggggttc aagtgattct cctccctcag cctcccaagc agctgggact   58920
acaggttcct gccaccacac ctagttaatt tttatatttt taatagatac ggggtttcac   58980
catgttggcc agtatagtct taatctcttg accttgtgat ccacctgcct cggcccccca   59040
aagtgctggg atgacaggca taagccacca ggtccggccc tttttttttt tttttttta   59100 attaacttct cagttgtaga gatggggtct tgttatgttt cctaggcttg tctcaaactc   59160
ctgggctcaa gtggattctc ctgcctcagc ctcccaaagt cctgggatta caagtgtgag   59220
ccactgggcc cagccactgg cctgattcct aaagatagta tttatcttat ttcttgccct   59280
cgttcacggt cgagttcatt aaaacctttg aaaacatcac tgcttacttc atatttcctg   59340
gcagtattta cggcagccat ataacgaata cctcttctgt gccagccact atgttgttag   59400
gctctgtctt ctgatggaag ggtctgtgct gtgcagagta gagttaattt gtattatcat   59460
aaccctatga atacataaaa tctataaaca caattggtaa atataatttg ggtaagggta   59520
actaattcct ttcaaacagc aaataagcta taatgatgtg gcataatgac aggaaacata   59580
ccagctcttt ttttcttgaa ggctgggaaa caagcagagc tctactctag tgtcataggc   59640
tggagtgaaa gctgcagttc tccatagcat ccactcaccg cactgaaaaa aatgcaccaa   59700
gggaccttct ctcttctttc ttggcctcct tgtcctgata gtgagtggct gctggctcaa   59760
ggaggttgtt tgcctttgaa gaagaacctg cagtggtttt caactctctg atctcatagg   59820
cctttcactg ttgtttttac agaacctgga gctggttgaa aaaggcttca gtaacttgaa   59880
gaaacaaatt gaaaatgcca gaatgtttgg aattccagta gtagtggccg tgaatgcatt   59940
caagtaagtg tagagtgtaa gcgaaaagga tgaatgtgga aaatctcctg gagctgattg   60000
tacagcactg cttttagctt tattttgttt ttcagttact gctattggtt atagcctgtg   60060
gttttagcct gcactgtgac aggcattgca tacgtcactg cgggctcacc acctcaccca   60120
ctgagggtcc caaagtcaga ttcagctcct atgggccctt ttccttttcca ctggggggaag   60180 taacacacaa gcctgaagtt caatgttcct ttttcatctt tagaggcctt ttatgctaac   60240
agaaggtcat aggcctatag tgttccatta ttttactaga tctggtggga tgttgtcttg   60300
acaaagaatt gggcatatta ctctggaagg ggtcatgcaa gaacttgtgt gggttgttta   60360
ggtattgcat tggtggtcag ggttttgtta taatggcctc accgtagtag aatgggaagc   60420
aaaaaatctt ttttttttt tgggggacga agtctgtctc tgttgcccag gctggagtgc   60480
agtggcacga tctccactcg ctgcaagctc tgcctcccgg gttcatgcca ttctcctgcc   60540
tcagcctccc tagtagctgg gactacaggt gcctgccacc atgcccagct aatttttttgt   60600 attttttagta gagacggggt ttcaccgtgt tagccaggat ggtctcgatc tcctgacctc   60660
gtgattctcc cacctcggcc tcccaaagtg ttgggattac aagtgtgagc caccgcgccc   60720
agccagcaaa attcttaaat gctagtattt actgattcct tctggagtgc tgggaatttt   60780
ccaagtattt tacatggatt taccatctga gtctcataac gtcccaatga aataagtgct   60840
gtgattattc gcgtattacc agggtggaaa ttgaggcaca taagattag gtaactggcc   60900 aaaagtcacc agctagtaag tttcggagct gagattcaaa cccaggccaa atttcttggt   60960
```

```
tagtgttcgt ttatcagtgg gtaattcaca tgaggtttaa tggcaaaaag aagacaattc    61020
tgtctctcca gccatttttcc atgctttgat atgaaatgct tcctttatag gacggataca    61080
gagtctgagc tggacctcat cagccgcctt tccagagaac atggggcttt tgatgccgtg    61140
aagtgcactc actgggcaga aggggcaag ggtgccttag ccctggctca ggccgtccag     61200
agagcagcac aagcacccag cagcttccag ctcctttatg acctcaaggt gggtgatttg    61260
ctgtctgcaa aaaagaaaa aagacgaaaa gggcacagtg aagtttctgt gtggctactt     61320
ctattagagc cccatgcttc gcagcttcag ccttgcggtt tgattcccac gtaggtgact    61380
tacacaacca cagcctggac tcccagctgt agacagcctt cttttattt ttgagacgga     61440 gtcttgctct tttgcccagg ctcgagtgca gaggcatgat ctcagctcac tgcaacctct   61500
gcctcctggg ttcaagtgat tctcctgcct cagcttccca agtagctggg attacaggcg   61560
tctgccaccg tgcccagcta attttcctta ttttttagt agagatgggg tttcaccatc    61620
ttggccaggc tggtctcgaa ctcctgacct cgtgatccac ctgccttggc ctcccaaagt   61680
gctggaatta caggcgtgag ccactgcgtc cgcccagaca gccttcttat aaacatatgc   61740
cactgcttac ttacagaggg gatttaagca ggaataccc agggtggagg gggaaccgtt    61800
gctcatatcc taacttcgaa aagggtcaaa gtacaggtgg cagaagagaa ggttacatat   61860
agaccaaata tgtaattcac tgtagccttt aaaacaaggc accaaccatg tagcagattg    61920
gtaaggggct gcatcgagct tacaaaattt ttctgatggc ttttcagtaa taggggaaag   61980
aagtgtgccc ccacgttcac ttcctggtaa ggtgctgcct caagttgagg gccctcacat   62040
gcaaaaccaa agtactccag gaagcttcat cattttttcc atcactaagc aaattaaatt   62100
acacctggtc taagtagagc cctgcttact ctatgataca ataaagttag ttcaggaaaa   62160
ggttcttatt atagggttgt gttttgtttt catttatctg tccagtgtat ttcaggatgt   62220
gatttgacat taagtagtat ggaaacaaca actggaaact tgttaggaa tatgagatat     62280 atgctgtagt taattttcc tattctctag gctagtttct ggcttgattt ttttgttttg    62340
ttttttgttt taagacaggg tcttgctctg ttgctcaggc tggagtgcag tggtacaatc   62400
atggcacact gcagcctcaa cctcctggac ccaagtggtc ctcccacctc agcccctga    62460 gtaggtggga ccacagacat gtactaccaa gcctggctaa tttgttttat ggccaggca    62520 cagtggctca cccctgtaac cccagcactt tgggaggccg aggtgggtgg atcacctaag   62580
gtcaagagtt ggagaccagc ctggccaaca tggtgaaacc ccatctctac taaaaataca   62640
aaaaattagc tgggtgtggt ggcaggcacc tgtaatccca gctacttgga aggctgaggc   62700
aggagaatcg cttgaacccg ggaggcggac gttgcaatga gctgagatca ctgcactcta   62760
gcctgggcaa caagtgcgaa acttcgtctc aaaaaaaaaa ttttgtttta ttttatttta   62820
tttttcttgt agtgactggg tctccctata ttgctcaggc tggtctcgaa ctcctgggtt   62880
caagtgatcc tcctgcctca gcctcccaaa gtgctgggat tataggcatg agccaatgtg   62940
cctggcctgg cttggttttt aatagataat catagacttt caaaaacagc cataaaaaag   63000
cagaaggaat aaacttatta ctcttgagtt ttagtgttct cttatttctc tttgccccctt  63060 gcagatataa tacacttaca gttaattaac attgacattg acattctcct gttgagcttt   63120
gattttatag gcaagttta aaatctgttc agcaatcatc cttttagaaa aatgccataa   63180
acacaaattt gcacacaaat gcaaagcatt tataggcacc ctctccaggc tccaatgcat   63240
agcacccaag gctggaagcc cagtccttga aaaccagcag gagacctgaa agagcaggga   63300
catatggact ttagaaccca tttctacttg caacttttat ccattctggc aaacaggagg   63360
```

```
ctgccacttt tgtcttact cagcgtctgc tagtcttaaa tcaccccttca accaaagtgc   63420 ttttgcttca gaagttctaa atgtgccttg gcatttatag agctccagtt atgagatgca   63480
tatgaaaata atctgtgttt catctttata aagtccttat tgaatgttca ctttattcat   63540
gcccattata taaagcccct tcataaatta tcattgttta gttcaaaagg aattttttgt   63600
ttttatagat agattattgc tccttttaaa aacaaaactt ggctgggcgc tgtggtcaca   63660
cctgtaatcc cagcactttg ggaagctgag gtgggtggat cacctaaggt caggagttcg   63720
agaccagcct gaccaagatg gtgaaactcc gtctctacta aaaatataaa attagccaag   63780
catggtggcc catgcctgtg atcccagcta cttgggaggc tgaggcagga gaatctcttg   63840
aacccgggag gcggaggttg cagtgagctg agatgacgcc attgcactcc agcctgggca   63900
acaagtgcaa aactctgtct caaataaata agaacctgcc taatatgttc ttttagcttt   63960
agttgctata aagacagata tattgcctaa tttttgtaat ttgctcatcc aaattaccca   64020
tgagtagctt tgcttctgat ttcctttagg caacctctcc gtatgctgtt ctctttgaat   64080
cttaatgccc tgaactagtc tacacagcat ttaagaagcc agctccactt ctctgaaggc   64140
tttgccccgg aggaaacagc ccatgggact gaggccctca ccagttagac cactggtctc   64200
tgtccactgc actgtttgct tcaggtgcca cagaaagtgg acatgcccaa tgcgtgttga   64260
tcatgtaaat cactgggttg ttttttctaa tacctgggtg attttgattt tatgactatt   64320
tcctaattcc tggtgcttgc acttaatcaa ttgtgttaag ggtggcatct gcctctcata   64380
tacagactgg gagttatgta gatggacatt ggttgtctta tttcataaac agtgtcccca   64440
ggtctggttt gacaggactg atctccagta ttagaataga acatctactt tttaattttt   64500
attattattt taaaattttt attttttaaa gagacagagt gttgctatgt tgcccaggct   64560
ggtttcaaac tcctgggctc aagtgatcct cctgccttgg cctcctccca aagtgctggg   64620
attacaggga tgagccacca tacccagcct gaacatctac ttttttattta tgaagaaata   64680 attattcttg ggtagtcagc aacactgttt atgatgtact tagcgagaga ttttaaatat   64740
gtacttatgt aagtatatat ttaaaaccttt aatatatatt aatatgtgta tctatatcta   64800
tatatatatg tatgtgtgta tatgtatatc tgcatatata gatataaaaa ctttacctct   64860
gtgggacatt ttcacttata aaatctgagg cttgatatta aaagaaagtg ttcctggctg   64920
ggtgcagtgg ctcacacctg taatcccagc actttgggag gccaaggctg gcagatcacc   64980
tgaggttggg agttcaagac cagcctgacc aacatggaga aactccgtct ctactaaaaa   65040
tacagaatta gccgggcttg gttgcgcatg cctataatcc cagctactcg ggaggctgag   65100
gcaggagaat cgcttgaacc tgggaggcag gggttacagt gaactgagat cgcgccattg   65160
cactccagcc tggcaacaga gcgaaactcc gtctcaaaaa aacaaaaaga aagtgttctt   65220
aacccaatca tcaacctcaa actatttgct tatgtatatg tatataaaaa ccatcttctg   65280
ccccttttag ggactctgac ctagaatgtg gctatgtcct ggttaaatgt cctcacatgt   65340
gtccagtcat ggtgtcccca tctctttctt gtgcattagc tcccagttga ggataaaatc   65400
aggatcattg cacagaagat ctatggagca gatgacattg aattacttcc cgaagctcaa   65460
cacaaagctg aagtctacac gaagcaggta gatgtttggt tagtttgtcc tttcaactct   65520
ttgcaaagca ggacttggag tcacaatctc tgggtcctcc cagccctgcc aagtacccgt   65580
tgcttcactt ctctgggtgg cagccttctc tcctctgaaa tactgagttt ggattaggtg   65640
gcacagtccc tggttctttta tttacccata ggcgttatat gaatgtgtag aaatccatga   65700
```

```
ggaaatacag aatgtcttac caaaatattg agaacgtctc cagttttttgt tattttgaga    65760 tagggtctgg ctccattgcc caggctagag tgcagtggca caatttcagc tcactgcagc    65820
ctctgactcc taggctcaag cgatcctccc acctcagcct cctgagtagc tgcgcctaca    65880
ggcacgcacc accacacctg gctaattttt gtgttttttg ttgagatggg gttttgccct    65940
gttgcccagg ctggtcttga actcctgggc tcaagcagtc cacccatctc agtctcccaa    66000
agtgctggaa tttataggca tgaaccactg cacctgaccc tctccaattt tattctcata    66060
tctactccaa actattattt taaattagtt ttatgttatt ccatagatg gaaataaaat     66120 attcacttgt ggactacagt tgtgagtacc taactccctc acccaacagt tctttttttt    66180 ttttttttggc ttaataaata agctggagga cagcaagata gagatgtata taaagggagt   66240
tggatgtttc gaataaattg aagaatccat gtaatcacag gcccagatg gtcattgctg     66300 ggttgtcatc tttcatttg tcctccctct cttcccttct ttcccaggg ctttgggaat       66360 ctccccatct gcatggctaa aacacacttg tctttgtctc acaacccaga gcaaaaaggt    66420
gtccctacag gcttcattct gcccattcgc gacatccgcg ccagcgttgg ggctggtttt    66480 ctgtaccccct tagtaggaac ggtaagtgca tgctgcaagg gagtagtggg cgcatctgca   66540
cttctcgtct gaagtgtgtt gccgaaacca tcaagcaaat gccaagtgag cagagttcac    66600
tgcccagaag aaaattggaa tcgggcctat tatgattgct gtggatcata agctataaag    66660
caggagctat atagctcttg ctgtggacca tcttggtgtc aaatcaagaa tgatgccagg    66720
actactcata ctgaataaaa aattctgttt cccaggaca gtatgctctt cactgaatct      66780
aggatgagcc cagttgatag gctggggtag tgctaacata atcacagtta atgtttattg    66840
ggagccttac atagattaac tcagtccccc cacagcccta ggaggtaggg acagaggttt    66900
tactgacagg cctagaactt acgtctgaaa ttcagggggt tcattatttt taagtaagga    66960
atttccccat taaaaaatgc aaatggaccc ttgagatatg aaaggtgagg ttgcttattt    67020
acgcttcaag gtgaacaagg tgtccattgc tttcttatct tacagatttt atgcatattc    67080
aaagaagaat attgccagtt gggaagcaga ggggagggat gcttaaggac ataatcatag    67140
tttgggctga cattgttcca aggttaactt ggatcctgaa tctaggttat cccctaaatc    67200
tgccctgtat cctgtatcta cagattgtac tgccatgcaa tacaggactg aaatattaaa    67260
ctaaatcaac acacatggaa aagaaaccaa catacatcct tttggattta tgtcattctt    67320
tcagtatagt aagaaagtgg taggaggtgg cattatagag ttgaaaacgt aggacattag    67380
agctgaattc attttcacct cttcagatct tggccttggg caaattatga aaggtgagag    67440
ccctgctgcc ctcagctcac actgtaggca acatcatcac atcacagtgg tgcttagcac    67500 aaaatgcctgc atctcactgc ctccttagct ctctatagag agcagaaggc ttagacttgc    67560
tatgatgtac atcagtctcc aggatttgta gaaatccctt gtggtaggaa ttttccacca    67620
tttttaccca gcaccttgaa tagtgcagaa atatgtgttg ttcttttttgg agaagttgtc    67680 agcagctacc agctgaaaga cgggtagctg tactctttct tgtcactttt gatcttcaca    67740
tgaagaaaag ggtaacagta gaggtgaaag caaatctgga agcagtcagg ccagtgagag    67800
tcaggctgta aggtggagag agacacagcc tgccgaactc aagactttct catttagaac    67860
aaagtatgtg tcagaggctt ttaacttaa ggttggaccaa ggcgtttcca cacatgatca     67920
aatggtttaa tcactattct aacaccttcc agttgccgtt ggggccttaa cgagactcag    67980
attatttgaa tattttctat attaattcaa agtgtgatgg cttatttttca gaactttata    68040 tctaggttca tacatgtgcg tacacataat attgtctttt tttgtatttt ttctgattat    68100
```

```
cagtgaccag tgtttaggag ggaaaatcct cttggggaat gagtgaaaat atcaaaaatc  68160
ctactcatca ctgtttaggg aaccatcttt agggttttct gctgacatgc acatgcccgt  68220
ctacaacaat gggcatgtgt cttttatctt tataatgtca tcttccggtt tttctgctgt  68280
gtctaaggac ccatcctttc ctctctccta cttgtctcac acctagcacc tccttacctc  68340
ttacacaata taagaatata aaccagttgt cagatcccta taatgtgttt tggggaatat  68400
tgattggtac tcagaagtca gtcagaatga ggttttctaa agtattgatg atgttttgtg  68460
ttacagaaga tgactctttt taaataacct ttttatagtt aagttttaga agtaacctaa  68520
gctgttttcc tgtctagatt tgatttggaa cttgtgtgta ttcattatat aggacattgt  68580
tacagataaa aatatacgga gttttcactt gcaagccgta catatttgca tctaagtaga  68640
aatttgtcaa agccgagtct ttagaaaagt agtgagtaca aatataattt gtaagcatta  68700
caagtttagt tttagaaggc cattttgggc cagtaagaat ggtgattata aaccatcta   68760 gattatgtac aaaagtgtct tggcccaagt taaaggatac taactcctac catcgtgttg  68820
ctgaagcaaa aatcacatgg gcagctcagc tagcaagact gaacgaaaca aaatttaaaa  68880
gcaggcaagc cctgtacctc cttttggtct tgcaaagcgt gagctgagga ggcgagtgag  68940
caactcctct actccccagc actcattctt gtaaggtgaa ggtggaaaca cctcctgcta  69000
ctgcttgtga ccacatggaa gatgatagtg aaggctggca tttggtttgc agaaggacat  69060
gaggaatcag tttcttttct tttccttttt ttttttttg atggagtc ttgctctgtc     69120 acccaggctg gagtgcagtg gcaagatctc ggctcactgc aacctccgcc tcccaggttc  69180
aagcgattct cctgcctcag cctcccaagt agctgggatt acaggcacac gccaccatgc  69240
ccagctaatt tttgtatttt tagtagagat ggggtttcac catgttggtc aggctggtct  69300
caaattcctg acctcaggtg atccatctgc cttggcctcc cagagtgcta ggattatagg  69360
catgagccac cacgcccggc agggatcagt ttctgagttt tttaacagga tcagtgactt  69420 gattttaat atgtaacaag agtacccact ttattgacaa ctataaaatg atgttctatc   69480
tttatgcctt gggctttctt tctgaaggaa aagtgaaagt aaagatgact ttacgtttat  69540
tttagacatg gccttgctct gtcgcccagg caatcggatg atcatggctc actgtggcct  69600
caacctccta gcctcaagca atcctcctgc cttagcatcc caagtagctg gaactacagg  69660
cacatgccat catatccagc taatttttta tttcctgtag atgggggt ctcactatgt    69720 tgcccagggt ggtttagaac tcctggcctc aagtgatcct ctccacctca gcctgggatt  69780
ataggcgtga gccactgtgc ccagcattag tttatttgta atgctttttt acatcctaga  69840
tgagcacaat gcctggactc cccacccggc cctgttttta tgatattgat ttggaccctg  69900
aaacagaaca ggtgaatgga ttattctaaa caggtaagtt gttactgggt ataatttgg   69960 cttttttcct catgtagctt atttatgaat tatagggctc aaactgacgc tataaaaatt  70020
cacattctaa tgctttcaaa acatttcttt tcagacttcc ctgaggggag aggggatagt  70080
aatgagagtt ggcaataacc aatgaattga aatatttata tttcaacaca ttttggaag   70140 aagcgcagca tggcttgtca caggttgaca gtgtagggga gaaaactgct gtccaataaa  70200
ctacagagga aactcagga gaggttagac tccctctgct gaagcccag gaggcttggg    70260 gttcagagtt gatgacacat tgcaggtcag gaacagctga cggtctgtat actctgaata  70320
ggtagttaga aggcaagaat tagcaaatgt cttaggaagt ataatagaaa agagaaggaa  70380
acaggaccaa tctggcagtt cttagggcct taggtgaaag ggccctgagt accgactgca  70440
```

```
atgagtgaca ttgcattgtt tgatattttt gaaatttcaa caggacgtgt ctctccttag    70500
gcagacccct ggggctgaag cagcaagttg cagtgtgcac ttatatccct agacacatcc    70560
tgttgaaact gcaaaaatat caaacatgaa atcctaaca tctttctcca gagacgaaaa     70620
aagtggcttg cctatgaaaa gaatgagaac tagacttaac gcccgtctta ctggcaataa    70680
gaagctttta gacaatggag gagtgtcctg taaggtcaca gggaagatga ctttcaacat    70740
gtgctcacac ctagccgaat ctatctggat attttcagac gtgcaagggt ttgccacccc    70800
acatctcttc ctaagaagtt atttagcaat gtacttagca aaatgaggaa ttaaccaaga    70860 aaaaggaag acgtgagttt tgggaaactg aaccctcatt tggacattag cgaaggggca     70920
ttctgataac catgcaaatg acctgaagtt acaaatcctg tgtggaacag gttggggag     70980 cacctgagaa aaactagaaa aagctagaaa agacaaggat atcaaagggt catagtataa    71040
aacaaaagct cttgcattat ttgagaaagt taaggtccaa gtagaagcaa actgtagttt    71100
gatgctagaa cactattctt tgagagggta tgtgtgatac tcgaaatgca gtcatggctc    71160
acggcttggt ctggtcttga acagtattca cacagtacta tggaaatacc atgcatcatt    71220
ttcaagtcca tttatggaca cgccctagaa gagctggtgg caggaaagga tgtaaatgtt    71280
aacagctttg gcaatgtgag tgggtaatgg tgcagtatgg aaggaacagg aaacatttca    71340
gtgcttgctt agagaaaaca tttatttctt gttttccctt ccagatcacc atccatcttc    71400
aagaagctac tttgaaagtc tggccagtgt ctattcaggc ccactgggag ttaggaagta    71460
taagtaagcc aagagaagtc agcccctgcc cagaagatct gaaactaata gtaggagttt    71520
ccccagaagt cattttcagc cttaattctc atcatgtata aattaacata atcatgcat     71580 gtctgtttac tttagtgacg ttccacagaa taaaaggaaa caagtttgc               71629
```

```
<210> SEQ ID NO 6
<211> LENGTH: 3613
<212> TYPE: DNA
<213> ORGANISM: Homo sapiens
<220> FEATURE:
<221> NAME/KEY: CDS
<222> LOCATION: (269)..(3205)

<400> SEQUENCE: 6
ccactccgca ccccaccctc tgtctggtac agcttaccaa accaaagtgc ccaaagccgt     60
gacatcccgg ccggcggctc gcaggccccc gccctccgca cgtcacggcc gccgggtgca    120 gtgccccta ggggccctg ggacgaggag gaagcgccag gtccttcccg ccgccgccgc      180
cgccgccgcc gcctgctccc ctggcacgcg cccgccgcc ctcggcagcc gcagctccgt     240
gtcccctgag aaccagccgt cccgcgcc atg ggc acg cgt ctg ccg ctc gtc        292
                                Met Gly Thr Arg Leu Pro Leu Val
                                 1               5 ctg cgc cag ctc cgc cgc ccg ccc cag ccc ccg ggc cct ccg cgc cgc       340
Leu Arg Gln Leu Arg Arg Pro Pro Gln Pro Pro Gly Pro Pro Arg Arg
        10                  15                  20 ctc cgt gtg ccc tgt cgc gct agc agc ggc ggc ggc gga ggc ggc ggc       388
Leu Arg Val Pro Cys Arg Ala Ser Ser Gly Gly Gly Gly Gly Gly Gly
 25                  30                  35                  40 ggt ggc cgg gag ggc ctg ctt gga cag cgg cgg ccg cag gat ggc cag       436
Gly Gly Arg Glu Gly Leu Leu Gly Gln Arg Arg Pro Gln Asp Gly Gln
                 45                  50                  55 gcc cgg agc agc tgc agc ccc ggc ggc cga acg ccc gcg gcg cgg gac       484
Ala Arg Ser Ser Cys Ser Pro Gly Gly Arg Thr Pro Ala Ala Arg Asp
             60                  65                  70
```

-continued

| | |
|---|---|
| tcc atc gtc aga gaa gtc att cag aat tca aaa gaa gtt cta agt tta<br>Ser Ile Val Arg Glu Val Ile Gln Asn Ser Lys Glu Val Leu Ser Leu<br>           75                    80                    85 | 532 |
| ttg caa gaa aaa aac cct gcc ttc aag ccg gtt ctt gca att atc cag<br>Leu Gln Glu Lys Asn Pro Ala Phe Lys Pro Val Leu Ala Ile Ile Gln<br>90                    95                    100 | 580 |
| gca ggt gac gac aac ttg atg cag gaa atc aac cag aat ttg gct gag<br>Ala Gly Asp Asp Asn Leu Met Gln Glu Ile Asn Gln Asn Leu Ala Glu<br>105                  110                115              120 | 628 |
| gag gct ggt ctg aac atc act cac att tgc ctc cct cca gat agc agt<br>Glu Ala Gly Leu Asn Ile Thr His Ile Cys Leu Pro Pro Asp Ser Ser<br>           125                    130              135 | 676 |
| gaa gcc gag att ata gat gaa atc tta aag atc aat gaa gat acc aga<br>Glu Ala Glu Ile Ile Asp Glu Ile Leu Lys Ile Asn Glu Asp Thr Arg<br>               140                  145              150 | 724 |
| gta cat ggc ctt gcc ctt cag atc tct gag aac ttg ttt agc aac aaa<br>Val His Gly Leu Ala Leu Gln Ile Ser Glu Asn Leu Phe Ser Asn Lys<br>155                  160                165 | 772 |
| gtc ctc aat gcc ttg aaa cca gaa aaa gat gtg gat gga gta aca gac<br>Val Leu Asn Ala Leu Lys Pro Glu Lys Asp Val Asp Gly Val Thr Asp<br>170                  175                180 | 820 |
| ata aac ctg ggg aag ctg gtg cga ggg gat gcc cat gaa tgt ttt gtt<br>Ile Asn Leu Gly Lys Leu Val Arg Gly Asp Ala His Glu Cys Phe Val<br>185                  190                        200 | 868 |
| tca cct gtt gcc aaa gct gta att gaa ctt ctt gaa aaa tca ggt gtc<br>Ser Pro Val Ala Lys Ala Val Ile Glu Leu Leu Glu Lys Ser Gly Val<br>               205                  210              215 | 916 |
| aac cta gat gga aag aag att ttg gta gtg ggg gcc cat ggg tct ttg<br>Asn Leu Asp Gly Lys Lys Ile Leu Val Val Gly Ala His Gly Ser Leu<br>           220                    225              230 | 964 |
| gaa gct gct cta caa tgc ctg ttc cag aga aaa ggg tcc atg aca atg<br>Glu Ala Ala Leu Gln Cys Leu Phe Gln Arg Lys Gly Ser Met Thr Met<br>               235                  240              245 | 1012 |
| agc atc cag tgg aaa aca cgc cag ctt caa agc aag ctt cac gag gct<br>Ser Ile Gln Trp Lys Thr Arg Gln Leu Gln Ser Lys Leu His Glu Ala<br>250                  255                260 | 1060 |
| gac att gtg gtc cta ggc tca cct aag cca gaa gag att ccc ctt act<br>Asp Ile Val Val Leu Gly Ser Pro Lys Pro Glu Glu Ile Pro Leu Thr<br>265                  270                275              280 | 1108 |
| tgg ata caa cca gga act act gtt ctc aac tgc tcc cat gac ttc ctg<br>Trp Ile Gln Pro Gly Thr Thr Val Leu Asn Cys Ser His Asp Phe Leu<br>               285                  290              295 | 1156 |
| tca ggg aag gtt ggg tgt ggc tct cca aga ata cat ttt ggt gga ctc<br>Ser Gly Lys Val Gly Cys Gly Ser Pro Arg Ile His Phe Gly Gly Leu<br>           300                    305              310 | 1204 |
| att gag gaa gat gat gtg att ctc ctt gct gca gct ctg cga att cag<br>Ile Glu Glu Asp Asp Val Ile Leu Leu Ala Ala Ala Leu Arg Ile Gln<br>               315                  320              325 | 1252 |
| aac atg gtc agt agt gga agg aga tgg ctt cgt gaa cag cag cac agg<br>Asn Met Val Ser Ser Gly Arg Arg Trp Leu Arg Glu Gln Gln His Arg<br>330                  335                340 | 1300 |
| cgg tgg aga ctt cac tgc ttg aaa ctt cag cct ctc tcc cct gtg cca<br>Arg Trp Arg Leu His Cys Leu Lys Leu Gln Pro Leu Ser Pro Val Pro<br>345                  350                355              360 | 1348 |
| agt gac att gag att tca aga gga caa act cca aaa gct gtg gat gtc<br>Ser Asp Ile Glu Ile Ser Arg Gly Gln Thr Pro Lys Ala Val Asp Val<br>               365                  370              375 | 1396 |
| ctt gcc aag gag att gga ttg ctt gca gat gaa att gaa atc tat ggc<br>Leu Ala Lys Glu Ile Gly Leu Leu Ala Asp Glu Ile Glu Ile Tyr Gly<br>380                  385                390 | 1444 |

| | |
|---|---|
| aaa agc aaa gcc aaa gta cgt ttg tcc gtg cta gaa agg tta aag gat<br>Lys Ser Lys Ala Lys Val Arg Leu Ser Val Leu Glu Arg Leu Lys Asp<br>395                   400                  405 | 1492 |
| caa gca gat gga aaa tac gtc tta gtt gct ggg atc aca ccc acc cct<br>Gln Ala Asp Gly Lys Tyr Val Leu Val Ala Gly Ile Thr Pro Thr Pro<br>    410                  415                  420 | 1540 |
| ctt gga gaa ggg aag agc aca gtc acc atc ggg ctt gtg cag gct ctg<br>Leu Gly Glu Gly Lys Ser Thr Val Thr Ile Gly Leu Val Gln Ala Leu<br>425                   430                  435                  440 | 1588 |
| acc gca cac ctg aat gtc aac tcc ttt gcc tgc ttg agg cag cct tcc<br>Thr Ala His Leu Asn Val Asn Ser Phe Ala Cys Leu Arg Gln Pro Ser<br>                  445                  450                  455 | 1636 |
| caa gga ccg acg ttt gga gtg aaa gga gga gcc gcg ggt ggt gga tat<br>Gln Gly Pro Thr Phe Gly Val Lys Gly Gly Ala Ala Gly Gly Gly Tyr<br>460                   465                  470 | 1684 |
| gcc cag gtc atc ccc atg gag gag ttc aac ctt cac ttg act gga gac<br>Ala Gln Val Ile Pro Met Glu Glu Phe Asn Leu His Leu Thr Gly Asp<br>    475                  480                  485 | 1732 |
| atc cac gcc atc acc gct gcc aat aac ttg ctg gct gcc gcc atc gac<br>Ile His Ala Ile Thr Ala Ala Asn Asn Leu Leu Ala Ala Ala Ile Asp<br>490                   495                  500 | 1780 |
| acg agg att ctt cat gaa aac acg caa aca gat aag gct ctg tat aat<br>Thr Arg Ile Leu His Glu Asn Thr Gln Thr Asp Lys Ala Leu Tyr Asn<br>505                   510                  515                  520 | 1828 |
| cgg ctg gtt cct tta gtg aat ggt gtc aga gaa ttt tca gaa att cag<br>Arg Leu Val Pro Leu Val Asn Gly Val Arg Glu Phe Ser Glu Ile Gln<br>                  525                  530                  535 | 1876 |
| ctt gct cgg cta aaa aaa ctg gga ata aat aag act gat ccg agc aca<br>Leu Ala Arg Leu Lys Lys Leu Gly Ile Asn Lys Thr Asp Pro Ser Thr<br>540                   545                  550 | 1924 |
| ctg aca gaa gag gaa gtg agt aaa ttt gcc cgt ctc gac atc gac cca<br>Leu Thr Glu Glu Glu Val Ser Lys Phe Ala Arg Leu Asp Ile Asp Pro<br>555                   560                  565 | 1972 |
| tct acc atc acg tgg cag aga gta ttg gat aca aat gac cga ttt cta<br>Ser Thr Ile Thr Trp Gln Arg Val Leu Asp Thr Asn Asp Arg Phe Leu<br>570                   575                  580 | 2020 |
| cga aaa ata acc atc ggg cag gga aac aca gag aag ggc cat tac cgg<br>Arg Lys Ile Thr Ile Gly Gln Gly Asn Thr Glu Lys Gly His Tyr Arg<br>585                   590                  595                  600 | 2068 |
| cag gcg cag ttt gac atc gca gtg gcc agc gag atc atg gcg gtg ctg<br>Gln Ala Gln Phe Asp Ile Ala Val Ala Ser Glu Ile Met Ala Val Leu<br>                  605                  610                  615 | 2116 |
| gcc ctg acg gac agc ctc gca gac atg aag gca cgg ctg gga agg atg<br>Ala Leu Thr Asp Ser Leu Ala Asp Met Lys Ala Arg Leu Gly Arg Met<br>620                   625                  630 | 2164 |
| gtg gtg gcc agt gac aaa agc ggg cag cct gtg aca gca gat gat ttg<br>Val Val Ala Ser Asp Lys Ser Gly Gln Pro Val Thr Ala Asp Asp Leu<br>635                   640                  645 | 2212 |
| ggg gtg aca ggt gct ttg aca gtt ttg atg aaa gat gca ata aaa cca<br>Gly Val Thr Gly Ala Leu Thr Val Leu Met Lys Asp Ala Ile Lys Pro<br>650                   655                  660 | 2260 |
| aac ctg atg cag acc ctg gaa ggg aca cct gtg ttc gtg cat gcg ggc<br>Asn Leu Met Gln Thr Leu Glu Gly Thr Pro Val Phe Val His Ala Gly<br>665                   670                  675                  680 | 2308 |
| cct ttt gct aac att gct cac ggc aac tct tca gtg ttg gct gat aaa<br>Pro Phe Ala Asn Ile Ala His Gly Asn Ser Ser Val Leu Ala Asp Lys<br>                  685                  690                  695 | 2356 |
| att gcc ctg aaa ctg gtt ggt gaa gaa gga ttt gta gtg acc gaa gct<br>Ile Ala Leu Lys Leu Val Gly Glu Glu Gly Phe Val Val Thr Glu Ala | 2404 |

-continued

```
                 700                 705                 710
ggc ttt ggt gct gac atc gga atg gag aaa ttc ttc aac atc aag tgc      2452
Gly Phe Gly Ala Asp Ile Gly Met Glu Lys Phe Phe Asn Ile Lys Cys
            715                 720                 725 cga gct tcc ggc ttg gtg ccc aac gtg gtt gtg tta gtg gca acg gtg      2500
Arg Ala Ser Gly Leu Val Pro Asn Val Val Val Leu Val Ala Thr Val
730                 735                 740 cga gct ctg aag atg cat gga ggc ggg cca agt gta acg gct ggt gtt      2548
Arg Ala Leu Lys Met His Gly Gly Gly Pro Ser Val Thr Ala Gly Val
745                 750                 755                 760 cct ctt aag aaa gaa tat aca gag gag aac atc cag ctg gtg gca gac      2596
Pro Leu Lys Lys Glu Tyr Thr Glu Glu Asn Ile Gln Leu Val Ala Asp
                765                 770                 775 ggc tgc tgt aac ctc cag aag caa att cag atc act cag ctc ttt ggg      2644
Gly Cys Cys Asn Leu Gln Lys Gln Ile Gln Ile Thr Gln Leu Phe Gly
            780                 785                 790 gtt ccc gtt gtg gtg gct ctg aat gtc ttc aag acc gac acc cgc gct      2692
Val Pro Val Val Val Ala Leu Asn Val Phe Lys Thr Asp Thr Arg Ala
        795                 800                 805 gag att gac ttg gtg tgt gag ctt gca aag cgg gct ggt gcc ttt gat      2740
Glu Ile Asp Leu Val Cys Glu Leu Ala Lys Arg Ala Gly Ala Phe Asp
    810                 815                 820 gca gtc ccc tgc tat cac tgg tcc gtt ggt gga aaa gga tcg gtg gac      2788
Ala Val Pro Cys Tyr His Trp Ser Val Gly Gly Lys Gly Ser Val Asp
825                 830                 835                 840 ttg gct cgg gct gtg aga gag gct gcg agt aaa aga agc cga ttc cag      2836
Leu Ala Arg Ala Val Arg Glu Ala Ala Ser Lys Arg Ser Arg Phe Gln
                845                 850                 855 ttc ctg tat gat gtt cag gtt cca att gtg gac aag ata agg acc att      2884
Phe Leu Tyr Asp Val Gln Val Pro Ile Val Asp Lys Ile Arg Thr Ile
            860                 865                 870 gct cag gct gtc tat gga gcc aaa gat att gaa ctc tct cct gag gca      2932
Ala Gln Ala Val Tyr Gly Ala Lys Asp Ile Glu Leu Ser Pro Glu Ala
        875                 880                 885 caa gcc aaa ata gat cgt tac act caa cag ggt ttt gga aat ttg ccc      2980
Gln Ala Lys Ile Asp Arg Tyr Thr Gln Gln Gly Phe Gly Asn Leu Pro
    890                 895                 900 atc tgc atg gca aag acc cac ctt tct cta tct cac caa cct gac aaa      3028
Ile Cys Met Ala Lys Thr His Leu Ser Leu Ser His Gln Pro Asp Lys
905                 910                 915                 920 aaa ggt gtg cca agg gac ttc atc tta cct atc agt gac gtc cgg gcc      3076
Lys Gly Val Pro Arg Asp Phe Ile Leu Pro Ile Ser Asp Val Arg Ala
                925                 930                 935 agc ata ggc gct ggg ttc att tac cct ttg gtc gga acg atg agc acc      3124
Ser Ile Gly Ala Gly Phe Ile Tyr Pro Leu Val Gly Thr Met Ser Thr
            940                 945                 950 atg cca gga ctg ccc acc cgg ccc tgc ttt tat gac ata gat ctt gat      3172
Met Pro Gly Leu Pro Thr Arg Pro Cys Phe Tyr Asp Ile Asp Leu Asp
        955                 960                 965 acc gaa aca gaa caa gtt aaa ggc ttg ttc taa gtggacaagg ctctcacagg    3225
Thr Glu Thr Glu Gln Val Lys Gly Leu Phe
    970                 975 acccgatgca gactcctgaa acagactact ctttgccttt ttgctgcagt tggagaagaa    3285
actgaatttg aaaatgtctc gttatgcaat gctggagacg tggtgaaata ggccaaagat    3345
ttcttcttcg ttcaagatga attctgttca cagtggagta tggtgttcgg caaaaggacc    3405
tccaccaaga ctgaaagaaa ctaatttatt tctgtttctg tggagtttcc attatttcta    3465
ctgcttacac tttagaatgt ttattttatg gggactaagg gattaggagt gtgaactaaa    3525
```

-continued

| | |
|---|---|
| aggtaacatt tccactctc aagttttcta ctttgtctttt gaactgaaaa taaacatgga | 3585 |
| tctagaaaac caaaaaaaaa aaaaaaaa | 3613 |

<210> SEQ ID NO 7
<211> LENGTH: 2937
<212> TYPE: DNA
<213> ORGANISM: Homo sapiens

<400> SEQUENCE: 7

| | |
|---|---|
| atgggcacgc gtctgccgct cgtcctgcgc cagctccgcc gcccgcccca gcccccgggc | 60 |
| cctccgcgcc gcctccgtgt gccctgtcgc gctagcagcg gcggcggcgg aggcggcggc | 120 |
| ggtggccggg agggcctgct tggacagcgg cggccgcagg atggccaggc ccggagcagc | 180 |
| tgcagccccg gcggccgaac gcccgcggcg cgggactcca tcgtcagaga agtcattcag | 240 |
| aattcaaaag aagttctaag tttattgcaa gaaaaaaacc ctgccttcaa gccggttctt | 300 |
| gcaattatcc aggcaggtga cgacaacttg atgcaggaaa tcaaccagaa tttggctgag | 360 |
| gaggctggtc tgaacatcac tcacatttgc ctccctccag atagcagtga agccgagatt | 420 |
| atagatgaaa tcttaaagat caatgaagat accagagtac atggccttgc ccttcagatc | 480 |
| tctgagaact tgtttagcaa caaagtcctc aatgccttga accagaaaaa agatgtggat | 540 |
| ggagtaacag acataaacct ggggaagctg gtgcgagggg atgcccatga atgttttgtt | 600 |
| tcacctgttg ccaaagctgt aattgaactt cttgaaaaat caggtgtcaa cctagatgga | 660 |
| aagaagattt tggtagtggg ggcccatggg tctttggaag ctgctctaca atgcctgttc | 720 |
| cagagaaaag ggtccatgac aatgagcatc cagtggaaaa cacgccagct tcaaagcaag | 780 |
| cttcacgagg ctgacattgt ggtcctaggc tcacctaagc cagaagagat tccccttact | 840 |
| tggatacaac caggaactac tgttctcaac tgctcccatg acttcctgtc agggaaggtt | 900 |
| gggtgtggct ctccaagaat acattttggt ggactcattg aggaagatga tgtgattctc | 960 |
| cttgctgcag ctctgcgaat tcagaacatg gtcagtagtg aaggagatg cttcgtgaa | 1020 |
| cagcagcaca ggcggtggag acttcactgc ttgaaacttc agcctctctc ccctgtgcca | 1080 |
| agtgacattg agatttcaag aggacaaact ccaaaagctg tggatgtcct tgccaaggag | 1140 |
| attggattgc ttgcagatga aattgaaatc tatggcaaaa gcaaagccaa agtacgtttg | 1200 |
| tccgtgctag aaaggttaaa ggatcaagca gatggaaaat acgtcttagt tgctgggatc | 1260 |
| acacccaccc ctcttggaga agggaagagc acagtcacca tcgggcttgt gcaggctctg | 1320 |
| accgcacacc tgaatgtcaa ctcctttgcc tgcttgaggc agccttccca aggaccgacg | 1380 |
| tttggagtga aggaggagc gcgggtggt ggatatgccc aggtcatccc catgaggag | 1440 |
| ttcaaccttc acttgactgg agacatccac gccatcaccg ctgccaataa cttgctggct | 1500 |
| gccgccatcg acacgaggat tcttcatgaa aacacgcaaa cagataaggc tctgtataat | 1560 |
| cggctggttc ctttagtgaa tggtgtcaga gaattttcag aaattcagct tgctcggcta | 1620 |
| aaaaaactgg gaataaataa gactgatccg agcacactga cagaagagga agtgagtaaa | 1680 |
| tttgcccgtc tcgacatcga cccatctacc atcacgtggc agagagtatt ggatacaaat | 1740 |
| gaccgatttc tacgaaaaat aaccatcggg cagggaaaca cagagaaggg ccattaccgg | 1800 |
| caggcgcagt ttgacatcgc agtggccagc gagatcatgc cggtgctggc cctgacggac | 1860 |
| agcctcgcag acatgaaggc acggctggga aggatggtgg tggccagtga caaagcggg | 1920 |
| cagcctgtga cagcagatga tttgggggtg acaggtgctt tgacagttttt gatgaaagat | 1980 |

-continued

```
gcaataaaac caaacctgat gcagaccctg gaagggacac ctgtgttcgt gcatgcgggc   2040
ccttttgcta acattgctca cggcaactct tcagtgttgg ctgataaaat tgccctgaaa   2100
ctggttggtg aagaaggatt tgtagtgacc gaagctggct ttggtgctga catcggaatg   2160
gagaaattct tcaacatcaa gtgccgagct tccggcttgg tgcccaacgt ggttgtgtta   2220
gtggcaacgg tgcgagctct gaagatgcat ggaggcgggc caagtgtaac ggctggtgtt   2280
cctcttaaga aagaatatac agaggagaac atccagctgg tggcagacgg ctgctgtaac   2340
ctccagaagc aaattcgat cactcagctc tttggggttc cgttgtggg ggctctgaat    2400 gtcttcaaga ccgacacccg cgctgagatt gacttggtgt gtgagcttgc aaagcgggct   2460
ggtgcctttg atgcagtccc ctgctatcac tggtccgttg gtggaaaagg atcggtggac   2520
ttggctcggg ctgtgagaga ggctgcgagt aaaagaagcc gattccagtt cctgtatgat   2580
gttcaggttc caattgtgga caagataagg accattgctc aggctgtcta tggagccaaa   2640
gatattgaac tctctcctga ggcacaagcc aaaatagatc gttacactca acagggtttt   2700
ggaaatttgc ccatctgcat ggcaaagacc caccttttctc tatctcacca acctgacaaa   2760
aaaggtgtgc caagggactt catcttacct atcagtgacg tccgggccag cataggcgct   2820
gggttcattt accctttggt cggaacgatg agcaccatgc caggactgcc cacccggccc   2880
tgcttttatg acatagatct tgataccgaa acagaacaag ttaaaggctt gttctaa      2937
```

<210> SEQ ID NO 8
<211> LENGTH: 978
<212> TYPE: PRT
<213> ORGANISM: Homo sapiens

<400> SEQUENCE: 8

```
Met Gly Thr Arg Leu Pro Leu Val Leu Arg Gln Leu Arg Arg Pro Pro
1               5                  10                  15

Gln Pro Pro Gly Pro Pro Arg Arg Leu Arg Val Pro Cys Arg Ala Ser
            20                  25                  30

Ser Gly Gly Gly Gly Gly Gly Gly Gly Arg Glu Gly Leu Leu Gly
        35                  40                  45

Gln Arg Arg Pro Gln Asp Gly Gln Ala Arg Ser Ser Cys Ser Pro Gly
    50                  55                  60

Gly Arg Thr Pro Ala Ala Arg Asp Ser Ile Val Arg Glu Val Ile Gln
65                  70                  75                  80

Asn Ser Lys Glu Val Leu Ser Leu Leu Gln Glu Lys Asn Pro Ala Phe
                85                  90                  95

Lys Pro Val Leu Ala Ile Ile Gln Ala Gly Asp Asp Asn Leu Met Gln
            100                 105                 110

Glu Ile Asn Gln Asn Leu Ala Glu Glu Ala Gly Leu Asn Ile Thr His
        115                 120                 125

Ile Cys Leu Pro Pro Asp Ser Ser Glu Ala Glu Ile Ile Asp Glu Ile
    130                 135                 140

Leu Lys Ile Asn Glu Asp Thr Arg Val His Gly Leu Ala Leu Gln Ile
145                 150                 155                 160

Ser Glu Asn Leu Phe Ser Asn Lys Val Leu Asn Ala Leu Lys Pro Glu
                165                 170                 175

Lys Asp Val Asp Gly Val Thr Asp Ile Asn Leu Gly Lys Leu Val Arg
            180                 185                 190

Gly Asp Ala His Glu Cys Phe Val Ser Pro Val Ala Lys Ala Val Ile
        195                 200                 205
```

```
Glu Leu Leu Glu Lys Ser Gly Val Asn Leu Asp Gly Lys Lys Ile Leu
    210                 215                 220
Val Val Gly Ala His Gly Ser Leu Glu Ala Ala Leu Gln Cys Leu Phe
225                 230                 235                 240
Gln Arg Lys Gly Ser Met Thr Met Ser Ile Gln Trp Lys Thr Arg Gln
                245                 250                 255
Leu Gln Ser Lys Leu His Glu Ala Asp Ile Val Val Leu Gly Ser Pro
            260                 265                 270
Lys Pro Glu Glu Ile Pro Leu Thr Trp Ile Gln Pro Gly Thr Thr Val
        275                 280                 285
Leu Asn Cys Ser His Asp Phe Leu Ser Gly Lys Val Gly Cys Gly Ser
    290                 295                 300
Pro Arg Ile His Phe Gly Gly Leu Ile Glu Glu Asp Val Ile Leu
305                 310                 315                 320
Leu Ala Ala Ala Leu Arg Ile Gln Asn Met Val Ser Ser Gly Arg Arg
                325                 330                 335
Trp Leu Arg Glu Gln Gln His Arg Arg Trp Arg Leu His Cys Leu Lys
            340                 345                 350
Leu Gln Pro Leu Ser Pro Val Pro Ser Asp Ile Glu Ile Ser Arg Gly
        355                 360                 365
Gln Thr Pro Lys Ala Val Asp Val Leu Ala Lys Glu Ile Gly Leu Leu
    370                 375                 380
Ala Asp Glu Ile Glu Ile Tyr Gly Lys Ser Lys Ala Lys Val Arg Leu
385                 390                 395                 400
Ser Val Leu Glu Arg Leu Lys Asp Gln Ala Asp Gly Lys Tyr Val Leu
                405                 410                 415
Val Ala Gly Ile Thr Pro Thr Pro Leu Gly Glu Gly Lys Ser Thr Val
            420                 425                 430
Thr Ile Gly Leu Val Gln Ala Leu Thr Ala His Leu Asn Val Asn Ser
        435                 440                 445
Phe Ala Cys Leu Arg Gln Pro Ser Gln Gly Pro Thr Phe Gly Val Lys
    450                 455                 460
Gly Gly Ala Ala Gly Gly Gly Tyr Ala Gln Val Ile Pro Met Glu Glu
465                 470                 475                 480
Phe Asn Leu His Leu Thr Gly Asp Ile His Ala Ile Thr Ala Ala Asn
                485                 490                 495
Asn Leu Leu Ala Ala Ala Ile Asp Thr Arg Ile Leu His Glu Asn Thr
            500                 505                 510
Gln Thr Asp Lys Ala Leu Tyr Asn Arg Leu Val Pro Leu Val Asn Gly
        515                 520                 525
Val Arg Glu Phe Ser Glu Ile Gln Leu Ala Arg Leu Lys Lys Leu Gly
    530                 535                 540
Ile Asn Lys Thr Asp Pro Ser Thr Leu Thr Glu Glu Val Ser Lys
545                 550                 555                 560
Phe Ala Arg Leu Asp Ile Asp Pro Ser Thr Ile Thr Trp Gln Arg Val
                565                 570                 575
Leu Asp Thr Asn Asp Arg Phe Leu Arg Lys Ile Thr Ile Gly Gln Gly
            580                 585                 590
Asn Thr Glu Lys Gly His Tyr Arg Gln Ala Gln Phe Asp Ile Ala Val
        595                 600                 605
Ala Ser Glu Ile Met Ala Val Leu Ala Leu Thr Asp Ser Leu Ala Asp
    610                 615                 620
Met Lys Ala Arg Leu Gly Arg Met Val Val Ala Ser Asp Lys Ser Gly
```

```
                625             630             635             640
Gln Pro Val Thr Ala Asp Asp Leu Gly Val Thr Gly Ala Leu Thr Val
                645             650             655

Leu Met Lys Asp Ala Ile Lys Pro Asn Leu Met Gln Thr Leu Glu Gly
                660             665             670

Thr Pro Val Phe Val His Ala Gly Pro Phe Ala Asn Ile Ala His Gly
                675             680             685

Asn Ser Ser Val Leu Ala Asp Lys Ile Ala Leu Lys Leu Val Gly Glu
                690             695             700

Glu Gly Phe Val Val Thr Glu Ala Gly Phe Gly Ala Asp Ile Gly Met
705             710             715             720

Glu Lys Phe Phe Asn Ile Lys Cys Arg Ala Ser Gly Leu Val Pro Asn
                        725             730             735

Val Val Val Leu Val Ala Thr Val Arg Ala Leu Lys Met His Gly Gly
                740             745             750

Gly Pro Ser Val Thr Ala Gly Val Pro Leu Lys Lys Glu Tyr Thr Glu
                755             760             765

Glu Asn Ile Gln Leu Val Ala Asp Gly Cys Cys Asn Leu Gln Lys Gln
            770             775             780

Ile Gln Ile Thr Gln Leu Phe Gly Val Pro Val Val Ala Leu Asn
785             790             795             800

Val Phe Lys Thr Asp Thr Arg Ala Glu Ile Asp Leu Val Cys Glu Leu
                        805             810             815

Ala Lys Arg Ala Gly Ala Phe Asp Ala Val Pro Cys Tyr His Trp Ser
                820             825             830

Val Gly Gly Lys Gly Ser Val Asp Leu Ala Arg Ala Val Arg Glu Ala
                835             840             845

Ala Ser Lys Arg Ser Arg Phe Gln Phe Leu Tyr Asp Val Gln Val Pro
850             855             860

Ile Val Asp Lys Ile Arg Thr Ile Ala Gln Ala Val Tyr Gly Ala Lys
865             870             875             880

Asp Ile Glu Leu Ser Pro Glu Ala Gln Ala Lys Ile Asp Arg Tyr Thr
                        885             890             895

Gln Gln Gly Phe Gly Asn Leu Pro Ile Cys Met Ala Lys Thr His Leu
                900             905             910

Ser Leu Ser His Gln Pro Asp Lys Lys Gly Val Pro Arg Asp Phe Ile
                915             920             925

Leu Pro Ile Ser Asp Val Arg Ala Ser Ile Gly Ala Gly Phe Ile Tyr
                930             935             940

Pro Leu Val Gly Thr Met Ser Thr Met Pro Gly Leu Pro Thr Arg Pro
945             950             955             960

Cys Phe Tyr Asp Ile Asp Leu Asp Thr Glu Thr Glu Gln Val Lys Gly
                        965             970             975

Leu Phe

<210> SEQ ID NO 9
<211> LENGTH: 1049
<212> TYPE: DNA
<213> ORGANISM: Homo sapiens
<220> FEATURE:
<221> NAME/KEY: CDS
<222> LOCATION: (108)..(935)

<400> SEQUENCE: 9
tccttcccgc cgccgccgcc gccgccgccg cctgctcccc tggcacgcgc ccgccgccc     60
```

-continued

| | |
|---|---|
| tcggcagccg cagctccgtg tccctgaga accagccgtc ccgcgcc atg ggc acg<br>　　　　　　　　　　　　　　　　　　　　　　　　　　Met Gly Thr<br>　　　　　　　　　　　　　　　　　　　　　　　　　　　1 | 116 |
| cgt ctg ccg ctc gtc ctg cgc cag ctc cgc cgc ccg ccc cag ccc ccg<br>Arg Leu Pro Leu Val Leu Arg Gln Leu Arg Arg Pro Pro Gln Pro Pro<br>　5　　　　　　　　　　10　　　　　　　　　　15 | 164 |
| ggc cct ccg cgc cgc ctc cgt gtg ccc tgt cgc gct agc agc ggc ggc<br>Gly Pro Pro Arg Arg Leu Arg Val Pro Cys Arg Ala Ser Ser Gly Gly<br>20　　　　　　　　　　25　　　　　　　　　　30　　　　　　　　　　35 | 212 |
| ggc gga ggc ggc ggc ggt ggc cgg gag ggc ctg ctt gga cag cgg cgg<br>Gly Gly Gly Gly Gly Gly Gly Arg Glu Gly Leu Leu Gly Gln Arg Arg<br>　　　　　　　　　40　　　　　　　　　　45　　　　　　　　　　50 | 260 |
| ccg cag gat ggc cag gcc cgg agc agc tgc agc ccc ggc gga cga acg<br>Pro Gln Asp Gly Gln Ala Arg Ser Ser Cys Ser Pro Gly Gly Arg Thr<br>　　　　　　55　　　　　　　　　　60　　　　　　　　　　65 | 308 |
| ccc gcg gcg cgg gac tcc atc gtc aga gaa gtc att cag aat tca aaa<br>Pro Ala Ala Arg Asp Ser Ile Val Arg Glu Val Ile Gln Asn Ser Lys<br>　　　　70　　　　　　　　　　75　　　　　　　　　　80 | 356 |
| gaa gtt cta agt tta ttg caa gaa aaa aac cct gcc ttc aag ccg gtt<br>Glu Val Leu Ser Leu Leu Gln Glu Lys Asn Pro Ala Phe Lys Pro Val<br>85　　　　　　　　　　90　　　　　　　　　　95 | 404 |
| ctt gca att atc cag gca ggt gac gac aac ttg atg cag gaa atc aac<br>Leu Ala Ile Ile Gln Ala Gly Asp Asp Asn Leu Met Gln Glu Ile Asn<br>100　　　　　　　　　　105　　　　　　　　　　110　　　　　　　　　　115 | 452 |
| cag aat ttg gct gag gag gct ggt ctg aac atc act cac att tgc ctc<br>Gln Asn Leu Ala Glu Glu Ala Gly Leu Asn Ile Thr His Ile Cys Leu<br>　　　　　　　　　120　　　　　　　　　　125　　　　　　　　　　130 | 500 |
| cct cca gat agc agt gaa gcc gag att ata gat gaa atc tta aag atc<br>Pro Pro Asp Ser Ser Glu Ala Glu Ile Ile Asp Glu Ile Leu Lys Ile<br>　　　　　　135　　　　　　　　　　140　　　　　　　　　　145 | 548 |
| aat gaa gat acc aga gta cat ggc ctt gcc ctt cag atc tct gag aac<br>Asn Glu Asp Thr Arg Val His Gly Leu Ala Leu Gln Ile Ser Glu Asn<br>　　　　150　　　　　　　　　　155　　　　　　　　　　160 | 596 |
| ttg ttt agc aac aaa gtc ctc aat gcc ttg aaa cca gaa aaa gat gtg<br>Leu Phe Ser Asn Lys Val Leu Asn Ala Leu Lys Pro Glu Lys Asp Val<br>165　　　　　　　　　　170　　　　　　　　　　175 | 644 |
| gat gga gta aca gac ata aac ctg ggg aag ctg gtg cga ggg gat gcc<br>Asp Gly Val Thr Asp Ile Asn Leu Gly Lys Leu Val Arg Gly Asp Ala<br>180　　　　　　　　　　185　　　　　　　　　　190　　　　　　　　　　195 | 692 |
| cat gaa tgt ttt gtt tca cct gtt gcc aaa gct gta att gaa ctt ctt<br>His Glu Cys Phe Val Ser Pro Val Ala Lys Ala Val Ile Glu Leu Leu<br>　　　　　　　　　200　　　　　　　　　　205　　　　　　　　　　210 | 740 |
| gaa aaa tca ggt gtc aac cta gat gga aag aag att ttg gta gtg ggg<br>Glu Lys Ser Gly Val Asn Leu Asp Gly Lys Lys Ile Leu Val Val Gly<br>　　　　　　215　　　　　　　　　　220　　　　　　　　　　225 | 788 |
| gcc cat ggg tct ttg gaa gct gct cta caa tgc ctg ttc cag aga aaa<br>Ala His Gly Ser Leu Glu Ala Ala Leu Gln Cys Leu Phe Gln Arg Lys<br>　　　　230　　　　　　　　　　235　　　　　　　　　　240 | 836 |
| ggg tcc atg aca atg agc atc cag tgg aaa aca cgc cag ctt caa agc<br>Gly Ser Met Thr Met Ser Ile Gln Trp Lys Thr Arg Gln Leu Gln Ser<br>245　　　　　　　　　　250　　　　　　　　　　255 | 884 |
| aag acg gag tct cgt tct gtc acc agg ctg gag tgc agg cgc gtg atc<br>Lys Thr Glu Ser Arg Ser Val Thr Arg Leu Glu Cys Arg Arg Val Ile<br>260　　　　　　　　　　265　　　　　　　　　　270　　　　　　　　　　275 | 932 |
| tag gctcactgca agctctgcct cccaggttga agtgattctc ctgtgaaagg | 985 |
| gaattatttt tgatgagtca ttaaagtata tccattccca gaatggtgct gcatttttcc | 1045 |
| tttt | 1049 |

<210> SEQ ID NO 10
<211> LENGTH: 828
<212> TYPE: DNA
<213> ORGANISM: Homo sapiens

<400> SEQUENCE: 10

```
atgggcacgc gtctgccgct cgtcctgcgc cagctccgcc gcccgcccca gcccccgggc    60
cctccgcgcc gcctccgtgt gccctgtcgc gctagcagcg gcggcggcgg aggcggcggc   120
ggtggccggg agggcctgct tggacagcgg cggccgcagg atggccaggc ccggagcagc   180
tgcagccccg gcggccgaac gcccgcggcg cgggactcca tcgtcagaga agtcattcag   240
aattcaaaag aagttctaag tttattgcaa gaaaaaaacc ctgccttcaa gccggttctt   300
gcaattatcc aggcaggtga cgacaacttg atgcaggaaa tcaaccagaa tttggctgag   360
gaggctggtc tgaacatcac tcacatttgc ctccctccag atagcagtga agccgagatt   420
atagatgaaa tcttaaagat caatgaagat accagagtac atggccttgc ccttcagatc   480
tctgagaact tgtttagcaa caaagtcctc aatgccttga accagaaaaa agatgtggat   540
ggagtaacag acataaacct ggggaagctg gtgcagaggg atgcccatga atgttttgtt   600
tcacctgttg ccaaagctgt aattgaactt cttgaaaaat caggtgtcaa cctagatgga   660
aagaagattt tggtagtggg ggcccatggg tctttggaag ctgctctaca atgcctgttc   720
cagagaaaag ggtccatgac aatgagcatc cagtggaaaa cacgccagct tcaaagcaag   780
acggagtctc gttctgtcac caggctggag tgcaggcgcg tgatctag                828
```

<210> SEQ ID NO 11
<211> LENGTH: 275
<212> TYPE: PRT
<213> ORGANISM: Homo sapiens

<400> SEQUENCE: 11

```
Met Gly Thr Arg Leu Pro Leu Val Leu Arg Gln Leu Arg Arg Pro Pro
1               5                   10                  15

Gln Pro Pro Gly Pro Pro Arg Arg Leu Arg Val Pro Cys Arg Ala Ser
            20                  25                  30

Ser Gly Gly Gly Gly Gly Gly Gly Arg Glu Gly Leu Leu Gly
        35                  40                  45

Gln Arg Arg Pro Gln Asp Gly Gln Ala Arg Ser Ser Cys Ser Pro Gly
    50                  55                  60

Gly Arg Thr Pro Ala Ala Arg Asp Ser Ile Val Arg Glu Val Ile Gln
65                  70                  75                  80

Asn Ser Lys Glu Val Leu Ser Leu Leu Gln Glu Lys Asn Pro Ala Phe
                85                  90                  95

Lys Pro Val Leu Ala Ile Ile Gln Ala Gly Asp Asp Asn Leu Met Gln
            100                 105                 110

Glu Ile Asn Gln Asn Leu Ala Glu Glu Ala Gly Leu Asn Ile Thr His
        115                 120                 125

Ile Cys Leu Pro Pro Asp Ser Ser Glu Ala Glu Ile Ile Asp Glu Ile
    130                 135                 140

Leu Lys Ile Asn Glu Asp Thr Arg Val His Gly Leu Ala Leu Gln Ile
145                 150                 155                 160

Ser Glu Asn Leu Phe Ser Asn Lys Val Leu Asn Ala Leu Lys Pro Glu
                165                 170                 175

Lys Asp Val Asp Gly Val Thr Asp Ile Asn Leu Gly Lys Leu Val Arg
            180                 185                 190
```

-continued

```
Gly Asp Ala His Glu Cys Phe Val Ser Pro Val Ala Lys Ala Val Ile
            195                 200                 205

Glu Leu Leu Glu Lys Ser Gly Val Asn Leu Asp Gly Lys Lys Ile Leu
        210                 215                 220

Val Val Gly Ala His Gly Ser Leu Glu Ala Ala Leu Gln Cys Leu Phe
225                 230                 235                 240

Gln Arg Lys Gly Ser Met Thr Met Ser Ile Gln Trp Lys Thr Arg Gln
                245                 250                 255

Leu Gln Ser Lys Thr Glu Ser Arg Ser Val Thr Arg Leu Glu Cys Arg
            260                 265                 270

Arg Val Ile
        275

<210> SEQ ID NO 12
<211> LENGTH: 236333
<212> TYPE: DNA
<213> ORGANISM: Homo sapiens
<220> FEATURE:
<221> NAME/KEY: misc_feature
<222> LOCATION: (33274)..(33274)
<223> OTHER INFORMATION: The number of "att" repeats staring at position
      33274 is seven, but there can be a greater number of such "att"
      repeats than seven.

<400> SEQUENCE: 12
ccactccgca ccccaccctc tgtctggtac agcttaccaa accaaagtgc ccaaagccgt    60
gacatcccgg ccggcggctc gcaggccccc gccctccgca cgtcacggcc gccgggtgca   120
gtgcccccta ggggcccctg ggacgaggag gaagcgccag gtccttcccg ccgccgccgc   180
cgccgccgcc gcctgctccc ctggcacgcg ccccgccgcc ctcggcagcc gcagctccgt   240
gtcccctgag aaccagccgt cccgcgccat gggcacgcgt ctgccgctcg tcctgcgcca   300
gctccgccgc ccgccccagc ccccgggccc tccgcgccgc ctccgtgtgc cctgtcgcgc   360
tagcagcggc ggcggcggag gcggcggcgg tggccgggag ggcctgcttg gacagcggcg   420
gccgcaggat ggccaggccc ggagcagctg cagccccggc ggccgaacgc ccgcggcgcg   480
ggactccatc gtcaggtgag tgtcgggtct ggccctggcc caggtctcca gcggctgtgg   540
ccccgaccca ggggcggagc gcccgggacc gccgtgggga gcggggcgcg gggctgcgag   600
tgtttggtgc caactcatta ggggggccgg gcggtgtgtc gggaaacgcg ggcttgggca   660
ctgcggccgg gagcgctggc ggagaacggg ggatccagta cccgaccggg cccgcagcgc   720
aggtgggcgt gggcatctcc aatgggcgcc tagcggcatg gaccgcacgc ccggctccac   780
gtgcgcagcc ggccgccggc tctgatgcaa tcgcgccggg cgcgacccag acggtaaagg   840
ggcggtgcgg ctgggcgga aaccagggga gggggcgagg agcaggagga gggcggggct   900
gcggctcggc gcgccggctg gcccggggtt cgggaagggc aagcgagct cgggagaggc   960 gggctcgggc ccagcgccgc ccgcgcgaag ctccctggtg ttgtgcgccc ttccccgcgc  1020
gcggcccctc ctgctgggct ggggtctgtg gctgacgtcc gcttttcccg gaacggcaaa  1080
ggtggagccg ggcccccggg acagccgccg ggggaatcc gagaggtctc agcgctggtt  1140
tccagcttcg ccgcgcagcg cccacggagt cccgcgcag ctgggtttgc agggtttcct  1200
gcgggcccag agcgaactgg gagccccggg cccggccttt cccgtcccgg tccccgcccc  1260
tgggctccag ccttcccgc cctcgcccag aggggcgcac gggtctcggg ccttgcaggg  1320
cgagcccttc gggacaactt gggggtggca agaaagcccc ttccgcctcc ctcggaactg  1380
```

```
ggattaggaa cgagttccag gatgcggttt ccccggccag cggaccacct cctccattca   1440
catcctcttc cctttccttc tagccttctt tcttagtcat tgcctgcttg cctttctctc   1500
tgcctttcct tcctccctct gctctcccat tttcctcccc actccccttc tcccatctca   1560
gtaaaatacg tttcctaggc tctttattat gtggcggatg attttaaggg gccatttatt   1620
tagttttttct tgttctctgt cttcttttttc ttttagaaat ggagtctcgc tttgttgctc   1680
aggctggagt tcagtggtgc catctcggct caatgcagcc tccgcctcct gggctcaagc   1740
gattctcccg ccttagcctc cagtgtaact gggaccacag gtgtgcgcta ccatgcccgg   1800
attattttat tttattttca tagagacaga gcaccactct gttaccaggc tggtctggaa   1860
ctcctgggcg caagccatca tccctgcccc caaaagcgct gggattaatt acacgtcagg   1920
tcattaggtt ttaacctgca cgttgctgag actcatctta ccggttagag tctgaagcca   1980
ggataggcgg caaaaaaact ctcccgtca tgctgttta ttttctaggt aaactgatta   2040
ttacctgaaa cttccttctt tgctcatttc ttgtctgtct cacccacctg gaatatgagc   2100
ttcatgagac agccgtctct tcggtgctat atcctaggtc ctggagagag tgcccagcat   2160
gtaataagca cttgtgaaat ggttacagaa ggaatgcttc aagatttggg gtcatctgtg   2220
ggttttattc atacatattc tttttttttt tttttttttt tgagacggag tcttgctctg   2280
tcactcaggc tggagtgcaa tggcacgatc ttggctccct gcaacctctg cctcccaggt   2340
tcaggcgatt cccctgcctc agcctcccga gtagctggga ttacaggagc acgccaccac   2400
gcccggctaa ttttttgtatt ttgagtaaag acaggatgtc tcaccatgtt ggccaggctg   2460
gtcttgaact cctgacctca ggtgatccga ctgccttggc ctcccaaagt gttgggatta   2520
caggcgtgac ccaccgcgcc tgggctattc atgcatactt ttaggtttaa agccatgact   2580
gccttagaga tgagtaaaga ggttagtagg gggctttagg gcctgcactg ggttctccaa   2640
actcaattcc ttcaggaaaa tgggaggagt aacagtactt acctcaaggg gttatggaaa   2700
caattatgtg agaggacaca tgcaaaatac atagcccagg actgtcacat acaagacaag   2760
tccctcaaca aatggtggct attaattttt tttttttttt tttgagacgg aatctcactc   2820
tgtcgcacag gttggagtgc agtggcggga tctcggctca ctgcaacctc cgcctcccgg   2880
gttcaagcga ttcccctgcc tcagcctcct gagtagctgg gattacaggc tcgcactacc   2940
acgcctggct tattttgtgt ttttagtaga cgggggttt caccatgttg gccaggctgg   3000
tctcaaactc ctgacctcgt gatctgcctg cctcagcctc ccaaagtgct gggattacag   3060
gtgtgagcta ccatgcccag caatattttt acaattcact aagccagggg tccacagacg   3120
ttttatatat aatgggccag atagtaaata ttttaggttt agtgatccta gaggcaaatc   3180
aaaattatta gtaggtacat ttataacaag agaaaagaca aatttaggcc aggcaccatg   3240
gttcatgcct gtaatcccag cactttgaga ggccaaagtg ggatgatcac attcccagga   3300
gttcaagacc agcctgggca acatagtgag acacccatct ctgtaaaaaa ttttaaaaaa   3360
ttaactgggc gtggcgcgtg cctgtagttc cagctactca gaaggctgag gcaggaggat   3420
cacttgagcc caggaggtca aggctacagt gagcggagat tgcgctactg cactgcagcc   3480
tgggcaatgg agtgagacct tattttttat ttttgcaatt aagtattttt aattaaggta   3540
tgtacatttt ttagacaatg cttttgcaca cttaatagat ggcagtatag ggtaaccata   3600
acttttattt ttattttcta ttttactttta agttctggga aacgtgccga acgtgcaggt   3660
ttgttacata ggtatacatg cgccatggtg gtttgctgca cccatcaacc cgtcatctag   3720
gttttaagcc ccacatgcat taggtatttg tcctaatgct ctccctcctc ttgccctccc   3780
```

```
acccccctgac agaccctggt gtgtgatgtt ccccctccctg ggtccacgtg ttcttattgt    3840
tcaactccca cttatgagtg agaacatggg gtgtttggtt tctgttcctg tgttggtttg    3900
ctgaggatga tggtttccag cttcttccat gtccctgcag aggacatgaa ctcatgcttt    3960
cttatggctg caatttttatt tttgtagaga tgaagtctca ctatgttggc caggctggtc    4020
tcaaactcct gggttcaagt gatcctgctg cctcagcctc ccaaagtgct gagattgcag    4080
gcatgagcca ccacgcctgg ctatattgta cctttcaatt gagttatgtg catggtttac    4140
tgaaactcta gccctgaatt gattctccga ggattggagc aaagtgggtg ggggtgtgtg    4200
tcagctagaa gtcacctgga atagacatcc aggagcggaa gtgtattagt cagaaaaatt    4260
aaagaatgag ctccctcaaa agcatagtga cctgttgttc ctggtgatgg gactagatga    4320
ccataatccc tcagcctccc aagtagctgg gattacaggc aggcaccacc acacccagct    4380
aattttttgta ttttttagtag agacggggtt tcaccatgtt ggccaggcta gtcttgaact    4440
cctgacctca aatgatccac ccgccttggc ctcccaaagt gttgggatta caggcatgag    4500
ccactgcccc tggccagtaa taatacattc tgtataatag tcacagtaat ggtgaaaata    4560
acaaagctgc tgctgatggc ttagttctga gttttagcta cacatggcaa cctagctaga    4620
gagctcacat tccttcccac tgtcctcaac caaagtggaa gctcacaagg ccattttttct    4680
gccccaagga catgaaaatc tctgattaga aacatttatg ctacttttttg gatttattga    4740
gcctaatgac tccttttttct ttcttgcttt gtcactgtag gaatgagtaa ccccaaaaaa    4800
tgaaacatta cacatataac aagttgtagg gagcatgaac ctattttgtt ttattagctt    4860
gggtggtagt agcgttgaac tccttttacat acctgtacag gcacccctaa gatattgtgg    4920
gttcagttgc agaccactgc aataaggga atatcgcagt aaaacgagtc acacaaattt    4980
tgtagtttcc cagtgcatat aaaagttatg tttagacaat actgtagcct attaagtatg    5040
cactagcgtt ttgtctaaaaa aaaaacccat atataaggcc gggcgtggta gctcatgact    5100
gtaatcccag cactttggga ggctgaagtg ggtggatcac gaggtcagga gttcgagacc    5160
agcctggcca acatagtaaa accctgtctc tactaaaaat acaaaaatta gccaggcatg    5220
gtggtgtgcg cctgtagtcc tggccacttg ggaggctgag gcaggagaat cgctttaacc    5280
cgggaggtgg aggttgtggg gaggcggagg ttgtggtaag ccactacact ccagcctggg    5340
aaacagagcg agactccgtc tcaaaacaaa acaaaacaaa aaacccaaa aaacatatat    5400
atatatatta tatatataaa atatatataa tataatatac cttaattata atataatata    5460
attatatata ccttaattta tatatatacc ttataatata tataccttaa tatatatacc    5520
ttaattatat atatacacac cttaatatat atataatata tattaatata tatcttaata    5580
tatatatata aggtaatata tatatacacc ttaataataa tatatatacc ttaattttaa    5640
aatactttat taccaagaaa tgccagtgat ctggtggagg atttgcctag atgttgatgg    5700
ttattgactg atcagggtga ttgctaaaga ttagggtggc tgtggcagtt ttttaaagta    5760
agacaatgag gtttgctgta ttgatggaac tcttcctttc ctggaagatt tctctgtagc    5820
agtgctacag agaaaatggt aacatttttac ccacagtagt aggacttctt tcaaaatggg    5880
cgtcaatcct ctcaaaccct gcaactgctt taccaagtac ttgatatcaa ctactgtaat    5940
cttttttttt tttttttttt tttttgagat ggaatcttgc tctgtcgccc aggctggact    6000
gcagtgctgc gatctcggct cgctggaacc tccgcctctc aggttcaagt gattctcctg    6060
cctcagcctc ctgagtagct gagactacag gcgcctgcca ccacgcctgg ctaatttttt    6120
```

```
tgtattttta gtagaaacgg ggtttcacca tattggccag gctggtctcg aactcctgac   6180
cttgtgatcc gcccacttcg gcctcccaaa ctgctgggat tacaggtgtg agccactgtg   6240
cctgcctaac tactgtaatc ttataaatcc tttgttgtca tttttatttta ttttaatttt   6300 attttatttt attttaattt aatttttattt tatttttattt tttgagacag tctcactctt   6360
tcacccaggc tggagtgcag tggcgcgatc tctgctcact gcaacctctg cctcccgggt   6420
tcaataaatt ctcctgcttc agcctcccga gtagctggga ttataggcgt gcaccaccat   6480
gccctgctaa tttttttatt tttagtagag acggggtttc actatgttgg ccaggctggt   6540
ctccaactcc tgacctcgtg atccgcccgc ctcggcctcc caaagtgctg ggattacagg   6600
tgtgagccac tgcgcccggc ctaataaggc tgttttctta tcatttgtgt atccacggga   6660
gtagcacttt taaatttctt caatagcttt cctttgcat tcacagcttg ctaactgtt   6720 tggctcaaga ggcctagctt tgacctatc ttggctttca atacaccctc ctcactaagt   6780
ttaattattt ctcggttttt atttaaagtg agagacctgc aactcttcac ttgaacactt   6840
agaggccact gtagttacta attgtcctaa tttcaatatt gttgtttctc agggaatagg   6900
gaagccagag gagagggaga gagaagggg aacagccagt ccagtgaagc agtgagaaca   6960
cacaccatca tgaaccatca tggccacggt ttggccaaca caattacaac agtaacatca   7020
aagatcgtca atcacacatc accagaacaa acatactaaa aatgaaaaag tttgaaatat   7080
tgtaagaatt atcaaaatgt gacacaaatt gagcagatgc cattggaaaa atgactccca   7140
tagacttaaa acacaggttg ccacaaactt tcaatttgta gaaaaacaca gtatctgtaa   7200
attgcagtaa agcaaagcac aaaaaatgat gtatgcctgt atttttttt ctatccacat   7260 ccaccccca actttttttt tttttttggt agagaccagg tcttgctatc ttgcccaggc   7320
tggccttgaa ctcctgagct caagtgatcc tctcacctca gcctcccaaa gtgctgggat   7380
tacaggcatg agccactgcg cccagccccc atccccaact attttaaaag tctaattact   7440
ttttgacgat tgccgactta cctatagaag tgttcctttc agcccggcga ggtggctcac   7500
ccctgtaatt ccagcacttt gggaggccta ggtgggcgga tcacgaggtc aagagatcga   7560
gaccaccctg gccaacttgg tgaaatcctg tctctactaa aaatacaaaa attagtggga   7620
cgtggtggca tgcaccagta gtcccagcta ctcaggagac tgaggcagga gaatcgcttg   7680
aacctgggag atggaggttg cagtgagccg agatcgtgcc actgccctcc agcctggaaa   7740
caaagtgaga ctccgtctca aaaaaataaa aagaagtgtt cctttcatca actatgaatg   7800
gatcaagact atgaatgttt ctgagaaaat tattgctgtt agtaagaatg tttttagtgt   7860
ttaagggtag ctttggggca cagaaaaaaa caaacgtaca tttataagaa aaagggaaa   7920 gagccactgt agtatacctg ttttacagat gaggaatctg agactcttag agacttgtcc   7980
acgctagtaa atgaaatgcc cagtaccaat cctgggccgt atttccactt agtgtctcag   8040
aattacctgg actctgttaa aaatgcacat ttctgggctc cactgagaca cgttgaatca   8100
gactttctag ggctggaact gttattttt ttgagacaga gtctcgctct gtcacccagc   8160
tggagtgcag tggcatgatt ttggctcact gcagcctctg cctcctgggt tcaagtgatt   8220
ctcctgcctc agcctcctga gtagctctgg gattacaggt gtgcaccacc atgcctggct   8280 aattttgta ttttactag agatggggtt tcaccatgtt ggccaggatg gtctcaaact   8340
cctgacctca gtgatccat ttcaccttgg cctcccgaag tactgggatt ataggtgtga   8400
gccactgcac ctggcctgga acctttactt ttaccaaact ctccagtgat ccttatacca   8460
tgaaccgctt gggtcccaca ctccggtgct ttcctggacc cagacaaaaa taagaaccca   8520
```

```
gcatagccaa attaacagtc acgacaggct ggaaagagtg cggtatatgg gcctcagtca    8580
cccattattg gatggatgga ttttagtgct tatttataag gtgatttgta aactttccca    8640
tatggtcaca tttattcagc acaataatac aattaattcc ctgggaatga agtagcttta    8700
tcccaagtgt ttccaaacaa aactaactga aatgttccca ggttatagac agttgcctgc    8760
acccagtcca tctgttccgg cccagctggc agtagaaaga ctggtcctgg ttgtgaatct    8820
gagcagctct ctcccctaaa gccccgcctg ggaactgcag tgcctctggt tccatttgtc    8880
agctgtgtct ctctgaaaac tggggaaagc ttcccgatgc ctttctgctc ttggcagtgt    8940
accgttgatg gcattggctg gaacttcttc accccgcatt tttgttaggt gcagtgcaag    9000
accctgtcgg agactgaaaa caaaatgtaa aggtggtctt agcactgaag cctgggggct    9060
cctgtggctg cgcctttggt ctattgtgag aggggggaaaa gccagctccc agtgctcatg    9120
tgctgctgag aacatatcat agggtggtgg cgaaggtagc ctctgcagtc actcatccca    9180
gaaggttcca taaagagctg agctcctaac acttttttt ttttttgaga cggagtcttg    9240
ctgtgttgcc caggctggag tgcggtggca caatctcggc tcactgcaac ctctgcctcc    9300
caggttcaag agattctccc gagtagctca gattataggc gcctgccacc acacccagct    9360
aattttttgta tttctggtag agacggggtt tcaccatatt ggccacggtg gtcttgaact    9420
cctgaccttg tgatccaccc gcctcagctt cccaaagtgc tgggattaca ggcgtgagcc    9480
accgctcctg gactttttt tttttctttt ttttaaaaag aaattgagtc ttgctctgcc    9540
acccaggctg gagtgcagtg gtgcagtcat agcttactac agcctcaaac tcatgggctc    9600
aagcggtcct ccagcttcag cctcccaagt atctgggact acagtcacgt gccatcacgc    9660
ccagctaaat tgtttataga gatgggatct cgttatgtta cccaggctgg tctcaaactc    9720
ctggtctcaa gcagtcctac cgccttggcc tctcaaagtg ctgggactac aggtgcatgc    9780
caccatgcca ggccttctac cacttttacc taggcctgct cacccaggc tggcacctcc    9840
ctcagaggtg ggaggtgaag gtggctgctg ctgggcattt aggaggtaca ggtgcagact    9900
atgttgtgga ttctcagagg actgagaagc tctctgtctc tctctctagg aggctttgat    9960
agtgttatca aagtgggtct ccagtgtttc tggaactttc ctcccctcc ttccttacct   10020
aattccttct ttaaattcca ggacctggaa tttatcctgt ctcgacactt cttgtccaac   10080
agtgagcccc ctgtcttcac ccccctaatc ccctgtcttc acatcccttct tccactttta   10140
tttgctttcc ccatggaccc atactcaggg ttttgggagg atggcagcgg agtatggtgg   10200
aggagagcga ttatttaaag tagaaaccca aagcttttat tatagtaaac ttggaaaata   10260
caagagaaaa attcacccct agaaaattat tgtaaacatc tagtttgttt ccctctgcat   10320
atttttaaaaa ctgattgcc gcattttacc ttgtgttagt gtcttgattt cattgttacg   10380
ccgcctaccc cctccacagt gtacacttgg agtgcgtcct tctgtggtct agttattttc   10440
acttggagga aggaactttc acagaaaatg tgttgtgtca gtcctttcta ctcattaacc   10500
aagaaatcac aatgttgttt tcttttctcaa tgtagagaag tcattcagaa ttcaaaagaa   10560
gttctaagtt tattgcaaga aaaaaaccct gccttcaagc cggttcttgc aattatccag   10620
gtaagccgag aacaaggttc agtcctacta ttttaggatg cctttcaatt tagaaaatga   10680
ttgtatacaa aagagcagct gcattctttg ccaaagagga gagggctcag ttggcaatgc   10740
tgttttcttt ggtctttgc ttctttggg tcacgggtga agtactgccc tgcttgagtg   10800
tgtcttcttt tgtgaatttt cctctctgag gtatgggtag ctttcagagg tctaggaggt   10860
```

```
aagcacttac atgcattgca ttacacagga tatatcgtgg tccatgtgtc ctcacaaatg   10920
cttaccaaat gtgatttgaa ggtgctgggg gaaaaagtgg cactttgttt caatggacac   10980
agatgctaga tgaaacatgg atatttggta atcttttttac tctatctttt aaaacctgcc   11040
ataaacttaa tgggacaaaa gtcattaccc tgtcaaaagg gctttgcatt ccacatactt   11100
cttttggctg caggctctgg ttctgagcca cagttggccc cagttgccat cctgcttggc   11160
acacttgtgt gatggcaggt gctgagaaat aaggaggtga gccaagcctg gaagcaaaca   11220
cagcctgaca gttgggctgc taccgcaggg cttggcatgc ccttagcgta tcaaaatagc   11280
agcctctggt tccaccgtgc tgcgtatttc aggattacag agctgtgctc aagttactta   11340
cattctctgg gatctgtagc cacatcttgt tacaaagaaa gacaagttag aacaatagaa   11400
agaaaattag attagggctc gggcctcctg ggaatctgct tactccctgg ctttccatct   11460
aaaggcaaac catttcaact cctacctttg gtatccccat ttttttggctt cttttttgtga  11520
tggggtcttg ctctgttgcc tgagctggag tgcagtggca tgatcttggc tcaccgtagc   11580
tttgaccttc tgggctcaag tgatcctccc acctcagcct cctgagtagc taggactgca   11640
ggcatgcacc atcacgccgg gctaatgttt gtattttttg tagagatggg gtttcaccat   11700
gttgcccagg ctggtctcga actcctgggc tcaagcaatc caccgcctca gccttctgca   11760
gtgctgggat tacaggcatg agccactgtg cccagtcggt gtcctcattt ttagagagga   11820
aagctggcta ggttactatg tcttctaata ggagggatat tattttcctt aaaaaagtga   11880
cataatttga aggcctgagg aattactctg ttaaatactg gccccaagtc ccttttttata  11940
agcagcaaga ttgttttttct gcaccttcca tattatcttt gtaattagat catctgtaat   12000
cacaaaattc atctctggat tatcttttgt gccttttcaa gctattttta tgttgttatg   12060
ttgtttttac cttcctaagg caggtgacga caacttgatg caggaaatca accagaattt   12120
ggctgaggag gtgaggactg ctgcttttaa aaaattcact ataacttttta acaatacatt   12180
ctcttatagt gacgaataac cttgtgttcc tttttcaggc tggtctgaac atcactcaca   12240
tttgcctccc tccagatagc agtgaagccg aggtaataat ggcagagctc taaactcttg   12300
cttcttcttt cctcttgaga cttaataggc ccattggcgt ctcttagtgg tggctgggac   12360
agatctaaga tttgcttgtg actgaatgtt agagggaaga cttcacttct tttctctagg   12420
gtaaatgctt catgatatcc ttgtttcttg tcatttgtat gtttctactg aagacttgag   12480
ttgcgacttg ttgagttcgg ttgtgtttct tcagctgcgg tggcagcgtc atctagtgga   12540
aattgtcagg ccgaggcgag gaaactggac cttggaccac agatccctgt gccagggccc   12600
ggcccttctg tggttagctt ttcttcctac tggcttcatg tgacagaaaa cctcaaataa   12660
tggaatctta ataatgtac aagtttattt ctctctctct ctcttttttt ttttgagatg    12720
gaattttact tttgttgccc aggctggagt gcaatggtgc catctcggct cactgcaacc   12780
tccgcctccc aggttcaagc aattctcctg cctcagcctc ctgagtagct gagattacag   12840
gtgcgtgcca ccacgcctgg ctaattttttg tatctttagt agagatgggg tttcaccatt   12900
ttggccaggc tggtcttgaa ctcctgacct caagtgatcc accctccttg gcctcccaaa   12960
gtgctgggat tacaagtgtg agctactgtg cccggcctag aagtgtattt tctgggaca    13020
tgaataaagt ttggaagtag gcagtccctg gttggtgata tcaccaagtc gcaggagctc   13080
aggctcctgt ccctctgctc tgccgccttt gtggtttggt taacaagcac tttgttctga   13140
ttgatcagtg aggcccagca ggtctgctag tcatttgtga gacaaagaat gggaatttgt   13200
agagtttgta tctggccttg tgctatgtaa acaaggggggc attggtgagt cttatttgag  13260
```

```
tcctatggag aagagcagtt ctttgcagta cacagaggct gcagggattt gttaaccttc    13320
cctcttttcc aggatcacag ggctcaggta aagttcgttg tcaccaagaa gaaaaaggaa    13380
ggacaaagac aggcccctgc tgtctttaaa gacatttcct gaaagtcaca gttctacatc    13440
catcccgttg tcccctactt agttgcctgg ccaactgcaa aggaggctgg gaagtgtagt    13500
ttttatacca ggaagcctta gatcatttat tagcaagcta aaaaccaaga gtttattact    13560
aagaagagaa aggaaactat atactgggcg ataagtgttt gccacacttg ccattgtagc    13620
gtggtacaaa tatgaagtgt taaatatgta acaaatacct atgataccag cagtgacagc    13680
atgcaaagga agttgttgtt catttgcacg atacccactg tctgcagcag aatttgcttt    13740 tcttttctttt tttttgagat ggagtctcgc tctgtcaggc tggagtgcgg tggtgcaatc    13800
ttggctcact gcaacctcta cctcccgggt tcaagtcatt ctcctgcctc agcctcccaa    13860
gtagctggga ttacaggcgc ccgccaccat gcctggctaa ttttttgtgt ttttagtaga    13920
gacagggttt catcatgttg accaggctgg tcttgaactc ctgacctcag gtgatggcct    13980
gcctctgcct cccaaagtgc taggattaca ggtgtgagcc actgcgccca gctggaattt    14040
gcttttcttt aggttgtttt gccactggtg tttttttttt tttttttttt tctgagacgg    14100
agtctcactc tgtcacccag gctagagtcc aatggcgcaa tctcctctca ctgcaacttc    14160
cacctcccat gttcaagtga ttctccctgc tcagcctccc aagtaactgg gtttacaggc    14220
acccgccatt atgcccagct aattttttgca tttttgtaga gacggggttt caccatgtta    14280
gccaggccgt tctcgaactc ctgacctcag gtgatctgcc ctccctggcc tcccaaagcg    14340
ctgggattac aggtatgagc cacctcacct ggccttgaca ctggtattaa tagcccttga    14400
ttttcgtcgt tgttgtttat aattgacaca taataattgt gcatgtgtgt ggggtacagt    14460
gtggtgtttc ggtacttgca tatgttgtgt aatgatcaaa tcaggttagt tacattcatc    14520
acctagaacg tttatcattt ctttgtggtg atagctttca agatcttttc tagctgtctg    14580
gaaatataca atacattgtc attagcttta gtcactctac tatgtaagag aacactggaa    14640
tttattcctc ctatctaagt gtaactttat acctactgat ggaccaacct ctccccattt    14700
cccctccccc atccctctcc agcctctggt aaccaccatt ctattctcta tttctatgag    14760 atcagcttc ctagattgca catgtaagtg acatccatg atatttgcct ttctgcacct     14820
ggcttatttc acttcatgtt atgtcctcca ggttcatcca tgttgccaca aatgacagga    14880
tttcattcct ttttatggtt gaatgatact ccattgtgta tacacaccac actttctttta   14940 tcctccatta atgggcattt ggattggttc catctcttgg ctactgtgaa tagtgctgta    15000
acaaacatgg gaatgcagac ggcttctcag catagcggtt tcagttccca tgcgtatata    15060
cctagtggtg ggaatggctg ggtcatatgg tagttgtttt tttaattttg tgagaaatct    15120
tcatactgtt ttctctaatg gctatattaa tctgcattcc caccaacagt gtacaagagc    15180 tccccttttcc acatatcctc gccagcattt gttattgtca tttttgataa tagccattct    15240
agcttgatat ctcattgtgg ttttgatttg catttccctg ataattaatg atgttgagtg    15300
ttttgtcata tacctgcagg ccatttgtat gtcctttggg agatgtctgt tcacgtcttt    15360
tgcacatttt ttatttgaat tatttgtttt tttgttatta agttatttga gttccttata    15420
tattctggat gttaacccct tgtcggacgc atactttgca aatatttttct cccattctgt    15480 aggttgtctc tgcttgttg attgtttgct ttgctatgaa gaatgttttt agtttgatat     15540
aatcccactg atgtattttt gctttcgttg cctattttgt tgaggtccta tccaaaaaaa    15600
```

```
ccttgtccag accaatgtca tgaagcattt ccctgtgtt ttcttctagt agttttatgg    15660
tttgagacct tatatttaag tctttaattc cttttgagtt gatttttata gaagtgagcg    15720
atgagggcct actttcattc ttctgcatgt ggatatccag ttttcccagt gctatttatt    15780
gaagaggctc tctttccaca atgtgtgttc ttagtacctt tgccttgact tatttttga    15840 caaggaatca tttattccgt attttttcttt gggaaaattc tcatagagtg aatttgtatg    15900
gtgttatatt gaaaagagt aggtacctta atttattagt taagatttgt gttggcattt    15960
gttgcttcta ccaaatgctt ggtacaggtg gcaatagttt cctcgcttca ttctggtctc    16020
tgcttggaca tcgtggcctc tgaccaccct ccacccatca tcactctgtt agccttttac    16080
cccactgaac cttatttttt ctgcatgtca tttattctttt ccagtgattt tattattatt    16140
attatttgga agggaggaac ttccctcctc cactagagta taagatccac gaggacagtt    16200
ttgtttatag ctgtatttcc tttacttaga actgatacag agtaagtgct caaaccattt    16260
gttgaatgaa tgaaagaatg ccaaatgaat gaaacaaagc tttctttctg attttgtacc    16320
tcaaatggtt tccctgcca ctgcacaggt agtgattttt gctaggcaat gaaacaaaaa    16380
tggtaaacca acccttcccc agagcctctg agtgagatct atatgcaaag ataagtatct    16440
tctcacttgt gagcaaatat ttttgttaag tgagatgaat caggatctta tctcctggca    16500
taaaatagac agagaggaca aagcattgct tatttagaga cacacccaga catttattag    16560
cttcccaaaa tgtagcttgg tcttttcct aaatagtgaa ttattttagt gtttcccata    16620
aaaggagctg tgcatgctaa gaattttct agcataagcc tttggaaagg cttcttgtgt    16680
gtcattgagg tccagataac ccgagggcct ctgtgactgc ttggacgtca tgattagtga    16740
gctgtgttga acacattgtg tttgaaacgc acaggcttag ctgggccaga ttggaatgct    16800
tcagattcat gcttcctgtc cttcctgaaa actggcagtg tgtttggctt aaagtatgct    16860
tgttgacaga gaagtgtcct ttgtctatct aaaccttaat agctgttgag ctttggtttt    16920
gttctgtttt gtctttttct ggcacagagt agagccatag aaaggcagag aagtcactaa    16980
aaaattcagc caagccttt aattttttt ttgagccttg tacacatgat gaaaagaaaa    17040
aaataggctt tttattatgc tttacaccaa gtttccaaca aggagcaaaa caacaacaaa    17100
ctataacaga tgcattttca tgaatccact ttttatataa agcttccttt gttgggtctc    17160
attttcacaa aactaatttt tattttgttt tttgttttc tctttagatt atagatgaaa    17220
tcttaaagat caatgaagat accagagtac atggccttgc ccttcagatc tctgagaact    17280
tgtttagcaa caaagtcctc aatgccttga accagaaaa agatgtggat gggtaagaaa    17340
ataaaatcaa ataatcaacc tttatggcta aatcacttttt tctattgtgc ctgcttttat    17400
ttttctaaat ttcttctatt tatttcaact gtgtcagtaa ttggataaaa aaatcatttt    17460
aaatatttca ggagtctata ggattttttt ttttttgaga tggagtctcg ctctgttgcc    17520
caggctagag tgcagtggcg tgatcttggc tcaccacaac ctccatctcc tgggttcaag    17580
cgattttcct gcctcagcct cctgagtagc tgggattaca ggcatgcgct accatgcctg    17640
gctaattttt gtattttag tagagacggg gttttaccat gttggccagg atggtgtcta    17700
tctcctgacc ttgtgatcca ctcacctcag cctcccaaaa tgttgggatt acaggcgtga    17760
gccaccgtgt ctggccatct gtagccttt aaaattctgc atgcaaaagt tacatatttt    17820
ggaaaataca ttagccctt tatagtgctt caatgccata tgatcttaca ccatcagatt    17880
catttaataa attccggtct gacttataca atctttagcc agctctattc ttctaatagt    17940 ttttccttg gtaattctac cagaccagag aagaaaactt agaaacctga ttccccagca    18000
```

```
gtaccatatt ctgtcttagt cccaggccag ttgagaaaag caaaataaat acttttctta   18060
atgacacaag gttttatttg aaatttggag gggaacatca taactattgg gtgctgtaat   18120
gttggcctgt gattcatgtc atggagtgac ataagcttca tagaacaaag gataccggcc   18180
gtctccagtg ggggataagc atgcttcctg gggattaaaa ccccattttc ctccatggaa   18240
atataggaag tgtttttgtac tgtggccaaa aagaacacaa tgtgttaatg gttataggtt   18300
gtaagcagat ttataaagtt agattccaga tccggtagac cctgcagggg ctggatgggg   18360
aggctaccac cttcctgaga cacccagcaa tcttccattc tagcctttta ttgtgacttg   18420
agtagaccca aacacaggct gaaaaggtgt catgaacacc tccagtcctg gctgggcaca   18480
gtggctcaca cctgtaatcc tagcactttg ggaggccaag gcaggaggat ctcttgatct   18540
caggaggtca agaccagcct ggacaacata gtgagacctc atctctattt ttttttttt    18600 tttttgagac agagtctcac tctgttgccc aggctggagt gcagtgacac gatctcggct   18660
cactgcaagc tctgcctcct gggttcacac cattctcctg cctcagcctc ccgagtagct   18720
gggactacag gtgcccacca ccacacctgg ctaattttg tacttttagt agagacgagg   18780
tttcaccgtg ttagccagga tggtctcgat ctcctgacct cgtgacccgc ctgcctcggc   18840
ctcccaaagt gctgggatta caggagtgag ccaccgcgcc tggccccttg tctctatttt   18900
taagtaaata attaaacatt tttttaaaaa acgacaatct ccagtcctgt cgtagactaa   18960
ctgtaaaagg agaagaagca ctaatccatg agaaaacttt cagaacttga aggtcctagg   19020
gcatagtttc aagtctttca taaaaggagg ggaattcatg ctgaggccca gccaggaaaa   19080
accaaccaaa caaaaacaac agagagtaaa aggagaaatt acgaaaatgg ttctaaatgt   19140
ctccattctg ttactgagat tgacgtgctc agtttaggct agatagctgt ggaatgtttt   19200
gtcctagatt tgaacaggga aaggcacaga acccttcaga agtgtgtggt cactcattt    19260 ttccactgcc ccccaccccg acttctcaag gagataaata tcgaggtcaa gttgaaatca   19320
gacctgtgac ctgtgcctca atcccaggtc ttactgggtc actccagatt tataggattg   19380
gttctgggtt ttgagtggac tgcaggacca tgcttctgtg taactctagg gatgctagtc   19440
cattggggtc cattgaaagg agctccctgg agttgcgaag tgaagccctg tatggcttta   19500
ggctgtgtcc tggtatattg gcagaaccgg aacacccaat gtcagggcca gggtgaagtt   19560
tcctaaggta ctgccttaga atttttctaag acctttattg aatggccttt attgcctgct   19620
ttctctttaa ttcattttt atgggttttt tttttttttt gagatggagt ctcgctctgt    19680
tgcccaggct ggagtgcagt ggcatgatct caactcactg caacctctgc ctcccaggtt   19740
caagcgatcc tcctgcctca gcccctagt agctgggatt acaggcacgt gccatcacgc   19800
ccagctacct tttgtatttt tagtggagtt gaggtttcgc catgttggcc aggctagtct   19860
cgagctcctg acctcatgtg atccaccccgc ctcagcctcc caaaatgctg ggattacagg   19920
cgtgagccac catgcctggt cctctttaat tcattttat gtattctgtc tatcaaacat    19980
tgacttggat gttatttggg gttaatatat gtacattaca cgtgagtgat ttttttggct   20040
gggctttgac ttaacctact tctttatttt ctgattcaga gtaacagaca taaacctggg   20100
gaagctggtg cgaggggatg cccatgaatg ttttgtttca cctgttgcca aagctgtaat   20160
tgaacttctt gaaaaatcag gtaggatgct ccttgagaaa tgccgctgat ttctatttat   20220
tggtatttac attattttta ataaggattt gtttggggaa gaattaaaaa ttttttaaa    20280 ttattattct gatatccttt taggatgttt ctagaagatt ctaattgaac atagaagtga   20340
```

```
tatttcacgt tgactttttt tattttctc atcttttggg agatacagat gaatacctag    20400 aaacttttc tagtaagacc atcttataaa ttaaaagaga aattagtaga gataaacgat    20460
tagccctgtt ttaaacatgc tcaatttctc tcatgaaaca gtcaaaataa ccacagtaaa    20520
atatgcttcc agtttcagct tactaaatct atcaatatgt agccttagat aagacttacg    20580
ttgaagactt aaatgaggcc aggcacagcg gctcatgcct ataatctcag tgctaggcga    20640
ggccaaggcc agaggatcac ttcaggccag gagttcgaga ccagcctggg caaacatact    20700
gagaccttgt ctctacaaaa aaaatttaaa aattagctgg gtatggtggt gtgcacgtgt    20760
agtcccagct atgctggagg ctcaggcggg aagatcgctt gagcccagga gtttgaggtt    20820
acagtgagct gtgattgcac cactgcactc tagcctgggc aatatagcaa gaccctgcct    20880
caaaaaaaaa aaaaaaaaaa aaagagaag aagaagaagc cggtagatgt agtttagggc    20940
acaggagcct aggttgggat ttattggtga gcagcttgct tttcagtagt caggacttaa    21000
tttccattgt tgtccccttg acttggcgtt tttatgtcag tgaaatagaa atgaatattt    21060
tctctttctt cattattaag tttaatgagt aaattactac caagtattta tatatttaag    21120
ggctttctga gaacataaag attcaactaa ttgggccggc acagtagctc acacctgtaa    21180
tcccagcact ttgtggagcc aagatgggag gattgcttga gcccaggagt ttgagaccag    21240
cttggggaac atagggagac tccatctcta ccaaaaaaaa tttttttttt aattagccag    21300
gtgtggtgac ttgtgcctgt agtcccggct acttgggagg ctgaggtagg agaatggctg    21360
gagcctggga ggtcaaggct tcagtgagct gtgatcacac cgcagcattc catcctgggc    21420
aacaagcaag atcctatctg aaaaaaaaaa aaaagaaaaa gaaaaaattc aacgaactaa    21480 atcttttct ctactccagt ttgaatagaa atgaagcaaa tgcccctccc tacccctgaa    21540
catccaacaa tcaagaaaaa atttcaaaaa tatatggcaa agttttatta aaaggttaac    21600
attcaggata tatgctttt ttggacagta atattaagct caaatctatg aaataatcca    21660
tatatacagt gctttttcat tacgtggatt atcaagatga agattctgag ccacttcatt    21720
agaaagtact caaagaaaag agtaaattag gctggtgagt tatagttaca tattgtggaa    21780
agaaattcag caacaggaat tggaaccaaa agggtttgaa tagagaattt ttgttgatta    21840
caacacccca ctcctagttc ctagtcattg taggttggtg ctgagaaagt tcaagttta    21900 aaagggtttt ttgttgttgt tgagacattc ttgctctgtt gcccaggctg gagtgcagtg    21960
gcgtgatctt ggctcactgc aacctctgcc tcccaggttc aagtgatttt cctgcctcag    22020
ccttctaagt agctgggatt ataggcatgt gccatgacgc ctggctaatt ttctatattt    22080
ttagtggagg cggggtttta ccatgttggc caggctgatc ttgaactcgt gacctgaagt    22140
gatccgcctg cctcagcctc ccaaagtgct ggaattatag gcatgagcca ccacacccag    22200
cctaaaaggg tcttttttc ttaagataaa gttcttaaag gaaggatctg aagttttgag    22260
tataatattg aattttcatt tggttagtag gtgtcaacct agatggaaag aagattttgg    22320 tagtggggc ccatgggtct ttggaagctg ctctacaatg cctgttccag agaaagggt    22380 ccatgacaat gagcatccag tggaaaacac gccagcttca aagcaaggta aatttcatgt    22440
tagaaacata catcttgaag gcttctgtta gaacagaaga aagtctagaa atgtataagc    22500
taagtgctta attcaagaaa ttagaggaag aaaattgaat agaccatat ccattaaaga    22560 cattgaatga gtctactcac cagacaaaca aacaagaaaa ggcaacaggt ggtttacaa    22620 atgagctcta tcaaacaaag aacagatcat tctaatacaa tccttttctc cagcaaatgg    22680
aaaaagaagg aacgtggcct aacagacttt atgagtgcca aaaccaaaga agggtaacat    22740
```

```
gctaaaggaa aattaacagg ccagtttcag ctatgaatat aaatgaaata atcgtgagcg   22800
aaatctgaga acaccaaata cagcaggaag tagggtttat tttaggattt ccaggtgatt   22860
gaacatgaga aagtctgtca ctgtaattca ccacattgtg attaaaaact aaattctcac   22920
catagtaagt acagaacagt catttggtaa atctaatatg cattatgacc ttttgaaagt   22980
aattataatt ttgatgaaaa ttattaagaa gacccatata aaagcagagg tatcatcttc   23040
atggagaaga tgcaatatct taaagatact aattgtctgc aaattttgta gaatttgaca   23100
gtctgattct gaaatccaaa tggaagcata aaggacaaag agagtcaaga caattttgtg   23160
gaaaaactag gtgggagaca ttcccagcca cacagtgtga attattatgc acttacagta   23220
attaggataa tatggtagac aaacagacga tcggaacaga agaaagtgga aatttatgca   23280
tatatggaag cttgagagca ggtaccacag atcagtgggg aaaagattaa ctattaaagg   23340
ccgggcgtgg tggctcatgc ctgtaatccc agcactctgg gaggctgagg cgggcaaatc   23400
acttgagctc aggagtttca gaccagcctg gccaatatgg tgaaacaccg tctctactaa   23460
aaatacaaaa aaattagccg ggcgtgtcgg cgcaagcctg taatcccagc tactcgggaa   23520
gctgaggcag gagaatcgct tgaacccggg aggcaggggt tgcagtgagc cgcgatcgtg   23580
ccactgcact ccagcctgcg cgacagagtg agactccgtc tcaaaaaaaa aagctaaaac   23640
attaactatt aaaaatggtg ctgacttaac tagttatgta tatgagtcta gcataggatt   23700
actaacctgc cactacatat aaaaatcact tctatattaa aataacctaaa tgtggaaagc   23760 aaaactgtaa aacttataga aaaaaatata ggcgtatgca tttaagaggt tggcgttgga   23820
aggatagctt aagagacccc aaaagcacag attgctaaag aaaaggtata taaatctgac   23880
tgcatccaaa ttttaaaaa ccccaaagtt tttctttctg aaaagaagtt cttaaaaaag   23940 tgaaagaca gctatagtgt agaagatatt tacaacaaac atttagccaa taattagtgt   24000
cttataaaag attcctacaa atcagtgaga caaagacaat ctgttagaaa aatggacaca   24060
tgacagacca ctaacaggtg aggaacccga ggtttaaaag acacgtgaaa agctgtctgg   24120
tttcctgctg tttttgctca ccagtcatat tggcagtagg taaaaagtgc cagttagcca   24180
tattgacaaa tgtctggagc tatgggaatt catatattgc tggcgggagt ttaaatttga   24240
aataggcatt tcgaaaagca gtttaatgga gtttgagcta ctctttgacc caggaatttc   24300
actctaaata tatatgatat ggccaggcat gatagctcac ccctgtaatt ccagcacttt   24360
gggaggctga ggcaggcaga ccacctgagg ttggggtttc aagaccagcc cgaccaacat   24420
ggagaaaccc catctctact aaaaatataa aattagctgg atgtggtggc acatgcctgt   24480
aatcccagct attcaggagg ctgaggcagg agaattgctt gaacccggga ggcagaggtt   24540
gcggtgagcc gagatcacac cattgtactc cagcctgggc aacaagaacg aaactccgtc   24600
tcaaaaaaat aataataaaa agtgtatata tatgtgtgtg tgtatatata tataaatag   24660 acaaaacttg cccatatata tacaaaggtg tgtttacaaa tggtcagagc agcatgttta   24720
tagtgcaaaa agttttgttt gtttgtttaa gacagagggg cagtggtggt tctgtgggtc   24780 ttggccccctt tctgctgtca gggctgagtt ggctccatga gttggtgaaa gcggtatcta   24840
gccaggttca agggagacag gggcaggatt tcgccttcac tgatgggcag gccagcggtc   24900
ccctgtggaa cggtgactat tgaatattga gaggacagta tccctccctg agcatcttct   24960
ggagcttgat gaccactagg gaatgtatct gagtcacgcg caccaaatgt gttaccggtg   25020
gcagctattc gagttatccc gagttcgtgc tggtgtatcc gtacagttct gcagcaactt   25080
```

```
cagctcttgc ctcctcggaa gaaagaattg gactgagggc cataaggcag aaggagagac    25140
tgaggcaagt ttcagagcag gacggaaagt ctagcaaaaa gctctagaac agtaaggaaa    25200
ggaaagaagg aaagtataac ttggaagaga gccaagcagg cgacttgaaa aaccaagtgc    25260
actgcaacaa gtatttaaac agtgatctaa atgcccatca gggtgaaagg ataaatcagt    25320
atagttgcat gtagagtatg catagtcata gttcataaaa caatgatata caagcagtga    25380
aaattaataa actagagctg tagatagcaa catgttttct tgttttgttt tttgtttgtt    25440 tgttttttg agacgaagtc tccctctatc ccccaggctg cagtgcagtg gcgcgaactc    25500
ggctcactgc aacctctgtc tcctgggttc aagtgattct tctgcctcag cctcctgagt    25560
agctgggact acaggtgtgc gccaccatgc ccagctaatt tttgtatttt tagtagagac    25620
agggtttcac catgttggcc aggctggtct ggaactcctg acctcaggtg atccgcccac    25680
ctcgacctcc caaaatgctg agattacagg catgagctac cgcgcccggg ctggaagaat    25740
tttttaaaac actgttcagt gaacaaaaac ccaagttgca gaaggatgta tttcatacaa    25800
caccatttat atgtgtctga aagcaacaca acatatatat atatatgtaa tctaatacat    25860
acatacatat aatatgtatt acatataatc cttatatata tatagaatct taatatatat    25920
atttaggtca ggacatttag atcactgttt aatatatata ttaggattat atataatata    25980
tattatatta ttatgtatta attatataat ccttatatat atattaggat tccatgcaaa    26040
tgaagtaaaa atataaagaa ataatgcaaa ctacgaacca aatccgaaaa gcatttattg    26100
aggcaaggat gtggatatag atggaaagga aacctagaca ccttcatgcc ttttttctta    26160
aactgggcaa taggtgttgt ctaggtatgt taggttattg ttttccattt ctatgtctga    26220
aatgattgtt tttcatttta aaaaatgatg gtacagctca cagatctaaa gcaaagtgaa    26280
gttttaaatg aatgcattaa gtacaatcag taactacaga atgtgatcta aaaatacatg    26340
ttcctcatgt tgcagggtga gaatggaaat gaggagtaaa ttgtaatcgt gccagggaag    26400
ccaggtgtct cagcagattt ggaatctttg catggcaggt ggatccaatt tatgtaatgc    26460
ttgggttaag acagctcagg aaggcagcct tgcaatgaaa cgtgaacctg tgtgcgtttt    26520
tagcagtcac cacatggtgg cagcctatcc aagaaaattc aagggcaata gtttgcactt    26580
gagagcccag aaattttgat ttggaagctc agtggaagag gaaataaaac cgtgccctgc    26640
actgaacagc tgtggtgaag agagaaaata ccttccttgg caattgaatg ttttcgcagc    26700
tgtcacagat acttttgcta gttgtatcta tattttgaa aaacaaagac atttttcaaa    26760 gtacttttt attacgggaa taaatcacct tgtctctgta ctttgggatg aatctcatct    26820
gaactttgag aacgattaag tggcttcact ttctggagaa tctggtcatt gggtaacatt    26880
cttgttttca tatggaccag aaggttctct ttcatagttg atgttgcaca cacgtttttt    26940
tccctaagtc cttggtattt atagtggcac cattgcgaat gttagaggct atcaactttc    27000
attcttatta ttgcttcatc tttgtagcca aaaatatggg aagaaatgtt catagccccg    27060
ccccatactt gtccccctct acctggccta cctacctacg tcaggctcct gtcccaccac    27120
aaatgacagc ctgtgtcttt catgttagca gctagtcttt cactagccac atacttcccc    27180
gtaacccata tgcctccctg tgtctgcctg acgtttgaat tgtcactatt ctgttgttgt    27240 attttttacaa gaagaatgta tgggggcagaa aaccccttgcc attcatttcc tgagtaggaa    27300
ttctagcctt ccttggagtc gtggtaatat ggagacatgg taatatgtgg attgtaccac    27360
tcaatggctg tctggaggcc acagtggtgc aaaaagccac ctaggcatgg gttagtgtcc    27420
tggggcaccc aatcaggaca ggacacctgg cacacccttg gaaaagcttc actgtgaaaa    27480
```

```
acactggaag taaaaatttt aacaacagat agggattttt ttccccttga gacagaggct   27540
cactctgtta cccaggctgg agtgcagtgg cgcgatctcg gctcactaaa gcctctgcct   27600
catgggttca agagattctc atgcctcagc cacctgagta gctgggatta caggcgagca   27660
ccaccatgcc tggctaattt ttatatttt agtagagatg gagtttcgcc atgttggcca   27720
ggctggtctc gaactcctga cctcaagtga tccacccaca tggccctctc aaagtgctgg   27780
aattagaggc ctgagtcact gtgcctggcc cacatgggga tttttgttgc ccagcttaat   27840
caaccaagaa taaagtgca ttttaagatt ataatctatt taacttctcc ttattggcaa   27900
tggtaaaaga gttaaggaaa aagagaata agcttaggat tatggctact aagtagaagg   27960
acgttatctt tgacgggcat ttctgttgtg cttatttgta cctgacatgg aacaagaccc   28020
ccccatcccc tcaacacata cctgctgtgg gacatctggc tagagatttc caaagctgag   28080
ggtgaaaggt ttgggcatcg gtgtgactgt gtaacactag agttctatct accatctctt   28140
aaactacagg tagtcttacc ggtgtgggct gaccttccgg ttatcaggca gcctgctgca   28200
accactagaa actgcctttg aaggtttcca gtccggcaca acatttgtgt tctcattaaa   28260
cagtagagca taggctttgg ggacacacag ctctgggctc aagccttagc tgttgctgct   28320
ctgagcctgt tccctcgcgt agaaaggcaa tcataatact ccctacttta tggggcagtt   28380
gtgggaatgg aattaaatgc taatgtgggc cgggtgcagt ggttcacgcc tgtaatccca   28440
gcactttggg aggctgagga gggcagattg cttgagccca ggagtttgag accagcctgg   28500
caacatggcg aaactccatc tctaaaaaag tacaaaaatt agccaggcgt ggtggctgta   28560
gtcccaggta cttggaggc tgaggtggga tgatcacctg aatctgggga ggtcgaggtt   28620
gcagtgagct gagattgcac caccgcactg caacctggag tgcaggctgg aggaagagaa   28680
atatatgggt caattaggca aatcactcag atcgtaagta gatatactag taaaatagcg   28740
tgacttaggg tccttcactg gaagcctggt attaatgctt ccattgtgtg ggtggggaa   28800 ggagagagtg tctccagctc tctgtctgtg aggtctccca gccgaatatt ggccaaggga   28860
gtgaaaccag aagcaagact accatgagac aacgttccag agaaggagg gactaaccag   28920 agcaggtgcc cagctttggc cagtcaggct catcttccag tcctcagtag attattatca   28980
actttaagtg atgtcacaga ctcccttcct ccaaagctgt ggacctcttc cttcccatgc   29040
ctcttgttac ttggaagtca ctctacttcc aaacatgtcg gctggagatc cctgatgggc   29100
cagttactac tttcaggctc tgtaggttta agaatggtt atatccagtt agttacaaat   29160
agaaatcgat cctttctctg tccgtctgtc taaacggaag gatattctgt ggacgctgat   29220
taggtataaa atctccacgg agcctgagca tgaagaattg accttcttag ggttccacag   29280
aaaccagaat agacttctgt gtttggtagc tttgtaactt acgcccgttg aggtgtacgg   29340
ttgaaaattg agaataaatt tcctgttctg tttctgagca tcttttccag gcttggagat   29400
gcgttgagca tttccacgga gaccctagag gtggggaggg gaagaacgcc tgggcatttg   29460
tccaaattag ccatatgctg tggagtgtca catgtcagga agccaaggca ctggagctag   29520 tgttttttggg cagggctagg gaacccccg cctttcctcc acccaaacgc aggcccccac   29580
acccagcgtc ctgggccctg cagggggaatg acactgttgg tttcactctc aggaatgagc   29640
ctagatttgg aggtaacctc ttcctgaccc cgatgatttc actctgatgc caaaaccagt   29700
ctgaagtggg tgtggttttg catttggtgt ttacaaggtg gagtggtgcc ctctgcacgg   29760
aagggagagg tgggcaggta cggcagggcc ctgctccctc gggagtctcc tctgaacctg   29820
```

```
tggttagggc acagctggac aatgctgaaa tggtctccag ctgggagatg aggtaaacct   29880
cagctgcatg ccgaagaaat aacctagaaa tcagagaacc gttttatttt gtttttctca   29940
gaggatctca tttctccctc tcctcctgag cacagagacc ctcaaaactg gtattcacag   30000
aaggaaaaaa tataggtctt tcacctttga aggatcaaag tgtctagggt tttttgtggt   30060
tttttttttt tttttttgaa caaagctgaa ctattacaaa gtccttttca gtttaaattt   30120
agtgcatggc atggctcatg aaagactttt aaaagtgaat tggaaaattc taaatgtact   30180
tgtattatac atgtgaaagg atgacttctt aaaaaagaa taatgtctgt cccaaacggg   30240
agaaggaagg aactctagct tttaaactgc actacattag tgagttacat gacaattctc   30300
cttttaacag gatggaatgc acttaaagca gtaatgtgct atggtgacag taatgacaga   30360
caatgttaat tgacagaatg gctactctga accaggcact gtcttgtact cctgttatct   30420
cagtggtctt cacacttatt ctgttaggca ggactgtcat cctccccaca ttacagatga   30480
ggaaactgac tgaggcttag agaggagact ttgcaaagat catgtgatta aaaaatggta   30540
gaggtggcaa aacagcctgt gtttttaaca ctgtcccatg tcagctctta ttccagatca   30600
tcacataaag tctaatctct aatcttgaaa accgaaaagc acctgccacc tcagataaga   30660
gagaccaaga ccctagacat tcgacttgtg ttgaattcac tcttattttg ttttgatgtt   30720
tgtaatccca gagccatact tgttaatgag ctgaagtaga gtgaatgctg tccctccct   30780 gaggcctggg gctcatcatc agctctccag gctccccttt cagaggggat ggtgagcacc   30840
ttcggagagg gcagggatgg acacacaaga cagcctcagt tatgtgagtt catcccctcc   30900
cctgcctgct gtgggtgaga tggagaaaaa agcactggac cctcctgggc atcacagcct   30960
tgtacttagc gagtggctga ggtcatcagt agcccaggtc atcagtagtg tggaattaag   31020
tgcactgaat agtgttggcc cctgagcttt gtttgacaga tttaggggt cagctcacca   31080 ctttccctc ttgcttctgt ctgatcattg ctctgttgt taataccaag gaagaaagtg   31140
aatagaactt tttagagagc caaaaaaact ttattagact ttatgccatt cattatactt   31200
agcagtgttg agggaaggat ttgtgagacg atatattcaa actaatgggc atgagaccaa   31260 gaagggggctg tgtggcgggc gcggtggctc acacctgtaa ccccagcact tgggaggcc   31320 gaggcaggtg gatcatgagg tcaggaatcg agaccatcct ggctaacacg gtgaaaccct   31380
gtctctacta aaaaaaaaa tacaaaaaca aaattagcag ggtgtggtgg caggcacctg   31440
aagtctctgc tactcgggag gctgaggcag aagaatagca tgaacccggg aggtggagct   31500
tgcagtgagc cgagatcgcg ccactgcact ccagcctggg caatagagtg agactccatc   31560
taaaaaaaag ccggttgggg tggggcatg taattaacag actgattggt cttaggtggc   31620
tcagaattta agctgagaaa ttaagattga gaagaaatga tgtattgtcg ttatatcaaa   31680
tatgtgagta aaaacataat taaaacacca tctatctcca gttttcccaa cattacctcc   31740
cttttatgat gcccttcctg taccttatta ggcaaaatat tctaatttca gtctcattgg   31800
attatgttct aaatgtttga aggttggtct gaacatggaa tgtattttct catagatata   31860
atagtataaa tggtgttagg gtcatgggat tgcgaagcca gttccactgc agtagaatca   31920
tattgacttg ctttccgatt tttctgtggg aaacttcatc tggagcttta atgcacttct   31980
tagctgtggg gtaagtttca gcctccatga cgcttgtgtt actttgtagt cacctgtggc   32040
caaccacaaa taaatctttg tggtcatcag gggccagtga agtgtatact gcacaaaaga   32100
gagcctaccc caattctgga agaagggctg caggcctgtg tccacacaaag aacaggcagg   32160 aagcatcacc ttcagcccac tggcagcagg tcatctccca tttgcttttc tgcactatca   32220
```

```
gcagagtctg gcttcctttt ccaccccctc tccaatgtga atgcttttta aggtcgtgga    32280
attagaattt aaaaaaaaaa ttttttttgag acagagtttt gctcttctcg cccaggctgg    32340
agtgcaatgg tgcaatctca gctcaccgca gtctccgcct cccaggttca aatgattctc    32400
ctgcctcagc ctcctgagta gctgggatta caagcatgcg ccaccacgcc cagctaattt    32460 tgtatttttta gtagggacag agtttctcca tgttggtcag gctggtctcg aactcctgac    32520
ctcaggtgat ccacccacct cggcctccca aagtgcaggg attacaggca tgagccaccg    32580
cgcctggcca gtattagaat cttttaatgg aacgtctta aacataacct ataacaatga    32640
agcaccttat aagtgtgtgg agatttcctt ttcatggctt ttcatatatg cctcgcactc    32700
acccagcaac cctgcaaact ggatgttata ctcaccagag agccttgacc ctgattgtca    32760
ctggcaagga gcagtgtctg gacttgaacg caggtcgcag gactccactc atggtgctct    32820
ccccactgca cctcaattcc tcacttttca aaggaggcag cggaagcctg gagagtttct    32880
caaaggaaac ggaatgcaga aatctgtctg tgtgcaatgt gaggctcaga actgaaaacc    32940
ataaatgtca ggaaatgcaa agcagaattt tcccctgcaa cggcagtttg catgaatatg    33000
aagacgctgt atggatgaaa gtttgtggct gcagcatgag cataaatcct cggggctgct    33060
gttcgtctag gagcctgact tgcctggtgt tgccctgaga actgcaactt gagcatttcc    33120
ttaattttgt actaaaggaa ccaaaatgag gtattttggt tctaagtctt tgtcatgtga    33180
aggaagcttc ctgttaccac cccccatcta catacacatt ctctttctta gcccacgtt    33240 tgaattttat gttttttccta aagtataggg aagattatta ttattattat tattttcttt    33300
ttcagacgga gtctcgttct gtcaccaggc tggagtgcag gcgcgtgatc taggctcact    33360
gcaagctctg cctcccaggt tgaagtgatt ctcctgtgaa agggaattat ttttgatgag    33420
tcattaaagt atatccattc ccagaatggt gctgcatttt cctttttatc atctgtcatg    33480 actttttaa gtgtgaagct tacttccaga ggaattgtct tttctagcat tttgacaca    33540 actaaatatc tttgatattt tcttctcata tgttgagcag taaattaagt tgaatggtga    33600
agtcagaggt gaacttagga acatttagaa aaaggaaggt catttattat ttttcagggg    33660
aaaagtttgg tagaaaaatg ctgtaatcct aattcccaga tgtccatttg gcttgtagtc    33720 atttgattt atgaaataat cataagaaat gtcttcaaat tttaaaagcc aataatttgt    33780
tctactaatc acagatgaga gtagaaataa aagaaacaca cccaattcct gaaaggaaaa    33840
aaattctccc aggatgagat cactgggtgg acgtgaagtg ggtaaaatac cttttgctgc    33900
aattgtcatc cccttatctt gccaaagtac gacaacatct gaatgaagat ggtttgatgt    33960 tcttagtttta gagtagttat actattattt taacattcct atttaatgat atgttttaat    34020
actgcagggg aaaggtagat acagattcat agctacaaag caatactctt atgatcaatg    34080
ttcatttaat ttcaaataca aagttagaca ttcagagtta aaaaaaatta atgcataggc    34140
tgggtgcagt ggctcacgcc tgtaatccca gcactttggg aggccgaggc aggcggatca    34200
tgaggtcagg agtgtgagac cagcctgacc aacatgggga aactccatct ctactaaaaa    34260
tacaaaaatt agctgggtgt ggtggcatgc gcctgtaatc ctagctactc aggaggctga    34320
gacaggagaa tcgttgaacc caggaggcag aggttgcagc gagctgagat tgcaccactg    34380
cactccagcc tgggccacag agtgagattc catctcaaaa aaaatagat atatatat    34440 tttttatatt atattatata ttatatattt atatttttat atatataaat gaataaacaa    34500
ggcatctgct tatgaaacag tctgcctgaa tgaaatctcc atttgcaggc aacacagtct    34560
```

```
acagtaatgg caggactgta ttaggcatgg ttcctaatgc ccatttctgt agcaaagtca   34620
ccagtagttc ctaattgcca aaagtgagtc accggtagtt cctaattgcc aaaagtgtat   34680
tttttgcttt tatcttgctt gaccacagct gtcatataaa cctgttggcc acacccttt    34740
cccttagcct gaatgaaaat gccccttcct gcccttcgta gctcctgagc caccaggaca   34800
tggtggtctc catcatctgt tcgttatctc taaccattta agattagtgc tccccaagga   34860
tgtctgttaa cctgctttcc ttcccattct gccagtttcc cctggggaat ccacacttct   34920
ggttttaacc atcacctaaa tgctgtgtgt cccgacccgc atccgcatgc tcccaggcca   34980
ttctcagttc cagacccggg cccccagctt cctgcagacg cctcctccag agatctcag   35040
tatcttgctt ttcctcctac cccttctaag gcattctcaa tccagcttcc agaggaatct   35100
tcctaaaaca catctgactg tgtgagccac atactgtagc caacctgac  agcttctttt   35160
ctatattaag aaaaagtgcg gccgggcgcg gtggctcacg cctgtaatcc cagctctttg   35220
ggaggctgag gcgggcagat cacgaggtca ggagatcgag accatcctgg ataacatggt   35280
gaaaccctgt ctctactgaa aatacaaaaa attagccggg catggtggca ggtgcctgta   35340
gtcccagcta ctcgggaggc tgaggcagga gaatggcatg aacccaggag gcggagcttg   35400
cagtgagccg ggatcgcgcc actgcactcc agcctggacg acagagtgag actcgtctca   35460
aaaaaaaaa  agaaaagaaa agaaaaagtg cacacatttt gacatctgag aaaagtgatg   35520
ttttttcttag aaaagtgaca tctaactctt tatagaaact ttgccacaag gtagtctagg   35580
agtcccctta ctacctaaga ttttcatgga catgccctgt ctgatcataa agcatgtggc   35640
acagtggctc acgcctgtaa tcccaacact ttggaaggcc caggcgggca gatcacttga   35700
gcccaggaat tcaagaccag cctgggcaac atggtgaaac cctgtctcta caaaaaatat   35760
ttaaaaaaca aaatgaactg agcatggtga agcacatcta tagtcccagc tacttagagg   35820
ctgaggtagg aggatcgctt aagcccagaa gtcagggctg cagtgagctg agactgcagt   35880
gccactgcat tccagcctag aggacagagt gagaccccgt ctccaaaaat aaataaatta   35940
attaaataaa gccttgtgaa gaatctgccg tgggagcataa tgtaacccat aaagccactt   36000
aactgggcgc acataaacta cataaactac agtgtgtccc agttcattga gagtgaaaat   36060
caagcaaggg accacctcag tgtggtagag ccccctccct gccctccaga ccctgctctg   36120
ttctctgtgt ctgaccattg actggccatc actcaggcac tagttgagaa tgccaatgtc   36180
tttagttatt gtaatttcag aagcacatcc ttgctggaca aagaacctac ctgttaattt   36240
tttaaagtaa tgttcatcat tttgaacatt gtttttcttc ttttttatt  agctgaccct   36300
catgaggaat ttaacttggt tttctgaact gtgttggtaa catttgaagg acatagaaac   36360
agttttcata ggtctcaagt gatataaacc acaattcttt agaaaatatc ttttttttt    36420
tacccattct ggattttgaa atatatacag atctcatacc tcagattctc atatgatatg   36480
aactgtttca aaacacattg atagcagaag atacatactg tcttctagtc aagagggtag   36540
cgctgtattt agtttaaaac atttaatgc attttatttg ctaaatacaa aattataata   36600
ttctgtataa ctttccaaat ctcatctgtc ctcccttcc cccatctctt tatattcaga   36660
tgcttgtccc tccagcttaa aaattcatga ctttgagaaa attcgtcttc atgttatcta   36720
aactactgca ccccccacacg ctccctgtta agtgtctgca tatctgtgtc ttactgttgt   36780
ttaaaattca cttgtctgcc tggggagtgg ggtggtttgc tttaagctgc tccactcaag   36840
tctcagcaga gaaagcaata atttgttatg agatagagtt ttaagccaag ctttggccag   36900
ggtctctccc atttgggagg aggaaaatag gaacaagtga gatgataatt ttccttgaat   36960
```

```
tttagctcat taaaatcttc ccttgtcctg ggcaggctat ttactgattt aagcatctag   37020
cacttttcct ttccagaaag aattaacatc tatgatgcaa tcattgctaa gggaggaggt   37080
ttttgtgttt tctctgtgga attagctgtt ctccagttgc agatgagcac agcccacttt   37140
agagttgtgt gtaggtatgg agttgagggg tcggaatgag atttccaaga tttataggta   37200
atgaaaagaa caggttgtat caaagacacc acgtgtagga aactaactgt tcttagggga   37260
cttgtgtgaa cctgtgatcc ttggctttct ccaaaatgaa catttcagcc ttgttcatat   37320
taacctcctt tttacagttg ttttaccgtg ttctggtttt gctgctattc tgcctgaaaa   37380
tctagcaaaa tggcgtttct tatctgcaga actgcgacaa agcttaaaca tttgtatttc   37440
tcttgaggat tactgtggtt gaatttttga cagtactata tataaatgaa gaaataaaat   37500
tttttataca gatgtttaaa atcctctttc cactagaaca tttctttctc cctaaatata   37560
ctattacctg gaactctagc tgttttcag atctgtagag atcataggtg cttaagggga   37620
ctagattgct ggtgatattg gctgcaaaat tttttttttt tttttttttt tttttttttt   37680
tgagacagag tcttgctcca tcgcccaggc tggagtgcag tggtgcaatc ttggcttcac   37740
tgcaacctct gcctcccagg ttcaagtgat tctcatttgg ctgcaaagtt cttagtgagg   37800
tttagtggta ttttggccct gtggcacaga agaatggtta tttagcaaat gtgttttgct   37860
tttgattttg ttttgttttt gagacagggt cttgccctgt tgcccaggct ggagtgaagt   37920
ggctcgatca cagctcactg cagccatgac ctcctgggct caagcgatcc ttccacctca   37980
acctcccaag tagctaggac cacaggcatg cctcaccaca cctggctaat tttattttta   38040
ttttattttt gtagagacag ggccttacta tgttgcccaa gctgttctca aacttttggg   38100
ctcaagcagt cttcccaccc tggcctccca aagtgctggg attacccagc atggcagcat   38160
gagccaacag gtctggcctc ggcaaaggtt ttagtagggc tttctctttt cttttgaaga   38220
tgattaatac agtagattca tacagccaga agctgaaaag cagggaatac tgtttggctt   38280
attaatggat aatcaatcag tgttaataca cttttcccta tttacatggt caaattgatc   38340
aaatatttcc aaggtattag cttttaaaag ttgactttgt cagctctatg aaaagacatg   38400
catttacatt tttatcgtgc tcctcctctg tcaggggact tggatctgtc cttgatcttg   38460
gcttttctgt tcataaacca ggtaggactg tcatgggttt gctcccatta ccatctcttg   38520
tcccaagatt tctaaaaggc atcacctgat gcacccttt gcccaaatag tgttaaaagt   38580
cctcaggctg aggagctgtc ctggttcttc tacaggatct ttaatgatca gcctgtctaa   38640
gctgagaatg gataagggtg tccccaacac gtttatttgg tggtttggtg ggggtagtga   38700 cactgggat gcttttgtgt gttgtaatct gccctctgt ctgtttgacc ccagagactc   38760
tgtggttagt tgcaggacat caaaatacgc aggaaagaca gtggggaag agaccatcag   38820 tcgccctctt gctgcctagg ttcactagaa tctctaagac tgaattcact aggagacaca   38880
ggacataccg tagagctgtt tatgtcttga gagccccagt ttcctagtct gttaaatgag   38940
catagtaaca ccaatctcac tccttggaa tattcaatgg tgtaatactt acaacatcta   39000
gctgacctgt acaattatag ctattctctt ctgcaagtct aatattccta ttcacccctc   39060
cctctgcata gggatccagt ttgaaatcat cagttgctca gtagggcctg gggagctagc   39120
tggtcattct ttggttaaag tcaaagccaa cctctttgcc tacctttttg tcttaatgtc   39180
aacttcctac cagacatgtt cctcccgcac tggatgatca aaatgcaaat aggatggaca   39240
cgatcaatgc attttgttgg agtggttgca ttcttctac tttcttaggg caaaaaatg   39300
```

```
aatggttgga caagagacta accaaggcct caaagaaagt gaaattcttt ctcaagctcc   39360
tgaaagtcct ttcatgggta tagtaacagt tctatagggg tctcattgtg atggtgccat   39420
tatacaggcc agcaagcccc ctgtgtgagc cagacctcat ggccttagcc cttgttttcc   39480 tcttttttt ttttttttt tttgagacag gtctcgctc tgttgttgga gtgcagtggt       39540
gtgatctcgg ctcactgcaa cctctgcctc ctgggttcaa gtgattctcg tgctgtagcc   39600
tcctgagtag ctgagattac aggccccac cagcacgcct ggctaatttt tgtattttta    39660
gtagagacag ggttttacca tgttggccag tctggtctcg aactcctgac ctcgtgatcc   39720
acctgcctca gcctcctaa gtgctgggat acaggtgtg agccactatg cccggctgcc      39780 ccatccttt tcttgatatt atagttagtg gtgaaaacat gtaaatgata atactccatg     39840
cagtatgtat gctgaagtga ctaccctgaa gacatttttt aagtcctatt ttcttttctt   39900
tctaggatat gataatcatt ttctgtttgt attaatacat gcttgaaagg aattagtaaa   39960
gcgattccat ccttgtcagc agcttggaac aaagctgtgg atctgggatt gtgtagaact   40020
catttgacat cagtagttac ttgtgtcttt atgcctcaga tcaagatgtg cgtgttttt    40080 tctttctcct tttagcttca cgaggctgac attgtggtcc taggctcacc taagccagaa   40140
gagattcccc ttacttggat acaaccagga actactgttc tcaactgctc ccatgacttc   40200
ctgtcaggta aatgtcttca cattggtgtt gagccactga ttaggtcaga tagttcaaag   40260
aaatgttaac ctttcctaa gaggttatgt ttctgaaatg ttagcagtcg tcaacattaa    40320
tatatagggt aggaaactta gactgtgggc tacctgatag aaccatgctg ttgagcaaag   40380
agagaccaag atggcggttg aggtgtctgc tcccacagtg aagtgccccc tactggcctc   40440
tagcagtcag gtcagttgtg acctcaagta gatgatttgt atgtgtgtga ggtaaactag   40500
aaatagcggt tttcacagtt tcttaaaaat tagtaaaacc ctttcttcca aagaaatctt   40560
cgtggaatct cactatgtaa aagcagatga gcgccggatt gttgggaggg atgggaatag   40620
gatcagcctg tgtgtctccc tgatttcctc ttgcattgac ccatgaagca catccttgga   40680
gccccagagt catctcagaa cagtatgaaa atcaccacta gatgcagaaa ctgttgtagg   40740
attggtcctg ctatttgatg gcattttgcc aaggtatcca ggaatactca agaccacacc   40800
aggcccactt tggggcagc ccaagcagtg cccgcaacag ggcagccagc agccccgggt    40860
ccagcaggag ccggcccaga gtgggttcct ttttccagtt cgtagaagga ctgaggctaa   40920
gaaagccttg gagcacaccc aggccctcag caagtccctg agtagcacag gtgagccaga   40980
gacgatggca cagggaggca gaggagagcc cctcttcctg attccttctg gctttggcct   41040
ccaaatgttt gtgtggaaga gaggactgtg ctgagctggg ctggaggaca ggggcagctt   41100
ttatccctaa agctgggcag aacatgcacc aaggttggca gcctctgctc tccttctcct   41160
ccaccaggac catacttgag gttgaaatct tgaaaccttg taggcagctc cataaaagca   41220
tgagccctag ccagaggttg ttactgaccc tcctctctag gaaatgtagc tcctgccaga   41280
attgaccgat cagattaaaa accccttggg ggctggagag ggtggaatgg aacagagtcc   41340
aaggaaagag gcattaagag ctgtggccct aatggctctt tttaacaaac agaaagcatg   41400
tactaaataa cattttaaaa atatgtgtaa tttattcata taacttttt tccctgaaa     41460 aaaaaaaaaa acaaagccta acctattaat agtggacagg gcttcctctg ttcagcatcc   41520
cagtcagatt aggaaaatca gttccaacat tgtttcttg taaatgaatg ctgctttgct    41580
gtaatattta cttgctgtgt tttattaaag ttttcatgta ggacagtttt ggcagtcatg   41640
gctggagata ggagtctact ttgatgttct ggaatctctt tgagctctgt ggttatatga   41700
```

```
cagtgacata tattttgtta gtgaaagtgc tttatttta ataaggtttc cttttaggac   41760 ccttatttt gaaaaaaagt attccctgaa atattagata tcaatgtaat gattctctgg   41820
gggaaaaaaa gaccaaggcg ttacagatgt tcctcgactg accatggggt tatgcacaga   41880
taaacccatc agaagttgaa aatatcatta gtaaaaaatg ggcatttgta gccaggatgg   41940
gatgtgaaaa cagaaaacaa cgtccaaaaa tgctggcagc acagtacgct gtagagtatt   42000
ggttgtttgg cctcgtgatt gcatggctga ccggaaacca cgatttgctg tcactgctgc   42060
ccagcgcctc aagacagcct tgttctttgt atagctggcc tgggaaaaga tcaaaattta   42120
aagcacagtt tctactgaat gcatgtccct ttcccaccat cataaagtgg aaaaatagta   42180
agtgaaaagg ttgtaaatca gggatggtct gtgtatttca aaatgattct ataagtagaa   42240
tttatttgaa atttatctgg cccaactgta atagttttct tgttggtttt tgaatgccca   42300
gtgtccagaa tagtacctga cgcttagtaa ccgctctgtg aaattttttt tttttttttg   42360
gagacagagt cttgctctgt caccctggct ttagtgcagt gggtgtgatc ttggctcact   42420
gcaacctcca ccttctgggt tcaggtgatt ctcctacctc agcctcccaa gtagctagga   42480
ttacaggtcc ctgtcaccac gcctggccaa tttttttttt ttttgtatt tttagtagaa   42540 gtgtggatgc accatgtttg ccaggttggt ttcgaactcc tgacctcaag tgatccaccc   42600
acctcggcct cccagagtgc taggattacg ggcatgagcc actgggcctg gctaactctg   42660
tgaatattga gtgtttgaca agttaataag catgaatcaa aattctactc tgcttgtagt   42720
tttaagttag tggcatgttt agaaacattt ccttgaattt gtctcccact taaagatggg   42780
gctgatggcc aggcacagtg gctcacgcct gtaatcctaa cactttggga ggccgaggca   42840
ggtggatcac ctgaggtcgg gagtttgaga cctagcctgg ccaacatggt gaaactcttg   42900
tctctattaa aaatacaaaa aaattagctg ggcttggtgg caggtgcctg taataccagc   42960
tactcgggaa gctgaggcag gagaatggct tgaacccagg aggtggaggt tgcagtgagc   43020
cgagattgca ccattgcact ccagcctgga tgacaagagc tttttttttt ttctcaaaaa   43080
aaaagaaaag aaaaaaaaat gggctcaact aggcagtcat tgagataaag atgaggaatg   43140
ctatgttgat gaaacagatg aacagtttcg gggtggtgct acccataata gcacatttct   43200
aaatagtcta caagttttaa ttttagcaac tttgtttagt atgaaaattt gatctaggaa   43260
taatggagaa aggttttttt tccctcttt ttttcataat cccactactg taaagaaatg   43320
aataaacttt ttgaaatatt aaaaagaaaa gagctcttat ttaaacttaa gatgagaaga   43380
acttttaata aacttgtggc tgggtgaaga cagagtttta taatgaaatt tttattctta   43440
ccttcatggt acagagtccc tcctccttac ccccgtaaaa atagatggga tgttgtgatt   43500
tatgatgagg caattctgta gagacatttt atggaatacg taatcctagg agagattttc   43560
ctgatggcta atatcccaga cacagagctc agaaaacaat tatacccagc tagttggttc   43620
tgttcactct actattgcat gagtccaatg tttagatttt aaaacaagga aatttcaaca   43680
ttctgttttc tagctgtaag agtaactact ttaaaaaaaa aaaaaagac aaccaaaaaa   43740 acctatttct tagaaaaagt cttgctctgt tgcccaggct agagtacagt ggcacgatca   43800
cagcctcaaa ctcctgggct ccagcaatcc tccctcctca gctaattaaa acaatttttt   43860
ttgttgttgt tgaggcaggg ttctcactgt gttgcccagg ctggtcttga actcccggcc   43920
tcaaatagtc ctcccgcctc cacctccaaa agtgctgag attactggtg taaaccacca   43980
tgtctggcct aaaaaaatta tttcaaatga aaaaactacg cactgctctt gtagtgccct   44040
```

```
gcttgctaaa cagcagattt catcataagc aaaatcattt tgtaccctaa atattaggac    44100
ttatttactg atgtaacaaa tgggaccaag gagaagctgg tcttccgtct taggctcaga    44160
aaacagtatc aaaacagcaa ctctgtggct cagagtaatt tatagcatca ttttaagcta    44220
atgtaattct atttagtgtg gaagagggga agagccctgg gatgctgatg tgctgggggt    44280
cccgagggac cttgagactt tctctcgtat ggctctgaag ggagacatta gaacttactg    44340
gaggctgggc gtggtgtggc tcatgcctgt aatcccagca ctttgggagg ccgaggccag    44400
tggatcactt gaagtcagga gttcgagacc agcctgagca acatagtgaa acctcatctc    44460
tattaaaaat acaaaagtta gccgggcatg gtggcaggca cctgtaatcc cagctacttg    44520
ggaggctggg gcaggagaat cgcttgaatc caagaggcag aggttgcagt gagccgagat    44580
cacgccattg cactccagcc tgggcagcaa gagcaaagct ccatctcaaa aaattaaaaa    44640
aaaaatgtag tggaaagaac atggactttg gagtcaggat taacctaact caaggacaag    44700
ggagctgttt ttgtaaaaaa aattcttggc cggatgcggt ggctcacgcc tgtaatccta    44760
gcactttggg aggctgaggc aggcggatca cctgcggtgg ggagttcgag accagcctga    44820
ccaacgtgga gaaaccccat ctctactaaa aatacaaaat tagccgggca tggtggcgca    44880
tgcctgtaat cccagctact caggaggctg aggcaggaga atcgcttgaa cccaggaggt    44940
ggaggttacg gtgagctgag atcgcgctcc agcctgggca ccaagagcga aactccatct    45000
caaaaaaaaa aaaaaagaa attcttaatt gcattgcact tacaggctgt gtgactttga    45060
ggaaataagc tctctgatta attaataaga ttcccaattt ctttgtgggt aaattgggag    45120
caaggctgtt gggaggaatg actgagatga tacctcgggg cagtgcctct ttgatggtag    45180
ctgccaataa atgctggtcc acttcctgca ttcctccctc cacttccttg ttgccatgtc    45240
acctgcacac aaaacagctt tcagactcca tcttggcaca atatacatttt atatttgaaa    45300 aatcaaaccc aagaaaggaa gaagtccaat gaaattctga acatgtaaga aaagtcagct    45360
ttagagaaat tggacatccg tgtaattttc attatgccaa agcaattgat ataaaattag    45420
gatctttgct tgtgactctt gaactttagt aattccaaaa tccattgtac ctatcactgt    45480
tttcttttat ttatttttc ctgtaaattc tggatattct agatctatcc ctgaagtata    45540
ttgccagttt tccatttcaa atttaatta gttctcaata caatgtattt aatattttgc    45600
tttttttaaa aaaagtaaag gttcatgtca tttagaatat gcagcactgt ataaatttcc    45660
ttgttaattt ggtttcagtg gtccaaatta agttattact aatagcttat tagtatcagt    45720
ttactaatat tttaattttt ttaatcatgt cttacattgc attctttaa aaactagtga    45780 tatgctgtca tttgacagta agaattcaaa taatttaaac taggattgca actctcaaga    45840
acactgtcac aaaaattta ccaaatgata tgtattagtc cattctcaca ctgctataaa    45900
gaaatacctg agactggta atttataaag aaaagaagtt taattgtctc acacttccac    45960
ggactgtaca ggtagtatga tgctggcatt tgcttggaag gccttctgga aggcctcagg    46020
aaacttacaa ttatagtaga aggggaaggg gaatcacata tatcttacat ggccagagca    46080
ggagcaagag agagggaggg cgtattagtc cattttcgca ctgctgataa agacatacac    46140
gagacgggga agaaaaagag gtttaattgg acttacagtt ccacatggct ggggaggcct    46200
caaaatcatg gcgggaggtg aaaagcactt cttacatggc agcagcaaga gaaaatcagg    46260
aagatgcaaa agcggaaacc cctgataaaa ccatctgatc tcatgagacg tatttactac    46320
catgagaaga gtatggggaa aaccaccccc atgattcaaa ttatctccca ctgggtccct    46380
cctacaacac gtgggaatta tgggagtaca attcaagatg agatttgggt ggggacacag    46440
```

```
ccaaaccata tcagaggagg aggtgcatac tacatacttt taaaaaccag atctcaggat   46500
aactcactca ctatcatgag aacagcacca atgggatggc gctaagcctt tcatgaaggg   46560 ccaccccat gatcctgtca cctcccacca ggccccaccc caacactgg ggattacaat    46620 tgaacatgag atttggtgga gacacagaac caaaccatat catgatactc attttattta   46680
ttgcatttta ctttatatcc tacaaagtca atatatttaa ctgaaaaact ggctaccagt   46740
gtttttgttt tttttttca agttctacct gtactgattt ctaatttta gccattcctg    46800 attttaaaac ctcgcataca ttttgggat aatttgttct cctagatggc gagaaaatat    46860
ttaagtctgt gggcttggag aatgctttt tgataagaag gatgcccttg ccagactgc    46920 atagaagctg agatgtttcc gcagagccga gatggcatga aggctgaaga attttcctgc   46980
atccctccca ctgcagtgat tgttctggca agttcccag ggtggtctct gcactgctca    47040
tattagtgaa agggtggttc tgatttctga ggaaggcatg ataacacttt ggccttaaat   47100 tttcttttg cagaaagttt gattatcatt agaagaatgg ccatctttta aagtgattca   47160
ttgacttgtc cctggagaaa tcatgagtta gatgagagtg tttagtggga agtgaaaaga   47220
cccgtccacg gtttcggatg agatcctcgt tggactgtga tcccaggata ttacccaggc   47280
ccagatcgta gacaacctcc caatggagtc ctgcccctac acgggcaggg ggtgaaataa   47340 tgattcccctt tcttaattt ctttagccat gaaatttatt aaaaatgtat gtctgattct   47400
gagttgccag tcttaattgc ttgagattct ctggattcag aacttatttt tatttttttt   47460 attttattt tttgagacag agtctcgctc tgtcatccag gcaggaatgc agtggcgcaa   47520
ctgcaggccc actgcatcct gagctcaagc gatcctcctg ccccagcccc caggtagctg   47580
ggactacaga catatgccac catgcccaac taatttttt ttttgaggca gagtctcgct   47640
ccctccccca ggctggagtg cagtggcatg agctcggctc actgcaagct ccgcctcccg   47700
ggttcacgcc attctcctgc ttcagcctcc cgagtatctg gactaaaagg cgcccgccac   47760
cacgcccggc tagttttttt ttttgtattt ttagtagaga cggggtttca ccgtgttagc   47820
caggatggtc tcgatctcct gacctggtca tccgcccgac tcggcctccc aaagtgctgg   47880
gattacaggc gtgagccacc gcgcccagtc ccaactgatt tttgtacctt ttctagagac   47940
gaggtttcac caggttgctc aggctgctct cgaactcctg gacttaagca atcctcctgc   48000
cttggcctct gaaagtgctg ggattacagg tgtgagctac tgcgcccagc ctgaatgcag   48060
tcttaaaact gaattagaaa atctgagtgc aggctagagt tatatataat taagagagtg   48120
tgggttttaa gttgtgtctt aaaattgtgt tgttttggt cgagtctggt ggctcacact   48180
tgtaatccca gcactttggg gggcctaagt gggctgattg cttgagctca cgagttcgag   48240
accagcctgg gcaacatagt gaaactctgc ctctacaaaa aatacaaaaa ttaagcccag   48300
gtgctgtggc tcatgcctgt aatcctagca ctttgggagg ccaaggctgg tggatcatct   48360
gaggtcagga gtttgagacc agcctggccg tggtgaaacc ctgcctctac taaaaaaata   48420
caaaaactaa ccaggcgtgg tggcacatgc ctgtagtccc agctacatgg gaggcagagg   48480
cagaagagtc ccttgaaccc aggaggcgga ggctgcagtg agccaagatc gcaccactgc   48540
actccagcct gggcgacaga gcaacagtcc gtctcaaaaa caaaaaacaa aaattagcca   48600
ggcattgtgg catgcgcctg tagtcccagc tacttgggag gctgaggtgg aagatggct   48660 tgagcctggg aggcggggt tacagggagc tgagatggtg ccactgtact ccagcctggg   48720
tgatcgggcc agaccttatc tcaaaaaaaa gtgttttaa ttacttgtaa ttttaattgc   48780
```

```
ttgtaattaa aaaacagtaa ttaaaaggac caaaagttaa ttttgcaggt agtaaacctt   48840
agcctactgt acgtaaaaat cagaaggcca aggcaggagg attgcctgag tccaggagct   48900
caagaccagc ttgggcaaca tagtgagacc ccgtctctat aaaacaactt aacaatgtgc   48960
caggtgtggt ggcacaccct tgcaatccca actactcagg aggctgaggt ggacggattg   49020
cttgagcctg ggaggtcaag gctgcaatga tcgtgatcac atcactgcac tccagcctgg   49080
gcaacagagc aagaccctct gtaaataata acagtaataa tcagaaagca acactgtatg   49140
tgaataaagt caccttacct agctgccggt ggacagcctt tggtgtttca aggacttagt   49200
ttttatgcgt tcctgctttc gatatttgtt gactgtgagc tttgggctta tccagggtcc   49260
atgaagaaga aatggctctt ccttatctca ggcttttgtt attttggggt gttttaaatt   49320
cctctcctgt ggttactcaa tccgacccta cttgcctctc tcttccacaa atttctcaaa   49380
tgtcattcat ggtacccttt taactcttac ggacttactt gttttttaaca tatctttat   49440 tcactttgaa tggagtttcg actgaaaata gagggtagtg ttgtgtgtac cacctaccat   49500
cttcagctag acactttcaa agagtttgtt ttgttaatta tatcttctta catggctcat   49560
tatgcttgtt gaaatttgca agatgcttta aaccaatcct gtccaaacca cagcctgtgg   49620
gccgcatgta gcccaggata gctttgaatg cagcccaaca caaattcata aactttctta   49680
aaacacgaaa tttttttgc aatttttttt ttccttagct catcagctat catagtgtta   49740
gtgtatttta tgtgtggcta tggcccaaga caattcttct tccagtgtgg cccagggaag   49800
ccaaaagatt acacattgct gaaaacttta gatgtatcag gaatcatata gcttttcaaa   49860
ataaaatatc cacactttg ctaagttcta tgctatgcaa gtgactgaac tataccagga   49920
cttatcttgt aaacttggaa gtgaaatatt cttcactcgc aagggtattt tgtgattaaa   49980
ttctggaaat atgcatttat aagttgatac cagctcctgg aatgtaactt tttcttttt   50040 cttttttct ttttagatt ttttgagatg aagtctcact ctgttgccca gggtggagtg   50100
cagtggcaca atcttggctc actgcagcct ctgggtcccg aggtcaagca attcgctggc   50160
ctcagcctct gagtaggtgg gactacaggc atctgccacc acagctggct aactttttt   50220 tgtatttta gtagagacag ggtttcacct tgttggccag gctggtcttg aactcctgac   50280
ctcaagtgat ccacccacct cggcctccca aagtgctggg attacaggcg tgagccaccg   50340 caccccggatg cttttttctca tttctccatc gcttaaagat agaggattga gagaggcccg   50400
tttgtggaca cgatcttaag tacagatctc tagtggttaa aacgaaacac aacaattctc   50460
tctcatcctc tagactcttg gcttttgcct aaatatgatt cataaagctg aagtgttgct   50520
aatctttaaa taacacccaa gggatatgat tatatgatta cccaacaccc taatacagtt   50580
taagaataga gtgatccaaa gaaggagaaa atagtgtctt caaaaatgtt gctattagaa   50640
atatttcttt tctctaaggg aggatgcagg ctaaagtatt tagcatgtgt gtttactttt   50700
ataaattttc taagtgatga aggaaggaag gtagaatctt tttttttttt tttttttttt   50760
tttttcagat agagtttcac tcttgttgcc caggctggag tgagtggtgt gatctcggct   50820
caccgcaatc tccgcctccc aggttcaagc gattctctgc ttcagcctcc ctagtagctg   50880
ggatcacagg tgtgcaccac cacgcccagc taatttttt tttttttt tttttttt   50940 ttttggtat tttagtaga gatggggttg accatgttg gccaggctgg tctcaaactc   51000
ctgacctcag gtgatccacc ctactcggcc tcctagagtc ctgggattac aggcgtgagc   51060
cactatgccc tgccagaagt agaattctta tcaacatctt tctaggttga taatcaggta   51120
atccctaaag ttaatacccct aaaatgcaat ttttagttt tgatggaaaa ttgattctat   51180
```

```
cccttttttt ttttttttt ttttttttt ttttttttt tttttgaggt ggagttttgc    51240
tcttgttgcc caggctggag agcaatggca cgatctcagc tcactgcaac ctcggcctcc    51300
cggttcaagc gattctcctg cctcagcctc ctgagtagct gggattacag gcatgtgcca    51360
ccacgcctgg ctaattttgt attttagta gagatggggt ttctccatgt tggtcaggct    51420
gttctcaaac ccccgacctc agatgatcca cccggcttgg cctcccaaat tgctgggatt    51480
acaggcgtga gccaccatgc ctggccggtt ctataacttc tatgatagag aattttaaa    51540 ttatcaaaaa agcctgatct ttcatgtaac actttgacca gtcttaccct gtgagtgttt    51600
tcatctgcct tctcacgctt tgcatccaca agtgaaagtg cttctatttt tctatgtatt    51660
gtacagtaaa gattttagag ctttctaggc caggcatggt ggctcgcacc tataacccca    51720
gcactttggg aggccgaggt gggcagatca ctgaggccag gagtttgaga ccagcctggc    51780
caacatggtg aaaccctgtg tctactaaaa atacaaaaat tagccgggag tgttggcagg    51840
tgccgtaatc ccagctgcta ataaggtgga ggttgcggtg agctgagatc gtgccattgc    51900
actccagcct gggtgacaga gagagactct atctcaaaaa taaaaaaaaa aaatttttt    51960 agatccttct aataagatga agcccactgt gtcaaaaaaa aatctaaagg ttaggatatg    52020
aagtcattct gacagattat gctgtggaag aatatatatc cctgttcctt tcttctgagc    52080
cttactttca tgttaatagt ttaaactaca tactatatgc caagaacttt atataccta    52140 tcatatttca ttttcacaaa attttaggag gttgatatta ctcacattaa ttaacaggcc    52200
caacatcaca atttctagca agaggaagag gtatgcttt aatgcaagtc tgactctgaa    52260
ttctgtggcc taatctgcag tctatgttgc atccacatgt tttaaatgtt cgctatgaat    52320
tctcttgagc tattattct atctctaatt atgccataat ttaaaaatca gaatacttgg    52380
gctcgtgtga agagatggtg tgcctagatg ttttcttcctg gctcagtgtg agatatgatt    52440
ttgaaagcac atgatgtgct tcattacatt ttttaaatcc attatccca ggttaatagc    52500 ttagatggcc ttttttttt tttttttttg agatggaatc ttgctatgtc gcccaggttg    52560
cagtgcagtg gcgtgatctt ggctcactgc aacctccacc ttccagcttc aagcgattct    52620
cctgcctcag cctcccaagt agctgggact acgggtacac gccaccatgt ccagctgatt    52680 tttatattt tagtagagat ggggttttgc catgttggcc aggctggtct tgaactgacc    52740
tcaggtgatc cacctgcctc ggcctcccaa agtgctggga ttacaggtgt gagccactgc    52800
acccggccag atggccattt ctctaatgta aaatgtgaag caggcccaat ggagggcccc    52860
aagcctgtgc cagaggtgac cagtctgcag ccgtgccccg catcctaac ttccttggtg    52920 aaaaatgaga ccactattca gtgtgctagc tgtttacaag gagcaattgg ttagaaatga    52980
cagtgtactg aaagtctttt ttttccctcc aatttttac agggaaggtt gggtgtggct    53040
ctccaagaat acattttggt ggactcattg aggaagatga tgtgattctc cttgctgcag    53100
ctctgcgaat tcaggtttgt tcaacatagc tgtctgagaa tcttgagttt ggaagtttga    53160
ttaatagttg ctaacatttt gcaagtggtt tctgtttacc aggtacagtg ttaaacactt    53220
cacacacagt gttaggccca tttgataagt gaagaaatgg tgattttgaa aaatgaagtg    53280
agttgcctat gatcacatgg cagtgtgggg caggaccca tcctggggac tgtgtatgtt    53340
atcttgtgct gtgtaataaa ttatcccaaa atttagcaac tgaagcaaca aggcatttat    53400
tatctcacag tttcttcaag tcagagattt ggtagtagat tagcagatta ggtggtatgt    53460
tagtccattc ttgcattgct ataaagaaat accagctact caggaggcta aagcaggagg    53520
```

```
atcgcttgaa cccaggagac agaggttgtg gtgagctgag attgcaccac tgaactccaa   53580
cctgggtgac agagggagac tgaaaaaaaa aaaaaagaaa tacctgagac tggttaactt   53640
agaaagaaaa cagatttaat tggctcacgg ttctttttt  tcccctgggg acagagtctc   53700
actttgtcac ccaggctgga gtgcagtggt gcgatcttgg ctcactgcaa cctccacctc   53760
ctgggtttaa gagattctca tgcctcagcc tcctgagtag ccgggactgc aggcacacac   53820
caccacgcct ggctaatttt ttgtatttt  agtagagaca gggtttcacc atgtcggcca   53880
ggctggtctc aaactcctgg cctcatgtga tccacccgcc ttggcctccc aaagtgctgg   53940
gattacaggc atgagccacc gcgcctgacc tggctcacag ttctgcaggc cttacaggaa   54000
gcataacaca ggcatctgct tctggagagg cctcaccaag cttccaagaa tggcagaaag   54060
tgaagggaaa gcaggcatct cacaaggcgg aacaggagc  agagagtgag ggatggtgct   54120
atatactttt aaatgaccag atctcatgag aactcattca ctatcacaag gacgctaccg   54180
agggagatga tgctaaacca tcatgagaaa ctagcccctg tgatcccatc accctccacc   54240
aggccccacc tctaacactg gggattacat ttcaagatgg gatttgggca gggacacaca   54300
tccaaactat atcaaattgt ttaggctcag gatctctcat gcatttgaag tgaagatgtc   54360
agctggggct gcagtcatct gaggcattaa ctggggctgg aggatctgtt tccaagatgg   54420
catactcaca tggctgtggg catgtgtatt tcattcctca ctggccatca gcaggatgcc   54480
ttggttcctc atcatgtcca cctctctgta gggctgctca cagtgtggca gctaacttcc   54540
cccagtgtga gcaatccaag ggaggcaacc aggaggagtc tgcagtgtgg atgacctggg   54600
ctctaacctc atgtgccgcc acttcctttt atcctgtttg ttagaagtag atcactaagt   54660
ccagttcaca ttcaagagaa ggagaattgt cctcacttct tcaagacagg agtattaaag   54720
tatttggagg catttttttca aaccaccacc acctgtgtga cctaaaggcg aaggtcatca   54780
gtgttccacc atataagctg agtgttctca tggtgctgga gcctgcagca gtggtggcct   54840
ctggcagtga catttagttc atttctttct tatgtacagg gtaatacaca attgaaactc   54900
tttacctcaa aatgggtcat tagacatttt tgtaaggatt ataagttaca tttccatcaa   54960
agccaaattt tattttttatt tatttttatt tcatttactt ataatttata tgcatacata   55020
acactactca gtagttcaat ttgcttgctc ttttatacca actatggaag gatggtattt   55080
ggaagctggg catccaagct gatcattcac gcagtcctat atttctttca tttttctttt   55140
ctaaattgga tgacgaacct attcagtata agtttatcca tgtacatgat gtcttttgtg   55200
aacacttaat ctatttattt atttatttat ttatttgaga cggggtctca ctgtgtcacc   55260
caggctggaa tgcagtggca cgatctcagc tcactgcagc ctccacctcc caggttcaag   55320
tgattctcct gcctcagcct cctgggtagc tgggattaca ggcacatgcc accacaccca   55380
gataattttt ttttttttt ttttttttt ttttgagaca gagtttagct cttgttgccc   55440
aggctagagt gtaatgtcgc aaactcggct cactgcaacc tccatctccc gggctcaagt   55500
gattctcccg cctcagcctc ctgagtagtt gggattacag gcacatgcca ccacacgcc   55560 cggctaattt tttgtatttt ttgagatgga gttttgctct tgttgcccag gctggggtgc   55620
aatggcacga tctcagctca ctgcaacctc cacctcccgg gttcaagtga ttctcctgcc   55680
tcagcctccc gagtagctgg gattacaggc gtgtgccacc acacccagct aatttttgtat   55740 ttttagtaga cggggtttt  ccatgttg  gtcaggctgg tctcgaactc ccgacctcag   55800
ttgatcccgc ctacctcagc ctcccaaaga ggattacagg cgtgagccac tgcacctggc   55860 ctaattttg  tatttttagt agagacaggg tttcaccatg ttgcccaggc tggtcttgaa   55920
```

```
ttcctgacct caagtgatct gcccacctcg gcctcccaaa gtgctgggat tacaggcatg   55980
agccacctca cctggcctat ttattcattt atttttaaag agacagaatc tcagctagga   56040
tgaagtacag tggtgtgatc ttgactcact gcagcctcaa acttctgggc tcaaacaatc   56100
ctcccacctc agcctcccga gtagctggga ttataggtgc gcatcaccac acctggattt   56160
tttaatagtg tattttctca cattttcctg ttttcttttt taaaatttaa caaaaacaat   56220
gaacatagtc agaagttctg gcctgtgact tgaaataacc ctggatgtac attttaaaa    56280 acattctcag attcattgct gtaagtatga agagctaata gtctgcaagg gaactataga   56340
attaagctgg atcatcaagt tcatgcatgc atatttaaga aacagagcag cttcttttaa   56400
tactatcaaa ctcttcagtg cgatattgaa tagttgtata tctaactagt ggttttcacg   56460
ttttcctttt taagaaaaac ctacaaacct agttacacgt gaataaaaat attcctaata   56520
tcctcctggc ttattgtgcg actcgataat cttgttttgt aacatccaca acaatattt    56580 ccatggttta agtgtgtgcc ctgtcagctt ttaccattct aacatgtttt cccctctatc   56640
cctgctgaag aacatggtca gtagtggaag gagatggctt cgtgaacagc agcacaggcg   56700
gtggagactt cactgcttga aacttcagcc tctctcccct gtgccaaggt aacactggtg   56760
ttttatttac actgatgtca gctcagcaca gtgccttagc cctagttagt catgggggag   56820
aagcacaact catggtactg tggttttgat ggtagataag tttctctatt cattaaattg   56880
ccaccctatt ttctctattg taaattctcc aaaattaaat cataatgaat gtattactgt   56940
gttctgtcaa ttctaagaag gcatattttt ttatttcaat gatgttttct atattaaatg   57000
gcagtttttt aatgatgttt taaaattaat ttatattaat ttaatttcaa tgatgtttcc   57060
tatatttaat ggcagtgttt tcccccccca ccctttttt ttttttttgag atggagtctt    57120 gctctgttgc ccaggctaga gtgcaatggt gcgatctcgg ctcactgcaa cctctacctc   57180
ccaggttcaa gcgattctcc tgcctcagcc tcccgggtag ctgagattac aggtgcacgc   57240
caccacaccc agctaatttt tgtattttta gtagagatgg gggtttcacc attttggcca   57300
gccggtctca aactcctgac ctcaggtgat ctgcccacct tggcctccca aagtgctggg   57360
attacaggcg tgagcgacca cgcctggcct ggcagtggtt tttcttctta gtggtccatg   57420
aagtaatggt tttaaatttg acaaaatatg gtaatgtaat atttggaata tgcttttcaa   57480
tgtcagaaat gcccaacacg tatatatccg cctggtgtta agggccatat aggtttctac   57540
tctggggata aaggaccgtc caaaccaaac attattccac gtgggaactg agctcagctt   57600
tcttcagaac gatctgatag aatagtctgt gctcgtcaag gtggatattt tcctcagagt   57660
gctctctgat gaggtctgag ctacatattc tatctataaa tttggaaata taaactgtag   57720
gtcatagtct cagcttgtgg tttagaatga ttgggtaggg atgatgtctg aatcagacag   57780
ctgcattttc cagcctgatg atgagtcatc tgtgtctgtc ccactccaag gaattggccc   57840 caccccatt atccaggtgt gcataatact aggtgtgcat cccaggtaa tctcatccag     57900 caacgttgga atgcacacag tgccgaggag ataaatccc tctagtaact gacactttat    57960
ttatttattt atttatttat ttattttttc tttttttttt tttttttttt gagacagagt   58020
cttgctctgg tcttgaactc ttgacctcag gtgttccacc tgcctcggcc taccaaagtg   58080
ctgggattac aagcatgagc caccgcaccg gggctgactc attttttacc tgataaccag   58140
ttgctttata gaattgaact ccatttcctt ggacagtcag atgaacaccc tggttcagtt   58200
ctacccacta ggagggtgtg accctcctgg acatgttttc atccctgcaa tagacgaaac   58260
```

```
atctcagtta tgctctctgt tcattaatta tataagttgc aatgaggaat gttattcttt    58320
gtaatatcat ccctgggctt gtgcaatctg tttcataaaa tatcttattt tagagttatt    58380
tttgttgtta taagaccttg gatttttaaaa gtaaatcaat aatttctact tacaaagtgc    58440
taaaaaagat taagatagat tccaccaaat tgtgtaccaa agtttcaaag taaattcttc    58500
ttgttaaata attaaatcct tttctccccc aagaagaatt tactttgaaa tcattgattt    58560
ctagacccac tgggcaaaga gaagcaggct gagtagttta taaatcaccc caaaaatcgg    58620
atgatgtctc tgtgactagc tagtaaagag aaaaccttac aggtgtttgt tttgttttgt    58680
ttttgagaca gagccttgct ctgttgccca ggctggagtg cagtggcttc atctctgctc    58740
attgtaacct tcacttcctg agttcaagcg aggacatctg gctaattttt gtattttag    58800 tagagacagg gtttcaccat gtttgccagg ctggtcttga actcctgacc tcaagtgatc    58860
tgccctcctg tgctcccaaa gtgctgggct tacaggcatg agccaccatg ccaggcctgt    58920
tttgtttgct tgtttgtttt ttgagacagt cttattctgt tgcccaggct ggagtgcagt    58980
ggtgcaatct cagctcacct caacctccgc ctcccaggtt caagtgattg tcctgcctcg    59040
gcctcccgag tagctgggac tacaggtgcc accaccacac ctggctaatt tgtttgtatt    59100
tttagtagag acgggatttt gctatgttgg ccaggctggt ctcaaactca tggactcaag    59160
tgatcctccc gccttggcct cccaaagtgc tgggattaca ggcgtgagcc tctgcagcct    59220
gccaaaagct tacacattgt tcaagattaa gctcttcaat ttaggagatt gtgggaagag    59280
agagacagaa aaaactatg gccaggaagg caaaacaaag taggaggcta gaaaggaaag    59340
gtcggatagg tggaggcctg gaaaggaata ctcagcggta cttgaggggg gtaacctgaa    59400
ctcctagttt ctctggtgcc cttttggagaa gtctgggtgg aggtgtgttt gctgttgcct    59460 cttaccccg ggtcaggccc ctacaggatc ctggaggaga gtctagggtg gtctgaacac    59520
tgagggtaga ttacctgcag tagctacaga aacagtcagg gccaagggc tgactaaagt    59580 ccactgaggg ggttgatctg cccaccgcaa ggaggcagac cacaacaaaa ataagtgttc    59640
tggggtgagt gaaggaatag ctgtcctctc tgatgcaacc tttaagggta gtcccccgcc    59700
gcgtggtctc ccggggttag tcttgctgct ggggaacag gtgtgccttc catctctcac    59760
tctcagacac atgaagggcc tgactgccca gcaaagaaat gactgagcac atgagcccca    59820
gaggaaagag tccagcatta cacatgctgg tatccagacc actcctgtaa gacgagcagt    59880
ggtggccagt aaaatagaag agttcagtta cgtgcccaat gactctctgg agttcctaca    59940
atttcctgtc tgaacttggg ctcagggcac taggtccttt taccgacagt tatgtaatta    60000 ataaacatt ttgaaatatg attttagact gtaaatagag aggggggaagt gtggacacag    60060 ataaaacgaa atagcatttc cacattttt ctttttttt gtacttaatc tctaatgtga    60120
tagtaatgtt cacattttg aatagccaag agaaacatgt ggccagcccg atcggagatt    60180
attatgcaat gaccctctat tcatcgctaa tgaataccat gatggcccat acagagcatt    60240
ttgctctgta gtcgaatcac acttgcagga gggttttgga cacattataa tatgctgttc    60300
ttgtctctat gccataggtg ttatacttcc acctggacac aattctagga tctttgtgag    60360 tttttggag ttgcatttct aaaatgatac accatttct catacacgtt aattattagc    60420
agttgtgctt attactgcct gggagaaagg accccaaagt aattgcattg atttcatcgt    60480
tggcgtgatg tgtggctgtt ttcactccag ttgtgaccac ctaagctgag aagccttttc    60540 tctcttttcgt attgtctttc ccctcagtga cattgagatt tcaagaggac aaactccaaa    60600
agctgtggat gtccttgcca aggagattgg attgcttgca gatgaaattg aaatctatgg    60660
```

```
caaaagcaaa gccaaagtac gtttgtccgt gctagaaagg ttaaaggatc aagcagatgg    60720
aaaatacgtc ttagttgctg ggtaagacac catctaacat ctacttgatc aagcagacat    60780
atttacaaaa ctcttcccta tttatctctc tcctcgtacc cctcaatcca tcctattctc    60840
acatttgaca tttcgtccat ttcatttggc atttctttat ttggtgtgag ataagttttt    60900
attttcagtg cagagcaaac tagtcgactc tacacaagat aaagtcaaac aagttgcagt    60960
gctttatctt ttgtttctca tattatgttg ttattacccc tgctcctcct tgacttttg    61020
aatttcattt ttcattataa aaatcaaaat aggaattgaa agtaaactat tttgaactga    61080
gcagtttgtt ttgtgcgttc tacttgaaat attttcgtgg aaaaggtaca gataatcata    61140
tgaaacatgt tttcctgtta atatccttga tcttacctac atattcacat ttcaaaagct    61200
cattatttcc cttttttctgc atttcaaaac taatgttggg ccattttcat ttgtgttggt    61260
tattttataa aagacaaatt catagttttt gtgaaaagga gtgtttgcct ttttcccctt    61320
cttttaaaa aagaagtac attcactagc tgaaagatg atagaaagca agggatttca    61380
aatatttatt cagtgtgacc tgagggaaca tcatgagacc atataaattc ctttgctgcc    61440
ttgaaatttc atttcagtga ctattgctta tgatgtatac aaagcttcag gcacaaaacc    61500
tatttgtcag gcagagacat ttcttgtaat tggaattgac tcctaggtaa ctttgttttt    61560
acgtatttaa ttattaatgt aagtgctttt ttctttatt cttttctgg ttataaaaag    61620
aatgtagttt cattgtagaa atattctaaa aattcagaaa acagaagtga aaaagtaaaa    61680
catcccaaac ccaagcactc agaggaaaca actgttgacc tgcgaggact gttttgacgc    61740
tgatagagtc tctcagccat gaggtcacac tcacatgcta ttgtgtaagc aacctgatta    61800
ttcaagcata tgtggcatac tgagctccat gtgagtgaat attgagctat gtcaccattt    61860
ttcatgacaa cataacattc catcactcac atcccagatt ctttttttt tttttttt    61920
gagacagagt cttgctctgt tgccaagact ggggtgcagt ggtgtgatct cagctcactg    61980
caaactctgc ctcccgggtt caagcgattc tcctgcctca gcctcccgag tagctgggat    62040
tacaggcatg cgccaccatg cccagctaat ttttgtattt ttagtcgaga tggggtttca    62100
ccatgttggc caggcttttc tcgaactcct gacctcaagt gatccaccca ccttggcatc    62160
ccaaagtgct gggattacag gtgtgagcca ccgcacctgg ccacatccca gattcttaaa    62220
catgttgggg aagcaggggc tgggggagta gcaaaatgcc caggatgagg gtggagatcc    62280
catcttacac atcttctggc acctctagtt ccatcaataa gtgctaccct ggtagttctg    62340
agtgtttcta attgtccaag tgcactgatg cagaaaaata atttgaacat agaatagga    62400
tgttccacaa cttacttgac caattttcta ttgatgggca atcaaagtgt tcccaatttt    62460
tgccatttta aactgctaga attaacaacc ttgggcatgt ggatttgtgc atctgtttaa    62520
ttatctcctt aggaaaaatc cccggaagtg agttcaatta tttataacca caaataaagc    62580
aaaaatatta tccaaaacag gccaagcgcg gtggctcaca cctgtaatcc cagctctttg    62640
ggaggccgag gcaggtggat cacaaggtca ggagatcgag accatcctgg ctaacatggt    62700
gaaaccccgt ctctactaaa aataccaaaa aattagccag gcgtggtggc aggcacctgt    62760
agtcccagct actcaggagg ctgaggcagg agaatggcgt gaacctggga ggcggagctt    62820
gcggtgagcc aagatcacgc cactgcactc cagcctaggt gacagagcaa gactgtctca    62880
aaaaaaaaa aaaaaaaaa aaatcacctc tttaatgata tagtgatttc ttcaaatcct    62940
ttttccctcc tcctgtccca ctttcctgtc ctcctctttc tccttctctt tgtgtagctt    63000
```

```
ttcttttttt tttttgagat gaagtcaccc aggctggagt gcactggtgc gattttggct    63060
cgctgcaacc tctgcccct  gggttcaagc aattcttgtg cctcagcttc ccaagtagct    63120
gggattccag gcatgcaccc ccacgcctgg ctaactgttt ttgtattttt atagagacgg    63180
ggtttcgcca cattagccag gctggccttg aactcctggc tcaagtggt  ccgcccgcct    63240 cctccttcca aagtgctagg attacaggtg tgagccatca tgcccagctt ctgtagcttt    63300
tttgtaagag ggacagacag ccagggcctc tctgaatccc tcagcagttg gcattgtaag    63360
gaattcatcc tttgctccac accttggttg cctgtggctt caccttctc  ccgcaggctt    63420 ccaggctcac tgcagttaga ttcctgagcc cctttccaac ctagaacccc aaacttaatg    63480
tccccataat cgagtgtggg aaagttcctg gctgagggga ggggttggct ccacctgcag    63540
gcaccctctg ggcccacacc ctgcaaggag ctgcctctgg ttagattggc tccgggtct    63600 ctgagtttag ggcacagttt agtcagggtt gttttatggc agtatgcttg atgcatattt    63660
gtctgcaatt aataaacaaa ctcttggcca ttaagacctt gaaaaagcat ttgatttgtg    63720
aaattggttc ctttcttcca ggcttcagat gatcttggta ggtgggtttg caggctttct    63780
caccctgttc agataggaac acttaaggaa aacttggtag gatgtgttgt ctgtttatga    63840
aggaagaatc ctgcagcaga ttttcttatc cagtccttgt gctttactcc attttgggct    63900
tgtcaataaa atcagaaatc cagatatgga tggctctgac cttagcttgg aacacaaaac    63960
tgatacttct aaaacaaagc tgtgatgata ctgttttcag gttccttact tgtaaacaaa    64020
gctgggcctc cagcctcatg ctggagaatg ctagctagca cgactgcctg gggttacagc    64080
caatgcagtc catggccagt agaacatttc tccacgctgg cttttttgcta gcattaatat    64140 gtataatcaa gctgaaattg gcctgccatg ttgtaaatag aaaagaagac taaagatgaa    64200
ttttcaagaa cagattaaac accaagggat caacaattct ttttctgaaa ttctaagttt    64260
ctttacctaa caaagacctt tgaaggaaca aaaattaaat ggcctgtctc ttttttaact    64320
gtagtggaaa aaaataaccg tgctggtaag attatgatat atgtatgcat ttgtggcaca    64380
gcttgaagat ttttaggaaa tagccacact ggattctata agggaagaat gaacagcccc    64440
ttctccccaa cacaacaaat gatatatttt ttagggctgt aaactgtcat cagtatctaa    64500
tcccttaata gctgaatatt gatatcagtt tagatcacag gcaactattt tatcgatagc    64560
ctaaagtggg cctggcatga cgggttgtgc ctataaccca attactctgg agactgtggg    64620
tggatcactt gaggccagga gttcaagacc agcctgagct gcatagcaag accccatctt    64680
taaaaaatac aaacaaacag caaaaagcag cactggttta aagcaacatt tgtaatctaa    64740
agtgaaaagt caatttgaaa taaaaatcat cttcatattt ttacatttga ccaggtcaag    64800
cgttaggggg aaatgactgt tatcaaacca ttatatgcac tgttgcaact tctttaaaaa    64860
tataaatgac ccctccatta aatggagaat tatttccttt ttctaaaagt cttttctaat    64920
tctgaaaata atattagctt attgtaaaaa atttaacata aagtaaaaag gagataacta    64980
ggtctctcat aactcaatat tttatttata tattcatctt tttacacatt gagatcatgc    65040
tataaatatc atttttgtcc tgccttttc  tctgaacact gtaacataaa tcttttttcca   65100 tgctttagaa gaattcaaat acccaagtaa ttttaaaata atactaaata acaatatatt    65160
tgttattaca tattttaatt tatatagaaa tgtgatttaa atatatcagc aatgggatta    65220
aaatataaaa caatgagatt ttttttaaatc ttctattatt aataactcaa atgcagaaca    65280
gattaattct tttaaaaagc cattcttcaa actttaggat ttcttattca gtcagaatca    65340
tctgcatttc atcaactaca tatcgcatgg tatttacacc tacacatcac tttatttgct    65400
```

```
ttgcctgaca aaatgaaaag tattgggaat tgttcaggga aatatgccaa aagaatctta   65460
gggactcatg agttttacat attttcccag ttacactaat gaaaaggaat tttgtttgag   65520
aacttgactt ggagtgcagc tgcagggcat ttgaatctca gtctccatca ggcctgcacc   65580
catttctgtg cagaagtttc tagaatttcc ctgaattggt tggacagagc agctaaaaaa   65640
gcagcccaaa ctgatctggg aatagactga atttcacatt aaagaaaaat ttgaatcatt   65700
cacatcattt catcttttt ttttttttt tttttttctg cagagggcca aatacccgat    65760
tggatttttt aaaaatgttt caacccttta tttcggtaca atgttaaaat aatctgactt   65820
ttctatgatt tggcttttct gccttgagta actatttaaa tatctgtgtg attttctttt   65880
atttgtgcta cttctagaac aaaacagagg tatttagaag aaaccacttc ccacagggcc   65940
tttgaaccgt ttacctaagt caagtgtaat gagaaacata accaaatgca ccatggggtt   66000
tattgttaga aataaaaagg cttaaaaagc ccctagaccc taaagatgcc tgggatggat   66060
gatttatgtt catatgctac ttgagcatgt agttttggag tgcatggtga ggcccatggc   66120
taatggcagt ggtgctattc aacaagattc tgggtcttta gaatagttca aagttttacc   66180
acttctctct ggataagcca tcttttttgac ctttgagtaa attataaact tcttttcaga  66240
ttgtgtccaa atggtcacag gtactttgac agttttact gtaactgcca ataagtaata    66300 ctcatctta aaagacatc attctggcag ggcatggtgg ctcacgcctg taatgccagc     66360
cctttgggag gccgaggcgg gcggatcatt tgaggtcagg agttcgagac cagcctggcc   66420
aacatggtga aaccctgttt ctattaaaaa tacaaaaatt agctgggcat ggtgatgggt   66480
gcctgtaatc ccagctactc aagagggtga ggcaagagaa ttgcttgagc ccgggaggtg   66540
gaggttgcaa tgagcagaga tcacaccatt gcagtccagc ctgggcaaca gagtgagact   66600
ccatctcaaa aaaaaaaaa aaaaaaaaa agcatcattc cattgtcaac ccttttttgc     66660
tgttctgtgc cctgaacagg tgatgtgata gcggtgcaaa gagggtgagc attgtccttt   66720
acctcaacaa gtgtgtggcc tggtaggcga gacaggcatg tcagaatgct tatcatgaag   66780
ccatctgaaa aattctagaa taatcatata atcaatgctc tagatatcag agaggggta    66840 cagaaatctg ccgggagaag tggaggaatg taatgaacaa aaatcacagt tccatctcta   66900
tgaactctaa gctcccatag aaaaagaaat tagagggctg ggcgtggtgg ctcacgcctg   66960
taatcccagc actttgggag gctgaggtgg gcggatcaca aggtcaggag tttgagacca   67020
gcctggccaa caaggtgaaa ccccgtctct actaaaaata caaaaattag ccaggtgtga   67080
tgacgtgcct gtagtcccag ctactcagga ggccgaggca ggagaattgc ttgaacctgg   67140
gaggcagaga ttgcagtgag ctgagattgt gccactgcac tccagcctgg gcaacaagag   67200
cgaaactcca tgtgtctcca aaaaaaaag agaaggaag aagggagga agagagggag      67260 ggaggaagga aggaaggaag gaaggaaggg agagagagta attagattac cttaaggaaa   67320
gaaggaagga aggaaggaag gaaagagag aaagaaagag aaattagatt accttggtgc    67380
tcattctttc gtatatcccc gttgatgatt tggaatctga gctaaagata ctgggggaa    67440 aactaaacca aattttgata ccaaatacag gaaggaggtg aaataagctt ttttattgta   67500
gctctccttt tattgctcac aataaatact tcctactttg tgattttccc gaactgtatt   67560
agttggcaga aagctgagca gtcctgtgtt tctaattaag aattggatgg ttagctggag   67620
ttttgaggag gtcatctctg ggcgtgtctg cttttggctt tcttgggcag ctatgctagc   67680
atatccttgg gaatgaaaat gtaatccttc atgtgacaca gtttaggtaa accacttagt   67740
```

```
cctttgcaaa caccaaatgc tcagtgcggt acttaaatga caccatattt gatgccacag   67800
tttctttaca ggctcttcta agattgtaat gcctgtgggc ttttaactgc ccttattgat   67860
gttgtatcca agaaaacaga aagttgactc caagcagaag tattaatatc tttgtataac   67920
tttcagtctt cacgttgacc ccactgcaga tctgctgttt agacagatgc agaggtgact   67980
gataagccgg ggtcatgtgg cttcaggagt cttaggtttc tccatgcagc ggtgtcagga   68040
taggctcacc agctcctggc cacagtgggt accagcgacc tccttgttgc tgaatccacc   68100
gaccactctc ggtcctcatc ctgcttcctg cctcagtggc gtttgacttt cctgttctgg   68160
aaacagtctc atccttggcc tccttctgag acttcctgtc atgttctgcc ttcttctcca   68220
gggtcctctt atttttttgtg tttttagaga cagggtctca ctatattgcc caggctggtc   68280
tcaaactccc tagctcaagc agtccttttta ccttggcctc ccaaagtgct aggattacaa   68340
gcatgaacca ctgcacacag ccgggttctc ttattttata ctacgccttc ttagtttcct   68400
tttggactct cttcttctga caactcatta caagcaaatg tgcttaactc ttctgtcctt   68460 atccctttttc tcactcggtg cactgtcctt gggtgatctt acccattcca tgctttaaat   68520
ggctatagtt atgatttcca tccatggaga acctggttaa gtcagatggc tggcttttgcc   68580 tcccagctct actgcttact agctgtgtga ctgtcggcaa gttgcttaca ctctgtgcct   68640
cagtttcctc atctatcaag tgagcgtaca aataattaac cccataaata tgaagcatag   68700
cacctctcct attaactgcc ccaatccact ctcagtttta tctagttaac atttattaat   68760
ttgccgggtc tcacctaaga tgttacttcc tacaggaaac attcccagat gttcaaatct   68820
agttagatcc tttttccatg taccctcata attcagtctg actgccctat ttccctgtct   68880
tagtgtttgt cacatttatc gtaattgctg atatattcag atcagctgga agctcgtgag   68940
gatagagatg aagtctgact ggatcatcat tttgtcccca gcgtctagct cagtgcctgg   69000
tacatagcag tacttgacaa atatttgctg aatgaatgac tcatggaatt gtagggtatg   69060
atgacgcctc taaagacatt cttttctttgt ggttacatcc ttaggttttg tagatcagaa   69120
aactctatta gattggttgt ggttgagtat ccttgacaac atggctgaca gtaactcatg   69180
gaagaccaaa ctgtaaaccc taatgacagc ctttaaattt tttaacgatg cttgagagct   69240
aagctggaag gacgtggggt gcttatccct cgtagaaatg cctgccaatg ctttctcatt   69300
tggacccaaa ctccagatcg ggagcagtct tatagctgga tcagctacca agagaaattc   69360
taaagcaaga agagaaaagc atttcaattt gggacattta tttgcacctg gaaatgggga   69420
atgggctatc agaccagact tctatcctgt ccaacctgcc ttcattcagt ccttccacat   69480
tgttattctg ggtttggact gtgctggaaa gacaactgtc ttatacaggc tgcagttcaa   69540
tgaatttgta aataccatac ctaccaaagg atttaacact gagaaaatta aggtaagctt   69600
gggaaattct aaaacagtca cttttcactt ctgggatgta ggtggtcagg agaaattaag   69660
gccactgtgg aagtcatata ccagatgcac agatggcatt gtatttgttg tggactctgt   69720
tgatgtcgaa aggatggaag aagccaaaac tgaacttcac aaaataacta ggatatcaga   69780
aaatcaagga gtccctgtac ttatagttgc taacaaacaa gacttgagga actcattgtc   69840
tctttcagaa attgagaaat tgttagcaat gggtgaactg agctcatcag ctccttggca   69900
tttgtagcct acctgtgcaa tcataggaga tggcctaaag gaaggacttg agaaactaca   69960
tgatatgatc attaaaagaa aaattttgcg gcaacagaaa aagaaaagat gaatatcaat   70020
atctattata tctgtgtgga gtaggttttc tctggtctga ttttgacaaa tagaagagtg   70080
tctacagcgt ggtttgcctg tctgccctcc tggatgctat taaagctttg ttttgttgaa   70140
```

```
caatcagatg cccaactctg ttgccttgtg gaagatgagt aaatgcagtg cttcttaaag   70200
tggtttcttc tccctacccc acacatcttt tggtactacc atttggggaa gccaagcaag   70260
gatagtaaat tgatcagaac acagttgtgg gaatttggcc tgaagttagt gaaataaaac   70320
tttaaagagt ggaaaaaaaa aattttttaac aatgcttgtg atgtactaaa gaacaatttt   70380
atgaggcctt acttggtaat gtaataggct ctcttcaata cctaatactg tgatgttatg   70440
aacatgggaa catttggttt tgcaaagtgt tgtcatcaac aataagattc tcaagagcag   70500
aagtttccgc catagtatgc acagggcctg tggactttt gaatatttga aggactgtca   70560 tatgaaagg gatcaggctt agtgtgtagg actccaagag ctaggacaca acatgaatgc   70620
agatgccttc tctctagaac aaagaacttt tgaactgtaa cagctgtctg taaatgagtg   70680
ggccacccca gaggtcatga ccttatcacc atctgtgttc aagcatggca gggagaagcc   70740
ctgggcaggg atatctggaa ggagaaggac aagtggggac tttagggtcc cttctaatcc   70800
tgagagtctg gcagtgccct actcacccaa ggaccgttga gctaggccct gtccccaaac   70860
cataggccct gtgcccacac cctgccccaa taaatggctc aggaagaaca actgctatat   70920
actcatcagc aagaaatgcc ccaccatcag ctgaattatt taaaccatt tgatgagtgg    70980 ttttatggcc tttcttgaaa ctgatgttgt tattagcact gcctaatacc tttccttt    71040 ttggtttctt ggtaaaggtg tgtctgtatc ttgactttag cttatgcctg tcctgtgtga   71100
tgtgagtaga ccataatagc ccgagaaaat taaattatgg agtgcatttt gaaatgagca   71160
ccctcagatt tgattctggt gtcttcggct ggttttgcat aggttgtctg ggaaatatta   71220
taaaattcac tttctccccc cgaactcagg atcacaccca ccctcttgg agaagggaag    71280 agcacagtca ccatcgggct tgtgcaggct ctgaccgcac acctgaatgt caactccttt   71340
gcctgcttga ggcagccttc ccaaggaccg acgtttggag tgaaaggtac tgtctttaac   71400
aactagtgta cttttcaggg caaagttggg gggagagaat tgtaaaaaga acattgtcaa   71460
cagataaaga gttaagactt ttcagggac ttggtacatt tcttcactgc acactcagta    71520
catagtggtc gccccatgtt ggttccccg gcatgaaaa agagcagtgg gagccgccag     71580
ggcttcactg gatgcctcag gagcctgttc ctggggctgc gttgctcaag gctcccgcct   71640
cgagtgcggt ctcccatttc atcagggcct tctttgccaa gtgatcttga aacacggcca   71700
tccatatcgg tgtttgatca tcccagtccc ggggaaaggt cttccctct gctttagtct    71760 cggctcattg gagttgctgt gtggggcccg cagagctctc tggagacgga ctggctgtgg   71820
acagcgagtc gtgatgaaat tcctccttgg ccgtggtcgg gctgatatct ggcacttccc   71880
cattcattac tctttcttcc ctgatttatc atgaaatcat tccttagctc actttacagt   71940
ggtggttatt gctgcaatta cagtttgtcc ttggcacttc gtgattttt aagaatattg     72000 catttgtatt actgttaaac atattaataa cgtatctcat aaagtactga taacgcacag   72060
agtgtcatgc atcgtgtagt ggaatgaaca ctagggttgg agcgagaaag ccaaggtttt   72120
ggtcacagct gtgtttccta ccgccatgtg acccttggcc acttgagcca gtcacaacct   72180
ctcggagccg catctctaaa agtccaaaat gctgagagcg gcaccaggct cacccagttg   72240
ttgtgaggat caaatgagaa agcacgtaaa gaacgagggc tactgtcaaa tgatacacac   72300
atgggcggtg ttgttctgct ttaggaaaga gcagtccttt tactctaaca accaacattt   72360
tgagggatac gcagcatgac aaatctcaca tactattatc tgaaataaat tgaagtttat   72420
aatttactca tttgaggtgg ttatgcggtg gttttttgt ttttgttttt gttttgttt     72480
```

```
tgagacagag tctcacttgg ttgcccaggc tggaatgcag tggtgcaatc tcggctcact   72540
ccaatctccg cctcccagtt tcaagtgatt ctcctgcctc agcctcccaa gtagctggga   72600
ttacaggcac ccgccaccat gcctagctaa ttttttatatt tttaatagag atagggtttc   72660
atcatgttgg ccaggccggt ctcgaactcc tgacctcaag tgatccgcct gcctcagcct   72720
cccaaagtgc tgggtttaca ggcatgagcc acctcgccca gccacagtgt attttttta   72780 aacaaagttt gctcagatat gaaatcatat acaattgatt tagataaagt atagtcacag   72840
agatctaata ataaattatc aaatattct catatcctgg tatgttttac agtaatgaca   72900
tctgctctat ttttaccttt tttttttaag caaagaaaca gaggtatagt tagacaaagt   72960 gtcaacttt tttgttgttg ttctgcttgg atataaccat tagtgtctct cactgccttt   73020
tgttacttca tcttgggtgt gacgcctctc tgttgggttt ggggagctgt gtcccttggc   73080
ctgtgtccat cgtggcagct gtacttggtg accgtttga aatgcctctt gctctgttgt   73140
ttaggaggag ccgcgggtgg tggatatgcc caggtcatcc ccatggagga ggtaagacct   73200
tgaagagatg cgggtcagct atcactgtgt ttccttcctg acatcttgtc tctgctccca   73260
tccacacagg cccacagacc ctcatccata atcccaaagt cattaaggct ctgaaacccc   73320
aaaatgtttg cataactcat gcagtgacaa acctagtat ttactgtgat gagctataat   73380
tatatggatt ttgtacgtgc tacttggcgt gaatattcat atacattgct gtggaaaaat   73440 tattttgat taacaggtgc tgacctagcc cctgcttggg gtgttttaca aataaactac   73500
atgtaaatca cactgccttc ctaaacttca aaaaattcag aatcttgaaa ccctgctggc   73560
cttgcgggtc tggatgagag aatgtgggtc tgtgcctccc ttgatcatct gctgtactgc   73620
caagttcacg aagacttgac gcttcccctc tgtcaattca ggctctagtg cgtgcctcgg   73680
cagcatagat actaaaactg gaatgacaca gagaggatta gcatggtccc tgcacgagga   73740
tgacacacaa atttgtgaag tgtcccatta aaaataaaag accccaaaat aaaagagttc   73800
cagaggaaaa tgggcaaaaa gaactgacgt tgttaattct cacttctgta agaactccac   73860 cttttgttcca cataacctct tgttgcctg taactaacca gtgaccagct ctttttcagtt   73920 tcactctctg catcagcctt atcattcagg gcctggacaa tcttccaaaa cccaaatctg   73980
agcaggtcac tttcctgttc tgtcatttcc gccgttgcct gtcaccctcc agcacagcac   74040
aggaggtcct cgtgggtggc tgctcctgct tccctgtcca caagtcccca cctgccttct   74100
ctctactgcg tcaagctcct tgcagactct ttttttttt ttttttttga cacagagttt   74160
tgctttgttg ctcaggctgg agtgcagtgg cacagtctcg gctcactgca acctctgcct   74220
cccaggttca agcaattctc atgcctcagc ctcctgagta gctgggatta caggcaactg   74280
ccattgtgcc tgactgattt tttgtatttt agtagagacg gggtttcacc atgttggcca   74340
ggcttgtctg gaactcgtga gctcagacaa tccactggtc tcagcctccc aaagtgttag   74400
gattacaggc gtgagccact gtgcccagcc cttgcagact cttttcctgt tctctcttgg   74460
ttccaggatt ttcccatgcc tggaacattc ttccttttct gtcctcttta cccagtttag   74520
tcaaggtttt ttgtcaaggt tcttctctac cccacagact ccctctgtgt ttacggctat   74580
ctggttcagt tggctgtggc gagttgcggg cctttcttga ggtctcaggt cccagcattg   74640
agcagagtgc ccagcacata gtaggaactc actagaaagt acttgttgac tttgttaaag   74700
gaatagaagt gttaccccat ggaggtctga gtgtcaggga agctaaagag aaaatctgta   74760
ggaacttcaa gtactgggag tgggggtgag aaagagtagt ccaaggcact gctgaaaaaa   74820
atcgtcccag gcctcaggtc agaatgggga tgggtaccat tcatgagcca gcaagaccca   74880
```

```
gaaccaggag gccaaattag aggtggtgta caaggggcat acacagggga atggctcggg   74940
tttagccagc aaattggaag acattggtg  tcccgctggt ttagggcatc agctgcgtgg   75000
cttggaggag agagctactt ttattttatt ttattttatt ttttgagatg gagtctcgct   75060
ctgtcaccca ggctggagtg caatggtgca atctcggctc gctgcaacct ctgcctccca   75120
ggttcaagtg attctcctgc ctcagcctcc cgagaagctg ggattacagg cacctgccac   75180
catgcccagc taattttat  attttaatac agatggggtt tcaccatgtt ggtcaggccg   75240
gtcttgaact cctgacctca ggtgacccac ccacctcggt cttcaaaagt gctaggatta   75300
caggcgtgag ccaccgcgcc cagccaagaa gactacctta tgagggtaga gtgggccaga   75360
cacactcagg caatttgttc cttgaagttg agtgcctcca gtctttcttc catctgtatc    75420
ctcccagctc tgagcaccgt gcctgacact tggtggatgt tgttgactg  tgtgccaggc    75480 acagacaata tgtactggac ggaacataat aaatcaccat aggggaaaat gttagaataa    75540
attccagatg ggctgaggaa ttgaaagtga aaacactatg actggaagga tgggaaggag    75600
ccggccttgt gaagaatgag ggagagcatt cagccagtgg gaactgctgg tgggaaagtc    75660
ctgaggcagg aaagggtgtg gcctgttcag ggaactggag gacaccaggg tggctggagc    75720
cccgtgggcc agcgggagtt ggggggttg  aggtagagaa gtgtgcaggc gccagctctg    75780
tcgagcgatt gcaatttgta gccaagaacc tggatttat  ttgaagtgcc aaggtcagcc    75840
attgaaggga tcttgacaga taacacaatg cagattgagt tttattaaaa tcaccctgtc    75900
ttctgtgtga tgaaaggacc aggggcctct cagtagacac gatgaatcca ggaggaagac    75960
tatggaagta gcctagggaa agatgtcagt gacttggccc aggatggggg cagtgaggat    76020 ggaaagagg  aaaaaacagt ttaagatttg tttgctgatg tttgcaggat tagatgttgg    76080
gggttagaaa agaggaggat tcaaggacga catccagggt actggcttga gcaactcagt    76140
agactcattt gttgaggcag agaacagggg agtgatggta tgaggtttga actgtgtggt    76200
gtggggtgtg gtggagggtg gtagtcagaa ggagggagtc agtttagagg cctatgaaac    76260
atgcaggtgg acatcaagta gacggctgga aagaaaaact tacattccag ttgtgaaatg    76320
gccaaagagt tcaatagaaa catcgaaaaa gaaatattaa ctaaatgcat attcatcttc    76380
accaataatc aagtaaataa atctacatta aaaccactat caggccgggc acggtggctc    76440
atgcctgtaa tcccagcact ttgggaggct gaggcgagtg gatcacctga ggtcaggagt    76500
ttgagaccag cctggccaac atggggaaac cctgtctcta ctaaaaatac aaaaagtagc    76560
tgggcgtggt ggcaggcgcc tgtaatccca gctccttggg aggcggaggc aggaggatca    76620
ctcaaacctg ggaggcagag gttgcagtga gccgagatca tgccactgca ctccagccca    76680
ggcaacaaga gcgagactcc gtctccaaat aaataaataa ataaaaataa aaccactatc    76740
agttaccatt ttacttgtca aattgacaaa attggattt  tcaaaatagt tatgatacca    76800
aattttggca aagaaattga atggactcc  cacacactgc tggaaagtgt atgttgataa    76860
aaacacttca ggaagaagag tagaaataca tattaagtgt tttaccgtgc atatcctttg    76920
gcccaaataa attcattttt agtgtaccct aaggaaaaaa tgaatgtatg gaatataga     76980 tcattttaaa ttaaatatac cctcacatag tttataacat taaaaatgg  ggggataata    77040 ataggacatc aggttaactg tattttgaag aatctttaat gatgtaaaaa tgcttgctat    77100
gttgagagtg taagagctaa agtataaact gttacgatgt tatgattcca atatttaaaa    77160
gtacaaatat atatttataa aatatatata catatgtaat ttttcatgtt ttctccagtt    77220
```

```
aacattattt tatgttataa agtaaaattt taacaagaaa atatttaacc ttccaagaaa   77280
ttaaggaaat gcagctttaa aaagaataac actttctcaa ctattaaatt atttcttagt   77340
ctaaaagtta ctttatttct gaagtaactg atctactact agtgttttgc agatgacact   77400
tcatctcttt caaaaagcaa tttggtgata ttatcaagat ctcaaaggcc ggatgtggtg   77460
gctcatgcct gtaatcccag cactttggga gtctgaggtg ggcagatcac aaggtcagga   77520
gtttgagacc agcctggcca acatggtgaa accacatctc tactaaaaat acaaaaatta   77580
accaggtgtg gtggcaggcg cctatagtcc cagctacttg ggaggcagga gaatcccttg   77640
aacctgggag gcggaggttg cattgagctg agatcatgcc actgcacacc agcctaggtg   77700
aaagagcgaa actccgtctc aaaaaaaaat aaataaaata aaaatacttc atccctttca   77760
aaaagcaatt tggtgatatt atcaagatcc caagggctgg gcgtggtggc tcatgcctgg   77820
aatcctagca ctttgcgggg ctgaagcgag aggatcactt gagtccagga atctgagacc   77880
aacctgtgca acatagtgag actgtgtctc tacagaaaaa aaaagaaaaa aaagaaaaga   77940
aagagagctc atttaaccta gtaactacct cctgaaaata tattactcat tagcaattaa   78000 ttttttttaat aaaaggaaaa gctatttgtg tatattcttt ataactgtgg cctttcttgt   78060
aaaagtgaac atttggtagt agcgtatata tccagcctga aacttttggt acatctaccg   78120
tatacagctt ctataaacta tacaaaagat tattatagaa aaagttttgt gaaaaacgaa   78180
acttggaagt ttgtaggaag atgattctac aaatgataat cgagtgtgct catgagactg   78240
gaaggaaaat aacagaatga gtagagtcat gagggtaaaa tactctattt ctccaaagtt   78300
ctgtaatatt tcatattatt ttattgttac tgtttatttt atgccctgcc tcactccaaa   78360
gtatatttga tatgatactg ttttctagat aataaaacaa tgaataaacg tagtgagtga   78420
ctataaggag attcattatt aaatgcatca gaatgttttg ccttaacctg aggatggaag   78480
aatttatgat ctgagtaatt gctcaaaggt tctttgttgt cacgtggaag gctttgacct   78540
tgattttctg atttaggcat tcctatagac tcagctcatt ataaggatat gtaatttgca   78600
tgctatttta tttattcagt ccttaaattc catagttgtt taaaacaaat aggaagatgt   78660
cttagccgag cacagtggcc caagagctca taaccagcct aggcaacata gcaagacccc   78720
catctccaca gaaaattcaa aaattagcca ggcacaatgg tgtgcaccta tagtcccagc   78780
ctactcagta ggcttaggtg agaggattgc ttgagcccaa gagtttgaga atacagtgag   78840
ctatgatcat gccactgcac tccagcctgg gcaacaaagc gagacccctat ttctgaaaat   78900 aaataaatag aaagatatct tatttctcta gttcaacctt cacttgactg gagacatcca   78960
cgccatcacc gctgccaata acttgctggc tgccgccatc gacacgagga ttcttcatga   79020
aaacacgcaa acagataagg tgagaaggat gccttgctag ccattttggg tattgtatcc   79080
tggaattcct ggattcttaa ggagtttgtg gaaagaattc tggtgtctgc aaactctgaa   79140
atgttattca attcaatttt gtgattttta catatgtccc tgtttcccaa ggagaaggag   79200
ccatcctttg atcagattct caaatgggtt tatgagcact gccaagttat tgggagaatt   79260
gtagtatgtt gtaaaagcca aatattctct aagatgagtc tttagtttta aagatggtag   79320
gtagaccagt tctcttcatt ctggtcatag gtccaatctc tgatctgttc taagggggatt   79380 ggacagatgt cgttttaaga ctaatgttat gtggagctat tttagatgtg ctgaaaagat   79440
gtcagagacc cttattgggc ttcatgtgct tgtaggttaa gagttaaacc acaccccaa    79500 aggggacagc ccaccagaag ctaattcctc acagatatag gacatagata aaaggggtac   79560
cttctggcac attttacaac aagggtcctc actttctttta attaaagtag ttccttagtg   79620
```

```
agtctttgct acataatcca gatacatctt catatggtag ttgtagcgat atagatcaag    79680
aaatatattt atgcaaactc tttgcaatgt gtattatttc agatcttgtc agttttatga    79740
aaatgacaga atttaagtca acattgttta tattagccca caaattttaa tagggtcttt    79800
tatctaaata gttcggttat aaatgcaatg aattttgtc atatcctgtg aattgtccaa     79860
gttcatggac aactaacttt tgtgtggtct cattttgtt ttgtgttttt aggctctgta     79920
taatcggctg gttcctttag tgaatggtgt cagagaattt tcagaaattc agcttgctcg    79980
gctaaaagta agtttccagt tagcaattct ttaaaaagaa aatatcgtag aaacgcatca    80040
gaaagattgt caaagcctga aattttcaac ttggtttgat tttggttttc agatatcctt    80100
ttgggtatta aactctatag agaccgaaca ctggagcaga gagagcacag tgttggaagc    80160
ctgaaccctg gttctacacg aaagagccag gtggacaaat taattaacct tttttggtct    80220
cagtttcttc gtctatgaaa tgagaggact gttttgctaa tttatgagta ctctagtcaa    80280
ctgacaagtt agctgggcac aggagcacat acatacctgt agtccgagct actcatgatg    80340
ctgatgtgag aggtttgctt gagccaagga gttcaaggtt tatagtgcac catgatggcc    80400
cctgtgaata gccactgcat gccagcctga gcaacacagc aagagcccat ctcttaaaaa    80460
aaaataacaa attagaattt ttggtgagtc cttctctttc taaagtgaaa tattttatg    80520 aaatttgtta aatttctagg aaattatagg ataacctttg aaaactcatc tatctcattt    80580
gtggttttct gtttttgttt gttttgtttt ttgagacaga gttttactct tgttgcccag    80640
gctggagtgc agtggcatga tcttggctca ctgcaacctc tgccttcctg gttcaagtga    80700
ttctcctgcc tcagcctccc aagtagctgt gattacagac acgcaccacc gcacctggct    80760 aattttgta ttttcagtac agatgggatt tcaccatgtt ggccaggctg gtctcaaacg     80820
cctgacctca gtgatccat ccaccttggc ctcccaaagt gctgggatta caggtgtgag     80880
ctactgcgcc cagcctcatc tacgttttg ttgcagcaaa cactacaatt atacttgcgt     80940
atgccatctt aattcttaaa acctgtctta tctttttct gatgccattt gctgcctctg     81000
gtcttctaat catattgctt gctactagcc ctgtttcaga gactaaaaaa taaccctaaa    81060
tggtataact taacaacctt actggttggt attaagtggt tttaaaaatt cacctcctgc    81120
ctcttactga accaagttca gtgtgttgaa ttagtgagta attccatcct cggcagctat    81180
aacaacatgc agtttctgtt tcccagatct ttttatgct tcattaaaaa tcactatttt     81240
gccaggcaca gtggctcacg cctgtaatcc cagcactttg ggaggccgag gcaggcagat    81300
cctgaggtca ggagattgag accatcctgg ctaacacggt gaaaccccat ctctactaaa    81360
aatacaaaaa attagccggg cgtggtggca ggcgcctgta gtcccagctt ctcgggaggc    81420
tggggcagga aatggcgtg aacccaggag gcggagcttg cagtgagccg agatcgtgcc     81480
attgcactcc agcctgggca acagagcaag actccatctc aaaaaagaaa aaaaaaaag    81540 aaaaatcact attttgtgtg tgtgtgacag tcttgctctg ttgctcaggc tggagtgcaa    81600
tggcacgatc tcggctcgct gcaacctccg cctcctaggt tcaagcagtt ctgcctcggc    81660
cttctgagta gctgggatta caggtgccca ccaccatgcc agcgaatttt ttgtattttt    81720
agtagagaag gggcttcacc atgttggcca ggctggtctc gaactcctga cctcaggtga    81780
tccacctgct tcagcctccc aaagtgctgg gattacaggc atgagccacc acacccagcc    81840
aaaaatcact ttcttaagat gttttattta cacaaaataa ataggaagat ttcttggctt    81900
ggtgtggtgg ctcacccctg taatctcagc actttgggag gccaagacaa gaggattgct    81960
```

```
tgagcccagg agttcatgac cagcccaggc aacatagcaa gacccccgtc tctacaaaaa   82020
atttaaaaat tggctgggca ttaaaagttt taattttttt ttttctcctc cataaattag   82080
gaataactta ctttgaaaca taggaataaa cttaacttga attactggta tttgtatttg   82140
aaaaactaaa gaactgcggc atcaattata tggacagaca gcagtttatg tctcttctga   82200
gcagcgtaca tggtgccac atagagcagc ccaaggagcc cctggctaac gcagccagca    82260
gcaggcacaa gtggtagtta gctgtatgct gtccactgca ggacatcttc agatcaatcc   82320
ttttcagagt ctattacgaa ctcacagtat cttactcgta gaagaaatct ggccataggt   82380
atttgtctga cttggcctaa cctataattc actcaaagtt cagtttagtt tagtttttt    82440 ttgtttgttt tttgttttt gttttttttt gagacggagt ttcactcttg ttgcccaggc    82500
tggagtgcaa tggcgcaatc ttggctcact gcaacttctg cctcccaggt taaagcgatt   82560
ctcctgcctc agcctcccaa gtagctggga ttacaggcat gtgccaccac gccaggctaa   82620
ttttgtattt ttagtagaga cagagtttct ccatgttggt caggctggtc tcgaactcct   82680
gacctcaggt gatctgccca cctccgcctc ccaaagcgct gggattacag gcgtgagcca   82740
ccacgcccag cttagttttg attttgtttt ttggttttt ttggagacag agtcttgctc    82800
tgtcactcag gctggagtgc agtggcagga tctcagctca ttgcaacctc tgcctcccag   82860
gttcaagtga ttcttctgcc tcagcctccc aagtagctgg gattacaggt gctctccacc   82920
atacctggct aattttttta tgtatttta gtagagacgg ggattcacca tgttggccag    82980
tctggtctcg aactcctgac cttaggtgat ccacctgcct ccaccttcca aagtgctggg   83040
attacgggca tgagccaccg cacctggccc agtttagtgt tttttttgtt ttgttttgtt   83100
tttgagatgg agtttcgctc ttgttgccca ggctggagtg caatggcacg attttggctc   83160
accgcaacct ccgcctccca ggttacagcg attctcctgc ctcagtttcc caagtagctg   83220
ggattacagg catgcgccac catgcccagc taattttttgc attttagta gagatggggt    83280 ttctccatgt tggtcaggct ggtctcgaac tcctgacctc aggtgatctg cccaccttgg   83340
cttcccaaag tgccagttta gttttttaaa aggctttacc aatcatggag aaaataaaat   83400
tagagggata attttggtga cccctttgctt tctgtttctt ctcaaacttc tcacctttt   83460 tcttcttaat cattagaaac tgggaataaa taagactgat ccgagcacac tgacagaaga   83520
ggaagtgagt aaatttgccc gtctcgacat cgacccatct accatcacgt ggcagagagg   83580
tgggtgctgg ggagatgcca gcaggctgat ggccaggtgg ggaggcgtgt tcgagccgaa   83640
gcgcttaaat tcagaaactt acagtttgat cctgtccagt gatcttccca gcctgtgctt   83700
catattccca ccatttattt cagttactat tatcgtacca ccctccctta tccttgcctc   83760
caattaaaac aaaaattctg tccagggtca atccctatct cctctgtgtc ttctaaattt   83820
ccaaggaaaa ttacctaatt ttctcttctg tttctctctc ctttggcctc ttgtatctat   83880
attaagaaaa aaaaaagaa acttttttta aagaccacgc ctcccggggct ttgtcctgct   83940 cctcctccac ccaccatccc accttcttct gttcacttcc ttaccactgg ctctcggcag   84000
ctctctgtgt gttccagtg ctggatttc ctccaagtct gatatgtgct ttcacccact    84060
taacgaggca tcgctccact gcttcacatg catccaggtg gagtccccgt gagctcccca   84120 ccacctgac ttccctgctt ccctctcagt tgtgaagtcc ccttccttct cccacactgc    84180
cctcagtctc atcgctcact atgggatgag acagagggaa atgcactaaa caggaagtta   84240
ggagccctga gtgtgtgtct cccctgccac tgactcactg catgatctcg agcaggtcgc   84300
atgcatgttc ttggcgttgg agatggagat ggtcacatac gctgcacaga aacacggcaa   84360
```

```
ccacatttta tgaaccctgt gcaactgcag aaatgttcaa tggcatggat ccctgattct   84420
tcctggatta ttcttctcat acttgtgccc tcatttacct ctttatgctc acatttggaa   84480
catatttatc agatgcgcat tttatagcag ttcccgacta atagattatc ttgcttccgt   84540
ttccatcccc cagttcagag ggttcacatt aacagagata tcccgttgtg atcagaggcc   84600
tccagtggct ccccacatcc tgggtgatac agttgccatc gcagagcttg gtcttcagga   84660
cacccgcagt ggcttccctc actctgctcc ctgcctgctt tctagtcagc agtgccgacc   84720
tccatcctcc tgccagccct agctgggcca tctccatcct gtcctgcc taggccagtg     84780 ttgccctcta agatgcaccc aggtctcgtc ccttcaggga gcttcccttc tgggaatcca   84840
cccagccagt ccattaagaa tttagtgtag tcccacaaac catgaggtag agagacaaag   84900
accagagact gagcgttggc tctgcggttt atgggctgca caactttgga cagactgctc   84960
actcagtttc ctcatcttta aaatggaatc ataattccag ctgccttgct gggaggcttc   85020
actgaaacat aagcatcctt tccagaccca aaagctctgc ccacacgatc atcagaagtc   85080
actgtggtga tagctgtatt gagtagagtt ttttgtttgt tgttattttg agacagagtc   85140
tcacttgccc tgtcacctag gctgaagtgc agtggtgcga tctaggctca ctgcaacctc   85200
tgcatcactg gctcagtcga ttctcttgcc tcatccttac gagtagctgg gattacaggc   85260
acacaccacc acacgtggct aattttttgta ttttactaga gatggggttt caccatgttg   85320
gccaggctgg tctggaactc ctgacctcaa acgatccgcc cacctcagcc tcccaaagtg   85380
ctgggattac atgcgtgagc cactgtgcct ggcttgggta gttttttga gtgtctttgt    85440 ctcccaaact aaactaaaat ctccttggaa actttatggt ttttttttg tttttttttt    85500 gagacagggc tcattctgt cacccaggtt ggagtgcagt agtgcaatct ccactcactg     85560
caagctctgc ctcccaggct caagcaattc tcctgcctca gcctcctgag tagctggagg   85620
ctgtgcgcca caacactcag ctaattttcg tattttagt agagatgggg tttcatcatg    85680
ctgcccaggc tggtctcaaa ctcctgagct caggtgatct tcctgcctcg gcctcccaaa   85740
gtgctgggat tacagacatg aaccactgca cccagcctag aaactttcaa ggatacattt   85800
ttcattttga aataagtaat aacattatag agattttgga aatgtctcaa aagaatttta   85860 aaaccttgc tatactaata aaactactat tcatagtttt ttgtgtgcat ctagtttttt    85920
ggtataactc tagttataac tttagtgtat agattttata tcctacgagt ttcattcatt   85980
tatatcataa gcattttgta ttttgttagc tctttgttgt aatggccatt ttaaatactc   86040
tagaatattc ctttgtggat gaaccacaac ttacttaagc aaggctcagt tcttgaaaac   86100
accaacagca tttaaataa tggacatgaa tactttaagc attttattga gaagcctaca    86160
tattttcttt gaaattttt tttataacta ggaagattta ttattaaaat gtcatcatgt    86220
ccaaaatgta ttgtcatctt ttttttttttc aaagcatttg tgattttgtg ttactcttca   86280
aaactttttt ggaggtttac tgatgatagg aaaatcagga aggtggaaat tagtgtattt   86340
taaaccaagc atatggatgt gctaaaagag aaagttttat gccaattggt attctttggt   86400
gtctgctttg gggttccagc ctgagcagcc atcagaaaca gggcaatggc ttagacatgg   86460
atcttggaag agaaaggcta catcatcttt tatacctggg tctggtctgc aattggtttc   86520
tctctggagc caggaaggac tgaagtgttt tgtggttgtg aatcacttt aatgaaagtg     86580 acaactttac aaaattcttc cggaaaaaaa tttgaattcc attattgttc agggcactga   86640
agtaaagaaa actttattgc tgtggacaag ctacctgggt cagaggaatt tggaatgaca   86700
```

```
tttgataagt agtttggctc ttatgaccat gaattaataa cagaaatagg actcttcatc   86760
aaaagaattg agaacatttg ctagtagggt tttttggctt aaacctagaa ctaatgtaac   86820
ccttgtgatg aaattggatc cttatttgat ttgacaacta gagcaggaca gtcagggtgc   86880
acggtggtgg gagtgagacc ctcttctcag gccatatgga tgttgcgcca tttaatgacc   86940
acccctccct ttcagcctgt gtacaaaatc tgatgattgt ttcatctttt tttttgagac   87000
agagtctcac tctcttgcca ggctggagtg cagtgtgcga tctcggctca ccgcaacctc   87060
caactccctg gatcaagcaa ttatcctgcc tcagcctccc gagtagctgg gactacaggc   87120
atgcgccacc atgcccagct aattttttgta tttttagtag agacggggtt tcatcgtgtt   87180
ggccaggatg gtctcgattt cctgacctcg tgatccgcct gccttggcct cccgaagtgc   87240
tgcgattaca ggcgtgagcc accgcgtcca gcagattgtt tcatcttatg cctcataccg   87300
aaagtttaaa ggcctcatgt tcctggaccc agagtggaac aaggaaccca cagacctttc   87360
cagaaatact aacataagc agaagaaaat atagacatac agccattttg ttacagagca    87420
taattttgca cagatgagcc tctgcctgtc cgagccccgg ggcctcacag gcttgccgtc   87480
tctccatctc cctcgcatgc ccaactcctg gccatggacc aagggcccac aagcctccct   87540
cagcctcagg gaatcaacca tcaagtggct ggttccttgc cccaacaaca ctctagggaa   87600
tcagtaccgt gtcttccact ggggccgaaa cagtggacct gccctgatt gaacaccttg     87660 tactgccagg ctcttggcca atattggctg tttcatcagc cattaggcat actgtggatg   87720
ttccttagga catagtcagc actgtagtat agtcagcact gtagtactaa aagggatggt   87780
ccagagcaaa aaataagcaa acagatctcc cccggctgcc tccaccccca cacccactgg   87840
cattgtccta gcatgcctta cataagaggc tggcactgtc ttcactatat ctctgtacag   87900
ctggctcggg actaggcaca agtagcccct caatacatac tccaggagtg aataagtgtt   87960
tcttattcca cctttagttc tatcattcag agaccaggaa ttccattttg gatcactaac   88020
ttagggttac tttctagtat ctttcttgtg ggctggaatt taaccttcac atttcttatg   88080
tatcactgat gcatcactta ccgggccatg ttaaaggcag aggtgggctt tggaggccac   88140
tgattctagt tgatcttgcc agacattttt tttttcttgtt ttctctttgc tagataaaaa   88200
acagctgaat ttctcttgtt gattttaaag aaatttgata aaaagattcc ctcaatctgg   88260
tgccaagatc gtgtatacta cagagcagga aagaggtttt tagttgattg actttgcacc   88320
ccatgtacat cttgggaaga acagtggtgg ctgaggatac tattgaaaag caggcctttc   88380
attttgtata tgctctgctt atagctgaaa aactcataaa gaaggtttct gtgtgtttat   88440
atgagtgtca gttggtgttt gtgtgagggt gtgagtgtgt ctgagagaga gggagcttgt   88500
tataaagact aacaacagcc gagtcaggga acagccatag gccaagaggg caagctggcc   88560
tgctggtgct ttgcgtatga aagaaaaggt taactttctt catcctacgg atgcctatag   88620
taccaaatac gtaatttcca tcaccatttt cataagtgct gtatcgtata cattgagtaa   88680
agtggatcta aattgtcaat gtggacagct tgttatttga agctgcataa attaacaaag   88740
tcagtgtact ggctttgttt tgttgcattg gtattcacta aaccaaacct aattttcaca   88800
aaatgtaaat aactgcaatt cttgttttgt tttgttttga cagggtct ggctgggtg       88860 cagtggctca cgccagttat cccagcactt tgggaggccg aggcaggtgg atcacatgag   88920
gtcaggagtt caagaccagc ctggccaaaa tggcaaaacc ccatctcttc taaaaataca   88980
aaaaattagc caggcatggt ggcaggcgcc tgtaatccca gctacttggg aggctgagac   89040
aggagaatcg cttgatccca ggaggcgaag gttgtagtga gccaagatca cgccactgca   89100
```

```
ctccagcctg catgacaaaa aaaaaaagag agacaaggtc tcacttccat ctcccaaatg   89160
ggagtgcaga gacacaatca tggtcattgc agcctcaacc cccaagactc aagcaatcct   89220
cccacctcat ttttgtattc tttgtagaga caaggtctca ctgtgttgcc caggctgttc   89280
tcaaattcct aggtgaccct cccgcctcag cctcccaaag tgctgggagg tgtgtgccac   89340
cacacccagc caataactga aattctaata agccagtgaa gaaataaag agaactggta    89400 cttgctctat tcaccattca ccccgccac ccccacaat tctactttat ttactttgc      89460 tttttaaaat tgtggtaaaa tatacataac gaaatatttt tccccatttg taagcacaca   89520
attcatggca ttaaatacat tcacaatgat tgcactatca tcactatcta tacccagaac   89580
cttttcatta tccccaacaa aaactcctta tccattaaat aattactccc ctcttctgcc   89640
cctgcctatt ctaggtgcct gatataagtg gactcatata gtacttgcct ttctgtgtct   89700
ggcatatttc actatgcacc atgttttcaa catccattca tgtatcaaca tgaccttctt   89760
ttatagccgt ctaatattcc attgcctgtc tgtgccacat tttgtttatc cattcacctg   89820
ttggtcgctt cctcctttg actattttga atagtgctgc tatgaacatg ggtgtacaga    89880
tatctgagtg tctcctttg gttctttcgg gtaatgccaa gaagggaagt tgctggttgg    89940
gttttttttt tttttttttt tttagaggg ggtctcactc tgtcgcccag gctggagtgc    90000
agtggtgcaa tctcagctca ctgcaacctc cgcctcccag gttcaagtaa ttctcctgcc   90060
tcagcctcct gagtagctgg gactacaggc acacacaacc atgcctggca aatttttata   90120
tttttagtag agatgggggtt tcaccatgtt ggccaggctg gtctggaact cctgacctca   90180
aacgatccac ccacctcagc ctcccaaagt gctgggatta caggcgtgag ccactgtgct   90240
tggcctctag tggattttttt tgtttgtttg ttgtttattt gattcttct ctatgtctac    90300 ccactagatg gtcagcttgg gggagcctga ccttttctct ttcaccctct gcaacttcct   90360
gagcatcaga acaatgccag acacacacca ggtggctggt ccatatttgt cgactgaatg   90420
actaatctgt tctctttcag tattggatac aaatgaccga tttctacgaa aaataaccat   90480
cgggcaggga aacacagaga agggccatta ccggcaggta ggtggtgctt tcttcccggg   90540
tgtggctctg ttcttacgtt catttctact ggcctgggag ctcactcttt gcctttcttg   90600
tctcatcccc aacctgttgt ggccagtggt tctctcactg ttttgggtgc tcagcagggc   90660
tgggagagga tcagaagaca tagaggctcc agtgtctttt taccatcttt tctatgtatg   90720
tttatttcat tttctttttt tcatgtatgt ttccaattgt gtttccagga agagccactc   90780
agggtattct ttgaatataa attctcactt attttattgg gaaccatcca ggtaatacta   90840
catctgcata actgataaat gaaaatctca gacacattac tcaaatttca tatatcaaag   90900
aacaaacacc tagttattag acttaatagc atgaggattt tttaaaggat aatggcttat   90960
taatacaaaa atggcttatt aataaaatac agagaatgca gaagaaaaat tatgtctgac   91020
ttcattgtaa tagatattgg atgtgcgtca atggcactta gggaatacaa attaattcct   91080
atgatttttc atccaggcac agtgggcttc taaattgtgt tgtgtttttt ttctttttga   91140
attgattata aactgtacat ttaagaacag ttttagattt ctgtccttta tgttaagttt   91200
ttattagtga aaaagagtc accttactat aataaccaat ccttacgcca aatagacttg    91260 tgacctttg aagtgtcttg aattaaaaag tgaatgtagg tattggatta agaagagaaa    91320
cttaagttcg tggacctcgt ctcctcccag tcctgtaact tacacacaca cacacaaaca   91380
gatttcaaat atccatgcta gcaaactgga atcattgcca tgaagtttta gatagttctg   91440
```

```
aaaaatagga agatggaatt agattgatga ttaaaaggac agcccaaaat atggtggact   91500
tccatcctta acaagcattc ttgcttttca tgttcttagc ctctcctgct aaagtgggag   91560
ctttataaaa gcagaggtta ttcccctttt tatttgctgc tgtgttccct atgttcagaa   91620
cagaactttg ttacatatag tcgtaagtgt tcagtaaata tctgttgaac aaatgagtag   91680
aataagtaaa agacaattta tggatacaga actaaaatgc caacataaaa agatgttcat   91740
gaataatcat aaaactgcaa attgaaacaa tggagtatca tttacctagg agcttgtcaa   91800
gtgaaaatag taggtactaa atgctagtga ggatgcaatg aaatgggggc atttatgcag   91860
cgttagtggg agtagaaatc cttttttggat gagtttgtta ttactaaaat ttgaaatgac   91920
ccaacaatta caactttgga actaaaaata ttttaatgaa agaacaaga aaatgtgtaa   91980 cgtacaggaa aaaattctgt gtattaggat atttgttgtg ccattatttg cagcggtgaa   92040
aattggaaac aatccaaatg tccaacagta gagatggttg catatatttg gtccgccatt   92100
ttgtcccatg ggagagttga aattaataaa tgtgcgtatg ggtgtcttga catgagtaga   92160
gagctctcat acaccattgg aaaggttgta aaaaccatt taaaactttg aagtaaaata   92220
ctgatattgt aaacctgttt atgttaagaa aaacccagcg tgtttactta cattataggc   92280
acttacaact tatttgtgta tataagtgcc tagaatgaaa agtagaaaga tgtatgccaa   92340
ctgttggcat tagttgcctg tgtaataaaa gcgagtattg aaaaggccct ttctctgcat   92400
agttttttac tgtttaggta ctggagagat ggaagattca cagtggcctt gatttcagtg   92460
cctactctgt gcattgtatt gatagttcca ttacatatat tagcacagtt catttgtaaa   92520
gctgatttgc aaatgaggaa attgggatgt tatgttaaaa aaacttgccc aaggttatat   92580
cttgtgttgc ttcgtgcata gatattttta agtaaaaagg ggttatagtg tatttaagag   92640
ctttaactgc ttttttattta tcataagact gtagtgaaga catctttttta tgtcgataaa   92700 ggtagacctg tatcttcatt tttaatgacc acatcatatc tcatagaggt accatagtag   92760
attcagccat ttccctgtta atgaacatgt agagtgtttg cagtttcagg ctatcacaag   92820
taagctgtag taagtataca catatatttg tgtgtatact tgatactatc cttaggatat   92880
tattccagat gtgtgattgc agagtccaag aggatacaaa tttccaatgt tgacatatgt   92940
tttgacatta acttccagga aattcatacc aattcacatc cttgccaata tcccatattg   93000
gcctttgttt aaatgtgtgc taaatccctc atttgcccta tcgtgattat tacacattgc   93060
atacctgtat cagaatagtt catgcaatcc acaaatatat acacctacta tatacctaaa   93120
aaaatgaaaa ggtaaatact aaatcaataa atgtgtgata agctgatgaa caataacgtt   93180
ttcattggca tctttatatg atttttgaaat attttatttg caaaacagaa atgagcagcc   93240
ttccgctatg cacgtcattt agtcattaaa gtgaatgaca gtgatacttt aattgaccca   93300
gtgtgtttca ttttttttat gctcaagatg tgaaattttg taattgtaac aattacaaat   93360
gaagagcttg aatatcgatt atatattatt cttatttaca cagctaatat ttcaagaatg   93420
tttctagtct catgttttgt acagaaaatc tccatatttt ttagtcattt tctcatatgc   93480
actgtttata atagaatggt agtatagaga accctaaatt tcatacaatg aaagaccact   93540
tatgtttgga atgagttata ttgagaatgt ataattgaa tatagttgta tttgactttc   93600
aggtaatatt ttttcactaa atcagtgact aatgcaatct caaccaggaa gtagccagaa   93660
agctccttat ttccttcctt tccttacttg tcagtgatgg aaatggataa taaaatgtct   93720
cataaggtga tcccaccagg gcacagccat tctctctctg cgtaagcttg aacttgtctg   93780
gctcacactc cccttgggaa gaagagaatt aagctggggc gtaatgaagt ggttctgtcc   93840
```

```
agagaaacat tcctagtggc tgaattatga ggaggaggaa gtacacattc ctgtgtccct    93900
tttattccat gttggacttc gtacaacgtg gagccacagc caagagatgg gaataggaag    93960
tcctagaact ttttgcaaaa agtctgtgct ctctagcttt cactactgaa agcttcaaga    94020
tctgatgtgg ccatatcctc ctgggcagct gaaaattgag tctgtgccac cagttgactg    94080
ggttgccctc cctgctgtgt tgagatccag ctctgggaaa gtagcctcac atgcaggaag    94140
ccagcatctt tcactgcccc ttatctctgt gccagacaga caatgcagcc ttcttgacag    94200
acctattact aacaagggag gtgggcccgta ggctagtcat taattcatct gatgcatatt    94260
gtatgcctac tgggtctcat gctccgtgct ggggattcag aagtgaacct gcctaatata    94320
gtccctgccg tcatggcact tacggtccag tggtagactg ataatgacca cactagactg    94380
ataatgacat tagtaatcaa ttaagtctga gacatgctac aacagcaaac catgtggtag    94440
tgctgtgagc gggtgtaaca ggggtcctaa ctcagcccac cctttgctga gcagagcatg    94500
gcaaagagca cattccgcct gggaggccac cctagggagc accaggcaca aaccctgcat    94560
ggtccagaca cgcagaaaac tgatgggatt gcatgcatgg cctttgagg gtagactctc    94620 tgggcctgtg gttgcttcat ggctgaagtc cagctccttg tgggaatggc catcccactg    94680
gcactgtcgc tgaccactac ctgtgtttgg gctggttcag gcgcagtttg acatcgcagt    94740
ggccagcgag atcatggcgg tgctggccct gacggacagc ctcgcagaca tgaaggcacg    94800
gctgggaagg atggtggtgg ccagtgacaa aagcgggcag cctgtgacag cagatgattt    94860
ggtgagtgtt tccaactcgg aagcttcagg gagtggacgg tcctcgttct tcgttaccag    94920
aaaaagaaag gttttcttcc ttttatcagt gagtgtaatg aggatacaga aaaagtttcc    94980
acacacacat ttcttccccg acaagcatgt ttgcctaact gcttcctaat gttctcatag    95040
tcatatatga cgtgcttatg cctggctgca acaaaaacat gtgaaattta tttcaggagc    95100
tttccaccat ccttgccaat cctgatctct gcttctgcct gggctgggga ggagtcaccc    95160
ccctgcagtc acttggtgac ttttaaaaaa tgtaccttct atgcctgcct gaaattgagg    95220
gcaaatcacc tttccaagga acagaaggaa gtggctctgc ttccatgaac aggaagataa    95280
agttaaaatt ggcacatttc tggcaccagc ctggcttatt atttaatttg gggccttaga    95340
tttgggtttt gtattataaa agcaaatctc tgcctcaatc agtcttgctt ttctagttcc    95400
cctttgagta gttgtggtgc tttctgtaaa gcttccatgg aacaccattt cctttttag    95460 tgcttttttct aattggcatg ctagtcttct tttcttcttc gtctttctgg tataataaca    95520 accttttcctg ttaactttttt tttttttttt ttttttttctg agacagtctg gctctgttgc    95580
ccaggctgga gtgcaatggc acgatctcag ctcactgcag cccctgcctc ccggattcaa    95640
gcgattctcc tgcctccgcc tcctgagtag ctgagattac aggcgcacgc caccacgccc    95700
agttaatttt tgtattttta gtagagatgg ggtttcacca ggttgtccag gctggtctcg    95760
aactcctgac ctcaggtgat ccacccaact tggcctccca aaatgctggg attacaggca    95820
tgagccacca cacctggcct tttccagtta acttaaactc cacatattcc ataggtgttt    95880
tgtttgcttg catttttgta tataagtgca tgggtgtgga cacaggcctc taagatagcc    95940
attactccaa atttaagttt actttcccat atactgaatc tcctacaata atggaactta    96000
aaatgcacac tggtgattgg taagcagttg tgaacagaga gaggcaaagt catatttttat    96060 taatttcaag ggcttagggt ataatttgaa ttctttttca aagtgtccgg attgtttttc    96120
agctgctttt gaagaaatga atctaactca tctcagaagt cttgtcaagt aaattcaata    96180
```

```
gatcaacgta tgtcgcagcc tatggaatac ttagtataaa aattgaagag aaaaccctca   96240
ggttgctata aaagtgctgc tttattaaaa ttaccaaaat ctcactattt ctatctaaac   96300
tgacatacta cagtttctgt ctaaatacat tgctctgtat tttattaatt tgtatggcaa   96360
taaatatgtg tcaggaacag ttttaaaact taatcctcaa atactgcttc cttaaatcta   96420
tttatttatt tttatttatt tatttttgttt ttgagatgga gtttcgctct tgttgcccag   96480
gctggagtac aatgccgtga tcttggctca ctgcaacctc tgcctcccag attcaagtga   96540
ttctcctgcc tcagcctccc aagtagctgg gattatgggt gcccactgcc acacccggct   96600
aatttttgta tttttagtag agatgggggtt tcaccatttt ggccaggctg gtctcgaact   96660
cctcaggtga tctgcccacc tcgacctccc aaagtgctgg gattcaggc atgagccacc   96720 acacccagcc cttaaatgta ttttttgtgtg agtgtatgat aaaaatcttg gatctggaac   96780
aaacccaaag attactcttt ttagttacct ttttaaataa actctttatt tatctttta   96840 ataaactctt tttagttatc ttttgtgttt cttgtttgca aaaagtaact aatttattaa   96900
attgtgcttc atccagtggg agctattgag agttggccac ccatagaaaa ttgagggagg   96960
attttaggaa ctgctgaagg tttctgccac atgcatgatt ctgatatacc ctggaagaat   97020
ccatctgagc cttccccaca tggacacaga gtgtggaatg ctagcagcac acagagggtg   97080
gcagagcttg ccctgcacgt gacagcacag gcgctgagat gtgtcccaga aaaatgagca   97140
ggtagaagcc tacctgagac atccaacaga aacatccctc ttaacttcct tcctcctta   97200 gtgttttgaa tcagtttatt tggttgggaa gtgtaagcaa ggatagtgta cagagaagta   97260
ggaaaactac tcctcttctt ccacctgctc tgcattagca caacaggaca actctcactg   97320
agccttcctg tcctgaagat ttcttttttc ttttcttttc tttttttttt ttttttttg    97380 agatggagtc ttgctctatt gcccaggctg gaatgcaatg gtgcaatcta agctcactgc   97440
aacctccaac tccaggttc aagtgattct cctgcctcag cctctcgagt tgctgggatg   97500
acaggcacct gccaccatgc ctggctaatt tttgtatttt tagtagagat ggggttttgc   97560
tatgttggcc aggctggtct cgaactcctg accccaggtg atccaccgc cttggcctcc   97620 caacgtgttg ggattacagg tgtgtgccac catgcccagc ctgtcctgca gctttcaaag   97680
tgaaccatct tcgtgtatgt ataatgagtg ggttgcattc atatcatgtg tgttttatac   97740
actgaggtag attccagtta cgtaggaata tagttagtaa tagtgtattc ctgaaaattg   97800
ctaagagtgg ttataaagta ttctcaccac caaaatgata actgtgaggt aatgcatatg   97860
ttaattaact aggtttaatc attccacagc atatacttca aaacatcatg ttatacacaa   97920
taaatacata cagtttttatc tgtcaatttg aagttaagga agaaaataga ttggattttc   97980
ttacaccttt taaatgatta aatattataa aaatagaaac caatcacatg agagaaacat   98040
ttactactgt tgttgataaa agtacgggga gaatgtaacg cactttagag tgaggaagat   98100
tctctggatt ctaccactgc atctgttagc gccatggcat actgtggtaa aatggcactg   98160
ttttccgatg ctatgtacag caagggatag cgccctgttt tccccccta gagctaccgt   98220 tacaagcatt tgcttatgtt atagccttcc aataactaat atgttgaaaa caccaagaca   98280
ccacttaagg tctttacaaa gtgagaagga attgggaaaa aagaaacaa aggccgggca   98340 cggtggctca cgcctgtaat gctagcactt tgagaggccg aggcaggcag atcatgaagt   98400
caggagttcg cgaccagcct ggccaatatg gtgaaacccc atctctgcta aaaatacaaa   98460
aaaaattagc cgtgtgtggt ggtgcatgcc tgtagtccca gctactgggg aggctgaggc   98520
agaagaatcg cttgaaccct ggaggcagag gttgcagtga gcctccagcc tgggcaacag   98580
```

-continued

```
agagagattc cgttctcaaa aaagaaaga aagaatgtg aatattgaca tcacattaaa    98640
aaataataac aaactttagc cttgtggcct ttttttggca catgttttcc gctagttctc    98700
atgcatcatc cctattctct ctcttctctg tcttttcttc atccaggaac agagaaagag    98760
gacttagaag gaactcaacc cagtacttcc taggattgga aggaagctgc cttatttcat    98820
gtataagtgg caccagcttg actgtaggaa gagagatagc gtgaagcctt tcacatctaa    98880
actagaaagc ttttaaacgt ggtagtttgt tgagttattc tctctctgtg gaatgaatga    98940
tgtagagatg gtgagaaatc agagtgggtg attttagaca tttcccttta ccctacttca    99000
ttcctgctct gtacagagcc ttgtttctgt tcttcacctt atttctttga gcaagagtaa    99060
agcctctgat tatgaaaata cactgtgcat aaatagccag aaaacacatt ttcttgcaat    99120
gaaagatttg ttttatggaa aatctcataa acaccatcaa ggaaggtttt ggaagaaggt    99180
caaatgtcct tcaaaatgct attacccat caccattcac atcttagtgt gactgacatc     99240
cgttctcagc tctggtgggg agaggtggac agagacagca gcactgtccc ctgtggccca    99300
gggttgcctg tggggacgcc cacccaagaa gcaggctgga gagaagtgcc aagggggttaa   99360
ccattgcctg gatgatattt tgtcaggaat ctaatgtttt tctctctcct gtaggggtg     99420
acaggtgctt tgacagtttt gatgaaagat gcaataaaac caaacctgat gcagaccctg    99480
gaagtaagtg gttttcttct tatagtaatt gtttgcatta actggattgc cacacaatgt    99540
gaacatttt agccaatatg aggcaggcat agagcatgcc tggggcagca gtgtgctttg     99600
caatctcagg cagaaagagt gaggatctgg ttaggaacct gtattagtcc attttgacat    99660
tgctacaagg aactacctga gactgggtaa tttatgaaga agcatcagaa taacttcttg    99720
gccaaccaaa aaaaaaatt tttaagtgta ttcatagctt ctttaatata agtcatgtct     99780
tggcttaatt gacccgagta gaaacttaga aagtcaatgt ctgaggccag gcgcggcggc    99840
tcatgcctgt aatcccagca ctttgtgagg ccgaggtggg cggattatga ggtcaggagt    99900
tcaagaccgg cctgaccaat atggtgaaac cccatctcta ctaaaaatac aaaaaaatta    99960
gccgggcatt gtggcacaca cctgtagtcc cagctatttg ggaggctgag gcaggagaat   100020
cgcttgaacc cgggaggcag aggttgcagt gagctgagat cgcaccaccg cactccagcc   100080
tgggcgacag agcgagactc cgtctgaaaa aaaaaaaaag agaaagtcaa tgtctaacat   100140
ttcaataggt tgtatggcca tgtttacaat ttattttctg tgttcccta atctctcata    100200
atcattgagt tgtggatttt ttggtttgct tttttattgt tgtttgtttg tttccaagca   100260
aaatacaata aatgccaaga cttttccagga aagcatttgc caaaggcaag tcaataaaca   100320
cacagcatgt tagttggtgg taaggtctgg agaagaaaaa tcagaggtca tgaggggcag   100380
agtgatgtgg ggtatgtgtg tctgtgcctg cccgcctgtt aaagcagtac cagcacagag   100440
ctgagtaaac caaggggggtg agccatgcac gtgtcttgaa gaacatttgg acagagggtt   100500
accttagtg caggggcctt gggcagcaag gtgttttgca atttcagaca gcaagagcga    100560
ggatctggtt aggaacctgt attagtttgt tctcgcattg ccgtaaggaa ctacctgaga   100620
ctgggtaatt taagaagaaa attggtttaa ttggctcaca gttctgcagg ctgtacagga   100680
agcatggctg gggaggcctc aggaaaactta tcatggtgga aggcgaaggg gaagcagaca   100740
agtcttcaca tggcagaaca ggagagagag ggcgaaggag gaagtgctac acactttaa    100800
acaactagat ctcatgagga ctcactcaca atcatgagaa cagcaagggg gaaattcact   100860
cccagaatcc agtcacctct ccccaggccc ctcctccaac attgaaggtt ataattcgac   100920
```

```
atgagatgtg ggtggggaca cagagccaaa ccatatcaga accaatatga cagaaatggg    100980
gggattggcc aggcacggtg gctcaagcct gtaatcccag cactttggga ggccaaggcg    101040
ggcagatccc ttgaggtcag gaacctcgag accagcctgg ccaacatagt gaatcccatg    101100
tctactaaaa atacaaaata aattagctgg gcatggtggc acgtgcctga atcccagct    101160
ccttgggagg ctgaggcagg agaatcactt gaacaggagg cgaagattac agtgaactga    101220
gattgcacca ctgcactcca gcctgggcga cagagtgagc tcttatctt ttaaaaaaag    101280
ggaatagaaa aaaatggggg gaccatttct gaaggtgccc agtgaggatg cagactgcag    101340
gtgtcccctg agctgaggaa gggaggactg aacgcctttg aacaggtgtc tgcagccccg    101400
ggggagggt gcaggatgca caggtgccaa ggccacaccc ttctgcggca ggttgtcctt    101460
cccgtctttc ctctcccctg atcattctgc cagcatgcac gtatcctcag aggtaggcca    101520
tcttaaaaag caaacaaaaa catttcaaaa acctcctgcc cccacctgca tcctcatcta    101580
gcttctgccc agctcttgtc tgtcactggg gtctccatgt taactgacct cgggttccac    101640
ctctcctgac tgcccttgtc caggtcactt ttcccttgga acaccaagt ctttgttgct    101700
gtgccctcct cagagaagct cagcagagtt tgacacagct gcccttgtct tccttcagga    101760
gcacctggtt cctctggcgt ctggggtccc ccctcccca ggcctgctcg ctgctcctcc    101820
tccgctttgc tggcttctct gatgacccct caccttttt gccccgttct cctccagaat    101880
tagccaggtg atgactccca aactcttgtt tggaatatca tgcacctgga atttcagact    101940
tgcaggtata gttaccagga gccacgtggg tggggaaaag ccatttcaaa ctgatacata    102000
aaccaggacc cacctcctac ctacttcctt ccagctcgct gcttccctga aaccttccca    102060
gtcattcaag gcagaaaccc gaggatgatc ctagaggcct gttttccctt ccctcttcc    102120
tgtgtccatc cctgcagagt tgtccttggt tacatgactc tgcccgtcc acgatgctca    102180
atgcctccct ccttcctgct ttagctgcca gcacgcccca cctgcacgag tgcagcagcc    102240
tcccaaccag tctctctgct gctactcttt tcttccaaaa tactctctcc tcagcagcca    102300
tagagactga aacctaatga agccctgttg ccttcctact tagagttctt ccatgattta    102360
cccatgtttc caccccggtc tgaaaagccc tagggatctg gctctcaccc cttccgctc    102420
cttgtccctt atcctcatct ctcatcctct gggggacctt tgcacggcta acaccactac    102480
ctgggccact tcctgatatt tcatgtcca gctccttcgc ctccctctgt tctcatgtca    102540
tgtaagcatc agctgctcag agaagccaca ggaatgtgca gcccccgtcc ctctgctgtc    102600
attgcagtac atggcacaga atgctgagag cttcctattt ccttatctgt tttctgtatt    102660
tctcctccca ccgagatgac agcaagacct tttccatcct gttcaccacc gtatctccag    102720
cttctagaaa gtgcccgaca cctattagag gttcagtaaa gacttgttga ataattaagt    102780
gaatgtttat tattttact acattctcct aaaaatacac atttattaat aaataactga    102840
ataagagaaa aaatacgaag tgatgtgata ttccttcata acacttctcc ctcaaagatg    102900
aatacttatt attagggata atcatttct ttattgttgt tgtttgtttt gttttgtttt    102960
gttttgtttt tttgagacgg agtctctccc tgtcgcccag cctggagtgc aatggtggga    103020
tctcggctca ctgcaacctc tgcctccag gttcaagcga ttctcttgcc tcagcctccc    103080
aggtagctgg gattataggc gcctgccacc acacccggct aatttttgta ttttttttt    103140
aagtagagat ggggtttcac cacgttggcc aggctggtct caaactcctg acctcaggtg    103200
atctgcccgc ctgagccccc aaagtgctgg aattacaggc gtgagccacc atgcccagc    103260
caggataatc atttcttgt tttaaataat tctttttttt tttttttttt tgaaacggag    103320
```

```
ttttgctctt gttgcccagg ctggagtgca atggtgtgat cttggctcac tgcaacctct 103380
gccttccggt ttcaagcgat tctcctgcct cagcctcctg agcatctggg attacaggcg 103440
cccgctacca tgcctggcta attttttgtat ttttagtaga cagggtttt taccatgttg 103500
gccaggctgg tctcgaactc ctgacctcat gatccaccca cctcggcctc ccaaagtgct 103560
gggattacag gcgtgggcca ccacgcccag caaattttg tattttagt agaggcaggg 103620
tttcaccatg ttggccaggc cagtctcaaa ctcctgacct caggtgatcc gtctgcctct 103680
gcctctcaaa gtactgggat tataggtgtg agccaccgtg cccggcctga gcactttta 103740
aaacataatc taaacctgtt atttctttgc tgcctaataa atcagagatt cagaacccctt 103800
aaaaagcaaa taaagtaag ggcaataaga cctgctgagg ctgaggcagg agaatagctt 103860
gaaccgggga ggtggaggtt gcagtgagca gagatcatgc cactgcactc cagcctgggc 103920
gacagattga gacataaaat agactgagac cctgcctcaa aaaaaaaaa aaagagtcct 103980
caaactgttc atatacagga ctgggcttgc tagggaaaga aggggaatt cttcagacta 104040
ctttacaagg acacaagaac tcctcaacct aaacaaagta tgaaggtaca tagacaagtt 104100
tcttgtaagt cggaaaacag agaaatccac agtaactata atacatccct taaaggataa 104160
gcatgcattt gtaggaagca aacaaagctt tccatagaga aaccacttcc accagatgat 104220
tatatggact tgggttttgt ttctgcatct gtcacttggc aaatgaagat accatcttca 104280
ggatgttccg tgtcatcgat ttcatttaag gcataggctg ttttaagatt actttaaaag 104340
atatggacct ttttacaaaa taaaacactg cattcactta aaatatttgc agacgtgaac 104400
tcttgtaccc tgatcctatg ttgtcactct gggttttatg tatctaatca ttgactagga 104460
atctatctca gcagataatc caaaaatcta gtttgactag ttggtagatt atgctttccc 104520
gctcacatct gaacacacct ggttgttagt ctggtaggag gtcatcaagg gccacatcct 104580
tacaggttgc caggagacca gtagttctta atcctgactg cacttgagaa gctcctggga 104640
aggtttaaga atattgattg attgatgccg ggctccccat cagacccagt gaacgtaatg 104700
tctgaggata aggcttgggt atcatgtatt gccagactga ggaagactta agacaagaaa 104760
acagtgagag ctgttaacat tttcccacag gttagccgtg tgtggtgttg atggaaactt 104820
cacatgcgag agcacactgt ccaatatggc ggccactgga catgtggcca tttcaatcta 104880
aattacctaa acttcaataa aatttggaat tcagttcttc agtcatttta gccacatttc 104940
catttatgca tttatttgtt tatattttac tgttcatatt taagtgctta gaactctggt 105000
aagctaacaa ttacttgaaa ttacttgaaa tattaatctt atgaaatgtt tgaaagggcc 105060
attatggaga atattcatag caagatagtt cctgccttat tttcctgagt gttctgcatg 105120
taaaataaaa cccagaactc aagataaatg tgtgtatgcc tttgagttag tcatagaatt 105180
ttttaagcaa catgtttaat ttgatgtact gtatcttata gctatatcca tgtttgagtg 105240
tgcaagtgtg tgtgtacctg tgtttggaag tctaacaatg acattccaat atttttttct 105300
caccaactcc atactgggag ttttaaaacc agagccctaa tcttgactta attattaatt 105360
tcctccgtgg ccctgaagaa ttcccttagc ctctctgggc cttaaatttc tggataaaga 105420
agttggctgc ttcgtgctct caacattatc tgattctgtg atttctagct aaagctacat 105480
ttatacaaaa atataaagtg cttttgcaaa gtaaagagta gaatagtggt tatcagaggc 105540
agtgggggat ggagaagttg accaaataat acaaaattcc agttagacac cacctgtgta 105600
ttcataaaca tgtgtcccta ggtttttattt atttattttt atttattatt ttttcatttt 105660
```

```
ttgagtcaga gtcggtctgt cacccacact ggagtgcagt ggtgcgatct cagctcactg 105720
caacctccac ctcccaggtt caagctgttc ttgtgcttca gcctcccgag tagctgagct 105780
gggtttacag gagcacacca ccacaccctg ctaaattttg tattttttagt agagacgggt 105840
ttcactgttg gccaggccag tcttgaactc ctgacctcag gcgatccgcc catcttggcc 105900
tcccaaagta cggggattac aggcgtgagt cactgtgccc agccaattgt aatgattttt 105960
atggttacct tttcttgaat ggaatcattt cttaattaaa aaataaata tacctttat 106020
accatcaggg tttaatttca ttcttttaaa aaatatagt gcatggcaac ataaataag 106080
gtaaataatt tatttcatgg tcattgaggc aactaacaaa atggtttaac aatatttttgg 106140
aaggaagtga ctgtattctc acagttttgt ctctcaggtt cagcattaaa tgtagaataa 106200
catttttcta gaatccggag ggaatttggt cctttgattg agtcagggtg ttttgactgt 106260
ctttgaaata ttttatgcat taaatatgca gtattcataa aagctttcct accccatttg 106320
ccccaaattg atcttggttt ccatgcttct gtttgtcttt tgggattttg atttgctttt 106380
tcacttctct aggggacacc tgtgttcgtg catgcgggcc cttttgctaa cattgctcac 106440
ggcaactctt cagtgttggc tgataaaatt gccctgaaac tggttggtga agaaggattt 106500
gtaggtaagt tatttctttt aaatttagtt gttgtagaat attgaagaaa tctaaaagct 106560
gatgactgga atggagtgat atccatcctg acatgaaaca tattctttca ggcaccctct 106620
ttcatagagg gtctcaataa tggaaaagcc ctaaggtctg gtctatactc gtgaaattat 106680
gcttgtgctt gaatcataga gtctggtatc aagtacatat gggtttgagt ataaactctg 106740
actcttgcaa actgagtgac attggacaca ttttaattac tactgagctt cggttttctt 106800
gtgtgtaaaa tagtgataac aatactgtat caaaccttttt agggttgtta tgaaaactga 106860
atgagatatt ttagtcattc agcaaatgtt ttttgagaac ctaccactta gaaggcatgt 106920
tagctaggga tccagtggta agcaaaacag ataggcgcag tggcacatgc ctcgctactc 106980
aggaagccga ggcaggagga ttgctcgagc ccaggagttt gtgtccagcc tgggcagcat 107040
agaagaccct gcctctgtga aaaaattaaa attaaaacaa ccagccttag ccctgctcc 107100
tgtggagcgt actgtctaat ggtaattgaa taagagaaag tgctcattga ctgtcagcca 107160
ttactaccct tactatgtag tactgataac ttgaagtcgt gggtttattt ccatgtacag 107220
tttctccttg tttttttgtga gctaatatag gagagattcc caaccagtag acttagaaat 107280
gttaattggt agtactgcac accttttgct gctgtcaagt tctttgcaga acctgttcct 107340
ctttggcttt tcttgcatat tccagctaga aagaaggggc aactctcata gagttttacta 107400
agtcagtgcc agcccccagtc tcacccacaa tactaaggca gcaaggaaac aaaagacaaa 107460
accaaaacac aggcattcat ggaggagtcc cttaatctga catatgaggg actgcattgg 107520
cagatttccc atgctaacag gtaattccca ttaaccacac gtatacctat aatcggagac 107580
agcaatctct tctttcactc ttatcatcag ctttggatca aactcaaaag agttatttta 107640
ttagaagaga gtgtgctgga caaaagaact tggcactgca ttttatgctc agacatcaca 107700
aagttcattc agtgttattg agactctttt aagaattcct tgtggactgg cagtcaggat 107760
cagatgaggc ttggtggagc tccactcctc catgatctgt tttctgcagc tctcatgtac 107820
tttgctcctt cggtagcaaa tccactgcaa gagtggctag acatactgtc taagtggatt 107880
tgctcaattg atcgctgcct aattgtagag ctaatggacg aggaggctgg gtcagggcgg 107940
gcactggaaa gttgggtgct taagtgaagt ggtggttctg atgcatcagc tctgcaaata 108000
aagtagcttc tagaaggaag cactctattt tatgctgaca gagatctctg cccataccag 108060
```

```
ttcttacttt gtcaaacaca tatttataaa atacatgtta tcatggcaga atactttcaa   108120
agatataaac tgatgatgta tgcaaagcaa acgagccctc tgtgtgacct tgaacaagcc   108180
attagcctct ctgggtgtgt ccctgtaga cattctcatc tgaaaatga gaagttggac    108240 cagatgagga gttggatgtg gatgtgtagc cgtggactca gagttagaca ctgtggaatt   108300
ggagccctga ctggtagtgt gttttcattt ctctagggct caattttta tttaataaaa    108360 agaatacttc tgtattttaa tgaataggat caagtgagaa actgctttgt aaaatatgaa   108420
ctatgttcag gtcagcaatt atactaattc tttctatgat ctcatctagt ctaagatgcc   108480
gtaagtgggg gggttttca tgaggatgaa atctgtccgt tgccagatgg ttcaaagggc    108540
aagccctaag tcagaggttt tacctcaact gctttcaagt cacagataac cttgggcaca   108600
tgaacccttc tcttccttgg tttccctacc tgtaaaatag ggctttggat agggcttccc   108660
tctcgaaagg acttggtagg tttgaaatga ggcatcaatg agatcatggg gttgagtcct   108720
ggcacctgac acatggtaag actcaatcct tcttggccac tcctggctgt cattgttacc   108780
cccactattg atacactact gatgaaggtt acatttctt ttttctttgg atcttttat     108840 tttttggatg attttatta tagttgttat aaaatacacg taacatgaaa gttaccatct    108900
tcaccatttt tgagtgtacg ttcattagtg aagtacacct tcattgttgt gcaaccaagc   108960
tgcagaaccg aagtcccatg cccattaaat attcctcatt ctccagcccc tggcagtgcc   109020
cttctacttt ctgtctcaat gaagttgact cctggatacc ccatgtgagt ggaatcatgt   109080
agtatttgtc cttctgtgac tgacttattt cacttagcat aatgtcctca aggttcatcc   109140
atgttgcagc aggcgtcaga attctcttcc ttttttttt tttttttttt attttttgtg    109200
agatggagtt tcgctcttgt tgcccaggct ggagcgcaat ggcacaatct cagctcactg   109260
caacctccgc ctcccaggtt caagcgatcc tcctacctca gcctcccgag tagctgggat   109320
tacaaacatg caccaccacg cccagctaat tttgtattt tttagtagag atggggtttc    109380
tccatgttgg tcagtctggt ctcaaactcc tgacctcagg tgatccaccc atatcagcct   109440
cccaaagtgc tgggattaca ggtgtgagcc accacacccg gctagaattc tcttccttt    109500 taaggcggaa taatattcca tcgtatggat agaccatact ttgtttatcc actcatccta   109560
cattggacat ttgacttgtt tccacctttg gctcttatga ataatgctgc tatgaacata   109620
gatgtacaaa tatattttaa tgtctaaaaa tcgtgctcta tgatgtctaa atatgtgatg   109680
gcaatgactt atattcacaa atacgtacca cggaactcta gccctgtaat gttgaactct   109740
cccgaaggtg gtgtgtccat gctgtggctc tgttggaatg ctggtggcaa agccagtgta   109800
ttgcacagtg ggaacggggt gtggtcagga gacagtgttc cttgcccatt gcttggtcaa   109860
gcctgcactg tggggctcgt tcattccttg cccttggatg aagtttataa tagttccctc   109920
tcattctcag ttaatatcta gtccctctaa cacatatatt ttttaattcc tctggtcact   109980
ttcaatcata agaatagccc ctaaaattaa aaatgcatat ccagttgtat atcaaaacca   110040
aaaactccaa atgtcactca gacttgagct cctctcctcc cctgtctggg cctcctctgg   110100
ctgacagtgg gaaggggaag gtggctgctt gcttctctgc cacccttgtc ttgcacttgg   110160
gctcgccctg gccctccta ggttgaagct ttggcatgaa atggtgccca tgtagcctct    110220
accagcagac gtcctcacac ttttggcaga agccccctga gcagtacctc atttagcttt   110280
tcctacctct gattccacac ctggtctcgg gtaccacaga cctctgacct ctggctgggg   110340
acacgccctg agccttgcca actggtcttc tggtcctcac ttgtggctta aggggaagc    110400
```

```
ggggacgcca aggcgggtgg atcacctgag gtcaggtgtt caaaaccagc ctggccaaca    110460
tggtgaaacc ccgtctctac taaaaataca aaaaaattta gcggggcttg gtggcgcatg    110520
atgtaatatc agctactcag gaggctgagg caggagaatc gcttgaaccc caggaggcag    110580
aggttgcagt gagctgagat cacaccattg cactccagcc taggcaacag agacagactc    110640
tgtctcaaaa aataaaaata aggggaagc agcttcgcat gctcttcact gggagctggg     110700
aggggagctg gatgtggcac actgataact ttctttgaag aaattctttc ccaggttcta    110760
acccgtcaac ccttttgaag cctcaatggg ctaaggcata caaatctat ttcaaactgc      110820 tttgcaaacc ctcccaggtc agccagcacc atcctttggc atgtgagcaa attgacacca    110880
atttgaggcc cgaaacaaaa gtgagacaaa aagacgttca tttcaacatc cttctacaga    110940
agttaaatag agtaggcaca tctgaggtgt atctgaagtc tgagcaggaa ttcatgttct    111000
tcaaaaagtt gtcgtttata gtagactatc tttatgacct cataataggg aaggatctct    111060
taaaatatga aaagctcaaa ccatagaaa aaatgtcgat aatttggcct gcattaagaa      111120
gtaaactgta tgtgataaaa gatacaagga taaaaacaa gtgacagatt ggaaagaaac      111180
gtttgcaaag atagtagaca atgattagca ttgagaatat gtaaacact aaagactaaa      111240 gactgataag agaaagacaa ataatccaat acaaaaatag agaatttgaa aaggtgattc    111300
gcagcaaatg agcaatttgg tggaatttct aggtagaact gaaaatgaac aaatgattta    111360
gcaatttcac ttctatgtat actctggaaa agaagtagtc aaaaatatat ttaagtcctt    111420
tgaaataatt gacttcagta cccctttaat gagcatttat taagcttctg ctatatgtca    111480
agtactatct gctaggagct gggaatcaaa tatgaataag acaggtttct tgccctccag    111540
taattgatga tgtgctgtga gagacaagaa cttcaatggt aagtacaatg cacttgatta    111600
agtactatat tagttaaggt tcttaactaa gaatttcaag ggatgatggg catctcttag    111660
atagaactgt ctccatatta ctggttttgc tgatttagtc taattttgt tctaacaaaa     111720 agcatacaca aggaaggaat tatttgtct attctgaata attagtctaa gataatagaa     111780
tcagtagtcc atttagactt aaaacagagt gacatttatt ttaaaaagc atgaatttgc      111840 aaaacacttt atgagaattt ttcaaaaact gctgtgatca ctgttgtggc tgtttcttcc    111900
gttagtcagc agtcctcatg ggagttcacc taacttccat ttacatgctg taaaggcaaa    111960
cagatatttg gcatcgaatt ctaatcatgt attacattta aaaataaag caaaggaaa      112020 gaaagaaagg aaaaagcagt attgagttcc tggattttaa aaacattatt atctcatctt    112080
taaactattt gtaggaattt caaacttacc cattaactta ggattttta atttgttttc     112140 tgctctctca gttggttttg attccagttt tcagataaag atcttgtctt tgcagaggag    112200
tgcagaatgc aattgtgtat ccttataggc aggtgtcatt aactgagggt caccagccac    112260
tggtggactc ctggatagac ttcgatctac aactctgtcc cataattaaa tataggttcg    112320
tgcatatgga gacatatata tatacacctt tttttttttt ttttgagatg gagtcccact    112380
ctgtcttcca ggctggagtg cagtggcgtg acctcagctc acggtgacct ccacctccca    112440
ggttcaagcg attctcctac ctcagcctct tgagtagctt ggattacagg cgcatgccac    112500
cacactcggc taattttgt atttttcagta gagacctggt ttcaccatgt tagccaggct    112560
ggtctcgaac tgacctcagg tgttccaccc gcctcggcct cccaaagtgc taggattaca    112620
ggtgtgagct gccgcacctg gccacctttt tttttaacc tggagaaaat tacacaattc      112680
ttggattctc acaggggacc atgacataag agagagaaag aactgttggt gcatatctca    112740
aagcctagct ctacttttga cggtagcttt cgatgtccca tacacatttg gcatttatta    112800
```

```
tccttatcca gaggtgcttg tcaagaagct acctaattga ttgcaactct gctgcttgct    112860
ctctgtagag aatcacacag acctggctgt gttccccagg tgcttcctgg gtacatgagc    112920
ataaacactc atgcagcaga ggagaaatat gagacaagtg cccaattaaa acacagggtg    112980
atctttgcct cagacatttc aggattagga tttagaaatc agaatgaatc gacttagcag    113040
ttccaagaca aattgaatgg gattgggaaa caaagccttg ttaatatttt cattaaaaac    113100
gcccccgttt ctgagccatt cctgagcatt agaccggtgc tgagactatc atataccttc    113160
tcactcaatc cttaaaaccg tctgtgggat cagtgttact atcctcatct tacagatgat    113220
gtaacagaag cttagcaaga tgatgataca tgtccacgat caatcagaga gtaagtgaca    113280
gaggacgtga cctgagggct cctcctcgcc aaagcttgtg ggtgatcagg cggctattgt    113340
gctcagtgtt tttctcaatg ctctttacct ggttgccacc ctctcccatt aaaaaataat    113400
tttagctggg cgcagtggct cactcctgta atcctagcac tttgggaggc cgaggtgggt    113460
ggatcacttg aggtcaggag ttcgagacta gcctgaccaa catggtgaaa ccctgtctct    113520
gctgaaaata caaaattagc cgagcgtggt tgtgggccct gtaatcccag ctacttggga    113580
gggtgaggca ggagaatcgc ttgaacctgg gaggcagagg ctgcagtgag ctgagattgt    113640
gccatcgcac tccagcctgg gcaacaagag caaaactctg tctcaaaaaa ataagaagaa    113700
ttttgggtga gctgtctaca gcagatggtc acagttacag gaagtaccaa tataactata    113760
ttgtaccaat atatcgtaat gtgcgccaac agtggtggtc cttttggtc ctttttttct    113820
tttctgtgtt ctactttaac atttcttcct cccaagtagg ttactgattg aagatgacct    113880
tatcgagtcc cactgtttcc ttgctctacc tctcaacctg tattttggg ggacagtttt    113940
ttaattttt tattttcctt ttttgagacg gagtctcact ctgtctccta ggcttgagtt    114000
cagtggcacg atcttggctc actgcaacct ccgcctcccg ggttcaagcg attctactgc    114060
cttagcctcc caagtagctg ggattacagg cacgcaccac catgcccggc tagttttgta    114120
tttttagtag agatggagtt tctccatgtt agccaggcta gtctcaaatt cctgacctca    114180
ggcgatccac tcacccctgc ctcccaaagt gtagagatta tagctgtgca ccactgcacc    114240
cagcctaggg gacagtttta taatcagtct tcttggcctt cagaggactc tgctggtggc    114300
tatacccagc tagtggcttg ttctctcttt ccacttttat tgccctgaaa ttctaaatat    114360
tccatcattt tggtagaaga aaaccagacc aaactaaaca ttctcatgat ttcatccacc    114420
tttaaaaaaa aaaaaaaatc tgacgtcaag tgatcctgca gctctaagct gtaattctcc    114480
cagaccttgc cctgtttaca ttatttaaaa acactgatct cagcctgggc tccacttttg    114540
ttattatgat gcttccaggt tttttgtctt tagtaaattt attcataatt aaatcaaggt    114600
tgagaagtgc tggcttatta gagactctgg ctgaaggtca tgtgcgaact caggaaactg    114660
ctaatcacag gtcgtgtttt tcagcccctg tcttcaggaa ggcttaactc taagggaggg    114720
ttgttttgtg tcatctccag agctctcatt tctcctgtgt ggcttggtgc cgaagctcat    114780
tcgtcccctc gctgtctgtt cggcccttgt cctacctccc ctttctcttt ccacgctttt    114840
gtgtaaagta gccctctttc aagctgctcc tctgtccttt gaaacaaat gaaaaagcaa    114900
aatgttcttc atatacacta aacaggaaag tatgcaaagt aatgttacaa acacccatgt    114960
tcccaccact ctgtttcatc aaaatcttaa catgtcgctg tgtgtccttt agtttttttg    115020
ttttttttaaa gagatacgtt tagctgggca tggtggcgca tgcctatagt cctagctact    115080
tgggagtctg aggcaggagg atcaattatg cccagcagtt taattctcct gggcaacaga    115140
```

```
gtgagaccct gtctctaaaa aaaaaaaaaa aagaaagaaa gaaaagaaaa gagagaagag    115200
aagaaatcag atattagaga cacagttgaa gttcccgtgg accctcctga tcccgttctt    115260
ttttctgctt ctctcctgat ttgagtgatt atcgtttccg ggtgtgtgtt tctactttga    115320
ccacacacat atatgtacac tagagatctg tagcggaggt tctcagactt tctctgctcg    115380
tgaccattaa tggcccagca attttttca tggtaccgcc cgggcaagag aaatacctaa     115440
catgtccatt tattaaatag gtccaaacaa cttaatgagt atttatgtcc ttacaactaa    115500
gtggccacct gaaaaaaaaa tacatatgaa ttcgaaggaa aaaataacat catttcattt    115560
ttaaattacc accatatgtt atgaatgaga tgtgtgtcct tgtcaggcac cagacaactt    115620 ctgaccettt gtaaccagtt gacacccgca cctcatttcc tgttccacgt tgattttcac    115680 acgattttg cattttgctg cggtacctgc caaaaacttt gctttgcaaa tatatgatgt     115740
catggaaagg gatgtagagc actattgttg aagcagtgaa aaacctcaca tgagtagtat    115800
ttgcagtgtc caacggatgt cctgtattac cgcgtttccg tcaaaaattt aaaataccc     115860 acggtgcctc tgagtttgct gcaatgcctc acggcacctc attgcacatt agaatcacag    115920
atgtgcggct tttcttggta ttttttatgt gttttcaaat tttatatatt aatagatatt    115980
aactgactgc attgttctct aatgaggtca ctgcactttt tctgtaaatg gcaagatcat    116040
aaatagtttg ggtcacagag tctctgtccc aagtactcaa tttagaaagc agccataggt    116100
aaagcatgaa ttcataaact agtccatgtt taggaatgag tctggctgtg ttccaacaga    116160
tgttattatt ggttcctaac atttgaattt catataattt tcacgtgtaa taatactctt    116220
ctgatattgt tggcaacatt ttaaaaggtg gccaggcaca gtggctcatg cctgtaattc    116280
cactgctttt ggaggccaag gtgggaggat tgcttgagcc caggggttca agaccagact    116340
gggcaacata gcaagatccc atctctataa aaaaaattt taattagcca ggtttggtgg     116400
cacatgcctg tagttccagc tactcgggag gctgaggtgg aagatcact tgagtccaaa     116460 agtttaaggc tgcagcaagc tatgatcaca cctagctact tggtaagcta ctatggacaa    116520
catggtgaaa ccctgtcttg aaagaaagag agagagagag ggagagggggg agagagagag   116580 ataatacttt ttaaaagaga aagaaagaaa agaaagaaag agaacacttt ttaaaaggat    116640 aaataaatttt taaaaactta ataatttaac atgtaaaaaa aaaagatgt agaccatata    116700 caaaacccag aggcacctgg atttgtcctg ctagccatac tggccaaccc ctgctctata    116760
acttgatatt tttgtgcaac ataacagttt tgcatttctc tatgtcactg tgatccaaaa    116820
agcctcattt tgcctgcagt ttagccttct gtgcgtgcat gtagcacgtg catttgtgca    116880
ttatttgtca aggggctttc agattgcttc cagtgttctg ctgttacaaa taatgctacg    116940
ggggacattc ttgtccatgt ctctgagatt tagtctaaaa ggtcttctag ggactatata    117000
caggagtgag atttgggggg ttaaaagtac gcttagcaac aacttaatag ataaagccaa    117060
attgttctgc aacgtaatac caatttatat cactaccaat tgtgtgtgtg agatttctga    117120
cctctccacg tttgtcctga cacttctttt ttttttttt cttgagacag agtctctctc     117180
tgttgcccag gctggcgtgc agtggcatga tctcagctca ttgcaacctc cacctcccag    117240
gttcaagcaa ttctcctgcc tcagcctccc aagtagctgg gcttacaggt gcacccatc     117300 acacgtggct aagttttgta ttttttagtag agatggggtt tcgccaagtt gaccaggttg   117360
gtttcaaact cctgacctca ggtgatccac ccaccttggc ctcccaaagt actgggatta    117420
caggcatgag ccactatgac cggctgaacg cttctattgt tagatttttt tagctcttgc    117480
taatctgatg gtagttcatt atagttgtga gatttagcat ctttatggct gtttctgggc    117540
```

```
atttgtgaat tgtctatttt gtattgtgct atttaccttt ttcttactaa ttaatggaaa   117600
tcctttatag attccgaata cgaatacttt gccattatga gttacaaata tcttctcccc   117660
tgtatggctt atcttttaaa tatgcttgtt gtaccttttc ttgtccaccc ttttctttat   117720
gatttctgct tttggaggtt ataaagataa tcatttgtat tgccttataa ctgttgtctc   117780
ttgcattgag gcctttaatc atcttagaat ttgtttgtgt aatggtgtct tttttcctta   117840
actcttacag tttgtgagac ttttctgccc tggtgatatg tgcatcagtg gttgttagcc   117900
cagccctatg aaaagggcca gctggcctcc atagatctaa ggcagccgag agtgctgtcc   117960
cctttgtccc aggctctgca gcatccaagg cgagtgcaga tggggccagc tgttcttcca   118020
aaaccatcat ctcttcttta cctgctcctt ctgagcttca cctgacatgg ctgtgcagtc   118080
cccaggaaaa agaaagtctc tcttgtcttc ctacttccta agtcaatcct aggaactgtt   118140
acgttcaatt ccaagcagtt gtcataaaag aagtttcctt ggaactttga aaacaaaaga   118200
aagggtttaa ttttcttctt ttcgttttgt tttgttttgt tttaattttt ttgagacaga   118260
gtctcgttct atcccccagg ctaacagctc actgcaacct ctacctcctg ggctcgagcg   118320
atcctcccac ctctgcctcc tgagtagctg agactgcagg cacaatccac tacacccagc   118380
caattgttca attttttttct ggagatgagg tctcactacg ttgcccaggc tggtcttaaa   118440
ctcctgagct caagtgatcg cctgcctcag cctcccaaaa tgctgggatt acaggcatga   118500
accactgcgc ccatccaaaa ggatttaatt ttatggtcaa attctacatt gtctattgac   118560
tttaatattt ttataaaatt cttaaataa aatgtcttta cctggaatac cttcaatgta   118620
cttactggat tagaggcagg taggtcctgt ttgtatggct agtatgttca ttaaatatga   118680
aagtaatgga aagatgttta tgacataagg agagaggaac cttcgcctgt caggataata   118740
gaaattgaaa gattttttatg acctggctca gcagaaaaag gagtatatga tgttagcaat   118800 ttttttagaat tgatttttca gaagaaacat gcaaaacaaa tgagaattaa gtagctagaa   118860
agcctttttc cccccttttat tcagataaag taactgaaga cttttaatga gaagcctggt   118920
ttctgtcttt ctacacggtg cactgggaat agtaagctgt tagaagtcag tgcttagaag   118980
tacctaccat cctaaacaca ggaaccaaaa acaagggaaa aaaaaaaaa aaggaagata   119040 aataaagtaa aagtaaaaaa gtacctaccg tcccaaattt tgtatatgat gatgttcacg   119100
tttttgaact tacacatatt cttctgtata agtaaaatat ttcataaaat taaaaatgtt   119160
ttataaaatt aggaacagaa tttcttaaag atcaacatgg tactaataca tcttacaatc   119220
tgtctttcaa agtttcaata gacttaactt agagtcattt tttaaattgc attttgatgc   119280
caatataatt catgtgtcat tttccgctat aatacaatga aaatccagat aatggagatg   119340 gatttcttc tgagtagcca cgcatattag gtttcaggct ccaattgcct ggttttgaat   119400
tgctctttgc catgtgctgt ctgtgacctt gggtgggtca cttcacctcc cccaaatcta   119460
ggtttctcca ataccstacct ccaggcttgt tctaggcatg aagtgcagtg atgatggaga   119520
aggcatggac tgtggcacaa atagaagagt caggggttgg cagctcctat tcccactgta   119580
cgatgccaag gatctttacc tataggataa gccttcagaa acataatttg gtctttcaag   119640
tgctgaatac ctctgtgagt atactttttt ccatcttttt tcttttggta aatgaaactc   119700
actgagaaat ttgacttctg ataatgggaa acagtgctgc ttatgtgttc tccttgtaca   119760
aaggtgtctg ggaccattat acttagaggt gatctgagaa atcggagggg ctctgattgt   119820
tttgaaaact ctcctttgag gtcgggcaca gtggctcatg cctgtaatcc cagcactttg   119880
```

```
ggaggccgag gcgggtggat cacttgagac cagcttggcc aacatgatga aacctgtctc    119940
tactaaaaat acaaaaatta gccgggcttg gtagcatgca tttgtaatcc cagctacttg    120000
gggggctgag gaaagagaat tgcttgaacc tggaaggtgg aggttgcggt gagccaagat    120060
cacaccattg cactccagcc tgggtgacag agtgagactc tgtctcaaaa aaaaaaaaaa    120120 aaaaaagaa agaaagaaaa agaaaactct cctttgaatt aaggtaatcc ttcttgaaag     120180
gcttgtttaa aatgtttcct tgttacctgg gagagagcag gaagcactgg gaaatagcac    120240
gtcactggtg cctcgtgcca tttccgtgcc tttccctgtc ttgcctcagc cttgcactgt    120300
ggaatgcaaa agagtagaag aaactccaac gtgaaaattg tcgacaaaca atgcagagaa    120360
tcttcggtgg cattaaacat taaaattaaa gacacatggt cttaaattca gctgatatac    120420
ttgacacctc agatatactc ttggtgccaa aagggatgtt aagcaaaatt tgagggattt    120480
gactccttat ttgggaaaga ccatgactac caaggggaga gaaaccagag gcaaacctta    120540
ttgaaaaatg gagtagctaa gtcattttgt atatgttact tttacccagc caagtacagt    120600
ctgtagtttt acacagtgaa tttgatcttt actctaaatt cttttccttt aatgaaagtg    120660
ctagtcagta atgcagaact tgggcaagtt ttataaatat gtttgcttta caaccagtct    120720
tattaagtca gggtatcatc taagggccca atcaaggact tttcatttaa aaaagaaaaa    120780
ctctaaattg cattgtgata taacccttaa attccaactg tcatggggaa tcccaagacc    120840
tacatctgta tgtatgtgct gtgttctaaa cactgctccc caacctttt ggcaccaggg     120900 accggtgtct tggaagacaa catttccgtg gttttgggat taaacggttc cacctcagat    120960
cataaggcgt gggtcctaga tcccttacat gcgcagttca cagtagcatt cacactccta    121020
tgagaatcta atgccactgc tgatctgaca ggaggtggag ctcaggcagt aatgctcact    121080
tgcccgctgc tcacctcctg ctgtgcgacc cagttcctta caggggctgc agaccagggg    121140
gttaggggtc tctgttttg ttttttgga gatcaagtct cactctgtcg cccaggctga      121200
agtgcagtgg cacaatatcg gctcaccaca ctcttcacct cccaggttca agtgattctc    121260
ctgtttcagc ctcccaagta gctgggacta caggcatcta ccatgcccag ttaatttttg    121320
tcattttagt agagactgag tttcaccatg ttggccaggc tggtctcgaa ctcctgacct    121380
caagtgatct gcccccctca gcctctcaaa gtgctgggat tacagacgtg agccaccgcg    121440
cctggctggg gacctctgtt ctaatatgct taccatgcca aatgcattat gaagaaaaac    121500
agaaacaagg cttttaatgt taaagtctta ttttctcgct actgaaatag gcaaatgtt     121560 tcaattttgc aaaaataata tagtattgtg tataggatct tccctaacct gcttttaca     121620 tttaattagg cttctacgag tcattcgggt agttgcatct agcaggctat ttatccattc    121680
tttatagacc ctttagaggt ttgagacccc tttatagagg tttgagagcc ctttcttgcc    121740
ccagttctct tgtctgtaaa gctgtaggaa ataatatgac ctaacataca aggcagtgtg    121800
aggacagcag aagtgacttc tgtaatgcat atggtgctgt tccaggcatg gataaatctt    121860
tgctaacagt cgtaagagtt tacctcctgt gaggacctgg ctacgtgctg agcaccctgc    121920
ttggtgcttt gtacattgtg actcattcag ttgctcaaac aacaccatga gtagtttacc    121980
agaattaccc ccatcttgca ggtgagaaaa ctgagcatcc gagtgagtta gtagtttgct    122040
caaaggcagg cagctagcgc aagggggagc aggaatttga acctgagtgt cggcccaca    122100 gcctttgctt ttaccaccgt gctttgccac ctctgaatgt tcactttcat tccatagcag    122160
catcatacag ccctgtgcat aacaggaagt gcacgtttgt taaatgagaa actagtaaca    122220
cttctggtag ctgaatgact taactactgg taaacctgtc tgcatggcca ctaggctttt    122280
```

```
tatggtgaac acaggcatat tttccatgtg ctgtgttgaa gcagcaatta aataaatcag 122340
gtaaaagagt aattaaattt aaaaggtaaa acgttttgga aggagttttg aggtttaggg 122400
ctgtctaacc tgaccttgac tgtttctcta tgtgctgtaa gatgcagatt gattttcaat 122460
gagatattca gcccatccct gcttatgatt tatatatatt ctaagtaata tgcttagaat 122520
gtagttctgc ttaccatcat aaaatgtgga gttaaaataa gatccttgtc aaaacattgt 122580
catgcagaga ttagtgctat gaaagttaac attaaatgat tttaaaatgt gatccagagg 122640
ttaaactgaa gttttgaaat tcataaaatg cataagcttt ttgagaattt ttaaaaatat 122700
ccgttacata ataactttaa aattacgtta tatgattgct atcttacccc atcttagcca 122760
agagcattca gcctgaggat actcaaaaag agtcaaatta ccccttcctt gtataagcta 122820
tagtttagga tattgcaatt atatgaggtc gttttaaagt ttttagcaac gtttggtata 122880
attacaatat tgtgctgttc ttacacaaag aaaacataac agaattttga gctaggaata 122940
ttgggaaacc agccattgct aaaggaagat gcatttagtg tatcttcta tgtacctctt 123000
aacatctttt gtggggtgta gaaaacaga ttattagggc tttctttttt tgtgggggg 123060
gcgggagcgg ggatggagtt tcactcttgt tgcccaggct ggagtgcaat gatgtaatct 123120
cggctcacca caacctcctc ctcccaggtt taagtgattc ttctgcctca gcctcccaag 123180
tagctgggat tacaggcatg tgccaccaca cccggctaat tttgtatttt tagtagaggt 123240
ggggtttctc catgttggtc aggctggtct cgaactcctg acctcaggtg atctgcccac 123300
cttggcctcc caaagcgctg ggattacagg catgtgccac catcccagc taattttgta 123360
tttttagtag agatgggggtt ctccatgtt ggtcaggctg tgtcgaact cctgacctca 123420
ggtgatctgc ccacctcagc ttcccaaagt gctgggatta caggcgtgag ccaccacgcc 123480
tggcctatta gggatctcta aaagccgcaa gcctcttgct agccatagct gtgaatgttg 123540
tcttaaccat taatgcttca gtataaataa tatcaattta aaagctgcct aagatttaaa 123600
agtactatgc aaattacaaa ctgcttgggt atctagatca aaataaagca gagcaaagaa 123660
gtaactttag gaatgaaagg gtatctaagt ggaatgataa aggaagactt catgcaacag 123720
aagaatttaa gtaaaactga aaaactgaaa ctaatgtgat catggcatta aatagtgtaa 123780
ccctgaagac gcatccagta tataaggaac accacagcag tgcctatact caccgttatt 123840
attcatcatt attctgaagc atgaataaga acaatttcaa aaattataaa tattggaaag 123900
gaagagacac attttattat ttatgtacag aataattata taactagaaa attcaagaga 123960
ggcaactgac aacttatttt aagtaataaa agttttagtt tgctagtgga tgcaatgtaa 124020
atatgtaaat gtcaatagtt ttctttttt gttagccata aatacatact gtaatagaga 124080
aaatgtccta cttatacatg tcccccaaag gatagaatac ttaggaaata agtttagcaa 124140
gaaatgagca catagaataa aactataaaa ctttattgaa agacaaacaa caagacctga 124200
ataaatggta agacacatga catactctta gatgggaata actggtatta atcatccttc 124260
ctctgtcaaa ctaacaccta aattactata aaattactat actatatcat gccacactat 124320
actatactgt atttactgta aaaactgcag aggaaaatga acttcgtggt taaattaatc 124380
acagcatttg tctagattct gcaagaatga attcatgagg atggatttaa aagcttttc 124440
aaggccgggc gcagtggctc acgcctgtaa tcccagcact ttgggaggcc aaggtgggca 124500
gatcacttga ggtcaggagt tcgagaccag cttggccaac atggtgaaac cctgtctcta 124560
ctaaaaatac aaaaattagc caggtgaggt ggtgcgtgcc tgtagtccca gctacttggg 124620
```

```
aggctgaggc aggagaatcg cttgaaccag ggaggcagag gttgcagtga gcctagattg 124680
taccactgca ctccagcccg gcgacggagt gagattctgt ctcaaaaaaa aaaaaggctt 124740
tttcaagaac catgatggat gattaaacta attgtaagta tcagaacaag ataaccctat 124800
agcaaaacag ttaatagcag aggaataccc tggagtgtcc tgagatagat ttcttccagt 124860
agtaatttga taagatgaca tttttatttt attttttattt ttttcttttc ttttattttt 124920
ttgagacaga gtttcactct tcttgcccag gctggagtgc aatggcgtga tcttagctca 124980
ctgcaacctc cacctcccag gttcaagtga ttctcctgcc tcagcctccc gagtagccgg 125040
gattacaggc atgcgccacc atgcccagct attttttgt attttttagt agagacaggg 125100
cttcaccagg ttggccagcc tggtcttgaa ctcccaacct caggtgatcc atctgccttg 125160
gccttccaac gtgctgggat tacaggcatg agccactgca cctggccaga tgacatttta 125220
aattagtggt gaatggatgg gatactgatt aaatgatgtt ggaacatttg actaataatt 125280
ttaaaacata aaccatagag tttgttgttg ttgttgtttg aaatgtagtc tcgctctgtc 125340
acccaggctg gagcgcagtg gtgcgatctc agctcactgc aacctccgcc tcctgcgttc 125400
aagtgatttt cctgcctcag cctccctgag tagctgggat tacaggcaca tgccaccatg 125460
cctggctaat ttttgtattt ttagtagaga cggagtttcg ccatgttgtc caggctgctc 125520
ttgaactcgt gacctcaggt gatccatctg cctctgcttc ccaaagtgct gggattacag 125580
gcatgagctg ccatgccctg ccaaaatata aaccatagag ctttgtatca caatatattc 125640
aaaataaaga tagagtgact ttttactttt tagtgtgcaa attaaacata aagcttccag 125700
gaaaaagcaa aaaaaaaaaa ttattgttgg tatcctatca aggctagtaa aagaataga 125760
taaatgtata catggaacat gggaaaacat tcacaaaata taagttaaa aaaatcaggt 125820
tgtaaaataa tatatctcca atttgtatga gatttatatc tatatatgga atgaagagat 125880
atagaagtat atcaaatgat tattttttgtt tgcctggagg taatgaaatc atggtgattt 125940
tcacttcaca ctttgtgatt tggcattctc aaattttac aattactgtg tattactttt 126000
gtagtagttt tttttataaa aggaaaaaat gacttgaaaa atcaagtaat ttgacatgta 126060
gacacaggga aattacattc gaggcagaga gcaaacgaca ggcatgtgac tgtagctgac 126120
aagtgtcagc agattgtggg catagtttag agtctaagac atctggggga gatgagtttc 126180
atcattagat gaagtcatat tctggagggg aataaatgct aatctgaaat actatgcttt 126240
caattgccag tgaggagaaa ttgacagttt tgaaatagtg gtttcaggaa ggctctcctg 126300
agaagatggc actgaggcga gccttgaaga aggtgagagg ggagaaagat tggcctgtgt 126360
tcaaggaatc aaaatagttc gctagttcag agacaggggta aagcaaatag actggagtct 126420
cattcaatgt ctttaaaagt catggagaag agttagtata gttctaatc catgaggact 126480
tcctgaatga ttttgccagg actgtacttt aagatactgt ttcttccaa cccccccatca 126540
gataagtcat accactttc tgaagtcgaa taagtgaagg gaaagagtgg acaaattgtt 126600
atctaacagg gctccctccc caggaaagga ctccttcgtc agtaagagat gtgcacgtgg 126660
tataaccaac aatgctactt ctgggtatgt ccacactgct ggagctcaga aatgcacaat 126720
gaaaaaacaa aacgggttgt ggaagtgtgt atacaatctg ttacattttt gaaaaacaca 126780
taacacaatg ctatattctg tttatgcatg tgtgcttatg tagaaaaagt ctgaaaacct 126840
gatctgcata agctctgagt tcataggagt tatgaccatg ggaagaagta gaggggtggg 126900
atgagcgcat gggatactga actcagctat gctgctttac ttctctgaaa gaggaacaat 126960
cttaagtaat catggtaaaa tgttaatgtt tgtccatttc agggtgggga aggaaattta 127020
```

```
ggtctgtaat ttaggagaga ggttgaggcc agagccaaga ttggcagttg tgatgagtat  127080
gtggttacat cttcactttt tttagaacta aatctggatg tcaatggcca tgtttagtgg  127140
gccaggggcc ttacattact ttcttgcagc actgatggct tttgtttgag gctgcacaaa  127200
ttcctgcatt tcccttgggt tgaatggtag ggatgcgggc agttggtgac tgggtgaacc  127260
acctgacttg agcagggcta cgactctctc tgcaaacgaa acccagagac atgaacagtg  127320
ctgagatttc tcagtggttt cccatgtagg ctgctttcca agggcagcaa gcatggcttc  127380
atcactcacc cagtgcttct gattcagcac tgtgatgctc ggttaagttt taatgaggtt  127440
ttaaatttt tcgtatgttt gagtgtttat gcaaacaaag atgctgaatt gtaaacacca  127500
gcaatctgag taccttcttt tgatttctct ctccatattg tttagtccct ttttctttgt  127560
ttgttttatg aaattgcata gatgttttgg ttgagagtag attgttttta cttttcaggg  127620
acaggcaaca atttcatgat ataacttcta aaatatttt aaacaagtat gaaaatagtt  127680
ttttcttcca aaaaccatt tcttcatttg gcacatacac aaacaaatga gcagaattta  127740
gagtaattta gagacagaat ttagataatt tgggtgggtt ttttttttgga cagtcttgcc  127800
ctgttgtcca ggctggagtg cagtgatgtg atctcggcgc accacagcct cctcctccca  127860
ggctcaagcg attcttgtgc cttagcctct caagctacag gcacacacca ccacgtccag  127920
ctaatttttg tatttttatt agagacgagt ttttgccatg ttgcccaggc tggtcttgaa  127980
ctcctggcct taagtgatcc tcctgcctcg gcctccttaa gggctgggat tacaggcatg  128040
agccaccaca gccggcctag tgtgaaagca gttttaagg acagttgaac aggaaagctc  128100
ctggattcct gcacatagat cttgtgcccc tccaaagtgc cgtaagtacc gatttctgct  128160
gtcttgattt aactcagtgt ctggagctta cgatccttcc tctctgtttc cttcagtggc  128220
gtagcttggg ggtgtcaatt aaagagttat gcaagatct cagcctctga agtttagct  128280
tattcatcag caaaacttta agcaagtctc acctcttcta aattagaatt gtaaccttga  128340
ctttagtctc agagttaaca ttgtgcagaa aaagaaaaca ctgcgcagtg ttgaagcagt  128400
ttgcaaactg aaatgataca aatgaaaaat gctatgatgt ttctcagtag tctctgtatt  128460
tgcaaatgag tcagttagga ttagttttac ccacaaataa caacaacagt aaaaaaaaaa  128520
aaaaaagaaa gaaagaaaga aagtgaccca gcactataat acaagtttat ttctctctca  128580
catcaaggaa gttcagggta gccagtctgg gctggtttag caactccttg atcatcatgg  128640
gttctgtgct acctggtagt ccaggatggt tgcacaagct ccagccattg catctgtatc  128700
ccaatcagca agaaaaagga agaaaggcat acccccttt caggaggctt cctggaaatc  128760
acatacaaca tacctggtta catctcatca gtgaccttag tcacacagcc atacttagct  128820
gcaagacaag cgaagacatt cagattctac ctcttcttct tgaaatagaa aggtgagttg  128880
ccaatccact gtcagcgtga cgacagttca agaggttttc ctagacacag agttgagtta  128940
atcccgtcat ctgtgtcatc gtctctattt tgacagcatc tgtcaggtgg tcaaccagag  129000
tttaggcaag aagacctatg acttctctac acagacatga ttaggattat cttctaaatc  129060
aaccaaactg accagcccac cctttcattc ttctgtgcat cacagatcat ttttgaaaaa  129120
gagtttagga cacatccaat agtaagagtg tagttttata aatcaggact cagtcttaca  129180
gtggaagatt atatggtagt tagtgtcatg gagaaaagct tcatattaga ttagttgaat  129240
cgattgggat acagaaccgt ctttagagca tggcatcgtt acattgcaga taaagcatgt  129300
aggtagagaa tgatatcttt gttggggaga gccccaaact gctcttcagg aacctttctc  129360
```

```
cgagatttgc aagccaatta ggcataatga aaccttgttt ttaatgcata tcttttgcca    129420
gtataataaa cataataatt aaatgtttat atatctttcg tattttcctg tataatacaa    129480
ctaatcatat ttttgtcagg ctgaggacat ctcaagagga gggaaaggtg gcaaattgag    129540
ggtctgttct tcttttatac cagatggcaa ttataacaaa ttacttctgg acttagggat    129600
gggggagggg tggggagatg ggaacatgag aattattcct gatttttgtt acttttgtc    129660 ctgtaaaata tgcttaccag gccgggcacg gtggctcacg cctgtatccc agcactttgg    129720
gaggccgagg caggcagatc gcctgaggtc gggagttcga gaccagcctg accaacatgg    129780
agaaacactg tctctactaa aaatacaaaa ttagccaggc gtggtggcac atgcctgtaa    129840
tcccagctac taggaagggt gaggcaggag aatcacttga acctgggagg cggaggtggc    129900
ggtgagctga gatcacgcca ttgcattcca gcctgggcaa caagagcgaa actccgtctc    129960
aaaaaaaaaa aaaaaaatgc ttaccgggac atctcaagga catcattcct tgtcaacgg    130020 tacaaagata acctgagaca taaagtgaaa atgatttatg gttttttgtt ttcttcctta    130080
cattaaattt tccaataaca tatcgctaat aacatatttc ttttgttttg agacggagtt    130140
ttgctcttgt tgcccaggct ggagtgcagt ggtgcaatct cgactcaccg caacctccgc    130200
ctcccaggtt caagtgattt ctcctgcctc agcctcccaa gtagctggga ttacctgcca    130260
ccacatcagg ctaatttttt gtattttag tagagacggg gtttcaccat gttggccagg    130320
ctggttttga actcctgact tgtgatcca cctgccttgg cctcccaaag tgctgggatt    130380
acaggcgtga gccacggtgc ctggccaaca tatttctaat aatatattaa tttgataaac    130440
agaagttatt ttggaaataa gccaaaacaa caaaaaatgc tcatccctgc ttttcaaggc    130500
tattatctgt agtttgaggt tttatcaaat gtagatatga actgcgggcc tcttcaggat    130560
gtcctcattg cttctgttaa tgcttttacc atccagtacc actgaacagg cagcagggtg    130620
ccttcttggg cacaccggaa ggacccagga aaaggaagat agtgtggcct gttcttgtct    130680
ccatgcccca aaatggacca ctacaccagt ggggtaggaa atagcaggtg tgttatgggt    130740
tgagtttgga gaccttgact tgatcaacca tctgctcacc caggtcatct ttccttttt    130800 tgcagaggtg aggtctcact atcttgccca ggctggtctc ctgggctcaa gtgatcttac    130860
cgcctttacc tcccaaagtg ctggtattac aggtgtgagc caccatgcct ggttcttgtc    130920
accattctta acatcagcag cagcagaaaa accccctgtt tagccttcaa tgttaatttc    130980
ctccttgatc tatgtgttct acacaaacca ctcccttgtt gtcccccata tattacattt    131040
gtggactctt ctcaaactct gcagctcagc cctggttcct gctgagccta cagccccagg    131100
cctgagcagc cggctgggcc aagttaccct cagtctcaag atgacttcct cacaaggcaa    131160
aacatttctc cagctgggtt ggagacctaa gctgggaac tgggctctca cattccaaga    131220
tagaggtttg cctatggacc cctgaaagta ggcgtgtaga agcaggttcc tctgatggca    131280
gaggccctct gtttatctct gaaagatcct gaatgctatg cttctttcat ccctctgcc    131340 ttgaattcgc ctgctttcta ggtgcggtgg agaaagctgg gaaaagagcc acctctgctc    131400
ccaggggcca ctgagagggt agaacactga ccgaatccca gactcactac ctcagggct    131460 gagatgggtc caaggggcc cttaacctct cacttgatca cctgactctt accgctgtca    131520
ttgatctgac atgttctcct gggcgctgtc ccagctctgt cccagcttct cagcactgtg    131580
tcctggtcag ccctgagggc tcatttcctt tatccatact gaggaccaag acctgtcttt    131640
cctgtagggc agtgagggcc acgggctagt gcctgagccg atgagtgcac tgctggtact    131700
gtgctgagcc ctggacaagg gtgtaggttg ctctaaaaaa caacttccca atattctaca    131760
```

```
aaataacgtt caaactgaac agagcttgac tgaagattct tcttacttca tttgttttca    131820
tgctacattt ttgctgtccg gctccaagtc tgtgacaatg ggtcacggga tcagtgcgag    131880
taacagtgaa gatgttttc ttcatctttg ggctatgatt gtgctttgtg atcctaagta    131940
taaatacatt gaggctgggc acggtgtctc acacctgtaa tcccagcact tgggaggcc    132000 aaggcaggtg gatgcctcga gcccaggagt tcgagaccag cctgggcaac atgtcaaaac    132060
cccatctcta caaaaaaaat acaaaaatta gccaggtgtg tggtgtgca cctgtggtcc    132120 cagctgctca ggaggctgag gtgggaggat cacctgagcc ctggagatca aggctgaagt    132180
gagttatgat cgtaccactg cactccagcc tgtctcaaaa aacaaaacaa aaaaaataca    132240
tacactgact aataacacca gcaatattgt ttcatgggag ctgcctctgc tgtttgtacc    132300
aaaactgagc agattctta ggccaggccc gagtaatcat taaatcgatc tgcttgtgag    132360
aaaccggtag gtctaggcat gagcacaaag tggcaggtcc gtctcttccc ttcttaaata    132420
aggaatcacc agaggtagac tctgtgcctg tgactcttga atgtttaact gaaatccaga    132480
gcagcaattg catttatat gacaccatgt gtgtgcaaaa actgaatcaa atcttgtga    132540 aacagtgcta ctttcactta ctatatatga tgtagtctaa taattttcta tcctatttta    132600
tttccttttt ttaaatgctg gttgaaattc tgtaaattta taatgaca aactactggg    132660 actctatctt ggttcaaaag tccatgatca gcctgcttgt attgagttac tacattgtac    132720
gatcttataa ttgtaaagtt taagatattt tccttctgtc tgtcttaatt tattctgtaa    132780
tctaagttgt cctgccagga atgctggcat atttactttg ttttttgaatt caataatcat    132840 agtttctctt gctaagttac attaatggta ccaaaaaaaa gttactgcat ggttttgaa    132900 actgttcttt cctaggaagt tttaaagtaa aatgttttta ccttttattg tttacacagg    132960
ttaagcatcc ctaattcaaa aatccaaaat ccaagaagt gctcaaaaat ccaaagtttt    133020
ttgagtgaca acatgatgcc accagtggaa aattccacac ctgatctcgt gtggcgggtt    133080
gcagtcagca tgcagttaaa tctttcatat atgcacaaaa ttattaaaac tattgtccag    133140
ggccaggcac agtggctcac acctgtaatc ccagcatttt gggaggccag gcaggcaga    133200 tcacttgagc tcaggagttc gagaccagcc taggcaaggt gatgaaaccc tgtctcctct    133260
aaaaatacaa aaaaaaaaa aaacattag ctgggcacgg tggcacacac ctgtagtccc    133320
agctatttgg gaggctgagg tgggagaatc acttgaactg ggtggcagag gttgcagtga    133380
gccaagatca tgtcactgca ctccagcctg gcaaacaga gggagaccct gtcttaaaaa    133440
aatatatata catatatata tatagtttag gctatgtcta taaggagtat atgaaatata    133500
aatgaatttc atgtttagac aggggtccca acccaagat atctcgttat gtatatgcaa    133560
atattacaaa atctgaaaaa atttaaaagc caaaaatcac ttcagtctgg tgccaaccat    133620
ttttgcataa ttgcattttc catgttgcat tttgcaacca ttttgcataa ttctgtactt    133680 cttccctt tgggtttgtt ttcataactg ctcagtaaaa agtgttctgt gtcatctttc    133740
cattattttg ggctaaatca tgttaatggc caagcctgtc agaattcatt tgttttgagt    133800
taacttcctg gtgtccagtt ctcaggagtt gcaagaatag agctcttccc tcatgcaatc    133860
atccaaaatc ccaggcctct aaccaggatt ggggaacacc actgttggcc aagagcagaa    133920
ggcttaaagc tctggtcata gtcatggcac tgtacaaact gttcttgttc cctacaagaa    133980
catgggaact atttggataa tggatttatg aatttaattc tgatggattt ttataaagga    134040
gctaaaaata agcctatata atttattaca tgtataatca tataattta aatgtgtata    134100
```

```
atttataata ttcatcgaaa catttctttt tggaaattaa atttcactt  ggtcaaaatc 134160
atcttacaaa acaagatgac tcatgatggt tctaaataat gtaaaccggt gtctgtaact 134220
aattaatgct ctggaggaag gaaattctga gttctgacac aaaagcacgt ctaagtggta 134280
ttggtatttt caaagctttt actacaacca aaaatatgtt cacgtgtacc tgtctcctct 134340
ttacactgct tactttctct atcgctttc  ccaaatacgt ccccagtaac ttcctcatgt 134400
tctgtgcacc acctccaatc ttcccctaat gtgtatgaac ttggtcatca ccaaagaggt 134460
ggaaaggaag aagggcatgt gctaatatta atattgaggt ttgggctggg tgtggtggct 134520
catgcctgta atcccagaat tttgggaagc cgaggcaggt ggatcacgag gtcaagacat 134580
tgagaccatc ctggccacat ggtgaaaccc cgtctctact aaaaatacaa aaattagctg 134640
agtgtgatgg tgcacaactg tagtcccagc tactcgggag gctgaggcag gagaattgct 134700
tgaaccaggg aggtggaggt tgcagtgagc cgagatcgtg ccactgcact ccagcctggc 134760
aacaggagga gactctgtct caaaaaaaaa aaaaaaaga aaaaaattga ggtttgtgcc 134820
agtttctttt tcctttaggt ctcctgatat gtgtctagtt agttctatat acttcctgga 134880
aattcgactc caagatattt aataaaacta aacagggtta tatgttgaat agacaaatcc 134940
taaagagcag aaaggattta gtggttagtg aaatttcatt gacttaagat gagttggatc 135000
ctcaaaatta atatattcta aacaaagttc tattttaag  ctgcagtaat aatgccgaat 135060
ttctcttata gttaattgaa tgatttatcc tggtgttgtc tcctggtagt cactgaaaaa 135120
gtcattacaa tcctcacttt ctccccttta attcaagttc agaattcatg tgttgctgtg 135180
actttttttg agtttatctg cagacagctg ccattgaata aacatgttta tagggcag   135240
aaaaaggcag cctgaagatt ctactttcta tttcttttag cactgtttgg cagttaacac 135300
caacagcgct tcagaatgag gtactgtcca gcatacacct tgcttgttcc tctacaaagc 135360
ttctattttt gttttgatt  tgttgtgagg aagcaaagtg tagcctttac ttgaatgaaa 135420
gctacagttt tattttctt  tcttatttac aagaaattct tttgatgatt aagttagcca 135480
gatacgcccc gtgcgctcat atttcttaac ctattttgag ctgagctagt tgcaaggact 135540
agttcttctg tgaaacctct ggcagtccat aaattcaagt tcgtgtccag acgtaatggt 135600
gaactcaata tgttgtatat ttgatatatg tttgttgcac acatggagag aaaagttgct 135660
accattgtga agtagccatg aaatccgaca gttctaattt ctttatcttc tgagtaccca 135720
tggaataaag gacctcttag tgccatagca aggcagaagt ttaatttgca attctggtgg 135780
caacatccag gtatttcaag tagaaattaa gaaaacttta cggaaaaact atctcagcac 135840
ttcagtttaa ctattttca  aagtccaagg agggttttcc ccagtgtaaa agcagaaatg 135900
agaatttcag atctaaagcg gttcttgcct tttcttttcc ctccatgcac atgtgctgac 135960
aacagaaagt aaaatttgaa agaaaaccc  aggctagagc attggggtca ctcatttccc 136020
atccagcgaa gggagagctg gtgcctggct ggggaggtt  aggaaggcaa gtcttgggat 136080
ctgatcactc ggctgggagt gggtaaaata cctggacctc aggaggccgg attgcagcgc 136140
cagtgttctc tacctgtgtg gcctgttcct gcctgggggtt gggtaccaag tccaggtgga 136200
agtggtccct ggagcatcct ctctctgaag tgtttctttg tcaaacagaa tactccctgc 136260
tgctgcccca gaactcatca ctgttgacac atggaccaag aactagcaga ggaggtgatt 136320
tataatctct aaatgaattg ctctaaaaga gacaacaagc actctgactt aagtaaagga 136380
agggagggtg ggtggaaagg aaggaggatc ataagaaca  ttctagattg catactttgg 136440
taatcacagc agggccttat tgcagttaga acaaaagcct ggacacactt acctctcagt 136500
```

```
tcaggaaaat aatttagagc tacttgttaa atgctggagt attattgaag taccaagtgt   136560
taagattttc actgaaagca aaactgacca agcagctcag ctagggaaat gctatgtgat   136620
cagttgattg tttgatgagg agtatggagc agggactttg gcagaggttg ctagcagaca   136680
ggccttggtt ttagtccaag ctctatcgct taatagctgt gtgaccttgg ggaaaattat   136740
aaaattttcc agtccttagt atcataaact gtaaatggag gagaaagatg cctcacagat   136800
gttgaaggtg aagtgagaca ggacacctag tacattgcct ggctacatag aaaatgtttc   136860
acaaatgtta acttgaggcc ctctccccat gcctcggtct cttagaatgg ttttttcccca  136920 tcgtgtgcac attgagcggt aaggcggaca gctgccgccg cccatgctgc cccatgttga   136980
gagcatttct gttgaccttc ccttcttccc tgtgaagctg gttcagcagt cacctcatca   137040
ctgtttttct tctccagaga gtgctgggtt gtagcgacca tactgttgac gcaacacatc   137100
ccaaccacgc tggacggaat ttttactgcg ataattcata ttccaggatc ttacagtgca   137160
cagggttaca acgattagca taatgatctt gcacaatctt tctgcctagc atgtagtgca   137220
ttcgtaatat tctcagagga ggcgtctaga aagcgccagg ctccttcctc ctgcgtgagc   137280
cactgcaagc tgtcggcgcc tcagtgctat ggagaccttg ggtggattat tccttgttgg   137340 cgggggagg gtcccagctg tcctgtgcat tataggatat ttagcagcat ccttgctaga    137400
tgccatttac aacaatcaaa aatgtctcca ggcattgcta agtgtccagg tggggagcgg   137460
aataggcaga accgcctcca gtcgagaagg gctgaactgt acttaggatt tgtgattctg   137520
cagaaatggg ttctgtgaat gcactaaagc atgagaacat ccaaaaatca gtgtggcaca   137580
gaactgaatt caaatttacc tggatccagg taaataagca caattttgaa agtaccaaac   137640
agaattcaag aaaaacaaca acaacaacaa aaaacacatt aaaaacagaa aagttggccg   137700
ggcgccgtgg ctcacgcctg taatcccaac actttgggag gccgaggtgg gcggatcacc   137760
tgaggtcaga agttcgagac cagcccgacc aacatggtga aaccctgact ctacaaaaaa   137820
tacaaaaatt agccgagcgt ggtggtgggt gcctgtagtc ccacctactc gggaggctga   137880
ggcaggagaa tcgctcgaac ctggagggcg gaggttgcag taagccgaga tcgcaccatt   137940
gcattccagc ctgggcaaaa agagtgaaac tccatatcca aaaaaaaagg ggggaaaggt   138000
cagaaagacg ttcttttttca ctaggtgatg aattaatctt tcccatctttt gtcatgttaa   138060 aaatgtgcct gtggctgttt ctccactaaa tgaagacact ggcacacaga tgattgtgtg   138120
taaacactag gcaagacact aggcacaatc gtaggggttc agtaattatt gaatgagaag   138180
aaagaaaggt tgttcttgaa ttctgtgatg tgagtgttta atgatgtttt tgaggagaat   138240
gccatatgta gcagacagaa ccctgggctg ggcatcagag ggaccgggggg caccacactg   138300 ggctttgtgt cattatctcc agaaagtaac tggcctggtg cacaggagaa agttagagta   138360
cattgtccat acagttccca catagctgta gggttttatg aacccatatt ttaaagggcc   138420
ttctaatgaa gtgaggatgt taatgctttt ttttaaaaaa aaaaaaaaaa aaagagagag   138480
agagattggt gattacttta aaatctgagt cctggccagg actcacgcct gtaatcccag   138540
cactttggga ggctgagacg ggcagatcat ttgaggtcag gagttcgaga ccagcctggc   138600
caacatggtg aaatcctgtc tctactaaat acaaaaatca cgctcctgta atcccagtta   138660
cttgggaggc tgaggcagaa gaatcacttg aacgtgggag gcggaggttg cagtgagcca   138720
agatcacacc actgcactcc agcctgggca acagaatgag actccatctc aaacaaaaca   138780
aaaaaatcca agtcctaatt atcgctgcag cttttcttttaa tgtgtgcagt aaggtgggga  138840
```

```
catacagaat aacttaagat gtagaaatcg tctctccctc cctgaagaat atcatggata   138900
ctacatttgc ctgccaggaa tgttgtgttg ttctggtgtt ctcgtttctg ccgttatcat   138960
tgtttctgct taattttttac aacacaactc tggccgcacc cgtggatgat catggaaagg   139020
cagctgcctg gctttccaga attgtttga  ctctccatct gaacccagag ctctgtttcc    139080
tgtacaggtt gctagcagta tttacccaaa ttgtcccttc ccaactcaga cccactgacc   139140
cttcctttct cagctgatta cgggtttaag tttgaatcaa accatgctat agaatcacta   139200
tctagcagct tctgtgcttg cacaataaga gtattagtca gcgtttcctg ttttcattca   139260
tattgtaagt tgaatagctg taacaaaagg gaaagagatt gccaagacaa ataattctta   139320
tggcttgtgc aaacaattta ttacaagcct tattaaatat gcagctttca gaagtctacg   139380
tgatatgcct ttcagcaaag ctaaatccta ctatgtggac ttgcttcatg acttaagaac   139440
aagtctatat tgaatttaac attaaataat tatttggcct gtatctcttt taagctttgt   139500
taagaactgc aaatatgata agggaataaa ttgctcattt caagtcacta agaaaaccta   139560
acctataggt tatatatgtt ggcagttccc aagaagtacc taggaaatgg aaccttccta   139620
taagagtggt ttgtcccctt ctcacgagat gggtcttcat atcaaggccc cctaaggcac   139680
agatacacag cactccacag tgtccaagtt cgtagtaatt ggtggcacct tattaaagta   139740
gttttactt tcataattac tgattacaca tcagcatacc ttttccatgt tctgtttcct    139800
tggcagcctg atatttgaat acaaacgaca taaaagtgat tacatgcagc atttcaggac   139860
agttttcaaa ctgagagaat ttggcacttt cttttatttt cttcccattc ttcgtctatt   139920
tcctttgcat ttggaagcca aactcctcga acctttactt ctgcatgttg ttttcgtccc    139980
ctagctagag ttctctttat tactactttt ttgtttccaa ttggtctctt tttaaaaata   140040
aaacatggtg aaaccccatc aatacaaaaa ttagccgggc atgatggcgg gtgcctgtga   140100
tcccagctac tcgggagact gaggtgggag aatcaattga acccaggaga cggaggttgc   140160
agtgagctgt gatcgtgcca ttgcactcca gcctgggcga caagagtgaa actccgtttc   140220
aaaaataaat gaataagtaa attaaaatat gaaattaagc ttagctagcc tgtgtagatg   140280
ttttagatgg tcatatcttt atcggatatg acatttatgc ctttcagtaa aaccattgta   140340
gtattgtaag aaaaaaaggg aagtatgata gggaggacta agaacatatt tgtacttcta   140400
tgtaatgcta ttttatgtgt ctatttccat tgaagtgtgg ccttgacatc actggctccc   140460
aagtcccatc ctgttttttc attgacctgc ttgtgccagg tactgcgtta ggaagtggag   140520
ctaccagatg aataaggcgt ggtcccgccc tccatgtggg agacggcacg tcagtgtact   140580
taggatgctg catgtggtga cagatgaggg ccctgcaagg gagcacacca cagggccggg   140640
agggtgggat gggcgggagg agtagccaac tttgcccgaa agcatcagga caagcttcca   140700
ggaaatggca catccaagct gagtcttgga cagcgggtta agaggcaga gaggggagag    140760
aggaatgttc cacatgggaa aagaggtctg gaggtgacaa caagtaacat agagtatgtg   140820
ggctgtgccg aagcttgat attacagagg cacgaagtct gaggcaggga gtgtgaagga    140880
agatgaaggt aggggaagga agtttacaca agggtggcct tgactttat attaaggcac    140940
tttagggaag caggaaccac tgaagacagg agaacatggt gactacacgg gcgcattgaa   141000
ggggggagga gctaggtttt tgaagggaat ttgagcttgc aatttttcaa gggcattcaa   141060
tggttataaa tgaaactttt cattaatata tttgtgtcca agtgttttta gatgtgcttt   141120
tctgctactc tcttttttatt tggtttggag atagatggtg acttttcctc agtgcttct    141180
atgtgtcttg acatgttaat gtctcaaaca catggtccgt atcatcatgg agcttgcaat   141240
```

```
ctaacagggt agtttaacac ataaatatgc atccagttgg aaagaactta gagatcactt   141300
gatcagcccc cgttatgtaa aatgtatgca acaatctacc tccaactata gggcgacatt   141360
aaacagtttt tcaaaatacc atggcattga aaaaaatgcg taacatttgg gttacttcag   141420
tcccactccc cggtactaat caggccagtg aaccagtctt gctggtgaaa taatgacttc   141480
tccagtcatg atggatgatt tcccttcatc atgaccattt cttccctggc tctgcccttta  141540 cctatgaatc tcttctttcc tccctctcct tcctcctctt ggtctctgcc tgccatacccc  141600 aactccacat ttctctgctt ggaaaaatcc tacttgattc tcagagcctg actccatcac   141660
cccctctctc caaccctccc aggcaaactc cgtccctccc agtgtgccgc cctccagctc   141720
tctctagttg aatagcagat gttctctctc ccacttccct gcagggcttc agggtagtga   141780
ccctaagagt gagcttctac cagtgagaaa aacgcctgga tggagcagga attcccacaa   141840
atgcttagga attcaatatg attttttagca agtgggagaa ttatccttttt ggttacaaag  141900 atgtgaacta ttttttgtgag ttctcagtat gcaccaagaa aaacccccagt gactcagtaa  141960 tgtacctgtg ccgtctcact taaccccttcc aacaaggaac ttgccaaggt gcacagctgg   142020
gagggatccg gggtcccgtc cgtgtgctaa cctgcaggac agcgccgcat aatccagtac   142080
tggggcctta ttgtccagcc ttccacctcc aggagcccac tcagtgatga cttttgacaa   142140
aagtcacccg gattatccct cttttgggt ccatgatgcc accaacggct aaagttaaca    142200
aatgcattac caggaggtac cactgaggta aggattgtta ctgtaagtga tttttctctga  142260 ttttgaccac tacaagtaaa atcacaagat ttgtcccaaa tactatataa agaggaatgt   142320
cttttatttc tcgaaattgt tctgccactt tgtttgttca aataacacat aataaaggat   142380
aaatggcttg tagctatatt tatccaaatt gaacattttt gatgtaattt ttttaatttg   142440
tcaaaagcat atcaatggtc ataaaaattt tttatgtcct ctggcccctat taccttaccc  142500 ttgggaattt attccaagaa cgtaatttga aagagattaa agcacatagg cacaaatatt   142560
ttcagtgcag tattgtttat attggaaaca acccaaatgt tcagtaacag ggggaacaat   142620
tttgtaaatc ttgctacagc aacttaacaa aattataagc tgccacttat aattgtaaat   142680
tttgaaagtt tgtagcacag caaggaaact gatcatgtta aatgtttctg atatcttagt   142740
taatttttct cccgccagtt ccgatcggtg tcctggtcat accgtcagca tataagtatg   142800
tatttcataa acatttactt tgtattaact cagtagtatt cccttcctag agtggtttgc   142860
ttcccagatt gtaatggaca atcatctcac ctggggatct tgtaacaatg tgattctgat   142920
tctgtaaact ttgtggggag cccaagattc cacatgtctt agaggctctc agatactgct   142980
gatgctgttg atcacgaatc acgcattgag cagcaaggtc ctagagctct ttgtgtatga   143040
agaagatact actgacccag tgcctcgcta tcttgaaagg cagctgtgac cttttctagca  143100 actgagggggg tggggactag aaacgagtgt tttctggtgt ttctctaata aagctgctgt   143160
cttgtatcca gattgaccat cagtatcctt atgcccttca actaacttga aatttgtcag   143220
ttaacagaaa ttactgggtg gcactaaaat aaaattattct taatataaag ggtaagaaag   143280
ggtcgggtgt ggtggctcat gcctgtaatc ccagcacttt gggaggccaa ggtgggcaga   143340
tcacctgaga tcaggacttt gagaccagcc tggccaacat ggcaaaaacc cgtctctact   143400
aacaataaaa aaaaaaaatt agccgggtgt ggtggtgggt tcctgtaatc ccagctactt   143460
gggaagctga ggcaggagaa tcgcttgaac ccggggaggcg gaggttgcag tgagctgaga  143520
ttgtgccatt gcactccagc ctgggggaca agagcgaaac tccatctcaa aaaaaaaaa   143580
```

```
aaaaaaaaga gtaagaaagg atcttccatt gtaatcatac tatcattgcc ttttgaaaca   143640
atttggaacc tgattacaaa gttgaaaatc cccatctgta tgaagaaaag cttcactggc   143700
tggtcacctt ggctcaacgc ctgtaatccc agcactttgt gaggctgagg cgggtggatc   143760
acaaggtcag gagtttgaga ccagtctggc caacatggtg aaaccccatc tctactaaaa   143820
atacaaaaat aaaaaattag ccaggtgtgg tggcaaacac ctgtagctac tcaggaggct   143880
gagtcaggag aatcgcttgt gcccgggagg cagaggttgc agtgagccga gatcatgccg   143940
ctgtactcca gcctgtgcga cagggcaaga caccatctcc aaaaaaaaaa gcttcactgt   144000
gagttatgat atgggaagaa aagtcttggc ctggccacca caaggaatcc ctcaggcctg   144060
gcggtgggaa gcagaggagg gcgcagtctc tttagggcag aaagtgaaga acatttctat   144120
gacaatgggg aaatcagttc acctttgtgt tggtaaacaa aaggaatgta agctgtcctt   144180
tgagctcgaa tcatagtggt gattgccaaa acctacctt gtttttagaa gataatagca   144240
catattccac ttgcttcccc acagtgaccg aagctggctt tggtgctgac atcggaatgg   144300
agaaattctt caacatcaag tgccgagctt ccggcttggt gcccaacgtg gttgtgttag   144360
tggcaacggt gcgagctctg aagatgcatg gaggcgggcc aagtgtaagt gcccacaccg   144420
ccttcctaat accaaagaaa tttcattatg ttaaaacaga attgagcatt tgaaaaattc   144480
ctgcccattt aatgactata gttttctaga gtattttct taaaactttt ttttcctgt   144540 agacctccct cgtggacatc taaaacgttt tttgttttgt gttgttttt gtttttccc   144600 aacaccacca tagggcactt tgagtttagt aagttcgagt aaacagtaac acccacagtt   144660
ctttctaaac aatatttttgg aaaggagcat aatgcaacca ctttttagtc tcaagcttca   144720
catctgatac tcaggccaag attgtataac catatggtaa tgggaggtta gaggctcttg   144780
tccctgaacg aagaacaaga ggattagagt gagttctttg atgacagaga tttttcattg   144840
tttgtacaga tagtttttcg gttcactgat gctgcaactc atcagatttc atctaaaact   144900
attttccttc tctttctgtt tattatgatt tctcctcaca actctgttat aatactggat   144960
tgtttctaag agcttggctt ggaaaacaca aattcgattt taacttcttt aaagactttt   145020
tatatttacc tatcctaata tatatagaaa ttacagacat tataaaggaa atatattcct   145080
ttccacagaa aacctgtgca tagattttgg ggggttttt tgttgttgtt tgcttgtttg   145140
ttgttttttt gtttcatttt taggaatttc caagtggaga ataagacatt ttatactgat   145200
taatcatttt gaaataaaat aaaatttctc tatcataata ttcacatatg agacgaactg   145260
ccaaatctga tttcttaatt ggtatactgt actgtgtatg tgacaaaagt catatattca   145320
atgattattg catagtcaaa acaagtagca ggtttgccat catgaaacgc tgtaaagcaa   145380
ttctttctcc tgggagaggt ggacatgatt tttataccat tttacagata aggaagctga   145440
gttttgatag gctagggaa tatggacaat gtcagcaggc cagcagagag ccgagaactt   145500
cagatctaaa tctcctacta tgtccaccat gcagagctgg atgttaatga agggcagaag   145560
ttttctaaat ccaaatccac tcctaatacc cgacacttaa gcacttcatt tttgcctaaa   145620
gcttcatcat catttcaaat gcaagaatga tataatacag attaaaagta gtaaatcata   145680
aagaattctg acttcactca aaacacccct tgttgctaca gtccttcctg gatttttagac   145740 attgaatctg tataacaact tctatttta aaaactactt ccgcccatgt aggatgcatt   145800
tggaattctc cctccctgcc ctgccaccct gaaaattata gaaagggctt agagattgtc   145860
tgatctcatt cagtctttat aaagagaaaa tctctgaggc acagggagac gcagtgactt   145920
gagtggtgtc acacatctat ttcagggact gatcagatct acagtcctgg tctcttgaca   145980
```

```
tcagtcccat agttttccag actctggtct ctgtcctgta aaaattctct acatggttta 146040
caatcctatt tcattcatct taacatatgt gctctgttat tcagtggttg cactttcgtg 146100
ccacattaat cctttgtgtc tcttccactg ctgcttaatg tcatggttct cagccagtga 146160
tcatggtaac atggaacagg gttagtaggc acagatatgg gtggaggata agaaaaggtg 146220
gggaccagcc aggcgtggtg gctcatgcct gtaatcccag cactttggag gctgaggcag 146280
gtggatcacc tgaggagttc aagaccagtg gtggcgggcg cctgtaattc ccactactca 146340
ggaggctgag gcaagagaat cgcttgaact tgggaggcag aggttgcagt gatctgagat 146400
tgcaccattg cactccagcc tgggtgacaa gaacaaaagt ccatctcaac aacaacaaca 146460
acaacaaaaa aaaaaaaaaa aaaaaaaaaa aaaaaaacca gcagggacca ggaagccctg 146520
tgaagctagg catccctctc ctgggctcca gtagtaccct ctgcctcaca ttgtttcatg 146580
aatgccttgt tctgtgtctc cctatgtaat tctcaattcc ttgagtttag ggactgtgtc 146640
ttattaattg gtatggtcca agtgtctggc atggtctata tgcagggagt gttttcaata 146700
atggcaagat aaatgaactt tcatcctctt aatcctctat tccatagtgc tcatctcggt 146760
gtccttcctt catattgaat agctctgtat ttttgaacca tgattattca tttctacttc 146820
tgttttcttt tttctttttt gctacaaata ctgcgctggg atcgacttcc ttttgatcat 146880
tacacaaata accatggctg cctcttatgt ttattcagct tgttttttttt ccataatttg 146940
tacagtggaa aatcttgtgg cccttgaatt tgcccatttt aaatttgccc tcagtcattt 147000
taaactcaca tcctgtcccc cagagtgctc ggccattccc agtgcaatcc aataactaat 147060
attgtgctat gctttgggat ccacagattc tttcacaatt agatctttaa actaaccatt 147120
gtatgaatca gcattcttca cacatagaac caataaggat gtgtgtatat atagagaaag 147180
atatttattg taaggaattg ggtcacatga ttacagaagc tggcaagtcc aaaatctgca 147240
ctgtgggctg gcaagctgaa gacccaggag aggcagtggg gctaatgcag tctgaaggca 147300
gcagtctgct ggagaattct cctgctctca ggggaggcca gtcttttttgt tgtactcaaa 147360
aaggcctttg actggtcagt tgagacccac ccacattatg taggacaact tgcctactca 147420
gaggctgctg atttccatat caatttcatc atagacaccc tcacagaaac acgcaaaata 147480
atgtttgaac aaatactgga caccctatgg ccccagcaaa gttgacacat aagattaacc 147540
acaaggccag gcacagtgtt tcaccctgta atgccagcac tttgagaggc cgaggtggga 147600
ggactgcttg agcccaagag ttcgagacca gcctggggaa gatagcaaga cctcgtctct 147660
acaaaataat aaaaaattat ctgggtgtgg tggtacacac ctgtattcct agctactggg 147720
gaggctgagg caggaggatc acttgagccc aggagtttga accgcagtg agctgtgatt 147780
gtgccactgc cctccagcct ggacaacaga actttatggc aattaccgta aatgatttc 147840
gaatggtgat gtactctgta taaatcaagt attaaacata ttattagttt tatgttctaa 147900
tttgaaccaa tgtttgagaa gtttcatact gttccattgg ctcaaattag aatcatccag 147960
ggagatttta aacattactg atcccaggtt cccctcccag aacttctgct ttcattggtc 148020
tgggtggagc ccagggatca gtgttttcta aaagcttccc gcaggagttt aggtttagcc 148080
agtgctgcca gctactgttt taaaagcaca aacatagag gtacatttct aaaaattgaa 148140
tgtgattatg ttgttctttc tttcagatcg gttgtgtaag cattttttata ggattattct 148200
tcatgttttc tctccttatt tcaggtaacg gctggtgttc ctcttaagaa agaatataca 148260
gaggaggtaa gaggagctgt ttagatgctt atgtgaagaa tctcttaaat ccagtgactc 148320
```

```
gttggctttc agtgaatgag ccctccttca gtggcctctt agaaaagtgc tgttctgtcc    148380
gggcgcagtg actcacacct gtaatttcag cactttggga ggccaaggcg accggatcac    148440
atgaggccag gagttcaaga ccagccaggc aaaacccatg ccaacatgg caaaacctca     148500
tctctactaa aaatacaaaa attagctggg catggtggct cacgcctgta gtcccagcat    148560
gagaatcgct tgaacctggg aggcagaggt tgcagtgagc tgcgatcgca ccactgtact    148620
ccagcctgga cgacagagtg agactctgtc tcaaaaaaaa gaaaagaaaa gtgccgttct    148680
aagaatccga gaggaaatgg atgggatgaa aggataaaat tcattcagtt aactcttaaa    148740
tatcaagaaa agatggatat aggctttgtc tactattgtg tactcccagg gtagccatca    148800
gagcaggaac tcaaggtctc caggtcagaa acaaatatga agcttacact tctgtattct    148860
tttgtcatgg aaggtctata tacagttggc tttatgattt acaggagtgg cttactcttt    148920
tctgtaaata gactttgatt tgctggcagc agtacctctt agctcctaca ggtggcgcca    148980
gggatctgag ccaggaatac ctggtcagag ctcctcaccc acctgggcc ttgtgcctgt     149040
caggcctcaa cctgcagagc atgggcgcat tgcatagacc ctgcagcctg tcctcagcag    149100
ggtgagctgc caggcttcag acccacccat atgccattgg atccagaatc attttagaaa    149160
ttattttgaa gacgaaccctc tttattcttg cagccatctt tcttggagga aaaagtgaaa    149220
aaagatgtag caaatcctgc cagagaggtg ctggcagttt agcttggcag gtttggtggg    149280
agacaataca caggggtctg ggttttgctt ttttctttt tacagaacat ccagctggtg      149340
gcagacggct gctgtaacct ccagaagcaa attcagatca ctcagctctt tggggttccc    149400
gttgtggtgg ctctgaatgt cttcaagtaa gtccagcctc ctcctttaaa tgtgggcatt    149460
atcactaggc caccctgtga acgatatttg tgtcttgggg tatttggtct ttctgtgctt    149520
catctaaaag tatacagaaa tacccagttc tttctgtttg tttatttggt ttggtttcat    149580
tttagcaaat gtgttctcac aatgttatta aggaagtgaa atttatatat agtgagttac    149640
tatctccttg gcttttttt tttttttt tttaattct acccagcatt tttgtctgaa         149700
acaaactgtg aatgatcaaa gggatatgtt atggaattt cttgataaca cccttaacga     149760
cttgaaatat ttgagtcact ttagagagga ctttttttt ccatgcttta agtctgattt      149820
atttaaacac gatgtgacca cttttgatgt ttaaaatgta ttcagtgtta gggagcgaag    149880
ttctgtataa atggtgagtc tttctttgaa aacatagcta aatggataca gatgcaaaac    149940
cacaaacatt ttcttcacta ggaccgacac ccgcgctgag attgacttgg tgtgtgagct    150000
tgcaaagcgg gctggtgcct ttgatgcagt ccctgctat cactggtccg ttggtggaaa     150060
aggatcggtg gacttggctc gggctgtgag agaggctgcg agtaaaagaa gccgattcca    150120
gttcctgtat gatgttcagg taagatctag taaaaacaat ggctcacatt tcttacacct    150180
tagcatgggt tgtcccattc tgttgtcacc acaaccctac agataagaaa actaaagata    150240
gaagagttta ggcccggtgc agtggctcac gcctgtaatc ccaacacttt gggaggctag    150300
ggcgggcaga tcacttgagg tcaggagttc gagaccagcc tggccaacat agagaaaccc    150360
catctctact aaaaatacaa aaattaggtg gcatggtgg cgtgcaccta tagtcccagc     150420
tactcgggag gctgaggtgg gagaattgct tgaacccagg aggtggaggc tgcagtgagc    150480
caagatcgga tcacaccac tgcactccag cctgggcgac agagtgagac cctgtctcaa     150540
acaaacaaac aaaaaggtag aagagtttaa gccatatgac aaagtcacat ttccaagtac    150600
agaccctagc tccttgtccc aaagcctgtg cttttgaaga ctcccaaatc gcagtcctaa    150660
gtgaggaggt actttagcga acaggatttg acagctgacg ctttcaggag ttgcacagga    150720
```

```
acaagagcaa tttcgtgagg attgggaaac catgggaggt attttccttg ttcatttctc   150780
tttttttttt ttgagacagt ctctgttgct caggctggag tacagtggtg caatctcggc   150840
ttactgcaac ctctgcctcc caggttcaag cacttctctg cctcagcctc ctgactagct   150900
gggattacag gcacctgcca acacgtctgg ctaagttttt gtattttag tagagacggg    150960
gtttcaccat cttgggcagg ctggtctcaa actcctgatc tcatggttca cccacctcgg   151020
cctcccaaag tgctgggatt ataggcatga gccaccacac ctggcctctg cttgttcatt   151080
tctgttatgg ttcttttctc ttgtggtttt attgaactat gtctagtgta tgtgtgtgta   151140
tatatacata cataatatat ttatttattt tcattgtggt aaatatatat ataacaaaat   151200
ttactatctt agccttttt ttttttttt ttttttgaga cagagccttg ctctgttgcc     151260
caggctggag tgcaatggcg tgatctcggc tcactgcaac ctccacctcc cgggttcaag   151320
caattcttct gcctcagcct cccaagtagc tgggactaca ggcgcaagca agcgtgcctg   151380
gctaatttct tttttatttt agtagagtcg gggtttcacc gtgttgcccg ggctggtctc   151440
gaactcctga gctccggcag tccacccgcc tcggcctccc agagtgctag gttgcaggg    151500
gtgagccacc acacctggcc catcttaacc attttaagt gcacgtcagt agtgttaagt    151560
acattcacat tgtcatgcag ccaatctcca gaacgctttt catcttgcaa aactgaaact   151620
gtacccactg aacaactccc catgcccctc cctacagtcc ctgccagcta ccattctcct   151680
tcatttccat gaatgtaaca actccaggga cctcatgtaa gtagcatcat actgtggctg   151740
gcttatttca cttagcataa tgtgcgtgca tgttgtagag tgtcagaatt tcccttcttt   151800
tttttttttg agatggagtt tcgcttttgt tgcccgggct ggagtgcaga ggcaccatct   151860
cagctcaccg caaccttctg ctctcgggtt caagcaattc tcctgcctca ggctcccgag   151920
tagctgggat tacaggcgtg caccaccacg cccagctaat ttttgtattt ttagcagaga   151980
cagggtttca ccatgttcgt caggctggtc tcaaactcct gaccttgtga tccacccacc   152040
tcggcttccc aaagtgctgg gattacaggt gtgagccacc gcgcccggcc agaatttcct   152100
ttatttttcg ggctgaatac gctcccattc tttggatatc ccacattttg tttctttgtc   152160
catctgtgga tggacacttg agctccccct cacagctatt gtaagtaatg ctgtatgagc   152220
atgcgtgttt atggcatatg gcatatgtac aagtatccct tcaagaccgt gttttctttt   152280
tttttttttt tttttttga gacggagtct tgctctgtcg cccaggctgg agtgcagtgg   152340
cgcaatctcg gctcactgca agctccgcct cccgggttca tgccatgttt tcaattcttt   152400
tggaaatgta ttcccagaag tgggattgct gggtcctcta ggatattttt aagcacatgt   152460
cgatggttca gtcagaagac ctgagcttcc cagggctcac tctcctcctc agatcgtctg   152520
tctttgcacc cgtctgacat ctccattctg aattttgtgg ttccgattct ggctgatgga   152580
tttgtcttca ggggtagtgc atgattgtgg agtgcccagg cttcaagctg attgctgctt   152640
ctcctgttcc ttcatccctc acatattcta ttgttgagtc actcagatgt cacagacact   152700
cttctttcct gttcagtggc ataaatcaat agcataagtg aagaagaaat ccgtgaagca   152760
agagcttagc agcgttgttg ataagcctgg agtcacagtg gtgagagaac ggggctgatg   152820
tattaatatt taatattacc acagctctcg cttttaagga gttgtttgtg agctgggtat   152880
atgggcgctt tgcacatgtt cacctctttg gtcctaacat ccctcttagg tggaaactgg   152940
tgatatcttc ccattttaca gacaagaaaa ctaaagcacg aagagactaa gtcaactgct   153000
cagtgtccca tagctaggaa gaggcagagc tgggagaaag aatatccaga tggttgaggt   153060
```

```
catcaccctg ctctgttctt cagagctaag tactgtgctc aaaagtgtgt gtgtattgga    153120
ggtctggggg gagacatagt taaaggggac agtgactgag tgaccccct gaagagaaag    153180
ggtgacagtg atgggcatag gcacagattc catgccacac aggggacatc atcgctggca   153240
cgcagtcagt gtttacggaa ggaaggacac agggaattaa ttggaggcta gctcataaaa   153300
ggtttttcat ttttatgagg ccattttgtg aatgaggaac tagaatattc tggactacag   153360
aggcggtaga gatcaattga gggagaagat tttggatgag tgaaaagaaa aatgttccag   153420
ttggaagctt tgagttctca gacctagagg tgttcagcgc aaaatagatg tagccctgct   153480
gtgggcaagt cagaggcatt gaagccaact cagatggcag gtggccaagg agaccctggg   153540
ttcctgttct ttggtcctgg gtaaggcttg ccagggtacc tacaacccct ggcacatgcc   153600
agagcctttc tacataaacc actgtaggga gagtcacccc cagatcctgc tgtgagtgtg   153660
cctctgatca tgccatctga tcatgccatc ttgccgtctg atcatgaacc accccactct   153720
gcatagcaaa ggcagttatt ttcatgaatg atttcacaaa gtgcggctct tttcaaggaa   153780
aacatcccag gtgaaaaaga ggtcagtaat cagaagaaat gcttctgagt tatgctgtct   153840
cagacatgca ctaaccctaa catgaaccct ttcctttcc actgatattt caatttttt    153900
ttctgaattc ccattcttca tgcagataat gctgctaaaa tgtcagctct cttctgaaag   153960
gaggaaaatg tttaataata atgtggtcta aagtcctcta ttgataggcg acctcaaggc   154020
caggatccct gcctcctttg ccaacacact tctcgctttt cttgtaacag aaattcgatt   154080
tgagctgcat aattgtttgt tagataatca gcctcccagc ctactgcagc atgacagttc   154140
atgaaaagag ctgctgctgc tgctggctct ctttgtactg tctgcctgtt agctgtgttc   154200
ctcacaccag caagatttag atcatctaag accatttaca gtcttgtctt gtcaccatgt   154260
aaaaatctga attcattggt gcagtcagta atagagctca agccttcttt gccccggatt   154320
tcttgcattg attggtgctg gtaaaacttt agtaacttaa gtaatggttt tctggaagcc   154380
cttttacct ccctacaac cccacaccct cacaaccaac ccttgggtgc tgggcagtga    154440
gaaagatatg gcattgctct ataggagaaa gaagttataa atgctttgca tatgacactc   154500
tcccaccttt gcttctcaaa gcaaactggg tttctgtgtg ccccttggtg tctccccaga   154560
ctttatatcc ccaagaatgt attcagtaca agactaatgg catcttgtgt gctattcttt   154620
ctccacccca gtcttgtgga aggaaaacac cggagatgat ttagggtaat gggaaatagt   154680
gctagagccc agggcatgac tgcatttgaa tgtgaagtag aaattgtctc ggaaccccac   154740
tggagagtga ttcagctgga gagagtgggg cacctggctc tcagaggcac tgtgcggcca   154800
gacagcagtg tgctggactt cctaatggcg agctcacagg ttaagtgaga aacaggctgc   154860
acttctgact tgggagtctc tgctgaactt tatagaaaac tgacttcagc agcaactgct   154920
gtctagagaa caatttggca tctctttttg ccagagtaac ttctaactca agagtaggca   154980
acttttaatt atggtaccgg atggaggcag caatgaataa tttagaataa agattgaaaa   155040
atatggaata aggtgtagta gactaattgc tcagaagaag ttttattgtg tgaaaatgaa   155100
tgtgtttaaa cttgaaatac agaggatcat ttcctctcta cccttgaggg tgattgcagt   155160
ccctttttaag aagctgttaa aagtccccct caagatcatc ttctctttga attttccttt  155220
ctaatgtgac ttttgacaat tatatctttta tcgttcacta agagaatatc tccatgtctg  155280
cagggatgca gggaaatatg atggctgaaa gaaacgctaa tctacatgcg cactttatta  155340
gctaagaaat ccctcctcca tacgttcttc caggcatgcc tccgcacatc ccatctgcta   155400
tgtgggctca actctgcatt atagatggga aggtgatgga cttgtccata agaaatggac   155460
```

```
gcttgatagg agaaggaaca tattacatag agctaacagg ctaaagcttt gggatcatgc  155520
aaattaagtt taaaccttga gtaggcctcc tactgtggac acaatttggg gaagctgact  155580
aatctctcga gcctcagcat cctcatttgt acaatggtgt ctgacagtga caccaacttc  155640
accaagttgc tgtgagaccc aaatgaaatg ccccagagta aaatgctgga acatagaaag  155700
caggcaatga aggccaggag tggtggctct cgcctgtaat cccagcacct tgggaggctg  155760
aggcaggtgg atcacctgag gccaggagtt cgagaccagc ctgggaaaca tggtgaaacc  155820
ccatctctac taaaaataca aaaactagac aggtgtggtg tcacgcacct gtagtcccag  155880
ctactcggga ggctgaggca ggagaatcgc ttgaacctgg gaggtagagg ttgcagtgag  155940
ctgagatcac accactgcac tccagcctgg gcaacagagt tagactctgt ctcaaaaaga  156000
aaaaaatgga ggaaagtagt caatcaatgc tggttcttcc tcctgtcatg ttcacttgga  156060
aagagagtgg gcctcctgaa ttcaccttca agaattctcc tgtaactcaa ggtaactttg  156120
tcaaactcca agattggttt attttgctct gggttaaaac caggaattag aagtcaagtc  156180
tcctaaagca ctactgaact aaaccaagac actgacgttt ttccttctcc gtgagaattg  156240
ggagccctta gtgatatcat aaaacatcag tcattttgc aaagaaggag gtatgacccg  156300
gagaagtcag cttgacattc agtcggaata ttgtttgtta aatgaggagt taaggttgaa  156360
aatcatctct gtatccttcc tctagccttg caaacatttt aaggtgtagc cttgacagca  156420
agacaggata gtgtttgttt ttattaaaag gtctttcctg ttccttgcgt gaagccattc  156480
tcttgatccc agtgggggct ggatgaagga agagcaaaac aaaccacgaa gacagcctgg  156540
agccgcagcc agctctgctg acttctgaac ttcacgctct cactgcccag atggccaggg  156600
gtgtttcctc ctctgctggt cttttttaag gcaggatgtt tgttgttatt gttgttgttt  156660
ttctggttgg ttcttaagaa attattttct acatcttgaa aatgccagct ggaacctaca  156720
ccagttgttg gtggggtgtg agaactatcc tttacatgga cttggagcat ttgcaactag  156780
agcctccaca ttgaaataaa catttaaaaa tgcatatcta tggatataca gtgggggatc  156840
ttccattgtg gtaaaaatat gtataacata caatttcccc tttaatcgct tttacatgta  156900
tagtctgtgg cattaagtac attcacattg tacatacagg gtttaattaa taggatctta  156960
aaacttaaaa gggtattgat gcacatctct gttgcctttt acatttcaca gtaattagaa  157020
gggaaaaaac acactctagg ttgaaaggct gtcctttctt ttggttgtcc ttgtccctgg  157080
aaaagctgtc ttcccccctca gggcctttga cctccccgg ctctccctcc catcttcaga  157140
cacgcccagg gccagcctga gtcagtagcc ctttcttcag cgctccctct tctcctgttg  157200
tgcattagaa tgtttggagt gttctgtgga aagctggtcc ttacatttc cagtcagtta  157260 tgcatctcac tcataaacct gtttcttccc ccatgctctt taatattctg ctttcttaat  157320
tatggttgag ctgcctttaa acagtcttag attgttcaat gtgagtggct tcaacaagcc  157380
tcccataagc ctcttatccc ctggcccct ttccatgatc caaccccaaa tctccagata  157440 cccctgctt tttttatgtt ttttgtttg ttggttggtt ggttggtttt tgggttttt  157500 ttttttttt gaggcagagt ctcgctctgt cacccaggct ggagtgcatt ggcacgatct  157560
cggctcactg caacctccac ctccggttt caagcaattc ttctgcctca gcctcctgag  157620
tagctgggat tacaggtgtg gccactatg cccagcaaat ttttgtattt ttagtaaagg  157680
cagagtttca ccatgttggc tgggctggtc tcgaactcct gacctcaagt gatctgtcct  157740
cctcagcctc ccaaagtgcc gggattacag gcatgagcca ctgcaccaag ccccggatac  157800
```

```
ctcctgcttg accagacctt ctgcaaacac accttagatc cctctcaaat ctagatgctt   157860
ctccaacact ggcttctagg ttctttatga aacctctgct ggccggcagt atataaccca   157920
ccacccagcc tgccaggcac gtcattcagc tgtgttagac agtttcgagg gatctgcacc   157980
tgtcatgagc actggcccaa ccttctcaaa gcatcccact catccctgtg attctggcaa   158040
agcttgcccc agctttcttt cctcgatggt tgaaatagca cccaatgaga aaaaaacagt   158100
ggcctgtatt tattatactt acacatgtca caagaatccc tgtagtgtca ttgaaagctt   158160
tcttctagca tgcaaaatga ttgtcactat gatgtaagtt tctagaaatg ccttatttca   158220
tctaaaatta tgagagaagg taaaatgatg aactatcaaa gtcacactac atgttggccg   158280
gctgccttct accactcact ccatccctcc ccaggctttc tgacttaaat ttagatcaca   158340
tgagaccatt gcagtggaga gagtgtccac tttctcaatc taaaagcaag ctcgtgaaga   158400
ccattaaata tgatcacagg aacaaacatt aaaggtacca cacgtaatgg accacttaag   158460
acagaaaact acgatcttag ggtttagggg aaaaaaacac tcaaacagca caggcttcca   158520
gtctccccag tctctgagag gttgggattt tttttttttaa taaagtacaa gggctccttg   158580
aacatgaaca cggaacgagc gttgcacctg tattcattca tttcgctctt gtaacacatt   158640
gatgttccta agtcagattt gtagaagagg aacgagcaga tgcatcatga gaacactgtg   158700
cttggccagg cgcggcggct catgcctgta atcctagcac ttagggaggc caaggtagga   158760
ggatcgctag aatcgaggag ttcaagacta acctgggtga catggcagat cctgtctcta   158820
ctaaaaatat tttaaaaatt agccaggcat agtggcacat gcactgtagt ctcagctact   158880
caggaggctg aggtgggagg attgcttgag cttgggaggc agaggttgca gtgagccaag   158940
atcaccccac tgcattccag cctaagcaac agagccaagc tcaaaaaaaa aaggccaggc   159000
acgatggctc cctcctataa tctcaaccct tgggagact gaggcgggca gatcacttga   159060
agtcaggagt tggagaccag cctggccaac atggcaaaac cccatctgta ctaaaaatac   159120
aaaaatgagc cgggcatcgt ggtgcgtgcc tgtaattcca gctactctgg aggctaaggc   159180
ccaagaatca cttgaacctg ggaagtggag gttgcggtga gccaagaaca tgccactaca   159240
caccatcatg cccggcctgt tttttttgtg tgtgtttgtt ttgggttttt tttgagcctg   159300
ggcaacagaa caagactctg tctcaaagaa aacaaaacag aacactgtac atgagtgttc   159360
ctgggcccag cagagtgctc gaaccagtca gcactttgcc ctcttttggg tgagatgaga   159420
tctttaaaat cacttattcc catatattcc gttttttggc attgctacac tattctattt   159480
gagagtaata aaagattacc catgtggatt tcttactatt tcatgtggag aaatgcagct   159540
tttctagcgg cgagcctttc ttccatttcc cagagtccgg ttaccctcac cgcaccccag   159600
gtttgccgta gaaggatgag attccctaca tgtaggcgtc ttcagagtga acctgttgct   159660
cagggcccgc gagcccacag ggctccatgc ccactgagca ggctcgtgga cgtcggcacg   159720 tagctcgat gtgctgattt ccagccaagg acatgctttg tgtcaacgat acaggggcct   159780
gttgttctca gtaacaaggg cagagccgct cccgggactc cagttggtat tggtaatgca   159840
agcccttgca cctagtgtgg tgtggtcagt ataaattaat atcgacagct tcatgttgta   159900
ctttaatttg aagtacagga aaggctgctt gccaaactgt atttgtagat catttaaaat   159960
ttatgcttca tttaaaatgc aaaatacgaa tggaaataat tactgtgtat ccggaaatgt   160020
ctattcaact tacaagttta ttaattgatc cttctcttta catgtttac gggacttga    160080 atacactttg ctaatatcac agcataggaa gatttaaccc atatgaattc aactctgtag   160140
ccttggtgaa agaaaagaac catgtatttg tcattcactg tggccccga tgtatgccaa    160200
```

```
cgacttcatt tggtgcaggg ctgaagaaat ggcagtgtgt tccaatactt cacaacagtg    160260
gggcctcatt aagagatgct agggtattga gagtggagtg ttacatagtg tttttcatag    160320
gtcttctaaa agattttca gagttgctga cttaagaatt tggcctctga gtaagatgag    160380
acgcccctac tacgttataa agccttcatg gatctttatt tctaacagtt cattttaaa     160440 cttttgttcc atttcatttt attttgtcca tttttgtca tcaaaaatt attttaaaat      160500 gtaacagctc ttctagaatg tacagatcaa ttttattcca ctaaaaaaca ggacttcaat    160560
aatttaattg aagaattcta gtgagcattt ccagagcctt ccaagaaag ctatactgtt     160620 taactttgag tgactcagct tctaggaccc tggtccacca cacctacaaa atgaatttaa    160680
taaagcatga aggtcaccaa atcctctact atttcttcgt ggagtcattc agctagtgtt    160740
tatgttgtgc ctgctctgtg cgagagactg tgccaccaat ataaccactg gtcacagtta    160800
ttttctagag ccatactgcc tgatatccca tgtggctaag attgacagtt cagtttctgg    160860
attgttccag tcccatttcc agtgctttta atagccacat gaggccagtg aacacacgat    160920
acatcttcca ttgtgataga aagtggcagt ggacagcttt gttctagagt atttccgttt    160980
ctgaaataca tgtttaagaa gtttggaaag gaattagtgt agagtatgag aagggttaca    161040
tttttggtga atatgaagat ttaacataat gttagttcaa aaatgaccaa agacacaagt    161100
gtagacacca ggcttttgaa gtagctaata tgttaagcag ctgtgcatta tatagacaga    161160
atattcacta tgtcccactc agccctgtgt ttgacaccat ttcaccttgg cttctgcctt    161220 tctttcccctt ctttgcctat tgagattttt cctgtccttt ctatccttt ttttttttt     161280 tttttttttt tttgaggcag agtcttgctg tgtcaccagg ctggagtcca gtggcacgat    161340
ctcagctcac tgcagtctcc acctcccggg ttcaagtgat tctcctgcct cacccctccca   161400 agtagctttg actacaggaa tgcgccacca ctcccagcta attttgtat tatttaaata     161460 gagatggggt ttcaccatgt tggccaggat ggtctcgatc tcttaacctc atgatccgcc    161520
caccttggcc tcccaaagtg ctgggattac aggtgtgagc caccgcacca ggcctcctgt    161580 cctttctttta atgcactatt ccagctttttt ttttaatatc ttgccagctt ttgctgattt   161640
tcatgcctcc ctctgcaacc tgtgatctct tgactttaat agtaatgttt atacagagtc    161700
ttgactgcac actctcttct gtcatcgttg tttgttgtgt ctcattgtcc ccaatccatc    161760
agaagttctt ggtacacaaa gtccctgaag ctgtatgaac aatgcccctga cgtcttgaaa   161820 ggacttgcca taggtggtta tttgatcact tagcagatgc ctttgggatc ctactttgtg    161880
caggccactc tccaaggcac aatgtggcaa gtaaatatat tagtcaatat ttacagaacc    161940
aagagaaagc cagcaatgat taatgcataa acagtcataa attggccatt ttatttgttt    162000
ataaaagcta tcatttacta cagagaagta caagtgaata tcaagctcag atcaagacct    162060
ttggactgag cttggctttt tttttttttt tctttaaaga ttacacttct cccccaaatc    162120
aagcagatta accataggaa gttccttgcc tgctaacaga atataaatag attgcatgca    162180
aggggaagga ccttatcagg gcagatttta gtatttacac taaacccaaa agattatttc    162240
cttaattgta cttgtgagtg aaaaacaaaa attgtagcag gagtcccaag agcactctgg    162300
ccatgggctt ttgagctgtg agttgaagca ctttattcag catgtggctg cagggttgta    162360
gctcaggttg tagacagtgc attctcttca ggtcccagga aacagtgtca tacctgtgga    162420
agccaccaga atgcaccttc atcttctcca gtggtggcga ggttgaggcc aagcatcaga    162480
agtgctgagt gctgggaaac tgtggggctg gatagatggc agtgcctgct gggaagcaca    162540
```

```
cagccctggg ttgaggcagg gaagcagggc cgcccagttg ggattcattc gtactactgg 162600
cccctcacag taccgtcatg tgtgggtggt cgcgcttgtc ctacaggaag taaaccacaa 162660
ctactcatct cacacagtca gcccggcacc tccttggaat tcccaaaaca ctttccaata 162720
aacattggaa aggaagaaag tttagttggt aacaaaaaaa tgtatgttgc cttacgccca 162780
aaagcattga aagcagggac tcaagcaggt actcatgcag ccctgttgat agcagcattg 162840
ttcccagtag ctgaaaggtg ggaaccccct tgtctgtcag cggggatcag ctaaatatgg 162900
cacacacata ctatggaaca ttattcagcc ttgggaagga cacctcctat cacacggatg 162960
aaccttgaga acattatgct aaatgaaata caccagacac ggaaggacag atactgcttg 163020
attccacttg tagggcctg tagagccgtc acattcatag acaggaagta aatggtggt 163080 tgtcaggggc caaggggagg ggcatggaaa gttgctgctt aatgggtaca gtttcagttt 163140
tgctaaatac agagagttct ggaggttggt tgcccgacac cataaatgga cttaacgcta 163200
ctgaactgta cacttagaaa tggttaaaat ggtaaattag gccaggcatg gtagcttgcg 163260
gctgtaatcc cagcactttg gaagtctgag gcaggcagat cacttgagcc caggagttca 163320
agaccagcct ggacaacata gcaagacccc catctctaca acaattttag aaattagctg 163380
gtggcttaca cctgtagtca tagctacaca gtatgctgag gtaagaggat cacttgagcc 163440
caggaagttg aggctgcagt gagccgtgat cacatcaccg aactccagaa tgagaccctg 163500
ggtcacaaaa aagaaaaga agatggtaaa ttatatgtta tgtgtacgtt accaaaatta 163560
aagttcttaa aaatatatat tttaggccag acacagtggc tcacacctga atcccagca 163620 ctttgggagg ccgaggcagg cagatcacct gaggtcagga gttcaagacc agcctggcca 163680
acatagtgaa accccatctc tactaaaaat acaaaaatta gccaggcgtg gtggcggag 163740 cctgtaatcc cagctgttcg ggaggctgag gcagaaagaa ttgcttgacc cagaaggcag 163800
aggttaccgt gagccaagat cgcgccacta cactaccagc ctgggtaaca gagtgagact 163860
ctgtctcaaa taaataaata aataatatat atatacatat tatatagata gatagataga 163920
tttcttacaa aacattttcg tgtttaaaaa taacaaatca ggccaggcac agtggctcac 163980
gcctgtaatc ccagcacttt gggaggccga ggcaagcgga tcacctgagg tcaggagttt 164040
gagaccagcc tgaccaacat ggtgaaaccc tgtctctact aaaaatacaa aattagccgg 164100
gcgtggtggc acatgcctgt aatcccagct acttgggagg ctgaggcagg agaatcactt 164160
gaacccagga ggcagaggtt gcagtcagcc aagatctcgc cattccactc caccctgggt 164220
gacagagtga gtctctgtat aaaaaaaatt tttttaaata acaactcagc catccactcg 164280
catcaattta ttcactagtc attcgattgc tattactttg ctcccatgtg agttttttaa 164340
attattaaca gaaaaatcac actctttatt tttgaattat gatcttgagt tcagtaaaga 164400
atgcattctg ttgattaaat gtgttatgag taacagtatc ttgttttgct gtacttccaa 164460
gcaaaatgta attctttcag tcctccctac cgttctcact ccataataat atgacttaag 164520
gtttgtatag catgacgttt acaacgtgct tgcgttttac actgactcaa cgtgtgcagt 164580
acagtgatgt atagtgaagt attcacatcc tcatcttaga aatgaggaaa taaattcagg 164640
gaggttacat gatttaacca cacataagga ggggctgcat tctctctgag cccttctacc 164700
tcacacagcc accaagctcc tttgtgcaga gcccatggag ggttggagtg gccacactgg 164760
ggtaggtgca ggccagagac tggatgcaac aggaacattg cctgcttccc aaaaccactg 164820
ttctactgcc cggagaacac acccttctgg gagctgactt ctaacaaagc aaggtccttg 164880
gacttgccct gcggcttctt tcctgcaaga agtatcttcc agcatcctac caacttttat 164940
```

```
ttcttaaaaa aggttgttcc ttgccaggca ttggttgatc agcagaggag ctcgcattag 165000
tttcagtgca gtgttgggag caagcacttg agtgcccagc aacataggct gctcatgatc 165060
taagattcat ggaaaaagtc ttctgcgctg ttgcctgcag cacatcaaca cctgaatttt 165120
cttatcatct tgtgtggcta ttgaaccaca gggaacccaa gcttagtcaa taggaaatat 165180
agaaatattc attggttcaa ctgtataggg agggccttgt atatattcca ggggctgtat 165240
cctatcttgc ctctaggtaa ataagagatg gtcccgaggc tcaaagagtt tatcaaccat 165300
tctttattct tcagctaata tgaacattga atcttttaca ttagaagttg cccatgcagg 165360
gcacgcctgt aatcccagca acctgggagg ccaatgcagg aaaatcactt gaggccggga 165420
gtttgagacc agcctgggca acatggtgag acctcatctc taccaaaaat aaattttaaa 165480
aaaagttacc cttaaatttc tttctctaac ccagcctcaa ctttgtactc aggcagtaac 165540
tctttgtaca acattcctgg caccatattc agcttataca gaaccctcca ggcaaggaca 165600
ggtcactgct aagtgagaga gctctggtta ttatagttct tccttaaaca ctgcactcaa 165660
aacgacttcc ttctaacgtt tgtcccttgg ttcacattct gccctccttt cgattttttg 165720
tatggcatgg ccctccaaga gatttcagtg tcagtgtggt gctgccaagt ctgtgtgact 165780
gttcacacac tcgggctcca ttcacacacc ccaagattgc atgagctttt gctgcagcca 165840
ctcacagtca ggccccagtg aatccctgtc tctgaagct gcaggtagga gcgccccaag 165900
ggcatctaga tgtcaaagaa gaggatgctc acatgtgcct aaggttcatc catgaaggct 165960
tcgtggagga ggtggctttt gggatagatc ttagaaagct cagagagttt taacaaagat 166020
tggtccttga agattactaa tcttttgact ttataaatac ttgcatatat cttcttccag 166080
tctgtctctt atttttgac cttatttata atgtcttctt aaaacaagtt ttaaattttg 166140
ctgtagtgaa atctatatat catttccttt atgggttatt ctattgttac ctcatttaag 166200
aaatccttct ctacttcaga ataatagagt tcccactgtt ttcttccaat atgtagagtt 166260
ataattttca agtttatgcc tttgttccat attgggttta tttggaggcc tggtatgtgg 166320
taggaatata attttatttc tctccagcca aaagtcagat ggtagtcagc cttttctctgt 166380 tgatttgtgt cacctctgtt atatactatc ctgcacatgc tgagtgtctt tgtgggttct 166440
ttcttctttt ccgttgatta atttgtctat acttgtgcca gtacccatgg aatttattag 166500
catagttttg tggtatgatt gatagctagt agaaaagtcc tctttctttg ttcttttggt 166560
tttgttttat ttttaaagtt atctgactat ttatgccatt accctgtgtt agttcactct 166620
cgagttgcta taaaggcatc cctgagactg gttaatggat aaagaaaagt agtttatttt 166680
ggctcatggt tctgaaggct gtgcaagcat ggcaccaaca tctgctgggc ttctggtgag 166740
ggcctcagga agcttccact cagggcagaa ggtgaaggcg gggggagcca gtgcatcaca 166800
tggcaagagc gggagcaaga gatggggtgg gaggtgccaa caagcagacc tcctgagaac 166860
tcagagtgag aactcactca ttatcgtgag gacagtacca agccattcat gagggatccg 166920
cccccgtgat ccaaacacct cccacctggc cccacctcca acattgagga ttacatttca 166980
ccatgagatt tggaggggac caccatccaa accacatcaa ccctttattg taagtttcag 167040
aactaattgg ccaagtaacc aaaaatgagc ttgggatttt tattggactt gcattgaact 167100
gagtaagttt cagagaagtg acgtctgtac agtgttaagt ctcctcatcc atgagcaaac 167160
tattttcctc cattgactca gactcttttt atgtccctca gtgaaaggtt ataaggcttg 167220
caccttcatt tcttttttatt tgttagaata ttcaatattt atgttccaga ccacagaaca 167280
```

```
cctctacagt aataaaaact gtagtaatga aaaacacgtt ttaaagcagt tttgggttct  167340
atcagggttg ggaggggaag agtgctagct tttatttatt ttctcttggg taactcttgt  167400
atcaatagta tttcatacaa atgtgacact agctgttgcc aagcaaagtc cttgaggcac  167460
atcacgggag acttgtgccc cttggttgac atctgttcca tcagcatttg gttcagcagt  167520
tgttcaccaa acagtaaatc cactaattgc atcatgcata tgctttcttt ttttttttt   167580 ttgagacaga gtcttgctct gtcacccagg cttgaagtgc agtggcgcga tcttggctca  167640
ctgcaacctc tgcctcccag ggtcaagcga ttctcctgcc tcagcctcct gagtagctgg  167700
gattacagaa gtgcgctgcc acacccagct gattttgta cttttagcag agacggggt  167760 tcaccatgtt ggccacgctg atcttgaaca cctgacctca agtgatccac ccacctcagc  167820
ctcccaaagt gctgggatta caggtgtgag ccactgcacc tggccacata tgcatcttta  167880
cccacaggag gattgtagat aattttgcca aatgtgtttc ttaaatttag aattacttta  167940
tctgtggaat attattttcc taatgaatca ttcttgtttc tgaagatccc ttgccgtatg  168000
ctatcaatag tctgtgtcct ggttttcaat ctaacattat ggaaatcttc tcctccaaca  168060
cacttatttg cctgtatcta gtcttctcac atttcttcca tgccacatga cttctcataa  168120
tttgcttaag tgacagtagg ttcaacctct gattttccaa tatagtgttt gatcacatca  168180
gcatttatgt taaatctca atccattact gctcatgaaa aaatacttgt ttttaatact  168240
atgaacccgt attcagaccc acttaaaaac cagcactcac aatttcgttg ggagactcct  168300
gtcctgacat atatgattat ttgaaaatta tagtaaacag gccaggcgtg atggctcatg  168360
cctgtaatcc cagtactttg ggaggccgag gtggacagtt tgcttgagcc caggagttca  168420
agaccaacct gggcaacgtg gtgaaaccca gtctctacaa aaaatgcaga aaaaaatta   168480 gcttggagtc atggtgcacc cctgtagtcg cagctactca ggaggctgag atgggaggat  168540
cacttgagcc tgggaggttg aggctgcagt gggctgagat tgtgccactg cacgacagag  168600
tgatactgtc ttaaaaaaaa aaagaaatt atagtaaact atatttttt aatgctacaa   168660 tggataaaaa tggttacaac tagataagaa gcctctaaat tgcctgaaca cctaagactt  168720
atttgctagt tgacatctga tctatttctg acactgaaaa tttcagtgct ttagggtgct  168780
aaaaggaaaa aagagggttt gctaggaatc ctgcagttgc tgagggggta ctctgataag  168840
ggaattttaa gcaattacag aacatctcac taaagttttt aaaaaatctt taaccagatt  168900
aaacttatac aattttgtta taatttgtgt ttctccaggt tccaattgtg gacaagataa  168960
ggaccattgc tcaggctgtc tatggagcca aagatattga actctctcct gaggcacaag  169020
ccaaaataga tcgttacact caacaggtaa aagttctact tttagggaa aagaaaaaat   169080 tcaccttagg ctctcagaat actcagcttg acttgaggat ttgtacatat cgcaccagct  169140
aacctttgct taatctattg tatggttaac aaagatgaag gtaatatcct cgggtagagt  169200
gtagactata tttagaactt tatggtgagg catatatcct ctgatccatg catcatttac  169260
ttctgtgact ataaatgtgt ctgatatggg tggtatccct gttttaggt gatgtgtgat   169320 ctttcatccc tcccactcag ccctgaatgt tgaagctatc ctttggagta gagctgcgga  169380
gtcagattta gatgaattgc aatgcttcct cttccttaca ggcctcttac ttactacctt  169440
aaaaatgcta gcgtggtgcc agggtaggca gataggagtg cagcctataa agatgggaat  169500
gtttgctgtt cttcttatgc aagcggttca ctggcttttt actgagcttg tccgctgaga  169560
ttgaaggctc catcatcttc tacctctagc cactgacaaa ggcaagtagg caaacagctg  169620
ggaaggtggc tgtgatctga cagcatgcat caccatctag tccagtgaca gtcatgatca  169680
```

```
atcaactcca ctacaggagg ctcagccacc ttcaccaaaa ggaccgtatg cctcgagtgt 169740
ccctcctact ttggtgtagt cggatagata gcagtcagaa cactttaaga gcctgctggc 169800
taaagaactt catgatgggt agcgttgacc ttttctttaa aaaaaatctc caactcctta 169860
ttcttttttg taaacccatt tgaaattttg ttaaatgctg ccgttgccag ccagggtatt 169920
tgttctccta ggtttggtaa aatagtcagc aactcaggaa gttctaaatt cttagaattt 169980
tccctgtatg ttcttggctt atcctttaca aaaaggattc ccaagcactg ctctgtgcac 170040
aggcattgtg gtgaaatttt cattcatgtg caatgaacca agtaaaataa ggtcattctc 170100
ataaggttgg tttgttttt tttccgtgag tttttaataa tgatatttaa gactatcatt 170160
tattctaata ttaagtcttt tctcctttca gtgttaaaat ggtatttctt ttatgaagta 170220
atctggtgag agtatatggc atattggttg gttttttct ttttaatatg cctactgaca 170280
aaatttttac attagcaaac ctgtattagt tcatagaaat tacttcaata tttaaccatg 170340
tctgaaattt aaaattctgg caccatttct gaaagacagt tgtgattgtc actcagcaaa 170400
attcttatcg gtatagaaga gtggagattt caaaaagaaa atggcccaa gtccaagtcc 170460
tccctgagtt gataagactc taagatcttc caaatagttt taggctaagt cttatgaaaa 170520
tttaactaaa gatttcattc cctttatctc tatcaaggaa atattcctta aaagtgatgt 170580
caaccgggca cggtgctcac acctgtaatc ccagcacttt gtgggtcaa ggcagaggat 170640
cagttgaagc caggagtttg agaccactct gggcaacata gcaaaacctc catctctatt 170700
tttattttt ttttaaagtt agtgtcaagt atgtggttgc aatgaattag caaagcctct 170760
aaaggaacac tgtgtgccat ttaatcagaa ccaggctttg aggacactgt gcttttgtg 170820
agacaccaca tgtgacttcc tgctctttca cctttggaac tctgggtcag acatagactt 170880
tggtccttaa aaacaagaag cttaaatagt gacctcatct tagttcttat aatgtaattg 170940
cagatcaaat agccatgatt cataaaccaa cacaaaggaa ccctttgctt cctgactgac 171000
tccagaatga gtgaacaaca tgagtaagag cctcgtcgca gagcctttct ccagactacc 171060
ttgctgggtc ccggatatta atagtcttgg aaagtggttt ctacagctgc tgctttgcct 171120
gaaaatagcc atgctttccc caaacatgca cataacactg ccttctctta aagagagcct 171180
ccaaaataaa caatagtcac ccttgacctg ctaaacagtc atcacatgga gatgagtttt 171240
tatcctcacc ttcttgcttc ttcagtgaac aagtagtaac aagcagctcc tgcgtgtgcc 171300
tcgatctgag ccggcatacc attgctgccg agactgtata aagtgcaaat tgaaaagcac 171360
aggagactaa catctgtatc agtgaacaca ttttctttcc tttctcacag ggttttggaa 171420
atttgcccat ctgcatggca aagacccacc tttctctatc tcaccaacct gacaaaaaag 171480
gtgtgccaag ggacttcatc ttacctatca gtgacgtccg ggccagcata ggcgctgggt 171540
tcatttaccc tttggtcgga acggtgagtg agtcacattt tccaaaaacc ctccccattc 171600
tgcattgctg tggtgcctca aatcgttatg ctccgcccgc tctttaaaaa tcatggatta 171660
gggaaaattg ggagtaatta atagtacagt attcgctatt tttctaaaca ctgtgtctca 171720
cctacttttg ccattgtggt ttggattttt ctttttttag atcatgtgtt cagggtcctt 171780
agagtcataa tactaatttc cttcctaagg tgagtaagaa cataacttgg gagaattcag 171840
tctgttattt aaatggtaga atggcttaag acagtggttg tcaaccttta tcacacatag 171900
cacccaaaat gatgtcatca cggtgggggtt gactgctcac accagacagg atctgcccag 171960
tcaccccaag ggctggggaa agcagtcctc accctctctc acttccccag cacgtcaggt 172020
```

```
gggaagctct ggcttaggaa attactgaat cataggagtt ctcattttg atgttgttgt   172080
gatgggatca tgttgctatt ggatgattat tctgttattt tgtgttatct atgggggtaa   172140
aggagatggg cagataaata aaagcttatc aaagtgctta aaatccatga agatgggctt   172200
catttggtac agctacacag tgatagcctt ccgttggtac cgtcagtggc ctaaatttga   172260
cttcttgtct ttgggagtgc tcctaaattt ggtttagaac aaaaaagaat tcttacaacc   172320
tagcagatcc catggcaagc aaagaaaaaa atattctaac ccatcattat cgtcatcatt   172380
agtgcaaagt gatctgagct taaacagcat acattatcat aatttttat aataaaccat    172440
gttgctttat tgtgcaaaca agcaatagat agataaaaag tgcagattct tgccttgata   172500
tttacatact tcatctaata ttggacacaa tgttttttca atcagcattt tttgaattct   172560
tcctgcatgt gaggcacaga gattttagga tgagcaggtg tgagacgcat gggtttgaat   172620
agcacagagg tatctggaga gcactgtgtt ggtattctga atgccctcag agcccagggg   172680
gataacagct cattatgcct ggggtagaac ttacccagga tgtggaagaa gaggggattc   172740
ttcaaaaaga gctcagcctc tgaactggca aaacagtgag ttttgactca aaggcaccaa   172800
agtactaata catgacatcc tctcctgggg tgatccgatg tggctggagt tggatgaggg   172860
ggggtggctg gggatgggaa tgggaatggg attgggatag caggacaggg tcacatggcc   172920
aaggatcttg aagaccatct catggaactt gaatctgatc tctacacact ggggagccac   172980
ggtagggtgg gttttttgtt tgtttgtttc ttggtttttt gttttttgg ttttaaataa    173040
ggaggagaag aatgtggtct gatgtgtatt ttagaaaaat agctctggca gcaatatgga   173100
gaatgtttag tgaaaagaga accaggccca gagaggtggg ttaattcagc tcgggccaga   173160
ggcaatcaag gtccgcactt tggccacaga agtagataca gagagtgggg gtgaattgca   173220
gacatactct aaaagtatcc tcctaccgtg ggggccgggg aagggaccg ttctagcttg     173280
gtgactctgg ctagtgatgc catcggtcat ggaaaggaca cggagaagg cagattggca     173340
gagccagaaa tgagcctggc ttgaacagag agagctcaga gggttaatag gatctaagga   173400
atagtctgtg tctccactgg aaatacagac acagtgcttc aaagaaagag gcaggaaggt   173460
caccctggtg ggtttaagga tatgggtgaa ggcagtcgtt aaacaagaga cacagggata   173520
gctggaaatc agtgagaaga cagtgaagga agacacccct gaaacaccca cgttaatgca   173580
gccgactcct agcagggtg ccttccagga ggcgggaagg aaggagcagc ggcatggcag      173640
agaacgtcca gaaaaatccc acagacaccg ctcgtagcag tgttggcaca gggagaaggg   173700
cctggatgaa atgggttctg aatgacattt tcaggtctac agttcagatc agtggttgcc   173760
aggagttggg ggaggggaag cgtttgactg cagaggggca ggaggaact ttttgggata    173820
atgcaaatac cctatgtttt gacgtggtag tgattccatg gctatataca ttcttccaga   173880
ctcatagacc tattcacgtg tgttgcccag gctggactca aactcctggg ctcaagcaat   173940
cctcccacct cagcttccca agtagctgtg actacaggct catgccactg tgccaggcct   174000
gtgtataatt taattatacc tcagttaaca aaaatgggtg ctgaagagct tgctttatat   174060
tcgttagaat ggcctcagtc agccgggtgc ggtggctcac gcctgtaatc ccagcacttt   174120
gggaggccga ggcgggcgga tcacaaggtc aggagttcga gacctgcctg gccaaaatgg   174180
tgaaacccca tcactactaa aaatacaaaa atttgccggg cggggtggtg ggcacctata   174240
atcccagctg ctcaggaggc tgaggcagga gaatcgcttg aacccgggag gcagaagttg   174300
cagtaagcca agattgcgcc attgcacttc agcctgggtg acagagcaag acttcatctc   174360
taaatacata catacataca tacatacata catgcataca tgcatacatg catacataga   174420
```

-continued

```
atggcctcag tgatggccac tttactcctg agctttagct ggtgaaagcc ttggcttagg   174480
gataagaggg cggctggaca gtgcaggccc agagagactg gaccatcagg ggaggtgagg   174540
ggtgacggag gtgcccaaac agagcatgaa atggtagagt agctgagaag gttagcctca   174600
gtcacgatct gtcctgtcct accctctgag gactctaaac cccgcagtag ttcacccaac   174660
aaattcattc actcggccaa tgctgcataa ggcactcagc tcgggctac agggagcccc    174720
aactttaaga agctttctct gcttcaggta gtttacaggt ggtagacgca gatagaagtg   174780
aattagtaaa gagaatagtt tggtgtaaaa attgtgcatt taactgaaac cttaattcac   174840
tactgagcat ttaatagcca ttaaataaaa accagggccc gcacagtggc tcacacttac   174900
aatccgagca cttttggaag ccaaggtaga aggattgctt caggccagga gtttgagacg   174960
cctgggcaac atagccagac tttgtctcta cttaaacaaa aattagccag gagtcatggc   175020
acgcacctgg agtcccagct actcaggagg ctgaaatggg aggattactt gagcccagga   175080
gtttgaggct acagtgagct atgatcatat cattgcactc cagcctggga gatagagtga   175140
gatctctgtc tctaaaaaaa tgaaataaaa taataaaaaa cacaatataa tttaaaatct   175200
ttggagtcac taaacaaata tacaatgtga atctcctctc actccagcta acgccaccat   175260
atccaacact aggtaaagac caaagccgtt ctggaaaatc agaatctgtt gccatggctc   175320
atgcctggac accaggctgt ccgctcctga cgtcactctt tcacttacga cttgttagaa   175380
aatgaatgtg tggaatggcc ctggatagct gctgcagctc cctggtttcc tgaagtgagc   175440
cctctgtgtc attatctggt cttctcagcc ctcagccgag ttcctcctgt ggccacacac   175500
ggggtcgcag tgagcgtcag tgcacagtga tgaaatctcc tggaacagtc gggtgtgggg   175560
catgaggaag ggagtggtgc ctgactacag aagttcctgg aggtcaggaa actctcactg   175620
gaggcggtgg ccctagaggg ctgctttcta tgacagagca ggaagctgca tgtgtagtgg   175680
gacacacgca ccagagggc caggatctcc taataaggac tggtatttat ttttacttga    175740
ccccattctg ggccttgcca cagtctgctg aaatgccttg aacattcatc acccgtgtgg   175800
gagacaggat agtaatttcc tgctgagatg actgagggga cggggaatgg ggacaccagg   175860
gggactggct cctgcaggtg ggaaaattct agcaaaatga atcactcttc tgcttagtca   175920
cccaatgtgc acttattagg gtgctgctga aatacatatt catctatcca ctccagaaag   175980
atagtccaaa ctgagacctc aggatcagaa agcctcccat tctcctgcag ggttcattca   176040
tttactcagt gaattattaa atgcctacag cacgcagggc catcagcccc acagctatga   176100
gaaagattca gtccttccct cacaggcctt atgatagact ccagtaaata aaaccataca   176160
ggcacagaat gcggcgggct ttataacaaa ggcagaaagc ccctcttgtt gtgtcctcaa    176220
gggaggcaga gaagctcccc tctggctcta gttggagaat cccaacccaa gcaagtccat   176280
ccttaaacaa taaacatctc cagcattgct ggctttggaa gaccccatgg tgagatgctg   176340
gagcttttt ccgctccaga tttcgcttct aaatatttac ttttactttc catgttcact    176400
tataggccag ggtttttttt tcctaccatt gaattatttc gtcatgttct atttaattat   176460
tgctttaatt ggcattggtg accacaaata ataataaata ctattaactg gtgtaacagc   176520
ttcactagtc tatttcactg ccccatgctg ttgtaactga agcccccagc acaagcattc   176580
ccagctcgtg gtcatctaag acctttgagg tcattcttac atgcattgct agtgttttcc   176640
atattccttg atggtagcca attttccctt cttaaaataa ctttcttcat tcctagtaag   176700
cttcatatgt atttttatgta ttcttccctc tttttttatga catgatacat attattgaaa   176760
```

```
gctaggaaat aatgcaagat tcttgaacga cataatacca cttagtacat cttttttgtaa    176820
gagatagttt ttctaataca aatctttgat atgggaagaa acaagcaagt tgttttttaa    176880
ggttttccaa ccctatattc tactacaaat taccctgtta tggtatgctt ccaaaattct    176940
ttcaaggatt atggtttata gagttcaata aacctaatag tttataaaac ttctcaaaaa    177000
ataatctcat gccaaaaata atttagtagt aggtggtctt tgtcttgtgg tcacatggtt    177060
ttgatattgt ctttaagttt ctataattta caagggctgt ttaatcagtt ggcataaatt    177120
tcatgacaaa aatactaata tgtaagcaaa gtatatgaaa caatattatt gagaagtaaa    177180
ttacattcca tgtagaaaaa gactagaaag acaacaccaa aaccttaaat tagacagtgt    177240
tattatgagt agcttttttt cttctctttt tccatataga tcaaattact acattgggcg    177300
tatatcactt ttataacatg aaaatacagt aaatagggcg atgataaact gcaagtgctt    177360
ggggagaatg cttaactcag gccagttgca agagagtgag aacacacacg cagcctgtgg    177420
gagcgggctc catgccatca cctggccggt cctggctgtg ttgctgtgtt ttcgcacctc    177480
aaaagttggg acagcaaaga aaggccataa gagctagaac gtttccataa gaagtgtatt    177540
cagtatgatt tgtctagctc tgactaatgt gtgcaaaccc cacattccac taagcaaatg    177600
caagattgtt tttccctgtt catttgttcc tgggcccttc ttgcttactg tgttgggagt    177660
tggagagggg ataattgact tctttcttct cacagtgttt tctctttttt tttttttttt    177720
ttttttttga cagagtat tgctctgtcg cccaggctgg agtgcagtag catgatctcg    177780
gctcactgca acctccgcct tccaggttca agtgatactc ctgcctcagc ctcccaagta    177840
gctgggacta caggtatatg ccaccacatc tggctcattt tttgtatttt tcaaagagac    177900
tggggtctca ccatgttggc caggctggtc tcaaactcct gacctcaagt aagccactgc    177960
gcccggccat ctctcacagt gttttttaaa acaacaatgc attttcataa cagttggcct    178020
ggagaggtgt ccgaccaagt tggaattcat agtagaatcc attggaagtt aatttttgat    178080
gtatttgact gttttccatt gacttcgcat tgaggcagtg agagagactt gaagaactta    178140
gaatacgcac cctttttgtca ctggcaaaca tgggacatag aggcgtgtct tgacagcaat    178200
ttgtggcaac actctgggct ggaatctagg ggttagacag cctggccggt tttgtaaatt    178260
agatagccag gccaccctca gagtcagttt gagggttgag tgggaagcct gaataaaaag    178320
agaagttaaa cttttaagaa aagggtcaag ctttaaaact ggaattgggt tttcaaattt    178380
aatgaggaaa aagaaacccc aaaactggaa ttgtaattgt ggagaaatac aactgataat    178440
atttggaata tcatctacaa ggaatgaaac tatccagaag catttagatg gtagtcagtg    178500
ccatgtaggg cacctctggg ggcagggtgg ctcctggcac tgtggagaaa gacgactggt    178560
gcttccttct cccaatcgga ggaaagggat acactgtgga ggtcccagca gcttagggcc    178620
tgcccccccat gtggttatct ctgtgccgtt tccttccctc tgtcttcctg taactccttc    178680
acttggccc ctctgcccctt tctgggcaga gggtgacagg aggcaccgca tgggtacatt    178740
ctttttttttt tttttttctttt tttttgagac agagtctcac tctgtcacct gggctggagt    178800
gcagtggcgc aatctcgact cactgcaacc tccatctccg ggtttcaagc gattctcctg    178860
cctcagcctc ccgagtagct gggattacag gtggccgcca ctacgccccg ctagttttt    178920
gtattttttaa tagagatggc atttcactat gttgttcagg ctggtctcaa actcctgacc    178980
tcgtgattca cctgcctcag cctcccaaag tgctgggatt acaggagtga gccactgcgc    179040
ccggccaact acatgctttt ttcctcctgt cgggattggc ctgggctgta cctatctcat    179100
ggtggaaacc tgcccaggga ccaggcccta gaagaccagc agtttattta actgggttgg    179160
```

```
cctttgtccc cactccctgt gacccggccc tgccacatct ttacccaggt gcaccactga   179220
catcatcgct tggctggact ctggaaagca ggaaactgct ggagcgtgtt tggggcatca   179280
gtgatgtcac ccgctacaaa tgctgggtgg ggttactgga ctgagggcca tgaaaaaga   179340 aagctgcggc cccggcccgt ggactcactg ccattctgct ctttctcacg tttcagttca   179400
gctcggtttg ttttccgtcc ccctccctct actgtaaaag tatgtactca gtgtttcgtt   179460
tcctgctgga tctgattcag gtcagtgatg aagttatttg tgaactcagt ggggaggtgt   179520
ttcctcccct ttgtaccggc cctacttagg gatgcacggt tggttatacg cttgcttcac   179580
tcggttaggc atggaggaga attcattcag ccctcatagg tttaaatcaa atgcatgacc   179640
cttcacattt tccagagatt tacgccagt tacaatgaga caattaaaca ttcacccccc    179700
cgccaagctg cacttggaga tgtgtaagca gtaatgtagt catgcgctcc ccatgatgtg   179760
agagcgtgca gaacgccact cccccagca ggtccgccag gacctccgca gggagcatct    179820
tgcctgcaaa atcacacatc ccttttccc cctctctcca ctttccctac tacttttcca     179880
ctcccacacc cacaaataaa caagaaacc ttgagcttat tttacaaaag tctttgaaat     179940
ggccctcgtc tctccaatgc tcctgggtcc tggtttggcc ccatctgtgc aatctctctg   180000
atgagtgtga ataagccag gtttggctca tgctctgccg gtgagcttgc cctccccatg    180060
agcctgtcct ctccatctgg cctcacttg tttgtgtccc tgtgtccttt gtctcccatc     180120
ctgggatcct ggtggtttcc tcctcccctc ccagcatgag tccttttccc cagggttctt   180180
ccctatctct acatcagaat ttcctgcttt ctcccaaata tgcatttccc tggcccaggc   180240
atccactgct tcctctcatc gtgaggtccc tgccgcaggc tgctgatggt attgtggccg   180300
tgccttcctc cacaacccag ggaaagctac gtgtgtgtct gtcccatagg gaaggagtca   180360
tccctgtctc ctcagtgtgg tgtgttcagg aggaaggaaa gtaaccagcg tcgttctcaa   180420
tttccagaaa ctgtttatca tattgacaag aagaagaaag ctttgtgact catgagaatg   180480
atgttttcct ctctggtaca taaggttatc taggtccaat ccatttgtgt agaggatctt   180540
ctctccccta gtgtgatatg cacttatttt tagcacaagt ataaaactac tttaaatgaa   180600
atcagcctca gccagggaaa tatgctgagt aataatgttg ccaggtacta taccactgag   180660
ttgagtttgt aattcactgc tattaatccc tgtgtattag ttctgatttt ttactctttg   180720
catacataga aaaatggtgt ttctcttcag agtcaaggag ggaaaaaag aaaagataaa     180780 agatgcttat aacacttttg tgtccacccc taaaatcagc atattgatct attattttt    180840 ctaggtattg atgagatgtt gactcatata cttttcataca actggtaata tatatatata   180900
tataatatgt gtgtgtgtat atatatatat atatatatat atatatatat atatatatat   180960
agactcattt ttcttccact ttcatctaca gcctacttgt tttcttcccc ccattttcg    181020 tatggattca tagcataaat tgacaacaaa gatacatctc aatttagagc ttccaaaagg   181080
cacccataaa agtatctggt gctcatggaa ttgctctttc ttctatgtct cttagttaca   181140
cttttctctt attacacttt tctatcccag ccatggctaa gaggcgtata atcagaagca   181200
gctaagcaat atatgcaagg gaaataaaat gaatgcaaac caagataccg gttttgtaaa   181260
ttagatagcc aggccaccct cagagtcagt ttgagggtat agtgggaagc ctgaataaaa   181320
agagaagtta aacttttaag aaaagggtca agctttaaaa ctggaattgg gttttcaaat   181380
ctaatgagta aaaagaaacc ccaaaactgg aattgtaatt gtggagaaat ataacgdata   181440
atatctggaa ctcgcggcag tttacaggct taactatgta tgtgttcctt aaattatcca   181500
```

```
cccgcagata tcagattaca ataagtcctc acttaatgtc attgataggt tcttggaaac   181560
taccactta  agcaaaaaga catgatgcat atgaaaccag ttttcccata gtctaattga   181620
taggaaaaag agttaagtta tgcagccaca cagtacctcg tttggcttaa agtcactgtt   181680
tccaagaacc tatccacaat gttaagtaag gacttaccgt atatgaaaat atttgcagta   181740
aattgctttt gagagaattg gttatcacac tcttctctgg gtatcattga aaattcagaa   181800
tgtttaatta catcaggcta tactcactgg tataaaatca gggagcaagt ataaagtagg   181860
tgtagggaaa taatttatgt tggattaaat gatccaatga agggatttta ttaagcccct   181920
agaagtccca gaatgaaaat gtataactgc atgactaacc cctaagaatt tgctggggtt   181980
tctgcattaa gtacgcttcc caggccattt gtaatgaagg taccgtgatc tgttaaggaa   182040
gagacctaca gctgggaaca aaagagccaa attccatcct agacatcagt ctcctgtttg   182100
actcattcca accccaagaa tatgttgtag agtgtaggac ccatgaaagt tacttactgt   182160
gcttccctgt accttccgtc atccagttcc cagacatatc tgtgtttctt ctctgaatgc   182220
ctagttactt gggatcccat gctgtattgg tctgttctca cactgctgta aagaactacc   182280
tgagactgga tagtttataa agaaaagagg tttaattgac tcagtttttac aggctatacg   182340
ggaagcatgg ctggggaggc ctcaggaaac ttacaatcat ggtggaaggc aaaggggaag   182400
caagcacatc ttcacatggc ggcaggaaag agagagagtg aagggcagt  gccacacact   182460
tttaaacaac cagatctcat gagaactcac tatcacgaga acaacaaggg ggaaattcac   182520
ccccatgatc cagtcacctc ccaccaggcc cctcctccaa cactgaagat cataattcat   182580
catgagattt ggctggggat acagcgccaa accatagcac atgcctttcc caggactggt   182640
gatggaggaa cggtgccctt gtcacaccta ccagaatata ctcacccacc tccagacact   182700
ccatttctct ttcaagcaca cctcttcact tgtgccgcca gctaaggttt actgcagtta   182760
cttcctttgt gtgtcctctt accttaccaa gtcgcctcac ccaccatcta ctgttaatta   182820
aattaccacc tcccccactt cccacctcca gagtagagac tgtgtcttca gttctcttgg   182880
ccttcccaca atgggaagtc cagtgtagaa catacccctag gagccaacta atgtgctag   182940
tggcctgcca accctgcaga gggctaggga atcttcaagg agtctgctgc cagtgaaact   183000
caccagtact agaatcccag gctccaaaga agtctagaaa agtacatctt ttaaggaggt   183060
aataagaggc tcaagtgccc acaaatccta tctgctcttg gcctagttct tttgggatca   183120
atgtgctagt ctctcttgtc gaaccagtta ctgaccagca agactaaaaa accaggccca   183180
aacacattct attcatgtgc ttagatatgg acctacggat caaatatccc actgtaaagc   183240
aaaacagcaa actgttttc  ccttgtactt tcacactcaa caatagcacg cttctgtggc   183300
tggctgtgtg gggctttc   cttacacacc aaatatttct cacaaacacc aaccaggtgt   183360
cctcttattc aattcaatcc tgacactgtc tacctggaga tggtgtcgga tcccacagat   183420
tgacggctca gtcccatgag accagcccca cttcaggcac taattgcaaa tccaggccat   183480
gcatacttct ctgactgcct ggctaaaaac cgcattcaca gccgggcacg gtggctcatg   183540
cctgtaatgc caaacctttg ggagaccaag gtaggtggat cacttgaggt cggaggttcg   183600
agaccagcct ggccaacatg gtgaaacccc atctctatta aaatacaaa  gattaggccg   183660
ggcacagtgg ctgacgccag taatcccggc actttgggag gccgaggcag gcagatcacg   183720
aggtcaggag attgagacca tcctggctaa cacagtgaaa ccctgtctct actaaaaata   183780
caaaaaatt  agccaggtgt ggtggcagac gcctgtagtc ccagctactc aggaggctga   183840
ggcaggagaa tggcgtgaac ccgggaggcg gagcttgcag tgagcggaga tcgcgccact   183900
```

```
gcactccagc ctgggcaaga cagcgagact ccgtctcaaa aaaaaaaaaa aaaaaaaatt   183960
agctgggtgt ggtggcgggc tcctgtaagc caagctacta gggaggctga ggcaggagaa   184020
tcgcttgaac ccaggaggcg gaagttgcag tgagttgaga tcctgccact gcactccagc   184080
ctgggagaca gagtgagact ccatctcaaa aaaaaaaaa aaaatgggt tcgcatgagc   184140 cccctccttg ggttcaatta agttcctagg atggctcaca gaactgagag aaacacttat   184200
ttacagaggt gttatgatat atattgattt tcgtccatgg ttcctggttc ctgaatccca   184260
taaaccttct tacagccttt tgttataatg ttgggggtgt cacgcctcag ggcaggcct    184320 ctgaccttcc ctgccctcct tgcactgtaa tgtttccccc atttctgatt gtgagtctta   184380
agaccctccc atgagagggt cccaccctac accttgtggg aaggaatgtg gatgtcatga   184440
agtgtccata aaaacccaag aggacagggt tcaagggat tccagatagc cagacatgtg   184500
gagcttcctg gaaggcaggg cacccaggtc gggcatggaa gttctgcacc tcttccccca   184560
tacctcgccc tacacacctc ttcatatgtg tcctttgcaa tatcttttg ttgttgtgt    184620 ttgtttgaga cagagtctcg ctctgctgcc caggctggaa tacaatggca tgatcttggc   184680
tccctgctac ctccgcctcc tgggttcaag cgactctccc acctcagcct cctgagtagc   184740
tgggattaca ggcatccacc atcatgcctg gctagttttt gtattttgt agagacgggg   184800 tttcaccatg ttggccaggc tggtcttgaa ctcctgacct taggtgaccc gcccgccttg   184860
gcctcccaaa gtgctgggat tacaggcgtg agccaccgtg cctggcctgt agtatccttt   184920
ataataaact ggaaatgtta agcatgtgtt tcctttagtt ctgttagctg ctccagcaaa   184980
ttaatcaaac ccaaagaggg gagtcctagg aactccaatt tgaaaccagt tggtcagaag   185040
ttccagaggc ccagacttgc gactggtatg gtgggggca ctcggccctg tgggatctga   185100
cactatctct gggtagacag ggtcggaact gaactggaag ccaccccacc tggtgtctgc   185160
tgcttggtgt atgggaaac cccatacaca tttggtcaca gaagtcttct atgttgatga   185220
ctgttgtggt gcgacagcag aggaaaacac ggtttgagga gagcttttcc caacacgctt   185280
atgtgtgcca gtttattata gaagacacag atgaacacca gatgaagaga tgcatagggc   185340
atggtctgtg gagttggggt tcacctccct cctggcacaa ggatgccttc accaacccag   185400
aaactcatca agtcttgttc aaggattttt gtagagctta atctccactc cccgccctcc   185460
acccttcctg gaggttgatg ggtggggctg aaagttccag ccctccaatc ttctacttac   185520
ttggtctttc catcctgagg ctagctggag gcccaccccg tcactccatt accttaagct   185580
caggtgttat tgaaggagct ccttatgaat agagcaaaat caccccctatc agaaatttca   185640 agagttttag gaaacctgtg actggaacca aggacaaaga tgaaatatat tttgtatgat   185700
agcacaccca ccagattgga tcgtggggcc atatggcctt tagtgtggaa gctgcttgac   185760
cacattttcc gcccatgcac tgccattctc atttcaggct gcgtcatcat catcatcacc   185820
atcacctgtt cttagcaaag gtcgcacacc ttccaaatgc tttgtataga ttagctcatc   185880 actcccata ctcaccctgg gagcatagtc agggataaga ggtagagttc tagcgctctg   185940
tggctactat ggtttatggg atctttgcgc aggaataact ggactttaaa catcttggct   186000 tttctttca gtaggtcagt cggcatgtac tcacagggcc gtgcatgctg agcattgaga   186060
cacatcacaa gggagtgaaa acctgctgcc ataccccccc agaggcagca ggatgtttgg   186120
ataaataagg cataaacacc tggagaatta aagcaagtac aattagtgca gcctttgcca   186180
agagaaaggt gtaagtgcta aatgcagtag atgttcaaat acggcagaga ccacagtggg   186240
```

```
cagggtaggc caagaatgct gcctaaggag tggggcttgg ggtgaaactg gggcatttga 186300
gacactgcag gcccatcacc ctggctgcgc cctcctgagg gaggcaggga ctgaggcggg 186360
aggcctggag aggtctgtgc gtgagcctgg gggctcattg ataaggagct tccagtgggg 186420
gcaataacat tggaagtgga gaggatggca tgtgtgccgg gagacgcagt ggagtggaag 186480
tcgccggaac tgacaaggga tgggatgtga gcaaggagtc caggtgagtc ctggggacct 186540
gaaaggatgg acccagagag ataaacgact tcaaaccggc acggcagtga agtgactgac 186600
ccgcgagtgc cctgcaccga ggctgacatt tgacttcctg ccaagttggc catcagacag 186660
ttagaaatca attttggagt tcaggagaga ggccagagct gaaaattggg gagttgttta 186720
cattgggagt gatatacagt ctctacattt ccatccagtt caaaacattc ttgcgtgtct 186780
gctatgcact gtgcactgag gttaccaaga ctggaaagac ccaatccctg tcctggaagc 186840
ttagtgttgg caggaggcag acaagctgat acatgcaaac aaagggctca caggtgccag 186900
gatgccaagg gatacagaag aaggatggtt gcttctctac ccaggagtgc cctgaggtgt 186960
cttaaaaaga ggagcattta tgactcaggc agggtggcac attccagacg gcagtgggca 187020
ggagcctgac tccagagcgc cttagaggct gccgctggga gttgagctgg accctgaagg 187080
cagtagggta agccataaat tagggttaag gaaccaaggg aataagggga tcagaccatt 187140
gcatagctcc agcagcacca ttactagcag cctgtgtgaa tgatggtccc ctcttacatg 187200
cccaccatgc aagggctcta ggccattctt cactctttaa tgcagaaaag caaaacttcc 187260
agctgttttc ccctacccaa aatgtgtgag cctgagccca gccccaggat ggatcttgtc 187320
ctaggtaacc aagaaggcct taagtgtcag aagaggtagc tccaggctga ataaagggac 187380
aaatgaagca ttactgcact gagatcgccc gtcgtgggt gggtctatac ccatctagtc 187440
attaagcctc aataatttgg tttctaaatg gactattatt tgctacagat caaaagttgt 187500
tggaaactat attacacaga taaatagaat tgtcctgcaa ataaaggaag taatctcttc 187560
tctgtttgag ataccatgca gtatttgtcc aacttgtaca aatagttctg atccatgaga 187620
atcctccact ttcaacttac ttgctgctat atcccaacta ttataaggcc atggagacca 187680
gtagcctggt ttccattatc tttgctctgt ttttttttat ggcatggttg acactacctc 187740
cagtagcaaa gagttaactt gtcatcagag ctataaaatc acaatgataa gtgaaaagtt 187800
ctcttttgta ctttagcatc caagagaagt gtaattccca actacaatgc tcaaaataat 187860
agagagtttt tactttgggc ctgaaaatac ttataggtca ggtctcctag ttgggtccat 187920
gctgttgttg gtgttccctc ccaagtaaat acatactgaa tttagcaaat tattcatttg 187980
tgatcctctg tgccatctaa aaatatatat agtttaaaac gctggccagg cgcagtggct 188040
catgcctata atctcagcac tttggggagc tgaggcaggt ggatcacctg aggtcgggaa 188100
ttgaagacca aactggccaa catggtgaaa cccctctct actaaaaata caaaaattag 188160
ctgggcatgt tgttggactc ctataatccc agctactagg gaggctgagg caggagaatc 188220
tcttgaaccc gggaggtgga ggttgcagtg agccgagatt gtggcactgt actccagcct 188280
gggtgacaga gtgagactcc atctcaaaaa aaaaaaaaaa aatgcttatc attgcacaga 188340
tagctgtaca gttttttatt atttatgata acggtaactg actttttgtt aaagctggtt 188400
tggaatctgg aggttatttt aattttgata actttatgat tttaactttt aattttaact 188460
ttatgatgtt tgtcataaaa gagtggaatg tgctcctatt ttgagatgga acatttcgg 188520
cagggagaga gaagagagac accaaaccac ctaacagcca ggttccaagg ggagattcat 188580
tcagcgtctt tgaagcattg ttagtttttca tttgaggcat aaattggaaa cttatatctt 188640
```

```
tctttggagt aggaagtatt tcagacagaa aaaaaatgat tgctacaaca acatcacgaa 188700
aaagaacaga aggtttcatg aagagtaata aagttaagtt tatgaattag agcttcagat 188760
gggaaatctt atttggacag taaatggtta atggtacagg acaccatga tgggggatct 188820
ttgcagcatt gaaaaaacac gcgtccataa atccttctct agcacttctt tgtgatcaca 188880
gagtcaagct gaggacaatg atggagtgct ccagttcatc cgaagtgcac gagtcccctt 188940
tgcagcagac tctgacattc ccggcccctc tccggagtgt tatcaacatg cagtcagtgc 189000
tctctacgtc attactttaa aaacaaaaac tcggccagca gcagttcagt acatcttcaa 189060
agatcttgac ttgtaatttt ttcccctgca tcttctctat tgagcacatg aactgacatc 189120
tttctacccc caaataatca gttctttccc cctaaataaa atgggtaatc caaaaaagac 189180
ccatcaaaag gaagctaaag atagtaatgc ctaggtagtt tcgggaccag aatgattgtc 189240
tctaaatatg tacatgtaca gtgattacgt gtttaaaatg tttaatgact tggagaaata 189300
gtgtgttgag tggagaaaaa tgagatttag tagagcataa cgtcaacagt gtaaaaatac 189360
atagaaaagc aagcaggaat aaaggaatgt ttaaataaat tacaaagata aaaattaaaa 189420
ccgtaattca gccgagcctg gtgggtcatg cctgtaatcc cagcactttg agaggctgag 189480
gcaggcagat cacttgaggt caggattttg agaccagcct ggccaacgtg gtgaaacctc 189540
atttctacta aaaatacaaa aattagccgg gcatggtgtt gggtgcctgt aatcccagct 189600
actcagaagg ctgaggcaga agaatcgctt aaacccagga gatggagttt gcagtgagcc 189660
tagttcgcgc cactggacta gactaggtga cagagggaga ctccgtctca aggaaaaaaa 189720
aaaaacttaa ctagaacatt tattgagcac ttactaggtg ccagctagtg ctctgagtgc 189780
tttgtgtgta ttaactcatt aatgccccca gcacctcttg aggtagatta aaatctccat 189840
ctcggtttta catgcaagga aaccagagca ggaagagctt caggaacttg ccctcctagt 189900
aaagatagaa agtagcaaac ccaggattca accccagaaa tattatatac tatgtttgtg 189960
ctgaatcttt ttttttttt tttgttttg gagatggagt tttgctcttg ttgcccaggc 190020
tggagtgcag tggcgcgatc tcggctcacc gcaacctccg cctcccaggt tcaagtgatt 190080
ctcctgcctc agcctcccaa gtagctggga ttgcaggtgc tcactaccac gccggctaat 190140
tttgtatttt tagtagagac agagtttctc catgttggtc aggctgttct caagctcccg 190200
acctcgggtg atctgcctgc ctcggcctcc caaagtgttg ggattacagg cgagagccac 190260
cgcacctggc ctttgtgctg attctatagt cttattttca catcctatca gttactgtaa 190320
gtaactcttg attccaagaa ctgtataata ggaaagggta gcttccaatt atctactctt 190380
gcttgataat gcattaattc cacatagcct ttaaaagttt agtaaatttt aggataaatt 190440
ttcgaactgt tatttcctat tggctgttag aaaattgtgt tgctcaaagg ggaacatgtc 190500
tattgtgcct tgtggagatt ttcctacagc ttttctggct gacccgtcac ttgcactctg 190560
gaactctcct aaaccagata cggcccacca cgtggcatgg tgtggatcct ggactttctg 190620
tcatccgtta ggttcatatt cttgaagcaa gtctagaact attttctgag agattccctg 190680
gctgttgttc tgtgtttggg tgggttagtc accttttttag gtgagagact tgatttgggt 190740
acacagtttc acaaaagtat tgtcaaccct gctggcaaag tgactgacgt gctgggcatg 190800
ggagcacact ccatcggcat ggcagagtgg attcactcca tgccattgcc agagaatagg 190860
actttgaacc acagccaccc ggcttttct gaaaggcctg cttgggcaat gatgcctgga 190920
gaattatctg aagaatgcag tctgtccatt cctctggaga tggtctagtt tttatcccca 190980
```

```
gaccaagctg aacctcttag agctgtgcat ttatattgtg tggaattgcc ttcagcgacg    191040
tgttctataa cgtcgtgttc ttgtcacctt ttgagggaca ctggtgctgt ggggaagatc    191100
ctcaccaata cgcaacagca gggccctgtt ctctcacctg ccatcccctc tggaaagctc    191160
acagagaggg tttcctgggt tgctcctttt ccaagcagga cttctactgt agacttacag    191220
ctccagttac aagcctgtgt gcttgtctgt ttccccacaa ggtgttctga cctggggggg    191280
aagggacgga atcctattca tctctgaatc ctaaatgcca ggcctagcac ttggcacaca    191340
gtgggttcca gttgtggaat gaattttttt cagtcctgac aataaatgtt ggggttcttt    191400
agtttgtttg ttgttattgt ctgttttatt tgtattttgg ggttttttgc ttttccccc     191460
agggaatgaa aatgccttct ccatatgaac cagacatatc ctggggctgg ggctgagtgt    191520
cctttgttgt ttgctctaat tataactaat gaacagttca gctctggtaa ttgtaggctt    191580
gctggaccca gtgcctgcct tctaactgaa tcttgactct gctccattat gtattttcca    191640
tgatcctgat ttctgtcaat ctaattttta aatttcattc taaggcaaac ctgctcatgt    191700
tcttcgctga aatcaacctc cccttctgg aatggacata tggaaaattg gaggcaaaat      191760
ataataatgg tggtgactca gactgcttta aggcctgaga accggccag gtactgtggc      191820
tcacgtctgt aatcccaaca tttgggagg ctgaggtggg tggattgctt gagcccagga      191880
gtttgagacc agcctgggca acataatgaa aactcatctc tacaaaaagt tactgggctc    191940
agtggtgtgc acctgtagtc ccagctactc aggaggctgg ggtgggacca tcgcttgggc    192000
ccaggaggta aaggctgaag tgagctgtga ttgcgccact gcactccagc ctgggcaaca    192060
gagtgagacc ctgtcttaaa aaaacaaaaa gacccatgag acctagactc ccctgtcaa     192120
aaatactcac acacacacat atacgataag atagtatttc tacctttct ttctcaaaac     192180
attccacaga acagtcttac cttcgaggag agccgtatgc atgacctttt gtttgtttgt    192240
ttgagacgga gtctggctct gtggcccagg ctggagtgca gtggtgccat ctcggctcac    192300
tgcaacctcc gcctcccagg ctcaagtgat tttcctgcct cagcctccca gtagctggg     192360
attacaggcg cgtgccacca tgcccagcta attttttgtat ttttagaaga acagtttca    192420
ccatattggc cagactggtc tcaaactcct gaccgcacat tatctgcctg ccaccacctc    192480
ccaaagtgct aggatttcag gcataagcca ccatgcccag ctggaggcct tatttttact    192540
gctattcaga gaacctgtgg cttatccatg gagggcttaa gctttgcctt ttctcttgct    192600
catttccata cctagcaaga gcttaagctg gtttattgca ctgacattct aatgaaatat    192660
aaatagcttc tcaacagaga gataagaaag aggagtatct agtacagcaa gaccctctgg    192720
gtgggtcagg gccagctggg gccgtgccgg ggctctgagt ggaggaggtg gcgtgggagc    192780
actgatgctc gggctctgtc acatccgttt ttggcatttg tcctggcaaa ggctgcattt    192840
ctgatctttc agaaagctgt gggtacactg tacagaaatg tgttttgctt gctttgaagg    192900
atgacctact ggctgacagc cagccagaat taattccata tacatttgca gattttcagt    192960
atgagagacg gcaattagcc tacagaaacc catttaaccc ccgaggtgga gctgtatggt    193020
gaagactgtt atttatggga gtctgtgtaa tttgcctctg tgacaaggga cagccatggc    193080
tcaggagggc ccacgccacc ctccttttca aggactcctg ccctgcctg agtggcttgg     193140
cctggcctgg ccatgtgagt cttgtggaca cgtgcacatc agtcagggac ccctgtggta    193200
tggaccaaag ggttgttttt tactgttttta acttatttaa tagcatctca tcagtattac    193260
aggcatgtgc cgccacgcca ggctaatttt ttttgtattt ttaatagaga cggggtttca    193320
ccatattggc caggctggtc ttgaactcct gacctcaggt gatcaccccg tgtcagcttc    193380
```

```
caaagtgctg ggagtacagg cgtgagccac cgcacctggc ccacagagct tctaaaggaa 193440
atgtgttggt tttttaatca aagttgaggc agtgcctcag tgaggggcag gctggagcag 193500
tggtaagcgc gctgaaggag tcgggctctc tgggcccaaa gtcctgccct ggccacagag 193560
tggctccctt cccctgagg tgggatgatg ttctccaggg ccttttagct ccaggctgct 193620
acagttctaa actggtggtg gtggtggtgg tggtggtggt tgtggtggtt gttttagatg 193680
cagtctcact cttttcccca ggctgggatg cagtggcatg atctcggctc actgcaacct 193740
tcgcctcctg ggttcaagcg attttcctgc ctgcgccacc acgcacagct aattttgta 193800
ttagtagagt tggggttttg ccatgttggc caggctgctc tcgaactcct gacctcaggt 193860
gatccgctca cctcagcctc ccaaagtgct gggattacag atacgagcca ccgcacctgg 193920
ccatgattgt tgttttata aaatcagaat ataaaatttg aaaatgttct tttttggtga 193980
gaaatgagaa ctaccaaagg agtaaaatgc tctaaaagcc atcaggtcct tcccacagta 194040
ttgaggctct gctcttacca ttttgttaaa taagttttgt tcctaacact ctttgtgata 194100
tgaagtattc ttgctaatca agctgcccgg agactggcgt ttcccagagc agtttcgaaa 194160
gtggaaatga tgctgcattt cctacccaca gtctggaggg tggctgtgct ctctgcacgg 194220
tgggtctgtg ctgctcagtt acgggatggt aagggaaggc tctaactcgg tgtcttacac 194280
catgcactag ggagtcgccc gctttattta cgagcgagtt gatgctttca gtgggttttg 194340
gctttgcctg gttccagact caagcccttc ctctaatgta gggcgggtac aagagagact 194400
tgagcaagga tattgggatt taagggaagg gcagtgcagg ccaaggtcag caagaggaca 194460
tctctaagat gaacagcact gcatttgtgg gaagcaaccc tgccataaac aactcagtta 194520
acgtttacat agtaaataat tgcattgcct tgggctggaa tagggacgcc agaaggtata 194580
ggaccatgtg gaattcagaa aagggagccc tgaagaatga gatttttattg ttcttaccag 194640
gagagtccag gtgctagagt tctctccttg taagtgacta accttctccc ttttggtaca 194700
caatcctcag atgaacggag atgattcatt aggccattct agcttaatgg atgcatcact 194760
gtgcaaccac gcaaatgcct catttctgat tcactcattt aatatttatt gaggagtgct 194820
gggtactagg ccattagaag aacaaacaac aacaacatag gcctggacct tgcacttgca 194880
gagttcacag gctagagagg cacacaagtt aaatatagac acagctgaaa gagctgacgt 194940
ctgggacaga gggagccccc tgctccagga gccagggagc agatgccatg ggggctggc 195000
agggataggg aagtcaggcc aggaatgggg ttacctaagc cggatcatga aggacgagaa 195060
cagactcacc aggggtcgag ggacaaggag gcagcaagtc cgcagcatga aggcaggaga 195120
gaacattgct gtaagccttt accatggcca ctgcatgggg aggaaacagg agatttgaa 195180
tgagctgtga cactgggcag gaaagcaaga cccaggtctt gtgaggcctt gagcgtcaag 195240
cttaggagtc aggacctggg gattttaagt acagcaatat cataattaca ttcatgtttc 195300
agagagatca ctcaggcagc agtctggaag gtggagtgga aaacggagaa attagtcatg 195360
aagacctatt tagaaagtag taggcaagaa atacccaggg cctaacctga ggtgtaggca 195420
ggggatggga atgagagcaa ttaccgaact agaatgaact aaactcaatg aacaggagcg 195480
gggaagaggg aatgcagaaa tggctctcag atttctgact tgttcgctta atgactgggg 195540
ttgtcatttg tttagataag caataaagaa cctagaaaca attttaggcg gaagatagtt 195600
gtgttgggag cccctaagac catgattat tacagcacaa ggatacaaag caaaattagc 195660
aaaaggaaac agcacgtggg gtcaagtcca ggggagctca ggcgcaagct tccagagtac 195720
```

```
tctcccata gagtcacaca agatacactt agttcctcca gcattgaact atgacgacac  195780
ctgaaatatt gtctgcagaa gaggctcatt agagactcag tccccaaggt ttttattggg  195840
taatggtcac gtaccaaatt tcagtctctc agaacaaaag caaatgttca gcatagacca  195900
ttttgtttgt gaaatttagg cacagtgagc ccctcttgtc agttagagga tagttgaaac  195960
cctcccacaa tccaagttct cagactcagg cctgctacat tatttctttc ctacacagta  196020
gtggatttgg ttactaacat gttggatctg aagcatttgt tgtaatttac agtgaagatg  196080
tccactgcac agttccgtat tgagtctgag gttcactgga gacatctgtg ctatcaatga  196140
aagtttctgg agtcattagc ccctcaaagg gtcattaaaa ccaggtcttc tagagagaaa  196200
gtctaaccct gtattccttt aaaccaccat agagaccatc tagttcttca cattataaaa  196260
atgagaaaac tgagtcccca gcgatgtggc ttggttgcac attttctat ttcaagtctg  196320
ttactccttc catcatacca gactgcctca caaaatgaca aagtcaggca ttgttcataa  196380
aagaacaaaa tggcatttag gttataaatc aggcccttgt aagtttggtt aatacaactt  196440
atttcccaaa gatcctggtc ctcagaccct caaaggaga gctgatcaca tcaaggcctc  196500
tacctggaag gaatttctaa gcagcctcta agtcaactgt tcatgttcag tccaccttga  196560
tttacaaaga acagtgaatc attaagacct ttctctccaa ggccgggtgc ggtggctcac  196620
gcctgtaatc ccagcacttt ggaaggccga ggcgagcgga tcacgaggtc aggagatcga  196680
gaccattcta gctaatacga tgaaaccccg tctctactaa aaatacaaaa aaaattagcc  196740
aggcttggtg gcgtgcacct gtagtcccag ctactcggga ggctgaggta ggagaatggc  196800
gtgaatccgg ggggcagagc ttgcagtgag ccaagatcgc gccactgcac tccagcctgg  196860
agaacagaga ctccatctca aaaaaaaga ccttttgctc ctctttgctc ttgtgtctgt  196920
ttaacagatt tttatgttaa caggcactct gtttgccact aggaataaaa agataaatgg  196980
gacaaagtct ttgcccctcaa gttacttata ttctagagcc aagaaagaga tagatgaaga  197040
acacatctta tatattagga ctgtgttggg ggcaggagta ggcagagtaa cccttggat  197100
atgggaaatg aaaataaatc aaactcaaaa caagtttatt atttgcttga agctctggta  197160
aaagataaag tgaaacctgc aaactgtaaa atgaagttgc tgctacacat ttctccagtt  197220
ttggatttca ttcttggatg gcctttaact tggatagaag gatacaagac agccatatat  197280
atatatatat acagctgttg ctcttttaaga tatccacttc accctgttgt ggggtgggag  197340
gagggggggag ggatagcatt aggagatata cctaatgtaa atgtcgagtt aatgggtgca  197400
gcacaccaac atggcacatg tatacatatg taacaaacct gcaccttgtg cgcatgtacc  197460
ctagaactta aagtacaata aaaaaaaaaa ttaaagaaaa gagatccact tcgctcagca  197520
catgtgattt ggctttggtc tttggtgtta atttggatgc ctaaagaact gactttcctt  197580
gatgctcact ccagccttt taggactaga ttggatacat ttacatgttt gctggctgtt  197640
ttttctacag tcacacatcc tacccataat aatattgcaa tattctaagt tgtcttggag  197700
gatatcatca agtaggtgtc aagtaaaact taatggtaga ctgtaaattt taaaacaagt  197760
tacaggtcat ttgtgtagtc tctctctcta tatatattaa aagaaacaaa acttttccct  197820
cttgaatctt tattcctatc tcagcttcat ttattgcctc gtttgtcatc taaatggtct  197880
ttgttctttc agctttcaaa catgattaat tgacattgtg cagcatagca cagggaaaag  197940
gctgaatatt ttgtatgatg agtaatctag ttaaacgccc atctttcttt tcaactttac  198000
caacaaatgt gtcttatgca gatgtaaggg cggtttgctt atttccctgt tcaaaatttt  198060
atgctattag cctagcatag catgtttctt ttccattgag ctagccaaaa ataatattga  198120
```

```
caaattcatg aagccttcca tctgatactg ttgcaaactt atgcaaatgt attttagact 198180
gttaagggaa tgtaagaatt aaataattaa acatccaaat gtcaagaatg ggataggaag 198240
aagtaactgg cctcatgttg gaagttaatg aaatatttga aaatataacct ttaaaatcaa 198300
agacatgaat ttgtgttttg ggttttttt tttcagattt gaataaagca gagtataata 198360
ttatagttgc tgcaggaagt tatgagcatt tctggaagtg cttattttca gcacatgcta 198420
cttagaattt taaaggacat tcagtgtatc tttgtcatga atctttctac tgggaccagg 198480
ccactcctgg atgaactcac agattgagag cttctcaaaa tgtaaaatca aattgtcttt 198540
taaaatatgc tattttaaag ttctggagaa tcaatgaact ttaaatgaaa atcggccaat 198600
acttggcaaa aagtcaattt gaagagttgt ctctttataa tctctgattt cacttataga 198660
gcttgcttcc aaaaaagta ctacgtatgt cataaatctg aaatgttttg cttttatgcc 198720
attttaagt cctgataaat attcttgaag tgttaaatta ttattattat tattatttga 198780
gatggagtca ctctgtcgcc caggctggag tacagtggtg tgatcttggc tcattgcaac 198840
ctccgcccc ccggattcga gtgattctcc tgcctcagcc tcccgagtat ctgggattac 198900
aggtgcctgc cactgcatcc ggctaatgtt ttgtattttt agtagagaca gggttttacc 198960
atcttggcca ggctgttctt gaactcctga ccttgtgatc cgcctgcctc ggcctcccaa 199020
agtgctggaa ttataggcat gagccgccgt gcccagccag tgttaaatta ttttttaactt 199080
gttagaaata attgtcccac aacttactga aggttggttt aatattcact attgttccca 199140
aaaaactctt aaaatattaa accaactcat agctcataac ttttcaaggt agcaagtgtt 199200
tgctaatctt aaaatgtgtt actattctt ttttgttttt tttttgtttt tttgtttttt 199260
tgttttgaga tggagtctcc ctctgtcacc caggctggag tgcagtggtg tgatcttgga 199320
tcactgcaac ctccacctcc tgggttcaag tgattctcct gcctcagcct cccaagtag 199380
ctgggattac aggcgtgcca ctacgcccag ctaatttgct tgtattttta gtagagatga 199440
ggtttcacca tgttggccag actggtctcg aacccttgac ctcaggtgat ccacccgcct 199500
tggactccca aagtgctggg attacaggtg tgagccacca tgcccggcca ctattcttaa 199560
gtgaccttct gcacatctct gtagttttat gcctggtgat ggcgtttaat ttaggagtat 199620
ctggcatgcc actccagtct gacagctagg ggcatgttag caaaggggc attttcagg 199680
tgagtgggtg agcatagccg tgctgaccat cttcctatc cagagggaag gcctagcagg 199740
gactcacgcc atcttgactt gcctgcccca ggctccctct cactgctccc ctggcctctt 199800
cctcttctcc agacaatggg gccttatgct cgctgtgttt gtcagaactc tcttgtggtt 199860
gtggctgcaa gtaagagaaa ctcaactcga gcttattcag aaagaggga tggattgacc 199920
cagataacag aaaagtgcta ggctagatct ggccttagcc acagctggat ccagccttct 199980
ggcatttgtg ctccgttcct cagccctgcc ccactgggag tgatgccttc tgttcacagt 200040
gtgatctgct tcatactcaa aactccctat ccagaggaag aggaatcttt tctctcccac 200100
catctgcaca gcagtattca ggaatcccct gccaggctct gttggcctca tgtgcccgt 200160
cctaatccac cactgtgccc agccagggtg tggccataca tgcccatcct gtgcataggg 200220
caggagcaga cccacctgca ccacatgcgg tggccgccat gaccacaaga ccaggatagg 200280
agtgctgatc aggccagacc ccaagggctg ttgctcagac cataccctggc ctgtagagta 200340
gaagaactaa atgtctcaca caggcaaaga ctactcttca attcctttaa ttgcaggtgt 200400
atgttggagt ccatgaaata caaagttatt gagaagcata actaaattta tagtagctcc 200460
```

-continued

```
tcattatata ttttcatgtt gataggattc tgccccatg ggaattaatt ttcttcatca    200520
aaagtgatct ccatactcac aaacactgaa tagctttggg cttttaaaaa caatgttttg    200580
gctttaaaag aaccacagga ggctgggcgc ggtggcttac gcctgtaatc ccagcacttt    200640
gggaggccga ggcgggcgga tcatgaggtc agaagattga gaccatccta gctaacatgg    200700
tgaaaccctg tctctactaa aaatacaaaa aaatcagcct ggcgtggtgg caggcacctg    200760
tagtcccagc tattcaggag gctgaggcag gggaatggtg tgaacccagg aggcagagct    200820
tgcaagtgag ctgagatcat gccactgcac tccagcctgg gcgacagagc aagactccat    200880
ctcaaaaaaa aaaaaaaaa aaaaagaac catggcaaaa gtgtccttta gccgggtgcg    200940
gtggctcaca cctgtaatcc cagcactttg ggaggccgag gcgggtggat cacgaggtca    201000
ggagattgag accatcctgg ctgatacagt gaaaccccgt ctctactaaa catacaaaaa    201060
attagccagg cgtggtggca ggcgcctgtt gtcccagcta ctcaggaggc tgaggcagga    201120
gaatggcgtg aacccgggag gcggagcttg cagtgagcca agattgcgcc attgcattcc    201180
agcctgggca atagagcaaa actccgtctc aaaaaaaaaa aaaaagtgt cctttagtct    201240
actgttggtt cttccaaaga gccatccttt cgctgatgct ttaggaactc caacctggg    201300
tcctgtcaag gataagctct catcttattc ccacaaaatt cctagagtta ctcatcattt    201360
tcctttcata ttcagctcat aaagcagtt tgtaggtctc tgtagtccat attagtaagt    201420
gttaaaaatg tatcaatttg attttttttt tttttttgag acagagtctt gctctgtagc    201480
ccaggctgga gtgcagtgtt gcaatcatgg ctcactgcaa cctctgcctc tgggtttaa    201540
gggattctcc tgcctcagcc tcctgagtag ctgggattat aggcgtgcac caccacgcct    201600
ggctaatttt tgcatttta gtagaaacgg gtttcacca cgttggtcag ctggtcttg    201660
aactcctgac ctcatgagcc accgctcccg gccatcgatt tgattattat aaaatcaggt    201720
tatattggtt tgaccagtta aaaacatcac aggttattta atcttttat ttatttattt    201780
atttattgag acagagtctg gctctgtcac ccaggctggt gtacagtggt gcaatctcag    201840
ctcactgcag cttcgacctc ctacgtccaa gcaattatcg tgcctcagcc tcctgtgtag    201900
ctgggattcc aggtgtgcgc caccacaccc agctaatttt tgtatttta gtagagacca    201960
ggcttcacca cgttggccag ctggtctcg aactcctggc tcaagtgat ccacccgcct    202020
tggcctccca aagtgctggg attacaggtg tgagccactg tggccagcta atcactttt    202080
taaatcacaa tttgtgttac gttcatgagt aatgggtgcc agaaataatg ttgtgtgtta    202140
aacataaatg tagatgggta accatgtata caaatgcata tctcctcaac ccagagagtg    202200
aaatttcccc accccagtga ccctgcctcg ctgtatggtt cattcttctc caggaattga    202260
aacatggtgg cagcctgcca gcttggcgtt accattaatt cttattctct tccctgccg    202320
atgtcatggg gacaccagcc aaatgaactc tgatgtgtct cacgtaatgc atgtggactt    202380
ctggtgcatg taaacagagg gtggttattc ttgattgcac atttgtgatt tttagtgagg    202440
ctctaaggga gaagcaagag gacttgaata acagatttat tctcgggcac tggtacatga    202500
aagagatgag taatgccaaa caataacac aattctgatt cacgccattg gtaatggagg    202560
agacttctgg gtaaacaaac caaagtaaca gctagaatgc agatctgatc acagcagtgt    202620
gttttgattc agtctaaaga tgacaaagaa agtttctgc tggtcctatc tgtagcaaca    202680
agggcctgcc cgcctgacca cactgcagtg aacagccac attgtgattt gcgggcctg    202740
aagcctttcg tctggtgacc ctttaagagg aacttgagcc aagatcttat cagtgatgga    202800
gatggagaca cctcaggatt ttccagtatc gttttcact ttttgttctt ggacatagtt    202860
```

```
aataacgctg ccaggtcttt caaatgctga ggcatttcct catagctcca agtagctgct    202920
gcgggtcaga ttctgcttga accgagggtt caattacaac atccgtatgc tttccagccc    202980
actctctgac ctttgttctt tttttcagta ctttttcagg ctcttaatgt ttccatccac    203040
taatctcagg agactctgta aatattctga gtatacatag cccaattact tttgaaaagc    203100
taatttaata gaaacttctt gatatgaatt gaataaattt tttaacttaa aaatcattta    203160
cttacaactt aagacagtta aacttgagag tatttgaaag ctagtaaact tcagagcttt    203220
cttcagtagg cacgaacttt accatttttc tgacactcag cacggtcagc aatgacacat    203280
tcattggagg actcatcaat atccctaaaa atagtagcag tactcgtgca cagcctgatt    203340
tcttttgaac ttggctcaat ttcttggaag cattgatcat gggatcccgc tttgattcct    203400
tttctgtaga ctagtgccag tttgcccagt ttcattacat ttttggaaag agctaaaact    203460
atggtatcgt tttattgcag tcctcacatc aatcataatt tggagcagtc ttggtgaaag    203520
atgaggaatt cagactggga tcctgggcaa ggcaggtcca gggggcaaga gggatggaat    203580
gcagtgagta cttattttat atcataagta cagccacctc agcctcatga cttttttagcc    203640 acggcttcat tccaaagtga ccacagtcat aaggcccaaa actatcttct ctctctttct    203700
ctctctctct ctctctctct ctctctccct ccctctctct gtcataggga cctccctaat    203760
cctccaggtt gtacagccag gaagggtaag gtattgtcaa aaacaagtga ggtacccct    203820 tgatagctca gtgggccaga gggcctctgg atgctggctg atcatggcaa aaactaaata    203880
cagaatccat acagtggatt ctctgtgctt tttctcttca cccctcctta cccttgacca    203940
aatttctgac tgtgttattt tcttattgca gtcctccctg ctagatatac aactttgact    204000
ttcatcagaa gaaagtgctc ccattgcatt attagctaaa ccatgttgca gtggcaacgc    204060
tccttcttcc agcttgcctc ggtgtttctg tagttagcat caggtgtcct tggttctgtt    204120
taccagcctg tccagggatc acttccctgg tgggatctct ctggtgaccc tcatctcaga    204180
gctcagcggt gcctttgggg ctacttgcca gacaactcca tgtgacagag gccaggtcc    204240 aagtgctcga tcaccccagc caccatttca gagttctcgg attatagatc cctcaacgag    204300
tcccagtgag acaccgaaca tgccatagaa gctatgtttt tctatttcag cacacagtaa    204360
aacactacct cttagatgtc gatgagtaca tgctgctttt atgttgacgc agaggacctg    204420
tgttgactct tcatcggcaa ggtgtctttt ttttaagttt caattgacac ataccacctc    204480
tggcccaagt ggaccacaca gttatgcatg ccctttggtg caagatacat cacgtctcca    204540
agaactcggg tgttttttctg atcatggaga attagattcc acatatagct tgtatttagg    204600
atctgcagat taggttttat aaattatgtt tggcaaatga taatccacaa agtagattct    204660
aagttaaaat actataaagt actataattt atgtttaaat gtctttcaac ctgagagtta    204720
ctctccctta gaagtcccca aaaatgctga aaccacacca ggttgatatc tgaccttttca    204780 cttttggaaa atgtgtatat tgttgaacct ctaatctaga ttcggacacc atcaccaacc    204840
agcttctctc tttcagttgc catctgcact ttactgttta gttttgttg tctttaggga    204900 aagttgtaaa atacccacat tcttctcaag ttcttcaagt cttttggttt ttagtaaacc    204960
cttttgtgac attgtctttg agaacagagg tcaacaaaca tttccttaat ggactagata    205020
gtagatatat caggacttgc agaccacatg gtctctgtcc taactactca actctgccgt    205080
tatagcacaa aaccagccgt actcaatata taaatgaatg accctgtggc tgtgttccac    205140
taaaacttca taaaaataag cagctggcca gatttgctgt gtgggtctta gtttgccaac    205200
```

```
ccctgatcta gaagaaaaga gttttgtgta atgtttgggt aataaaataa acataccaaa    205260
ccatctcagg aatccctaac cttttcctca ttgggaacta ttttcccagt atccccaagt    205320
actggtggga atgagataaa aagggccagg catgccattc cctaaagcag atagccaacc    205380
ctctttcttt ccctgtggaa atcccctctg cctacaggga ggagaagcaa ctggtttgga    205440
agctgccagc cagtccgttt atttagaaaa ttctaagccc agttccagat cactttgcgt    205500
caactctaaa atacagccac aaatgaaata atgttgttt ataatcctac caagtctagt    205560
aggtgtgtat gtgcttgagg ttaaacttt gtgtaagctc cagacttact ttaggtttat    205620
agaaaattac atcgcaattg atacaatggt tgtgttgggt gatggagata gaaagaggga    205680
gaagaagtga aagtgaaatt ttggtcaaaa ttggatacca ccctaataag ccgggagata    205740
aggggtgctg cagaactgtt ttctgtgata cagtgcatct acattgataa tttgtgtttt    205800
atgtactttt aaaatgaggc tttattggct tgatttctgt gagaaaaatc actaatgggc    205860
tgatcgtact gctctacttc aacatgcaag agaattgctc agacgcttgt cagatgcctg    205920
aaccacatac ttatttgaga atgtgccatc ataggaagct ttcattcacc aaggtcaccg    205980
agagggcagc ccagggaagc acgttgaact tcgcatggtt ctggccactc gtgtcagtag    206040
caaagcaagg aaataaggag ctgacttgcc caaaaattac aagttcagag aaaacggact    206100
tgttttgttt ggaaaaggca gataacggag cagtaactaa agaatcctct ttttttatta    206160
ttattgttgt tgctcaattt ataaacctaa acagaaaatg tgtgttgcct tatttcctct    206220
tcttttctac agataacttt cttttaaaac attctaaata ttaagcaaca ttgtaagtac    206280
agattttttt tttttttttt ttttgagtt ggagtctcac tccgatcatc cagactggag    206340
tgcaatggcg cgatcttggc tcactgcaac ctctgcctcc tgggttcaag cagttctcct    206400
gcctcggcct cctgagtagc tgggattcca ggcacccacc accacatttg gttaattttt    206460
gtattttag tagagatggg gtttccccat gttggccagg ctagtctcga actcctgact    206520
cacctcagcc tcccaaagtg ctgagagtac aggcgtgagc caccacgccc ggctagtaca    206580
gaatttttta tggccccttt taaagactgc aaaccttttt ataccaaaaa aaaattattt    206640
ttcctgtatt tattttacac attagtaaat gaatgaaatt ttggctctag gtttagaaag    206700
caatttcatt ttaagctcat tttactgtgt cattggactt tttattaatt ttattcttga    206760
actacttagc tgaaaatcga attctgtcat tatatgtaat catataatgc ttctcataat    206820
gttacacttt aattagatgc agttgaataa taacctaaaa aatcttcata gtctataaaa    206880
ttcacactta tatttataag acaatattat ctcacccatt gatacataat gttatgttaa    206940
aagtacacaa tatggccagg tgtggtggct cacacctgga atcccagtac tttgggaggc    207000
tgaggcggca gatcacttga gcccaggagt tcgacatcag catgagcaac atgttgaaac    207060
cccgtctcta ccaaaaatac aaaaattagc caggcatggt ggcgcacatc tgtaatccca    207120
gcaacttggg aggctgaggc aggaggatca cttgaaccca gggacagag gttgcagtga    207180
acagaggttg cagtgagcgg agattgtgcc tcctctgcac tccagcctgg atgacagagt    207240
gatactctgt ctcaaaaaat aaaaagagta cacaatatta tctcacccat tgatacataa    207300
tgttatgtta aaagcacact gcattctaga gaaggtagag taacagggtc ttactttacc    207360
ctcccacttg aaacaagtaa aaaactggac aaagtatatg aaaaatacat cactcagggc    207420
attggacacc aggcagcaaa aaacagtggc ccctgagaaa ttggaaacaa agtgagtcct    207480
ataattgtcc ttatctagaa aaagtttcct ggctactgtg tagagagaag gaacccagga    207540
gaaagagctc aactgtctcc ctgagttgaa gacagagctg gggatacatc aagggaaacc    207600
```

```
aaggcagcta gtttgcagag gtggaggacc ggagaggaga gaactgcata gagagagctt    207660
tgcggatgta cagagtcctc cttgagcatg caagtgcgta ctgatcaaag tgtggttgtg    207720
agaaaactac ccatcaccag agaaaggatc acccgaaaga atgagggaac agtgcctgcc    207780
tcccacacag tagccaagaa gaggtgcctg ttgccaacag ctagagtgaa aacctctgaa    207840
tgcaggggca ctggttagaa tactaagaag ggtcttgcca gacatccaat ccaaaattag    207900
caggcatgca aagatctagg aaaataccac ctaaaatgag aaaagtcaat caaaactaac    207960
ccattataca gatgatagaa ttcatagaca cggacattaa agtagttgtt gtgactgtag    208020
tttgcatgtt taagaaacta gaagaaggat ttaacatgtt aaatagagac aaagaagata    208080
taacaaagat ataaatcaaa ctgaagagat gaaaactgca gtgcctgaaa tgataaaaaa    208140
aaaaaactct taattaatag cagattagac attgcaaaag aaaagcctag ttaacttaaa    208200
gacatgcagt agaaactatc tgaaatgaaa cagaaaaagg ctgaaaagaa gcaagagagc    208260
aacattgagc tttgggatca ttttaagtag ccaaaaatat gtaaaactag agtcccacag    208320
gagtggaaaa aaggaactga aaaatatttg aagaaataat gggcaaaacg ttttcaaatt    208380
tgatagaaac tataaactca tacattcaaa aaaatgagaa cattttaaaa agagaggata    208440
aatgacacat tatgtagaga ggaacaaaga taaattggct gatgatttct tgttggaaac    208500
aacacaaact agaaggtggt aggtcaatat ttttaaagca gtgaaagaaa attcacagcc    208560
tagagttttt tacctggtta aaatatcttt ccaaaacaaa gctgaaataa agactatttt    208620
agacacgtaa aagctgaaaa aattcatcac tagctaacct gaagtacaaa aagtgttaca    208680
gaaattcctg ctggcagaaa gaaaatgata ccagttggaa acctgaatct acccaaagga    208740
atgaagaaca ccaaaaatag taaccgcatg gatagaaaga cttgttctta ctgtttatct    208800
taaaagctat tactgtatac agtaattact gcataaagca aaaataataa aaatgtagta    208860
tagcgttaaa aacatttaga agctaaatat atggcaacaa taacacaaag tctaagagga    208920
gagaaataga agcatgcttt tgtaaaattc ttaggctata tgtgaagtag tataactata    208980
tgtggtgtgg tagtataatt atatgtgaag gtagactgtg caaagtgaaa tgtgtatgta    209040
gtcatgtgct gtataataac gttttggtca aaaacaaacc gtgtatacaa cagcagttcc    209100
atcagattat aatactgtat tttttactgt accctttcta ttgtatgttt gcatgtataa    209160
atacttacca ttctgttaca gccacctact gtattcagaa caataacatg ctatgcaggc    209220
ttgtagccct ggtgcagtag gctgtaccat acagccaagg tgtgtaggag gctataccat    209280
ctaggtttgc aagtacactg tatgatgttc acacagtgac aaaatcaccc agtgatgtgt    209340
ttctcagaat gtacccgtct ttaagcaaca caggactgtg ctgtaaatgc aaggtaacca    209400
tttcagtaat tcaacaacgt tatagttaaa gagttgtaac cttgttatag ttaacaaagt    209460
taatatatag ttatctacaa agtagataaa atgaaatcat taaaaataat ccagaggaag    209520
cagaaagggg aaaaaggaac aaagaacaga taggacaata agaaaaagaa tagcaaaata    209580
gtagatttaa actcaactat atcgataatc acactagata taaatgtcct aaatacacta    209640
attaaaatgc aaagaatgtc agattggcta aaaatgcaag agccgactat tactgtcaac    209700
aagaaaccct ttttaaatct aaagacataa gtaggttaaa ggtaaaagga tggaaaagcg    209760
ctaatactaa tcaaaagaaa attgaattgg tatatcaata tcaaagtaga actagagcaa    209820
agagtagtac caaggatata aaagaggctt gtttcattat gacaaagggg ccgtttcacg    209880
aacaggacat agcagttcta agtgtttaag catataataa cagagcatca acataaatga    209940
```

-continued

```
agaaaaaaaa agataaaatt atagggaaaa atagaaaatc cacaaatata gtcagaattt   210000
tttaaacccc tctcagaaca agtagagtaa aaatcaataa ggatttagaa gacttaaaca   210060
atgctacaat tcagcttgac tccacccaac aacagcagat tacgcattct tttcaaacgt   210120
acacagaaca tttgccaaaa tagaccatat tctgagtcac aaaatgtctt aataaatttg   210180
taagggctca aatcatacaa aatatgttct ctaaccacag tgggattaaa ttagaaatca   210240
acactgaaag acatctggaa acactccaaa tatttggaaa taagctacag agtgggagaa   210300
aatatttgca agttatctat ttgatataag gatttgtata tggaatacta aaactcaaaa   210360
ctcaatgaga aaataacgct tttaaaagat gactgaaaga tttgaacaca tatttcaccc   210420
aagaaaatac atgaaaatat gcttaccatc acaggcatta gggaaatgga aatttaaacc   210480
acagtgaata ccgctgcata gctattagaa tgtctacaat taaaaagatt gaccagctaa   210540
gcacagtagc tcatgcctgt aatcccaaca ctttgacagg cagaggcagg aggatggctt   210600
gagcccagcc tggacaacat agggaggaga ctctgtgtct acaataaaag aaaaagaaaa   210660
ttagccagtt gtggtggcct agctgctcac ttgggaggat gaggtgggag gattgcttga   210720
gcccaggttg aggctgtagt aagctgtgat tgcaccactg cactccagcc tgcaagacag   210780
agcaagaccc tgtcccaaag aaaaaaaaga ttgggctggg cacggtggct cacagctgta   210840
attgcatcac tttgggaggc tgaggcaggt ggatcacttg aggtcaggag ttcaagacca   210900
gcctgggcaa catggggaaa ccccaactct actaaaaata caaaaaatta attgggcatg   210960
gtggcacacg cctgtaatcc cagctactcg ggaggctgag gcccgagaat tgcttgaacc   211020
caggaaacag aggttgcagt gagccaagat tgtaccactg cactccagcc tgggtgacag   211080
agtgatactc tgtctaaaaa aaaaaaaaaa aaagactgac cataccaaat gttggcaagg   211140
atgtggaaca actggaaccc tcatacactg ctggtaggaa tatataacag taccaccccc   211200
ttggaaatca atttggggtc gtttcttaaa aagttaaagt gcacctgcca tatagtcaag   211260
acattctctt tctaaatatt tacccaagag aaatgcagta tatgtccatg taaagatccg   211320
tgcatgaatg ttcgtagcag cttttttgta ataatataca gtaagcttta cactttgaca   211380
tgtgcagttt attgtatgta atttgcctca ataaagtttt taaataatac aattttatcc   211440
aaaataaagt tgtgaaaagt agaaaaatga ggaaaaagtt tcaaaggtta gagggtcag   211500
tccaggagac ctaacatcta actaatggga attccaataa gacagaagaa accagaaggg   211560
aagaaattat cagagaaata atcctcagcc ttccacccaa aattttctct cctagaactg   211620
aaggactccc aaatcaaaag ggtcagcaaa ataaatgtat agactcacac caacacactt   211680
catcataata gtaaaaagaa cagtagagtc aaaaagagga tactaaaagc tttcagaggg   211740
ggaaaaaaca aaacatgcaa ataatctgga acccgaatgg catcagactt ttcaacggta   211800
atactgggct gggtgcagtg gctcacgcct gtaatcccag cactttggga ggccaaggca   211860
ggtgaatcac ctgaggtcag gaattcaaga ccagcctggt caacctgatg aaaccccatc   211920
tctattaata gtacaaaaat tagcttattt cttaaaagcc agcaaggggg atggtttttt   211980
ccttgggctg gtggcacgca tctgtaatcc tagctactcg ggaagctgag gcatgagaat   212040
tgcttgaact tgggaggtag aggttgcagt gagccaagat cgtgccacta tactctagcc   212100
tgggcggcag agtgaaactg tgtcttaaaa gaaaaaaata aataaaagtt atcaaaaaac   212160
aaaaacaaaa ccataatact ggaggctaga ttacaataga gcaatatctt caaaattcaa   212220
ggaaaatggc caggcgcggt ggctcacgct tgtaatccca gcactttgga aggccgaggc   212280
gggcggagca cgaggtcagg agatccagac cacggtgaaa ccctgtctct actaaaaata   212340
```

```
caaaaaatta gccgggcgtg gtggcaggcg cctgtagccc cagctactcc ggagaggctg   212400
aggcaggaga atggcatgaa cccaggaggt ggagcttgca gtgagccaag atcgcgccac   212460
tgcactccag cctgggcgac agagcaagac tctgtctcaa aaaaaaaaaa aaaaaaaaaa   212520
tcaaggaaaa taatataccc agctaaacca tcatgaagtg tgataagaat aatgacgaag   212580
ccagacattt tagaaaaatc taccoctagc gccctttttc tcaagaagcc actagaggag   212640
tatttcactc aaatgagcaa gcagaggaag gaggattgct tgagcccagc ctgggcaatg   212700
tacagagacc ccatgtctac aaagaaataa agaagaaaa ttagccaggt gtggtggcct    212760
gtagtcctag ctactcactc aggaggatga ggtaggagaa ttgcaagtaa atgagcaagt   212820
aaaccacaga agaatattaa ttttctcttt tttctgctgc ataacaaatg agcacacatt   212880
tagtggctta aaacagctca catgtattat cttccatttc tctgggtcag cttagctggg   212940
ttctctgctt cagactgcga aaattgtctc atctgaggcc tgggttcctc atcaaagctc   213000
atttggcaga attccattcc ttgaagttgt gggactgagg gcccagcttt tgctggctg    213060 tcagctggag gccacaccca ggtcccagag gccatgtggg tttttgccat gagaccttct   213120
ccttcgtcca ttcacagcat ggcagcttat ttcttgaaag ccagcagggg ggatgggttt   213180
tctctggaat ctgttagatg aagtgacctc ccttcactgt cactcgtgcc atattctgct   213240
ggtgagaagc aagtcacagg cctcacctgc actcaggagg ggactcactg ggagtcgccg   213300
ccacagtgtg gctccaggaa tggaaactac cacactgcag aggtgcaggg aatccccagg   213360
attatggtca agaaagagcc cactaagtgt tttgttcagt aggcctgcag gatgaagggt   213420
gccaggagga tggctccatg aaagactgag cctatacgtg aacgtactga aagctgactt   213480
acagttcagc cagtgtggtg gtatgtgatt gacagcgccc tagcaagatg agcaacaaag   213540
atacaagact ccagcagaaa caagctgcag aagaacagga gtgtaatcaa taaatcagat   213600
ggccttgctg tgaacggtta catagctctg ataaatcctg atctaaccaa aagtcatgac   213660
agctcgatat ttgggagctg gaggggtgg ggagtagggg tagtaggata tgaaggagct    213720
aagtccccat tgttgatatt agaaatccag tgggtaacat ctgaacggca agaccaggac   213780
agcagcgaaa ggcaaaaaga caccactgag tgttgacagt ggctgccttt caggagtggg   213840
aatgccactg ggggcagggc agtgggggc agggaacagg ttttctgtt tgttttttgt     213900 ttgtttgttt gttttgtttt gagatggagt ttcactcttg ttgcccaggc tggagtgcga   213960
tggcatgatc tcggctcaca gctggagtgc gatggcgtga tctcggctca ccgcaacctc   214020
cgccccccgg attcaagcaa ttctcctgct tcagcctctc aagtagctag gattacaggc   214080
atgcaccacc acgcccagct aattttgtat tttagtaga gacggagttt caccatgttg    214140
gtcacgctgg tctcaaactc ccgacctcat gtgatctgcc cacctcggcc tcccaaagtg   214200
ctgggattac aggtgtgagc cacttcgcct ggccatggga acagtcatgt tgcatagtaa   214260
gccctaaaga gcagtgtgat ctcttaagcc agcacgtgat ttactttggt aaaaattaaa   214320
ttaaaaaaaa agaaattagg ccaggcgtgg tggctcacac ctgtaatccc aggactttgg   214380
agagccgagg taggcggttc acctaaggtc aggagttcaa gaccagcctg ccaacgtgg    214440 tgaaaccccg tctctactta aaatacaaaa aaaatagctg ggcgtggtag tgcacatcca   214500
taaatcccag ccactcggga ggctgaggca ggagaattgc ttgaacctgg gaggtggaga   214560
tttcagtgag ccgagattgc gccattgcac tccagcctgg atgacggagt gagactctgg   214620
cccaaaaaag aaaaaaataa tcctattggt ctcatagtgt ttctctgtat ttttaatata   214680
```

```
ctgtgtatgt gcttatgaga aaccgaaaga gaagtgattt gtgaacgatt tgaggacttt   214740
tggtccacgt ttttttctcc cacttatact tgtggcataa tccagaggaa gaagggcagc   214800
tgcggagtcc cagcagtgtt gcgggtatca gggcagccag tgagaggatg gaggagaaac   214860
ccaggagagg gcagaggagg agggacagct gtgcccacct ggtcctttca ttgttgtctg   214920
cctctgccct tgcagttaga aaagagtgt tctgtgtata gaagcctttg caagtagcat    214980
agttaggagt ctttcggtcc aggaattgaa ggtgctaaag caggaggaaa acatacatag   215040
aagaaaggaa atgtccacat aagtaagtgt attagtctgc tagggctgcc gtaacaaaag   215100
accatagact gggtggcttc aacaacagaa gtttatttta ttttctcaca gttctggagg   215160
cgggaagtcc aagatcaggg tgctggcagg gctggtttct gctgaggcct ctcttcttgg   215220
cttgcagaca gctgtcttcc ctgtatgtcg tcttctctgt acacaaacat ccctgtgacc   215280
tcttcctctt cttttaagga cactcagtcc tattggatta gggccccatg cttatgacct   215340 ttttggggttg ttttttgtgt ttgttttgag atggggtctt gctctgtcac ccaggatgga   215400
gtgcagtggc acgatcatgg ctccctacag cctcgacttc ctgtctccaa atgtagtcgt   215460
attgggggat taggatgtca atataggggt tttgaggga tgcagttcag tccattatat    215520
acagtaagcc acttctagac ccagtctgaa gtcctgagca ttcagctggt atctggagtg   215580
gatcacctaa gaaacattac agaacaatat aggcctctgg tatttaaaat agtttaatta   215640
cgtcacaggg tagtcctgaa ttcttttccta cttcagccag tcttggccag ccgagtttca   215700
gggtagtgat gagcactgat gaggtgactc cccttctcc aaactcttcc tttgccactg    215760
tcccaagaaa accataaagg ggaagtttaa atgatggatg taattttcct gacttgggct   215820
gggcgcagtg gctcacacct gtaattccag cactttggga ggctgcggtg cgcagatcac   215880
ctgaggtcag gagttccaga ccaggctggc caacatggtg aaacgctgcc tctactaaaa   215940
atgcaaaaaa aaaaaaaaa aaaaaaaaat agccaggcat ggtggcacac gccagtaatc    216000
ccagctactt gggaggctga ggcaggagaa ttacttgaac ctgggaggca gaggttgcag   216060
tgagctgaga tcttgccact gcaccccagc ctgggtgaca gagactgtct caaaaataat   216120
aatgatttcc ctgtcttatg ttttttctact acacagctta ttatctctgg gcaggagctt   216180
tcccagggtc ggagggggcaa gggtctagtt gtgagggaga gaggtgaaag caaaaggaa    216240 atgctaaatg acatggcaca gcaagcaagg tctaggcagc tgcgcctttg ataacaagct   216300
gcttgaagag aaagaccaga tcggctgagt gaaagcactg tccatcctcc ccacccttc    216360 cttcctgctt cctcctcttc ccatctcctc cagcttctcc ttaaagggac taccgaatga   216420
tgatttcctt gccagtagga ccttgacata aaacccagcc cacaacatca cagttgattt   216480
tcaagggatg agcttctcag aaaccagaat ttaattactt aatttgtgagt ttccaaacaa  216540 taaaatatat tattaaattg atttgttttc cacacgtagt ggagatttc atggtgtgct    216600 acctgtcggt caaacggctg atgaatgagt atgtcgcaaa aactctaggt gggaatatga   216660
cacatgagga atggaatttg tgcttcagct cttcccagca tcttcttggg ctgcacaaga   216720
gttggtagtc tttcatctcc taaggactga agggccattt agaatcacac ctgtttgag    216780 tttatagtca cgcttctgaa actttctctc ttacagcctt atctgacctc aatcaagcta   216840 ccctgttca tttaaatact ttaggtcttg gctattggtt tagcttaaca tttgattgcc    216900
ataaataaga actacagaaa gcgtgacttg taaaattgta gacccagaaa aattagggaa   216960
caatctcata atactaatga aaccttttt cccataaaat aaatacataa ttagatatag    217020
aagatttttt ttttggttta agctatcttt tcctatttct atcttaaata atttacaact   217080
```

```
ctcctttaat ccaggcaatt atcaattcta taataaaata acaacaatgg gtactgtgta 217140
ttaaactcta aactagggtc cttcatctca tttgaatttt gaaatgactc cataatatat 217200
tgttatactc atgctgtagt tatagataaa gaacgagggc tgacctttga caatcacaat 217260
caaaaaaaac aaaacaaaag aagtgaaggc tgagcgaagt aactcaccca gcaagatgca 217320
attcgtatag ggtagagtcc cctgtctccc gataatgctt tgcccacac ctgaaagtct 217380
tgatctggtt cccattaccc ctcagacttt gggtccccag tagaaccttt gcacttgcag 217440
ttctccttcc taatgggctc agggaaactc acatgactgc ctggaggctg tttctgcacc 217500
tgtagatggg aatgggcaag tctctcccga ctcacttgtc tcatagtgtt gttgaaaggc 217560
tcaggtgtga tcattacagt gaaataagga aaggcaggga agaatctcca tcgttctcca 217620
aatacgaaga atgaaatgca attttttttt ttttcttttt gagacgaagt ctcactcttg 217680
tcacccaggc tggagtgcag tggtgccatc tcggctcact gcaacctctg cctcccaggt 217740
tcaagcgatt ctcctgcctc aacctcccga gtagctgaga ttacaggcac ctgccaccat 217800
gcccagctaa tttgtgtatt tttagtagag atggagtttc accatgttgg ccaggatggt 217860
ctcgatttct tgacctcgtg atctgcccac ctcggcctct caaagtgctg ggattacagg 217920
cgtgagccac agcgcccggc cacaaataag tttatacct tgtagtcatg gcctttcttt 217980
tatctttctg gtaatgaata aaatgaagc atataagtga cagagaaacc agctacttga 218040
tcaatagtgg cattgtttca caattgtctg tattggattt tgccaaccca ctagagagtt 218100
accaaagcac atttctgaca taactatgat tgattttttt ttaattttg actaaatatg 218160
ttactttgac taaattggtt acttcattgc ataatggtga ccatttacac ttttcagata 218220
ggtacaaaaa atctgtgtat tctagctggc catgaaagag tagcaagcct gttattttta 218280
agaaaaaagc tcgagtagtt actgtatttg tatcattttg gaaatctctc attttctaa 218340
tcagcaaaat ggggataatg taaataacaa taaccctgac ctcacagggt tcttgggatt 218400
aaatgagata tggtgcatac aacgtgctta gcatggcgcc tggagtatgg tcagaactta 218460
acaaacacaa gttataaatg aggtcccgaa atacaagaaa ttcacttcct cagaaacctt 218520
ccttgagcct ggctacatct atagctacat tttctacatg ttaaatgcct ccctcagaag 218580
tgtcactgtt ggagttgcca gggcaccaat ttattacttt gaaaatagat aaataaaaga 218640
atcaagacaa aagaaaaagg tgctaccaaa gaagacattc tgtcttacac tggatcacac 218700
gagatgtgga tatttggccc ggaactgctc acatgggtca gcaagcctga gaatgaccgt 218760
ggagagaaat ggctggggct gcaggactca gccaagcctg gcacgcgtgt cttccgggca 218820
ccggagcagg acgttgtctg aaaacatgaa gaatgaaatg gaagtaatgt aatacctggg 218880
gtcggggctg ggggaagctt tctaagtaca ggcagggtct ttctatgttg cccagggtgg 218940
tcttgaactc ctggccccaa gcgatcctcc cacctcggct tcccaaagtg tggggattgc 219000
gagtgtgggc cactgtgcct ggcctaatta ctgatttaa atattaatct ttctaaaagt 219060
caaactccag aactgtgcat gtagaactat tcaatttctg tatataacta tagaaatata 219120
tattagacgg gccgggcgtg gtggctcatg cctgtaatcc cagcactttg ggaggccgag 219180
gcgggcagat cacgaggtca ggagatcgag accatcctgg ctaacacacg gtgaaacccc 219240
gtctctacta aaaatacaaa aaattagcca ggcgtggtgg cgggtgcctg tagtcccagc 219300
tactcgggag gctgaggcag gagaatcgct tgaacccggg aggtggagct tgcagtgagc 219360
cgagatcgcg ccactgcact ccagcctggg tgacagagtg agactccatc tcaaagaaaa 219420
```

```
aaaaaaaaaa atatatatat atatatatat gtatatattt atatatgtat atacacacac   219480
acacacatta gataagcaca ttgtttatat aggaatcaaa aattacctgt gagtaatttt   219540
tatttatgta atttaataat tacataaaaa ttatttgcag aggttacctc tggaagcagt   219600
attagaagtg gaggactttt ttcttctatg ttgaaaatat tttaagtaaa ttttttaaaaa  219660
cgaatagaaa tttaatcagg aacaggcttt ctaccattaa aaaactttat agtcttcttt   219720
acaaagaag  agaaataatt gtacttgttc agtcattcaa ggccactgaa ataattggca   219780
tagcttgagc tctgtagtac tgtcacaata tgcaaacaca gtgtggtaat ttttatagta   219840
attgaacatg acttacgtct tagaaagtca taagttagga atttattctg ttcgttcttt   219900
tgaagtgaaa agtaaagaaa gcaaaacatt ttttggccgg gcgcgttgtc tcacgcctgt   219960
aatcccagca ctttgggaag ccgaggcggg tggatcacct gaggtcagga gtttgagacc   220020
agcctggcca acatggcaaa accccatctc tactaaaaat tcaaaaatta cctggccatg   220080
gtggtgggtg cctgtaatcc cagctactcg ggaggctgaa gcaggagaat cacttgaggc   220140
caggaggcag aggttgcagt gagcagagat tgtgctacta cacttcagcc tgggcgacag   220200
agcgagactc tgtctcaaaa aaaaaaacaa tgactttgac ctgaatgtcc caagggtctg   220260
ctttgtgtag tctgcccctc tacaagcagg gaccaggtct tggtcacctg gtgtccttgt   220320
agtaagctct tagcagggac tgggtcctgg tcacctgggt gtcctggtag taagctctta   220380
gcagggactg ggtcctggtc acctgggtgt ccttgtagta agctcttagc aaaggttgct   220440
gagtcgaatg aacttcaccg tttcggtcct ttggtacagt aacaggcact caagagagtc   220500
cacgctgtag ggttgatcag ccaccatgag agagaagtat actctaagag cacacaccat   220560
caacccccaga gcatccctgc cgaccaggaa tgtagttaca gcggtgcagg ttcccagcta  220620
ccccaaagaa atcccaggag agtccatctc tactaagtca agcaaataga aattgcaact   220680
gtagcagcac aatctatttt cattatatag tgtgtgtctc tctctcccct catctctctc   220740
tctctctcct ttcccctcgg tcacttgaca ttgatactgg gccatttatc ctcgtgcatc   220800
atcttagagt tacatttgta taattatcaa catggccatt tgatataaac aattccgtcc   220860
ctcacatcca aagaaaaggg aagagacaga aagaaaaggc ctaatttctg agcaattttt   220920
gttgtttgtt tcccatttg  taattgtcct ccatctttac tcatctgttt ttttaaaatat  220980
taattatttt tttgagacag ggtctggctc tgttgctcag gctggagtac agtggtgcac   221040
atggcttact gtagcctcga cctcctgggc tcaagagatc ctcccacctc agcccctaa    221100
gtaactggga ccacaattgt gcaccaccac acctggctaa ttttttgttt gttttttgtag  221160
agatggggct ttgccatatt gcccaggctg gtcttgaact cctgggctca atccatcctc   221220
ctacctgagc ctctcaaagt gtcaggatta caggcgtgaa ccaccatgcc tgaccaaaaa   221280
tactttctga gggtctaata ttgccaggca ccgtgttaac aattcagaaa atactcctgc   221340
ttaataaata aagacttgaa ttttttttagt tacttcattg aaaagaaaat cttttttattt  221400
aaattgtatc gtcagccagg cgcaattgct caccccctata atcccagcac tttgggaggc   221460
cgaggcagac gaatcatttg agtcaggagt tcaagactag tctggccacc gtggtgaaac   221520
cttgtctcta ccaaaaatac aaaaattagc caggcatggc ggcgggcacc tgtaatccca   221580
gctatttggg aggctgagac aggagaattg cttgaaccca cgaggcgag  gctgcagtga    221640
gctgagatca cgctgctgca gtccagcctg ggcgacagag ccagaggcca tctcaaaaat   221700
aaataaataa ataaataaat aaataaataa ataaataaat aataaaattg tgatgtagtt   221760
aactggtata atcttttcag ttattttaa  attttttgaaa caacacgctg tatatcagcc    221820
```

```
atccatcaga gaaggaaaga aatatgtaga aggactgtct tctgcttcag atcatgaact 221880
gtaggaacaa aatagatatg tgtaaaaatg ctgctccttt tctgaaccaa aataaaatta 221940
gattttttgtt gttgtggttg ttgttggaaa aggtagtaga tttcaggcaa aatcagaaaa 222000
taaattattt cagaaacaca acaaaactaa gtacaacgat attttggtta agaaaattat 222060
ggttagaaat tatgattcta tcactttatg aaacagaatc tttaataatt tttcagctta 222120
taccaaggat attcttttat ttcttaatga ctagttttaa atatatgact attctctctg 222180
tacagatttt taattaatgc tcataaaggc tattgataga actcattctt tctccaaaat 222240
ggagttaacc cgaaatgggt agagattcag aagcttcatt gtagttaaaa ttagggtcat 222300
gaagggcaaa agcccaggta tttcagcctt tgtagaagaa tccattaatg cagcattaca 222360
agtaagtgta atttagtggc tccttagtta ttttaagcaa gaggcctcct taaagggcac 222420
acagataaag tcaacataga tctccactga ccccaggcgt gcggccagag gtcaactccc 222480
aacggctgtc tgggctcctt tttccctgca gtgctgtatg tctgggggg tgacaatcct 222540
ttgataacag ttttttttat tgggagaaaa tttgtgggaa tgcataaggt cttgctaaca 222600
taattccaca ttatgcttgc tcaacaggag aagttttagt ttaaatgtag acttattgga 222660
gatggctgta tatctgcagg tcagggagtc tcgcgtctgc agattctttg tggtttctcg 222720
tctgtcgtcg cttatcccaa ataagtagct gcacttcttg gaagagatga ttgcgtcact 222780
tgaaggggtc atgggagtct actgattgaa ctcattttc tcccatctga aagaaagaaa 222840
agttgaaaca agaggaaaga catttcacac tttctggcat ttaatatttc ggctagtttt 222900
tgtttgtttg tttctttttt gagacagatt ctctctctgt tgcccaggct ggagtgcatt 222960
ggtgcactct cggctcactg caacctctgc ctcccgagtt caaacgattc tccttcctcg 223020
gcctcccaag tagctaaaac gacgggtgct cattaccaca cccagctaat tttttttttt 223080
ttttttttgt atttgtagaa gagacagagt ttcgccatgt tggccaggct gacttcaagt 223140
gatccgcccg cctcggcctc ccaaaatgct gggattacag gcatgagcca ctgcgcccgg 223200
cctggccagg tttagatcct ggttttgtga aagaatcaga atgactagaa gattcatgtt 223260
ccgatccact gcagctaaca aatacagctc caggaaccgc acaaatcctg catcgccttt 223320
catcagcaga tagttaaagg cggagaattg ggttttcttg tttgtaaaga tagtgcgtgt 223380
aaacaagcat gcagtaaatt atgttatctg cagtagagtc ttccattggt agctttggtc 223440
agacgagctg aaatacactg ccttcagggt tcttcttggt ttgtcaccgt gagtagagat 223500
ttgaatttac actgcctcat ctgtactgaa ttctgcccct gctgtgaatc atgtcacagt 223560
ctcagaagca gcagcagcca tagagtccag tgacatcctt accagtaaga tacctttgac 223620
ctagagagtt catttcaggg gtggggcagc atcagtgtgg ctaaatgtga atattcattt 223680
cttttttctta aactataaaa tgcttgttct tttccaaatc catagctagg cacagattat 223740
agaggcatct taaaaagcct tctatagctg ggtgcagtgg ctcacgcctg taatcccagc 223800
actttgggag gctgaggcgg gtggatcact tgaggtcagg agtttgagac cagcctagcc 223860
aacatggtca aaccctgtct ctaccaaaaa tacaaaaaat tagccgggca tggtggcagg 223920
tgcctataat cccagctact cgggaggccg aagcaggaga atcgcttgaa cccgggaggt 223980
ggagattgca gtgagccgag atcgtgccac tgcactccag cctgggtgag agtgagactc 224040
tgtctcaaaa acaaaaacct cctataaatg ccatagatg ccggcaaatg ccatctcaaa 224100
atgcagttag gcaggaaaat tacctggtat gagttgtaac ctaggcaact ggaaaaaaat 224160
```

```
atgtgtccac cagttaccct tgtgtttgat gtttcaagta gtagaacagt ataagtgtgg    224220
ttttctttct ggggtctccc ccattgtatg cactcactgt agtaaccaga ggaaaatgtt    224280
accttcctgc tgggaacctt aacttccgag gctgtgatac ccatcttcat acctaaagtt    224340
ttaacatata gcaagtcccc acctacaagc aggtcttatg tcaaaagtgt agttgcagtt    224400
tattgcctgg aacccggaat ggattttccc ataggcgtgt tatgaacggc agctgtattc    224460
caggcagctg tggaagcctt tttagcccat ttatatacct gaagtgcagt catgtgcaat    224520
tagcaagaca agaaccagcc atcatccatc acaatgtttt atgtgttccc ccagcctccc    224580
cactcccact ctcagttggc ccagctaggc agggaagggg gtgttaatga ggcctgcagg    224640
tgcacagatt tactccccac ctgctgcatc tgcaggggtt aaaccggctt ttccctcccc    224700
ttcgctctca ccattccttc tctccctctc cccaccccca gtctcccttt ccctgtgctg    224760
aaggggctgg gcagtgaagt gaggaagggt ggctggagct gttggggct gaggccacat    224820
tgtgcagttc acatcagaac cccctgggga cttgctccag ttgcagattc aaatgcagca    224880
ggtctggggt gggctctgaa attccgaata tctaacaggc tcccaggtaa tgcccatgca    224940
caggcccaca ggccccattt gagtaacagg agtctctaaa caccatgcag ggaggagagg    225000
ctggtgaaga gggaaacctc gagtcacgac tgaaaggcag tggagggtga gagctgagtt    225060
ctattctcta ggccttaggg aggtcccttt tacactgaga acttttttgcc acatgggaag    225120
aagcaggcaa accctggatg ccatcaggtg ctggcacatc gcagcctcat ctcatgcaag    225180
gtgttcttgg ccagggcctg tggaggttct acatgatatg gcattaaccc tcgggagagc    225240
aggcacagta gaacctgaat gtctcctcca agcgactggg tgcagcatcg ctccatgtga    225300
ctgggtgcag catcgcccca tgcgactggg tgcagcattg ccccatgcga ctgggtgcag    225360
catcgttcca tgcgactggg tgcagcatcg ttccatgcga ctgggtgcag catcgcccca    225420
tgcgactggg tgcagcatcg ttccatgcga ctgggtgcag catcgttcca tgcgactggg    225480
tgcagcatcg ccccatgcga ctgggtgcag catcgttcca tgcgactggg tgcagcatcg    225540
ttccatgcga ctgggtacag catcgttcta tgtgactggg tgcagcatcg ccccatgtga    225600
ctgggtgcag catcgttcca tgcgactggg tgcagcatcg ttccatgcga ctgggtgcag    225660
cattgcccca tgtgactggg tgcagcatcg ttccatgcga ctgggtgcag cattgctcca    225720
tgtgactggg tgcatattgc tccatgggca tggtttgtat gaaacactca ctattaaagc    225780
acagtaggaa atgctgaaat ggaaaaggaa tgggtcatcc gggagcccca ggatctagac    225840
cctggagcag tgtttcaggg cctgaggatc cgtcaagggg gccagcatca gaagcccag    225900
cacacagggg gcttctgatg caggaggaga gtgtgcggtt tgaagatctt tcatcccaac    225960
acagcaaggc ggtgaagaac cagttttcat cctgtctcca ccactaacta gccatgtgtc    226020
cttgagctca taccctcatg cctaagtgtc ctctgtcctc atccgtaaag taaggctaaa    226080
atgagtacct acctcattag ggtgctggga agctcaatga gattatttct gtaaaaccct    226140
tagactgtcc attaagtgtc acaaaagcag tcgtaggggt ggctgtggcg tatggtagt    226200
ggtgaaatga gtaatttgag attataggcc taaagtcaaa tttctggttt tgcaacttt    226260
tactagtgtg acctgggcaa gtgacttagc ctctccaaac ctcagtttct tcccttgtaa    226320
aatgaaaata ataaagttc ctacctgcta tattattgag aggataaaat gaggaaagca    226380
cgtagcacag tgcccatcac aaagcaagct ctcagtagat atcagttact gttattgagg    226440
gagaccgggg tgacgactgg catctgaaca ggagttttcc agctgtgctc caggagctat    226500
aggttttaca aaaatgtgtc ttgggggtga gaaggaggcc attattcacc ctgcccacac    226560
```

```
ctgctgcccc cttcaacctg atgggcttgt ctttgttggc gttcagcatg aagatttat    226620
tgagaagaaa aggtttggag tttggaagat cactgttttg tagttcgggt gtgttatggg    226680
gccacaggga aggtaaatgg tctcaatttt caggaagttg acatttgcct tttctacttc    226740
atttccttaa acaaaaattg aaatatcaga tgacaaattt aaagagatat atcccatata    226800
aaacctaaag ttctatgagg ctgtattgaa cgatagagtt aatttgcatc atcagatgtt    226860
gtggccgctt tgtagcattt gctaatctgt aacgcttggt tttctccccc agatgagcac    226920
catgccagga ctgcccaccc ggccctgctt ttatgacata gatcttgata ccgaaacaga    226980
acaagttaaa ggcttgttct aagtggacaa ggctctcaca ggacccgatg caggtaggct    227040
gatgtgcttc aacttttttct ctctttgttt ttttccagtt catatccttt ttttgtcatt    227100
tttttttttct gataccacag aagtgatctg ataaatcctt tccttccttt gttactcaaa    227160
ttcctaccaa atgattttcc gtgactggag ttcactcctg ggtgtggctg tgagttacat    227220
gctcagatgc tcagtacaca acccttagtg tcctgcgctc gagtccagtg aaagccaagt    227280
tatgtcatcc ctgaatatag atgtgtttag agcatctctg accataacag aactctgtaa    227340
actcattgtt cttttccagg attaaaacca gcgtctgtta taattttaaa agagtaactt    227400
cctaccttcc tgccacgtat ctcttggtac agagctagaa tcatgtgaaa gaggaatctt    227460
ggtgtatccg tttcctgggg ctgccatgac aaagtatcgc aaactgggtg gcttaaaaca    227520
gtggaaagtt tgaaacagtt ctggaggcta aagtccaaa gtcaaggtgt cagccaggcc    227580
atacgccacc tcgagactct gggtggaatc cttgctggcc tcttcctagc atccagtggt    227640
ggctgtcact ccctggcgtt cccaccttgc agctgcgtca ctcccgtctc agcctctgtg    227700
gtcccaccac gttctccctg tgtctgtgtc ttcacatgat gttcacctct tataaggacc    227760
ccagtcctat tggattaggg cccacctaa gaacctcctt ttaacttgat tactctgcaa    227820
agaccctcct tccaaataag atcactctca gccaagcact tgggaggcc gaggtggtg     227880
gatcacgaag tcaggagttc aagaccagcc tggccaagat ggtgaaaccc cgtctctact    227940
aaaaatacga aaattagctg ggcgtgttgg tgggcacctg taatcccagc tactcgggag    228000
gctgaggcag agaattgctt gaacccggga ggcggaggtt gcagtgagct gagattgcgc    228060
cactgcactc cagcctgggc gacagagcaa gactctcctt ctaaaaaaaa aaaatcact    228120
ctcacaggtg ctcagggtta ggacttaagc atatctttta ggggacacag ttcaacccag    228180
aacactcaac tgtgtggcac aacaggtgtg ttcggctctc ttgtccctgg acagacacat    228240
agccatggga cagaccattt aactagaggg ccccatgggt tccaggaagg gcagggcagc    228300
agaaagtagg ccactgatg acttcgggtt tgcacagtct caggttgggc tttgactctg     228360
agctgtctta ggcagcccag acctggggac tctcggtctt attcatgtcc acgccacagc    228420
actgcagcca tacctgctgg cttctatcct gactccccat cgtgaagaaa aatgaccaca    228480
ttcctaaacc tcttccctgg gagacaactc ctaatcagaa gcttgaaagg ctcagggctg    228540
cttctcctac cccagggatc aaacatgtcc tcaccatatt ctaaagacac attctttccc    228600
cgcaagcacc ccgcctcctt ctccccactg actcctgttc ctgagcccag aacctctccc    228660
tcttgccagc atattctcgg cctttgcaga tgagcttttg tggcctaaag accttcttct    228720
tcaaccatct ctgagttacg gctccaagcc aggcacccag gattctcatt tcatttgttt    228780
cactaccagg agtccacttg aggacttgtt gttgttgttg ttgtttgaga cagagtctcg    228840
cgctatcacc taggctggag ttcagtggcg tgatctctgc tcactgcaac ctccgcctcc    228900
```

```
cgggttcaag caattctctt gcctcaccct cccaagtagc tgggattaca ggtgtgtgcc   228960
accacgcccc gctgattttt gtattttatt tatgtattta tttatttgcg acagagtctt   229020
actctgttgc caaggctgga gtgcagcggc actgtgtggg ctcactacaa cctctgtctc   229080
ctgggttcaa gcaattctcc tgcctcagcc tcccaagcag ttgggattac aggcgtccac   229140
caccatgccc agctagtttt tttatttta gtagagacag ggtttcacca tgttggccag   229200
gctggtctcg aactcctgac ctcaggtgat ccacccgcct cagcctccca aagtgctgag   229260
attacaggcg ggagccacca cgcccagcct aattttgta ttttaataga gatggggttt   229320
taccgtgttg gccaggctgg tctcaaactc ctgacctcaa gtgagccacc tcgtctggcc   229380
aagttttttt gttgaggctt tgttgctaaa acactaaaga cctaggctat ggtgagaaag   229440
ataagggaac cataaatgaa attacattaa acaaagtgt gaaattgttt gttttgagtt   229500
gtggatgttg tttggggggtg tttgtatgtg ttttttgctg aggagcggga gctgtgttaa   229560
gtttgagcca taactgcatc tttgatcttt gttatttcag aaaaaataaa actctagaaa   229620
atgaagtaag ggagactagt ttaacaaaga aacccataaa ctcaagtgtt gataaaatgt   229680
tgtttcatct tttggtgtga gcttgtgtgt tgccaatgtc ttccattccc cagtaaggct   229740
gtggggaaat aattgctatt tccccaattg ctagttggcc tagcaattct cttttatgt   229800 caggaaccca ttatgttaca tttctgccat ttgtcatttt tctccagaat aagtgtgttt   229860
gattctccca tctctcttgg acagtatttt tccagctttt ggtgagtttt cacatgctct   229920
ccaagtaggt catataagtc caattatacc ttaatcactg tagttaggac tcaggtccta   229980
ctcagggata catccttagc attattaatg catacccta aatcctttat tacctactcc   230040
ctaacaagaa ttcctccaga tcttatatac ggggcctgca gggcaggaca caggcctatg   230100
gtaattactt ccaatgtatc gggcattgtg ctaagcactt tgcatgggtg gtcacagcac   230160
ctctggagcc aagtgttgtc ccataagggc cacaaggctt caagaggacg gagcctaccc   230220
cttggtcact gagggggtggc cctggtctgc aaggctacag aactgccttg ccaccctgtg   230280
gcactgcctc tcatttcata gctggcacat gtcattttgc cacccccatc acatgtcatg   230340
ctggcatcaa cccagggagg tgggtagtat ttttgttgaa gagctgcaag aactctgccc   230400
agagaagtcg acaacctgct caagttgtgc agctaataac tacaaaagcc aagactcaac   230460
tcagatctgt tgactctcag tattacccca acctttatgc cccaaaccaa aggatgccct   230520
tttcatttca gtcacgggta aaatgaactt tggcccattc cgaaagatga taccagctat   230580
ttgaacagac aggtacttga ggataatgag gtaattttt ctaataagta aagataattg   230640
tttgggtatt aaaagctatg attttgtcat aattcttttt agtccaagta taatagagcc   230700
agctctttcc taattctcta atggaatggc atttctaccc cttacccacc ccccaatcca   230760
aggcctcttt cttctttgtg aattgctaaa tacagttctg ggctagtggg cagtggttca   230820
aaacccatcg tttgaccctg cttgaacaat caaaaacaga tccagtgtcc taagataaaa   230880
ccactataca aagcaaacat tccctctcag tggctcctcg gtaatgaccc agcaagtatt   230940 gtctgttcc cgtgcctctc actatagcca tcagggacca cttctactaa taatcagagg   231000
tctgcggcta ttcaaaatgc ataaaataaa aatgttaaag cttaggtgac agcttggaca   231060
aacgtgggca tctgaaagga aatgtctggc ttgctgacgt tgctccttca gggatcacac   231120
cgtagatggt gtgcataccc aggtgcggag cagcacactc attattcccc caggaaagtg   231180
ttgaaggcgc gttccactca ggaagaagat tgtgcttggt tgatgacaac tttctgtcct   231240
tcccttcctc acctttctag cctgtctcac ctcctaggaa accgtgtgaa accaaaggtg   231300
```

-continued

```
aacattatat gccaaaaaac atcagaattg gagctctcct tgctccctct tcccaagact 231360
tctctgtagt gccttcactg tggttagaat aagggcatga ctcattcttt tggatgtcac 231420
taaatagaac taattaaaat agattttttg tcccagtgaa attgatccgg ctgttgagtc 231480
ttttgtttaa agattattgg aatgaaggat ttgatacttt tccccccatt ctttttttctc 231540
acttggaaac tttatcatat ttctgagctt tggcaagatt cattcaaatg aacacacaat 231600
aaagtctggc aaatttcctg aagaattcaa ggactcccct acttctttat tgtactgtgc 231660
aaagttacgt tgagtacgga atcagattca ctccagtcct gctacaaatg tttgttattt 231720
acaaaagaat tgcttttttct tgaattacat acacagaaat aagttcagga aagaaattag 231780
tttctttcct aaactggctt tagggcatct acagacaaat ggttaaagaa aatgtggtat 231840
gtatagagag tggaatacta cttagccatt aaaaagaat gaaataatgt catttacagc 231900
agcatggatg gaagtggaag ttattatgtg aaataagctg ggcacggaaa gactaatgct 231960
gcatgttctc actctcatgt ggaagctaaa aagcttaccc tcatagacag aataaatggt 232020
agataccaga ggctgggaag gatgggtggc tgggaggagg ttatgaagaa aggttggtta 232080
tgggtacaaa catacagtta gacgaagaaa taagctctaa tgtttgatag caaactagga 232140
tgactatact cagcaacaat attttgtata cttcaaagta acaggaagag agtgggggtgt 232200
acttgaaatg ataccaacat acagtagtaa tgataaatac tcaagataat ggacacccca 232260
ggtaccctga cttgatcact acacattcca ggcacataat aaacactcat atataccca 232320
taagaatata aaatattagg ccaggtgtgg tggctcatgc ttctaatctc agcagtttgg 232380
gagtccgagt gggtggatca cttgagccca ggaattcgag accagcctgg gaaacatggc 232440
aaaaccctgt ccctactaaa aatagaaaaa ttagccaggc gtcatggcac gcacctgtaa 232500
tctcagctac tcaggaggct gaggcaggca aatctcttga acccaggagg tggaggctgc 232560
agtgagctga gatcatgcca ctgcactcta gcctgggtga cagagcaaga ctcggtctca 232620
aaaatatata taatgtatca atacaaggga aaaatgggca gaaattttca atgatattta 232680
ataaccataa attaatcttg agttgggttg ctgcctgcca gcccttctgt gaacatgatt 232740
tgttcagtcc caagtcacaa accacagggt tacaaagtac cctgggaggg tgcctgagct 232800
ctgtggtttt agtcttgaaa ctttatctttt tcacaaagca attcaaaaat tgctcatcac 232860
cattgtgttc cgagaaaagg ggcgccaagg catcaccctg agccatccga ggagtgctgt 232920
gtgccttctt ccttttctgct tccaagtagg atggaagctc cagctttata cttaaataat 232980
cctcatcaac atctaaaaga tagtgataat taaatctctc ctatctaact aaaatggaat 233040
gttttaaagc ttaggtaaca attctgaaat tcttaattcc ccccaaaaca aacttttttct 233100
gagcacattt tgatttctta ttcccatgcc agaatagact gttttgtata tggtatcttc 233160
caagatattt tccccactgag ttaacttctg aaattgcttc ttccaacgca taagcaataa 233220
acaacagatt cgttttttaca ttctcacctt agctattgca tctctgattg ttttcatcta 233280
taatgagact ttctatactt tggccagtcc ttctgttttt cttaaaatgt gggaccacag 233340
gccaggcacg gtagctcgca tctgtaatcc cagcaatttg ggaggccgag gcaggcggat 233400
cacctgaggt caggagttca agaccagcct ggccaacatg gtgaaacccc atctctacta 233460
aaaatacaaa aattagtcgg gcatggtggc gggtacctgt aatcccagct acttgggaag 233520
ctgaaccctg agaattgctt ggacccagga ggcgaaggtt gcagtgagct gatatcgcat 233580
cgctgcactc cagtgtgggc aacagagcaa gactccatct caaaaaaaaa aaaaaaagt 233640
```

```
gggaccacat actctaagca cctttagaca aaaccacagg atacaaatgt aatgtggcta  233700
atcagctggt cttccaccac ccacctctgg agcatggaag gccttgtcca gccttgcctt  233760
gccaagccaa gggtcatctc tagtccactg agcccaccct taccctagc acccctcctg  233820 tcccaagagt cattgaccct caggtcaagg gataccagag ccactacagt gaggctggcc  233880
gtgtctctga aatattttct tttttttttt ttgcccttct ctcttcctcg cgctgcctca  233940
tggaggtggc agccatctcc tcctcggcat cttggccgcc ctcagacccc ttgtgaagcc  234000
caagatcgtc aaaagagaa ccaagaagtt catccggcac cagtcagacc attatgtcaa  234060
aattaagcgt aactggtgga aacccagagg cattgacaac agggttcgta gaagattcag  234120
ggtccagatc ttgatgccca acactggtta tgggagcaac aaaaaaacaa agcacatgct  234180
gcccagtggc ttccggaagt tcctggtcca acgtcaag gagctggaag tgctgctgat  234240
gtgcaacaat cgtacttgtg ccgagatcgc tcacaatgtt tcctccaaga accgcaaagc  234300
catcgtggaa agagctgccc aactggccat cacagtcacc aacccagtg ccaggctgtg  234360 cagcgaagaa aatgagtaga cagctcgtgt gcacattttc tgtttaaata aatgtaaaaa  234420
cagccatctg gcatcttcct ttaaaaaaaa agaaaagaaa gaatatttt ctttctttc  234480 tttttttttt ttttttgag acgcagtctc gctctgtcac ccaggctgaa gtgcagtggc  234540
acgatctcgg ctcactgcaa gctccgcctc ccgggttcac gccattctcc tgcctcaacc  234600
tccagagtag ctgggactac aggcacctgc caccacgccc agctaatttt ttgtatttt  234660 tttaatagac acggggtttc accgtgttag acaggatggt cttgatctcc tgacctcgtg  234720
atccacccgt gagccaccgc gcctggcctg aaatatttta ttttgttca tctttgttgt  234780 gcttataata ctcctgtttt ctgtttattc ccctgacttg aaccagatgt taggggagta  234840
tttgaagctc ctcgttccct ctcttcatca atatcttctg tctagaaact aaccaagcac  234900
cttatctggc tccagacctc tcagtgatct gtgggaggcc aactcgcagg atttcagcag  234960
agtttgcact ttctaggcct aaaagataag tccttccatg tgtaagttca gattaaaggc  235020
aacatattgc atttacattt tagagaggtg aacacattat tttctgggac ttaagtgttg  235080
ttttgtttct tttttttttt tttaatgtag tttatttctc tttctaagag attacaggat  235140
tcaagaatgg caatgaatct taatagcctt tgggagaaag cagcaaagct ttaatactaa  235200
gttccaggac catgaacttc catgttgtcc taaatgcatt tttcaaacat tgctttctgt  235260
gcctactcta taaaacctaa aaatccaagg tgacagtatt ccttatctaa aatcctaaac  235320
aaggctgggc gtggtggttc atacctgtaa tcccagcact ttgggaggac aaggcaggcg  235380
gatcacttga gcccaggagt tcaagaccag cctggccaac gtggtgaaac ctcgtcttta  235440
ctaaaaatac aaaaattagc cgggcatggt ggtgcacact tgtaatccca gctactccgg  235500
aggctgtggc gggaggattg cttgaacccg ggagacggag gttgcagtga gccgagatct  235560
cgccactaca ctccagcctg ggcgacaaag tgagactctg tctcaaaaaa ttaaaaaaaa  235620
atttttttaa atcctaaata ttctcattcc acaggatcct gcaaactgta gatcccaaac  235680
ttggaagttc tgggaattct gccagtatcc ccaagtaaat ctcttgggaa gtttagaatg  235740
ctgcatggcg tagctgtgcc tgctcttata gagtggtgca gactctgctt ctccacgtct  235800
gctaagtaaa atattccaaa cacagatcag ccttatctag cgaaccatca ctctgctctt  235860
gaatttcctt ttggcctcaa actctagagc tataacatgt taacggttta acaccagagg  235920
agaaagctat tcttaaacta ctcaaacatg gttttttttt ctattttca gactcctgaa  235980 acagactact ctttgccttt ttgctgcagt tggagaagaa actgaatttg aaaaatgtct  236040
```

-continued

```
gttatgcaat gctggagaca tggtgaaata ggccaaagat ttcttcttcg ttcaagatga    236100
attctgttca cagtggagta tggtgttcgg caaaaggacc tccaccaaga ctgaaagaaa    236160
ctaatttatt tctgtttctg tggagtttcc attatttcta ctgcttacac tttagaatgt    236220
ttattttatg gggactaagg gattaggagt gtgaactaaa aggtaacatt ttccactctc    236280
aagttttcta ctttgtcttt gaactgaaaa taaacatgga tctagaaaac caa           236333
```

<210> SEQ ID NO 13
<211> LENGTH: 30
<212> TYPE: DNA
<213> ORGANISM: Homo sapiens
<220> FEATURE:
<221> NAME/KEY: misc_feature
<222> LOCATION: (5)..(5)
<223> OTHER INFORMATION: The number of "att" repeats starting at
      position 5 is seven, but there can be a greater number of such
      "att" repeats than seven.

<400> SEQUENCE: 13

```
gaagattatt attattatta ttattttctt                                     30
```

<210> SEQ ID NO 14
<211> LENGTH: 1987
<212> TYPE: DNA
<213> ORGANISM: Homo sapiens
<220> FEATURE:
<221> NAME/KEY: CDS
<222> LOCATION: (159)..(1442)
<220> FEATURE:
<221> NAME/KEY: misc_feature
<222> LOCATION: (259)..(259)
<223> OTHER INFORMATION: Xaa at position 259 of the amino acid
      sequence = Arg or Gln
<220> FEATURE:
<221> NAME/KEY: misc_feature
<222> LOCATION: (934)..(934)
<223> OTHER INFORMATION: n at position 934 of the nucleic
      sequence = c or g

<400> SEQUENCE: 14

```
gcagacttag ccgtgcattg caggcatgga ggattaatca gtgacaggaa gctgcgtctc    60
tcggagcggt gaccagctgt ggtcaggaga gcctcagcag ggccagcccc aggagtcttt    120
cccgattctt gctcactgct cacccacctg ctgctgcc atg agg cac ctt ggg gcc   176
                                          Met Arg His Leu Gly Ala
                                            1               5 ttc ctc ttc ctt ctg ggg gtc ctg ggg gcc ctc act gag atg tgt gaa    224
Phe Leu Phe Leu Leu Gly Val Leu Gly Ala Leu Thr Glu Met Cys Glu
            10                  15                  20 ata cca gag atg gac agc cat ctg gta gag aag ttg ggc cag cac ctc    272
Ile Pro Glu Met Asp Ser His Leu Val Glu Lys Leu Gly Gln His Leu
        25                  30                  35 tta cct tgg atg gac cgg ctt tcc ctg gag cac ttg aac ccc agc atc    320
Leu Pro Trp Met Asp Arg Leu Ser Leu Glu His Leu Asn Pro Ser Ile
    40                  45                  50 tat gtg ggc cta cgc ctc tcc agt ctg cag gct ggg acc aag gaa gac    368
Tyr Val Gly Leu Arg Leu Ser Ser Leu Gln Ala Gly Thr Lys Glu Asp
55                  60                  65                  70 ctc tac ctg cac agc ctc aag ctt ggt tac cag cag tgc ctc cta ggg    416
Leu Tyr Leu His Ser Leu Lys Leu Gly Tyr Gln Gln Cys Leu Leu Gly
                75                  80                  85 tct gcc ttc agc gag gat gac ggt gac tgc cag ggc aag cct tcc atg    464
Ser Ala Phe Ser Glu Asp Asp Gly Asp Cys Gln Gly Lys Pro Ser Met
            90                  95                 100
```

-continued

| | |
|---|---|
| ggc cag ctg gcc ctc tac ctg ctc gct ctc aga gcc aac tgt gag ttt<br>Gly Gln Leu Ala Leu Tyr Leu Leu Ala Leu Arg Ala Asn Cys Glu Phe<br>               105                    110                    115 | 512 |
| gtc agg ggc cac aag ggg gac agg ctg gtc tca cag ctc aaa tgg ttc<br>Val Arg Gly His Lys Gly Asp Arg Leu Val Ser Gln Leu Lys Trp Phe<br>120                    125                    130 | 560 |
| ctg gag gat gag aag aga gcc att ggg cat gat cac aag ggc cac ccc<br>Leu Glu Asp Glu Lys Arg Ala Ile Gly His Asp His Lys Gly His Pro<br>135                    140                    145                    150 | 608 |
| cac act agc tac tac cag tat ggc ctg ggc att ctg gcc ctg tgt ctc<br>His Thr Ser Tyr Tyr Gln Tyr Gly Leu Gly Ile Leu Ala Leu Cys Leu<br>                    155                    160                    165 | 656 |
| cac cag aag cgg gtc cat gac agc gtg gtg gac aaa ctt ctg tat gct<br>His Gln Lys Arg Val His Asp Ser Val Val Asp Lys Leu Leu Tyr Ala<br>          170                    175                    180 | 704 |
| gtg gaa cct ttc cac cag ggc cac cat tct gtg gac aca gca gcc atg<br>Val Glu Pro Phe His Gln Gly His His Ser Val Asp Thr Ala Ala Met<br>                    185                    190                    195 | 752 |
| gca ggc ttg gca ttc acc tgt ctg aag cgc tca aac ttc aac cct ggt<br>Ala Gly Leu Ala Phe Thr Cys Leu Lys Arg Ser Asn Phe Asn Pro Gly<br>200                    205                    210 | 800 |
| cgg aga caa cgg atc acc atg gcc atc aga aca gtg cga gag gag atc<br>Arg Arg Gln Arg Ile Thr Met Ala Ile Arg Thr Val Arg Glu Glu Ile<br>215                    220                    225                    230 | 848 |
| ttg aag gcc cag acc ccc gag ggc cac ttt ggg aat gtc tac agc acc<br>Leu Lys Ala Gln Thr Pro Glu Gly His Phe Gly Asn Val Tyr Ser Thr<br>                          235                    240                    245 | 896 |
| cca ttg gca tta cag ttc ctc atg act tcc ccc atg cnt ggg gca gaa<br>Pro Leu Ala Leu Gln Phe Leu Met Thr Ser Pro Met Xaa Gly Ala Glu<br>                    250                    255                    260 | 944 |
| ctg gga aca gca tgt ctc aag gcg agg gtt gct ttg ctg gcc agt ctg<br>Leu Gly Thr Ala Cys Leu Lys Ala Arg Val Ala Leu Leu Ala Ser Leu<br>          265                    270                    275 | 992 |
| cag gat gga gcc ttc cag aat gct ctc atg att tcc cag ctg ctg ccc<br>Gln Asp Gly Ala Phe Gln Asn Ala Leu Met Ile Ser Gln Leu Leu Pro<br>280                    285                    290 | 1040 |
| gtt ctg aac cac aag acc tac att gat ctg atc ttc cca gac tgt ctg<br>Val Leu Asn His Lys Thr Tyr Ile Asp Leu Ile Phe Pro Asp Cys Leu<br>295                    300                    305                    310 | 1088 |
| gca cca cga gtc atg ttg gaa cca gct gct gag acc att cct cag acc<br>Ala Pro Arg Val Met Leu Glu Pro Ala Ala Glu Thr Ile Pro Gln Thr<br>                          315                    320                    325 | 1136 |
| caa gag atc atc agt gtc acg ctg cag gtg ctt agt ctc ttg ccg ccg<br>Gln Glu Ile Ile Ser Val Thr Leu Gln Val Leu Ser Leu Leu Pro Pro<br>                    330                    335                    340 | 1184 |
| tac aga cag tcc atc tct gtt ctg gcc ggg tcc acc gtg gaa gat gtc<br>Tyr Arg Gln Ser Ile Ser Val Leu Ala Gly Ser Thr Val Glu Asp Val<br>          345                    350                    355 | 1232 |
| ctg aag aag gcc cat gag tta gga gga ttc aca tat gaa aca cag gcc<br>Leu Lys Lys Ala His Glu Leu Gly Gly Phe Thr Tyr Glu Thr Gln Ala<br>360                    365                    370 | 1280 |
| tcc ttg tca ggc ccc tac tta acc tcc gtg atg ggg aaa gcg gcc gga<br>Ser Leu Ser Gly Pro Tyr Leu Thr Ser Val Met Gly Lys Ala Ala Gly<br>375                    380                    385                    390 | 1328 |
| gaa agg gag ttc tgg cag ctt ctc cga gac ccc aac acc cca ctg ttg<br>Glu Arg Glu Phe Trp Gln Leu Leu Arg Asp Pro Asn Thr Pro Leu Leu<br>                          395                    400                    405 | 1376 |
| caa ggt att gct gac tac aga ccc aag gat gga gaa acc att gag ctg<br>Gln Gly Ile Ala Asp Tyr Arg Pro Lys Asp Gly Glu Thr Ile Glu Leu | 1424 |

-continued

```
                410         415         420
agg ctg gtt agc tgg tag ccccctgagct ccctcatccc agcagcctcg   1472
Arg Leu Val Ser Trp
        425 cacactccct aggcttctac cctccctcct gatgtccctg aacaggaac tcgcctgacc   1532 ctgctgccac ctcctgtgca ctttgagcaa tgccccctgg gatcacccca gccacaagcc   1592 cttcgagggc cctataccat ggcccacctt ggagcagaga gccaagcatc ttccctggga   1652 agtctttctg gccaagtctg gccagcctgg ccctgcaggt ctcccatgaa ggccacccca   1712 tggtctgatg ggcatgaagc atctcagact ccttggcaaa aaacggagtc cgcaggccgc   1772 aggtgttgtg aagaccactc gttctgtggt tggggtcctg caagaaggcc tcctcagccc   1832 gggggctatg gccctgaccc cagctctcca ctctgctgtt agagtggcag ctccgagctg   1892 gttgtggcac agtagctggg gagacctcag cagggctgct cagtgcctgc ctctgacaaa   1952 attaaagcat tgatggcctg tggacctgca aaaaa   1987
```

```
<210> SEQ ID NO 15
<211> LENGTH: 1284
<212> TYPE: DNA
<213> ORGANISM: Homo sapiens
<220> FEATURE:
<221> NAME/KEY: misc_feature
<222> LOCATION: (776)..(776)
<223> OTHER INFORMATION: n at position 776 of the nucleic
      sequence = c or g

<400> SEQUENCE: 15
atgaggcacc ttggggcctt cctcttcctt ctggggtcc tggggccct cactgagatg   60 tgtgaaatac cagagatgga cagccatctg gtagagaagt tgggccagca cctcttacct   120
tggatggacc ggcttttccct ggagcacttg aaccccagca tctatgtggg cctacgcctc   180
tccagtctgc aggctgggac caaggaagac ctctacctgc acagcctcaa gcttggttac   240
cagcagtgcc tcctagggtc tgccttcagc gaggatgacg gtgactgcca gggcaagcct   300
tccatgggcc agctggccct ctacctgctc gctctcagag ccaactgtga gtttgtcagg   360
ggccacaagg gggacaggct ggtctcacag ctcaaatggt tcctggagga tgagaagaga   420
gccattgggc atgatcacaa gggccacccc cacactagct actaccagta tggcctgggc   480
attctggccc tgtgtctcca ccagaagcgg gtccatgaca gcgtggtgga caaacttctg   540
tatgctgtgg aacctttcca ccagggccac cattctgtgg acacagcagc catggcaggc   600
ttggcattca cctgtctgaa gcgctcaaac ttcaaccctg gtcggagaca acggatcacc   660
atggccatca gaacagtgcg agaggagatc ttgaaggccc agacccccga gggccacttt   720
gggaatgtct acagcacccc attggcatta cagttcctca tgacttcccc catgcntggg   780
gcagaactgg gaacagcatg tctcaaggcg agggttgctt tgctggccag tctgcaggat   840
ggagccttcc agaatgctct catgatttcc cagctgctgc ccgttctgaa ccacaagacc   900
tacattgatc tgatcttccc agactgtctg gcaccacgag tcatgttgga accagctgct   960
gagaccattc ctcagaccca agagatcatc agtgtcacgc tgcaggtgct tagtctcttg   1020
ccgccgtaca gacagtccat ctctgttctg gccgggtcca ccgtggaaga tgtcctgaag   1080
aaggcccatg agttaggagg attcacatat gaaacacagg cctccttgtc aggcccctac   1140
ttaacctccg tgatggggaa agcggccgga gaaagggagt tctggcagct ctccgagac   1200 cccaacaccc cactgttgca aggtattgct gactacagac caaggatgg agaaaccatt   1260
```

```
gagctgaggc tggttagctg gtag                                          1284
```

<210> SEQ ID NO 16
<211> LENGTH: 427
<212> TYPE: PRT
<213> ORGANISM: Homo sapiens
<220> FEATURE:
<221> NAME/KEY: misc_feature
<222> LOCATION: (259)..(259)
<223> OTHER INFORMATION: Xaa at position 259 of the amino acid
      sequence = Pro or Arg

<400> SEQUENCE: 16

```
Met Arg His Leu Gly Ala Phe Leu Phe Leu Leu Gly Val Leu Gly Ala
1               5                   10                  15

Leu Thr Glu Met Cys Glu Ile Pro Glu Met Asp Ser His Leu Val Glu
            20                  25                  30

Lys Leu Gly Gln His Leu Leu Pro Trp Met Asp Arg Leu Ser Leu Glu
        35                  40                  45

His Leu Asn Pro Ser Ile Tyr Val Gly Leu Arg Leu Ser Ser Leu Gln
    50                  55                  60

Ala Gly Thr Lys Glu Asp Leu Tyr Leu His Ser Leu Lys Leu Gly Tyr
65                  70                  75                  80

Gln Gln Cys Leu Leu Gly Ser Ala Phe Ser Glu Asp Asp Gly Asp Cys
                85                  90                  95

Gln Gly Lys Pro Ser Met Gly Gln Leu Ala Leu Tyr Leu Leu Ala Leu
            100                 105                 110

Arg Ala Asn Cys Glu Phe Val Arg Gly His Lys Gly Asp Arg Leu Val
        115                 120                 125

Ser Gln Leu Lys Trp Phe Leu Glu Asp Glu Lys Arg Ala Ile Gly His
    130                 135                 140

Asp His Lys Gly His Pro His Thr Ser Tyr Tyr Gln Tyr Gly Leu Gly
145                 150                 155                 160

Ile Leu Ala Leu Cys Leu His Gln Lys Arg Val His Asp Ser Val Val
                165                 170                 175

Asp Lys Leu Leu Tyr Ala Val Glu Pro Phe His Gln Gly His His Ser
            180                 185                 190

Val Asp Thr Ala Ala Met Ala Gly Leu Ala Phe Thr Cys Leu Lys Arg
        195                 200                 205

Ser Asn Phe Asn Pro Gly Arg Arg Gln Arg Ile Thr Met Ala Ile Arg
    210                 215                 220

Thr Val Arg Glu Glu Ile Leu Lys Ala Gln Thr Pro Glu Gly His Phe
225                 230                 235                 240

Gly Asn Val Tyr Ser Thr Pro Leu Ala Leu Gln Phe Leu Met Thr Ser
                245                 250                 255

Pro Met Xaa Gly Ala Glu Leu Gly Thr Ala Cys Leu Lys Ala Arg Val
            260                 265                 270

Ala Leu Leu Ala Ser Leu Gln Asp Gly Ala Phe Gln Asn Ala Leu Met
        275                 280                 285

Ile Ser Gln Leu Leu Pro Val Leu Asn His Lys Thr Tyr Ile Asp Leu
    290                 295                 300

Ile Phe Pro Asp Cys Leu Ala Pro Arg Val Met Leu Glu Pro Ala Ala
305                 310                 315                 320

Glu Thr Ile Pro Gln Thr Gln Glu Ile Ile Ser Val Thr Leu Gln Val
                325                 330                 335

Leu Ser Leu Leu Pro Pro Tyr Arg Gln Ser Ile Ser Val Leu Ala Gly
```

```
                    340                 345                 350
Ser Thr Val Glu Asp Val Leu Lys Lys Ala His Glu Leu Gly Phe
        355                 360                 365

Thr Tyr Glu Thr Gln Ala Ser Leu Ser Gly Pro Tyr Leu Thr Ser Val
370                 375                 380

Met Gly Lys Ala Ala Gly Glu Arg Glu Phe Trp Gln Leu Leu Arg Asp
385                 390                 395                 400

Pro Asn Thr Pro Leu Leu Gln Gly Ile Ala Asp Tyr Arg Pro Lys Asp
                405                 410                 415

Gly Glu Thr Ile Glu Leu Arg Leu Val Ser Trp
                420                 425

<210> SEQ ID NO 17
<211> LENGTH: 30
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n at position 16 of the nucleic
      sequence = c or g

<400> SEQUENCE: 17
tgacttcccc catgcntggg gcagaactgg                                      30

<210> SEQ ID NO 18
<211> LENGTH: 19887
<212> TYPE: DNA
<213> ORGANISM: Homo sapiens
<220> FEATURE:
<221> NAME/KEY: misc_feature
<222> LOCATION: (8450)..(8450)
<223> OTHER INFORMATION: n at position 8450 of the nucleic
      sequence = c or g

<400> SEQUENCE: 18
gcagacttag ccgtgcattg caggcatgga ggattaatca gtgacaggaa gctgcgtctc       60
tcggagcggt gaccagctgt ggtcaggaga gcctcagcag ggccagcccc aggagtcttt      120
cccgattctt gctcactgct cacccacctg ctgctgccat gaggcacctt ggggccttcc      180
tcttccttct gggggtcctg ggggccctca ctgagatgtg tggtgagtaa ctcgcctcta      240
tcctgtgcct ctttcctcct gggtccttag tggggtggct agggcatagg atgagggaac      300
ttacctgccc ttctaagctc ccatagcagt ttgggcttag ctggacctca gcatttaaca      360
catcctattg tgattgatta tatgtttgac tcctcaccag acaagatctc cgttaattca      420
gtcattcgtt cacacattca ttcagcgcat actgagcctt ttctgtgtca ggcccagtgt      480
tagcctttgg ggaacgtgca aagcatgaga caagtctaat ccctgccatc ctagagctta      540
tgttctaggg aaggggggaca gacaaaagaa atggttaggt gctcccacct gaaatctcag     600
cattttggaa ggctgaggcg ggaggggagg atcgcttgag ctcaacagtt caaggtcagc      660
ctgggcaaca tagggagacc ccatctctac aaaaaataaa aaaaattaaa aaatagctgg      720 gcatgggggaa gactttctga agaccaagag gacacatggg agctgaaact cgaaggaaga    780
aaaggagctg gcaggaaagg agtgggggac acacattcta ggcagcagga agtgagcctt      840
cggaggtcct gcctgctcca gctctgtgcc ccaagggggtc tcttggagca cagtctcctg    900
ggacctgtct atgagtctga gcttagaggc tcagggctgc tccttcagac aggaggcaga      960
aggcaggctt tgggaacttt gggccgccca cgcgcctttt ctcctcctct gcacctagga     1020
```

```
ttacgttgag caatacactt tcaccccat ggtctcttga gaccctgggg aaaccctgag   1080
aggtgggtgc agtcatgtcc aggtgtcaag tgaagaagtc gagggttgga ggggctgagt   1140
gacccactca gggtgctcca ccttttccag agctttgctg aacttagttt ttagaacttg   1200
aagcctcgtt tgttttcgtt ttgttttttg ttgagagagg ttctccctct gttgcccagg   1260
ctggagtgca gtggcacgat cttggctcac tgcagcctct gccttgtggg ttcaagtgat   1320 tccccacct cagcctccca gtagctgga gactgcatgt gcatactacc atgcttggct    1380 aattttgta ttttttgta gagacagggt ttcgccatgt tgcccaggct ggtctcgaac    1440
tcctgggctc aagtgaaact cttgcgtcgg cctcccaaat tgctgagatt acaggcgtga   1500
gccaccgtgc ccggccagaa ctccaagcct ctcatctgtg ttccataaat gcaatcagac   1560
acctcaggtc tgggcccagg aaccccagct cttggttcat gtccggacag tccccagggg   1620
agttctgggt tcaaccagca agagctcttc ctcctggctg atctggtcct cagccttgga   1680 cagtagtcc attaacctga ccccacagga gccccaatcc cttggggtct ggggaatctt   1740
gaactggggt ttggggtgca atatctgca ctgagtcact taattgcacc cagcctcatt    1800
cctttatctg taaagtgggc taagaatgct ccctgcctt cctcctcggt gtagtacaag    1860
gaaggatccc atgacacctg ctctcccagt ttaaagctct atatgtatgt tgtgaaattg   1920
acagggatcc tgcacaaac gctaatgcaa agtgggctcc tgtgcttcct tttctctttc    1980 ttcttcttt tttttttttt aattttcttc tagagatgag gtctcactat attgcccagg    2040
gttggtttca aactcctagg gtcaagcgat cctcccacct tggcctccca aactgctggt   2100
attacaggcg tgagccactc tgtctggctc ctgtgcttgt gaatgtcaac agcaatcagc   2160
ccttagctgg cagggctggg ttggtagggc gagagctcac ccaaggctgc ttttattacc   2220
ctgcgtgaat ctgcctggcc ccttccttct aaggaggttg ctctgtggtt gtcagtctct   2280 cccttttacag ctggatcctg atctttcagt ttctaaccct gtgctgactc atcgtgctgg   2340
aagtgagagc ccggggtgag gtcagggaac tcccttgcgc gtttcaagaa aagggaaaag   2400
gaaagagagg tgaggagggg ggcagatgac cagagagaca caggctgaga gagactgaga   2460
cagacccaga gagcctcaca cattgagtga cagagacgga gaaatggaga taggcaccaa   2520
aaaatggttc tcagtgacag aaagggaaaa agcaaccccc ccagtctctc ttaacatctg   2580
gtgagaaacc agccatgtgc tttggtctgg gcccacacag caaaggatta tgtagggttt   2640
catgctggtg gatggtcacc ttatagcaac aggtatctgg ggctgtcggg aaaacagaca   2700
cgaggttgtg ggacccagac ccacagagat ggagctgttc taggagctct ggtcctcgtt   2760
ctggtcccct gggatatggc acagtgaagg ccaccatcag gcagctggag cccagcagca   2820
actgggaggc agtaaacagg gaccgaaagt gcaaggttac ctccgaggca aactactcta   2880
agctaccctg tgctgagctc aagtcccttg gaactatccc taaggcttcc gcttccagag   2940
tgtttgagta ttttcgttgc acagcttcga ataaatccca cagcaacagg taaacggctg   3000
caagctgtga ctgttttcta agagctcatc tcacaatctc aggtcctctt catttaaaca   3060
gagatggcag gaaaggcgtt attttgagat ctgcatggag gaagttcacc aggcagcctc   3120
aattcaccag ctggaagttt gcgttgtttg gaaatttgat gtgtaacacg ttctgcatgt   3180
gggctgatgt ttttgtaaac gggtagcaca cacattcagc agggcaccaa agagcggggg   3240 cttttgcagtt aggtccatcc ttggctctgc agccttgtgt aagacatgac acgactttga   3300
acttctgttt cctcttctgt gcaaagcaat gatgacagta tctacatcac aggactggca   3360
tgaggaccaa gtgagattgg gcaaggtgcc cgggcacacc agtctcactg tcactgctga   3420
```

```
tgggcagagt ggttgcctgg cagtagcatc ctctatcttc agcccaccac ctctcttgct   3480
ggctcactcc aactgctctt tagagataca cgcttccect cttttctcct cccactgcct   3540
ttcagtatgg ctgcatttcc ccctgcaagt tggtgtgtgc tgggtggagg tgggggtgag   3600
gacatgtatt ctctggagaa ggccctggta acgtcaaagc acttctttgc tggtggcctg   3660
gccctgtgac ctcatttgta ccattttctt ttctaagaaa taccagagat ggacagccat   3720
ctggtagaga agttgggcca gcacctctta ccttggatgg accggctttc cctggagcac   3780 ttgaaccca gcatctatgt gggcctacgc ctctccagtc tgcaggctgg gaccaaggaa   3840
gacctctacc tgcacagcct caagcttggt taccagcagt gcctcctagg gtattgccac   3900
actctctttt tccatgtctt gctccacata ctaagagatg ggaaacttgg gtactagttt   3960
gggcctgtca ccactttgtg ggcagacctt aggcaaattt tctccatcta tagaatggag   4020
gacctttgtc catctataga atgaaggggt tggttggatt agatcagaga tgctaatgca   4080
aggctccttt tgctactact gtccatcatg tgtctgaggc agacataact aatccgtgac   4140
tatactcttt gatgatgagc ccaggagcag catctgactc tatgctccct tagtgtgcct   4200
gaggcagata tcactaatcg atgactgcag tcttctacat tgagcttaga agcagcatct   4260
gactctgtat gctcccctcc catgcatgag gcagacatca gtaatccatg accgcattct   4320
ttcatactga gcccagaagc agcatctttt cttttcttc ctctcactct gttgcccagg   4380
ctagagtgca gtggcacaat cttggcttgc cccaacctcc aattcccggg ttcaagtgat   4440
tctcgtgcct cagccacctg aatagctggg attacaggcg tgtgccacca tgcccagctg   4500 attttttgtat ttttggtaga gatagggttt caccatgttg gccaggctgg tcttgaactc   4560
ctgacctcag gtgatccgcc tgtcttggct tcccaaagtg ttgggattat aggcatgagc   4620
cactgcacca atccaaaagc agcatctttg tgctcccttt tcaagaggca tcacagagag   4680
gcctgttttg gggtttgaat gagaggcgaa gaatcagcca tggagtgcct ctttctcaga   4740
ctccctcttg agaagtggat gcaggggtgg agagaaaaga agactaggca tagtggctca   4800
tacctgtaat cccaacattt tgggaggctg aggcaggaag attgcttgag ctcaggagtt   4860
tgagaccagc ctaggcaaca tagtgagacc acatctctta aaaaaagaa aaagaaaaaa   4920 aatgagccag gtgtagtgac tcatgcctgt ggtccccact tctccggagg caaaggtggg   4980
aggatctttt gaggctgaga atcgaggct acagtgagcc atggtggcac cactgcactc   5040
cagcctggga gacagagaga ccctatctca gtaaaaaaaa aaaataaaaa tatggctggg   5100
tgtggtggct cacgcctgta atcccagcac tttgggaggc caaggtaggt agatcacatg   5160
aggttaggag ttcgaaacca gtctggccaa catagtgaaa ccctgtctct actgaaaata   5220
caaaaaatta gccaagggtg gtggtgggca actgtaatcc cagctacttg ggaggccgag   5280
gcagaagaat cgcttgaact cgggaggcgg aggttgcagt gagctgagaa catgccactg   5340
cactccagcc tgggcaacaa gagcgaaact ctgtctcaaa gaaataaat aaataaaata   5400 aaaaataaa aaaggagggg gcatatgggt gaagtatgga caaatagtg gggcaggcac   5460 agatgatctg gacacaggag cccttggagt ttattcttga atctaactgt tcatctttat   5520
taaatatttg tggcatacac ctcacaacaa catagccaac acacctcctt ttggagcttt   5580
tatcaaagtt tcccactgtt aagattttt cccgctttgt gatgcgggtg gggtgggtgc   5640
tgtaagcagg cttacggggt ggcagttct cacaaaggca ttaactggcc ttgtcctagg   5700
tctgccttca gcgaggatga cggtgactgc cagggcaagc cttccatggg ccagctggcc   5760
```

```
ctctacctgc tcgctctcag agccaactgt gagtttgtca gggccacaa ggggacagg    5820 ctggtctcac agctcaaatg gttcctggag gatgagaaga gagccattgg tgagcagaca   5880
ccatccgctg ggggtgggga gcagctggga gggctcatca gatgatattc tccaatgaga   5940
atcagaactt tgggttttct ccccaggcgt ctttcccacc atccattctg cccatctcac   6000
tgcctacgta gaggctcgaa cctgtcccca tagccatcct tgacccagct tttcccgcgc   6060
tgcacacata ctattgacag gtgtgtttcg tggttttttg ttttttgttt gtttgtttgt   6120
tttgagttgg aggtttgctc ttgctgccca ggctggagta caatggcgca atctcagctc   6180
accgcaatct ctgcctcctg ggttcaagca attctcctgc ctcagcctcc tgagtagctg   6240
ggattacagg catgcgccac cacacccagc taattttgta tttttagtag acgtggggtt   6300
tctccatgtt ggtcaggctg gtctcgaact cctgacctca ggtgatccgc ttgccttagc   6360
ctccgaaagt gctgggatta caggcatgag ccactgcgtt aggcccactg acaagccttg   6420
tattggctag ccaccaagat tgacttgatt atccaccttc gggacaactg gacagcctgc   6480
ttatgactta cgccatagtc tgtctctact agctctcctg ccctgacttg acccagcata   6540
caacagccag agccagcctt ttcaatataa acctgatctt gctggcactg cttaaaccct   6600 gcagggcct cgcactgctc catggcccag cctgtctacc cttaccttct gcccaggctg    6660
tgctcatcca ttctctgcct cccacacacc tgccctctgt gggctccagc cataccatct   6720
ctcaactcat aagccagttt tttcatacag gctccctcca tctggactgg cttccctgcg   6780
tgcagttcac tcctgctcta cctttggctc tgcctccacc catcctcagc cgtctccagc   6840
attacctcct tggagaatcc tgccttgact tcccagccac ccaaatatca ctacttggtc   6900
tgcattctcg ttgcaattgc agtcgcatga gcaattgctg tggttgaggc ccgaactgcg   6960
cagtgcctgt ctgccatggg tctcctgctt cctctaagca cagtgcctga cacacagtga   7020
gacctcagca cgtatgggct gaggcaatga aggaatgaag gatccatga  cccaaaagag   7080 cgtgttggaa agtgcaggcc agggtcccag gtgctggcgg ggctggctgc tgggtggggg   7140
cagagaggca acccctctgt ttttttccct ctcagggcat gatcacaagg gccacccca    7200 cactagctac taccagtatg gcctgggcat tctggccctg tgtctccacc agaagcgggt   7260
ccatgacagc gtggtggaca aacttctgta tgctgtggaa cctttccacc agggccacca   7320
ttctgtgggt gagtaggtca gaccgtgcca aggccaggct ggcactccct cagtcccag    7380 gtctgcactg atgacctcca taccctggcc cccacactca cctttccttg gggctcctcc   7440
gaatcaagtc ctttagggac gaattggcga gggctcatgg gtgatgcttc agctgtgagc   7500
cagctttgga gctggtaggt ggatctcttg aggccaggag ttcaagacaa cgtggtgaaa   7560
ccccatctct actaaaaata aaaagttag  ccgggcatgg tggcacatgc ctgtagtccc   7620
agctactcgg gaggctgagg caggagaatc acttgaacct gggaggcgga ggctgcagtg   7680
agtggagatc gcaccactgc cctccagcct gggcaacaga gtgagtgaga ctctgtctca   7740
aaaaataaaa aataaaataa aactcccct  agtgattccaa tgtgcagcta agtttggaaa   7800
taggtggtat ggggtcaagt cctcttgggc ctccctcctc cagtccttct ccctaacctc   7860
tagccctcaa gttgcagagt gatcagccaa accagtttgc ccagaaatga gcagtttcct   7920
gggacacagg atttttcagag tccagacaag gaaagtcttg gcagaccag  gttgagttgg   7980 tgcccttagc tgatctgacc atgttgccct tcttctccaa gccctcctgt ggttgtccat   8040
agctacaagg gcctgaccct caagcccctg cctgtcctgg cccctttggc tctccagctc   8100
attgcatgtt ctgtccccca cttcaagaca cagcagccat ggcaggcttg gcattcacct   8160
```

```
gtctgaagcg ctcaaacttc aaccctggtc ggagacaacg gatcaccatg gccatcagaa    8220
cagtgcgaga ggagatcttg aaggcccaga cccccgaggg ccactttggg aatgtctaca    8280
gcaccccatt ggcattacag gtgggaaaga gaccctggag ccatggccac cctggggaac    8340
agtcaggggt ggagtggtca ggtgctggaa cacctagccc ctccctgccg gctgacttcc    8400
tctctctctt cctcactcta tcaccagttc ctcatgactt cccccatgcn tgggcagaa     8460 ctgggaacag catgtctcaa ggcgagggtt gctttgctgg ccagtctgca ggatggagcc    8520
ttccagaatc tctcatgat ttcccagctg ctgcccgttc tgaaccacaa gacctacatt     8580
gatctgatct tcccagactg tctggcacca cgaggtagcc caactttttg tggaagcaca    8640 gcccttaca atctgctgcg cacccattga cgtcccagtg aggggaggtt gcttcatcct     8700
gatttgctga gtcagcacaa gattgtgggt gtgcatggga cacagcagcc aaaatgtggt    8760
catagcttct agaagctcac agtgtgggga ggaagacagt aaatggagat ccctgggcat    8820
atcgcttgtg tgatacccag tacagaaatg tttggatgga tggatggatg gatggatgga    8880
tggatggatg gatggatgga tgaggagaga cacattttgg ttaactctaa tacaacatga    8940
taagccccag tagcagcatg atccaggctt tctctgagag agggtctgag gacgtgactg    9000
ggatttgcca attaagaatg gagaaagagg ccaggtgcag tgactcatgc ctgtaatccc    9060
aacactttgg gaggccgagg cgggtggctc acctgaggtc aggagttcga gaccagcctg    9120
gctaacatgg cgaaactcca tctattaaaa atacaaaaaa gtagctgggt gtggtggcga    9180
gtgcctgtaa cccagctaa gctactcagg aggctgaggc aagagaatca cttgaacctc     9240
agaggtggag gttgcagtga gccaagatca tgccactgca ctccagtctg ggtgacagag    9300
taagactatg tctcaaaaaa aaaaaaaaaa aatgagaag aaggaagctg acatggtgg      9360 ctcgtgctta taatcctagc actctgggaa gctgaggcag atggattgcc tgagcccagg    9420
agtttgagac cagcctgggc aacatggtga accctgtct ttactaaaat acgaaagatt     9480
agccaggcat ggtggtagac acctataatc ccagctacta gggaggctga gccacaagaa    9540
tcacttgaac ctgggagaca gaggttgcag tgagccgaga tcgcgccatt gcacttcagc    9600
ctgggcgaca gtgtgagact ctgtctccag aaaaaacaag aatggataga gtggagccaa    9660
gaagaggcag gaagaacaaa gacacagagg tgcacagagt ttgggggaat tttgaggaat    9720
ggtcttgcaa aagagtggga tctgggagaa tgagtgggag tggaaagcag atgaatgaag    9780
agaaggtgag cgcatcaggg taacagagat gcgttgtgaa caaatgcatg ttctaggaag    9840
agccctctgg agtgctaggt gccagagagg tgggaggaag gatactggaa gcagagaaac    9900
cagtgagggg cctgatcttg ggtggtgggg aatgagggac aggggaggcc gggatggaag    9960
ccaggtggtg gggaatgagg gacaggggag gccgggatgg aagccaggtt tcagctgagc   10020
aggtggcggt ggcattgatg gagatgagga catgggaag acaaagtcc aggtgtcctt     10080 gagggaagac aagaagacaa ataatccagg ctctctgtcc tcacaccagc tgcccgcccc   10140
tttcttcctg gcacagtcat gttggaacca gctgctgaga ccattcctca gacccaagag   10200
atcatcagtg tcacgctgca ggtgcttagt ctcttgccgc cgtacagaca gtccatctct   10260
gttctggccg ggtccaccgt ggaagatgtc ctgaagaagg cccatgagtt aggaggattc   10320
acgtgagact cccacctccc agtcctcacc ccacccaacc tcacatgcct gataacaggg   10380
tcacagaaga gacggggaac agaggagagg gttccctcgg gagagacact ggccctgctt   10440
ctgcttctac ctgctcagct cctttcttgc ccacggtgtt atggaaacag ggagccatag   10500
```

```
gccagcattg tcactgagag agcaggcttt ggaggcagag ccccccagtt ggaatcccaa   10560
ctctaaccag ctaggttcca ggtaggcacc cacaattcac cgaggagaac agttgtgccc   10620
cttccctgca gggccagtgt gaagagtcca ggagttagta cacatagaga tagtggcatg   10680 tgcttttat atgtgcaagg tccagcacat agcaagcgct caacacagcg ttgctttcat   10740
cagagtaaga actgtttttt gtttgtttgt tgtttgttt ttaagagaca gggtctcaat   10800
cttatcaccc aggctggagt gtaattgtgc aatcacgtct cactgcagtc tcgaactctg   10860
gggatgaagc aaccctactg tcctgcctca gcctcccaaa tagctgagac tataggcacg   10920
tgccacacaa ccctgggtaa ttttttttt ttttttttt gagatagggt ctctgtctgt   10980
tgcccaggct ggtctcaaat tcctggcctc aaaccatcct cacacctgag gcgctcaaaa   11040
tattgggatt ataggtgcga gccatcatgc tcagccagaa taataactgg ttttttttgt   11100 tttttttt gagacagagt ctcactctat acccaggct ctggaggccc aactcgtgtt   11160
tgtgtatttg tttatttta tttatttatt tatttcgaga cagagcctct ctctttcacc   11220
taggctggag tgcagtggcg caatctcggc tcactgcaac ctccgtctcc tgggttcaag   11280
tgattgtcct gcctcagcct cctgagtagc tggcgctaca ggcgcgtgcc accatgccca   11340 gctaatttt gtattttag tagagacagg gttttactat gttggccagc tggtttctaa   11400
ctcctgaact cgggtgatct gcctgcctcg gcctcccaaa gtgctgggat tacaggcatg   11460
ggcctccgtg cccggccatg tatttattta ggcaaggtct ctctctgtta tccaggctga   11520
agtgcagtgg cacattcata gctcactgca gcctcaaatt atccaagtaa cagggactac   11580
aggcatgcac caccaccc atctactttt ttttgagatg gagtctccct ctgtcgccca   11640
gactgggttg cagtggcaca atttcagctc atggcagcat ctacctccca ggttcaagcg   11700
attctccttc ctcagtctcc cgagtagctg ggactatggg catgcaccac catacctggc   11760
taatgtttat atttgagta gagatggaat tttgccattt tggccaggct ggtcttgagc   11820
tcttgacctc aagtgatatg tctgcctcag cctcccaaag tgccgggatt acaggcatga   11880
gccactatgc ctggcccaga ataagaactt ttatttatt tgagacaggg tcttactctg   11940
tcacctaggc tagagtgcag tggcacaatc acagctcact gtagcctcaa tcttccgggc   12000
tctgatcctc ccaccttagc ctcccaggta gctgggaaca acaggcatgc gccaccacgc   12060
ttggcaaata tttttaaa atttttgta gacatgggat tgcttcatgt tgcccagact   12120
ggtctcaaac tcctggactc aagcgatcta cccaccttgg cctcccaaag tgctgagata   12180
acaggcgtga gccgccgtgg ctggccagaa taagaacttt tattatgaaa taagtttggc   12240
cctatcctgt tattaattac ctcaaagagg ttggacaatg tccttacact tgcttctcac   12300
cctgagctta gaatagtttg agaatgagca tgtctggact gttgtttgac aggtcctgtc   12360
catgatgaaa taagatgaat gtaattctca tgttatcagt ggggagtcca gcccagagaa   12420
gttgaatgcc ttccaccagg tcacgcacac cacagacttc tcccctagaa tcatgggcct   12480
atctctgtcc ccagtgggag ttcctggaaa acagcatcct gcatccaggg agggcccaca   12540
gttggttcct tcgggtcctc taggctagag aatctcagac cggagaaatg caaagactcc   12600
tctgaagtac aaacattctc ccagacccca ggttaagtta tttcttctat aatatcactt   12660
agatgtgtac tgataatttt attaaatata aagtctttgg ccagctggtg gctcactc    12720 ctgtaattcc agtgatttgg gaggctgagg caggaggatc acttgagcct aggagtttga   12780
gaccagcctg gcaacatag tgagactgcc atctcttcaa aaaaatttt ttaattagct   12840 gggcatgatg gtgtgcacct ataatcctag ctacccagaa ggctgaggtg gaggactgc    12900
```

```
ttgagcccag gagttcaagg cggcagcaag ctatgatgac gtcactgtcc tgtagcctgg    12960
atgacaaaac tttttttttt tttttaaaag acaaagggct gagtgtgatg gctaacacct    13020
gtaatcccag cactttggga ggccaaggtg ggcagattac ttgaggccag gagttcaaaa    13080
ccagccgggc aacgtggcg  aaagcccgtc tctaccacac acaaaaaaag tcctttctct    13140
ttctagctct agacagctat aaatccccaa caactttata aattaaatag aaagtataa     13200 aaaccaatac cattcaaata aggatgctct gcggaggtgc tggcctgcac tttagcacct    13260
ccctgtattc aagctgcagt gaagcctggg cactcctggc ctggctcagc cacttcattc    13320
actatgaggg ccacctccgt ttccttcctg tggcctatgg cacataacgc aatgctgctg    13380
ggcaccagcg cagtcactga tggccacgca taggctgagt gcccttggga gggctcagac    13440
ccacagactg agattaccca gaaccagctg gtattcatgt ttgaatattg tcatcaaaat    13500
gaaagacaat tagaatttaa cgttttttatt cagagctcgg ggatctctgg gaagacactg    13560
tggactccag tctgagaaat ggttctcttg ttagtgtgca tggatgcctc aactgggttc    13620
aggcatgaag actatgtttg aggcccctga atgcacagca gagaaagctc aactgcagac    13680
acagatagac agatgtggag agaggtagcc ctgtgcagcc acatggccct gcagagttaa    13740
ggaatgggaa aagggctact ctgtgacatt ccttagaaca gtagtttccc ttcgctaaag    13800
tcaccccaaa tagggtggtg gttgttgttg ttgttttgag acggagttgc attcagtcgc    13860
ccaggctgga gtgcagtggc acgatctcgg ctcactgcaa cctccacctc ctgggttcaa    13920
gcgattctcc tgcctcagcc tcctgagcag ctgggattac aggggcccac catcacacct    13980
ggctagtttt tgtattttta gtagaaatag ggtttcacca tgtgagccag gctggtgtca    14040
aactcccaac ctcaggtgat ccacccacct ccgcctcctc aagtgctggg attacagatg    14100
tgacccaccg cgccccacct gtgtttctta aaaccaaaaa aatccctcta agactgcaac    14160
catcgataac ttagggctgt attacccccag agagcacttt gtagaagatg cgtttgttca    14220
catcacttcc ctgttacttt gacggtctca cctccttttc agtcatttgc attctcccag    14280
aacctgctca tttgttgttt tttgtttgtt tgcttggttt tgttttttgag aagcagtctt    14340 gctctgttac ccaggctgga gtgcagtggt gcgacctcag gtcactgcaa cctccgccta    14400
ctaggttcaa gtgattctcc tgcctcagtc tcctgaatag ctgggattac aggtgtgcac    14460
caccatgccc agcctaattt ttgtattatt agtagagatg gggtttcacc atgttgtcca    14520
ggctggtcat gaactcctga cctcaagtga tccaccgct  ttggcctccc aaagtgctgg    14580
gattacaagc atgagccaca gtgcctggcc tgaccctgct cttttgaaag accattcccc    14640
caaattctgt gcacctgtgt gcctttcttc tctctgcctc ctctcagctc tgccccgctc    14700
tcctcccttc tcctctggca aatcccactc atctcttgaa gcccttcttc caggggaagc    14760
cctgatcatg ctgctttctc ctgtgggagg gatgaaggac gtggcccacg gagtttgttt    14820
tgttttgttt tgagatggag ttttgctcat gttgcccagg ctggggtaca atggtacgat    14880
ctcagctcac tgcaacctct acgtcccggg ttcaagcggt tctcctgcct tagcctcccc    14940
agtagctggg attactggca tgaaccacca cacctggcta attttgtgtt tttagtagag    15000
atggggtttc ttcatgttgg tcaggctggt ctcgaactcc caacctcagg tgatctgcct    15060
gccttggcct cccaaagtac tgggattaca gggttgagcc actgtgcctg gcccaggccc    15120
acggagtttt aagaggcttc ctgtggcagt ggcatccaga cggagtgcag aaactcaaag    15180
ttgaaggcca gaagctcagg gaaggggag  tgtgagttga ggagtctctt ggctgccagg    15240
```

```
gccagaaacc gaactccaag cctctccaca acagcgggtg tagagcatgt agaatcagag    15300
aggaggctga gccatgcagc cccgagaaga ggggaatgcc actgagccac agagacccag    15360
tgccactgcc aggtgtctct gcctccactt cccatgaccc tgcctgtctc tgtatgcagg    15420
cttcaccctc tctcgttgta cattgtacac attctaggtg acaccagcag cttctgattc    15480
tcatccccca taacatcagc cccccagaga ggggacaact gctgagctga taacataata    15540
gatgcccctt tcctggaggc catggtcatg gtcagcgtgg agaggatgaa gcctgagcag    15600
gcaggatcgg gggtctggag gggaaggagg tggaagttga gatcacagac ctgtggccag    15660
gtggcctggg aagggtttga cgagtgtcgg cccaaagagc ttggaaggga ttttgctgct    15720
gtgggtgagc actgcctctc cccttaggga caacagccac ctcttctctc cccatttgcc    15780
tttcccttct gtagatatga aacacaggcc tccttgtcag gcccctactt aacctccgtg    15840
atggggaaag cggccggaga aagggagttc tggcagcttc tccgagaccc caacacccca    15900
ctgttgcaag gtgagtcatg gcctgacact ctggatgtgt cccctacccc aagcttactc    15960
agccaagagg cttcatcaac tcaccccagc tttccctagc accctcctgg ccacaccctt    16020
cacaaaatca ctgatgctca aagttggata taatatattg aactgaagcc ttagaatttt    16080
tatgcaagtt actgtggaaa ttctaggaaa ccagacagat tacaaaaaaa aaaaaaaact    16140
agaagaaaat taacatcacc taggatatac tacctaggaa taacgtcttt tattttgaga    16200
tggagtttcg ctcttgttgc ccaggctgga gtgcagcggt atgatctcgg ctcgctgcaa    16260
cctccgcctc ctgggttcat gtgattcttc cacctcagcc ttcctagagc caagtggtc     16320 tgcctgcctc tgcctcccaa agttctggga ttacaggcat gagccaccgc acccagccaa    16380
aattacttaa cttttcttct agatactttt taaaaatatg gcagtaagtt tttcataaaa    16440
aatggagcca tgctatccag tggaaattta atgttgccca catgtataac ttaaaaattt    16500
catatatgtg tatacatata tatgaaatat atatatatac agacacacat atatatgtat    16560
acatatatat acacacatat atatgtatat atatatacac acatatatat gtatacatat    16620
atacacacat acacatatat acacacacat acacacacat atacacacac atacatacac    16680
atacatacac acatatatac acacatatat acacacatat atatgtatac atatatatac    16740
acacatatat atgtatacat atatacacac acacatatgt atacatatat acacacacat    16800
atatatgtat acatatatac acacatatat atgtatacat atatacacac atatatatgt    16860
atacatatat acacacacac acacacacat atatatatat atatatattt tttttttttg    16920
agatggagtc ttgctctgtt gcccaggccg gagtacaatg gcgaggtctc agctcactgc    16980
agcctctgcc ttctgagctc aagcaattct cctgcctcag cctcccaagt agctgggatt    17040
acaggtgtgt gccaccatgc ccagttattt ttgtattttt agtagagacg gggtttcacc    17100
atgttggcca ggctggtctc aaactcctga cctcaagtga tctgcctgcc tcagcctccc    17160
aaagtgctgg gattacaggc gtgagccacc acgcctggcc tgcaaacaga cccttaaaag    17220
tcatctgttc ctactcttgt tatttaagtt gctttgatac tccacccctg aagaactttt    17280
atggggcact taccatgtgt caagcattgt ggcgagtgct tatagagaag gtgggacttt    17340
ctgagggagc ccacaaaaaa gcattctttt cttgccctca ttctgaataa attgaggaat    17400
aaaaaatagg agctacagat ggagacccca agtctggcca gttctattac tgataaagac    17460
aggagggtga gagctaggtg gacccagcca ggaagcagac ctgggcagtt gtagcctcta    17520
tctccttccc cctctgccct tgagtctaga aggaagcccg ctcccaggag aaaaatagcg    17580
cccaggctac acatgcctag tttattcttc ccaaatcaac cagttgcata aatcactcct    17640
```

```
ctatcttcct tggggtggaa agtggatggg agttataatt tgagttctct tttgtcttag    17700
tccattgaag ctgctattac aaaataccat aaactgggtg gcttataaac agcagaaatg    17760
aggccgggtg cggtggctca tgcctataat tccagcactt tgggaggcca aggcaggtgg    17820
atcacctgag atcagtagtt caagactagc ctgaccaaca tggtgaaacc ctgtctctac    17880
taaaaataca aaaaattagc tgggggtggt ggcgggcacc tgtaatccca gctactcagg    17940
aggctgaggc aggagaatcg cttgaaccca ggaggcggag gttgccgtga gctgagatca    18000
cgccattgca tttcagcctg gcaacaaga gtgaaactcc atctcaaaat gaaataaaat    18060
aacagaaatg tatttcttaa cagttctgga ggttgggtgg gcagtcccag atcaggacac    18120
tgacagattc agtgtctgat gggggcccac tttctggtgt tacctgctgg ctgtgttctc    18180
acatggtgga aggaacatgg caactttctg gggccttgtt ttttaattta aaaaaaaaaa    18240
atattttcct ggcccttgcc tgctgaagga acctcttttta taatggtact taaaaatttt    18300
tttttttgag atgggggtct cactctgtca cccacgctga gtgcagtatc acaatctcag    18360
ctcactgcaa cctctgcctc cctggcttaa gcgatcctcc cacctcagcc tcctgagtac    18420
gtgtgaccat aggcccatgg cacaaagccc agctaatttt ttgtattttt agtagaaatg    18480
tggtttcacc atgttgcata ggctggtctc gaacttctga actcaagtga tctgcctgcc    18540
ttggcctccc aaagtgctgg gattctaggt atgagccacc ctgctcggcc tataatggca    18600
ctttcctatc ccattgatga ggctctactc tcatgaccta atcatctccc aaaggcccta    18660
aggcctcctg ataccatcac ctttggggtt aggttttaac atatacattt tgggggggaca    18720 cagacatttt agaccatagc acctccattg aaaggaaaca tttctgacac ctggctatct    18780
caaagggccc tttcagttcc cctgcaggct gcattcccac atcaccaaca agagcagcga    18840
cactcactca gaggttaaat aacttgtcca gagtcacagc agtaatgaat gacagagctg    18900
gggcttgaat ccaggcgtcc tcctagagcc tggattctgt gtagtgagtg aaagctgact    18960
cctgggagac ttctgcgtgg tcctggttct ctctccagac tgcactgcgc aagtttctct    19020
tcctgatggt ccctaggta ttacaaagac agtggccctg cctgtcaggt gtttttatta    19080
ccagatgagg tcatggcctc aggaaccctg tgggaagctg agttcagagt ctttgagcag    19140
gctttaggga ggttccagct tcccaccacc aagcccagg tggattctta cagactctag    19200
cctcagggtg gggggtctgg aagatgaggt tgcggggtgc gatattctgc ccaattcgcc    19260
cctccttgct caatctgttt ctgcaggtat tgctgactac agacccaagg atggagaaac    19320
cattgagctg aggctggtta gctggtagcc cctgagctcc ctcatcccag cagcctcgca    19380
cactccctag gcttctaccc tccctcctga tgtccctgga acaggaactc gcctgacccct    19440 gctgccacct cctgtgcact ttgagcaatg cccctggga tcaccccagc acaagccct    19500 tcgagggccc tataccatgg cccaccttgg agcagagagc caagcatctt ccctgggaag    19560
tctttctggc caagtctggc cagcctggcc ctgcaggtct cccatgaagg ccaccccatg    19620
gtctgatggg catgaagcat ctcagactcc ttggcaaaaa acggagtccg caggccgcag    19680
gtgttgtgaa gaccactcgt tctgtggttg gggtcctgca agaaggcctc ctcagcccgg    19740
gggctatggc cctgaccca gctctccact ctgctgttag agtggcagct ccgagctggt    19800
tgtggcacag tagctgggga gacctcagca gggctgctca gtgcctgcct ctgacaaaat    19860
taaagcattg atggcctgtg gacctgc                                        19887
```

<210> SEQ ID NO 19

-continued

```
<211> LENGTH: 20
<212> TYPE: DNA
<213> ORGANISM: Homo sapiens

<400> SEQUENCE: 19
cactccagtg tttgtccatg                                          20

<210> SEQ ID NO 20
<211> LENGTH: 19
<212> TYPE: DNA
<213> ORGANISM: Homo sapiens

<400> SEQUENCE: 20
gcatcttgag agccctgac                                           19

<210> SEQ ID NO 21
<211> LENGTH: 20
<212> TYPE: DNA
<213> ORGANISM: Homo sapiens

<400> SEQUENCE: 21
ttctctttct tagccccacg                                          20

<210> SEQ ID NO 22
<211> LENGTH: 21
<212> TYPE: DNA
<213> ORGANISM: Homo sapiens

<400> SEQUENCE: 22
agagcttgca gtgagcctag a                                        21

<210> SEQ ID NO 23
<211> LENGTH: 22
<212> TYPE: DNA
<213> ORGANISM: Homo sapiens

<400> SEQUENCE: 23
ccatcgtcag agaagtcatt ca                                       22

<210> SEQ ID NO 24
<211> LENGTH: 20
<212> TYPE: DNA
<213> ORGANISM: Homo sapiens

<400> SEQUENCE: 24
ctggttgatt tcctgcatca                                          20

<210> SEQ ID NO 25
<211> LENGTH: 22
<212> TYPE: DNA
<213> ORGANISM: Homo sapiens

<400> SEQUENCE: 25
ggtctttgga agctgctcta ca                                       22

<210> SEQ ID NO 26
<211> LENGTH: 21
<212> TYPE: DNA
<213> ORGANISM: Homo sapiens

<400> SEQUENCE: 26
ttgcagtgag cctagatcac g                                        21
```

-continued

```
<210> SEQ ID NO 27
<211> LENGTH: 20
<212> TYPE: DNA
<213> ORGANISM: Homo sapiens

<400> SEQUENCE: 27
gatcacaccc acccctcttg                                               20

<210> SEQ ID NO 28
<211> LENGTH: 21
<212> TYPE: DNA
<213> ORGANISM: Homo sapiens

<400> SEQUENCE: 28
cctcctttca ctccaaacgt c                                             21
```

METHODS AND MATERIALS FOR IDENTIFYING POLYMORPHIC VARIANTS, DIAGNOSING SUSCEPTIBILITIES, AND TREATING DISEASE

CROSS REFERENCE TO RELATED APPLICATIONS

This patent application is a continuation-in-part of copending International Patent Application No. PCT/US05/021288, filed Jun. 16, 2005, which is incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 493,070 Byte ASCII (Text) file named "701903.5T25," created on Dec. 17, 2007.

BACKGROUND OF THE INVENTION

An important enzyme involved in one carbon metabolism is the NADP-dependent trifunctional enzyme MTHFD1 (5,10-methylenetetrahydrofolate dehydrogenase, 5,10-methenyltetrahydrofolate cyclohydrolase, 10-formyltetrahydrofolate synthetase) [Hum et al., J. Biol. Chem., 263:15946-15950 (1988)]. MTHFD1 is often referred to as the "C1-THF synthase" and catalyses the interconversion of tetrahydrofolate to 10-formyl, 5,10-methenyl, and 5,10-methylene derivatives. These derivatives form an important part of de novo DNA synthesis. Promotion of DNA synthesis is desirable in placental and fetal development. In other contexts, such as cancer treatment, blocking of DNA synthesis is desirable. Maternal folate status and/or homocysteine levels have been implicated in a range of pregnancy-related complications, most notably in pregnancies affected by a neural tube defect (NTD).

A polymorphic variant at position 1958 of MTHFD1 at which guanine is replaced with an adenosine results in the substitution of a conserved arginine amino acid with a glutamine at position 653. One study has disclosed that this polymorphic variant is a maternal risk factor for neural tube defects (NTDs) [Brody et al., Am. J. Hum. Genet., 71:1207-1215 (2002)]. Neural tube defects (NTDs) are common congenital malformations that can be presented as anencephaly, encephalocele, and spina bifida. NTDs' etiology likely includes both genetic and environmental factors. Intervention trials have shown that maternal supplementation with folic acid in the period before pregnancy can prevent the majority of NTD-affected pregnancies.

Abruptio placentae or placental abruption is thought to arise from a sudden rupture of the spiral arteries, resulting in the premature separation of a normally implanted placenta [Anath et al., Obstet. Gynecol. 88:309-318 (1996); Eskes, Eur. J. Obstet. Gyn. R. B. 95:206-212 (2001)]. This event leads to increased risk of adverse outcomes to both mother and baby. The underlying cause of abruptio placentae is unknown, but several factors have been suggested to increase risk including folate deficiency, hyperhomocysteinemia, preeclampsia and history of a prior pregnancy abruption [Kramer et al., Obstet. Gynecol. 89: 221-226 (1997); Misra et al., J. Clin. Epidemiol. 52: 453-461 (1999); Ray et al., Placenta, 20: 519-529 (1999); Eskes, Eur. J. Obstet. Gyn. R. B., 95: 206-212 (2001).] Non-genetic risk factors have been described including cigarette smoldng, preeclampsia and increased maternal age [Misra et al., J. Clin. Epidemiol. 52: 453-461 (1999); Eskes, Eur. J. Obstet. Gyn. R. B. 95: 206-212 (2001)]. Additional risk factors include elevated homocysteine [Goddijn-Wessel et al., Br Med. J., 2: 1431-1436 (1996); van der Molen, et al., Am. J. Obstet. Gynecol., 182: 1258-1263 (2000)] and low folate levels [Hibbard et al., Br. Med. J., 2: 1431-1436 (1963); Streiff et al., N. Engl. J. Med., 276: 776-779 (1967); Whalley et al., Am. J. Obstet. Gynecol., 105: 670-678 (1969); Hibbard, S Afr Med J 49: 1223-1226 (1975); Goddijn-Wessel et al., Br. Med. J., 2: 1431-1436 (1996)].

A substantial proportion (15-50%) of second trimester pregnancy losses remain unexplained [Gaillard et al., Arch. Pathol. Lab. Med, 117:1022-1026 (1993); Faye-Petersen et al., Obstet. Gynecol. 94, 915-920 (1999); Incerpi et al., Am J Obstet Gynecol 178, 1121-1125 (1998); Drakeley et al., Hum Reprod 13, 1975-1980 (1998)]. Although placental insufficiency is a common finding in these cases {Faye-Petersen et al., Obstet. Gynecol. 94, 915-920 (1999)], its etiology is often unknown. Sub-optimal folate or $B_{12}$ metabolism due to either a deficient diet or a genetic predisposition appears to increase the risk of a number of pregnancy complications including spontaneous abortion.

Polymorphisms have been studied in the context of a variety of cancers and other diseases. [See, e.g., Chen, et al., Int. J. Cancer, 110, 617-620 (2004), Krajinovic et al., The Pharmacogenomics Journal 4:66-72 (2004); U.S. Pat. Nos. 5,449,605; 5,688,647; 5,719,026; 5,942,390; 6,294,399; 6,312,898; 6,537,759; 6,548,245; 6,627,401; 6,664,062; 6,759,200; 6,818,758; 6,833,243, and 6,872,533; and U.S. Patent Application Publication Nos: 2005/0084849; 2005/0089905; 2005/0095593; and 2005/0112680.

Methylenetetrahydrofolate dehydrogenase (NADP+ dependent) 1-like (MTHFD1L) is a trifunctional enzyme localized to mitochondria which has been reported to have one or more enzymatic activities in common with MTHFD1. MTHFD1L has been shown to be transcribed into two mRNA transcripts: 1.1 kb and 3.6 kb in size. The shorter transcript is produced by splicing Exon7 with alternative Exon8A and therefore it lacks the 10-formyltetrahydrofolate synthase (synthetase) sequence [Prasannan et al., J. Biol. Chem., 278 (44):43178-43187 (2003)].

Methylenetetrahydrofolate reductase (MTHFR) is involved in the remethylation of homocysteine to methionine by generating the necessary methyl group donor 5-methyltetrahydrofolate from 5,10-methylenetetrahydrofolate. Polymorphisms within MTHFR have been extensively studied in relation to a wide variety of diseases including NTDs, cancer and pre-eclampsia. The MTHFR polymorphic variant at 677 where a C is replaced with a T has a functional effect on the MTHFR enzyme and is associated with elevated plasma homocysteine levels when folate status is low. A relatively small number of studies have examined the MTHFR polymorphisms in relation to abruptio placentae and results have not yielded a clear indication of increased risk for the disorder.

Coagulation factor II is proteolytically cleaved to form thrombin in the first step of the coagulation cascade, which ultimately results in the stemming of blood loss. F2 also plays a role in maintaining vascular integrity during development and postnatal life. Mutations in F2 can lead to various forms of thrombosis and dysprothrombinemia.

Coagulation factor V (F5) is an essential factor of the blood coagulation cascade, and circulates in plasma, and is converted to the active form by the release of the activation peptide by thrombin during coagulation. Once activated, factor V is a cofactor that participates with activated coagulation factor X to activate prothrombin to thrombin. Defects in this gene result in either an autosomal recessive hemorrhagic diathesis or an autosomal dominant form of thrombophilia, which is known as activated protein C (APC) resistance. A variant of factor V with a particular single point mutation associated with APC resistance is known as factor V Leiden [Bertina et al., Nature, 369:64-67 (1994)].

Transcobalamin II (TCNII) is a member of the vitamin $B_{12}$-binding protein family. TCNII binds cobalamin and mediates the transport of cobalamin into cells. TCNII polymorphic variant 776C>G (P259R) has been reported to confer an increased fetal genetic risk of early spontaneous abortion [Zetterberg et al., Hum. Reprod., 17:3033-3036 (2002)] and influence levels of circulating vitamin $B_{12}$ bound to TCNII [Afman et al., Eur. J. Hum. Genet., 10:433-438 (2002), Miller et al., Blood, 100:718-720 (2002)]. TCNII 776C>G polymorphic variant may interact with the MTHFR 677TT genotype to confer an even higher fetal genetic risk of spontaneous abortion than either polymorphism separately [Zetterberg et al., Hum. Reprod., 18:1948-1950 (2003)].

Chemotherapy of cancer has involved use of highly toxic drugs with narrow therapeutic indices, and, most adult solid cancers remain highly resistant to treatment. Chemotherapy often results in a significant fraction of treated patients suffering unpleasant or life-threatening side effects while receiving little or no clinical benefit; other patients may suffer few side effects and/or have complete remission or even cure. Chemotherapy is also expensive, based not only on the cost of drugs, but the medical care involved with their administration. Tests are needed that better predict chemotherapy efficacy; such tests would allow for more selective use of toxic drugs. In those cases where toxicity of chemotherapy or other drug regemin is at least partially a result of genetic differences, the identification of relevant polymorphic variants will allow for more effective and safer drug use.

Accordingly, to better diagnose and treat pregnancy complications and neoplastic disorders, cardiovascular disorders, Alzheimer's disease and other conditions associated with one carbon metabolic pathways, there is a need to identify polymorphic variants that indicate a relative susceptibility to such diseases and/or relative response to treatments for such diseases.

BRIEF SUMMARY OF THE INVENTION

The invention provides a method of screening for an increased susceptibility for at least one pregnancy-related complication selected from the group consisting of second trimester miscarriage and placental abruption. A sample from a subject is screened to detect the presence or absence of a polymorphic variant of a polymorphism in at least one chromosomal copy of the MTHFD1 gene, wherein the polymorphic variant is associated with an increased susceptibility for at least one pregnancy-related complication selected from the group consisting of second trimester miscarriage and placental abruption. The susceptibility of the subject for at least one pregnancy-related complication selected from the group consisting of second trimester miscarriage and placental abruption is diagnosed based on the presence or absence of the polymorphic variant of at least one chromosomal copy of the MTHFD1 gene.

The invention provides a method of testing for an increased susceptibility for a complication related to a defect in a one-carbon metabolic pathway. A sample from a subject is screened to detect the presence or absence of a polymorphic variant of a polymorphism in at least one chromosomal copy of the MTHFD1L gene, wherein the polymorphic variant is associated with an increased susceptibility for a complication related to a defect in a one-carbon metabolic pathway. The susceptibility of the subject for a complication related to a defect in a one-carbon metabolic pathway is diagnosed based on the presence or absence of the polymorphic variant of at least one chromosomal copy of the MTHFD1L gene.

The invention provides a kit. The kit includes a nucleic acid comprising at least 30 nucleotides of SEQ ID NO: 2 or a complement thereof, the nucleic acid further comprising the sequence of a polymorphic variant associated with an increased susceptibility for at least one pregnancy-related complication selected from the group consisting of second trimester miscarriage, placental abruption, and severe placental abruption. The kit includes instructions for screening a sample from a subject using the nucleic acid. The kit further includes instructions for diagnosing an increased susceptibility for one of said pregnancy-related complications if the polymorphic variant of at least one chromosomal copy of the MTHFD1 gene is detected in the sample.

The invention provides a kit. The kit includes a nucleic acid comprising at least 30 nucleotides of SEQ ID NO: 12 or a complement thereof, the nucleic acid further comprising the sequence of a polymorphic variant associated with an increased susceptibility for at least one complication related to a defect in a one-carbon metabolic pathway. The kit includes instructions for screening a sample from a subject using the nucleic acid. The kit further includes instructions for diagnosing an increased susceptibility for a complication related to a defect in a one-carbon metabolic pathway if the polymorphic variant of at least one chromosomal copy of the MTHFD1L gene is detected in the sample.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION OF THE INVENTION

Determination of Polymorphisms

This invention involves one or more polymorphic variants useful in the field of diagnostics and therapeutics for optimizing efficacy and safety of drug therapy for specific diseases or conditions and for establishing diagnostic tests for pregnancy-related and other complications affected by one carbon metabolic pathways. Methods are presented for identifying polymorphic variants and determining their utility in diagnostic and therapeutic methods, along with probes, kits, and related materials that are useful, for example, in identifying the presence and genotype of a particular polymorphic variant in an individual.

In identifying new correlations between polymorphic variants and disease susceptibilities and treatment approaches, different population groups based on racial, ethnic, gender, and/or geographic origin can be studied. Individuals with a particular disease or condition of interest or altered relative susceptibility thereto can have a higher frequency of certain polymorphic variants than the general population. The polymorphic variants can be predictive of differential, increased or decreased, susceptibility to various disease states, conditions, and complications, independent of ethnicity, race, or geographic origin, even if the polymorphic variant and disease association was originally identified in a particular population, for example, European, Celtic, and Irish populations. Distributions for some of the polymorphic variants are discussed herein.

"Differential" or "differentially" generally refers to a statistically significant different level in the specified property or effect. Preferably, the difference is also functionally significant. "Differential binding or hybridization" is a sufficient difference in binding or hybridization to allow discrimination using an appropriate detection technique. "Differential effect" or "differentially active" in connection with a therapeutic treatment or drug refers to a difference in the level of the effect or activity which is distinguishable using relevant parameters and techniques for the effect or activity being considered. In some embodiments, the difference in effect or activity is also sufficient to be clinically significant, such that a corresponding difference in the course of treatment or treatment outcome would be expected, at least on a probabilistic basis.

"Population" refers to a geographically, ethnically, racially, gender, and/or culturally defined group of individuals or a group of individuals with a particular disease or condition or individuals that may be treated with a specific drug. In most cases a population will preferably encompass at least one hundred, one thousand, ten thousand, one hundred thousand, one million, ten million, or more individuals, with the larger numbers being more preferable. In some embodiments, the population refers to individuals with relative susceptibility to a specific disease or condition and/or amenability to a particular drug regimen. The frequency of one or more polymorphic variants that is predictive of a differential susceptibility to a disease response and/or a response to a particular treatment is determined in one or more populations using a diagnostic test.

Nucleic acid samples, for use in polymorphic variant identification, can be obtained from a variety of sources as known to those skilled in the art, or can be obtained from genomic or cDNA sources by known methods. For example, the Coriell Cell Repository (Camden, N.J.) maintains over 6,000 human cell cultures, mostly fibroblast and lymphoblast cell lines comprising the NIGMS Human Genetic Mutant Cell Repository. A catalog (http://locus.umdnj.edu/nigms) provides racial or ethnic identifiers for many of the cell lines. Cell lines may also be obtained from the Beijing Cancer Institute.

"Allele frequency" is the fraction of genes in a population that have one specific polymorphic variant or set of polymorphic variants. The allele frequencies for any gene should sum to 1. In some embodiments, a polymorphic variant has an allele frequency of at least 0.001, 0.01, 0.05, or 0.10. Another measure of frequency known in the art is the "heterozygote frequency" namely, the fraction of individuals in a population who carry two alleles, or two forms of a particular polymorphic variant or variant form of a gene, one inherited from each parent. Alternatively, the number of individuals who are homozygous for a particular form of a gene may be a useful measure. The relationship between allele frequency, heterozygote frequency, and homozygote frequency is described for many genes by the Hardy-Weinberg equation. Most human polymorphic variants are substantially in Hardy-Weinberg equilibrium. The allele frequency, heterozygote frequency, or homozygote frequency can be determined experimentally.

To establish the association between a specific condition and one or more polymorphic variants, a study is commonly performed in controlled clinical trials using a limited number of patients that are considered to be representative of the population with the disease or relative susceptibility for the same. The populations should preferably be large enough to have a reasonable chance to find correlations between a particular genetic variant and susceptibility to the disease of interest. In addition, the allele frequency of the genetic variant in a population or subpopulation with the disease or pathology should vary from its allele frequency in the population without the disease pathology (control population) by at least 1%, by at least 2%, by at least 4%, or by at least 8%.

The association between case-control status and genotype can be examined using a number of standard odds ratios. In order to have a common approach for all analyses, a log linear model can be employed. The statistical software (SAS PROC NLMIXED) allows estimation of nonlinear functions of the parameters of the model, and provides standard errors calculated using the delta method [Agresti, Categorical Data Analysis (1990)]. The parameterization of the model can easily be modified for the computation of different odds ratios. This approach enables the researcher to estimate log odds ratios and their standard errors for the computation of confidence intervals, as well as to check the goodness of fit of different models. Potential gene-gene interaction effects can also be examined. Tests of interactive dominant or recessive effects of specific combined genotypes can be performed using a series of non-hierarchical logistic regression models [Piegorsch et al., Stat. Med., 13, 153-162 (1994)]. Statistical significance can be assessed using likelihood ratio chi-square tests.

The polymorphism variant(s) showing the strongest correlation with an altered relative susceptibility for a disease state within a given gene are likely either to have a causative role in the manifestation of the phenotype or to be in linkage disequilibrium with the causative variants. Such a role can be confirmed by in vitro gene expression of the variant gene or by producing a transgenic animal expressing a human gene bearing such a polymorphic variant and determining whether the animal develops a relevant disease. Polymorphic variants in coding regions that result in amino acid changes can change relative susceptibility for a disease state by decreasing, increasing, or otherwise altering the activity of the protein encoded by the gene in which the polymorphism occurs. Polymorphic variants in coding regions that introduce stop codons can change relative susceptibility for a disease state by reducing (heterozygote) or eliminating (homozygote) functional protein produced by the gene. In some embodiments, stop codons result in production of a truncated peptide with aberrant activities relative to the full-length protein. Polymorphisms in regulatory regions can change relative susceptibility for a disease state by causing increased or decreased expression of the protein encoded by the gene in which the polymorphism occurs. Polymorphic variants in intronic or untranslated sequences can change relative susceptibility for a disease state either through the same mechanism as polymorphic variants in regulatory sequences or by causing altered splicing patterns resulting in an altered protein.

Types of Polymorphisms

As used herein, a "gene" is a sequence of DNA present in a cell that directs the expression of a "gene product," most commonly by transcription to produce RNA and translation to produce protein. An "allele" is a particular form of a gene. The term allele is relevant when there are two or more forms of a particular gene. Genes and alleles are not limited to the open reading frame of the genomic sequence or the cDNA sequence corresponding to processed RNA. A gene and allele can also include sequence upstream and downstream of the genomic sequence such as promoters and enhancers. The terms "gene product," or "polymorphic variant allele product" refer to a product resulting from transcription of a gene. Gene and polymorphic variant allele products include partial, precursor, and mature transcription products such as pre-mRNA and mRNA, and translation products with or without further processing including, without limitation, lipidation, phosphorylation, glycosylation, other modifications known in the art, and combinations of such processing. RNA may be modified without limitation by complexing with proteins, polyadenylation, splicing, capping or export from the nucleus.

A "polymorphism" is a site in the genome that varies between two or more individuals or within an individual in the case of a heterozygote. The frequency of the variation can be defined above a specific value for inclusion of variations generally observed in a population as opposed to random mutations. Polymorphisms that can be screened according to the invention include variation both inside and outside the open reading frame. When outside the reading frame the polymorphism can occur within 200, 500, 1000, 2000, 3000, 5000, or more of either the 5' or 3' end of the open reading frame. When inside the reading frame, the polymorphism may occur within an exon or intron, or overlapping an exon/intron boundary. A polymorphism could also overlap the open reading frame and sequence outside of that frame. Many polymorphisms have been given a "rs" designation in the SNP database of NCBI's Entrez, some of these designations have been provided herein for the polymorphisms that can be screened according to the invention.

A "polymorphic variant" is a particular form or embodiment of a polymorphism. For example if the polymorphism is a single nucleotide polymorphism, a particular variant could potentially be an "A" (adenosine), "G" (guanine), "T" (thymine), and "C" (cytosine). When the variant is a "T", it is understood that a "U" can occur in those instances wherein the relevant nucleic acid molecule is RNA, and vice versa in respect to DNA. The convention "PositionNUC1>NUC2" is used to indicate a polymorphism contrasting one variant from another. For example, 242A>C would refer to a cytosine instead of an adenosine occurring at position 242 of a particular nucleic acid sequence. When 242A>C is used in respect to a mRNA/cDNA, it can also be used to represent the polymorphism as it occurs in the genomic DNA with the understanding that the position number will likely be different in the genome. Sequence and polymorphic location information for both coding domain sequence and genomic sequence is described herein for the genes relevant to the invention. "Polymorphic variant allele" refers to an allele comprising a particular polymeric variant or a particular set of polymorphic variants corresponding to a particular set of polymorphisms. Two alleles can both be considered the same polymorphic variant allele if they share the same variant or set of variants defined by the polymorphic variant allele even though they may differ in respect to other polymorphisms or variation outside the definition. For a mutation at the amino acid level, the convention "AA1PositionAA2" is used. For example, in the context of amino acid sequence, M726L, would indicate that the underlying, nucleotide level polymorphism(s) has resulted in a change from a methionine to a leucine at position 726 in the amino acid sequence.

A "genotype" can refer to a characterization of an individual's genome in respect to one or both alleles and/or one or more polymorphic variants within that allele. A subject can be characterized at the level that the subject contains a particular allele, or at the level of identifying both members of an allelic pair, the corresponding alleles on the set of two chromosomes. One can also be characterized at the level of having one or more polymorphic variants. The term "haplotype" refers to a cis arrangement of two or more polymorphic variants, on a particular chromosome such as in a particular gene. The haplotype preserves the information of the phase of the polymorphic nucleotides—that is, which set of polymorphic variants were inherited from one parent, and which from the other. Wherein methods, materials, and experiments are described for the invention in respect to polymorphic variants, one will understand that can also be adapted for use with an analogous haplotype.

A single nucleotide polymorphism (SNPs) refers to a variation at a single nucleotide location. In some cases the variations at the position could be any one of the four nucleotide bases, in others the variation is some subset of the four bases. For example, the variation could be between either purine base or either pyrimidine base. Simple-sequence length polymophisms (SSLPS) or short tandem repeat polymorphisms (STRPs) involve the repeat of a particular sequence of one or more nucleotides. A restriction fragment length polymorphism (RFLP) is a variation in the genetic sequence that results in the appearance or disappearance of an enzymatic cleavage site depending on which base(s) are present in a particular allele.

A diagnosis for a given susceptibility in accordance with this invention includes detection of homozygosity and/or heterozygosity for a given polymorphism(s). Heterozygosity and homozygosity are relevant wherein the cell tested has two chromosomal copies. In other contexts, such as in a sperm or egg, only a single chromosome is present so that the issue of homozygosity or heterozygosity does not directly present itself. In the some embodiments, such as those involving cancer, homozygosity or heterozygosity can be lost or at least obscured because of deletion or inactivation of one of the two gene copies.

In those embodiments where a sample is screened to detect the presence or absence of more than one polymorphic variant associated with a given condition, the combination of the polymorphic variants can be additive, synergistic, or even antagonists in regards to correlative strength—although not overly antagonist if the susceptibility or drug effect probability is lost. When screening for multiple polymorphisms all can be heterozygous, all can be homozygous, or a combination with one or more polymorphism homozygous, and one or more polymorphism heterozygous, depending on the particular susceptibility relationship for a given set of polymorphic variants and a condition or drug response.

The polymorphic variants described herein can be associated with an altered susceptibility to one or more complications and/or therapeutic treatments. How a polymorphism is associated with this susceptibility need not be known for the usefulness and operability of the invention. The polymorphism need not actually cause or contribute to etiology or severity of the condition. In some embodiments, the polymorphism can cause or contribute to the condition. In some embodiments, the polymorphism serves as a marker for another polymorphism(s) responsible for causing or contributing to the condition. In such a situation, the polymorphism(s) screened for can be in linkage disequilibrium with the responsible polymorphism(s).

Linkage is the tendency of genes or DNA sequences, for example, polymorphisms, to be inherited together as a consequence of their physical proximity on a single chromosome. The closer together the markers are, the lower the probability that they will be separated during DNA crossing over, and hence the greater the probability that they will be inherited together. If a mutational event introduces a "new" allele in the close proximity of a gene or an allele, the new allele will tend to be inherited together with the alleles present on the "ancestral," chromosome or haplotype. However, the resulting association, called linkage disequilibrium, will decline over time due to recombination. Linkage disequilibrium has been used to map disease genes. In general, both allele and haplotype frequencies differ among populations. Linkage disequilibrium is varied among the populations, being absent in some and highly significant in others.

Linkage disequilibrium (LD) or allelic association means the preferential association of a particular allele or genetic marker with a specific allele, or genetic marker at a nearby chromosomal location more frequently than expected by chance for any particular allele frequency in the population. For example, if locus P has alleles x and y, which occur with equal frequency, and linked locus Q has alleles w and z, which occur with equal frequency, one would expect the haplotype ac to occur with a frequency of 0.25 in a population of individuals. If xw occurs more frequently, then alleles x and w are considered in linkage disequilibrium. Linkage disequilibrium may result from natural selection of a certain combination of alleles or because an allele has been introduced into a population too recently to have reached equilibrium between linked alleles.

A marker in linkage disequilibrium with disease predisposing variants can be particularly useful in detecting susceptibility to disease or association with sub-clinical phenotypes notwithstanding that the marker does not cause the disease. For example, a marker P that is not itself a causative element of a disease, but which is in linkage disequilibrium with a gene Q that is a causative element of a phenotype, can be used to indicate susceptibility to the disease in circumstances in which the gene Q may not have been identified or may not be readily detectable. Relatively young evolutionarily alleles are expected to have a larger genomic segment in linkage disequilibrium. The age of an allele can be determined from whether the allele is shared among different human ethnic groups and/or between humans and related species.

The polymorphisms described herein can also be used to establish physical linkage between a genetic locus associated with a trait of interest and polymorphic markers that are not associated with the trait, but are in physical proximity with the genetic locus responsible for the trait and co-segregate with the responsible variation. Such analysis is useful for mapping a genetic locus associated with a phenotypic trait to a chromosomal position and thereby cloning gene(s) responsible for the trait [Landau et al., Proc. Natl. Acad. Sci. (USA), 83, 7353-7357 (1986); Landau et al., Proc. Natl. Acad. Sci., (USA) 84, 2363-2367 (1987); Donis-Keller et al., Cell, 51, 319-337 (1987); Landau et al., Genetics, 121, 185-199 (1989))]. Genes localized by linkage can be cloned by a process known as directional cloning. [Wainwright, Med. J. Australia, 159, 170-174 (1993); Collins, Nature Genetics, 1, 3-6 (1992)]. Linkage studies can be performed on members of a family. Available members of the family are characterized for the presence or absence of a phenotypic trait and for a set of polymorphic markers. The distribution of polymorphic markers in an informative meiosis is then analyzed to determine which polymorphic markers co-segregate with a phenotypic trait. [See, e.g., Kerem et al., Science, 245:1073-1080 (1989); Monaco et al., Nature, 316:842 (1985); Yamoka et al., Neurology, 40:222-226 (1990); Rossiter et al., FASEB Journal, 5:21-27 (1991).]

Linkage is analyzed by calculation of lod (log of the odds) values. A lod value is the relative likelihood of obtaining observed segregation data for a marker and a genetic locus when the two are located at a recombination fraction 0, versus the situation in which the two are not linked, and thus segregating independently [Thompson & Thompson, Genetics in Medicine (5th ed, W.B. Saunders Company, Philadelphia, 1991); Strachan, "Mapping the human genome" in The Human Genome (BIOS Scientific Publishers Ltd, Oxford), Chapter 4]. A series of likelihood ratios are calculated at various recombination fractions (O), ranging from $\theta=0.0$ (coincident loci) to $\theta=0.50$ (unlinked). The computed likelihoods are usually expressed as the $\log_{10}$ of this ratio, known as a "lod" score. For example, a lod score of 3 indicates 1000:1 odds against an apparent observed linkage being a coincidence. The use of logarithms allows data collected from different families to be combined by simple addition. Computer programs are available for the calculation of lod scores for differing values of 0, for example, LIPED, MLINK [Lathrop, Proc. Nat. Acad. Sci. (JSA), 81:3443-3446 (1984)]. For any particular lod score, a recombination fraction may be determined from mathematical tables. [See Smith et al., Mathematical tables for research workers in human genetics (Churchill, London, 1961); Smith, Ann. Hum. Genet. 32:127-150 (1968).] The value of $\theta$ at which the lod score is the highest is considered to be the best estimate of the recombination fraction. Positive lod score values suggest that the two loci are linked, whereas negative values suggest that linkage is less likely (at that value of $\theta$) than the possibility that the two loci are unlinked. By convention, a combined lod score of +3 or greater (equivalent to greater than 1000:1 odds in favor of linkage) is considered definitive evidence that two loci are linked. Similarly, by convention, a negative lod score of –2 or less is taken as definitive evidence against linkage of the two loci being compared. Negative linkage data are useful in excluding a chromosome or a segment thereof from consideration. The search focuses on the remaining non-excluded chromosomal locations.

In those embodiments where the screened for polymorphic variant(s) is responsible in part or whole for the condition(s), the polymorphic variant(s) can result in a change in the steady state level of mRNA, for example, through a decrease in transcription and/or mRNA stability. Some polymorphic variants can alter the exon/intron boundary and/or effect how splicing occurs. When the polymorphic variant occurs within or overlaps with the protein-encoding sequence of the gene, the polymorphic variant may be silent resulting in no change at the amino acid level, result in a change of one or more amino acid residues, a deletion of one or more amino acids, addition of one or more amino acids, or some combination of such changes. For some polymorphic variants, the result is premature termination of translation. The effect may be neutral, beneficial, or detrimental, or both beneficial and detrimental, depending on the circumstances. Polymorphic variants occurring in noncoding regions can exert phenotypic effects indirectly via influence on replication, transcription, and translation. Polymorphic variants in DNA can affect the basal transcription or regulated transcription of a gene locus. Such polymorphic variants may be located in any part of the gene but are most likely to be located in the promoter region, the first intron, or in 5' or 3' flanking DNA, where enhancer or silencer elements may be located. A single polymorphism can affect more than one phenotypic trait. A single phenotypic trait may be affected by polymorphisms in different genes. Some polymorphisms predispose an individual to a distinct mutation that is causally related to a certain phenotype.

Determining what effect if any a polymorphic variant has on the disease state, condition, or complication with which it is correlated can be useful in the context of certain aspects of the invention, for example, choosing a proper therapy. Methods for analyzing transcription are well known to those skilled in the art. Transcriptional run off assay is one useful method. Detailed protocols for useful methods can be found in texts such as: Current Protocols in Molecular Biology edited by: F. M. Ausubel, R. Brent, R. E. Kingston, D. D. Moore, J. G. Seidman, K. Struhl, John Wiley & Sons, Inc. (1999), or Molecular Cloning: A Laboratory Manual by J. Sambrook, E. F. Fritsch and T Maniatis, Cold Spring Harbor Laboratory Press, $2^{nd}$ edition (1989).

RNA polymorphic variants can affect a wide range of processes including RNA splicing, polyadenylation, capping, export from the nucleus, interaction with translation intiation, elongation or termination factors, or the ribosome, or interaction with cellular factors including regulatory proteins, or factors that may affect mRNA half life. An effect of polymorphic variants on RNA function can ultimately be measurable as an effect on RNA levels—either basal levels or regulated levels or levels in some abnormal cell state. One method for assessing the effect of RNA polymorphic variants on RNA function is to measure the levels of RNA produced by different alleles in one or more conditions of cell or tissue growth. Such measuring can be done by conventional methods such as Northern blots or RNAase protection assays, which can employ kits available from Ambion, Inc., or by methods such as the Taqman assay, or by using arrays of oligonucleotides or arrays of cDNAs or other nucleic acids attached to solid surfaces, such as a multiplex chip. Systems for arraying cDNAs are available commercially from companies such as Nanogen and General Scanning. Complete systems for gene expression analysis are available from companies such as Molecular Dynamics. See also supplement to volume 21 of Nature Genetics entitled "The Chipping Forecast." Additional methods for analyzing the effect of polymorphic variants on RNA include secondary structure probing, and direct measurement of half life or turnover. Secondary structure can be determined by techniques such as enzymatic probing with use of enzymes such as T1, T2, and S1 nuclease, chemical probing or RNAase H probing using oligonucleotides. Some RNA structural assays can be performed in vitro or on cell extracts.

To determine if one or more polymorphic variants have an effect on protein levels and/or activity, a variety of techniques may be employed. The in vitro protein activity can be determined by transcription or translation in bacteria, yeast, baculovirus, COS cells (transient), CHO, or study directly in human cells. Further, one can perform pulse chase experiments for the determination of changes in protein stability such as half life measurements. One can manipulate the cell assay to address grouping the cells by genotypes or phenotypes. For example, identification of cells with different genotypes and phenotype can be performed using standardized laboratory molecular biological protocols. After identification and grouping, one skilled in the art could determine whether there exists a correlation between cellular genotype and cellular phenotype.

Correlation between one or more polymorphic variants can be performed for a population of individuals who have been tested for the presence or absence of a pregnancy complication or a disease state such as cancer or an intermediate phenotype. Correlation can be performed by standard statistical methods including, but not limited to, chi-squared test, Analyses of polymorphic variant, parametric linkage analysis, non-parametric linkage analysis, etc. and statistically significant correlations between polymorphic form(s) and phenotypic characteristics also can be used.

Genes and Polymorphic Variants

MTHFD1

Methylenetetrahydrofolate dehydrogenase (NADP+ dependent) 1, methenyltetrahydrofolate cyclohydrolase, formyltetrahydrofolate synthetase (MTHFD1) is a trifunctional enzyme localized to the cytoplasm. MTHFD1 has the further aliases HGNC:7432, MTHFC, and MTHFD. MTHFD1 has the further designations 5,10-methylenetetrahydrofolate dehydrogenase, 5,10-methylenetetrahydrofolate cyclohydrolase, 10-formyltetrahydrofolate synthetase; C1-THF synthase; MTHFC; MTHFD; NADP-dependent cyclohydrolase/formyltetrahydrofolate synthetase; cytoplasmic C-1-tetrahydrofolate synthase; methylenetetrahydrofolate dehydrogenase (NADP+ dependent), methenyltetrahydrofolate cyclohydrolase, formyltetrahydrofolate synthetase; methylenetetrahydrofolate dehydrogenase 1. MTHFD1 has been assigned Gene ID 4522, and is positioned on chromosome 14 at locus 14q24. Further information for MTHFD1 is found on the NCBI wesite in the Entrez Gene database and Online Mendelian Inheritance in Man (OMIM) website under entry +172460.

MTHFD1 nucleic acid and amino acid sequences relevant to the invention include genomic, cDNA, and fragments thereof. The particular sequences identified herein by sequence identification number and/or accession number are representative of MTHFD1 sequences. One of skill in the art can appreciate that there can be variability in the gene or gene fragment distinct from the polymorphism(s) of interest and that such allelic variants still fall within the scope of the invention. As the polymorphism will be reflected in both strands of the DNA, the screening in the context of the invention can involve one or both of the strand sequences. Accordingly, where the sequence for a given strand is provided, the invention also includes the use of its complement.

The following are representative sequences for MTHFD1. NM005956 includes coding nucleic acid sequence of MTHFD1 (SEQ ID NOS: 1 and 2, with SEQ ID NO: 2 providing the nucleic acid sequence of the coding region) and also provides the amino acid sequence of MTHFD1, which is the translation of the coding region (SEQ ID NO: 3). Other relevant sequence information includes J04031; NP005947; BC001014, AAH01014; BC009806; AAH09806; BC050420; AAH50420; J04031; AAA59574; P11586. Screening with a fragment of at least 30 nucleic acids is within the scope of the invention, however, smaller fragments are also possible provided that they comprise the relevant polymorphism(s) and provide a sequence unique in the human genome. An example of such a fragment is provided in SEQ ID NO: 4. The genomic sequence is provided in SEQ ID NO: 5 and corresponds to positions 63924886 and 63996474 inclusive in NC_000014. Screening with a genomic fragment of at least 30 nucleic acids is within the scope of the invention, however, smaller fragments are also possible provided that they comprise the relevant polymorphism(s) and provide a sequence unique in the human genome. An example of such a fragment is also provided in SEQ ID NO: 4. SEQ ID NOS: 1-5 indicate the variability corresponding to the MTHFD1 1958G>A polymorphism (at the nucleotide level: position 2011 in SEQ ID NO: 1; position 1958 in SEQ ID NO:

2; position 15 in SEQ ID NO: 4; 63978638 in the NC_000014 genomic sequence corresponding to position 53753 in SEQ ID NO: 5) and the Arg653Gln polymorphism in the amino acid sequence (SEQ ID NOS: 1 and 3). This polymorphism is given the designation rs2236225 in the SNP database of NCBI's Entrez. Allele frequencies for the MTHFD1 1958G>A polymorphic variant are as follows:

| Geographical/Ethnic Populations | A Allele Frequency |
|---|---|
| Ireland | 0.45 |
| The Netherlands | 0.45 |
| Germany | 0.40 |
| Italy | 0.45 |
| Turkey | 0.45 |
| Africa | 0.16 |
| Israel | 0.47 |
| Pakistan | 0.50 |
| Northern China | 0.24 |
| Mexico | 0.61 |
| Brazil | 0.79 |

[Brody et al., Am. J. Hum. Genet., 71: 1207-1215 (2002); Hol et al., Clin. Genet. 53:119-125 (1998); Akar & Akar, Acta Haematol., 102:199-200 (1999); Konrad et al., J. Neurol., 251:1242-1248 (2004); Cheng et al., Biomed. Environ. Sci., 18:58-64 (2005); Shi et al., Birth Defects Res Part A 67:545-549 (2003); DeMarco et al., 48th Annual Meeting of the Society for Research into Hydrocephalus and Spina Bifida, Dublin 23-26 June, 2004.]

MTHFD1L

Methylenetetrahydrofolate dehydrogenase (NADP+ dependent) 1-like (MTHFD1L) is a trifunctional enzyme localized to mitochondria with enzymtatic activity similar to MTHFD1, sharing at least one enzymatic activity with that enzyme. MTHFD1L has the further aliases HGNC:21055, DKFZp586G1517, FLJ21145, FTHFSDC1, dJ292B18.2, and further designations RP1-292B18.2; formyltetrahydrofolate synthetase domain containing 1; mitochondrial C1-tetrahydrofolate synthase; mitochondrial C1-tetrahydrofolate synthetase. MTHFD1L has been assigned Gene ID 25902, and is positioned on chromosome 6 at locus 6q25.1. Further information for MTHFD1L is found on the NCBI website in the Entrez Gene database.

MTHFD1L nucleic acid and amino acid sequences relevant to the invention include genomic, cDNA, and fragments thereof. The particular sequences identified herein by sequence identification number and/or accession number are representative of MTHFD1L sequences. One of skill in the art can appreciate that there can be variability in the gene or gene fragment distinct from the polymorphism(s) of interest and that such allelic variants still fall within the scope of the invention. As the polymorphism will be reflected in both strands of the DNA, the screening in the context of the invention can involve one or both of the strand sequences. Accordingly, where the sequence for a given strand is provided, the invention also includes the use of its complement.

The following are representative sequences for MTHFD1L. NM0015440 includes coding nucleic acid sequence of MTHFD1L (SEQ ID NOS: 6 and 7, with SEQ ID NO: 7 providing the nucleic acid sequence of the coding region) and also provides the translation of the coding region (SEQ ID NO: 8). These sequences correspond to a 3.6 kb transcript. AY374131 includes coding nucleic acid sequence of MTHFD1L (SEQ ID NOS: 9 and 10, with SEQ ID NO: 10 providing the nucleic acid sequence of the coding region) and amino acid sequence (SEQ ID NO: 11) for a 1.1 kb transcript of MTHFD1L. Other relevant sequence information includes NP056255; AA478842; AL117452; AV704883; BE735249; BQ062382; AL035086; CA142788; CAI42793; CAI42794; CAI42795; AL133260; CAC03667; AA478842; AB127387; BAD93193; AK024798; BAB15009; AK127089; AL117452; CAB55934; AV704883; AY374130; AAQ82696; AAQ82697; BC008629; AAH08629; BC017477; AAH17477; BE735249; BQ062382. Screening with a fragment of at least 30 nucleic acids is within the scope of the invention, however, smaller fragments are also possible provided that they comprise the relevant polymorphism(s) and provide a sequence unique in the human genome. The genomic sequence is provided in SEQ ID NO: 12 and corresponds to positions 151278805 and 151515137 inclusive in NC_000006. Screening with a genomic fragment of at least 30 nucleic acids is within the scope of the invention, however, smaller fragments are also possible provided that they comprise the relevant polymorphism(s) and provide a sequence unique in the human genome. An example of such a fragment is provided in SEQ ID NO: 13. SEQ ID NOS: 12 and 13 indicate the variability corresponding to the "ATT" short tandem repeat polymorphism at starting at position 151312078 in the source genomic sequence (position 33274 of SEQ ID NO: 12 and position 5 of SEQ ID NO: 13). This polymorphism is given the designation rs3832406 in the SNP database of NCBI's Entrez, and also corresponds to position 55374834 in NT_025741. As this polymorphism is located in an intron, the polymorphism is not designated in SEQ ID NOS: 6-11. In some embodiments, the relevant polymorphism has an effect on splicing, and accordingly an effect on the transcription and amino acid sequence encoded by the same.

Allele frequencies for the MTHFD1L rs3832406 "ATT" Intron 7 tandem repeat are as follows with Allele 1 comprising "ATT" repeated seven times, Allele 2 comprising "ATT" repeated eight times, and Allele 3 comprising "ATT" repeated nine times.

| Geographical/Ethnic Population | Allele 1 | Allele 2 | Allele 3 |
|---|---|---|---|
| Ireland | 0.64 | 0.21 | 0.15 |

The MTHFD1L gene produces two mRNA transcripts. The shorter one originates from the use of an alternative exon 8A that may be derived from an Alu element. Although not wishing to be bound by any particular theory, it appears that these alleles affect how efficiently alternative exon 8A is used. Any putative effect is relevant to folate metabolism since alternative exon 8A produces a premature stop codon that translates into a protein product that lacks a synthetase domain.

Other Diagnostic Genes and Polymorphic Variants

Polymorphic variants to be screened for are principally located in or in close proximity to the MTHFD1 and/or MTHFD1L genes. Representative, polymorphic variants that can be tested for in addition to MTHFD1 and/or MTHFD1 variant(s), include those associated with following described genes without limitation to polymorphism or gene. In some embodiments, the screened for polymorphic variants are correlated with the same disease. In some embodiments, the screened for polymorphic variants are correlated with different diseases.

MTHFR 5,10-methylenetetrahydrofolate reductase (NADPH) (MTHFR) is an enzyme involved in one-carbon metabolic pathways such as folate-dependent one-carbon pathways. MTHFD1 has the further alias HGNC:7436. MTHFR has the further designations methylenetetrahydrofolate reductase; methylenetetrahydrofolate reductase intermediate form. MTHFR has been assigned Gene ID 4524, and is positioned on chromosome 1 at locus 1q36.3. Further information for MTHFR is found on the NCBI website in the Entrez Gene database and Online Mendelian Inheritance in Man (OMIM) website under entry *607093. Polymorphic variants that can be screened for in addition to one or more of the MTHFD1 and MTHFD1L polymorphic variants relevant to the invention include the polymorphic variant described in the OMIM MTHFR entry *607093 as allelic variant 0.0003 MTHFR 677C>T, Ala222Val. Frosst et al., Mammalian Genome, 7:864-869 (1995), reported the 677C>T mutation in the MTHFR gene, resulting in an Ala222Val substitution. Polymorphic variants that can be screened for in addition to one or more of the MTHFD1 and MTHFD1L polymorphic variants relevant to the invention include the polymorphic variant described in the OMIM MTHFR entry *607093 as allelic variant 0.0004 MTHFR 1298A>C, Glu429. Van der Put et al., Am. J. Hum. Genet., 62:1044-1051 (1998), identified another polymorphism of the MTHFR gene: a 1298A>C mutation resulting in a Glu429Ala substitution.

MTHFR nucleic acid and amino acid sequences relevant to the invention include both genomic, cDNA, and fragments thereof. The particular sequences identified herein by sequence identification number and/or accession number are representative of MTHFR sequences. One of skill in the art can appreciate that there can be variability in the gene or gene fragment distinct from the polymorphism(s) of interest and that such allelic variants still fall within the scope of the invention. As the polymorphism will be reflected in both strands of the DNA, the screening in the context of the invention can involve one or both of the strand sequences. Accordingly, where the sequence for a given strand is provided, the invention also includes the use of its complement.

The following are representative sequences for MTHFR. NM005957 includes coding nucleic acid sequence of MTHFR and also provides the translation of the coding region. Other relevant sequence information includes AF105977; AAD17965; AF105978; AAD17965; AF105979; AAD17965; AF105980; AAD17965; AF105981; AAD17965; AF105982; AAD17965; AF105983; AAD17965; AF105984; AAD17965; AF105985; AAD17965; AF105986; AAD17965; AF105987; AAD17965; AF398930; AAN40863; AAN40864; AAN40865; AJ249275; CAB81551; CAB81552; AL953897; CAI15885; CAI15886; CAI15887; CAI15888; CAI15889; AY338232; AAP88033; AB209113; BAD92350; AJ237672; CAB41971; AY046560; AAL17646; AY046561; AAL17647; AY046562; AAL17648; AY046563; AAL17649; AY046564; AAL17650; AY046565; AAL17651; BC011614; BC018766; AAH18766; BC053509; AAH53509; P42898. Screening with a fragment of at least 30 nucleic acids is within the scope of the invention, however, smaller fragments are also possible provided that they comprise the relevant polymorphism(s) and provide a sequence unique in the human genome. The genomic sequence corresponds to positions 11780945 and 11800248 inclusive in NC_000001. Screening with a genomic fragments of at least 30 nucleic acids are within the scope of the invention, however, smaller fragments are also possible provided that they comprise the relevant polymorphism(s) and provide a sequence unique in the human genome. The variability corresponding to the 677C>T polymorphism occurs at position 11790510 in the genomic sequence. The variability corresponding to the 1298A>C polymorphism occurs at position 11792412 in the genomic sequence.

Allelic frequencies for MTHFR 677 C>T are as follows:

| Geographical/Ethnic Populations | T Allele Frequency |
| --- | --- |
| Ireland | 0.29 |
| Spain | 0.34 |
| France | 0.36 |
| Germany | 0.29 |
| The Netherlands | 0.27 |
| Russia | 0.27 |
| Italy | 0.41 |
| Southern Italy | 0.46 |
| Israel | 0.26 |
| Ashkenazi Jewish | 0.48 |
| Northern Han Chinese | 0.44 |
| Southern Han Chinese | 0.34 |
| Australian white | 0.29 |
| Mexico | 0.57 |
| African Americans | 0.12 |
| U.S. Caucasians | 0.32 |
| U.S. Hispanics | 0.45 |
| U.S. Asian | 0.21 |
| Canadian White | 0.25 |

[Wilcken et al., J. Med. Genet., 40:619-625 (2003); Rady et al., Am. J. Med. Genet., 107:162-168 (2002); Kirke et al., BMJ, 328:1535-1536 (2004); Konrad et al., J. Neurol., 251: 1242-1248 (2004).]

Factor II

Coagulation factor II (F2) is a factor that is cleaved from prothrombin to thrombin in the blood clotting cascade. F2 has the further aliases HGNC:3535 and PT. F2 has the further designations prothrombin; prothrombin B-chain; serine protease. F2 has been assigned Gene ID 2147, and is positioned on chromosome 11 at locus 11p11-q12. Further information for F2 is found on the NCBI website in the Entrez Gene database and Online Mendelian Inheritance in Man (OMIM) website under entry +176930. Polymorphic variants that can be screened for in addition to one or more of the MTHFD1 and MTHFD1L polymorphic variants relevant to the invention include the polymorphic variant described in the OMIM Factor V Deficiency +176930 entry as allelic variant 0.0009; 20210G>A. Poort et al., Blood, 88:3698-3703 (1996), described this common genetic variation in the 3-prime untranslated region of the gene that is associated with elevated plasma prothrombin levels and an increased risk of venous thrombosis: a G-to-A transition at position 20210, see Degen and Davie, Biochemistry 26:6165-6177 (1987).

F2 nucleic acid and amino acid sequences relevant to the invention include both genomic, cDNA, and fragments thereof. The particular sequences identified herein by sequence identification number and/or accession number are representative of F2 sequences. One of skill in the art can appreciate that there can be variability in the gene or gene fragment distinct from the polymorphism(s) of interest and that such allelic variants still fall within the scope of the invention. As the polymorphism will be reflected in both strands of the DNA, the screening in the context of the invention can involve one or both of the strand sequences. Accordingly, where the sequence for a given strand is provided, the invention also includes the use of its complement.

The following are representative sequences for F2. NM000506 includes coding nucleic acid sequence of F2 and also provides the translation of the coding region. Other relevant sequence information includes M17262, V00595, AF478696; AAL77436; AF493953; AAM11680; AJ544114;

CAD80258; M17262; AAC63054; S50162; AAB24476; AY344793; AAR08142; AY344794; AAR08143; BC051332; AAH51332; M33031; AAA60220; V00595; CAA23842; P00734. Screening with a fragment of at least 30 nucleic acids is within the scope of the invention, however, smaller fragments are also possible provided that they comprise the relevant polymorphism(s) and provide a sequence unique in the human genome. The genomic sequence corresponds to positions 46697331 and 46717631 inclusive in NC_000011. Screening with a genomic fragment of at least 30 nucleic acids is within the scope of the invention, however, smaller fragments are also possible provided that they comprise the relevant polymorphism(s) and provide a sequence unique in the human genome. This polymorphism is provided in the SNP database of NCBI's Entrez.

Factor V

Coagulation factor V (proaccelerin, labile factor) (F5) is a factor in the blood clotting cascade. F5 has the further aliases HGNC:3542, FVL, PCCF, factor V. F5 has the further designations activated protein c cofactor; coagulation factor V; coagulation factor V jinjiang A2 domain; factor V Leiden; labile factor. F5 has been assigned Gene ID 2153, and is positioned on chromosome 1 at locus 1q23. Further information for F5 is found on the NCBI website in the Entrez Gene database and Online Mendelian Inheritance in Man (OMIM) website under entry +227400. Polymorphic variants that can be screened for in addition to one or more of the MTHFD1 and MTHFD1L polymorphic variants relevant to the invention include the polymorphic variant described in the OMIM Factor V Deficiency 227400 entry as allelic variant 0.0001, Arg506Gln, 1691G>A, "Factor V Leiden." The Factor V Leiden polymorphic variant was reported by Bertina et al., Nature, 369:64-67 (1994).

F5 nucleic acid and amino acid sequences relevant to the invention include both genomic, cDNA, and fragments thereof. The particular sequences identified herein by sequence identification number and/or accession number are representative of F5 sequences. One of skill in the art can appreciate that there can be variability in the gene or gene fragment distinct from the polymorphism(s) of interest and that such allelic variants still fall within the scope of the invention. As the polymorphism will be reflected in both strands of the DNA, the screening in the context of the invention can involve one or both of the strand sequences. Accordingly, where the sequence for a given strand is provided, the invention also includes the use of its complement.

The following are representative sequences for F5. NM000130 includes coding nucleic acid sequence for F5 and also provides the translation of the coding region. Other relevant sequence information includes AH005274, M14335, AF119360; AAF32515; AF285083; AAG30113; AY046060; AAL09164; AY136818; AAN12307; AY364535; AAQ55063; L32755; AAB59401; L32779; AAB59401; Z99572; CAB16748; CAI23065; AJ297254; CAC82572; AJ297255; CAC82573; M14335; AAB59532; M16967; AAA52424; M94010; AAA52416; P12259. Screening with a fragment of at least 30 nucleic acids is within the scope of the invention, however, smaller fragments are also possible provided that they comprise the relevant polymorphism(s) and provide a sequence unique in the human genome. The genomic sequence corresponds to positions 166287379 and 166215067 inclusive in NC_000001. Screening with a genomic fragment of at least 30 nucleic acids is within the scope of the invention, however, smaller fragments are also possible provided that they comprise the relevant polymorphism(s) and provide a sequence unique in the human genome.

TCNII

Transcobalamin II (TCNII) is a Vitamin $B_{12}$ binding protein. TCNII has the further aliases HGNC:1 1653, D22S676, D22S750, and TC2. TCNII has been assigned Gene ID 6948, and is positioned on chromosome 22 at locus 22q12.2. Further information for TCNII is found on the NCBI website in the Entrez Gene database and Online Mendelian Inheritance in Man (OMIM) website under entry +275350.

TCNII nucleic acid and amino acid sequences relevant to the invention include both genomic, cDNA, fragments, and products thereof. The particular sequences identified herein by sequence identification number and/or accession number are representative of TCNII sequences. One of skill in the art can appreciate that there can be variability in the gene or gene fragment distinct from the polymorphism(s) of interest and that such allelic variants still fall within the scope of the invention. As the polymorphism will be reflected in both strands of the DNA, the screening in the context of the invention can involve one or both of the strand sequences. Accordingly, where the sequence for a given strand is provided, the invention also includes the use of its complement.

The following are representative sequences for TCNII. NM000355 includes coding nucleic acid sequence for TCNII (SEQ ID NOS: 14 and 15, with SEQ ID NO: 15 providing the nucleic acid sequence of the coding region) and also provides the translation of the coding region (SEQ ID NO: 16). Other relevant sequence information includes AF047576; AAC05491; AF076647; AAG24506; BC001176; AAH01176; BC011239; AAH111239; CR456591; CAG30477; L02647; AAA61056; L02648; AAA61057; M60396; AAA61054; P20062; AAB25526. Screening with a fragment of at least 30 nucleic acids is within the scope of the invention, however, smaller fragments are also possible provided that they comprise the relevant polymorphism(s) and provide a sequence unique in the human genome. An example of such a fragment is provided in SEQ ID NO: 17. The genomic sequence is provided in SEQ ID NO: 18 and corresponds to positions 29327715 and 29347601 inclusive in NC_000022. Screening with a genomic fragment of at least 30 nucleic acids is within the scope of the invention, however, smaller fragments are also possible provided that they comprise the relevant polymorphism(s) and provide a sequence unique in the human genome. An example of such a fragment is also provided in SEQ ID NO: 17. SEQ ID NOS: 14-18 indicate the variability corresponding to the 776C>G polymorphism (at the nucleotide level: position 934 in SEQ ID NO: 14; position 776 in SEQ ID NO: 15; position 16 in SEQ ID NO: 17; position 8450 in SEQ ID NO: 18-position 29336164 in the source genomic sequence) and the Pro259Arg polymorphism in the amino acid sequence (SEQ ID NOS: 14 and 16). This polymorphism is given the designation rs1801198 in the SNP database of NCBI's Entrez.

The invention also includes use of other polymorphic variants of the genes and proteins described herein. Use of both the nucleic acids described herein and their complements are within the scope of the invention. In connection with the provision and description of nucleic acid sequences, the references herein to gene names and to GenBank and OMIM reference numbers provide the relevant sequences, recognizing that the described sequences will, in most cases, also have other corresponding allelic variants. Although the referenced sequences may contain sequencing error, such error does not interfere with identification of a relevant gene or portion of a gene, and can be readily corrected by redundant sequencing of the relevant sequence (preferably using both strands of DNA). Nucleic acid molecules or sequences can be readily obtained or determined utilizing the reference sequences.

Molecules such as nucleic acid hybridization probes and amplification primers can be provided and are described by the selected portion of the reference sequence with correction if appropriate. In some embodiments, probes comprise 5, 6, 10, 12, 13, 14, 15, 16, 17, 18, 19, 20, 23, 25, 27, 30, 35, 40, 45, 50, or more nucleotides.

Diagnosis

The terms "disease" or "condition" are commonly recognized in the art and designate the presence of signs and/or symptoms in an individual or patient that are generally recognized as abnormal. Unless indicated as otherwise, the terms "disease," "disease state," "condition," "disorder," and "complication" can be used interchangeably. Diseases or conditions can be diagnosed and categorized based on pathological changes. Signs can include any objective evidence of a disease such as changes that are evident by physical examination of a patient or the results of diagnostic tests which may include, among others, laboratory tests to determine the presence of polymorphic variants or variant forms of certain genes in a patient. Symptoms can include a patient's perception of an abnormal condition that differs from normal function, sensation, or appearance, which may include, for example, physical disabilities, morbidity, pain, and other changes from the normal condition experienced by an individual. Various diseases or conditions include, but are not limited to, those categorized in medical texts.

Unless otherwise indicated, the term "suffering from a disease or condition" can refer to a person that currently has signs and symptoms, or is more likely to develop such signs and symptoms than a normal person in the population. For example, a person suffering from a condition can include a developing fetus, a person subject to a treatment or environmental condition that enhances the likelihood of developing the signs or symptoms of a condition, or a person who is being given or will be given a treatment that increases the likelihood of the person developing a particular condition. Methods of the invention relating to treatments of patients can include primary treatments directed to a presently active disease or condition, secondary treatments that are intended to cause a biological effect relevant to a primary treatment, and prophylactic treatments intended to delay, reduce, or prevent the development of a disease or condition, as well as treatments intended to cause the development of a condition different from that which would have been likely to develop in the absence of the treatment.

Combined detection of several such polymorphic variants typically increases the probability of an accurate diagnosis. Analysis of the polymorphisms of the invention can be combined with that of other polymorphisms or other risk factors such as family history. Polymorphisms can be used to diagnose a disease at the pre-symptomatic stage, as a method of post-symptomatic diagnosis, as a method of confirmation of diagnosis or as a post-mortem diagnosis. Ethical issues to be considered in screening and diagnosis are discussed generally in Reich, et al., Genet. Med., 5:133-143 (2003).

Pregnancy-Related Complications

Pregnancy-related complications include not just complications that occur during the course of pregnancy, but also include infertility complications. That is, a pregnancy-related complication can also, or in the alternative, involve a complication that prevents pregnancy from occurring or diminishes the probability that pregnancy will occur. Accordingly, the polymorphic variants relevant to the invention can be correlated with infertility. Particular pregnancy-related complications are described as follows without limitation to other relevant pregnancy-related complications correlating with one or more polymorphic variants relevant to the invention. Screening for polymorphic variants in the context of pregnancy-related complications can include screening of the mother as well as the father and the unborn child(ren). Both males and females can be screened using the methods of the invention. A female screened may be of any age, born or unborn, and need not be pregnant when screened. In some embodiments, the subject screened is female and has had complications becoming pregnant, which can include any number of different infertility factors. In some embodiments, the woman screened has been pregnancy previously but has suffered complications during pregnancy. In some embodiments, the woman screened is pregnant, but is not carrying an embryo or fetus with a neural tube defect. The sample screened from any subject may be derived from any number of different sources such as cells, tissues, and organs. In some embodiments, the sample comprises blood. In some embodiments, the sample comprises an egg and/or sperm. In some embodiments, the sample screened comprises a somatic cell.

Placental Abruption

The diagnosis of abruptio placentae or placental abruption can be based on hemorrhage and accumulation of blood between the placenta and the wall of the uterus. In some embodiments, diagnosis is based on a sudden rupture of the spiral arteries, resulting in the premature separation of a normally implanted placenta. Severe placental abruption is generally characterized by more extensive manifestations of placental abruption and can also comprise worse clinical outcomes such as death of the mother and or children. In some embodiments, severe placental abruption is diagnosis based on a retroplacental clot and/or accidental haemorrhage with associated clinical signs of abruption and/or a statement in the case records that the patient was a definite case of abruptio placentae. Data on gestational age at delivery, maternal hypertension, maternal blood transfusion, and pregnancy outcome can be collected. Control pregnancies can be selected from women with no history of abruptio placentae, and can be matched for the same date and clinic as the cases where the genetically tested blood sample was provided.

Diagnosis for an increased susceptibility for severe placental abruption is rendered when a particular polymorphic variant that has been correlated with severe placental abruption is identified. In some embodiments, the polymorphic variant is an adenosine at position 1958 of MTHFD1. In some embodiments, the subject tested is homozygous for the 1958A variant, in some embodiments, the subject is heterozygous for the 1958A variant.

Miscarriage

Miscarriage is the loss of one or more children before birth. In some embodiments, the miscarriage occurs in the second trimester. In other embodiments, the miscarriage occurs in the first or third trimester. In some embodiments, the miscarriage has no clinical explanation. A miscarriage can comprise a spontaneous abortion and/or fetal death.

Diagnosis for an increased susceptibility for miscarriage is rendered when a particular polymorphic variant that has been correlated with miscarriage is identified. This correlation can be with first, second, and/or third trimester miscarriage. In some embodiments, the correlation is with unexplained second trimester miscarriage. In some embodiments, the polymorphic variant is an adenosine at position 1958 of MTHFD1. In some embodiments, the subject tested is homozygous for the 1958A variant, in some embodiments, the subject is heterozygous for the 1958A variant.

Neural Tube Defects

Neural tube defects include, for example, anencephaly, encephalocele, iniencephaly, and spina bifida, and are diagnosed by symptoms commonly accepted in medical field. Diagnosis for an increased susceptibility for a neural tube defect is rendered when a particular polymorphic variant that has been correlated with a neural tube defect is identified. In some embodiments, the increased susceptibility for a neural tube defect is rendered when a 7-repeat variant of the MTHFD1L ATT polymorphism rs3832406 (position 55374834 in NT_025741) is identified. In some embodiments, the subject tested is homozygous for the 7-repeat ATT polymorphism, in some embodiments the subject is heterozygous for the 7-repeat ATT polymorphism. In some embodiments, one or two copies of a 8-repeat repeat variant of the MTHFD1L polymorphism rs3832406, wherein the 8-repeat variant is correlated with a protective effect, that is a decreased susceptibility for a NTD. In some embodiments, diagnosis is based not only on a polymorphic variant in the MTHFD1L gene, but also with the MTHFD1 1958A variant. In some embodiments, the subject tested is homozygous for the 1958A variant, in some embodiments, the subject is heterozygous for the 1958A variant.

Neoplastic Diseases

Diagnosis for an increased susceptibility for a drug dosage complication can be rendered based on a polymorphic variant in MTHFD1L that has been correlated with such a complication. In some embodiments, the increased susceptibility for a neural tube defect is rendered when a 7-repeat variant of the MTHFD1L ATT polymorphism rs3832406 (position 55374834 in NT_025741) is identified. In some embodiments, the subject tested is homozygous for the 7-repeat ATT polymorphism, in some embodiments the subject is heterozygous for the 7-repeat ATT polymorphism.

As used herein, the term "cancer" is meant any malignant growth or tumor caused by abnormal and uncontrolled cell division that may spread to other parts of the body through the lymphatic system or the blood stream. The cancer can be, for example, breast cancer, prostate cancer, lung cancer, colon cancer, rectal cancer, urinary bladder cancer, non-Hodgkin lymphoma, melanoma, renal cancer, pancreatic cancer, cancer of the oral cavity, pharynx cancer, ovarian cancer, thyroid cancer, stomach cancer, brain cancer, multiple myeloma, esophageal cancer, liver cancer, cervical cancer, larynx cancer, cancer of the intrahepatic bile duct, acute myeloid leukemia, soft tissue cancer, small intestine cancer, testicular cancer, chronic lymphocytic leukemia, Hodgkin lymphoma, chronic myeloid cancer, acute lymphocytic cancer, cancer of the anus, anal canal, or anorectum, cancer of the vulva or cancer of the neck, gallbladder, pleura, malignant mesothelioma, bone cancer, cancer of the joints, hypopharynx cancer, cancer of the eye, cancer of the nose, nasal cavity, neck, or middle ear, nasopharynx cancer, ureter cancer, peritoneum, omentum, or mesentery cancer, or gastrointestinal carcinoid tumor.

Those skilled in the art will understand whether the polymorphic variants or gene forms in normal or disease cells are most indicative of the expected treatment response, and will generally utilize a diagnostic test with respect to the appropriate cells. Such a cell type indication or suggestion can be contained in a regulatory statement, for example, on a label or in a product insert.

Alzheimer's Disease

Intermediates and defects in one carbon metabolic pathways have been shown to play a role in Alzheimer's disease. Accordingly, the invention includes methods of and materials for predicting altered susceptibility to Alzheimer's disease and response to Alzheimer's disease therapeutic agents based on correlation with the polymorphic variants discussed herein. The invention is also relevant to other central nervous system (CNS) diseases and therapeutic agents.

Cardiovascular Disease

Intermdiates and defects in one carbon metabolic pathways have been shown to play a role in some cardiovascular diseases. Accordingly, the invention includes methods of and materials for predicting altered susceptibility to cardiovascular disease and response to cardiovascular disease therapeutic agents based on correlation with the polymorphic variants discussed herein.

Detection Probes

The detection of the presence or absence of a polymorphic variant can involve contacting a nucleic acid sequence corresponding to one of the genes identified above or a product of such a gene with a probe. The probe is able to distinguish a particular form of the gene, gene product, polymorphic variant allele product, or allele product, or the presence or a particular polymorphic variant or polymorphic variants, for example, by differential binding or hybridization. The term "probe" refers to a molecule that can detectably distinguish between target molecules differing in structure. Detection can be accomplished in a variety of different ways depending on the type of probe used and the type of target molecule. Thus, for example, detection may be based on discrimination of activity levels of the target molecule, but preferably is based on detection of specific binding. Examples of such specific binding include antibody binding and nucleic acid probe hybridization. Probes can comprise one or more of the following, a protein, carbohydrate, polymer, or small molecule, that is capable of binding to one polymorphic variant or variant form of the gene or gene product to a greater extent than to a form of the gene having a different base at one or more polymorphic variant sites, such that the presence of the polymorphic variant or variant form of the gene can be determined. A probe can incorporate one or more markers including, but not limited to, radioactive labels, such as radionuclides, fluorophores or fluorochromes, peptides, enzymes, antigens, antibodies, vitamins or steroids. A probe can distinguishe at least one of the polymeric variant described herein. The probe can also have specificity for the particular gene or gene product, at least to an extent such that binding to other genes or gene products does not prevent use of the assay to identify the presence or absence of the particular polymorphic variant or polymorphic variants of interest.

Nucleic Acids

The nucleic acid molecules relevant to the invention can readily be obtained in a variety of ways, including, without limitation, chemical synthesis, cDNA or genomic library screening, expression library screening, and/or PCR amplification of cDNA. These methods and others useful for isolating such DNA are set forth, for example, by Sambrook, et al., "Molecular Cloning: A Laboratory Manual," Cold Spring Harbor Laboratory Press, Cold Spring Harbor, N.Y. (1989), by Ausubel, et al., eds., "Current Protocols In Molecular Biology," Current Protocols Press (1994), and by Berger and Kimmel, "Methods In Enzymology: Guide To Molecular Cloning Techniques," vol. 152, Academic Press, Inc., San Diego, Calif. (1987). Nucleic acid sequences are mammalian sequences. In some embodiments, the nucleic acid sequences are human, rat, and mouse.

Chemical synthesis of a nucleic acid molecule can be accomplished using methods well known in the art, such as those set forth by Engels et al., Angew. Chem. Intl. Ed., 28:716-734 (1989). These methods include, inter alia, the phosphotriester, phosphoramidite and H-phosphonate methods of nucleic acid synthesis. Nucleic acids larger than about 100 nucleotides in length can be synthesized as several fragments, each fragment being up to about 100 nucleotides in length. The fragments can then be ligated together to form a full length nucleic acid encoding the polypeptide. A preferred method is polymer-supported synthesis using standard phosphoramidite chemistry.

Alternatively, the nucleic acid may be obtained by screening an appropriate cDNA library prepared from one or more tissue source(s) that express the polypeptide, or a genomic library from any subspecies. The source of the genomic library may be any tissue or tissues from any mammalian or other species believed to harbor a gene encoding a protein relevant to the invention. The library can be screened for the presence of a cDNA/gene using one or more nucleic acid probes (oligonucleotides, cDNA or genomic DNA fragments that possess an acceptable level of homology to the gene or gene homologue cDNA or gene to be cloned) that will hybridize selectively with the gene or gene homologue cDNA(s) or gene(s) that is(are) present in the library. The probes preferably are complementary to or encode a small region of the DNA sequence from the same or a similar species as the species from which the library was prepared. Alternatively, the probes may be degenerate, as discussed below. After hybridization, the blot containing the library is washed at a suitable stringency, depending on several factors such as probe size, expected homology of probe to clone, type of library being screened, number of clones being screened, and the like. Stringent washing solutions are usually low in ionic strength and are used at relatively high temperatures.

Another suitable method for obtaining a nucleic acid in accordance with the invention is the polymerase chain reaction (PCR). In this method, poly(A)+RNA or total RNA is extracted from a tissue that expresses the gene product. cDNA is then prepared from the RNA using the enzyme reverse transcriptase. Two primers typically complementary to two separate regions of the cDNA (oligonucleotides) are then added to the cDNA along with a polymerase such as Taq polymerase, and the polymerase amplifies the cDNA region between the two primers.

The invention provides for the use of isolated, purified or enriched nucleic acid sequences of 15 to 500 nucleotides in length, 15 to 100 nucleotides in length, 15 to 50 nucleotides in length, and 15 to 30 nucleotides in length, which have sequence that corresponds to a portion of one of the genes identified for aspects above. In some embodiments the nucleic acid is at least 17, 20, 22, or 25 nucleotides in length. In some embodiments, the nucleic acid sequence is 30 to 300 nucleotides in length, or 45 to 200 nucleotides in length, or 45 to 100 nucleotides in length. In some embodiments, the probe is a nucleic acid probe at least 15, 17 20, 22 25, 30, 35, 40, or more nucleotides in length, or 500, 250, 200, 100, 50, 40, 30 or fewer nucleotides in length. In preferred embodiments, the probe has a length in a range from any one of the above lengths to any other of the above lengths including endpoints. The nucleic acid sequence includes at least one polymorphic variant site. Such sequences can, for example, be amplification products of a sequence that spans or includes a polymorphic variant site in a gene identified herein. A nucleic acid with such a sequence can be utilized as a primer or amplification oligonucleotide that is able to bind to or extend through a polymorphic variant site in such a gene. Another example is a nucleic acid hybridization probe comprised of such a sequence. In such probes, primers, and amplification products, the nucleotide sequence can contain a sequence or site corresponding to a polymorphic variant site or sites, for example, a polymorphic variant site identified herein. The design and use of allele-specific probes for analyzing polymorphisms is known generally in the art, see, for example, Saiki et al., Nature 324:163-166 (1986); Dattagupta, EP 235, 726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. A nucleic acid hybridization probe may span two or more polymorphic variant sites. Unless otherwise specified, a nucleic acid probe can include one or more nucleic acid analogs, labels or other substituents or moieties so long as the base-pairing function is retained. The nucleic acid sequence includes at least one polymorphic variant site. The probe may also comprise a detectable label, such as a radioactive or fluorescent label. A variety of other detectable labels are known to those skilled in the art. Nucleic acid probe can also include one or more nucleic acid analogs.

In connection with nucleic acid probe hybridization, the term "specifically hybridizes" indicates that the probe hybridizes to a sufficiently greater degree to the target sequence than to a sequence having a mismatched base at least one polymorphic variant site to allow distinguishing of such hybridization. The term "specifically hybridizes" means that the probe hybridizes to the target sequence, and not to non-target sequences, at a level which allows ready identification of probe/target sequence hybridization under selective hybridization conditions. "Selective hybridization conditions" refer to conditions that allow such differential binding. Similarly, the terms "specifically binds" and "selective binding conditions" refer to such differential binding of any type of probe, and to the conditions that allow such differential binding. Hybridization reactions to determine the status of variant sites in patient samples can be carried out with two different probes, one specific for each of the possible variant nucleotides. The complementary information derived from the two separate hybridization reactions is useful in corroborating the results.

A variety of variables can be adjusted to optimize the discrimination between two variant forms of a gene, including changes in salt concentration, temperature, pH and addition of various compounds that affect the differential affinity of GC vs. AT base pairs, such as tetramethyl ammonium chloride. [See Current Protocols in Molecular Biology, Ausubel et al. (Editors), John Wiley & Sons.] Hybridization conditions should be sufficiently stringent such that there is a significant difference in hybridization intensity between alleles, and preferably an essentially binary response, whereby a probe hybridizes to only one of the alleles. Hybridizations are usually performed under stringent conditions that allow for specific binding between an oligonucleotide and a target nucleic acid containing one of the polymorphic sites described herein or identified using the techniques described herein. Stringent conditions are defined as any suitable buffer concentrations and temperatures that allow specific hybridization of the oligonucleotide to highly homologous sequences spanning at least one polymorphic site and any washing conditions that remove non-specific binding of the oligonucleotide. For example, conditions of 5×SSPE (750 mM NaCl, 50 mM Na Phosphate, 5 mM EDTA, pH 7.4) and a temperature of 25-30° C. are suitable for allele-specific probe hybridizations. The washing conditions usually range from room temperature to 60° C. Some probes are designed to hybridize to a segment of target DNA such that the polymorphic site aligns with a central position of the probe. This probe design achieves good discrimination in hybridization between different allelic forms.

Allele-specific probes are can be used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence. The polymorphisms can also be identified by hybridization to nucleic acid arrays, some examples of which are described by WO 95/11995. Arrays may be provided in the form of a multiplex chip.

One use of probe(s) is as a primer(s) that hybridizes to a nucleic acid sequence containing at least one sequence polymorphic variant. Preferably such primers hybridize to a sequence not more than 300 nucleotides, more preferably not more than 200 nucleotides, still more preferably not more than 100 nucleotides, and most preferably not more than 50 nucleotides away from a polymorphic variant site which is to be analyzed. Preferably, a primer is 100 nucleotides or fewer in length, more preferably 50 nucleotides or fewer, still more preferable 30 nucleotides or fewer, and most preferably 20 or fewer nucleotides in length. In some embodiments, the set includes primers or amplification oligonucleotides adapted to bind to or extend through a plurality of sequence polymorphic variants in a gene(s) identified herein. In some embodiments, the plurality of polymorphic variants comprises a haplotype. In certain embodiments, the oligonucleotides are designed and selected to provide polymorphic variant-specific amplification.

Proteins and Expression of Nucleic Acids

Polymorphic variant alleles or fragments thereof can be expressed in an expression vector in which a variant gene is operably linked to a native or other promoter. Usually, the promoter is a eukaryotic promoter for expression in a mammalian cell. The transcription regulation sequences typically include a heterologous promoter and optionally an enhancer that is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof. Host cells can be selected to process the variant gene product to produce an appropriate mature polypeptide. Processing includes glycosylation, ubiquitination, disulfide bond formation, and general post-translational modification.

The protein can be isolated by conventional means of protein biochemistry and purification to obtain a substantially pure product, i.e., 80, 95 or 99% free of cell component contaminants, as described in Jacoby, Methods in Enzymology Volume 104, Academic Press, New York (1984); Scopes, Protein Purification, Principles and Practice, 2nd Edition, Springer-Verlag, New York (1987); and Deutscher (ed), Guide to Protein Purification, Methods in Enzymology, Vol. 182 (1990). If the protein is secreted, it can be isolated from the supernatant in which the host cell is grown. If not secreted, the protein can be isolated from a lysate of the host cells.

In addition to substantially full-length polypeptides expressed by variant genes, the invention includes use of biologically active fragments of the polypeptides, or analogs thereof, including organic molecules that simulate the interactions of the peptides. Biologically active fragments include any portion of the full-length polypeptide that confers a biological function on the variant gene product, including ligand binding and antibody binding. Ligand binding includes binding by nucleic acids, proteins or polypeptides, small biologically active molecules or large cellular structures.

Antibodies

Another type of probe is a peptide or protein, for example, an antibody or antibody fragment that specifically or preferentially binds to a polypeptide expressed by a particular form of a gene as characterized by the presence or absence of at least one polymorphic variant. Such antibodies may be polyclonal or monoclonal antibodies, and can be prepared by methods well-known in the art.

Antibodies can be used to probe for presence of a given polymorphism variant for those polymorphism variants that have an effect on the polypeptide encoded by the gene. For example, an antibody can recognize a change in one or more amino acid residues in the resulting protein. In some embodiments, the antibody is used to recognize polypeptides encoded by differential splice variants. If the polymorphism introduces or eliminates a surface feature of the protein such as a glycosylation site, lipid modification, etc., an antibody can also be used to identify a particular variant.

Polyclonal and/or monoclonal antibodies and antibody fragments capable of binding to a portion of the gene product relevant for identifying a given polymorphism variant are provided. Antibodies can be made by injecting mice or other animals with the variant gene product or synthetic peptide fragments thereof. Monoclonal antibodies are screened as are described, for example, in Harlow & Lane, Antibodies, A Laboratory Manual, Cold Spring Harbor Press, New York (1988); Goding, Monoclonal antibodies, Principles and Practice (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

Polyclonal or monoclonal therapeutic antibodies useful in practicing this invention can be prepared in laboratory animals or by recombinant DNA techniques using the following methods. Polyclonal antibodies are raised in animals by multiple subcutaneous (sc) or intraperitoneal (ip) injections of the gene product molecule or fragment thereof in combination with an adjuvant such as Freund's adjuvant (complete or incomplete). To enhance immunogenicity, it may be useful to first conjugate the gene product molecule or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl, or $R^1N=C=NR$, where R and $R^1$ are different allyl groups. Alternatively, immunogenic conjugates can be produced recombinantly as fusion proteins.

Animals are immunized against the immunogenic conjugates or derivatives (such as a fragment containing the target amino acid sequence) by combining about 1 mg or about 1 microgram of conjugate (for rabbits or mice, respectively)

with about 3 volumes of Freund's complete adjuvant and injecting the solution intradermally at multiple sites. Approximately 7 to 14 days later, animals are bled and the serum is assayed for antibody titer. Animals are boosted with antigen repeatedly until the titer plateaus. The animal can be boosted with the same molecule or fragment thereof as was used for the initial immunization, but conjugated to a different protein and/or through a different cross-linking agent. In addition, aggregating agents such as alum are used in the injections to enhance the immune response.

Monoclonal antibodies can be prepared by recovering spleen cells from immunized animals and immortalizing the cells in conventional fashion, e.g. by fusion with myeloma cells. The clones are then screened for those expressing the desired antibody. The monoclonal antibody preferably does not cross-react with other gene products.

Preparation of antibodies using recombinant DNA methods such as the phagemid display method, may be accomplished using commercially available kits, as for example, the Recombinant Phagemid Antibody System available from Pharmacia (Uppsala, Sweden), or the SurfZAP™ phage display system (Stratagene Inc., La Jolla, Calif.).

Bispecific antibodies that specifically bind to one protein and that specifically bind to other antigens relevant to pathology and/or treatment are produced, isolated, and tested using standard procedures that have been described in the literature. [See, e.g., Pluckthun & Pack, Immunotechnology, 3:83-105 (1997); Carter, et al., J. Hematotherapy, 4:463-470 (1995); Renner & Pfreundschuh, Immunological Reviews, 1995, No. 145, pp. 179-209; Pfreundschuh U.S. Pat. No. 5,643,759; Segal, et al., J. Hematotherapy, 4:377-382 (1995); Segal, et al., Immunobiology, 185:390-402 (1992); and Bolhuis, et al., Cancer Immunol. Immunother., 34: 1-8 (1991).]

Transgenic Animals

The invention further provides the making and use of transgenic nonhuman animals capable of expressing an exogenous variant gene and/or having one or both alleles of an endogenous variant gene inactivated. Expression of an exogenous variant gene is usually achieved by operably linking the gene to a promoter and optionally an enhancer, and microinjecting the construct into a zygote. [See Hogan et al., "Manipulating the Mouse Embryo, A Laboratory Manual," Cold Spring Harbor Laboratory.] Inactivation of endogenous variant genes can be achieved by forming a transgene in which a cloned variant gene is inactivated by insertion of a positive selection marker. [See Capecchi, Science 244:1288-1292 (1989).] The transgene is then introduced into an embryonic stem cell, where it undergoes homologous recombination with an endogenous variant gene. Mice and other rodents are preferred animals. Such animals provide useful drug screening systems.

The nucleic acids relevant to the invention can be used to generate genetically modified non-human animals or site specific gene modifications in cell lines. The term "transgenic" is intended to encompass genetically modified animals having a deletion or other knock-out of an endogenous gene, having an exogenous allele that is stably transmitted in the host cells, and/or having an exogenous allele promoter operably linked to a reporter gene. Transgenic animals may be made through homologous recombination, where the allele locus is altered. Alternatively, a nucleic acid construct is randomly integrated into the genome. Vectors for stable integration include plasmids, retroviruses and other animal viruses, YACs, and the like. Transgenic mammals or relevance include cows, pigs, goats, horses, etc., and particularly rodents, e.g. rats, mice, etc.

Transgenic animals can be made having exogenous genes comprising the polymorphic variants relevant to the invention so as to "humanize" the animal in respect that gene(s), such a process involves deletion of the analogous endogenous gene when appropriate. The exogenous gene is usually either from a different species than the animal host, or is otherwise altered in its coding or non-coding sequence. The introduced gene can be a wild-type gene, naturally occurring polymorphism, or a genetically manipulated sequence, for example those previously described with deletions, substitutions or insertions in the coding or non-coding regions. Where the introduced gene is a coding sequence, it usually operably linked to a promoter, which may be constitutive or inducible, and other regulatory sequences required for expression in the host animal. A detectable marker, such as lac Z can be introduced together with the exogenous gene to demonstrate incorporatation of the exogenous gne.

The modified cells or animals are useful in the study of the physiological effect, if any, of the polymorphic variant. Animals can be used in functional studies, drug screening, etc., for example, to determine the effect of a candidate drug. By providing expression of a polymorphic variant in cells in which it is otherwise not normally produced, one can induce changes in cell behavior. Transgenic animals are also useful as part of a preclinical program.

DNA constructs for homologous recombination can comprise at least a portion of the polymorphic variant with the desired genetic modification, and can include regions of homology to the target locus. DNA constructs for random integration need not include regions of homology to mediate recombination. Conveniently, markers for positive and negative selection can be included. Methods for generating cells having targeted gene modifications through homologous recombination are known in the art. For various techniques for transfecting mammalian cells, see Keown et al., Methods in Enzymology 185:527-537 (1990).

Screening Techniques for Identifying Polymorphic Variants

The molecules and probes relevant to the invention can be used in screening techniques. A variety of screening techniques are known in the art for detecting the presence of one or more copies of one or more polymorphic variants in a sample or from a subject. Many of these assays have been reviewed by Landegren et al., Genome Res., 8:769-776, 1998. Determination of polymorphic variants within a particular nucleotide sequence among a population can be determined by any method known in the art, for example and without limitation, direct sequencing, restriction length fragment polymorphism (RFLP), single-strand conformational analysis (SSCA), denaturing gradient gel electrophoresis (DGGE) [see, e.g., Van Orsouw et al., Genet Anal., 14(5-6): 205-13 (1999)], heteroduplex analysis (HET) [see, e.g., Ganguly A, et al., Proc Natl Acad Sci USA. 90 (21):10325-9 (1993)], chemical cleavage analysis (CCM) [see, e.g., Ellis T P, et al., Human Mutation 11(5):345-53 (1998)] (either enzymatic as with T4 Endonuclease 7, or chemical as with osmium tetroxide and hydroxylamine) and ribonuclease cleavage. Screening for polymorphic variants can be performed when a polymorphic variant is already known to be associated with a particular disease or condition. In some embodiments, the screening is performed in pursuit of identifying one or more polymorphic variants and determining whether they are associated with a particular disease or condition.

In respect to DNA, polymorphic variant screening can include genomic DNA screening and/or cDNA screening. Genomic polymorphic variant detection can include screening the entire genomic segment spanning the gene from the transcription start site to the polyadenylation site. In some embodiments, genomic polymorphic variant detection can include the exons and some region around them containing the splicing signals, for example, but not all of the intronic sequences. In addition to screening introns and exons for polymorphic variants, regulatory DNA sequences can be screened for polymorphic variants. Promoter, enhancer, silencer and other regulatory elements have been described in human genes. The promoter is generally proximal to the transcription start site, although there may be several promoters and several transcription start sites. Enhancer, silencer and other regulatory elements can be intragenic or can lie outside the introns and exons, possibly at a considerable distance, such as 100 kb away. Polymorphic variants in such sequences can affect basal gene expression or regulation of gene expression.

The presence or absence of the at least one polymorphic variant can be determined by nucleotide sequencing. Sequencing can be carried out by any suitable method, for example, dideoxy sequencing [Sanger et al., Proc. Natl. Acad. Sci. USA, 74:5463-5467 (1977)], chemical sequencing [Maxam and Gilbert, Proc. Natl. Acad. Sci. USA, 74:560-564, (1977)] or variations thereof. Methods for sequencing can also be found in Ausubel et al., eds., Short Protocols in Molecular Biology, 3rd ed., Wiley, 1995 and Sambrook et al., Molecular Cloning, 2nd ed., Chap. 13, Cold Spring Harbor Laboratory Press, 1989. The sequencing can involve sequencing of a portion or portions of a gene and/or portions of a plurality of genes that includes at least one polymorphic variant site, and can include a plurality of such sites. The portion can be of sufficient length to discern whether the polymorphic variant(s) of interest is present. In some embodiments the portion is 500, 250, 100, 75, 65, 50, 45, 35, 25 nucleotides or less in length. Sequencing can also include the use of dye-labeled dideoxy nucleotides, and the use of mass spectrometric methods. Mass spectrometric methods can also be used to determine the nucleotide present at a polymorphic variant site.

RFLP analysis is useful for detecting the presence of genetic variants at a locus in a population when the variants differ in the size of a probed restriction fragment within the locus, such that the difference between the variants can be visualized by electrophoresis [see, e.g. U.S. Pat. Nos. 5,324,631 and 5,645,995]. Such differences will occur when a variant creates or eliminates a restriction site within the probed fragment. RFLP analysis is also useful for detecting a large insertion or deletion within the probed fragment. RFLP analysis is useful for detecting, for example, an Alu or other sequence insertion or deletion.

Single-strand conformational polymorphisms (SSCPs) can be detected in <220 bp PCR amplicons with high sensitivity [Orita et al, Proc. Natl. Acad. Sci. USA, 86:2766-2770, 1989; Warren et al., In: Current Protocols in Human Genetics, Dracopoli et al., eds, Wiley, 1994, 7.4.1-7.4.6.]. Double strands are first heat-denatured. The single strands are then subjected to polyacrylamide gel electrophoresis under nondenaturing conditions at constant temperature with low voltage and long run times at two different temperatures, typically 4-10° C. and 23° C., or appropriate ambient temperature. At low temperatures such as 4-10C, the secondary structure of short single strands, the degree of intrachain hairpin formation, is sensitive to even single nucleotide changes, and can be detected as a large change in electrophoretic mobility. Polymorphisms appear as new banding patterns when the gel is stained.

SSCP is usually paired with a DNA sequencing method, because the SSCP method does not provide the nucleotide identity of polymorphic variants. One useful sequencing method, for example, is DNA cycle sequencing of radiolabeled PCR products using the Femtomole DNA cycle sequencing kit from Promega (WI) and the instructions provided with the kit. Fragments are selected for DNA sequencing based on their behavior in the SSCP assay. Single strand conformation polymorphism screening is a widely used technique for identifying and discriminating DNA fragments that differ from each other by as little as a single nucleotide. The SSCP technique can be used on genomic DNA [Orita et al. Proc Natl Acad Sci USA. 86(8):2766-70, 1989] as well as PCR amplified DNA as well.

The basic steps of the SSCP procedure can be as follows. SSCP can be used to analyze cDNAs or genomic DNAs. If cDNA is used any suitable reverse transcriptase procedure and/or kit may be utilized such as a Superscript II kit from Life Technologies. Material for SSCP analysis can be prepared by PCR amplification of the cDNA in the presence of radiolabeled dNTP, such as dCTP. Usually the concentration of nonradioactive dCTP is dropped from 200 uM (the standard concentration for each of the four dNTPs) to about 100 uM, and .α32PdCTP is added to a concentration of about 0.1-0.3 uM. This process involves adding a 0.3-1 ul (3-10 uCi) of 32P cCTP to a 10 ul PCR reaction. In some embodiments, about 200 base pair PCR products for SSCP. In some embodiments, about 0.8-1.4 kb fragments are amplified and then several cocktails of restriction endonucleases are used to digest those into smaller fragments of about 0.1-0.3 kb, aiming to have as many fragments possible between 0.15 and 0.3 kb. In some embodiments, several different restriction enzyme digests can be performed on each set of samples, and then each of the digests can be run separately on SSCP gels. After digestion, the radiolabelled PCR products are diluted 1:5 by adding formamide load buffer (80% formamide, 1×SSCP gel buffer) and then denatured by heating to 90% C for 10 minutes, and then allowed to renature by quickly chilling on ice. The secondary structure of the single strands influences their mobility on nondenaturing gels. Even single base differences consistently produce changes in intrastrand folding sufficient to register as mobility differences on SSCP. The resulting single strands are resolved on one or more gels, one a 5.5% acrylamide, 0.5×TBE gel, the other an 8% acrylamide, 10% glycerol, 1×TTE gel, or other appropriate gel recipe known in the art. The use of two gels provides a greater opportunity to recognize mobility differences. Both glycerol and acrylamide concentration have been shown to influence SSCP performance.

Another method for detecting polymorphic variants is the T4 endonuclease VII (T4E7) mismatch cleavage method: T4E7 specifically cleaves heteroduplex DNA containing single base mismatches, deletions or insertions. The site of cleavage is 1 to 6 nucleotides 3' of the mismatch. The enzyme pinpoints the site of sequence variation, so that sequencing can be confined to a 25-30 nucleotide segment. The major steps in identifying sequence variations in candidate genes using T4E7 are as follows. First, 400-600 bp segments are PCR amplified from a panel of DNA samples. Second, a fluorescently-labeled probe DNA is mixed with the sample DNA. Third, the samples are heated and cooled to allow the formation of heteroduplexes. Fourth, the T4E7 enzyme is added to the samples with incubation for 30 minutes at 37° C., during which cleavage occurs at sequence polymorphic variant mismatches. Fifth, the samples are run on an ABI 377 sequencing or other suitable apparatus to identify cleavage bands, which indicate the presence and location of polymorphic variants in the sequence. Sixth, a subset of PCR fragments showing cleavage is sequenced to identify the exact location and identity of each polymorphic variant. A subset of the samples containing each unique T4E7 cleavage site is selected for sequencing. DNA sequencing can, for example, be performed on ABI 377 automated DNA sequencers using BigDye chemistry and cycle sequencing. Analysis of the sequencing runs can be limited to the 30-40 bases marked by the T4E7 procedure as having the polymorphic variant.

Denaturing gradient gel electrophoresis (DGGE) can detect single base mutations based on differences in migration between homoduplexes and heteroduplexes [Myers et al., Nature, 313:495-498 (1985)]. The DNA sample to be tested is hybridized to a labeled wild type probe. The duplexes formed are then subjected to electrophoresis through a polyacrylamide gel that contains a gradient of DNA denaturant parallel to the direction of electrophoresis. Heteroduplexes formed due to single base variations are detected on the basis of differences in migration between the heteroduplexes and the homoduplexes formed.

In heteroduplex analysis (HET) [Keen et al., Trends Genet. 7:5 (1991)], genomic DNA is amplified by the polymerase chain reaction followed by an additional denaturing step that increases the chance of heteroduplex formation in heterozygous individuals. The PCR products are then separated on Hydrolink gels where the presence of the heteroduplex is observed as an additional band.

Chemical cleavage analysis (CCM) is based on the chemical reactivity of thymine (T) when mismatched with cytosine, guanine or thymine and the chemical reactivity of cytosine(C) when mismatched with thymine, adenine or cytosine [Cotton et al., Proc. Natl. Acad. Sci. USA, 85:4397-4401 (1988)]. Duplex DNA formed by hybridization of a wild type probe with the DNA to be examined, is treated with osmium tetroxide for T and C mismatches and hydroxylamine for C mismatches. T and C mismatched bases that have reacted with the hydroxylamine or osmium tetroxide are then cleaved with piperidine. The cleavage products are analyzed by gel electrophoresis.

Ribonuclease cleavage involves enzymatic cleavage of RNA at a single base mismatch in an RNA:DNA hybrid (Myers et al., Science 230:1242-1246, 1985). $^{32}P$ labeled RNA probe complementary to the wild type DNA is annealed to the test DNA and then treated with ribonuclease A. If a mismatch occurs, ribonuclease A will cleave the RNA probe and the location of the mismatch can then be determined by size analysis of the cleavage products following gel electrophoresis.

In addition to the physical methods described herein and others known to those skilled in the art, see, for example, Housman, U.S. Pat. No. 5,702,890; Housman et al., U.S. patent application Ser. No. 09/045,053, polymorphisms can be detected using computational methods, involving computer comparison of sequences from two or more different biological sources, which can be obtained in various ways, for example from public sequence databases. The term "polymorphic variant scanning" refers to a process of identifying sequence polymorphic variants using computer-based comparison and analysis of multiple representations of at least a portion of one or more genes. Computational polymorphic variant detection involves a process to distinguish true polymorphic variants from sequencing errors or other artifacts, and thus does not require perfectly accurate sequences. Such scanning can be performed in a variety of ways as known to those skilled in the art, preferably, for example, as described in U.S. patent application Ser. No. 09/300,747. The "gene" and "SNP" databases of Pubmed Entrez can also be utilized for identifying polymorphisms.

Genomic and cDNA sequences can both or in the alternative be used in identifying polymorphisms. Genomic sequences are useful where the detection of polymorphism in or near splice sites is sought, such polymorphism can be in introns, exons, or overlapping intron/exon boundaries. Nucleic acid sequences analyzed may represent full or partial genomic DNA sequences for a gene or genes. Partial cDNA sequences can also be utilized although this is less preferred. As described herein, the polymorphic variant scanning analysis can utilize sequence overlap regions, even from partial sequences. While the present description is provided by reference to DNA, for example, cDNA, some sequences can be provided as RNA sequences, for example, mRNA sequences.

Interpreting the location of the polymorphic variant in the gene depends on the correct assignment of the initial ATG of the encoded protein (the translation start site). The correct ATG can be incorrect in GenBank, but that one skilled in the art will know how to carry out experiments to definitively identify the correct translation initiation codon (which is not always an ATG). In the event of any potential question concerning the proper identification of a gene or part of a gene, due for example, to an error in recording an identifier or the absence of one or more of the identifiers, the priority for use to resolve the ambiguity is GenBank accession number, OMIM identification number, HUGO identifier, common name identifier.

Allele and genotype frequencies can be compared between cases and controls using statistical software (for example, SAS PROC NLMIXED). The odds ratios can be calculated using a log linear model by the delta method [Agresti, New York: John Wiley & Sons (1990)] and statistical significance was assessed via the chi-square test. Likelihood ratios (G2) were used to assess goodness of fit of different models i.e., G2 provides a measure of the reliability of the odds ratio; small G2 P-values indicate a poor fit to the model being tested. Combined genotypes can be analysed by estimating, maximum likelihood estimation, the gamete frequencies in cases and controls using a model of the four combinations of alleles as described by Weir, Sunderland, Mass.: Sinauer (1996). Gene-gene interactive effects can be tested using a series of non-hierarchical logistic models [Piegorsch et al., Stat. Med. 13:153-162 (1994)] to estimate interactive dominant and recessive effects. A sample size as large as possible from a relatively homogenous population to minimize variables outside the focus of the study.

Genomic DNA can be extracted from cases and controls using the QIAamp DNA Blood Mini Kit from Qiagen, UK. Genotyping of polymorphisms was performed using PCR-RFLP (Restriction Fragment Length Polymorphism) using appropriate restriction sites for the gene(s) being studied [Frosst et al., Nature Genet., 10:111-113 (1995); Hol et al., Clin. Genet., 53:119-125 (1998); Brody et al., Am. J. Hum. Genet., 71:1207-1215 (2002)]. A polymorphism may be genotyped using an allele-specific primer extension assay and scored by matrix-assisted laser desorption/ionization-time of flight (MALDI-TOF) mass spectrometry (Sequenom, San Diego). Appropriate controls should be included in all assays. genotyping consistency can be tested by analyzing between 10-15% of samples in duplicate.

One type of assay has been termed an array hybridization assay, an example of which is the multiplexed allele-specific diagnostic assay (MASDA) (U.S. Pat. No. 5,834,181; Shuber et al., Hum. Molec. Genet., 6:337-347 (1997). In MASDA, samples from multiplex PCR are immobilized on a solid support. A single hybridization is conducted with a pool of labeled allele specific oligonucleotides (ASO). The support is then washed to remove unhybridized ASOs remaining in the pool. Labeled ASO remaining on the support are detected and eluted from the support. The eluted ASOs are then sequenced to determine the mutation present.

Two assays depend on hybridization-based allele-discrimination during PCR. The TaqMan assay (U.S. Pat. No. 5,962,233; Livak et al., Nature Genet., 9:341-342, 1995) uses allele specific (ASO) probes with a donor dye on one end and an acceptor dye on the other end such that the dye pair interact via fluorescence resonance energy transfer (FRET). A target sequence is amplified by PCR modified to include the addition of the labeled ASO probe. The PCR conditions are adjusted so that a single nucleotide difference will effect binding of the probe. Due to the 5' nuclease activity of the Taq polymerase enzyme, a perfectly complementary probe is cleaved during the PCR while a probe with a single mismatched base is not cleaved. Cleavage of the probe dissociates the donor dye from the quenching acceptor dye, greatly increasing the donor fluorescence.

An alternative to the TaqMan assay is the molecular beacons assay [U.S. Pat. No. 5,925,517; Tyagi et al., Nature Biotech., 16:49-53 (1998)]. In the molecular beacons assay, the ASO probes contain complementary sequences flanking the-target specific species so that a hairpin structure is formed. The loop of the hairpin is complimentary to the target sequence while each aim of the hairpin contains either donor or acceptor dyes. When not hybridized to a donor sequence, the hairpin structure brings the donor and acceptor dye close together thereby extinguishing the donor fluorescence. When hybridized to the specific target sequence, however, the donor and acceptor dyes are separated with an increase in fluorescence of up to 900 fold. Molecular beacons can be used in conjunction with amplification of the target sequence by PCR and provide a method for real time detection of the presence of target sequences or can be used after amplification.

High throughput screening for SNPs that affect restriction sites can be achieved by Microtiter Array Diagonal Gel Electrophoresis (MADGE)(Day and Humphries, Anal. Biochem., 222:389-395, 1994). In this assay restriction fragment digested PCR products are loaded onto stackable horizontal gels with the wells arrayed in a microtiter format. During electrophoresis, the electric field is applied at an angle relative to the columns and rows of the wells allowing products from a large number of reactions to be resolved.

Additional assays depend on mismatch distinction by polymerases and ligases. The polymerization step in PCR places high stringency requirements on correct base pairing of the 3' end of the hybridizing primers. This has allowed the use of PCR for the rapid detection of single base changes in DNA by using specifically designed oligonucleotides in a method variously called PCR amplification of specific alleles (PASA) [Sommer et al., Mayo Clin. Proc., 64:1361-1372 (1989); Sarker et al., Anal. Biochem. (1990), allele-specific amplification (ASA), allele-specific PCR, and amplification refractory mutation system (ARMS) [Newton et al., Nuc. Acids Res. (1989); Nichols et al., Genomics (1989); Wu et al., Proc. Natl. Acad. Sci. USA, (1989)]. In these methods, an oligonucleotide primer is designed that perfectly matches one allele but mismatches the other allele at or near the 3' end. This results in the preferential amplification of one allele over the other. By using three primers that produce two differently sized products, it can be determine whether an individual is homozygous or heterozygous for the mutation [Dutton and Sommer, Bio Techniques, 11:700-702 (1991)]. In another method, termed bi-PASA, four primers are used; two outer primers that bind at different distances from the site of the SNP and two allele specific inner primers [Liu et al., Genome Res., 7:389-398 (1997)]. Each of the inner primers have a non-complementary 5' end and form a mismatch near the 3' end if the proper allele is not present. Using this system, zygosity is determined based on the size and number of PCR products produced.

The joining by DNA ligases of two oligonucleotides hybridized to a target DNA sequence is quite sensitive to mismatches close to the ligation site, especially at the 3' end. This sensitivity has been utilized in the oligonucleotide ligation assay [Landegren et al., Science, 241:1077-1080 (1988)] and the ligase chain reaction [LCR; Barany, Proc. Natl. Acad. Sci. USA, 88:189-193 (1991)]. In OLA, the sequence surrounding the SNP is first amplified by PCR, whereas in LCR, genomic DNA can by used as a template.

In one method for mass screening based on the OLA, amplified DNA templates are analyzed for their ability to serve as templates for ligation reactions between labeled oligonucleotide probes [Samotiaki et al., Genomics, 20:238-242, (1994)]. In this assay, two allele-specific probes labeled with either of two lanthanide labels (europium or terbium) compete for ligation to a third biotin labeled phosphorylated oligonucleotide and the signals from the allele specific oligonucleotides are compared by time-resolved fluorescence. After ligation, the oligonucleotides are collected on an avidin-coated 96-pin capture manifold. The collected oligonucleotides are then transferred to microtiter wells in which the europium and terbium ions are released. The fluorescence from the europium ions is determined for each well, followed by measurement of the terbium fluorescence.

In alternative gel-based OLA assays, polymorphic variants can be detected simultaneously using multiplex PCR and multiplex ligation [U.S. Pat. No. 5,830,711; Day et al., Genomics, 29:152-162 (1995); Grossman et al., Nuc. Acids Res., 22:4527-4534, (1994)]. In these assays, allele specific oligonucleotides with different markers, for example, fluorescent dyes, are used. The ligation products are then analyzed together by electrophoresis on an automatic DNA sequencer distinguishing markers by size and alleles by fluorescence. In the assay by Grossman et al., 1994, mobility is further modified by the presence of a non-nucleotide mobility modifier on one of the oligonucleotides.

A further modification of the ligation assay has been termed the dye-labeled oligonucleotide ligation (DOL) assay [U.S. Pat. No. 5,945,283; Chen et al., Genome Res., 8:549-556 (1998)]. DOL combines PCR and the oligonucleotide ligation reaction in a two-stage thermal cycling sequence with fluorescence resonance energy transfer (FRET) detection. In the assay, labeled ligation oligonucleotides are designed to have annealing temperatures lower than those of the amplification primers. After amplification, the temperature is lowered to a temperature where the ligation oligonucleotides can anneal and be ligated together. This assay uses a thermostable ligase and a thermostable DNA polymerase without 5' nuclease activity. Because FRET occurs only when the donor and acceptor dyes are in close proximity, ligation is inferred by the change in fluorescence.

In another method for the detection of polymorphic variants termed minisequencing, the target-dependent addition by a polymerase of a specific nucleotide immediately downstream (3') to a single primer is used to determine which allele is present (U.S. Pat. No. 5,846,710). Using this method, several variants can be analyzed in parallel by separating locus specific primers on the basis of size via electrophoresis and determining allele specific incorporation using labeled nucleotides.

Determination of individual variants using solid phase minisequencing has been described by Syvanen et al., Am. J. Hum. Genet., 52:46-59 (1993). In this method the sequence including the polymorphic site is amplified by PCR using one amplification primer which is biotinylated on its 5' end. The biotinylated PCR products are captured in streptavidin-coated microtitration wells, the wells washed, and the captured PCR products denatured. A sequencing primer is then added whose 3' end binds immediately prior to the polymorphic site, and the primer is elongated by a DNA polymerase with one single labeled dNTP complementary to the nucleotide at the polymorphic site. After the elongation reaction, the sequencing primer is released and the presence of the labeled nucleotide detected. Alternatively, dye labeled dideoxynucleoside triphosphates (ddNTPs) can be used in the elongation reaction [U.S. Pat. No. 5,888,819; Shumaker et al., Human Mut., 7:346-354, (1996)]. In this method, incorporation of the ddNTP is determined using an automatic gel sequencer.

Minisequencing has also been adapted for use with microarrays [Shumaker et al., Human Mut., 7:346-354 (1996)]. In this case, elongation (extension) primers are attached to a solid support such as a glass slide. Methods for construction of oligonucleotide arrays are well known to those of ordinary skill in the art and can be found, for example, in Nature Genetics, Suppl., Jan. 21, 1999. PCR products are spotted on the array and allowed to anneal. The extension (elongation) reaction is carried out using a polymerase, a labeled dNTP and noncompeting ddNTPs. Incorporation of the labeled DNTP is then detected by the appropriate means. In a variation of this method suitable for use with multiplex PCR, extension is accomplished with the use of the appropriate labeled ddNTP and unlabeled ddNTPs [Pastinen et al., Genome Res., 7:606-614 (1997)].

Solid phase minisequencing has also been used to detect multiple polymorphic nucleotides from different templates in an undivided sample [Pastinen et al., Clin. Chem., 42:1391-1397 (1996)]. In this method, biotinylated PCR products are captured on the avidin-coated manifold support and rendered single stranded by alkaline treatment. The manifold is then placed serially in four reaction mixtures containing extension primers of varying lengths, a DNA polymerase and a labeled ddNTP, and the extension reaction allowed to proceed. The manifolds are inserted into the slots of a gel containing formamide which releases the extended primers from the template. The extended primers are then identified by size and fluorescence on a sequencing instrument.

Fluorescence resonance energy transfer (FRET) has been used in combination with minisequencing to detect polymorphic variants [U.S. Pat. No. 5,945,283; Chen et al., Proc. Natl. Acad. Sci. USA, 94:10756-10761 (1997)]. In this method, the extension primers are labeled with a fluorescent dye, for example fluorescein. The ddNTPs used in primer extension are labeled with an appropriate FRET dye. Incorporation of the ddNTPs is determined by changes in fluorescence intensities.

The above discussion of methods for the detection of SNPs is exemplary only and is not intended to be exhaustive. Those of ordinary skill in the art will be able to envision other methods for detection of polymorphic variants that are within the scope and spirit of the invention.

Polymorphisms are detected in a target nucleic acid from an individual being analyzed. For assay of genomic DNA, virtually any biological sample other than pure red blood cells is suitable. "Tissue" means any sample taken from any subject, preferably a human. For example, convenient tissue samples include whole blood, semen, saliva, tears, urine, fecal material, sweat, buccal epithelium, skin and hair. For assay of cDNA or mRNA, the tissue sample should be obtained from an organ in which the target nucleic acid is expressed.

Many of the methods described involve amplification of DNA from target samples. This can be accomplished by e.g., PCR. Other suitable amplification methods include the ligase chain reaction (LCR) [see Wu and Wallace, Genomics 4, 560 (1989), Landegren et al., Science 241, 1077 (1988)], transcription amplification [Kwoh et al., Proc. Natl. Acad. Sci. USA 86, 1173 (1989)], self-sustained sequence replication [Guatelli et al., Proc. Nat. Acad. Sci. USA, 87, 1874 (1990)] and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Single base extension methods are described by e.g., U.S. Pat. Nos. 5,846,710, 6,004,744, 5,888,819 and 5,856,092. Generally, the methods work by hybridizing a primer that is complementary to a target sequence such that the 3' end of the primer is immediately adjacent to, but does not span a site of, potential variation in the target sequence. That is, the primer comprises a subsequence from the complement of a target polynucleotide terminating at the base that is immediately adjacent and 5' to the polymorphic site. The term primer refers to a single-stranded oligonucleotide capable of acting as a point of initiation of template-directed DNA synthesis under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer but typically ranges from 15 to 40 nucleotides. Short primer molecules generally require cooler temperatures to form sufficiently stable hybrid complexes with the template. A primer need not reflect the exact sequence of the template but should be sufficiently complementary to hybridize with a template. The term primer site refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified. Hybridization probes are capable of binding in a base-specific manner to a complementary strand of nucleic acid. Such probes include nucleic acids and peptide nucleic acids as described in Nielsen et al., Science 254, 1497-1500 (1991). A probe primer can be labeled, if desired, by incorporating a label detectable by spectroscopic, photochemical, biochemical, immunochemical, or chemical means. For example, useful labels include $^{32}P$, fluorescent dyes, electron dense reagents, enzymes (as commonly used in an ELISA), biotin, or haptens and proteins for which antisera or monoclonal antibodies are available. A label can also be used to "capture" the primer, so as to facilitate the immobilization of either the primer or a primer extension product, such as amplified DNA, on a solid support. The hybridization is performed in the presence of one or more labeled nucleotides complementary to base(s) that may occupy the site of potential variation. For example, for biallelic polymorphisms, two differentially labeled nucleotides can be used. For tetraallelic polymorphisms, four differentially-labeled nucleotides can be used. In some methods, particularly methods employing multiple differentially labeled nucleotides, the nucleotides are dideoxynucleotides. Hybridization is performed under conditions permitting primer extension if a nucleotide complementary to a base occupying the site of variation if the target sequence is present. Extension incorporates a labeled nucleotide thereby generating a labeled extended primer. If multiple differentially-labeled nucleotides are used and the target is heterozygous then multiple differentially-labeled extended primers can be obtained. Extended primers are detected providing an indication of which base(s) occupy the site of variation in the target polynucleotide.

An allele-specific primer hybridizes to a site on target DNA overlapping a polymorphism and only primes amplification of an allelic form to which the primer exhibits perfect complementarily. [See Gibbs, Nucleic Acid Res., 17:2427-2448 (1989).] This primer is used in conjunction with a second primer that hybridizes at a distal site. Amplification proceeds from the two primers leading to a detectable product signifying that the particular allelic form is present. A control is usually performed with a second pair of primers, one of which shows a single base mismatch at the polymorphic site and the other of which exhibits perfect complementarily to a distal site. The single-base mismatch prevents amplification and no detectable product is formed. In some methods, the mismatch is included in the 3'-most position of the oligonucleotide aligned with the polymorphism because this position is most destabilizing to elongation from the primer. [See, e.g., WO 93/22456.] In other methods, a double-base mismatch is used in which the first mismatch is included in the 3'-most position of the oligonucleotide aligned with the polymorphism and a second mismatch is positioned at the immediately adjacent base (the pen-ultimate 3' position). This double mismatch further prevents amplification in instances in which there is no match between the 3' position of the primer and the polymorphism.

Amplification products generated using the polymerase chain reaction can be analyzed by the use of denaturing gradient gel electrophoresis. Different alleles can be identified based on the different sequence-dependent melting properties and electrophoretic migration of DNA in solution. [Erlich, ed., PCR Technology, Principles and Applications for DNA Amplification, (W.H. Freeman and Co, New York, (1992)), Chapter 7.]

Arrays provide a high throughput technique that can assay a large number of polynucleotides in a sample. In one aspect of the invention, an array is constructed comprising one or more of the genes, proteins or antibodies relevant to the invention, comprising one or more of these sequences. This technology can be used as a tool to test for differential expression, or for genotyping. Arrays can be created by spotting polynucleotide probes onto a substrate (e.g., glass, nitrocellulose, etc.) in a two-dimensional matrix or array having bound probes. The probes can be bound to the substrate by either covalent bonds or by non-specific interactions, such as hydrophobic interactions. Techniques for constructing arrays and methods of using these arrays are described in, for example, Schena et al., (1996) Proc Natl Acad Sci USA. 93(20):10614-9; Schena et al., (1995) Science 270(5235): 467-70; Shalon et al., (1996) Genome Res. 6(7):639-45, U.S. Pat. No. 5,807,522, EP 799 897; WO 97/29212; WO 97/27317; EP 785 280; WO 97/02357; U.S. Pat. No. 5,593, 839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734.

In some embodiments, an array comprises probes specific for one or more allelic variants for a given gene. Probes that specifically bind to the allele of interest can be used, and reaction conditions for hybridization to the array can be adjusted accordingly. The probes utilized in the arrays can be of varying types and can include, for example, synthesized probes of relatively short length (e.g., a 20-mer or a 25-mer), cDNA (full length or fragments of gene), amplified DNA, fragments of DNA (generated by restriction enzymes, for example) and reverse transcribed RNA. Both custom and generic arrays can be utilized in detecting differential expression levels. Custom arrays can be prepared using probes that hybridize to particular preselected subsequences of mRNA gene sequences or amplification products prepared from them. Many variations on methods of detection using arrays are within the skill in the art and within the scope of the invention. For example, rather than immobilizing the probe to a solid support, the test sample can be immobilized on a solid support that is then contacted with the probe.

Screening may also be based on the functional or antigenic characteristics of the protein. Immunoassays designed to detect predisposing polymorphisms in proteins relevant to the invention can be used in screening. Antibodies specific for a polymorphism variant or gene products may be used in screening immunoassays. A sample is taken from a subject. Samples, as used herein, include biological fluids such as tracheal lavage, blood, cerebrospinal fluid, tears, saliva, lymph, dialysis fluid and the like; organ or tissue culture derived fluids; and fluids extracted from physiological tissues. Samples can also include derivatives and fractions of such fluids. In some embodiments, the sample is derived from a biopsy. The number of cells in a sample will generally be at least about $10^3$, usually at least $10^4$ more usually at least about $10^5$. The cells can be dissociated, in the case of solid tissues, or tissue sections may be analyzed. Alternatively a lysate of the cells can be prepared.

In some embodiments, detection utilizes staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively or in addition, a second stage antibody or reagent can be used to amplify the signal. For example, the primary antibody can be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and protein encoded by the polymorphic variant in a lysate. Measuring the concentration of protein binding in a sample or fraction thereof can be accomplished by a variety of specific assays. A conventional sandwich type assay may be used. For example, a sandwich assay can first attach polymorphic variant protein specific antibodies to an insoluble surface or support. The particular manner of binding is not crucial so long as it is compatible with the reagents and overall methods of the invention. Binding may be covalent or non-covalent.

Other immunoassays are known in the art and may find use as diagnostics. Ouchterlony plates provide a simple determination of antibody binding. Western blots can be performed on protein gels or protein spots on filters, using a detection system specific for polymorphic variant protein as desired, conveniently using a labeling method as described for the sandwich assay.

The invention provides a method for determining a genotype of an individual in relation to one or more polymorphic variants in one or more of the genes identified in above aspects by using mass spectrometric determination of a nucleic acid sequence that is a portion of a gene identified for other aspects of this invention or a complementary sequence. Such mass spectrometric methods are known to those skilled in the art. In preferred embodiments, the method involves determining the presence or absence of a polymorphic variant in a gene; determining the nucleotide sequence of the nucleic acid sequence; the nucleotide sequence is 100 nucleotides or less in length, preferably 50 or less, more preferably 30 or less, and still more preferably 20 nucleotides or less. In general, such a nucleotide sequence includes at least one polymorphic variant site, preferably a polymorphic variant site which is informative with respect to the expected response of a patient to a treatment as described for above aspects.

Therapies

The invention provides methods for choosing a relevant therapeutic strategy based on the detection of one or more polymorphic variants. In some embodiments, the polymorphic variant indicates an altered susceptibility to a particular disease state. In embodiments, where the variant is associated with an increased susceptibility for that disease state. In some embodiments, for the MTHFD1 1958A variant, a resulting diagnosis for an increased susceptibility for a pregnancy complication such as severe placental abruption or a second trimester miscarriage would indicate a therapy that helps minimize or eliminate such complications. In some embodiments, for the MTHFD1L "ATT" seven repeat intron variant of rs3832406, a resulting diagnosis for an increased susceptibility for a pregnancy complication such as a neural tube defect indicates a therapy that helps minimize or eliminate such complications. In some embodiments, for the MTHFD1L "ATT" seven repeat intron variant of rs3832406, a resulting diagnosis for an increased susceptibility for a cancer drug complication would indicate that helps minimize such a complication. Accordingly, the invention provides a method for determining whether a compound has a differential effect due to the presence or absence of at least one polymorphic variant in a gene or a variant form of a gene. In some embodiments, the method comprises identifying a subset of patients with enhanced or diminished response or tolerance to a treatment method or a method of administration of a treatment where the treatment is for a disease or condition in the patient. General methods of testing effects of a polymorphic variant for an effect on drug efficacy are known to those of skill in the art and are provided in various sources such as U.S. Pat. Nos. 6,537,759; 6,664,062; and 6,759,200.

One or more polymorphic variants in one or more genes in a plurality of patients can be correlated with response to a particular treatment such as a drug or more specifically a drug regemin including dosage, administration, and other relevant parameters. The correlation can be performed by determining the one or more polymorphic variants in the one or more genes in the plurality of patients and correlating the presence or absence of each of the polymorphic variants (alone or in various combinations) with the patient's response to a particular treatment. The polymorphic variants can be previously known to exist or can also be determined de novo, or combinations of prior information and newly determined information may be used. The enhanced or diminished response should be statistically significant, preferably such that $p=0.10$ or less, more preferably 0.05 or less, and most preferably 0.02 or less. A positive correlation between the presence of one or more polymorphic variants and an enhanced response to treatment is indicative that the treatment is particularly effective in the group of patients having those polymorphic variants. A positive correlation of the presence of the one or more polymorphic variants with a diminished response to the treatment is indicative that the treatment will be less effective in the group of patients having those polymorphic variants. Such information is useful, for example, for selecting or de-selecting patients for a particular treatment or method of administration of a treatment, or for demonstrating that a group of patients exists for which the treatment or method of treatment would be particularly beneficial or contra-indicated. Such demonstration can be beneficial, for example, for obtaining government regulatory approval for a new drug or a new use of a drug.

In some embodiments, a first patient or set of patients suffering from a disease or condition are identified whose response to a treatment differs from the response (to the same treatment) of a second patient or set of patients suffering from the same disease or condition, and then determining whether the frequency of at least one polymorphic variant in at least one gene differs in frequency between the first patient or set of patients and the second patient or set of patients. A correlation between the presence or absence of the polymorphic variant or polymorphic variants and the response of the patient or patients to the treatment indicates that the polymorphic variant provides information about variable patient response. The method can involve identifying at least one polymorphic variant in at least one gene. In some embodiments, a first patient or set of patients suffering from a disease or condition and having a particular genotype, haplotype or combination of genotypes or haplotypes is identified, and a second patient or set of patients suffering from the same disease or condition that have a genotype or haplotype or sets of genotypes or haplotypes that differ in a specific way from those of the first set of patients is identified. The extent and magnitude of clinical response can be compared between the first patient or set of patients and the second patient or set of patients. A correlation between the presence or absence of a polymorphic variant or polymorphic variants or haplotypes and the response of the patient or patients to the treatment indicates that the polymorphic variant provides information about variable patient response and is useful for the invention.

Polymorphic variants of relevance include those that can affect one or more of: the susceptibility of individuals to a disease; the course or natural history of a disease; and the response of a patient with a disease to a medical intervention, such as, for example, a drug, a biologic substance, physical energy such as radiation therapy, or a specific dietary regimen. Variation in any of these three parameters can constitute the basis for initiating a pharmacogenetic study directed to the identification of the genetic sources of interpatient variation. The effect of a DNA sequence polymorphic variant or polymorphic variants on disease susceptibility or natural history are of particular interest as the polymorphic variants can be used to define patient subsets that behave differently in response to medical interventions. Useful gene sequence polymorphic variants for this invention can be described as polymorphic variants that partition patients into two or more groups that respond differently to a therapy, regardless of the reason for the difference, and regardless of whether the reason for the difference is known.

Once the presence or absence of a polymorphic variant or polymorphic variants in a gene or genes is shown to correlate with the efficacy or safety of a treatment method, that information can be used to select an appropriate treatment method for a particular patient. In the case of a treatment which is more likely to be effective when administered to a patient who has at least one copy of a gene with a particular polymorphic variant or polymorphic variants (in some cases the correlation with effective treatment is for patients who are homozygous for polymorphic variant or set of polymorphic variants in a gene) than in patients with a different polymorphic variant or set of polymorphic variants, a method of treatment is selected (and/or a method of administration) which correlates positively with the particular polymorphic variant presence or absence which provides the indication of effectiveness. Such selection can involve a variety of different choices, and the correlation can involve a variety of different types of treatments, or choices of methods of treatment. In some cases, the selection can include choices between treatments or methods of administration where more than one method is likely to be effective, or where there is a range of expected effectiveness or different expected levels of contra-indication or deleterious effects. In such cases the selection can be performed to select a treatment that will be as effective or more effective than other methods, while having a comparatively low level of deleterious effects. Similarly, where the selection is between methods with differing levels of deleterious effects, preferably a method is selected that has low such effects but that is expected to be effective in the patient. Alternatively, in cases where the presence or absence of the particular polymorphic variant or polymorphic variants is indicative that a treatment or method of administration is more likely to be ineffective or contra-indicated in a patient with that polymorphic variant or polymorphic variants, then such treatment or method of administration is generally eliminated for use in that patient.

The term "therapy" refers to a process that is intended to produce a beneficial change in the condition of a mammal, for example, a human, often referred to as a patient. A beneficial change can include one or more of: restoration of function, reduction of symptoms, limitation or retardation of progression of a disease, disorder, or condition or prevention, limitation or retardation of deterioration of a patient's condition, disease or disorder. Such therapy can involve nutritional modifications, administration of radiation, administration of a drug, behavioral modifications and combinations of these, among others.

The terms "inhibit," "prevent," and "treat," as well as words stemming therefrom, as used herein, do not necessarily imply 100% or complete inhibition, prevention, or treatment. Rather, there are varying degrees of inhibition, prevention, or treatment of which one of ordinary skill in the art recognizes as having a potential benefit or therapeutic effect. In this respect, the present inventive methods can provide any amount of inhibition of metastasis of a cancer cell, any level of prevention of metastasis of a cancer cell of cancer, or any degree of treatments of a cancer in a subject. The term "patient" refers to both human and veterinary subjects. The term "subject" or "individual" typically refers to humans, but also to mammals and other animals, multicellular organisms such as plants, and single-celled organisms or viruses.

If a given polymorphism variant correlates with an increased the expression level or activity of the protein encoded by the variant, the complications associated with the variant can be treated by administering an antagonist of the protein. If a given polymorphism variant correlates with a complication involving decrease in the expression level or activity of the protein encoded by the variant, the complications can be treated by administering the protein itself, a nucleic acid encoding the protein that can be expressed in a patient, or an analog or agonist of the protein. In the case of pregnancy complications and polymorphism variants of genes encoding enzymes involved in a one carbon metabolic pathway such as MTHFD1, MTHFD1L, and MTHFR, folate, Vitamin $B_{12}$, and/or other B vitamins are administered to the woman subject who is pregnant or planning a pregnancy.

Other treatments can include, but are not limited to, surgery, the administration of pharmaceutical compounds or nutritional supplements, and behavioral changes such as improved diet, increased exercise, reduced alcohol intake, smoking cessation, etc.

The invention comprises a method for determining a method of treatment effective to treat a disease or condition by altering the level of activity of a product of an allele of a gene selected from the genes described herein, and determining whether that alteration provides a differential effect related to reducing or alleviating a disease or condition as compared to at feast one alternative allele or an alteration in toxicity or tolerance of the treatment by a patient or patients. The presence of such a differential effect indicates that altering that level of activity provides at least part of an effective treatment for the disease or condition.

Information gained from analyzing genetic material for the presence of polymorphisms can be used to design treatment regimes involving gene therapy. For example, detection of a polymorphism that either affects the expression of a gene or results in the production of a mutant protein can be used to design an artificial gene to aid in the production of normal, wild type protein or help restore normal gene expression. Once designed, the gene can be placed in the individual by any suitable means known in the art. [Gene Therapy Technologies, Applications and Regulations, Meager, ed., Wiley (1999); Gene Therapy Principles and Applications, Blankenstein, ed., Birkhauser Verlag (1999); Jain, Textbook of Gene Therapy, Hogrefe and Huber (1998)].

There are several methods that can be used for assessing the medical and pharmaceutical implications of a polymorphic variant include computational methods, in vitro and/or in vivo experimental methods, prospective human clinical trials, and other laboratory and clinical measures. Informatics-based approaches include DNA and protein sequence analysis, such as phylogenetic approaches and motif searching, and protein modeling. Tools are available for modeling the structure of proteins with unsolved structure, particularly if there is a related protein with known structure. [Rost et al., J. Mol. Biol. 270:471-480 (1997); Firestine et al., Chem. Biol. 3:779-783 (1996).] Methods are also available for identifying conserved domains and vital amino acid residues of proteins of unknown structure by analysis of phylogenetic relationships. [Deleage et al., Biochimie 79:681-686 (1997); Taylor et al., Protein Sci. 3:1858-1870 (1994).] These methods can permit the prediction of functionally important polymorphic variants, either on the basis of structure or evolutionary conservation. Phylogenetic approaches to understanding sequence variation can also be used. If a sequence polymorphic variant occurs at a nucleotide or encoded amino acid residue where there is usually little or no variation in homologs of the protein of interest from non-human species, particularly evolutionarily remote species, then the polymorphic variant can be more likely to affect function of the RNA or protein.

Clinical Trial

A clinical trial can be used to evaluate differential efficacy of or tolerance to a treatment in a subset of patients who have a particular polymorphic variant or polymorphic variants in at least one gene. A "clinical trial" is the testing of a therapeutic intervention in a volunteer human population for the purpose of determining whether a therapeutic intervention is safe and/or efficacious in the human volunteer or patient population for a given disease, disorder, or condition. Clinical trials can comprise Phase I, II, III, or IV trials. In general, the polymorphisms relevant to the invention are useful for conducting clinical trials of drug candidates for the disease state, conditions and complications of the invention. Such trials can be performed on treated or control populations having similar or identical polymorphic profiles at a defined collection of polymorphic sites. Use of genetically matched populations eliminates or reduces variation in treatment outcome due to genetic factors, leading to a more accurate assessment of the efficacy of a potential drug. In some embodiments, the set of polymorphisms may be used to stratify the enrolled patients into disease sub-types or classes. In some embodiments, the polymorphisms are used to identify subsets of patients with similar polymorphic profiles who have an unusually high or low response to treatment or who do not respond at all. Information about the underlying genetic factors influencing response to treatment can be used in many aspects of the development of treatments, such as identification of new targets, through the design of new trials, product labeling, and patient targeting. Additionally, the polymorphisms can be used to identify the genetic factors involved in adverse response to treatment.

Diagnostic tests for a specific polymorphic variant or variant form of a gene can be incorporated in the clinical trial protocol as inclusion or exclusion criteria for enrollment in the trial, to allocate certain patients to treatment or control groups within the clinical trial or to assign patients to different treatment cohorts. In some embodiments, diagnostic tests for specific polymorphic variants are performed on all patients within a clinical trial, and statistical analysis performed comparing and contrasting the efficacy or safety of a drug between individuals with different polymorphic variants or variant forms of the gene or genes. Diagnostic tests for polymorphic variants can be performed on groups of patients known to have efficacious responses to the drug to identify differences in the frequency of polymorphic variants between responders and non-responders. In some embodiments, diagnostic tests for polymorphic variants are performed on groups of patients known to have toxic responses to the drug to identify differences in the frequency of the polymorphic variant between those having adverse events and those not having adverse events. Such outlier analyses are useful if a limited number of patient samples are available for analysis. Embodiments involving clinical trials include the genetic stratification strategies, phases, statistical analyses, sizes, and other relevant parameters.

Prior to establishment of a diagnostic test for use in the selection of a treatment method or elimination of a treatment method, the presence or absence of one or more specific polymorphic variants in a gene or in multiple genes is correlated with a differential treatment response. Such a differential response can be determined using prospective and/or retrospective data. The determination can be performed by analyzing the presence or absence of particular polymorphic variants in patients who have previously been treated with a particular treatment method, and correlating the polymorphic variant presence or absence with the observed course, outcome, and/or development of adverse events in those patients. Alternatively, the analysis can be performed prospectively, where the presence or absence of the polymorphic variant or polymorphic variants in an individual is determined and the course, outcome, and/or development of adverse events in those patients is subsequently or concurrently observed and then correlated with the polymorphic variant determination.

General methods for performing clinical trials are well known in the art. [Guide to Clinical Trials by Bert Spilker, Raven Press, 1991; The Randomized Clinical Trial and Therapeutic Decisions by Niels Tygstrup (Editor), Marcel Dekker; Recent Advances in Clinical Trial Design and Analysis (Cancer Treatment and Research, Ctar 75) by Peter F. Thall (Editor) Kluwer Academic Pub, 1995.] Additional design considerations include defining what the genetic hypothesis is, how it is to be tested, how many patients will need to be enrolled to have adequate statistical power to measure an effect of a specified magnitude, definition of primary and secondary endpoints, and methods of statistical analysis. The design of the trial can incorporate the preclinical data sets to determine the primary and secondary endpoints. Endpoints can include include whether the therapeutic intervention is efficacious, efficacious with undesirable side effects, ineffective, ineffective with undesirable side effects, or ineffective with deleterious effects. Pharmacoeconomic analyses can be incorporated in order to support the efficacious intervention, efficacious with undesirable side effects cases, whereby the clinical outcome is positive, and economic analyses are carried out for the support of overall benefit to the patient and to society. The strategies for designing a clinical trial to test the effect of a genotypic polymorphic variant or polymorphic variants can be modified based upon the data and information from the preclinical studies and the patient symptomatic parameters unique to the target indication.

A clinical trial in which pharmacogenetic related efficacy or toxicity endpoints are included in the primary or secondary endpoints can be part of a retrospective or prospective clinical trial. In the design of these trials, the allelic differences is identified and stratification based upon these genotypic differences among patient or subject groups are used to ascertain the significance of the impact a genotype has on the candidate therapeutic intervention. Retrospective pharmacogenetic trials can be conducted at each of the phases of clinical development, with the assumption that sufficient data is available for the correlation of the physiologic effect of the candidate therapeutic intervention and the allelic polymorphic variant or polymorphic variants within the treatment population. In the case of a retrospective trial, the data collected from the trial can be re-analyzed by imposing the additional stratification on groups of patients by specific allelic polymorphic variants that may exist in the treatment groups. Retrospective trials can be useful to ascertain whether a hypothesis that a specific polymorphic variant has a significant effect on the efficacy or toxicity profile for a candidate therapeutic intervention. Retrospective or prospective human clinical trials are performed to test whether the identified allelic polymorphic variant, polymorphic variants, or haplotypes or combination thereof influence the efficacy or toxicity profiles for a given drug or other therapeutic intervention.

In designing a pharmacogenetic trial, retrospective analysis of Phase II or Phase III clinical data can indicate trial variables for which further analysis should be obtained. A placebo controlled pharmacogenetics clinical trial design can be one in which target allelic polymorphic variant or polymorphic variants is identified and a diagnostic test is performed to stratify the patients based upon presence, absence, or combination thereof of these polymorphic variants. In the Phase II or phase III stage of clinical development, determination of a specific sample size of a prospective trial is described to include factors such as expected differences between a placebo and treatment on the primary or secondary endpoints and a consideration of the allelic frequencies.

A prospective clinical trial has the advantage that the trial can be designed to ensure the trial objectives can be met with statistical certainty. In these cases, power analysis, which includes the parameters of allelic polymorphic variant frequency, number of treatment groups, and ability to detect positive outcomes can ensure that the trial objectives are met.

The design of a pharmacogenetics clinical trial can include a description of the allelic polymorphic variant impact on the observed efficacy between the treatment groups. Using this type of design, the type of genetic and phenotypic relationship display of the efficacy response to a candidate therapeutic intervention is analyzed. For example, a genotypically dominant allelic polymorphic variant or polymorphic variants are those in which both heterozygotes and homozygotes demonstrate a specific phenotypic efficacy response different from the homozygous recessive genotypic group. A pharmacogenetic approach is useful for clinicians and public health professionals to include or eliminate small groups of responders or non-responders from treatment in order to avoid unjustified side-effects. Further, adjustment of dosages when clear clinical difference between heterozygous and homozygous individuals may be beneficial for therapy with the candidate therapeutic intervention.

In some embodiments, a recessive allelic polymorphic variant or polymorphic variants are those in which only the homozygote recessive for that or those polymorphic variants will demonstrate a specific phenotypic efficacy response different from the heterozygotes or homozygous wildtype. In some embodiments, allelic polymorphic variant or polymorphic variants organized by haplotypes from additional gene or genes are included to help explain clinical phenotypic outcome differences among the treatment groups. These types of clinical studies can identify an allelic polymorphic variant and its role in the efficacy or toxicology pattern within the treatment population.

Statistical Analysis of Data

A variety of informative comparisons can be used to identify correlations in the clinical data. In some embodiments, a plurality of pairwise comparisons of treatment response and the presence or absence of at least one polymorphic variant can be performed for a plurality of patients. The response of at least one patient homozygous for at least one polymorphic variant can be compared with at least one patient homozygous for the alternative form of that polymorphic variant or polymorphic variants. The response of at least one patient heterozygous for at least one polymorphic variant can be compared with the response of at least one patient homozygous for the at least one polymorphic variant. The heterozygous patient response can be compared to both alternative homozygous forms, or the response of heterozygous patients is grouped with the response of one class of homozygous patients and said group is compared to the response of the alternative homozygous group.

One approach to analyzing the clinical data is as follows. First, variability between patients in the response to a particular treatment is observed. Second, at least a portion of the variable response is correlated with the presence or absence of at least one polymorphic variant in at least one gene. Third, an analytical or diagnostic test is provided to determine the presence or absence of the at least one polymorphic variant in individual patients. Fourth, the presence or absence of the polymorphic variant or polymorphic variants is used to select a patient for a treatment or to select a treatment for a patient, or the polymorphic variant information is used in other methods described herein.

Polymorphic variants in a gene can be correlated empirically with treatment response, which can be used to identify polymorphic variants in a gene that exist in a population. The presence of the different polymorphic variants or haplotypes in individuals of a study group, which can be representative of a population or populations, is determined. This polymorphic variant information is then correlated with treatment response of the various individuals as an indication that genetic variability in the gene is at least partially responsible for differential treatment response. Statistical measures known to those skilled in the art can be used to measure the fraction of interpatient variation attributable to any one polymorphic variant. Useful methods for identifying genes relevant to the physiologic action of a drug or other treatment are known to those skilled in the art, and include large scale analysis of gene expression in cells treated with the drug compared to control cells, or large scale analysis of the protein expression pattern in treated vs. untreated cells, or the use of techniques for identification of interacting proteins or ligand-protein interactions.

The gene comprising the polymorphic variant can be involved in drug action, and the variant forms of the gene are associated with variability in the action of the drug. In some embodiments, one variant form of the gene is associated with the action of the drug such that the drug will be effective in an individual who is heterozygous or homozygous for the variant. In some embodiments, a variant form of the gene is associated with the action of the drug such that the drug will be toxic or otherwise contra-indicated in a homozygous or heterozygous individual.

In one embodiment, patients are stratified by genotype by one candidate polymorphic variant in the candidate gene locus. Genetic stratification of patients can be accomplished in several ways, including the following, where "X" is the more frequent form of the polymorphic variant being assessed and "x" is the less frequent form): (a) XX vs. xx; (b) XX vs. Xx vs. xx; (c) XX vs. (Xx+xx); (d) (XX+Xx) vs. xx. The effect of genotype on drug response phenotype can be affected by a variety of nongenetic factors, and it can be beneficial to measure the effect of genetic stratification in a subgroup of the overall clinical trial population. Subgroups can be defined in a number of ways including, for example, biological, clinical, pathological or environmental criteria. Biological criteria include sex (gender), age, hormonal status and reproductive history, ethnic, racial or geographic origin, or surrogate markers of ethnic, racial or geographic origin. Clinical criteria include disease status and disease manifestations. Pathological criteria include histopathologic features of disease tissue, or pathological diagnosis; pathological stage; loss of heterozygosity (LOH), pathology studies, and laboratory studies. Frequency of responders is measured in each genetic subgroup. Subgroups can be defined in several ways: more than two age groups, and age related status such as pre or post-menopausal. One can also stratify by haplotype at one candidate locus where the haplotype is made up of two polymorphic variants, three polymorphic variants or greater than three polymorphic variants. A variety of statistical methods exist for measuring the difference between two or more groups in a clinical trial. One skilled in the art will recognize that different methods are suited to different data sets. In general, there is a family of methods customarily used in clinical trials, and another family of methods customarily used in genetic epidemiological studies. Methods from either family can be suitable for performing statistical analysis of pharmacogenetic clinical trial data.

Conventional clinical trial statistics include hypothesis testing and descriptive methods. Guidance in the selection of appropriate statistical tests for a particular data set can be obtained from texts such as: Biostatistics: A Foundation for Analysis in the Health Sciences, 7th edition (Wiley Series in Probability and Mathematical Statistics, Applied Probability and statistics) by Wayne W. Daniel, John Wiley & Sons, 1998; Bayesian Methods and Ethics in a Clinical Trial Design (Wiley Series in Probability and Mathematical Statistics. Applied Probability Section) by J. B. Kadane (Editor), John Wiley & Sons, 1996.

Hypothesis testing statistical procedures include the following examples: one-sample procedures (binomial confidence interval, Wilcoxon signed rank test, permutation test with general scores, generation of exact permutational distributions); two-sample procedures (t-test, Wilcoxon-Mann-Whitney test, Normal score test, Median test, Van der Waerden test, Savage test, Logrank test for censored survival data, Wilcoxon-Gehan test for censored survival data, Cochran-Armitage trend test, permutation test with general scores, generation of exact permutational distributions); R×C contingency tables (Fisher's exact test, Pearson's chi-squared test, Likelihood ratio test, Kruskal-Wallis test, Jonckheere-Terpstra test, Linear-by linear association test, McNemar's test, marginal homogeneity test for matched pairs); Stratified 2×2 contingency tables (test of homogeneity for odds ratio, test of unity for the common odds ratio, confidence interval for the common odds ratio); Stratified 2×C contingency tables (all two-sample procedures listed above with stratification, confidence intervals for the odds ratios and trend, generation of exact permutational distributions); General linear models (simple regression, multiple regression, analysis of polymorphic variant—ANOVA-, analysis of copolymorphic variant, response-surface models, weighted regression, polynomial regression, partial correlation, multiple analysis of polymorphic variant—MANOVA-, repeated measures analysis of polymorphic variant); analysis of polymorphic variant and copolymorphic variant with a nested (hierarchical) structure. designs and randomized plans for nested and crossed experiments (completely randomized design for two treatment, split-splot design, hierarchical design, incomplete block design, latin square design); nonlinear regression models; logistic regression for unstratified or stratified data, for binary or ordinal response data, using the logit link function, the normit function or the complementary log-log function; probit, logit, ordinal logistic and gompit regression models, fitting parametric models to failure time data that may be right-, left-, or interval-censored; tested distributions can include extreme value, normal and logistic distributions, and, by using a log transformation, exponential, Weibull, lognormal, loglogistic and gamma distributions; compute non-parametric estimates of survival distribution with right-censored data and compute rank tests for association of the response variable with other variables.

Descriptive statistical methods include factor analysis with rotations, canonical correlation, principal component analysis for quantitative variables, principal component analysis for qualitative data, hierarchical and dynamic clustering methods to create tree structure, dendrogram or phenogram, simple and multiple correspondence analysis using a contingency table as input or raw categorical data. Specific instructions and computer programs for performing the above calculations can be obtained from companies such as: SAS/STAT Software, SAS Institute Inc., Cary, N.C., USA; BMDP Statistical Software, BMDP Statistical Software Inc., Los Angeles, Calif., USA; SYSTAT software, SPSS Inc., Chicago, Ill., USA; StatXact & LogXact, CYTEL Software Corporation, Cambridge, Mass., USA.

Genetic epidemiological methods can also be useful in carrying out statistical tests for the invention. Guidance in the selection of appropriate genetic statistical tests for analysis of a particular data set can be obtained from texts such as: Fundamentals of Genetic Epidemiology (Monographs in Epidemiology and Biostatistics, Vol 22) by M. J. Khoury, B. H. Cohen & T. H. Beaty, Oxford Univ Press, 1993; Methods in Genetic Epidemiology by Newton E. Morton, S. Karger Publishing, 1983; Methods in Observational Epidemiology, 2nd edition (Monographs in Epidemiology and Biostatistics, V. 26) by J. L. Kelsey (Editor), A. S. Whittemore & A. S. Evans, 1996; Clinical Trials: Design, Conduct, and Analysis (Monographs in Epidemiology and Biostatistics, Vol 8) by C. L. Meinert & S. Tonascia, 1986).

Parsimony methods can be used to classify DNA sequences, haplotypes or phenotypic characters. Parsimony principle maintains that the best explanation for the observed differences among sequences, phenotypes (individuals, species) etc., is provided by the smallest number of evolutionary changes. Alternatively, simpler hypotheses are used to explain a set of data or patterns, than more complicated ones [Molecular Systematics, Hillis et al. (1996)]. These methods for inferring relationship among sequences operate by minimizing the number of evolutionary steps or mutations, changes from one sequence/character, required to explain a given set of data. To obtain relationships among a set of sequences and construct a structure, such as a tree or topology, the minimum number of mutations that are required for explaining the observed evolutionary changes among a set of sequences are first counted. A structure is constructed based on this number. Additional structures are tried and the structure that requires the smallest number of mutational steps is chosen as the likely structure/evolutionary tree for the sequences studied.

If the computed frequency of the polymorphic variants and/or haplotypes is equal to the number of individuals in the population, then there will be a consideration of utilizing additional methods. For these cases and if there is a small population, then the number of haplotypes will be considered relative to the number of entrants. Homozygotes can be assigned one unambiguous haplotype. If there is a single site polymorphic variant (mutation) at one of the chromosomes then it will have two haplotypes. As the number of polymorphic variants increase in the diploid chromosomes, each of these polymorphic variants are compared with the haplotypes of the original population. Then a frequency is assigned to the new polymorphic variant based upon the Hardy-Weinberg expected frequencies. [See generally, Clark, Mol Biol and Evol. (1990).]

The statistical significance of the differences between polymorphic variant frequencies can be assessed by a Pearson chi-squared test of homogeneity of proportions with n−1 degrees of freedom. Then, in order to determine which polymorphic variant(s) is responsible for an eventual significance, one can consider each polymorphic variant individually against the rest, up to n comparisons, each based on a 2×2 table. This approach should result in chi-sequared tests that are individually valid; talking the most significant of these tests is a form of multiple testing. A Bonferroni's adjustment for multiple testing can be made to the P-values, such as $p^* = 1-(1-p)n$. The statistical significance of the difference between genotype frequencies associated to every polymorphic variant can be assessed by a Pearson chi-squared test of homogeneity of proportions with 2 degrees of freedom, using the same Bonferroni's adjustment as above.

Testing for unequal haplotype frequencies between cases and controls can be considered in the same framework as testing for unequal polymorphic variant frequencies, because a single polymorphic variant can be considered as a haplotype of a single locus. The relevant likelihood ratio test compares a model where two seqarate sets of haplotype frequencies apply to the cases and controls, to one where the entire sample is characterized by a single common set of haplotype frequencies. This comparison can be performed by repeated use of a computer program [Terwilliger and Ott, 1994, Handbook of Human Linkage Analysis, Baltimore, John Hopkins University Press] to successively obtain the log-likelihood corresponding to the set of haplotpe frequency estimates on the cases (lnL case), on the controls (lnLcontrol), and on the overall (InLcombined). The test statistic 2((InLcase)+(InLcontrol)−(InLcombined)) is then chi-squared with degrees of freedom, where r is the number of haplotypes. To test for potentially confounding effects or effect-modifiers, such as sex, age, etc., logistic regression can be used with case-control status as the outcome variable, and genotypes and covariates, plus possible interactions, as predictor variables.

Drug Screening

Drug screening assays can be performed on cells that have been transfected with a nucleic acid encoding all or part of one of the polymorphic variants relevant to the invention. In some embodiments, no endogenous equivalents of transfected nucleic acids are present in the cells. The cells can be transfected with RNA in which case expression of the polymorphic variant protein is transient. Alternatively, the nucleic acid can be stably introduced into the cell line. In those embodiments wherein the nucleic acid encodes a one carbon metabolic pathway enzyme, cells expressing protein are monitored for relative levels of pathway molecules. The control can be vehicle without an agent or can be an agent known not to have any effect on a one carbon metabolic pathway. The control can be a known agonist and/or antagonist of a one carbon metabolic pathway. Transfected cells are also useful for identifying genes whose expression pattern is altered in the presence of one or more of the polymorphic variants relevant to the invention relative to wildtype form. Such genes themselves are potential therapeutic or diagnostic targets.

In some embodiments, drug screening assays are performed on transgenic animals. Some transgenic animals have an exogenous human transgene bearing a polymorphic variant relevant to the invention. In some such animals, the endogenous equivalent(s) of transfected gene(s) transgene is/are knocked out. In other transgenic animals, the endogenous gene is mutated to contain one of the variant forms relevant to the invention. Potential agents are administered to the transgenic animal, and relevant parameters are measured. The performance can be compared with that of a transgenic animal administered a control substance or with a nontransgenic animal administered the agent or a control substance.

The invention provides a pharmaceutical composition that includes a compound that has a differential effect in patients having at least one copy, or alternatively, two copies of a form of a gene as identified for aspects above and a pharmaceutically acceptable carrier, excipient, or diluent. The composition is adapted to be preferentially effective to treat a patient with cells containing one, two, or more copies of the form of the gene.

The methods and materials of the invention can utilize conventional pharmaceutical compositions more effectively by identifying patients who are likely to benefit from a particular treatment, patients for whom a particular treatment is less likely to be effective, or for whom a particular treatment is likely to produce undesirable or intolerable effects. In some embodiments, compositions are adapted to be preferentially effective in patients who possess particular genetic characteristics, i.e., in whom a particular polymorphic variant or polymorphic variants in one or more genes is present or absent—depending on whether the presence or the absence of the polymorphic variant or polymorphic variants in a patient is correlated with an increased expectation of beneficial response. In some embodiments, one or more polymorphic variants indicates that a patient can beneficially receive a significantly higher dosage of a drug than a patient having a different polymorphic variant or polymorphic variants. An indication or suggestion can specify that a patient be heterozygous, or alternatively, homozygous for a particular polymorphic variant or polymorphic variants or variant form of a gene. In some embodiments, an indication or suggestion specifies that a patient have no more than one copy, or zero copies, of a particular polymorphic variant, polymorphic variants, or variant form of a gene.

In some embodiments involving pharmaceutical compositions, active compounds, or drugs, the material is subject to a regulatory limitation or restriction on approved uses or indications, e.g., by the U.S. Food and Drug Administration (FDA), limiting approved use of the composition to patients having at least one copy of the particular form of the gene that contains at least one polymorphic variant. In some embodiments, the composition is subject to a regulatory limitation or restriction on approved uses indicating that the composition is not approved for use or should not be used in patients having at least one copy of a form of the gene including at least one polymorphic variant. In some embodiments, the composition is packaged, and the packaging includes a label or insert indicating or suggesting beneficial therapeutic approved use of the composition in patients having one or two copies of a form of the gene including at least one polymorphic variant. Alternatively, the label or insert limits approved use of the composition to patients having zero or one or two copies of a form of the gene including at least one polymorphic variant. The latter embodiment would be likely where the presence of the at least one polymorphic variant in one or two copies in cells of a patient means that the composition would be ineffective or deleterious to the patient. In some embodiments, the composition is indicated for use in treatment of a disease or condition which is one of those identified for aspects above. In some embodiments, the at least one polymorphic variant includes at least one polymorphic variant from those identified herein.

The term "packaged" means that the drug, compound, or composition is prepared in a manner suitable for distribution or shipping with a box, vial, pouch, bubble pack, or other protective container, which may also be used in combination. The packaging can have printing on it and/or printed material may be included in the packaging. In some embodiments, the drug is subject to a regulatory limitation or suggestion or warning as described above that limits or suggests limiting approved use to patients having specific polymorphic variants or variant forms of a gene in order to achieve maximal benefit and avoid toxicity or other deleterious effect.

A pharmaceutical composition can be adapted to be preferentially effective in a variety of ways. In some embodiments, an active compound is selected that was not previously known to be differentially active, or which was not previously recognized as a potential therapeutic compound. In some embodiments, the concentration of an active compound that has differential activity can be adjusted such that the composition is appropriate for administration to a patient with the specified polymorphic variants. In some embodiments, the presence of a specified polymorphic variant may allow or require the administration of a much larger dose, which would not be practical with a previously utilized composition. In some embodiments, a patient requires a much lower dose, such that administration of such a dose with a prior composition would be impractical or inaccurate. The composition can be prepared in a higher or lower unit dose form, or prepared in a higher or lower concentration of the active compound or compounds. In yet other cases, the composition can include additional compounds needed to enable administration of a particular active compound in a patient with the specified polymorphic variants, which was not in previous compositions, for example, because the majority of patients did not require or benefit from the added component.

In some embodiments, a drug is explicitly indicated for, and/or for which approved use is restricted to individuals in the population with specific polymorphic variants or combinations of polymorphic variants, as determined by diagnostic tests for polymorphic variants or variant forms of certain genes involved in the disease or condition or involved in the action of the drug. Such drugs can provide more effective treatment for a disease or condition in a population identified or characterized with the use of a diagnostic test for a specific polymorphic variant or variant form of the gene if the gene is involved in the action of the drug or in determining a characteristic of the disease or condition. Such drugs can be developed using the diagnostic tests for specific polymorphic variants or variant forms of a gene to determine the inclusion of patients in a clinical trial.

The invention also comprises a method for producing a pharmaceutical composition by identifying a compound that has differential activity against a disease or condition in patients having at least one polymorphic variant in a gene, compounding the pharmaceutical composition by combining the compound with a pharmaceutically acceptable carrier, excipient, or diluent such that the composition is preferentially effective in patients who have at least one copy of the polymorphic variant or polymorphic variants. In some embodiments, the patient has two copies of the polymorphic variant or polymorphic variants. In some embodiments, the disease or condition, gene or genes, polymorphic variants, methods of administration, or method of determining the presence or absence of polymorphic variants is as described for other aspects of this invention.

The invention also comprises a method for producing a pharmaceutical agent by identifying a compound which has differential activity against a disease or condition in patients having at least one copy of a form of a gene having at least one polymorphic variant and synthesizing the compound in an amount sufficient to provide a pharmaceutical effect in a patient suffering from the disease or condition. The compound can be identified by conventional screening methods and its activity confirmed. Compound libraries can be screened to identify compounds which differentially bind to products of variant forms of a particular gene product, or which differentially affect expression of variant forms of the particular gene, or which differentially affect the activity of a product expressed from such gene.

The invention also includes methods of manufacturing a medicament comprising one or more of the materials of the invention in the treatment of one or more of the diseases of the invention. Therapeutic agents and regimens further include homocysteine monitoring, B vitamin supplementation, for example, folate, FOLTX®, $B_{12}$, and chemotherapeutic agents. Each FOLTX® tablet contains 2.5 mg of folacin (folic acid), 25 mg of pyridoxine (Vitamin $B_6$), and 2 mg of cyanocobalamin (Vitamin $B_{12}$).

Formulation

A therapeutic agent, which can be a compound and/or a composition, relevant to the invention can comprise a small molecule, a nucleic acid, a protein, an antibody, or any other agent with one or more therapeutic property. The therapeutic agent can be formulated in any pharmaceutically acceptable manner. In some embodiments, the therapeutic agent is prepared in a depot form to allow for release into the body to which it is administered is controlled with respect to time and location within the body (see, for example, U.S. Pat. No. 4,450,150). Depot forms of therapeutic agents can be, for example, an implantable composition comprising the therapeutic agent and a porous or non-porous material, such as a polymer, wherein the therapeutic agent is encapsulated by or diffused throughout the material and/or degradation of the non-porous material. The depot is then implanted into the desired location within the body and the therapeutic agent is released from the implant at a predetermined rate.

The therapeutic agent that is used in the invention can be formed as a composition, such as a pharmaceutical composition comprising a carrier and a therapeutic compound. Pharmaceutical compositions containing the therapeutic agent can comprise more than one therapeutic agent. The pharmaceutical composition can alternatively comprise a therapeutic agent in combination with other pharmaceutically active agents or drugs, such as chemotherapeutic agents, for example, a cancer drug.

The carrier can be any suitable carrier. Preferably, the carrier is a pharmaceutically acceptable carrier. With respect to pharmaceutical compositions, the carrier can be any of those conventionally used and is limited only by chemico physical considerations, such as solubility and lack of reactivity with the active compound(s), and by the route of administration. In addition to the following described pharmaceutical composition, the therapeutic compounds of the present inventive methods can be formulated as inclusion complexes, such as cyclodextrin inclusion complexes, or liposomes.

The pharmaceutically acceptable carriers described herein, for example, vehicles, adjuvants, excipients, and diluents, are well-known to those skilled in the art and are readily available to the public. The pharmaceutically acceptable carrier can be chemically inert to the active agent(s) and one which has no detrimental side effects or toxicity under the conditions of use. The choice of carrier can be determined in part by the particular therapeutic agent, as well as by the particular method used to administer the therapeutic compound. There are a variety of suitable formulations of the pharmaceutical composition of the invention. The following formulations for oral, aerosol, parenteral, subcutaneous, transdermal, transmucosal, intestinal, parenteral, intramedullary injections, direct intraventricular, intravenous, intranasal, intraocular, intramuscular, intraarterial, intrathecal, interperitoneal, rectal, and vaginal administration are exemplary and are in no way limiting. More than one route can be used to administer the therapeutic agent, and in some instances, a particular route can provide a more immediate and more effective response than another route. Depending on the specific conditions being treated, such agents can be formulated and administered systemically or locally. Techniques for formulation and administration may be found in Remington's Pharmaceutical Sciences, 18th ed., Mack Publishing Co., Easton, Pa. (1990).

Formulations suitable for oral administration can include (a) liquid solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or soft shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inhibitor in a flavor, usually sucrose and acacia or tragacanth, as well as pastilles comprising the inhibitor in an inert base, such as gelatin and glycerin, or sucrose and acacia, emulsions, gels, and the like containing, in addition to, such excipients as are known in the art.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The therapeutic agent, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non pressured preparations, such as in a nebulizer or an atomizer. Such spray formulations also may be used to spray mucosa. Topical formulations are well known to those of skill in the art. Such formulations are particularly suitable in the context of the invention for application to the skin.

Injectable formulations are in accordance with the invention. The parameters for effective pharmaceutical carriers for injectable compositions are well-known to those of ordinary skill in the art [see, e.g., Pharmaceutics and Pharmacy Practice, J. B. Lippincott Company, Philadelphia, Pa., Banker and Chalmers, eds., pages 238 250 (1982), and ASHP Handbook on Injectable Drugs, Toissel, 4th ed., pages 622 630 (1986)]. For injection, the agents of the invention can be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Formulations suitable for parenteral administration include aqueous and non aqueous, isotonic sterile injection solutions, which can contain anti oxidants, buffers, bacteriostats, and solutes that render the formulation isotonic with the blood of the intended recipient, and aqueous and non aqueous sterile suspensions that can include suspending agents, solubilizers, thickening agents, stabilizers, and preservatives. The therapeutic agent can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the inhibitor in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The therapeutic agent can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The exact formulation, route of administration and dosage can be chosen by the individual physician in view of the patient's condition. [See, e.g., Fingl et. al., in The Pharmacological Basis of Therapeutics, 1975, Ch. 1 p. 1]. The attending physician can determine when to terminate, interrupt, or adjust administration due to toxicity, or to organ dysfunctions. Conversely, the attending physician can also adjust treatment to higher levels if the clinical response were not adequate, precluding toxicity. The magnitude of an administrated dose in the management of disorder of interest will vary with the severity of the condition to be treated and the route of administration. The severity of the condition may, for example, be evaluated, in part, by standard prognostic evaluation methods. The dose and perhaps dose frequency, can vary according to the age, body weight, and response of the individual patient. A program comparable to that discussed above can be used in veterinary medicine.

Use of pharmaceutically acceptable carriers to formulate the compounds herein disclosed for the practice of the invention into dosages suitable for systemic administration is within the scope of the invention. With proper choice of carrier and suitable manufacturing practice, the compositions relevant to the invention, in particular, those formulated as solutions, can be administered parenterally, such as by intravenous injection. The compounds can be formulated readily using pharmaceutically acceptable carriers well known in the art into dosages suitable for oral administration. Such carriers enable the compounds relevant to the invention to be formulated as tablets, pills, capsules, liquids, gels, syrups, slurries, tablets, dragees, solutions, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the invention include compositions wherein the active ingredients are contained in an effective amount to achieve its intended purpose. In addition to the active ingredients, these pharmaceutical compositions can contain suitable pharmaceutically acceptable carriers comprising excipients and auxiliaries which facilitate processing of the active compounds into preparations which can be used pharmaceutically. The pharmaceutical compositions relevant to the invention can be manufactured in a manner that is itself known, for example, mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions can be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Administration

The invention also provides selecting a method of administration of an agent to a patient suffering from a disease or condition, by determining the presence or absence of at least one polymorphic variant in cells of the patient, where such presence or absence is indicative of an appropriate method of administration of the agent. The selection of a treatment regimen can involve selecting a dosage level or frequency of administration or route of administration of the agent(s) or combinations of those parameters. In some embodiments, two or more agents are administered, and the selecting involves selecting a method of administration for one, two, or more than two of the agents, jointly, concurrently, or separately. As understood by those skilled in the art, such plurality of agents is often used in combination therapy, and thus may be formulated in a single drug, or may be separate drugs administered concurrently, serially, or separately. Other embodiments are as indicated above for selection of second treatment methods, methods of identifying polymorphic variants, and methods of treatment as described for aspects above. The frequency of administration is generally selected to achieve a pharmacologically effective average or peak serum level without excessive deleterious effects. In some embodiments, the serum level of the drug is maintained within a therapeutic window of concentrations for the greatest percentage of time possible without such deleterious effects as would cause a prudent physician to reduce the frequency of administration for a particular dosage level. Administration of a particular treatment, for example, administration of a therapeutic compound or combination of compounds, is chosen depending on the disease or condition which is to be treated. In some embodiments, the disease or condition is one for which administration of a treatment is expected to provide a therapeutic benefit. In embodiments involving selection of a patient for a treatment, selection of a method or mode of administration of a treatment, and selection of a patient for a treatment or a method of treatment, the selection can be positive selection or negative selection. The methods can include modifying or eliminating a treatment for a patient, modifying or eliminating a method or mode of administration of a treatment to a patient, or modification or elimination of a patient for a treatment or method of treatment. A patient can be selected for a method of administration of a treatment, by detecting the presence or absence of at least one polymorphic variant in a gene as identified herein, where the presence or absence of the at least one polymorphic variant is indicative that the treatment or method of administration will be effective in the patient. If the at least one polymorphic variant is present in the patient's cells, then the patient is selected for administration of the treatment.

Dosage

The term "drug" or "therapeutic agent" as used herein refers to a chemical entity or biological product, or combination of chemical entities or biological products, administered to a person to treat or prevent or control a disease or condition. In some embodiments, the chemical entity or biological product is a low molecular weight compound. A "low molecular weight compound" has a molecular weight <5,000 Da, <2500 Da, <1000 Da, or <700 Da. In some embodiments, the chemical entity is a larger compound, for example, an oligomer of nucleic acids, amino acids, or carbohydrates including without limitation proteins, oligonucleotides, ribozymes, DNAzymes, glycoproteins, lipoproteins, and modifications and combinations thereof. In some embodiments, the biological product is a monoclonal or polyclonal antibody or fragment thereof such as a variable chain fragment cells; or an agent or product arising from recombinant technology, such as, without limitation, a recombinant protein, recombinant vaccine, or DNA construct developed for therapeutic use. The term "drug" or "therapeutic agent" can include, without limitation, compounds that are approved for sale as pharmaceutical products by government regulatory agencies such as the U.S. Food and Drug Administration (USFDA or FDA), the European Medicines Evaluation Agency (EMEA), and a world regulatory body governing the Internation Conference of Harmonization (ICH) rules and guidelines, compounds that do not require approval by government regulatory agencies, food additives or supplements including compounds commonly characterized as vitamins, natural products, and completely or incompletely characterized mixtures of chemical entities including natural compounds or purified or partially purified natural products. In some embodiments, the drug is approved by a government agency for treatment of a specific disease or condition. The term "drug" as used herein is synonymous with the terms "agent," "therapeutic agent," "compound," "therapeutic compound," "composition," "therapeutic composition," "medicine," "pharmaceutical product," or "product."

In treating a patient exhibiting a disorder of interest, a therapeutically effective amount of a agent or agents is administered. A therapeutically effective dose refers to that amount of the compound that results in amelioration of one or more symptoms or a prolongation of survival in a patient. The amount or dose of the therapeutic compound administered should be sufficient to affect a therapeutic response in the subject or animal over a reasonable time frame. For example, in the case of cancer, the dose of the therapeutic compound should be sufficient to inhibit metastasis, prevent metastasis, treat or prevent cancer in a period of from about 2 hours or longer, e.g., 12 to 24 or more hours, from the time of administration. In certain embodiments, the time period could be even longer. The dose can be determined by the efficacy of the particular therapeutic agent and the condition of the subject, as well as the body weight of the subject to be treated. Many assays for determining an administered dose are known in the art.

The dose of the therapeutic compound can also be determined by the existence, nature and extent of any adverse side effects that might accompany the administration of a particular therapeutic compound. The attending physician can decide the dosage of the inhibitor relevant to the invention with which to treat each individual patient using the correlation between polymorphic variant and disease and/or drug efficacies provided by the invention and taking into consideration a variety of factors, such as age, body weight, general health, diet, sex, inhibitor to be administered, route of administration, and the severity of the condition being treated. In some embodiments, the dose of the therapeutic compound is about 0.001 to about 1000 mg/kg body weight of the subject being treated/day, from about 0.01 to about 10 mg/kg body weight/day, about 0.01 mg to about 1 mg/cg body weight/day.

Toxicity and therapeutic efficacy of therapeutic agents can be determined by standard pharmaceutical procedures in cell cultures or experimental animals, for example, for determining the $LD_{50}$ and the $ED_{50}$. The dose ratio between toxic and therapeutic effects is the therapeutic index and it can be expressed as the ratio $LD_{50}/ED_{50}$. In some embodiments, compounds that exhibit large therapeutic indices are used. The data obtained from these cell culture assays and animal studies can be used in formulating a range of dosage for use in humans. The dosage of such compounds can lie within a range of circulating concentrations that can include the $ED_{50}$ with little or no toxicity. The dosage can vary within this range depending upon the dosage form and route of administration utilized. The therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

In connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by those of skill in the art.

In some embodiments, dosage is in respect to B vitamins administered as part of a therapy for a pregnancy-related complication. The following are dietary reference intakes (DRIs, per diem) for exemplary B vitamins. While in some embodiments, a subject is administered a dose about equal to that of DRI, generally the subject is administered one or more vitamin in doses greater than that of the DRI. Vitamin $B_2$ (riboflavin), DRI of 1.1 milligrams; Vitamin $B_6$ (pylidoxine), DRI of 1.3 milligrams; Vitamin $B_9$ (folic acid, folate, pteroylglutamic acid), DRI of 400 micrograms; and Vitamin $B_{12}$ (cyano-cobalamin) DRI of 2.4 micrograms. Analogous, pro-drug, salts, and bioactive equivalents of these vitamins can also be employed. For example other folate-related compounds include folinic acid (5-formyl-tetrahydropteroylglutamate), and other $B_{12}$-related compounds include methylcobalamin, hydroxycobalamin, and adenosylcobalamin (5'-deoxyadenosylcobalamin, dibencozide).

Kits

The invention includes kits for the detection of polymorphic variants associated with disease states, conditions or complications. The kits can comprise a polynucleotide of at least 30 contiguous nucleotides of one of the variants described herein. In one embodiment, the polynucleotide contains at least one polymorphism of the invention. Alternatively, the 3' end of the polynucleotide is immediately 5' to a polymorphic site, preferably a polymorphic site of the invention. In one embodiment, the polymorphic site contains a genetic variant. In still another embodiment, the genetic variant is located at the 3' end of the polynucleotide. In yet another embodiment, the polynucleotide of the kit contains a detectable label. Suitable labels include, but are not limited to, radioactive labels, such as radionuclides, fluorophores or fluorochromes, peptides, enzymes, antigens, antibodies, vitamins or steroids. The kit may also contain additional materials for detection of the polymorphisms. A kit can contain one or more of the following: buffer solutions, enzymes, nucleotide triphosphates, and other reagents and materials useful for the detection of genetic polymorphisms. Kits can contain instructions for conducting analyses of samples for the presence of polymorphisms and for interpreting the results obtained.

In some embodiments, the kit contains one or more pairs of allele-specific oligonucleotides hybridizing to different forms of a polymorphism. In some embodiments, the kit contains at least one probe or at least one primer or both corresponding to a gene or genes relevant to the invention. The kit can be adapted and configured to be suitable for identification of the presence or absence of one or more polymorphic variants. The kit can contain a plurality of either or both of such probes and/or primers, for example, 2, 3, 4, 5, 6, or more of such probes and/or primers. The plurality of probes and/or primers are adapted to provide detection of a plurality of different sequence polymorphic variants in a gene or plurality of genes, for example, in 2, 3, 4, 5, or more genes or to sequence a nucleic acid sequence including at least one polymorphic variant site in a gene or genes. In some embodiments, the kit contains components for detection of a plurality of polymorphic variants indicative of the effectiveness of a treatment or treatment against a plurality of diseases. Additional kit components can include one or more of the following: a buffer or buffers, such as amplification buffers and hybridization buffers, which may be in liquid or dry form, a DNA polymerase, such as a polymerase suitable for carrying out PCR, and deoxy nucleotide triphosphases (dNTPs). Preferably a probe includes a detectable label, for example, a fluorescent label, enzyme label, light scattering label, or other label. Additional components of the kit can also include restriction enzymes, reverse-transcriptase or polymerase, the substrate nucleoside triphosphates, means used to label, for example, an avidin-enzyme conjugate and enzyme substrate and chromogen if the label is biotin, and the appropriate buffers for reverse transcription, PCR, or hybridization reactions.

In some kits, the allele-specific oligonucleotides are provided immobilized to a substrate. For example, the same substrate can comprise allele-specific oligonucleotide probes for detecting any or all of the polymorphism variants described herein. Accordingly, the kit may comprise an array including a nucleic acid array and/or a polypeptide array. The array can include a plurality of different antibodies, a plurality of different nucleic acid sequences. Sites in the array can allow capture and/or detection of nucleic acid sequences or gene products corresponding to different polymorphic variants in one or more different genes. The array can be arranged to provide polymorphic variant detection for a plurality of polymorphic variants in one or more genes which correlate with the effectiveness of one or more treatments of one or more diseases.

The kit also can contain instructions for carrying out the methods. In some embodiments, the instructions include a listing of the polymorphic variants correlating with a particular treatment or treatments for a disease of diseases. The kit components can be selected to allow detection of a polymorphic variant described herein, and/or detection of a polymorphic variant indicative of a treatment, for example, administration of a drug.

The following examples further illustrate the invention but, of course, should not be construed as in any way limiting its scope.

EXAMPLE 1

Candidate polymorphic variant sites in folate/homocysteine-related genes were investigated for a potential maternal association with increased risk of developing clinically severe abruptio placentae during pregnancy. [Parle-McDermott et al., Am. J. Med. Genetics, 132A:365-368 (2005).] The polymorphic variants tested included MTHFD1 1958G>A (R653Q), which had not been tested previously in relation to abruptio placentae, and the MTHFR polymorphisms 677C>T (A222V) and 1298A>C (E429A).

Blood samples were obtained from 56,049 pregnant women attending the three main maternity hospitals in Dublin between 1986 and 1990. Samples were taken on the first visit to the clinic and the gestational ages ranged between 15 and 17 weeks. Approximately 90% of births in the Dublin area are delivered in these hospitals as previously described [Kirke et al., Obstget. Gynecol., 89:221-226 (1993)]. In a global context, the Irish can be described as a Caucasian Northern European population [Cavalli-Sforza, Princeton, N.J.: Princeton University Press (1993)]. Moreover, the low level of immigration into Ireland during the last century, means that population stratification is unlikely to confound genetic analyses. Pregnancies affected by severe abruptio placentae (n=62) and control pregnancies (n=184) were identified from hospital records in two of the hospitals. The diagnosis of severe abruptio placentae was based on having a retroplacental clot and/or accidental haemorrhage with associated clinical signs of abruption and/or a statement in the case records that the patient was a definite case of abruptio placentae. Data on gestational age at delivery, maternal hypertension, maternal blood transfusion, and pregnancy outcome were collected on all cases. Control pregnancies were selected from women with no history of abruptio placentae, and were matched for the same date and clinic as the cases where the blood sample was provided. Ethical approval was obtained for all samples collected and samples were anonymised prior to genotyping.

Genomic DNA was extracted using QIAamp DNA Blood Mini Kit (Qiagen, UK). Analysis of the MTHFD1 1958G>A (R653Q) polymorphism was performed by PCR-RFLP (restriction fragment length polymorphism) as detailed previously [Brody et al., Am. J. Hum. Genet., 71: 1207-1215 (2002)]. Analysis of the MTHFR 677C>T (A222V) polymorphism was performed by PCR-RFLP using Hinf I as previously described [Frosst et al., Nature Genet., 10: 111:113 (1995)]. The MTHFR 1298A>C (E429A) polymorphism was PCR amplified as described in van der Put et al., Am. J. Hum. Genet., 62:1044-1051 (1998) and genotyping was carried out via ASO (allele specific oligonucleotide) analysis as described previously [Parle-McDermott et al., J. Hum. Genet. 48:190-193 (2003)].

Allele and genotype frequencies were compared between cases and controls using statistical software (SAS PROC NLMIXED). The odds ratios were calculated using a log linear model by the delta method [Agresti, New York: John Wiley & Sons (1990)] and statistical significance was assessed via the chi-square test. Likelihood ratios (G2) were used to assess goodness of fit of different models i.e., G2 provides a measure of the reliability of the odds ratio (small G2 P-values indicate a poor fit to the model being tested).

Combined MTHFR genotypes were analyzed by estimating (maximum likelihood estimation) the gamete frequencies in cases and controls using a model of the four combinations of alleles as described by Weir, Genetic Data Analysis II, Sunderland, Mass.: Sinauer (1996). A gene-gene interactive effect of MTHFR 677C>T (A222V) with MTHFD1 1958G>A (R653Q) or MTHFR 1298A>C (E429A) was tested using a series of non-hierarchical logistic models [Piegorsch et al., Stat. Med. 13:153-162 (1994)] to estimate interactive dominant and recessive effects.

The case group (n=62) consisted of mothers whose pregnancies were affected by clinically severe abruptio placentae. As expected in severe cases of abruption placentae, there was considerable co-morbidity. Intrauterine fetal death occurred in 31 of 62 (50%) cases. Blood transfusion was required in 26 of 62 (42%) cases. Maternal antepartum hypertension preabruptio was present in 17 of 62 (27%). Preterm delivery (<37 weeks gestational age) occurred in 29 of 62 (47%). Genotyping of the abruptio placentae cases and controls was successful in 100% (246/246) of subjects for MTHFD1 1958G>A (R653Q), 99.2% (244/246) for MTHFR 677C>T (A222V) and 100% (246/246) for MTHFR 1298A>C (E429A). The allele and genotype frequencies and comparisons for each polymorphism are shown in Table I. Although several models were tested for each polymorphism, only the best fitting model (largest goodness of fit (G2) P-value) is shown in Table I.

The 'Q' allele of the MTHFD1 1958G>A (R653Q) polymorphism was more common in severe abruptio placentae cases than in controls due to an increase in 'QQ' homozygotes among cases (Table I). Thus, pregnant women who are homozygous for the 'Q' allele ('QQ') have a greater risk of developing severe abruptio placentae during their pregnancy (odds ratio 2.85 (1.47-5.53), P=0.002) compared to women who are heterozygous ('RQ') or homozygous wildtype ('RR'). Among women with severe abruptio placentae, those who were 'QQ' homozygous were not significantly more likely than women who were 'RR' homozygous wildtype or heterozygous to have hypertension, pre-term deliveries, or to require transfusions. However, an effect may have been missed due to the small number of individuals within each subgroup. The allele frequencies in the controls are similar to those previously reported in the Dutch [Hol et al., Clin. Genet., 53: 119-125 (1998)] and Turkish [Akar et al., Acta. Haematol. 102:199-200 (1999)] populations and in previously published Irish control population [Brody et al., Am. J. Hum. Genet. 71:1207-1215 (2002)].

the two polymorphisms in both cases and controls. However, analysis of combined MTHFR genotypes showed similar frequencies in cases and controls, indicating that there is no interactive effect of these MTHFR polymorphisms on risk of abruptio placentae; this finding was confirmed by the non-hierarchical logistic model analysis. Therefore, the MTHFR 677C>T (A222V) and 1298A>C (E429A) polymorphisms are in linkage disequilibrium but do not show an association with severe abruptio placentae risk in this cohort when analyzed either independently or in combination.

Combined analysis of MTHFR 677C>T (A222V) with MTHFD1 1958G>A (R653Q) genotypes by the non-hierarchical logistic model analysis also did not show any significant effects and therefore, there does not appear to be an interactive effect of these two polymorphisms and risk of severe abruptio placentae. Analysis of the MTHFR polymorphisms 677C>T (A222V) and 1298A>C (E429A) in the largest group of clinically defined severe abruptio placentae patients to date (n=62) and controls (n=182) does not support their role as genetic risk factors.

Pregnant women who are homozygous for the MTHFD1 R653Q polymorphism i.e., 'QQ', are almost three times more likely to develop severe abruptio placentae than pregnant

TABLE I

Comparison of MTHFD1 1958G > A (R653Q), MTHFR 677C > T and MTHFR 1298A > C Polymorphisms in placental abruption.

| MTHFD1 R653Q | Genotypes | | | Alleles | |
|---|---|---|---|---|---|
| | 'RR' | 'RQ' | 'QQ' | 'R' | 'Q' |
| Abruptio Placentae | 18 (.29)[1] | 23 (.37) | 21 (.34) | 59 (.48) | 65 (.52) |
| Controls | 60 (.33) | 96 (.52) | 28 (.15) | 216 (.59) | 152 (.41) |
| 'Q' vs. 'R' | Odds Ratio 1.57 (1.01[2]-2.44[3]), P = 0.047[4] | | | | |
| 'QQ' vs. 'RQ'/'RR' | Odds Ratio 2.85 (1.47-5.53), P = 0.002[5] | | | | |
| MTHFR 677C > T | CC | CT | TT | C | T |
| Abruptio Placentae | 26 (.42) | 31 (.50) | 5 (.08) | 83 (.67) | 41 (.33) |
| Controls | 80 (.44) | 80 (.44) | 22 (.12) | 240 (.66) | 124 (.34) |
| T vs. C | Odds Ratio 0.96 (0.63-1.44), P = 0.83 | | | | |
| TT vs. CT/CC | Odds Ratio 0.64 (0.23-1.76), P = 0.39[6] | | | | |
| MTHFR 1298A > C | AA | AC | CC | A | C |
| Abruptio Placentae | 25 (.40) | 31 (.50) | 6 (.10) | 81 (.65) | 43 (.35) |
| Controls | 91 (.49) | 75 (.41) | 18 (.10) | 257 (.70) | 111 (.30) |
| C vs. A | Odds Ratio 1.23 (0.81-1.86), P = 0.33 | | | | |
| CC/AC vs. AA | Odds Ratio 1.45 (0.81-2.60), P = 0.21[7] | | | | |

[1]Data in parentheses are allele or genotype frequencies;
[2]Lower limit of 95% Confidence Interval;
[3]Upper limit of 95% Confidence Interval;
[4]Assessed with use of chi-squared analysis;
[5]Goodness of fit statistic G2 P = 0.53;
[6]Goodness of fit statistic G2 P = 0.57;
[7]Goodness of fit statistic G2 P = 0.67.

Analysis identified the MTHFD1 G1958GA (R653Q) polymorphism as a genetic risk factor for having a pregnancy affected by severe abruptio placentae. Pregnant mothers who are 'QQ' homozygous have almost a tripled risk of having this pregnancy complication.

Case-control comparisons of the MTHFR polymorphisms 677C>T (A222V) and 1298A>C (E429A) did not reveal significant differences between cases and controls (Table I). The association between MTHFR 677C>T and 1298A>C was also examined and in agreement with previous MTHFR data [Parle-McDermott et al., J. Hum. Genet., 48:190-193 (2003)], there was clear evidence of linkage disequilibrium between women who are either heterozygous ('RQ') or homozygous wildtype ('RR') (odds ratio 2.85 (1.47-5.53), P=0.002). The possibility of fetal DNA differentially affecting the results due to fetal-maternal transfusion can be ruled out as all the blood samples were taken between 15-17 weeks gestation, prior to the diagnosis of placental abruption. Moreover, the genetic consequences of this possibility would be to increase the apparent number of heterozygotes in affected mothers.

Without being held to any particular theory of mechanism, the following theories have been contemplated. The effect of the MTHFD1 R653Q polymorphism appears to act through the 'QQ' homozygous genotype. Even if the MTHFD1R653Q polymorphism does not have a direct effect on folate and homocysteine levels, this polymorphism may alter nucleotide pools available for DNA synthesis and thus affect cell division. The MTHFD1 653 'Q' allele, which resides in the synthetase domain of the trifunctional enzyme, may be less efficient at DNA synthesis particularly when folate status is low. This lower efficiency may produce effects at the cellular level without causing major perturbations in plasma metabolites. Alternatively, this polymorphism may be in linkage disequilibrium with an unknown variant that alters enzyme activity.

EXAMPLE 2

This study investigated whether the MTHFD1 1958G>A, MTHFR 677C>T, or TCNII C667G polymorphism influences the maternal genetic risk of second trimester pregnancy loss. Cases and controls were derived from a bank of blood samples from 56,049 pregnant women drawn during their first clinical visit at the three main Dublin maternity hospitals between 1986 and 1990. These hospitals deliver approximately 90% of births within the Dublin area as previously described [Kirke, et al., Q. J. Med. 86:703-708 (1993)]. This bank of samples is representative of a homogeneous population and due to the low level of immigration into Ireland during the collection period population stratification is unlikely to confound the performed genetic analyses. Women with a history of at least one unexplained second trimester pregnancy loss (n=125), during a previous pregnancy were identified retrospectively from the computerised records of the Coombe Women's Hospital. Individual chart reviews were then performed to confirm the details of each case. Cases were women with a previous history of spontaneous abortion or in utero fetal demise occurring spontaneously between 13 and 26 weeks gestation. Women in whom a clinical explanation for the spontaneous abortion or fetal death was apparent were excluded. Thus, women with incompetent cervix, preterm premature rupture of membranes, preterm labor, placental abruption, maternal medical disease, or fetal malformations were not included. The control group (n=625) consisted of a systematic random sample of women from the same bank. Data on parity and maternal age when the blood sample was collected was available for all cases except one and for 118/625 of the controls. Personal identifiers were removed from all samples prior to genetic testing. Appropriate ethical approval was obtained for all samples collected.

Genomic DNA was extracted from cases and controls using the QIAamp DNA Blood Mini Kit from Qiagen, UK. Genotyping of the MTHFR 677C>T and MTHFD1 1958G>A polymorphisms was performed using PCR-RFLP (Restriction Fragment Length Polymorphism) using Hinf I and Msp I respectively as previously described [Frosst et al., Nature Genet. 10:111-113 (1995); Hol et al., Clin. Genet. 53:119-125 (1998); Brody et al., Am. J. Hum. Genet. 71:1207-1215 (2002)]. The TCNII 776C>G polymorphism was genotyped using an allele-specific primer extension assay and scored by matrix-assisted laser desorption/ionization-time of flight (MALDI-TOF) mass spectrometry (Sequenom, San Diego). Appropriate controls were included in all assays and genotyping consistency was tested by analyzing between 10-15% of samples in duplicate, resulting in 100% agreement.

The PCR conditions used for the experiment are set out in part in Table II. The reactions were set up on ice, and ran with thermocycle program "MTHFDRQ" using three GeneAmp PCR 9700 machines. When the temperature was approx. 90° C. the machine was paused and the tray was placed inside machine and the program was allowed to run. The program "MTHFDRQ" comprises the following parameters: 95° C. 3 mins, (94° C. 30 secs, 58° C. 1 min, 72° C. 1 min)×35 cycles, 72° C. 10 mins, Hold at 15° C. The primers used were R653Q Forward Primer 5' cactccagtgtttgtccatg 3' (SEQ ID NO: 19) and R653Q Reverse Primer 5' gcatcttgagagccctgac 3' (SEQ ID NO: 20). The primer stocks were diluted as follows: 1/25 60 µl+1,440 µl water for the forward primer and 1/23 65 µl+1,435 µl water for the reverse primer.

TABLE II

PCR Reactants

| Reagent | 100 Reactions | Per Reaction |
|---|---|---|
| 10 x PCR BUFFER | 500 µl | 5 |
| 25 mM MgCl$_2$ | 300 µl | 3 |
| 2.5 mM dNTPs | 400 µl | 4 |
| F primer 1/25 (10 pmol/µl) | 250 µl | 2.5 |
| R primer 1/23 (10 pmol/µl) | 250 µl | 2.5 |
| Taq (5 U/µl, Sigma) | 20 µl | 0.2 |
| H$_2$O* | 3180 µl | 31.8 |
| DNA* | 1 µl + 49 µl Mix | 1 µl |

*Adjust H$_2$O volume depending on how much DNA is added.

The PCR products were digested with restriction enzyme MspI as indicated in Table III. Digestions took place in 37° C. waterbath for at least 3 hours, and can also be left overnight.

TABLE III

PCR Product Digest Parameters

| Reagent | 100 Digests | Per Digest |
|---|---|---|
| Msp I (20 U/µl) | 100 µl | 1 µl |
| NEB2 Buffer | 300 µl | 3 µl |
| H$_2$O | 1,100 µl | 11 µl |
| PCR product | 15 µl + 15 µl Mix | 15 µl |

The products of the digest were with mixed with Orange G loading dye and loaded all on 1.5% agarose gel (use centipede with large combs: half a tray per gel) and allowed to run until orange G is just at the bottom of the gel. The bottom half of the gel can be stained in an ethidium bromide bath. The uncut product should be approximately 330 bp. For an AA genotype, the digest products should be approximately 267 bp and 71 base pairs. For a GG genotype, the digest product should be approximately 196 bp, 71 bp, and 55 bp. For an AG genotype, the digest product should be approximately 267 bp, 196 bp, 71 bp, and 55 bp.

The association between case-control status and genotype was examined using a number of standard odds ratios. In order to have a common approach for all analyses, a log linear model was employed. The statistical software (SAS PROC NLMIXED) allows estimation of nonlinear functions of the parameters of the model, and provides standard errors calculated using the delta method [Agresti, Categorical Data Analysis (1990)]. The parameterization of the model can easily be modified for the computation of different odds ratios. This approach enabled estimation of log odds ratios and their standard errors for the computation of confidence intervals, as well as checking the goodness of fit of different models. Potential gene-gene interaction effects were also examined. Tests of interactive dominant or recessive effects of specific combined genotypes were performed using a series of non-hierarchical logistic regression models [Piegorsch et al., Stat. Med. 13:153-162 (1994)]. Statistical significance was assessed using likelihood ratio chi-square tests.

The majority of cases (116/125) had experienced just one second trimester pregnancy loss. The remaining cases experienced two (n=7) or three (n=2) second trimester pregnancy losses. The average age of the study cases was 30+/−5.23 and controls were 26.3 +/−5.09 (data on just 118/625 controls). Among the case group 12% of women had a parity of 0 and 88% had a parity of 1. Among the control group where data was available, 43% had a parity of 0 and 57% had a parity of 1.

Three polymorphisms were genotyped in the second trimester pregnancy loss case (n=125) and control (n=625) groups with 98.9% of all subjects successfully genotyped for MTHFD1 1958G>A, 98.4% for MTHFR 677C>T and 97.8% for TCNII 776C>G. Comparison of allele and genotype frequencies between cases and controls is shown in Table IV.

TABLE IV

COMPARISON OF MTHFD1 1958G > A, MTHFR 677C > T AND TCNII 776C > G POLYMORPHISMS IN MOTHERS WITH A HISTORY OF SECOND TRIMESTER PREGNANCY LOSS AND CONTROL MOTHERS.

| MTHFD1 1958G > A | Genotypes | | | Alleles | |
|---|---|---|---|---|---|
| | GG | AG | AA | G | A |
| Case Mothers | 32 (.26)[1] | 58 (.47) | 33 (.27) | 122 (.50) | 124 (.50) |
| Control Mothers | 173 (.28) | 333 (.54) | 113 (.18) | 679 (.55) | 559 (.45) |
| A vs. G | Odds Ratio 1.23 (95% CI 0.93-1.63), P = 0.14[2] | | | | |
| AA vs. AG/GG | Odds Ratio 1.64 (95% CI 1.05-2.57), P = 0.03[3] | | | | |
| MTHFR 677C > T | CC | CT | TT | C | T |
| Case Mothers | 55 (.44) | 55 (.44) | 14 (.11) | 165 (.67) | 83 (.33) |
| Control Mothers | 271 (.44) | 270 (.44) | 73 (.12) | 812 (.66) | 416 (.34) |
| T vs. C | Odds Ratio 0.98 (95% CI 0.73-1.31), P = 0.90 | | | | |
| TT vs. CT/CC | Odds Ratio 0.94 (95% CI 0.51-1.73), P = 0.85[4] | | | | |
| TCNII 776C > G | CC | CG | GG | C | G |
| Case Mothers | 33 (.27) | 61 (.50) | 29 (.24) | 127 (.52) | 119 (.48) |
| Control Mothers | 184 (.30) | 306 (.50) | 121 (.20) | 674 (.55) | 548 (.45) |
| C vs. G | Odds Ratio 1.15 (95% CI 0.88-1.52), P = 0.31 | | | | |
| GG vs. CC/CG | Odds Ratio 1.25 (95% CI 0.79-1.98), P = 0.34[5] | | | | |

[1] Data in parentheses are allele or genotype frequencies;
[2] Chi-squared analysis;
[3] Goodness of fit statistic G2 P = 0.80;
[4] Goodness of fit statistic G2 P = 0.99;
[5] Goodness of fit statistic G2 P = 0.65

The MTHFD1 1958AA genotype is clearly enriched in the second trimester pregnancy loss case group compared to controls. MTHFD1 1958AA women have a significantly increased risk of having an unexplained second trimester pregnancy loss than women who are MTHFD1 1958AG or 1958GG (odds ratio 1.64 (1.05-2.57) P=0.03). The control group shows deviation from Hardy-Weinberg equilibrium with slightly more MTHFD1 1958AG heterozygotes than expected (P=0.03). Published frequencies from other populations including Dutch (Hol et al., Clin Genet. 53, 119-125 (1998)), Turkish (Akar et al., Thromb Res 102, 115-120 (2001)), Italian (De Marco et al., Annual Meeting of the Society for Research into Hydrocephalus and Spina Bifida, Dublin 23-26 (2004)) and Mexican (Shi et al., Birth Defects Res. Part A Clin. Mol. Teratol., 67:545-549 (2003)) are also skewed toward heterozygote excess although these deviations from Hardy-Weinberg equilibrium are not statistically significant.

Increased frequencies of the TCNII 776G allele (48% vs 45%) and the 776GG genotype (24% vs 20%) were observed in cases compared to controls (Table IV). Although this difference was not statistically significant, the TCNII 776C>G polymorphism cannot be completely ruled out as a risk factor for second trimester loss. Comparison of the allele and genotype frequencies of the MTHFR 677C>T polymorphism showed no difference between cases and controls. Thus, the MTHFR 677C>T polymorphism does not appear to be a significant risk factor for unexplained second trimester pregnancy loss in the Irish population.

Data was also examined for the possibility of combined genetic factors having an additive effect on risk of second trimester loss. The following genotype combinations for the possibility of an interactive effect: MTHFD1 1958AA and MTHFR 677TT (OR 1.25, P=0.75), MTHFD1 1958AA and TCNII 776GG (OR 1.20, P=0.75) or 776CG/GG (OR 1.16, P=0.77), MTHFR 677TT and TCNII 776GG (OR 0.81, P=0.78) or 776CG/GG (OR 0.70, P=0.59). The results of these analyses show no significant genotype interactive effects on the risk of second trimester pregnancy loss.

While there has been some evidence to support a role of the MTHFR 677C>T polymorphism as both a maternal and fetal genetic risk factor for early pregnancy loss [Reviewed in Zetterberg et al., Reprod. Biol. Endocrinol., 2:7 (2004)], analysis of the MTHFR 677C>T polymorphism in the second trimester cohort showed no evidence of an association.

The results indicate that the maternal TCNII 776C>G genotype does not independently contribute to risk of second trimester pregnancy loss. Although the 776GG genotype showed an increased frequency in the second trimester case group compared to controls (24% vs 20%), this result was not statistically significant.

Although the variants in MTHFR and TCNII were not found to be independent maternal risk factors, each may contribute to second trimester loss in combination with some other factor. For example, an interactive effect between TCNII 776CG or 776GG and MTHFR 677TT on early fetal loss has been reported [Zetterberg et al., Hum. Reprod.

18:1948-1950 (2003)]. While an odds ratio comparison showed that these genotype combinations were significantly higher in spontaneously aborted fetuses, a statistical method that differentiates between independent and interactive effects would have tested more effectively whether these polymorphisms act synergistically. Logistic regression analysis was applied to this data [reconstructed from Zetterberg et al., Eur. J. Hum. Genet. 10: 113-118 (2002), Zetterberg et al., Hum. Reprod., 17:3033-3036 (2002), and Zetterberg et al., Hum. Reprod. 18:1948-1950 (2003)]. This method confirmed that each polymorphism acts as an independent risk factor (TCNII 776CG or 776GG, P=0.0006; MTHFR 677TT P=0.033) but the interaction between MTHFR 677TT and TCNII 776CG/GG was not significant (P=0.77). Similarly, no evidence was found in the analysis of second trimester pregnancy loss cases and controls for interactive effects between the MTHFR 677TT and TCNII 776GG (P=0.78) or TCNII 776CG/GG (P=0.59).

The study did consider maternal age and the mean age among cases was 30 years, well under the threshold (35+ years) at which substantially increased complications related to maternal age are expected [Cunningham and Leveno, N. Engl. J. Med. 333:1002-1004 (1995)]. All losses with fetal malformations were excluded. Even if miscarriages due to unrecognized NTDs were present in the study, such miscarriages were unlikely to have had a significant impact on the analyses as the rate of NTD associated pregnancy losses is 1/50.

This experimental study has identified the MTHFD1 1958AA genotype as an independent maternal risk factor for unexplained pregnancy loss during the second trimester of pregnancy. Analyses of the MTHFR 677C>T and TCNII 776C>G polymorphisms did not indicate that these variants either independently or in combination had any significant affect on risk of pregnancy loss.

EXAMPLE 3

The second trimester study of Example 2 is repeated, but also gathering data for maternal risk factors such as tobacco or alcohol use, which contribute to fetal loss. In addition, prenatal diagnosis and routine ultrasound can be performed. Genetic testing as described above for MTHFD1, MTHFD1L, etc. is carried out. These genetic test results can be combined with the risk associated with alcohol or tabacco use. The resulting risk estimate provides greater accuracy than those based on genetic testing or environmental exposure measurements alone.

EXAMPLE 4

The second trimester study of Example 2 is repeated, but with further testing for inherited or acquired thrombophilia. This testing involves testing for the polymorphic variants described herein in respect to F2 and F5. By testing for multiple risk factors, one can achieve greater predictive value.

EXAMPLE 5

The results in Example 2 showed significantly more 1958AG heterozygotes in the general population than expected and the apparent selection against transmission of the 1958A allele in the earlier MTHFD1 NTD study suggested that the 1958G>A polymorphism in the fetus may also have a role in fetal loss. The second trimester study is repeated with the spontaneously aborted embryos/fetuses tested for the MTHFD1 1958G>A polymorphism with the tentative prediction that more than expected would carry the 1958AA genotype.

EXAMPLE 6

The following study revealed a correlation between neural tube defects and a particular variant of the rs3832406 polymorphism of MTHFD1L is predicative of an increased susceptibility for a having a child with a neural tube defect.

The study group consisted of NTD-affected children plus their parents (triads) who were recruited throughout Ireland from 1993 to date with the assistance of various branches of the Irish Association for Spina Bifida and Hydrocephalus. The NTD population comprised 387 NTD cases, 349 fathers of NTD cases and 386 mothers of NTD cases. The control population (n=280) was obtained from between 1986 and 1990 from 56,049 pregnant women attending the three main maternity hospitals in the Dublin area. Details of this collection have been described previously [Kirke, et al., Q. J. Med., 86:703-708 (1993)]. Informed consent and ethical approval were obtained for all samples collected.

Extraction of genomic DNA was carried out using the QIAamp DNA Blood Mini Kit, Qiagen, UK. Genotyping of the MTHFD1L intron 7 deletion insertion polymorphism, rs3832406, was carried out under the conditions outlined below. The sequences for the PCR primers were as follows: MTHFD1L.F 5'*TTCTCTTTCTTAGCCCCACG 3' (SEQ ID NO: 21) and MTHFD1L.R 5' AGAGCTTGCAGTGAGC-CTAGA 3' (SEQ ID NO: 22)*6-FAM (BLUE) LABEL. An ABI GeneAmp PCR system 9700 was used for the thermocycling using the following program conditions: 94° C. 3 mins, (94° C. 30 secs, 60° C. 30 secs, 72° C. 30 secs)×35 cycles, 72° C. 5 mins. PCR reactant parameters are provided in Table V.

TABLE V

| MTHFD1L PCR REACTANTS | | |
| --- | --- | --- |
| Reagent | 100 Reactions | Per Reaction |
| 10 x PCR BUFFER | 250 µl | 2.5 |
| 25 mM MgCl$_2$ | 150 µl | 1.5 |
| 2.5 mM dNTPs | 200 µl | 2 |
| F primer 1/90 (10 pmol/µl) | 200 µl | 2 |
| R primer 1/20 (10 pmol/µl) | 50 µl | 0.5 |
| Taq (5 U/µl, Sigma) | 10 µl | 0.1 |
| H$_2$O* | 1390 µl | 13.9 |
| DNA* | 2.5 µl + 22.5 µl Mix | |

PCR products were resolved on a 6% denaturing polyacrylamide gel on an ABI 377 DNA sequencer and sized using the Genescan software. Genotypes were analysed using the Genotyper software. Analysis of the transmission of alleles from parents to affected NTD case was performed using an extended transmission disequilibrium test as described by Sham and Curtis, Ann. Hum. Genet., 59(Pt 3):323-36 (1995), using the ETDT software. Allele and genotype frequencies were compared between NTD groups and controls and statistical significance was assessed by chi-squared analysis. The allele and genotype frequencies for MTHFD1L intron 7 deletion insertion polymorphism, rs3832406, are shown in Table VI. The alleles are represented by the following numbers: Allele 1=7×ATT; Allele 2=8×ATT; Allele 3=9×ATT.

TABLE VI

Allele and Genotype Frequencies in NTD Groups and Controls

|  | Cases | Fathers | Mothers | Controls |
|---|---|---|---|---|
| Genotypes |  |  |  |  |
| 1-1 | 184 (.49) | 134 (.39) | 164 (.44) | 107 (.39) |
| 1-2 | 74 (.20) | 91 (.27) | 84 (.23) | 75 (.28) |
| 1-3 | 69 (.19) | 66 (.19) | 75 (.20) | 58 (.21) |
| 2-2 | 10 (.03) | 14 (.04) | 10 (.03) | 14 (.05) |
| 2-3 | 23 (.06) | 16 (.05) | 22 (.06) | 10 (.04) |
| 3-3 | 12 (.03) | 19 (.06) | 18 (.05) | 8 (.03) |
| Total | 387 (96.1%) | 349 (97.4%) | 386 (96.6%) | 280 (97.1%) |
| H-W (2df) | P = 0.044 | P = 0.004 | P = 0.080 | P = 0.102 |
| Alleles |  |  |  |  |
| 1 | 511 (.69) | 425 (.63) | 487 (.65) | 347 (.64) |
| 2 | 117 (.16) | 135 (.20) | 126 (.17) | 113 (.21) |
| 3 | 116 (.16) | 120 (.18) | 133 (.18) | 84 (.15) |

Comparison of cases to controls showed that the "1-1" genotype appears to be associated with increased risk of an NTD. In contrast, the "2" allele appears to be protective. The ETDT test confirmed the case versus control comparisons and showed over transmission of the "1" allele from parents to affected offspring, while the "2" allele showed under transmission. A summary of this analysis is shown in Table VII.

TABLE VII

Case Vs Control Comparisons

Allele

1 Vs 2/ 3; OR 0.80 (0.64-1.01) P = 0.066
2 Vs 1/ 3; OR 1.41 (1.06-1.87) P = 0.020
3 Vs 1/ 2; OR 0.99 (0.73-1.34) P = 0.941

Genotypes 1-1 Vs the Rest; OR 1.51 (1.10-2.07) P = 0.011
2-2/1-2/2-3 Vs the Rest; OR 0.71 (0.51-0.99) P = 0.041
3-3 Vs the Rest; OR 1.10 (0.44-2.73) P = 0.837

If ignore Allele 3:

1-1 Vs 1-2/2-2 OR 1.83 (1.25-2.68) P = 0.002
1-1 genotype = Risk
1-2 or 2-2 = Protective
Other genotypes = no effect Logistic Regression TDT was performed using extended transmission disequilibrium test-Sham and Curtis 1995 Software ETDT, supra, results were as follows: Chi-squared for allele-wise TDT=2*(L1–L0)=9.496, 2 df, P=0.0087. Chi-squared for genotype-wise TDT 2*(L2–L0)=10.887, 3 df, P=0.0124. Chi-squared for goodness of fit of allele-wise model=2*(L2-L1)=1.391, 1 df, P=0.238. L0=Log likelihood that there is a probability of equal transmission, i.e., null hypothesis. L1=Alternative hypothesis that transmission probabilities are determined in an allele specific way. L2=Transmission probabilities may be independent for each genotype, that is, alleles are transmitted in a genotype specific fashion.

A summary of transmissions from all heterozygous parents is provided in Table VIII; maternal and paternal results are displayed in Tables IX and X respectively.

TABLE VIII

Summary of Transmissions from All Heterozygous Parents

|  | Allele 1 | Allele 2 | Allele 3 |
|---|---|---|---|
| Passed | 137 (58%) | 63 (38%) | 66 (51%) |
| Not Passed: | 100 (42%) | 102 (62%) | 64 (49%) |
| Chi-Squared (1df): | 5.776 | 9.218 | 0.031 |
| P-values$: | 0.0163 | 0.0024 | 0.8608 |

$these values can be corrected for multiple testing.

TABLE IX

Maternal Transmissions only

|  | Allele 1 | Allele 2 | Allele 3 |
|---|---|---|---|
| Passed | 65 (61%) | 28 (41%) | 27 (42%) |
| Not Passed: | 41 (39%) | 41 (59%) | 38 (58%) |
| Chi-Squared (1df): | 5.434 | 2.449 | 1.862 |
| P-values$: | 0.0198 | 0.1176 | 0.1725 |

Chi-squared for allele-wise TDT = 2* (L1 – L0) = 5.489, 2 df, P = 0.064
Chi-squared for genotype-wise TDT 2* (L2 – L0) = 7.115, 3df, P = 0.068
Chi-squared for goodness of fit of allele-wise model = 2* (L2 – L1) = 1.627, 1df, P = 0.202
$these values can be corrected for multiple testing.

TABLE X

Paternal Transmissions only

|  | Allele 1 | Allele 2 | Allele 3 |
|---|---|---|---|
| Passed | 63 (56%) | 30 (35%) | 35 (61%) |
| Not Passed: | 50 (44%) | 56 (65%) | 22 (39%) |
| Chi-Squared (1df): | 1.496 | 7.860 | 2.965 |
| P-values$: | 0.2214 | 0.0051 | 0.0852 |

Chi-squared for allele-wise TDT = 2* (L1 – L0) = 9.341, 2 df, P = 0.009
Chi-squared for genotype-wise TDT 2* (L2 – L0) = 9.404, 3df, P = 0.024
Chi-squared for goodness of fit of allele-wise model = 2* (L2 – L1) = 0.062, 1df, P = 0.802
$these values can be corrected for multiple testing.

The 1-1 genotype appears to be a risk for NTD cases. Preferential transmission of allele 1 is observed in the TDT. Having at least one copy of allele 2 appears to protect against NTDs i.e., 1-2, 2-2 or 2-3 genotypes. The TDT shows that allele 2 is transmitted significantly less than expected. Allele 3 appears to have no effect on risk of NTDs. The fathers and NTD cases are significantly out of Hardy-Weinberg equilibrium, presumably this situation is driven by the case genotypes.

EXAMPLE 7

The hypothesis being tested in the following series of experiments is that polymorphism rs3832406 within the MTHFD1L gene affects the splicing efficiency of the alternative transcript and could ultimately impact on the level of mitochondrial 10-formyltetrahydrofolate synthase.

Confirmation of the Alternatively Spliced Transcript

Total RNA was extracted from transformed lymphoblast cell lines using Ultraspec™ II (Biotex, Houston, USA). These cell lines were obtained from the Coriell Cell Repository, having been transformed by culturing primary lymphocytes with Epstein-Barr Virus (EBV). RNA from five cell lines was pooled, although pooling need not be carried out for this experiment. These five cell lines and their genotypes were 15083 (7ATT/7ATT), 17102 (7ATT/7ATT), 17133 (7ATT/8ATT), 17219 (7ATT/7ATT), and 17259 (7ATT/8ATT). DnaseI (Invitrogen) treated RNA (1 µg) was reverse transcribed using Superscript II (Invitrogen) as described by the manufacturer. PCR primers were designed to amplify both transcripts (Table XI), the 1.1 kb transcript only or the 3.6 kb transcript only (Table XI). The results of this experiment confirm the presence of both transcripts that are specific to the MTHFD1L gene.

TABLE XI

Primer Sequence Details for RT-PCR Assays

| Primer Sequences | mRNA | PCR Temp. |
|---|---|---|
| Forward (SEQ ID NO: 23): CCATCGTCAGAGAAGTCATTCA Reverse (SEQ ID NO: 24): CTGGTTGATTTCCTGCATCA | 1.1 kb and 3.6 kb | 56° C. |
| Forward (SEQ ID NO: 25) GGTCTTTGGAAGCTGCTCTACA Reverse (SEQ ID NO: 26): TTGCAGTGAGCCTAGATCACG | 1.1 kb only | 58° C. |
| Forward (SEQ ID NO: 27): GATCACACCCACCCCTCTTG Reverse (SEQ ID NO: 28): CCTCCTTTCACTCCAAACGTC | 3.6 kb only | 58° C. |

Determination of mRNA Levels

Taqman assays are performed to examine the levels of MTHFD1L mRNA in relation to the rs3832406 polymorphism. Lymphoblast Coriell cell lines that are representative of rs3832406 genotypes have been identified. Total RNA is extracted and DnaseI treated as described above. Taqman® assays have been designed to distinguish the expression level of the long and short transcripts of MTHFD1L. A control assay that detects both transcripts is localized between Exons 1 and 2 of the MTHFD1L mRNA transcript (Applied Biosystems (ABI) assay ID Hs_00920574). A second assay detects the longer transcript only and is localized to Exons 19/20 (ABI assay ID Hs_003836161). A third assay has been custom designed by ABI and is localized to Exons 7/8A. These assays will be used to examine the relative expression levels of both transcripts to determine if there are differences that are correlated with rs3832406 genotype.

Folate/Homocysteine Levels

A correlation between the rs3832406 polymorphism and folate/homocysteine levels is determined. A collection of DNA samples where folate and homocysteine levels have already been assayed are genotyped for the rs3832406 polymorphism using the procedures described herein. A correlation may be found between genotype and folate/homocysteine levels. As folate and homocysteine levels may predict vascular disease and cancer risk, genotypes at rs3832406 may prove useful in estimating the risk for these diseases.

EXAMPLE 8

The objective of these experiments is to determine if a polymorphism in MTHFD1L, for example, rs3832406, has an effect on the efficacy or proper dosage for a chemotherapeutic drug such as 5-fluorouracil (5-FU), and more generally whether a particular variant has an effect on the metabolic pathways that affect 5-FU/folinic acid (FA) action. Variable response of patients to administration of 5-FU or other drugs relevant to folate metabolism, or administration of the specific drugs can be used in identifying polymorphic variants responsible for such variable response. As described above, those polymorphic variants can then be used in diagnostic tests and methods of treatment.

5-fluorouracil (5-FU) is a widely used chemotherapy drug. The effectiveness of 5-FU is potentiated by folinic acid (FA; generic name: leukovorin). The combination of 5-FU and FA is standard therapy for stage III/IV colon cancer. 5-FU is used in the standard treatment of gastrointestinal such as colorectal, breast and head and neck cancers. Clinical trials have also shown responses in cancer of the bladder, ovary, cervix, prostate and pancreas. Patient responses to 5-FU and 5-FU/FA vary widely, ranging from complete remission of cancer to severe toxicity.

This study compares the variance frequency distribution in the MTHFD1L rs3832406 polymorphism between groups of patients with solid tumors, treated by weekly or monthly regimen of 5-FU+FA and defined by level of toxicity (graded according to the NCI common toxicity criteria) as: Group 1: patients with high toxicity (grade III/IV on NCI criteria) Group 2: patients with minimal toxicity (grade 0/I/II on NCI criteria). This study helps determine whether the seven, eight, nine, or other multiple "ATT" repeat polymorphic variant affects the efficacy of the 5-FU+FA regemin, and can be readily adapted to test other drug regemins as well. The groups differ in the degree of toxicity experienced with treatment, if any: patients with high toxicity (grade III/IV on NCI criteria), and patients with minimal toxicity (grade 0/I/II on NCI criteria). Analyses are performed globally, then by regimen (monthly vs. weekly) and by type of toxicity (gastrointestinal vs. bone marrow). The statistical significance of the differences between polymorphic variant frequencies can be assessed by a Pearson chi-squared test of homogeneity of proportions with n−1 degrees of freedom.

In one embodiment, the number of subjects in the study is as follows: about 50-100 patients to each group. However, prior to testing to identify the presence of sequence polymorphic variants in a particular gene or genes, it is useful to understand how many individuals should be screened to provide confidence that most or nearly all pharmacogenetically relevant polymorphic variants will be found. The answer depends on the frequencies of the phenotypes of interest and what assumptions were made about heterogeneity and magnitude of genetic effects. At the beginning, only known phenotype frequencies, for example, responders vs. no responders, frequency of various side effects, etc., are known. The occurrence of serious 5-FU/FA toxicity, for example, toxicity requiring hospitalization is often >10%. The occurrence of life threatening toxicity is in the 1-3% range [Buroker et al., J. Clinical Oncology 12:14-20 (1994)]. The occurrence of complete remissions is on the order of 2-8%. The lowest frequency phenotypes are about 2%.

In one embodiment, if homogeneous genetic effects are responsible for half the phenotypes of interest and for the most part the extreme phenotypes represent recessive genotypes, then one should detect alleles that will be present at about 10% frequency (0.1×0.1=0.01, or 1% frequency of homozygotes) if the population is at Hardy-Weinberg equilibrium. To have an about 99% chance of identifying such alleles would involve searching a population of 22 individuals. If the major phenotypes are associated with heterozygous genotypes then alleles present at about 0.5% frequency (2×0.005×0.995=0.00995, or about 1% frequency of heterozygotes) should be detected. A 99% chance of detecting such alleles would involve about 40 individuals. Given the heterogeneity of the North American and other populations, one should not necessarily assume that all genotypes are present in Hardy-Weinberg proportions; a substantial oversampling is performed to increase the chances of detecting relevant polymorphic variants: For initial screening, 50-100 individuals of known race/ethnicity can be screened for polymorphic variant. Polymorphic variant detection studies can be extended to outliers for the phenotypes of interest to cover the possibility that important polymorphic variants were missed in the normal population screening.

Two major dosing regimens can be used: 5-FU plus low dose FA given for five consecutive days followed by a 23 day interval, or once weekly bolus intravenous 5-FU plus high dose FA. The higher FA dose results in plasma FA concentrations of 1 to 10 µM, comparable to those used for optimal 5-FU/FA synergy in tissue culture, however low dose FA (20 mg/m$^2$ vs. 500 mg/m$^2$) has produced comparable clinical benefit.

Leukovorin (folinic acid) is the most widely used 5-FU modulator, however a variety of other molecules have been used with 5-FU, including, for example, interferon-alpha, hydroxyurea, N-phosphonacetyl-L-aspartate, dipyridamole, levamisole, methotrexate, trimetrexate glucuronate, cisplatin and radiotherapy. S-1 is a novel oral anticancer drug, composed of the 5-FU prodrug tegafur plus gimestat (CDHP) and otastat potassium (Oxo) in a molar ratio of 1:0.4: 1, with CDHP inhibiting dihydropyrimidine dehydrogenase in order to prolong 5-FU concentrations in blood and tumour and Oxo present as a gastrointestinal protectant. The experimental study can be carried out with one of these modulator in addition to 5-FU.

5-FU toxicity has been well documented in randomized clinical trials. Accordingly, during the course of the experimental study, participants are monitored for such toxicities. Patients receiving 5-FU/FA are at even greater risk of toxic reactions and should be monitored carefully during therapy. A variety of side effects have been observed, affecting the gastrointestinal tract, bone marrow, heart and CNS. The most common toxic reactions are nausea and anorexia, which can be followed by life threatening mucositis, enteritis and diarrhea. Leukopenia and stomatitis is also a problem in some patients, particularly with the weekly dosage regimen. Toxicity is a major cost of 5-FU/FA therapy, measured both in patient suffering and in financial terms (the cost of care for drug induced illness).

Many non-genetic factors can influence the response of cancers to drugs, including tumor location, vasculature, cell growth fraction and various drug resistance mechanisms. Accordingly, in performing the drug trial, these non-polymorphic variables are controlled for by selecting participants with common attributes.

There are many potential candidate therapeutic interventions or drugs that can affect the folate and pyrimidine pathways. Categories of these are 5-FU prodrugs, drugs that affect DNA methylation pathways, and other drugs that have been developed for similar indications as 5-FU. The study can be performed using one of these drug in the alternative or in addition to 5-FU. 5-FU prodrugs are generally modified fluoropyrimidines that require one or more enzymatic activation steps for conversion into 5-FU. The activation steps may result in prolonged drug half-life and/or selective drug activation (i.e. conversion to 5-FU) in tumor cells. Examples of such drugs include capecitabine (Xeloda, Roche), a drug that is converted to 5-FU by a three-step pathway involving carboxylesterase 1, cytidine deaminase and thymidine phosphorylase. Another 5-FU prodrug is 5' deoxy 5-FU (Furtulon, Roche), which is converted to 5-FU by thymidine phosphorylase and/or uridine phosphorylase. Another 5-FU prodrug is 1-(tetrahydro-2-furanyl)-5-fluorouracil (FT, ftorafur, Tegafur, Taiho-Bristol Myers Squibb), a prodrug that is converted to 5-FU by cytochrome P450 enzyme, CYP3A4. In some embodiments, drugs acting on DNA methyation pathways are substituted or used in combination with 5-FU.

A variety of drugs are being developed for similar indications as 5-FU, and/or are being tested in combinations with 5-FU/leukovorin. These drugs can be substituted or used in combination with 5-FU in this study. Identification of patients likely to respond to 5-FU with or without leukovorin, may be useful in selecting optimal responders to other drugs. Alternatively, identification of patients likely to suffer toxic response to 5-FU containing regimens can allow identification of patients best treated with other drugs. Other drugs with activity against cancers usually treated with regimens containing 5-FU or in the alternative include the platinum compound oxaliplatin (L-OHP), the topoisomerase I inhibitors irinotecan (CPTI 1, Pharmacia-Upjohn) and topotecan, Surarnin, a bis-hexasulfonated napthylurea; 6-hydroxymethylacylfulvene (HMAF; MGI 114); LY295501; bizelesin (U-7779; NSC615291), ONYX-015, monoclonal antibodies, for example, 17-IA and MN-14, protein synthesis inhibitors such as RA 700, angiogenesis inhibitors such as PF 4, and cyclooxygenase inhibitors. Additional drugs that can be substituted for or used in combination with 5-FU in accordance with this study include the following: quinazoline derivatives such as ZD1694 (Tomudex, AstraZeneca); ZD9331 (AstraZeneca); LY231514 (Eli Lilly); GW1 843 (1843U89, GlaxoWellcome); AG337; and AG331; trimetrexate (US Bioscience); edatrexate, piritrexim; and lometrexol. More generally, 5,8-dideazaisofolic acid (LAHQ), 5,10-dideazatetrahydrofolic acid (DDATHF), and 5-deazafolic acid are structures into which a variety of modifications have been introduced in the pteridine/quinazoline ring, the C9-N10 bridge, the benzoyl ring, and the glutamate side chain (see article below). Other drugs include 2,4-diaminopyrido[2,3-d] pyrimidine based antifolates.

EXAMPLE 9

The experimental study described in Example 8 is repeated using a relevant cardiovascular drug. This study and similar studies are helpful in improving therapies for atherosclerosis, thromboembolic diseases and other forms of vascular and heart disease. Homocysteine is a proven risk factor for cardiovascular disease. One important role of the folate cofactor 5-methyltetrahydrofolate is the provision of a methyl group for the remethylation of homocysteine to methionine by the enzyme methionine synthase. Variation in the enzymes of folate metabolism, for example methionine syntase or methylenetetrahydrofolate reductase (MTHFR), may affect the levels of 5-methyltetrahydrofolate or other folates that in turn influence homocysteine levels. The contribution of elevated homocysteine to atherosclerosis, thromboembolic disease and other forms of vascular and heart disease may vary from one patient to another. Such variation may be attributable, at least in part, to genetically determined variation in the levels or function of the enzymes of folate and one carbon metabolism described in this application. Understanding which patients are most likely to benefit from particular drugs assists in the clinical development or use of drugs to treat cardiovascular diseases. Such drugs include those aimed at the modulation of folate levels, for example, supplemental folate, and at other known causes of cardiovascular disease, for example, lipid lowering drugs such as statins, or antithrombotic drugs such as salicylates, heparin or GPIIIa/IIb inhibitors. In some embodiments, patients are included whose disease is significantly attributable to elevated homocysteine from treatment with agents aimed at the amelioration of other etiological causes, such as elevated cholesterol.

EXAMPLE 10

The experimental study described in Example 8 is repeated using a relevant central nervous system (CNS) drug. Phencyclidine, an NMDA receptor antagonist, has been shown to induce a psychotic state closely resembling schizophrenia in normal individuals has led to attempts to modulate NMDA receptor function in schizophrenic patients. The amino acid glycine is an obligatory coagonist, with glutarnate, at NMDA receptors via its action at a strychnine-insensitive binding site on the NMDA receptor complex, and consequently glycine or glycinergic agents, for example, glycine, the glycine receptor partial agonist, D-cycloserine, or the glycine prodrug milacemide, have been tried as an adjunct to conventional antipsychotics for the treatment of schizophrenia. Several trials have demonstrated a moderate improvement in negative symptoms of schizophrenia. Because the folate pathway modulates levels of serine and glycine, the endogenous levels of glycine in neurons may affect the response to glycine or glycinergic drugs. CNS drugs can also include drugs for treatment or prevention of Alzheimer's disease or other dementia.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of screening a human for an increased susceptibility to second trimester miscarriage, the method comprising:
   (a) screening a sample from a human to detect the presence or absence of a polymorphic variant of a polymorphism in at least one chromosomal copy of the MTHFD1 gene, wherein the polymorphic variant is at position 1958 of SEQ ID NO: 2; and
   (b) identifying the human as having an increased risk of second trimester miscarriage with the homozygous presence of the AA polymorphic variant in the MTHFD1 gene.

2. A method of screening a human for an increased risk of placental abruption, the method comprising:
   (a) screening a sample from a human to detect the presence or absence of a polymorphic variant of a polymorphism in at least one chromosomal copy of the MTHFD1 gene, wherein the polymorphic variant is at position 1958 of SEQ ID NO: 2; and
   (b) identifying the human as having an increased risk of placental abruption with the presence of the A polymorphic variant in at least one chromosomal copy of the MTHFD1 gene.

* * * * *

UNITED STATES PATENT AND TRADEMARK OFFICE
CERTIFICATE OF CORRECTION

PATENT NO. : 7,879,551 B2  
APPLICATION NO. : 11/958126  
DATED : February 1, 2011  
INVENTOR(S) : Brody et al.

Page 1 of 1

It is certified that error appears in the above-identified patent and that said Letters Patent is hereby corrected as shown below:

Title page, item (73) which reads:

"Assignees: The United States of America as represented by the Department of Health and Human Services, Washington, DC (US)"

should read:

--The United States of America as represented by the Secretary, Department of Health and Human Services, Bethesda, MD (US)--

Signed and Sealed this  
Fifth Day of April, 2011

David J. Kappos  
*Director of the United States Patent and Trademark Office*